(12) United States Patent
Adachi et al.

(10) Patent No.: US 10,497,883 B2
(45) Date of Patent: Dec. 3, 2019

(54) ORGANIC LIGHT-EMITTING DEVICE, HOST MATERIAL, LIGHT-EMITTING MATERIAL, AND COMPOUND

(71) Applicant: KYULUX, INC., Fukuoka-shi, Fukuoka (JP)

(72) Inventors: Chihaya Adachi, Fukuoka (JP); Takuma Yasuda, Fukuoka (JP); Takuro Nishimoto, Fukuoka (JP); Sae Youn Lee, Fukuoka (JP)

(73) Assignee: KYULUX, INC., Fukuoka-Shi, Fukuoka (JP)

( * ) Notice: Subject to any disclaimer, the term of this patent is extended or adjusted under 35 U.S.C. 154(b) by 1 day.

(21) Appl. No.: 15/125,286

(22) PCT Filed: Mar. 4, 2015

(86) PCT No.: PCT/JP2015/056285
§ 371 (c)(1),
(2) Date: Sep. 12, 2016

(87) PCT Pub. No.: WO2015/137202
PCT Pub. Date: Sep. 17, 2015

(65) Prior Publication Data
US 2017/0213974 A1 Jul. 27, 2017

(30) Foreign Application Priority Data

Mar. 11, 2014 (JP) .................. 2014-047342

(51) Int. Cl.
*H01L 51/00* (2006.01)
*C07D 403/10* (2006.01)
(Continued)

(52) U.S. Cl.
CPC .......... *H01L 51/008* (2013.01); *C07D 403/10* (2013.01); *C07F 5/02* (2013.01);
(Continued)

(58) Field of Classification Search
CPC ....... C07F 5/027; C09K 11/025; C09K 11/06; C09K 2211/1007; C09K 2211/1059; C09K 2211/1096; H01L 51/008; H01L 51/5012

See application file for complete search history.

(56) References Cited

U.S. PATENT DOCUMENTS 8,658,832 B2   2/2014  Yersin et al.
9,153,788 B2  10/2015  Adachi et al.
(Continued)

FOREIGN PATENT DOCUMENTS

CN    101687889 A    3/2010
JP    2001-66651 A   3/2001
(Continued)

OTHER PUBLICATIONS

Machine translation for JP 2005-166574 A (publication date: Jun. 2005). (Year: 2005).*

(Continued)

*Primary Examiner* — Dawn L Garrett
(74) *Attorney, Agent, or Firm* — Browdy and Neimark, PLLC

(57) ABSTRACT

A high light emission efficiency can be achieved by the use of a compound represented by the general formula (1) as a host material or a light-emitting material of a light-emitting layer of an organic light-emitting device. $X^1$ to $X^{12}$ each independently represent C or BH constituting carborane, provided that among $X^1$ to $X^{12}$, the bonding positions to A and D each represent C, and the other thereof each represent BH; A represents an acceptor bonded to the carborane through an aromatic ring or a heteroaromatic ring; and D represents a donor bonded to the carborane through an aromatic ring or a heteroaromatic ring.

(Continued)

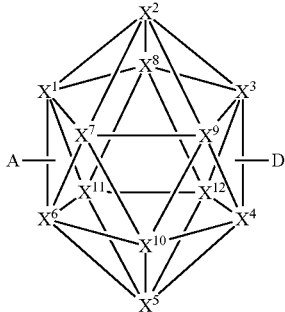

General Formula (1)

17 Claims, 5 Drawing Sheets

(51) Int. Cl.
*C09K 11/06* (2006.01)
*C07F 5/02* (2006.01)
*C09K 11/02* (2006.01)
*H01L 51/50* (2006.01)
*H05B 33/14* (2006.01)

(52) U.S. Cl.
CPC ............ *C07F 5/027* (2013.01); *C09K 11/025* (2013.01); *C09K 11/06* (2013.01); *H01L 51/0045* (2013.01); *H01L 51/0067* (2013.01); *H01L 51/0072* (2013.01); *H05B 33/14* (2013.01); *C09K 2211/1007* (2013.01); *C09K 2211/1011* (2013.01); *C09K 2211/1029* (2013.01); *C09K 2211/1059* (2013.01); *C09K 2211/1096* (2013.01); *H01L 51/5012* (2013.01)

(56) References Cited

U.S. PATENT DOCUMENTS

| | | | |
|---|---|---|---|
| 2008/0111473 A1* | 5/2008 | Kawamura | C07D 213/04 313/504 |
| 2009/0167162 A1* | 7/2009 | Lin | C07D 409/14 313/504 |
| 2010/0090209 A1* | 4/2010 | Ikari | H01L 27/3211 257/40 |
| 2012/0319088 A1* | 12/2012 | Lee | H01L 51/008 257/40 |
| 2014/0138669 A1 | 5/2014 | Nakagawa et al. | |
| 2014/0138670 A1 | 5/2014 | Nakagawa et al. | |
| 2014/0332792 A1* | 11/2014 | Tada | H01L 51/0067 257/40 |
| 2015/0048338 A1 | 2/2015 | Adachi et al. | |
| 2015/0105564 A1 | 4/2015 | Adachi et al. | |
| 2015/0141642 A1 | 5/2015 | Adachi et al. | |
| 2015/0144927 A1* | 5/2015 | Jin | H01L 51/008 257/40 |

FOREIGN PATENT DOCUMENTS

| | | |
|---|---|---|
| JP | 2005-166574 A | 6/2005 |
| JP | 4323935 B2 | 9/2009 |
| JP | 2010-505812 A | 2/2010 |
| JP | 2010-532399 A | 10/2010 |
| JP | 2013-116975 A | 6/2013 |
| JP | 2013-256490 A | 12/2013 |
| JP | 2014-009224 A | 1/2014 |
| JP | 2014-009352 A | 1/2014 |
| WO | 2008-041123 A1 | 4/2008 |
| WO | 2013-011954 A1 | 1/2013 |
| WO | 2013-011955 A1 | 1/2013 |
| WO | 2013-081088 A1 | 6/2013 |
| WO | 2013-088934 A1 | 6/2013 |
| WO | 2013-133359 A1 | 9/2013 |
| WO | 2013-154064 A1 | 10/2013 |
| WO | 2013-161437 A1 | 10/2013 |

OTHER PUBLICATIONS

International Preliminary Report on Patentability for corresponding PCT International Application No. PCT/JP2015/056285, dated Sep. 22, 2016, with English translation.
International Search Report for corresponding PCT International Application No. PCT/JP2015/056285, Year 2016.
First Office Action for corresponding Chinese Patent Application No. 201580013301.0, dated Apr. 19, 2017, with English translation.
Wee et al., Carborane-Based Optoelectronically Active Organic Molecules: Wide Band Gap Host Materials for Blue Phosphorescence, Journal of the American Chemical Society, 134:17982-17990 (2012).
Office Action dated Feb. 24, 2018 issued in the corresponding Chinese patent application No. 201580013301.0 with its English Machine Translation.
"Introduction to Organic EL", Chapter 3, Section 34, p. 80., Certified English translation of lines 6-13 in bottom part of 4, Apr. 26, 2008.
http://www.sigma-aldrich.com/mscatalog-jp, "Basics of Material Science", vol. 1, No. 1 published by Sigma-Aldrich Japan, Certified English translation of "3" to "5" in p. 7 of 2, Oct. 2009.
Office Action dated Aug. 21, 2018 issued in the corresponding Japanese patent application No. 2016-507471 with is English Machine Translation.
Chinese Office Action dated Sep. 10, 2018 issued in the corresponding Chinese patent application No. 201580013301.0 with its English Machine Translation.
Ayataka Endo et al., "Efficient up-conversion of triplet excitons into a singlet state and its application for organic light emitting diodes", Appl. Phys. Lett. 98, 083302 (2011), doi:10.1063/1.3558906.
Maya Parac et al., "A TDDFT study of the lowest excitation energies of polycyclic aromatic hydrocarbons", Chemical 292 (2003), pp. 11-21 Physics.
N. Nijegorodov et al., "Evolution of absorption, fluorescence, laser and chemical properties in the series of compounds perylene, benzo(ghi)perylene and coronene", Spectrochimica Acta Part A 57 (2001), pp. 2673-2685.
Chinese Office Action dated Sep. 10, 2018 issued in the corresponding Chinese patent application No. 201580013301.0 (English translation filed as NPL1 on Dated Dec. 12, 2018).

* cited by examiner

ORGANIC LIGHT-EMITTING DEVICE, HOST MATERIAL, LIGHT-EMITTING MATERIAL, AND COMPOUND

TECHNICAL FIELD

The present invention relates to a compound that is useful as a host material and the like, and an organic light-emitting device using the same.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing and combining an electron transporting material, a hole transporting material, a light-emitting material, a host material, and the like constituting an organic electroluminescent device. Among these, there are studies relating to an organic electroluminescent device utilizing a compound having a carborane structure.

Non-patent Document 1 describes the results of studies on the characteristics as a host material for blue phosphorescence of a carborane derivative represented by the following formula and a compound having a carbazolylphenyl group bonded to an o-position or a p-position of a carborane structure. However, the compounds described in Non-patent Document 1 are all symmetric molecules having the groups bonded to the carborane structure that are the same as each other, and a compound having different groups that are bonded to a carborane structure is not described.

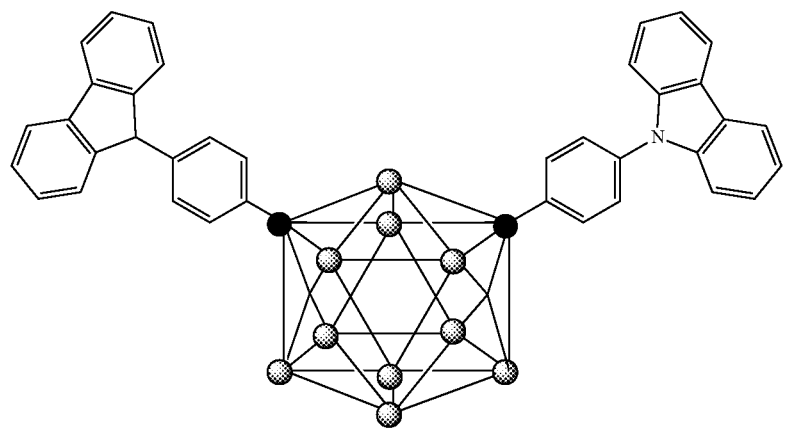

Patent Document 1 describes a carborane derivative having silyl groups bonded thereto represented, for example, by the following formula and a compound having a silyl group and another group bonded to a carborane structure, and describes an example using the carborane derivative as a host material in a light-emitting layer present between a pair of electrodes constituting an organic electroluminescent device. However, the carborane derivatives shown in Patent Document 1 are all compounds having a silyl group bonded to a carborane structure, and the literature does not describe a carborane derivative having combined therewith a group other than a silyl group.

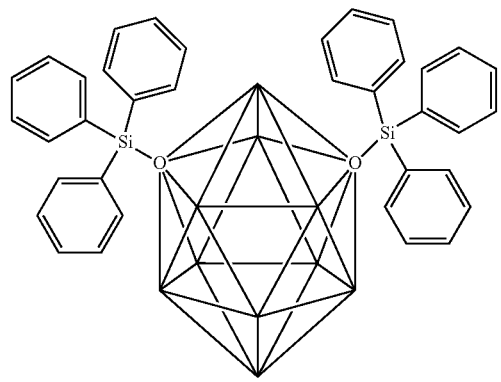

Patent Document 2 describes the usefulness of a carborane derivative represented by the following general formula as a material for an electron transporting layer of an organic electroluminescent device. In the formula herein, it is stated that $R^1$ to $R^8$ each represent a hydrogen atom, a substituted or unsubstituted alkyl group, a substituted or unsubstituted aryl group, a substituted or unsubstituted heterocyclic group, a substituted or unsubstituted condensed polycyclic aromatic group, or a substituted or unsubstituted condensed polycyclic heterocyclic group, and compounds, in which $R^1$ and $R^8$ are carbazolylphenyl groups, are described as specific examples thereof. However, Patent Document 2 does not confirm the usefulness of the carborane derivative represented by the following general formula as a host material and a light-emitting material.

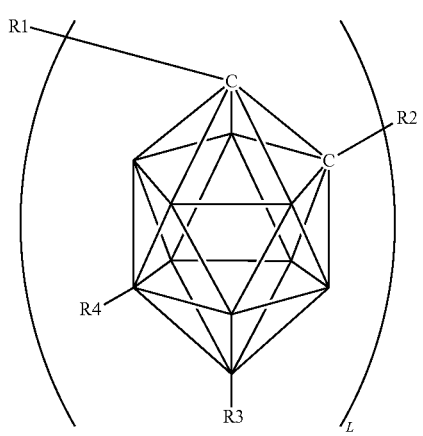

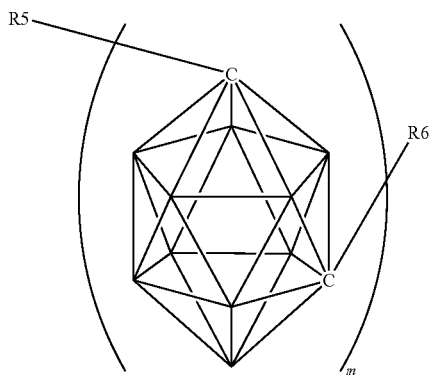

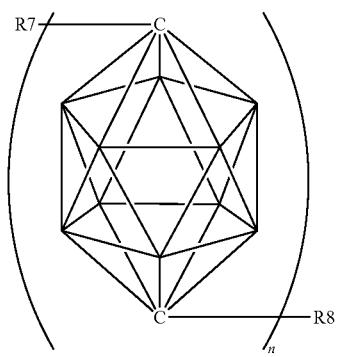

CITATION LIST

Non-Patent Literature

Non-patent Document 1: J. Am. Chem. Soc. 2012, 134, 17982-17990

Patent Literatures

Patent Document 1: WO 2013/088934
Patent Document 2: JP-A-2005-166574

SUMMARY OF INVENTION

Technical Problem

As described above, Non-patent Document 1 describes the results of studies on the characteristics as a host material of the compound having two carbazolylphenyl groups bonded to the carborane structure. However, as a result of actual evaluation by the present inventors of the characteristics as a host material of the compound having two carbazolylphenyl groups bonded to the carborane structure, it has been found that the characteristics are not sufficiently satisfactory, and there is a demand of providing a host material having better characteristics.

The inventors then start to investigate variously a group of compounds having a carborane structure, have firstly found that among many compounds having a carborane structure, a group of compounds having a structure containing a carborane structure having an acceptor and a donor bonded thereto has usefulness as a host material and the like, and have decided to continue further investigations. As described above, Patent Document 1 describes an example using the compound containing a carborane structure having silyl groups bonded thereto as a host material of a light-emitting layer. However, a silyl group does not function as an acceptor or a donor, and Patent Document 1 does not describe a compound containing a carborane structure having an acceptor and a donor bonded thereto. Patent Document 2 describes the usefulness of a compound containing a carborane structure having two carbazolylphenyl groups bonded thereto as a material for an electron transporting layer, and furthermore Non-patent Document 1 describes the result of investigations on the characteristics of the compound as a host material. Herein, a carbazolylphenyl group functions as a donor. However, Patent Document 1 and Non-patent Document 1 do not describe a compound containing a carborane structure having both a donor and an acceptor bonded thereto. Accordingly, for a compound containing a carborane structure having an acceptor and a donor bonded thereto, the usefulness as a host material, and the like of the compound cannot be estimated.

Under the circumstances, the inventors have further made investigations on the usefulness as a host material and the like of a compound containing a carborane structure having an acceptor and a donor bonded thereto, and have made accumulated studies for finding a compound having excellent characteristics as a host material and the like. Furthermore, the inventors have made earnest investigations for providing a general formula of compounds useful as a host material and generalizing the structure of an organic light-emitting material having a high light emission efficiency.

Solution to Problem

As a result of the earnest investigations performed, the inventors have found that compounds containing a carborane structure having an acceptor and a donor bonded thereto through an aromatic ring or a heteroaromatic ring has excellent properties as a host material and the like. The inventors also have found that the group of compounds includes compounds that are useful as a light-emitting material, such as a delayed fluorescent material, and have clarified that an organic light-emitting device having a high light emission efficiency can be provided inexpensively. Based on the knowledge, the inventors have provided the following inventions as measures for solving the problems.

[1] An organic light-emitting device containing a compound represented by the following general formula (1):

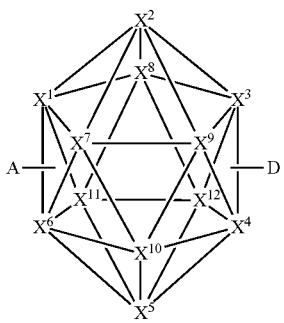

General Formula (1)

wherein in the general formula (1), $X^1$ to $X^{12}$ each independently represent C or BH constituting carborane, provided that among $X^1$ to $X^{12}$, the bonding positions to A and D each represent C, and the other thereof each represent BH; A represents an acceptor bonded to the carborane through an aromatic ring or a heteroaromatic ring; and D represents a donor bonded to the carborane through an aromatic ring or a heteroaromatic ring.

[2] The organic light-emitting device according to the item [1], wherein the organic light-emitting device contains the compound represented by the general formula (1) in a light-emitting layer.

[3] The organic light-emitting device according to the item [2], wherein the organic light-emitting device contains the compound represented by the general formula (1) as a host material.

[4] The organic light-emitting device according to the item [3], wherein the light-emitting layer further contains a delayed fluorescent emitter.

[5] The organic light-emitting device according to the item [2], wherein the organic light-emitting device contains the compound represented by the general formula (1) as a light-emitting material.

[6] The organic light-emitting device according to any one of the items [1] to [5], wherein in the general formula (1), D is bonded to the carborane through a benzene ring.

[7] The organic light-emitting device according to any one of the items [1] to [6], wherein in the general formula (1), D has a diphenylamino group or a carbazolyl group.

[8] The organic light-emitting device according to any one of the items [1] to [7], wherein in the general formula (1), D represents a group represented by the following general formula (2):

$[(R^1)(R^2)N]^{n1}$—Ar$^1$—    General Formula (2)

wherein in the general formula (2), $R^1$ and $R^2$ each independently represent a substituent, provided that $R^1$ and $R^2$ may be bonded to each other to form a cyclic structure; n1 represents an integer of from 1 to 4; and Ar$^1$ represents a substituted or unsubstituted aromatic group having a valence of (n1+1).

[9] The organic light-emitting device according to the item [8], wherein in the general formula (2), n1 represents 1 or 2.

[10] The organic light-emitting device according to any one of the items [1] to [9], wherein in the general formula (1), A has a heteroaromatic ring containing a nitrogen atom.

[11] The organic light-emitting device according to the item [10], wherein in the general formula (1), A has a triazine ring.

[12] The organic light-emitting device according to the item [11], wherein the triazine ring is substituted with a phenyl group.

[13] The organic light-emitting device according to any one of the items [10] to [12], wherein in the general formula (1), A is bonded to the carborane through the heteroaromatic ring containing a nitrogen atom.

[14] The organic light-emitting device according to any one of the items [10] to [12], wherein in the general formula (1), A represents a group represented by the following general formula (3):

(Het)$_{n2}$-Ar$^2$—    General Formula (3)

wherein in the general formula (3), Het represents a substituted or unsubstituted heteroaromatic ring group (provided that the heteroaromatic ring group contains a nitrogen atom as a ring structure constituting atom); n2 represents an integer of from 1 to 4; and Ar$^2$ represents a substituted or unsubstituted aromatic group having a valence of (n2+1).

[15] The organic light-emitting device according to the item [14], wherein in the general formula (3), n2 represents 1 or 2.

[16] The organic light-emitting device according to any one of the items [1] to [15], wherein the compound represented by the general formula (1) is an o-carborane compound or a m-carborane compound.

[17] The organic light-emitting device according to any one of the items [1] to [16], wherein the organic light-emitting device is an organic electroluminescent device.

[18] The organic light-emitting device according to any one of the items [1] to [17], wherein the organic light-emitting device emits delayed fluorescent light.

[19] A host material containing a compound represented by the following general formula (1):

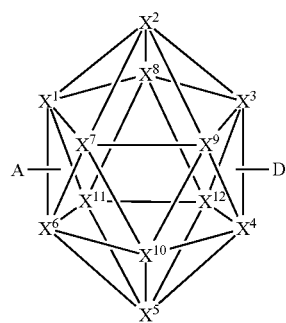

General Formula (1)

wherein in the general formula (1), $X^1$ to $X^{12}$ each independently represent C or BH constituting carborane, provided that among $X^1$ to $X^{12}$, the bonding positions to A and D each represent C, and the other thereof each represent BH; A represents an acceptor bonded to the carborane through an aromatic ring or a heteroaromatic ring; and D represents a donor bonded to the carborane through an aromatic ring or a heteroaromatic ring.

[20] A light-emitting material containing a compound represented by the following general formula (1):

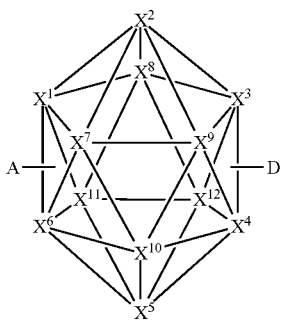

General Formula (1)

wherein in the general formula (1), $X^1$ to $X^{12}$ each independently represent C or BH constituting carborane, provided that among $X^1$ to $X^{12}$, the bonding positions to A and D each represent C, and the other thereof each represent BH; A represents an acceptor bonded to the carborane through an aromatic ring or a heteroaromatic ring; and D represents a donor bonded to the carborane through an aromatic ring or a heteroaromatic ring.

[21] A delayed fluorescent emitter containing a compound represented by the following general formula (1):

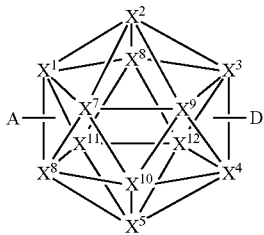

General Formula (1)

wherein in the general formula (1), $X^1$ to $X^{12}$ each independently represent C or BH constituting carborane, provided that among $X^1$ to $X^{12}$, the bonding positions to A and D each represent C, and the other thereof each represent BH; A represents an acceptor bonded to the carborane through an aromatic ring or a heteroaromatic ring; and D represents a donor bonded to the carborane through an aromatic ring or a heteroaromatic ring.

[22] A compound represented by the following general formula (1'):

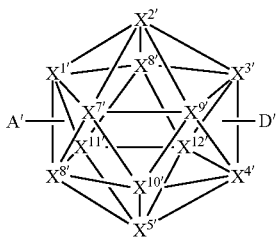

General Formula (1')

wherein in the general formula (1'), $X^{1'}$ to $X^{12'}$ each independently represent C or BH constituting carborane, provided that among $X^{1'}$ to $X^{12'}$, the bonding positions to A' and D' each represent C, and the other thereof each represent BH; A' represents an acceptor bonded to the carborane through an aromatic ring or a heteroaromatic ring; and D' represents a donor bonded to the carborane through an aromatic ring or a heteroaromatic ring.

Advantageous Effects of Invention

The compound represented by the general formula (1) is useful as a host material and/or a light-emitting material. The compound of the invention includes one that emits delayed fluorescent light. The organic light-emitting device using the compound of the invention as a host material or a light-emitting material is capable of achieving a high light emission efficiency.

DESCRIPTION OF EMBODIMENTS

Figure 1:
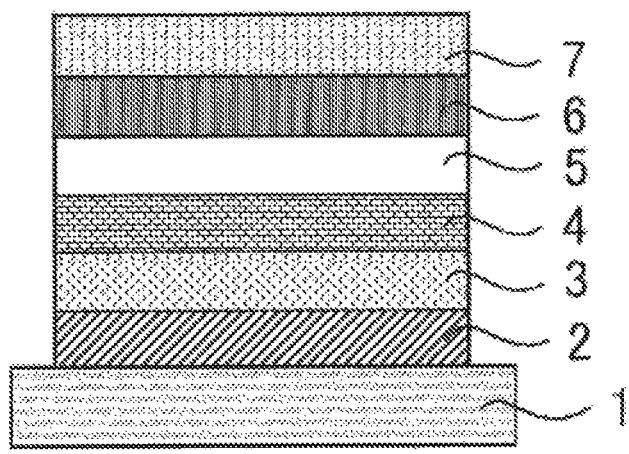
FIG. 1 shows a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in a molecule of the compound used in the invention is not particularly limited in isotope species, and for example, all the hydrogen atoms in the molecule may be $^1H$, and all or a part of them may be $^2H$ (deuterium (D)).

Compound represented by General Formula (1)

The organic light-emitting device of the invention contains a compound represented by the following general formula (1).

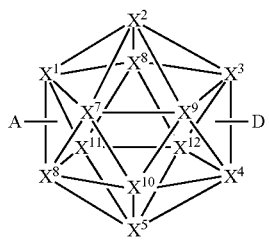

General Formula (1)

In the general formula (1), $X^1$ to $X^{12}$ each independently represent C or BH constituting carborane, provided that among $X^1$ to $X^{12}$, the bonding positions to A and D each represent C, and the other thereof each represent BH. Among $X^1$ to $X^{12}$, the bonding positions to A and D may be any of $X^1$ to $X^{12}$, and in the case where any one of A and D is bonded to $X^1$, the other thereof is preferably bonded to $X^2$ or $X^3$. Accordingly, the compound represented by the general formula (1) is preferably an o-carborane compound or a m-carborane compound. Among $X^1$ to $X^{12}$, BH may have a substituent substituting the hydrogen atom. For the descriptions and the preferred ranges of the substituent capable of being substituted on $X^1$ to $X^{12}$, reference may be made to the descriptions and the preferred ranges of the substituent that may be represented by $R^1$ and $R^2$ described later.

D represents a donor bonded to the carborane through an aromatic ring or a heteroaromatic ring. The "donor" referred in the invention means an aromatic substituent having an electron donating function to the carborane.

The donor represented by D has at least one aromatic ring or heteroaromatic ring, and is bonded to the carborane through the aromatic ring or heteroaromatic ring. Examples of the aromatic ring and the heteroaromatic ring include a benzene ring, a pyridine ring, a pyridazine ring, a pyrimidine ring, a triazine ring, a triazole ring, a thiazole ring, and a pyrrole ring, and the donor is preferably bonded to the carborane through a benzene ring among these. The bonding position to the carborane in the aromatic ring or the heteroaromatic ring is not particularly limited, and the donor is preferably bonded to the carborane at a carbon atom among the atoms constituting the aromatic ring or the heteroaromatic ring.

D preferably has a diphenylamino group or a carbazolyl group. The diphenylamino group and the carbazolyl group may be substituted with a substituent. For the descriptions and the preferred ranges of the substituent capable of being substituted on the diphenylamino group and the carbazolyl group, reference may be made to the descriptions and the preferred ranges of the substituent that may be represented by $R^1$ and $R^2$.

D is also preferably a group represented by the following general formula (2).

General Formula (2)

In the general formula (2), $R^1$ and $R^2$ each independently represent a substituent.

Examples of the substituent that may be represented by $R^1$ and $R^2$ include a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

$R^1$ and $R^2$ may be bonded to each other to form a cyclic structure. The cyclic structure may be an aromatic ring or an aliphatic ring, and may be a structure containing a hetero atom, and the cyclic structure may be a condensed ring containing two or more rings. The hetero atom referred herein is preferably selected from the group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, and a cycloheptaene ring.

n1 represents an integer of from 1 to 4, and preferably 1 or 2. In the case where n1 is an integer of from 2 to 4, the plural groups represented by $[(R^1)(R^2)N]$ may be the same as or different from each other.

$Ar^1$ represents a substituted or unsubstituted aromatic group having a valence of (n1+1). The aromatic group referred herein includes a monocyclic aromatic group and also includes an aromatic group having a ring aggregated structure containing two or more aromatic rings bonded through a single bond, such as biphenylene, and an aromatic group having a polycyclic condensed structure containing two or more aromatic rings condensed, such as naphthalene. Specifically, the aromatic group is preferably an aromatic hydrocarbon group having from 6 to 18 carbon atoms, more preferably a residual group of a benzene ring, a biphenylene ring, a naphthalene ring, a fluorene ring, or a triphenylene ring, further preferably a residual group of a benzene ring, and still further preferably a divalent residual group of a benzene ring having bonding positions at the 1-position and the 4-position (i.e., a 1,4-phenylene group). The aromatic group may be substituted with a substituent. For the descriptions and the preferred ranges of the substituent capable of being substituted on the aromatic group, reference may be made to the descriptions and the preferred ranges of the substituent that may be represented by $R^1$ and $R^2$ above.

A represents an acceptor bonded to the carborane through an aromatic ring or a heteroaromatic ring. The "acceptor" referred in the invention means an aromatic substituent having an electron withdrawing function to the carborane.

The acceptor represented by A has at least one aromatic ring or heteroaromatic ring, and is bonded to the carborane through the aromatic ring or heteroaromatic ring. For the specific examples of the aromatic ring and the heteroaromatic ring, reference may be made to the specific examples of the aromatic ring and the heteroaromatic ring of the donor bonded to the carborane. The bonding position to the carborane in the aromatic ring or the heteroaromatic ring is not particularly limited, and the acceptor is preferably bonded to the carborane at a carbon atom among the atoms constituting the aromatic ring or the heteroaromatic ring.

A preferably has a heteroaromatic ring containing a nitrogen atom. Examples of the heteroaromatic ring containing a nitrogen atom include a pyridine ring, a pyridazine ring, a pyrimidine ring, a triazine ring, a triazole ring, a thiazole ring, and a pyrrole ring, and a triazine ring is preferred. The heteroaromatic ring containing a nitrogen atom may be substituted with a substituent. For the descriptions and the preferred ranges of the substituent capable of being substituted on the heteroaromatic ring containing a nitrogen atom, reference may be made to the descriptions and the preferred ranges of the substituent that may be represented by $R^1$ and $R^2$ above. In the case where the heteroaromatic ring containing a nitrogen atom is a triazine ring, the triazine ring is preferably substituted with a phenyl group. In the case where A has a heteroaromatic ring containing a nitrogen atom, the heteroaromatic ring containing a nitrogen atom may be bonded to the carborane through a single bond, or may be bonded to the carborane through an aromatic group $Ar^2$ as a linking group, as represented by the following general formula (3).

(Het)$_{n2}$-Ar$^2$—  General Formula (3)

In the general formula (3), Het represents a substituted or unsubstituted heteroaromatic ring group (provided that the heteroaromatic ring group contains a nitrogen atom as a ring structure constituting atom). Examples of the heteroaromatic ring group containing a nitrogen atom include residual groups of a pyridine ring, a pyridazine ring, a pyrimidine ring, a triazine ring, a triazole ring, a thiazole ring, and a pyrrole ring, and a residual group of a triazine ring is preferred. In the case where the heteroaromatic ring group has a substituent, for the descriptions and the preferred ranges of the substituent, reference may be made to the descriptions and the preferred ranges of the substituent that may be represented by $R^1$ and $R^2$ above. In the case where the heteroaromatic ring group containing a nitrogen atom is a residual group of a triazine ring, the residual group of a triazine ring is preferably substituted with a phenyl group.

n2 represents an integer of from 1 to 4, and preferably 1 or 2. In the case where n2 is an integer of from 2 to 4, the plural groups represented by Het may be the same as or different from each other.

$Ar^2$ represents a substituted or unsubstituted aromatic group having a valence of (n2+1). For the descriptions and the preferred ranges of the aromatic group represented by $Ar^2$, reference may be made to the descriptions and the preferred examples of the aromatic group represented by $Ar^1$.

Preferred examples of the compound represented by the general formula (1) include a compound having a structure containing a m-carborane or an o-carborane having bonded thereto a donor D having a carbazole ring and an acceptor A having a triazine ring, and more preferred examples of the compound include a compound having a structure containing a m-carborane or an o-carborane having bonded thereto a donor D having a carbazole ring and an acceptor A having a triazine ring, in which at least the carbazole ring of D is bonded to the carborane through a phenylene ring.

Specific examples of the compound represented by the general formula (1) are shown below. However, the compound represented by the general formula (1) capable of being used in the invention is not construed as being limited to the specific examples.

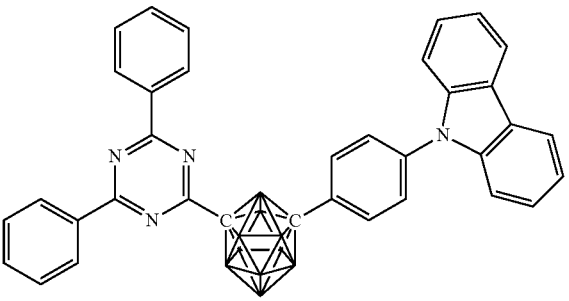

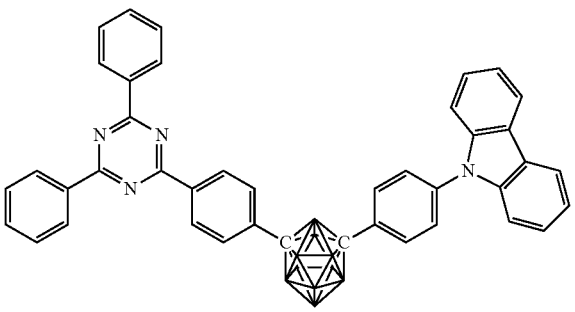

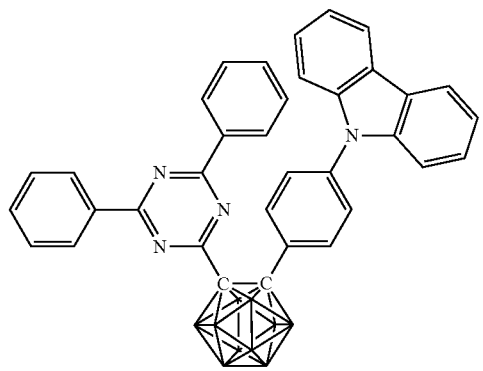

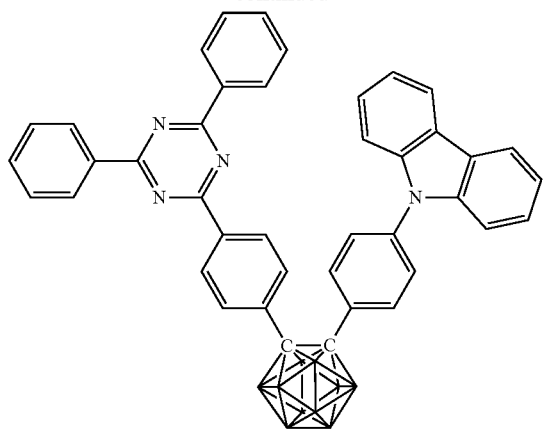
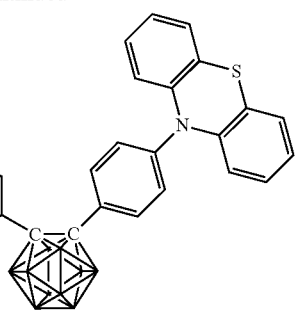
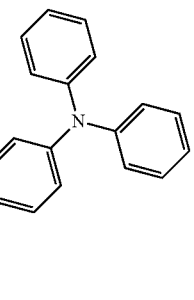
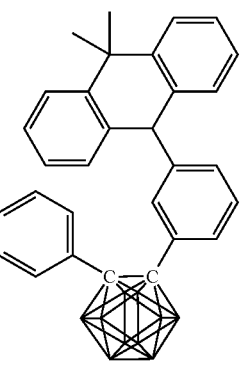
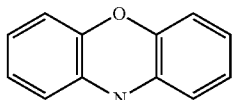
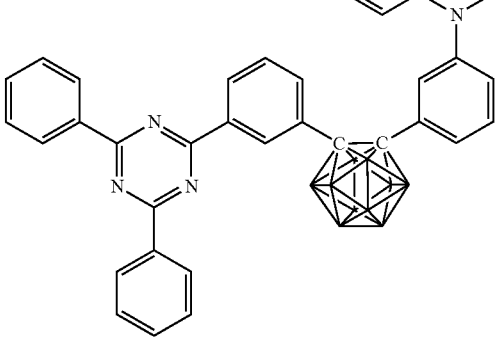

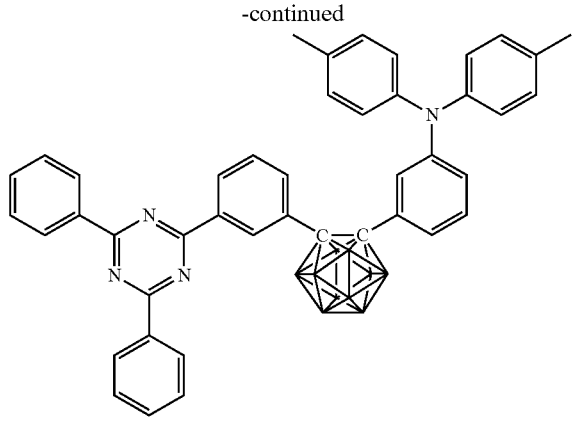
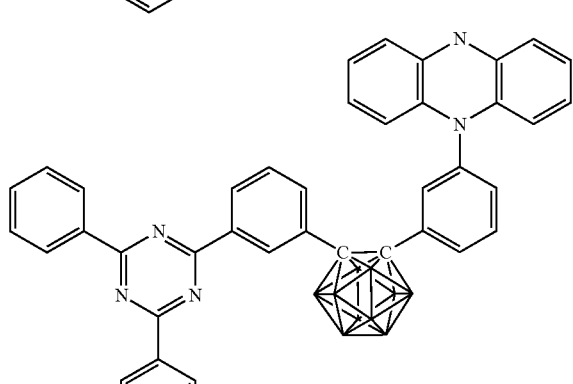
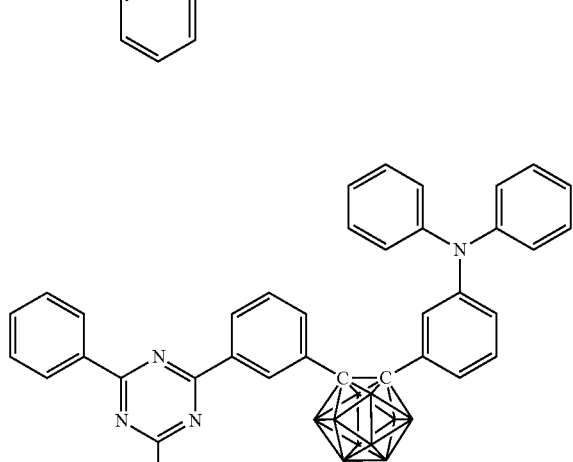
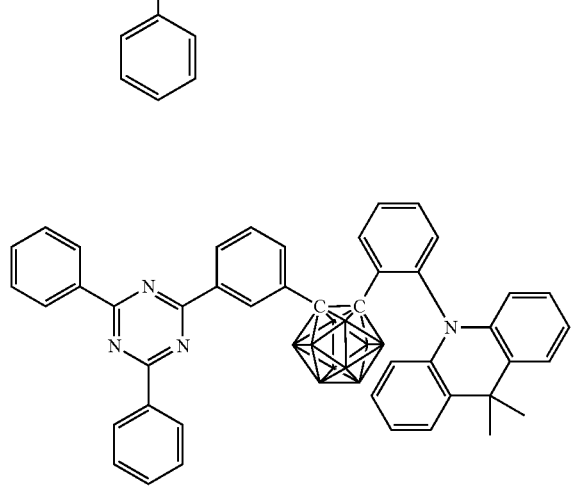
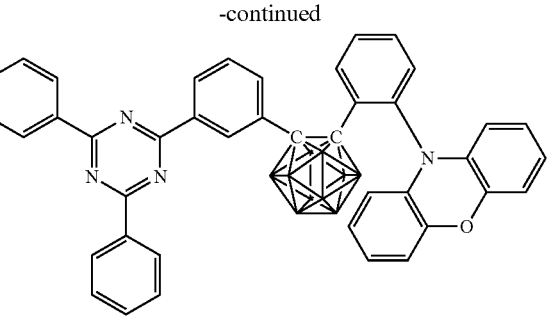
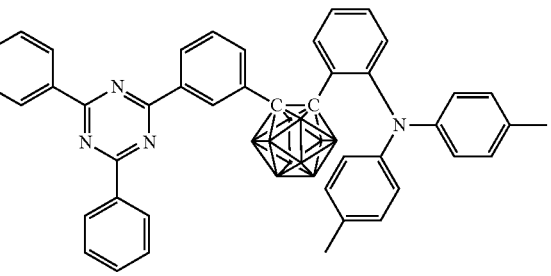
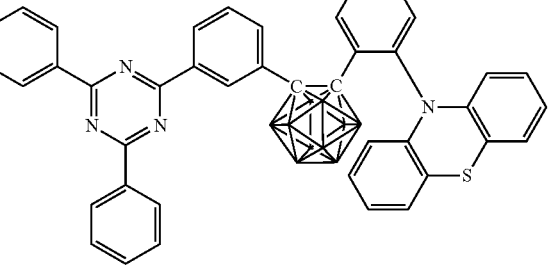
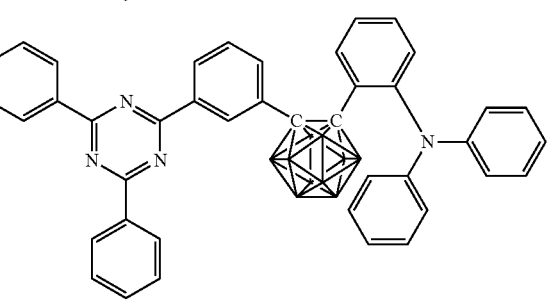
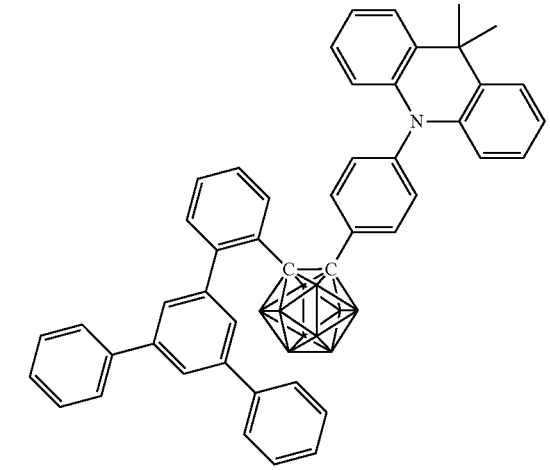

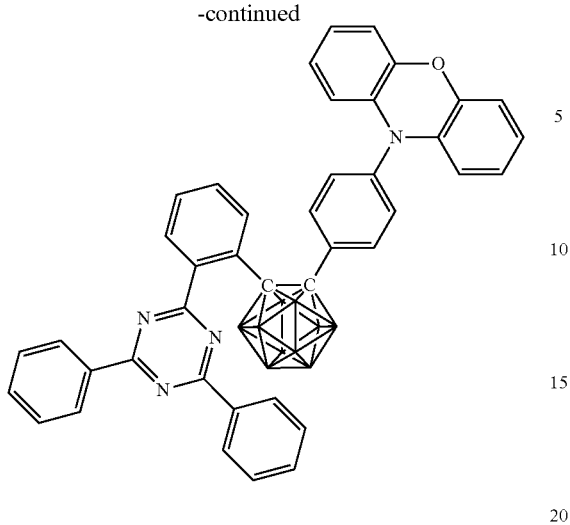
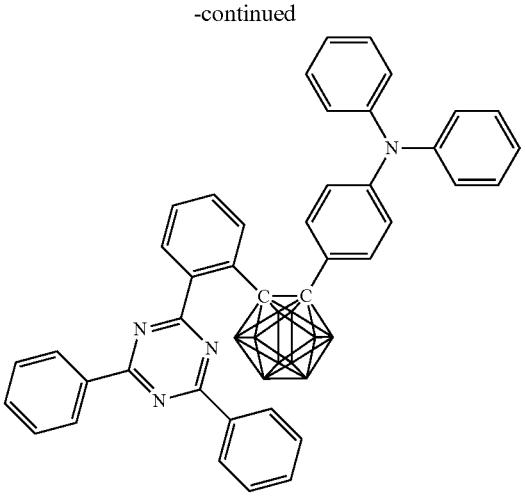
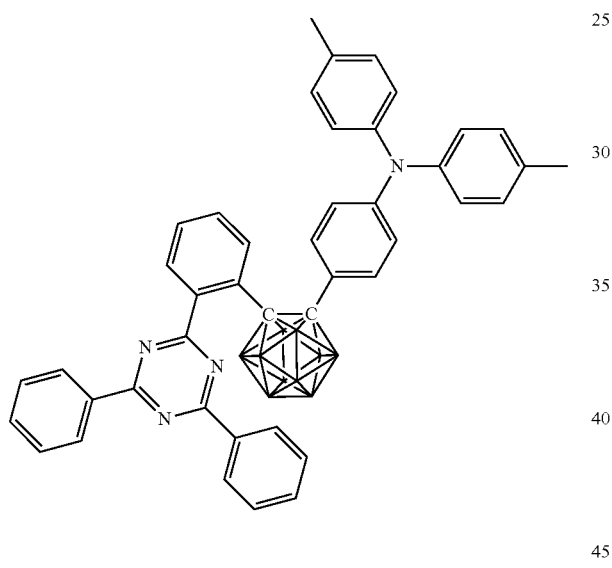
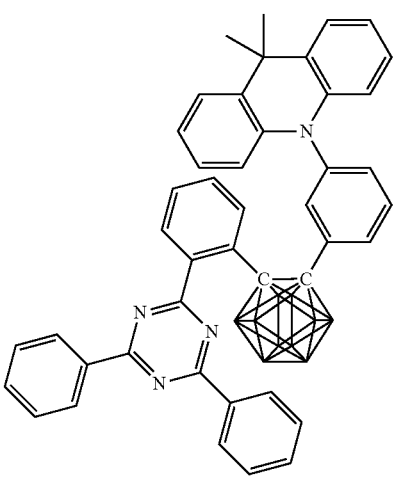
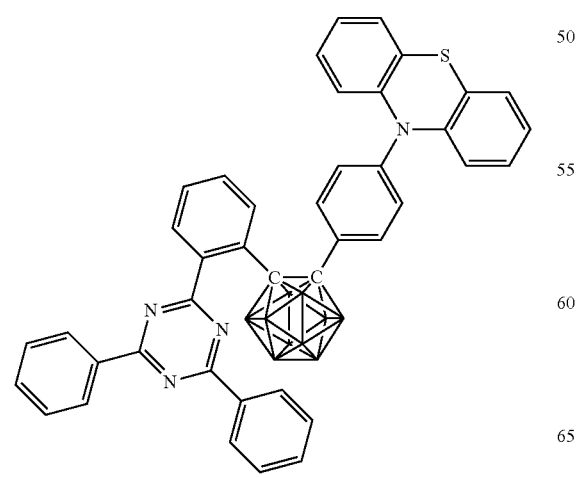
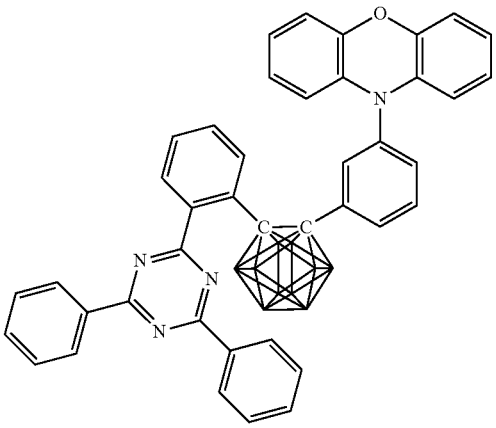

-continued
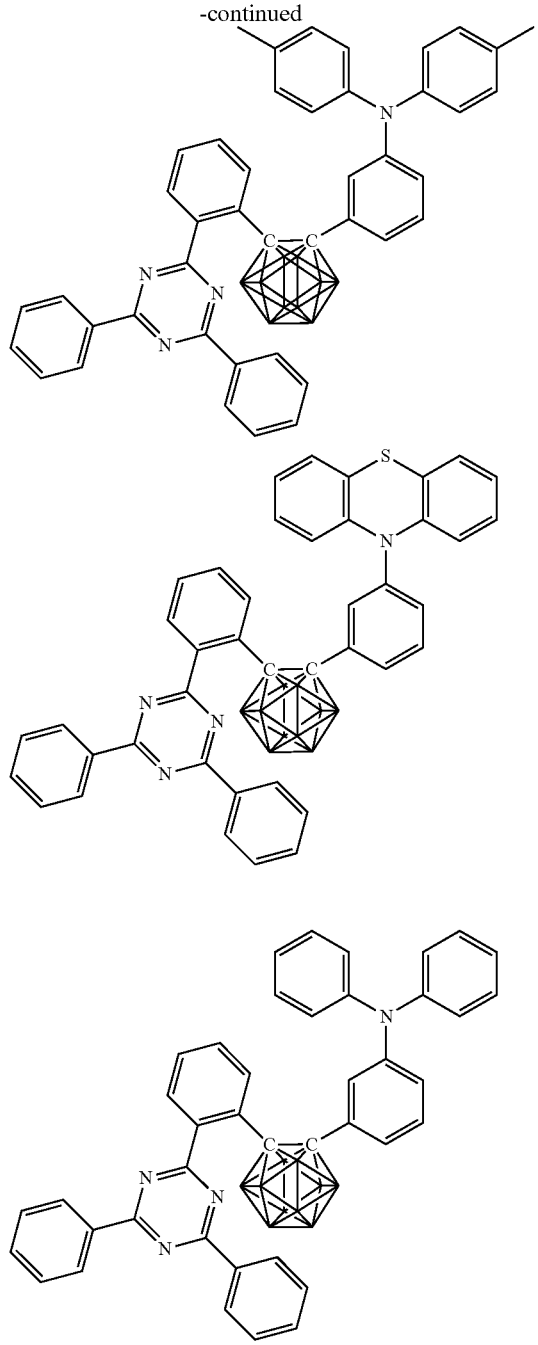
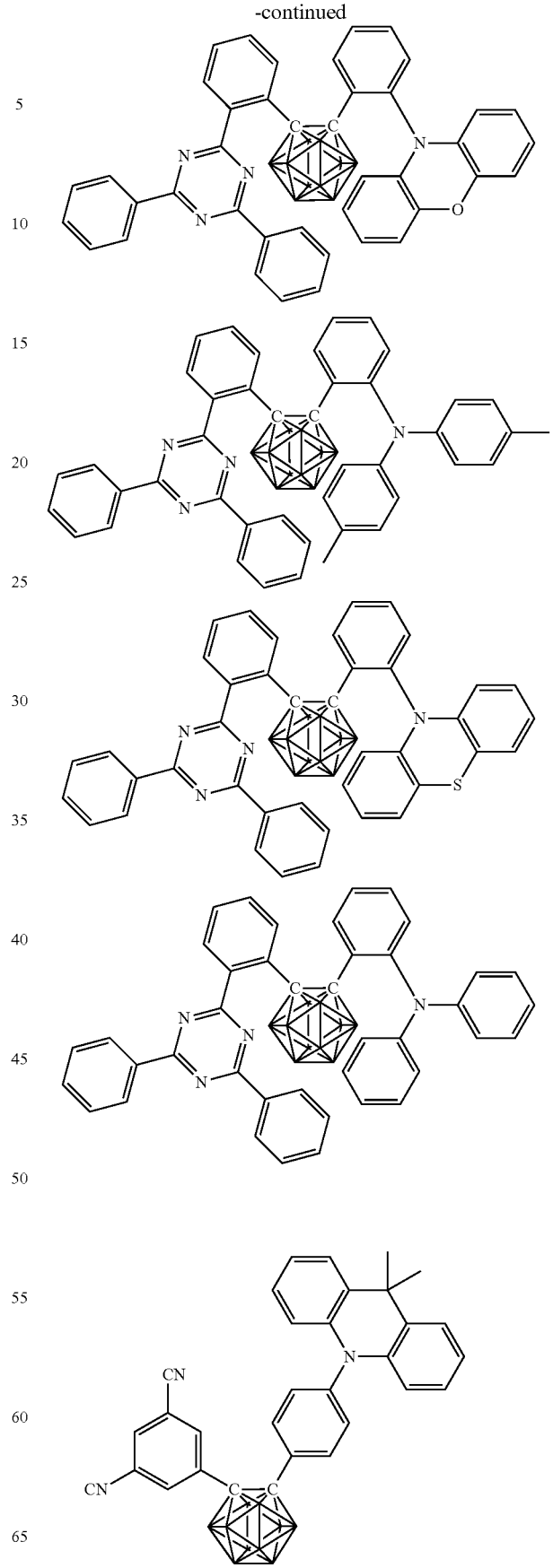

-continued
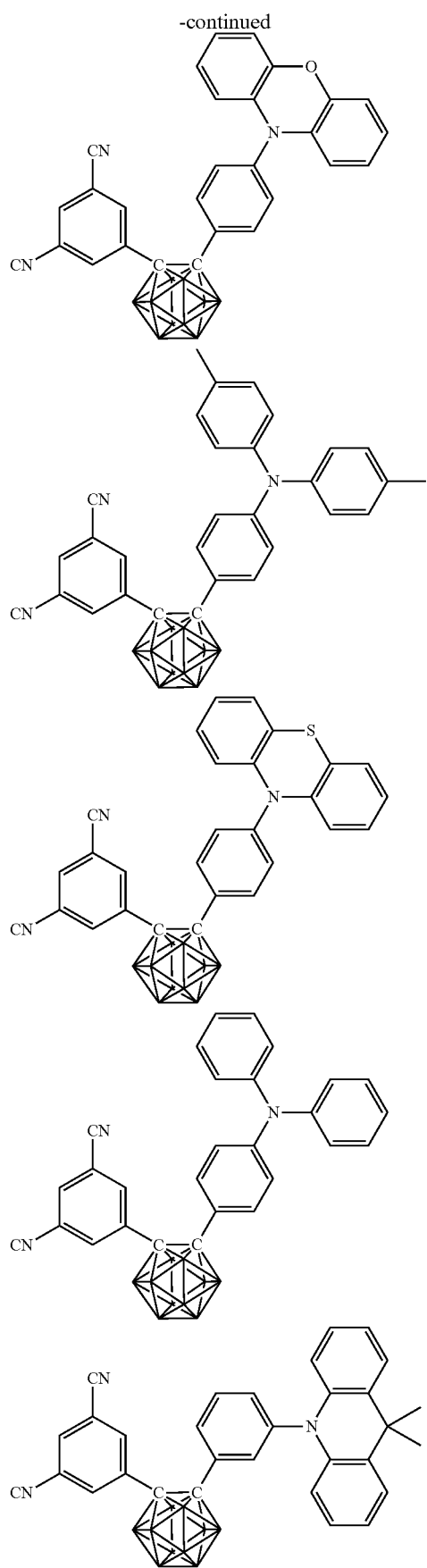
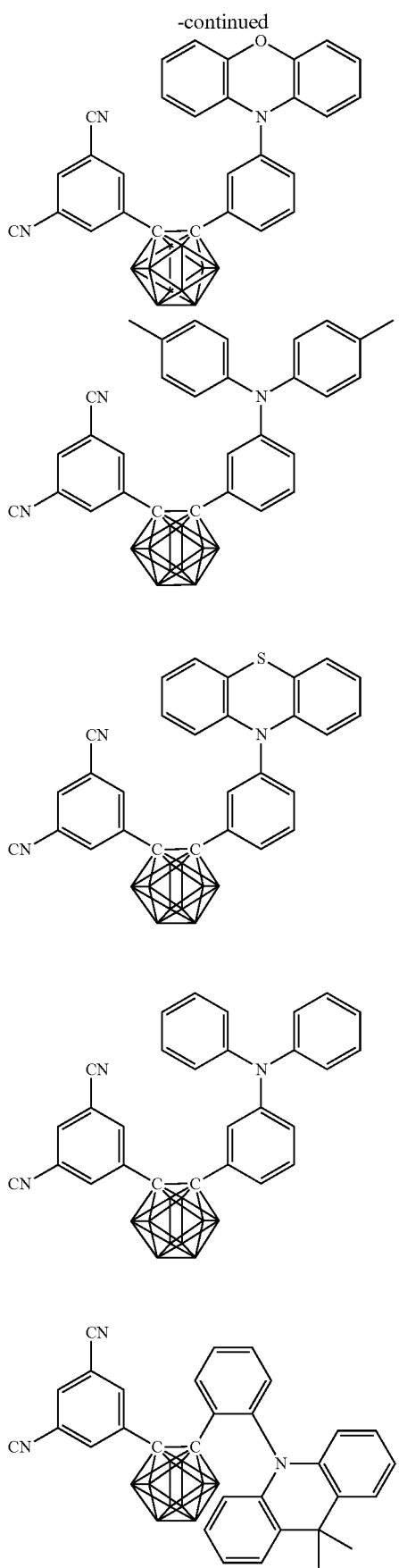

-continued
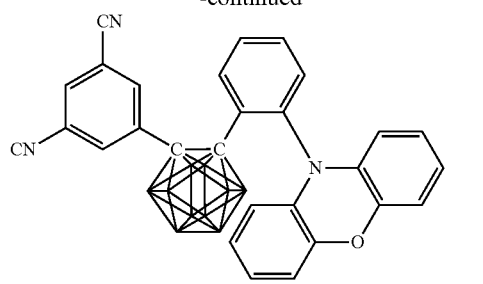
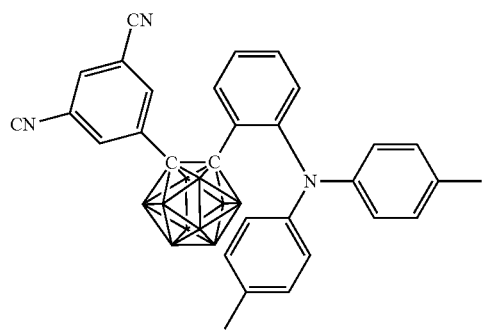
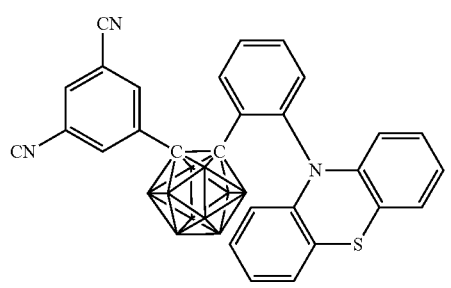
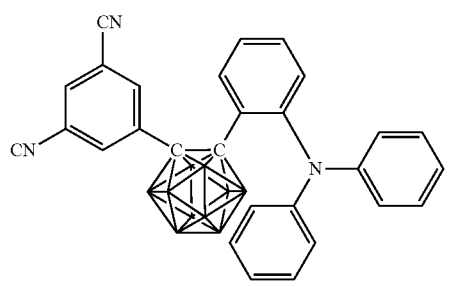
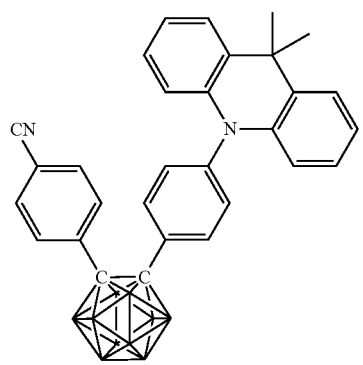
-continued
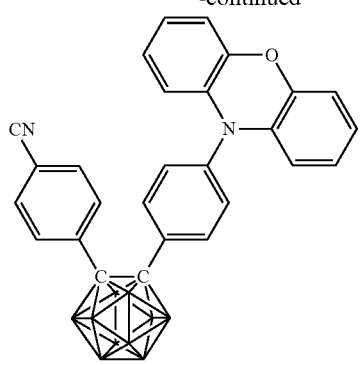
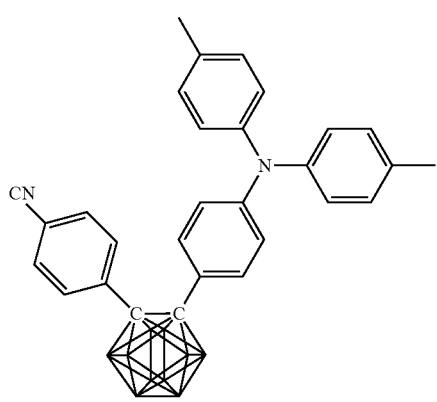
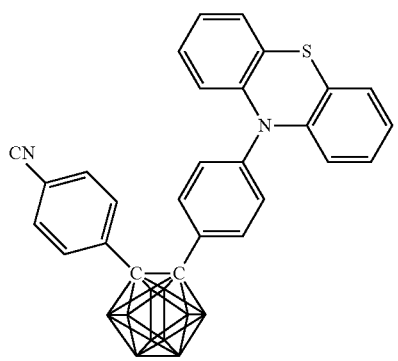
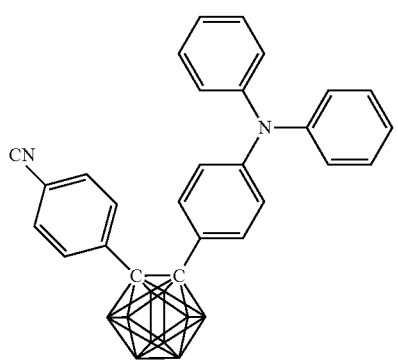

-continued
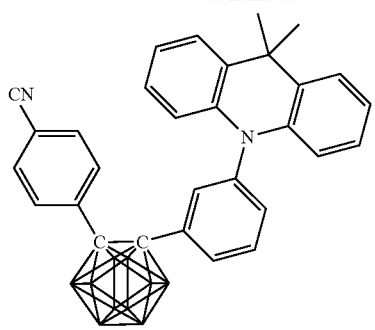
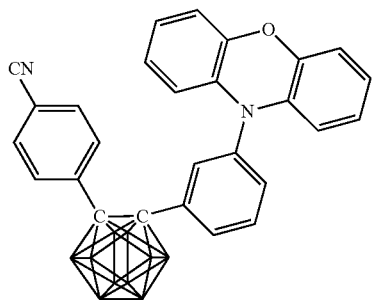
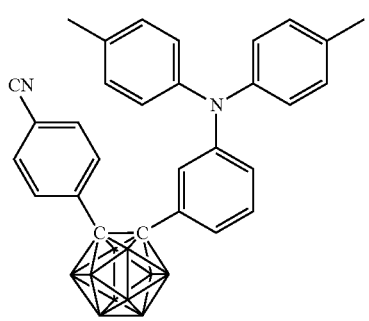
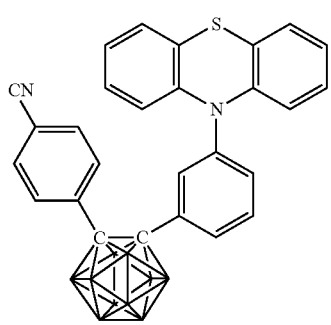
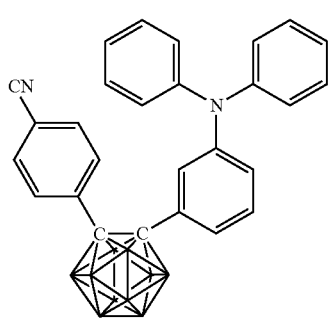
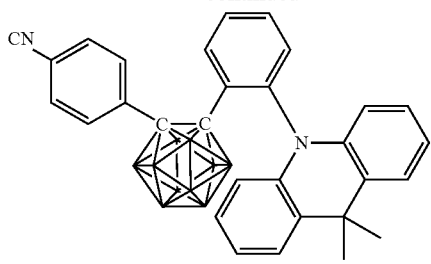
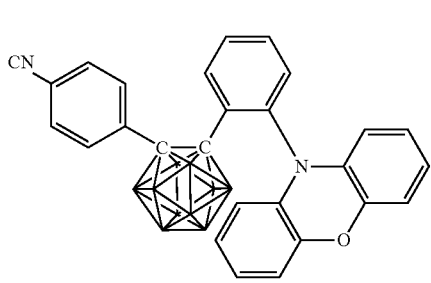
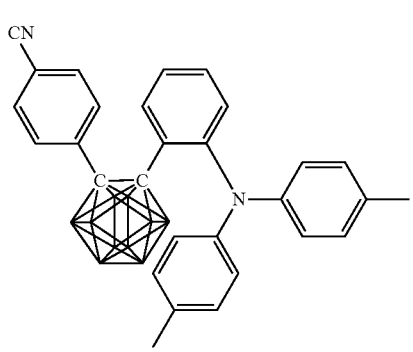
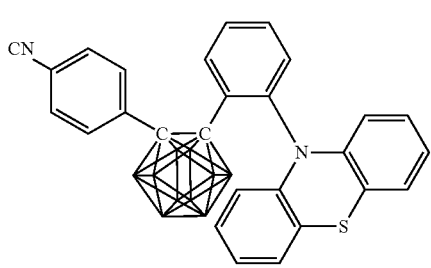
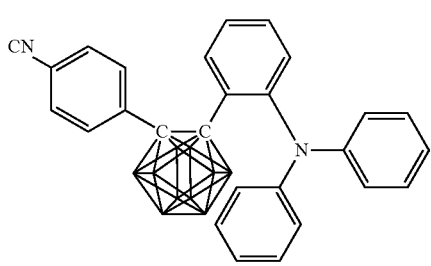

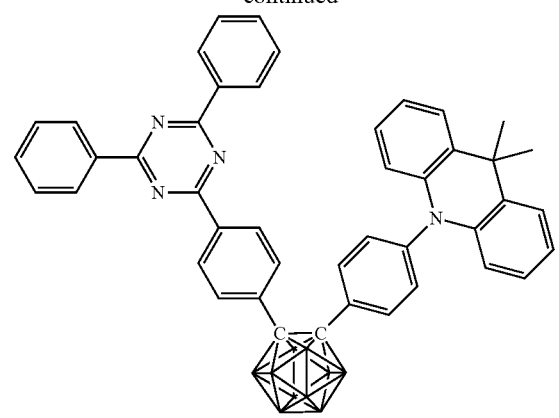
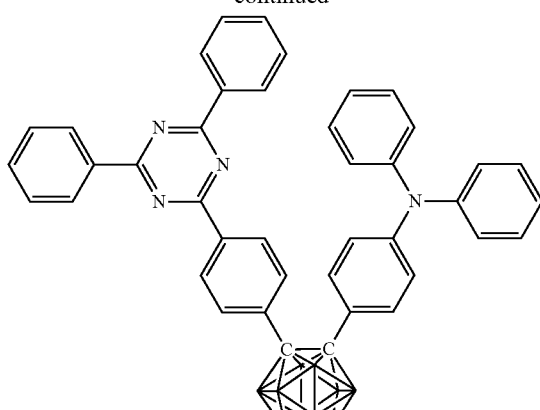
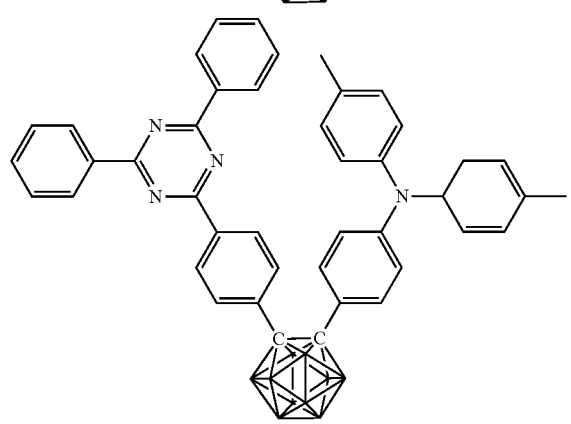
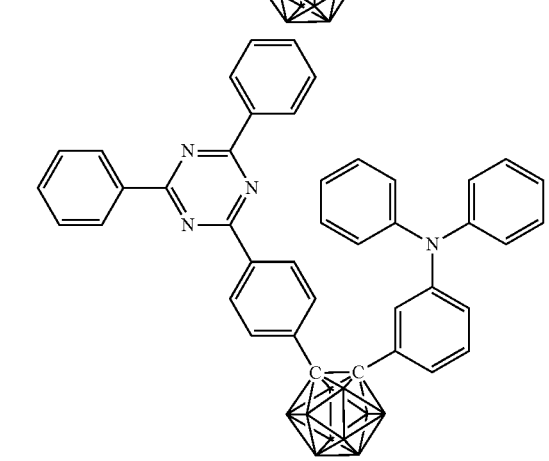
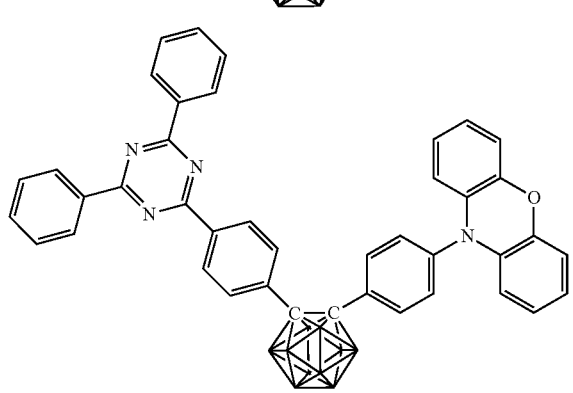
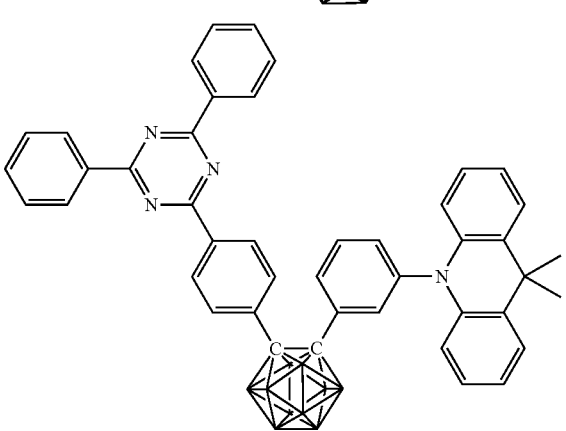
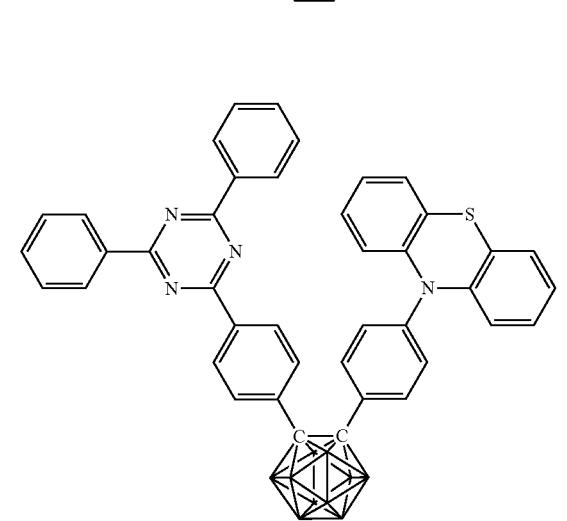
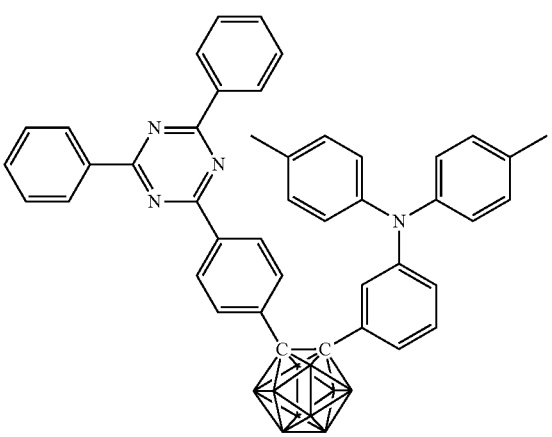

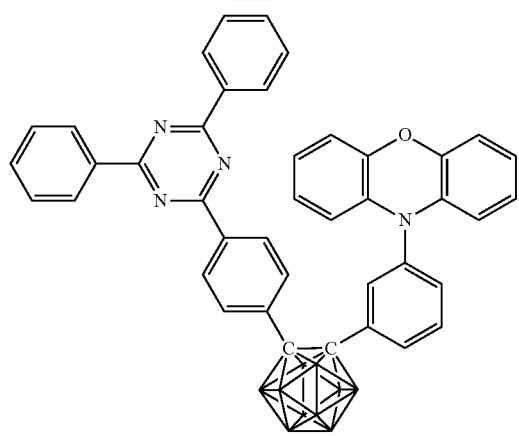
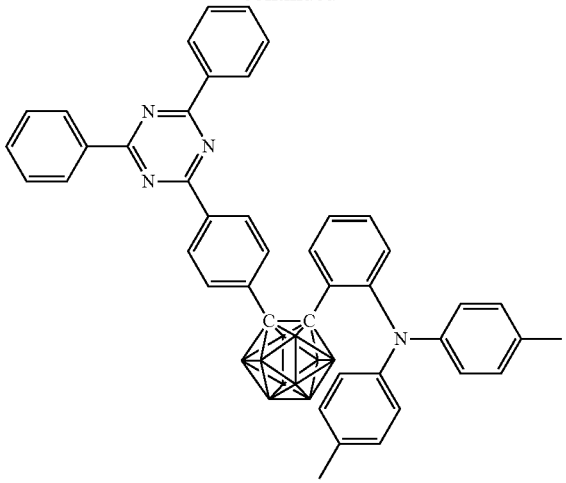
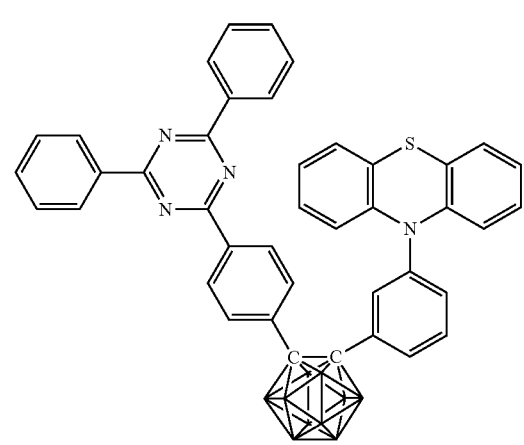
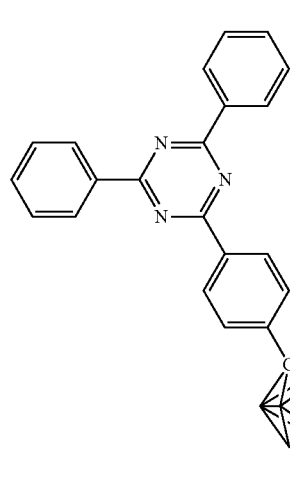
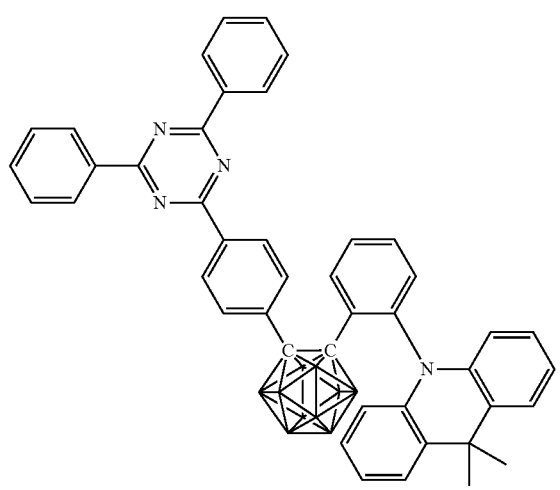
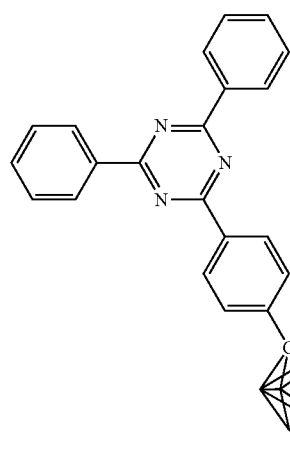

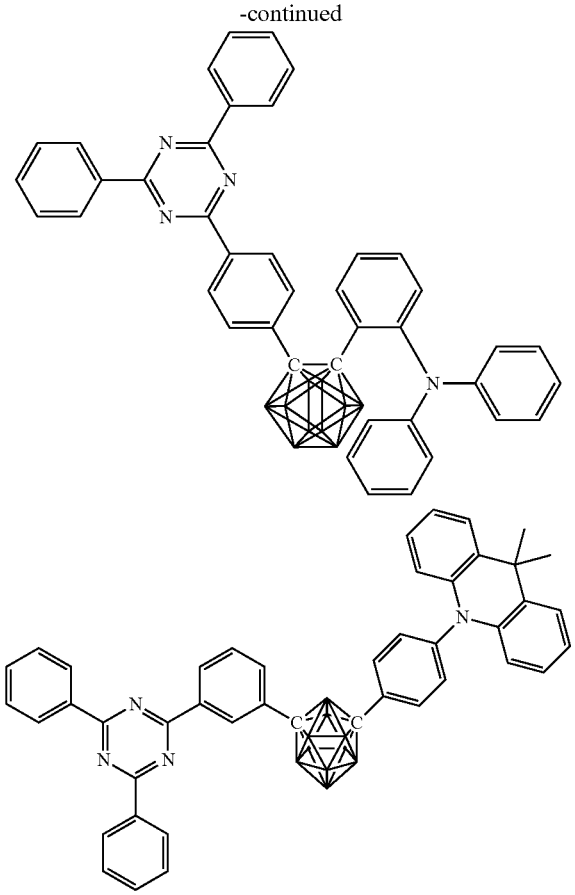
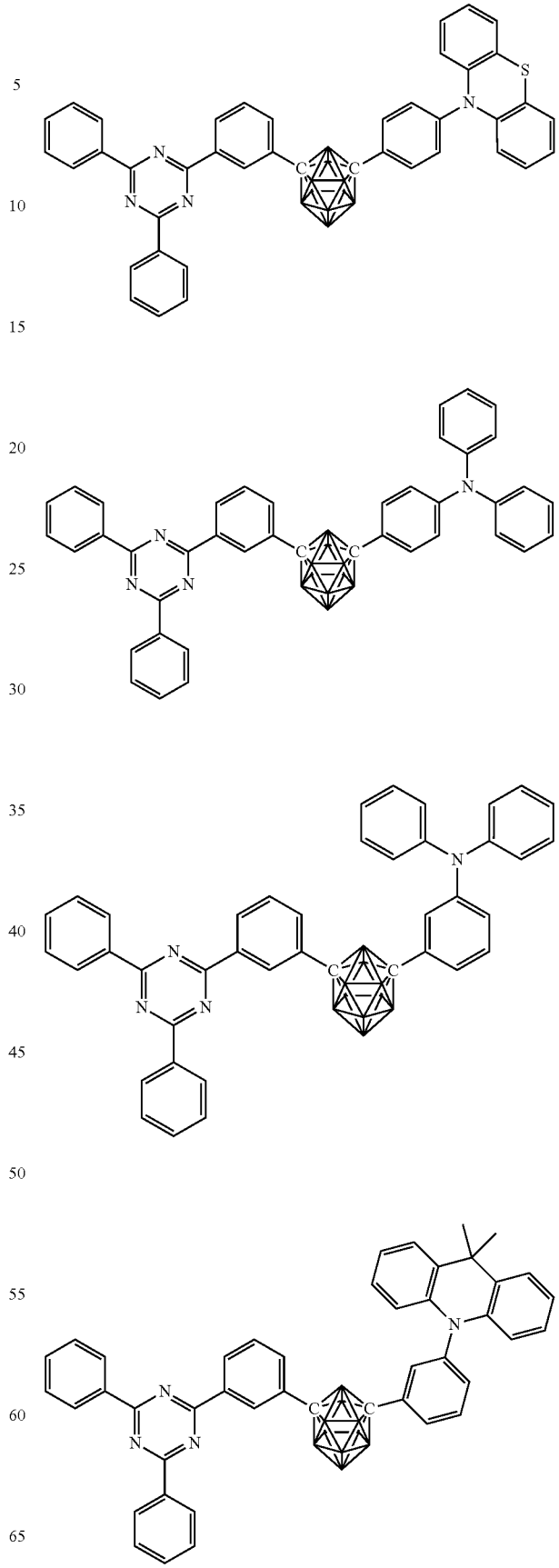

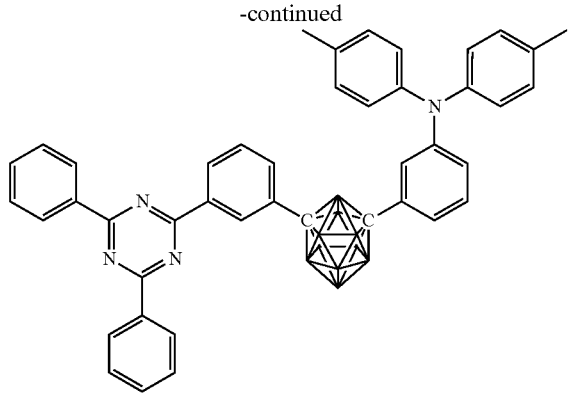
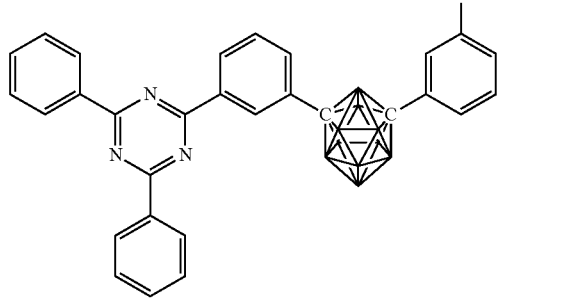
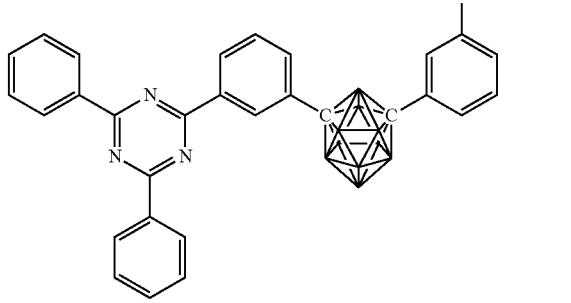
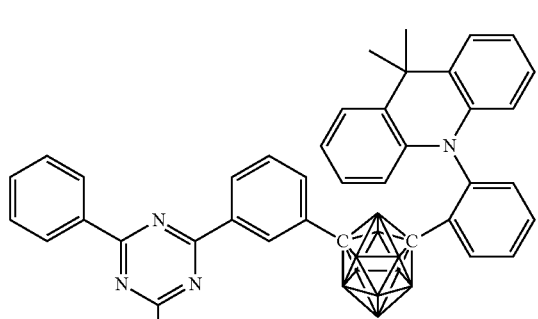
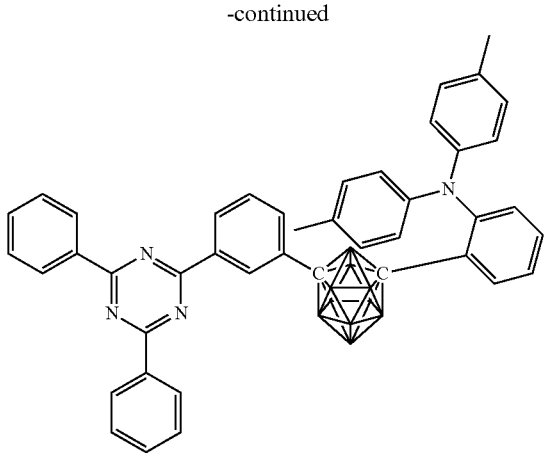
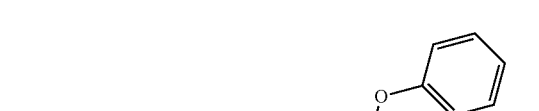

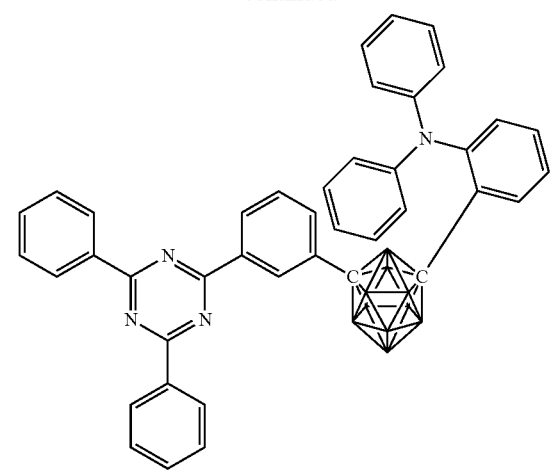
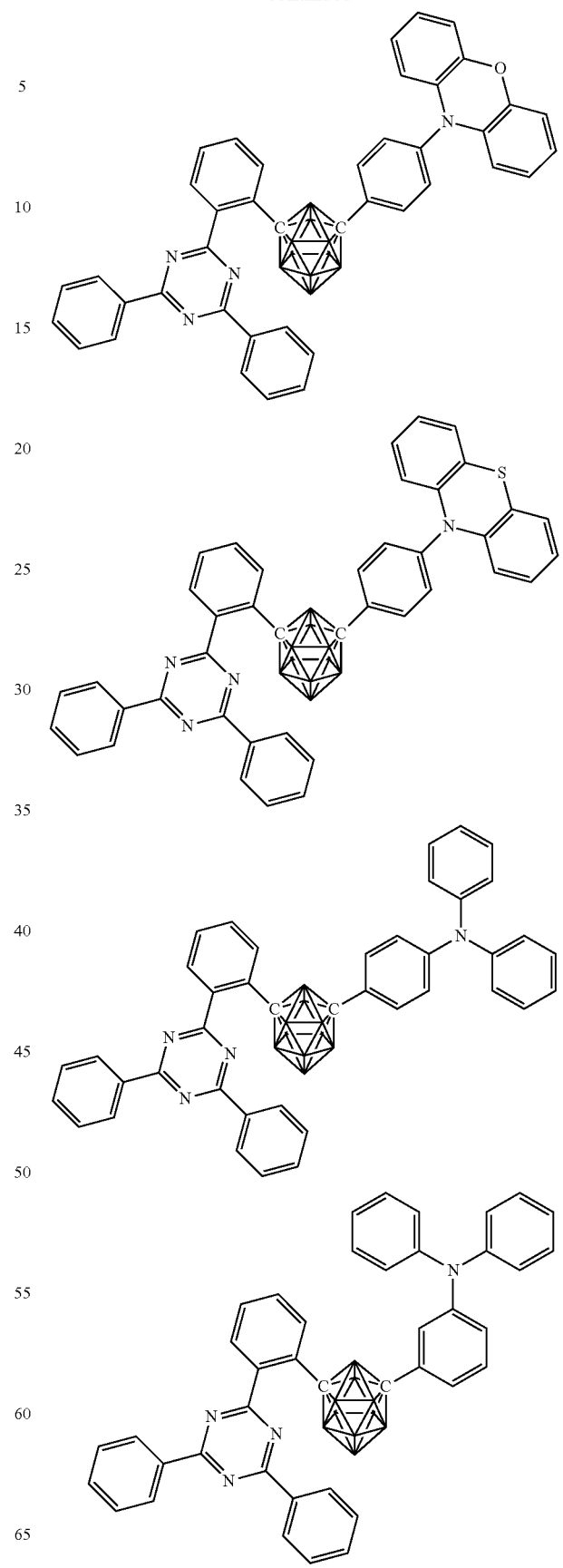

37
-continued
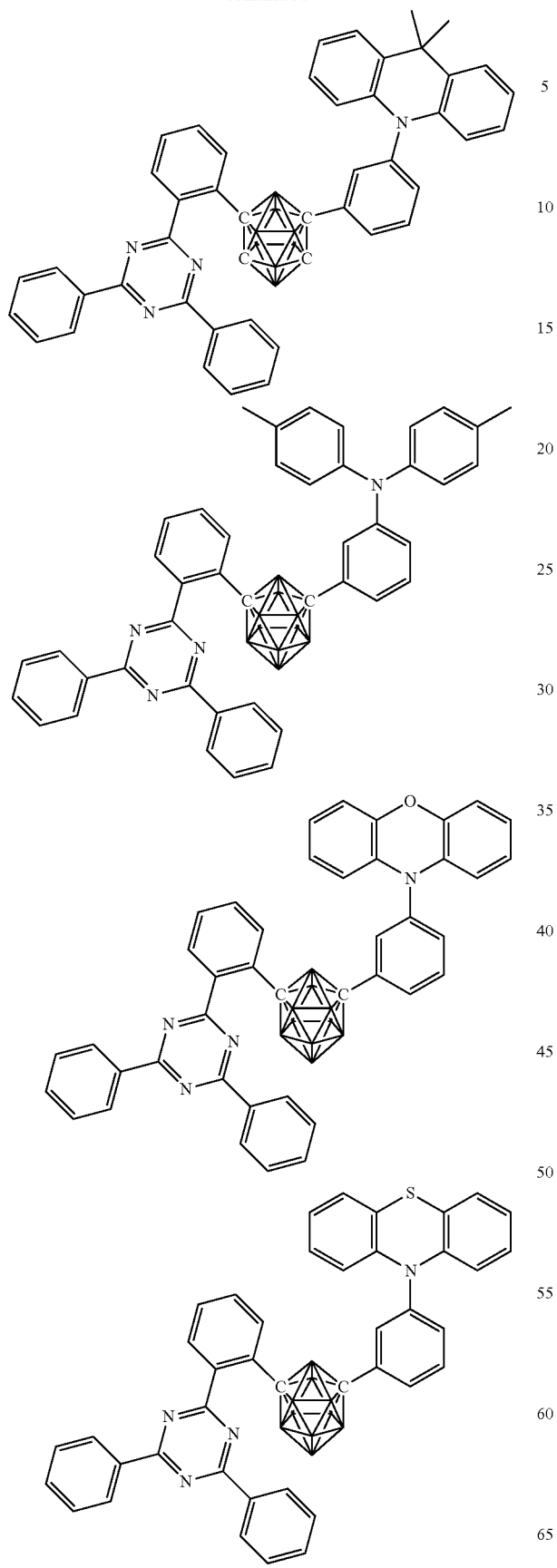
38
-continued
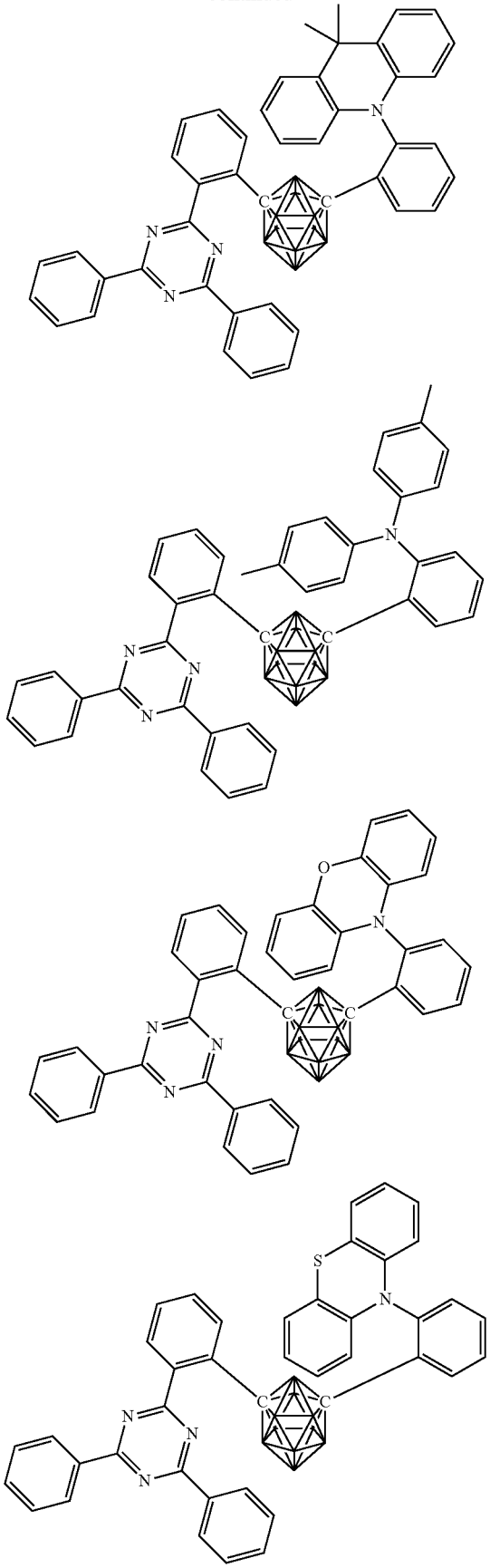

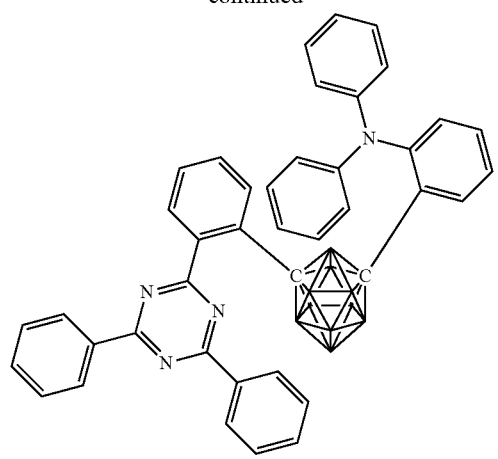
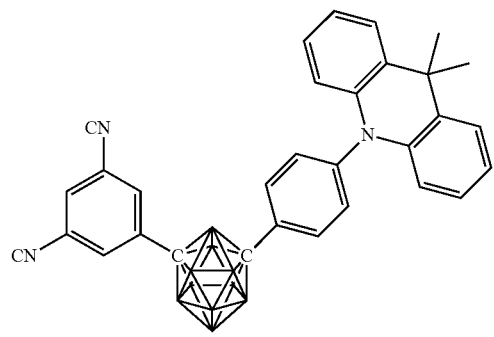
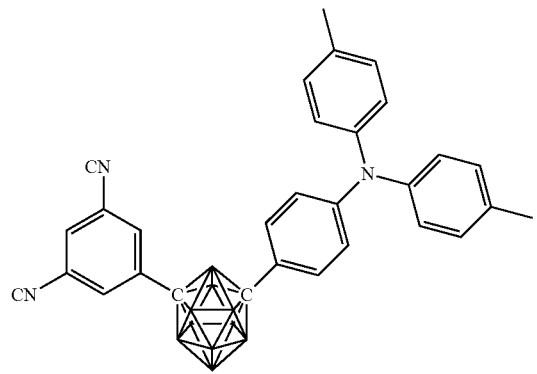
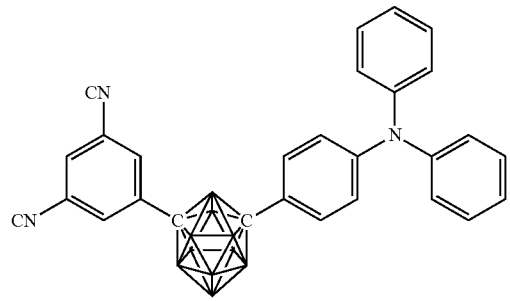
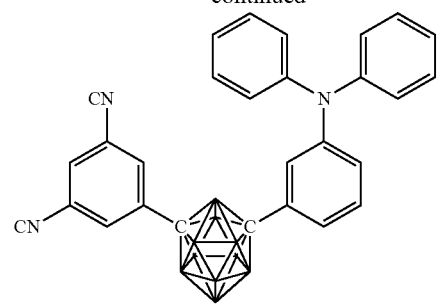
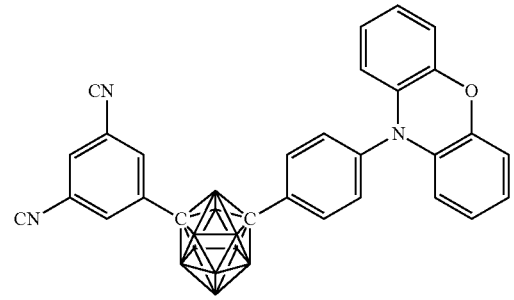
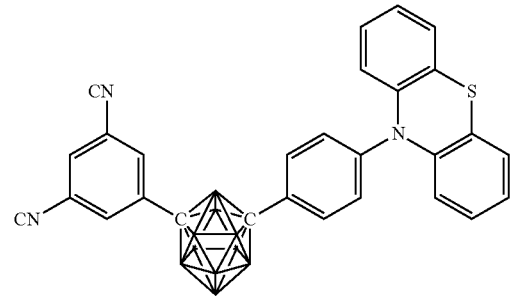
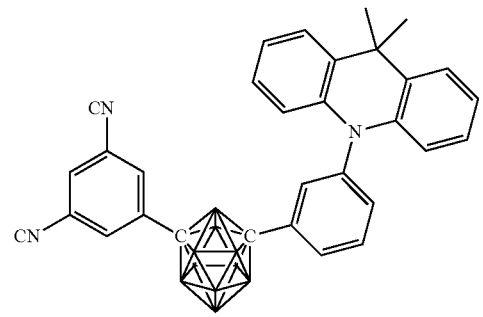
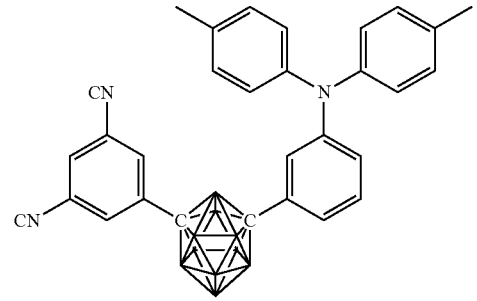

-continued
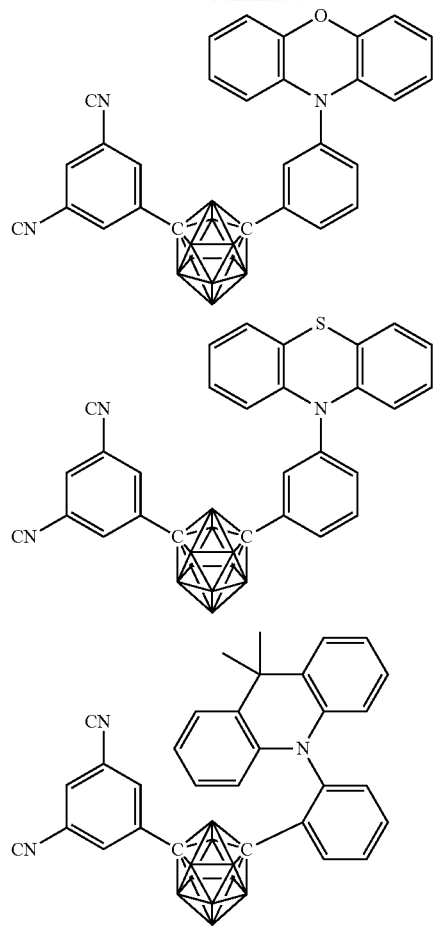
-continued
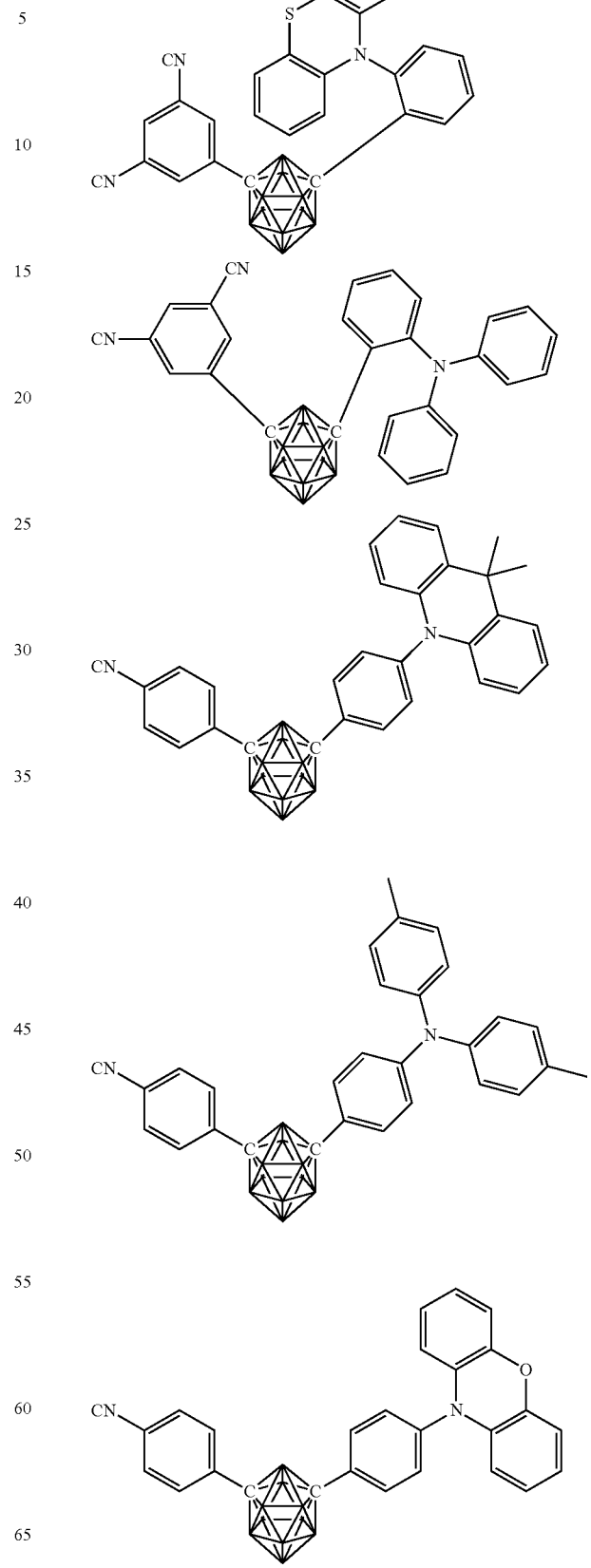

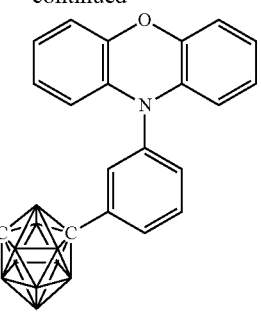
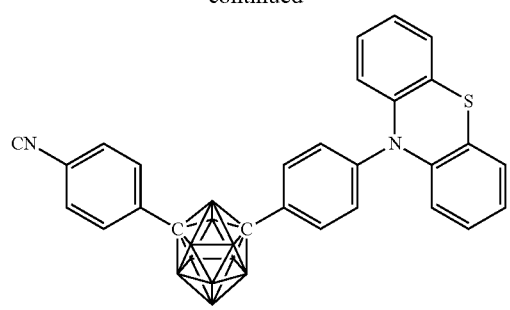
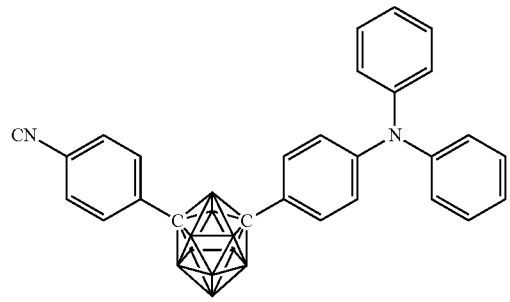
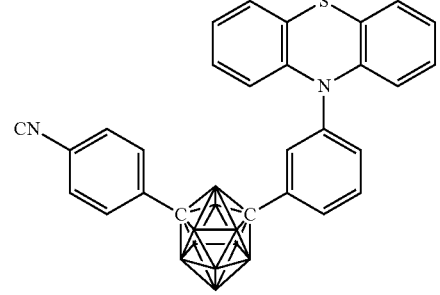
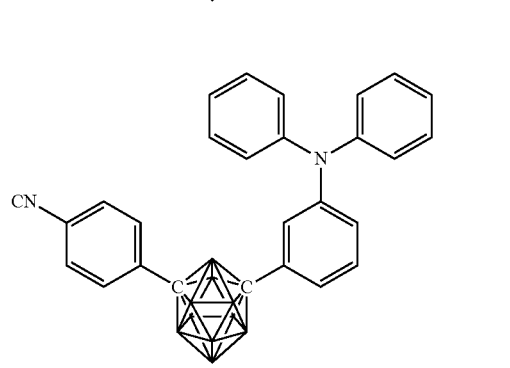
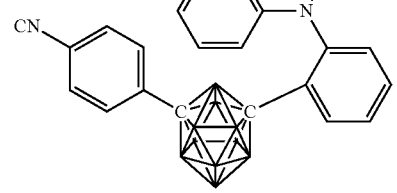
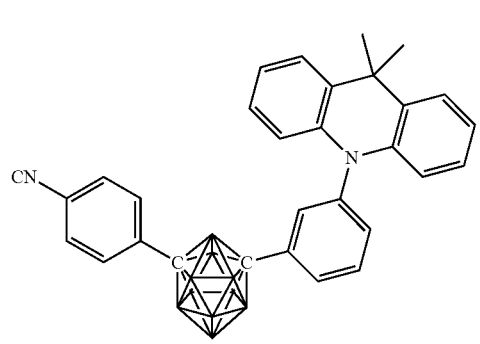
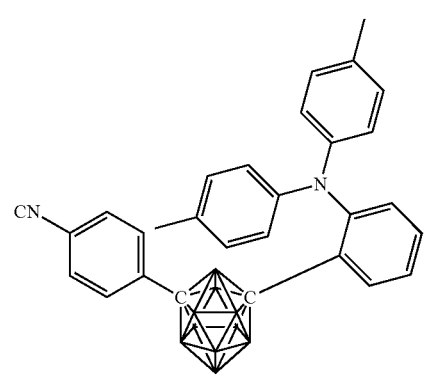
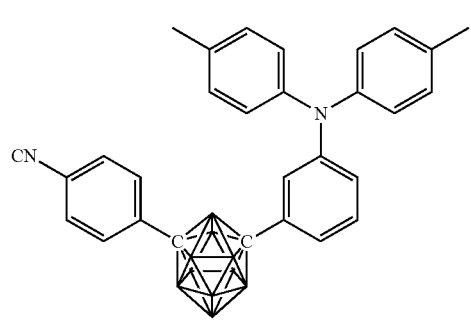
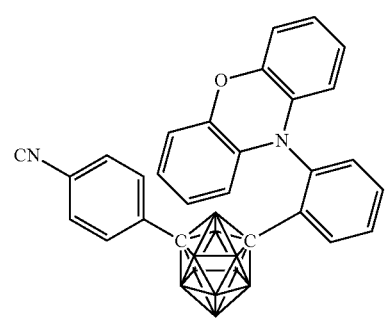

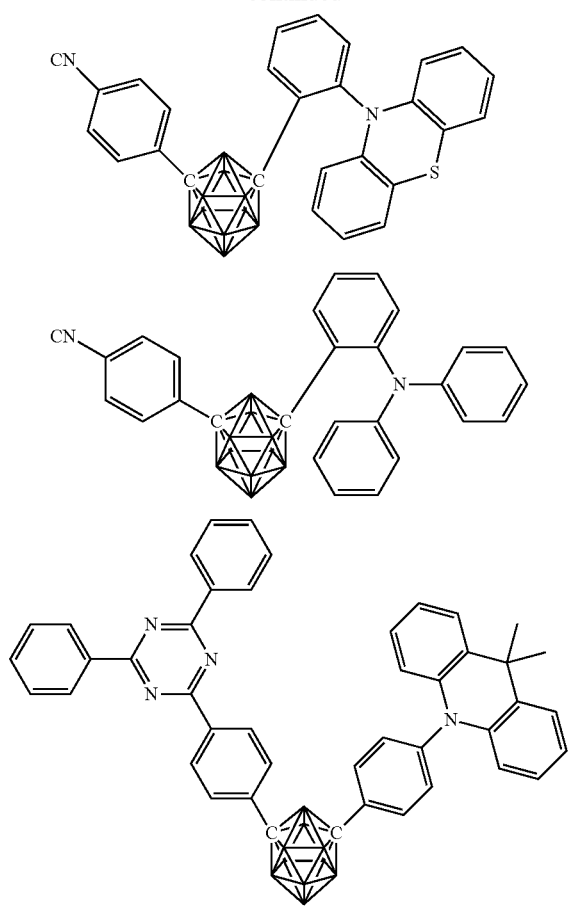
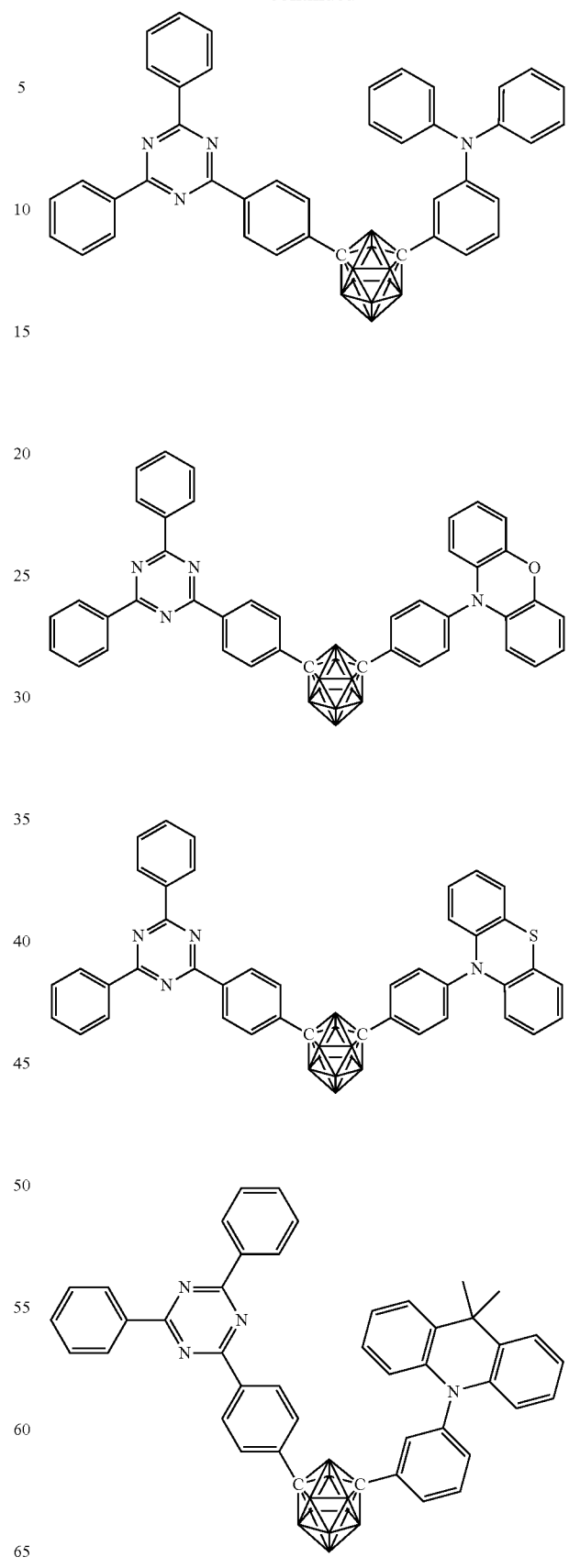

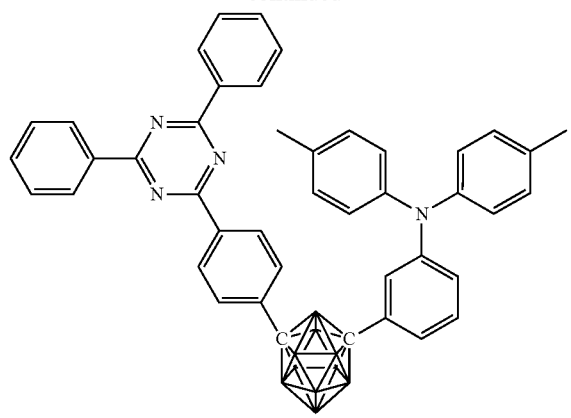
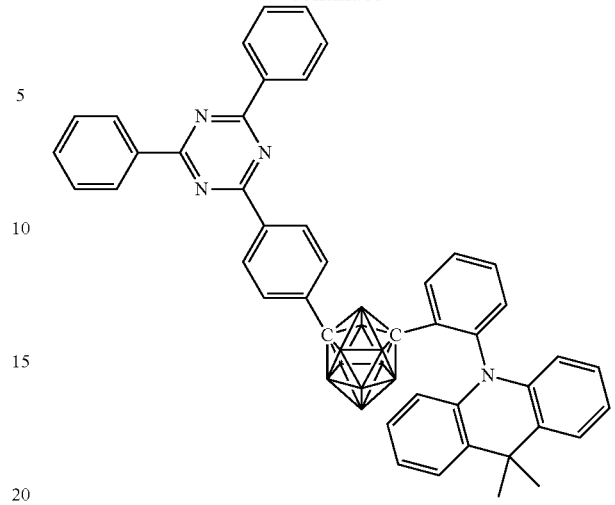
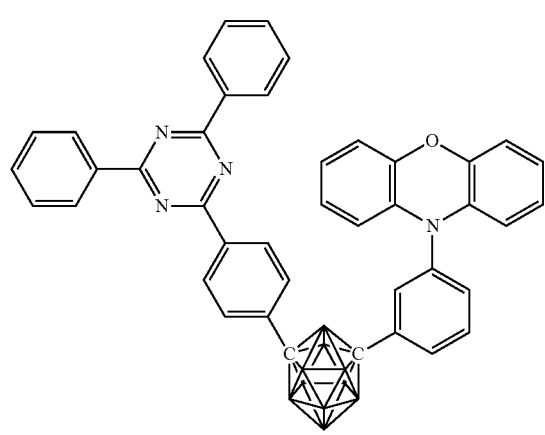
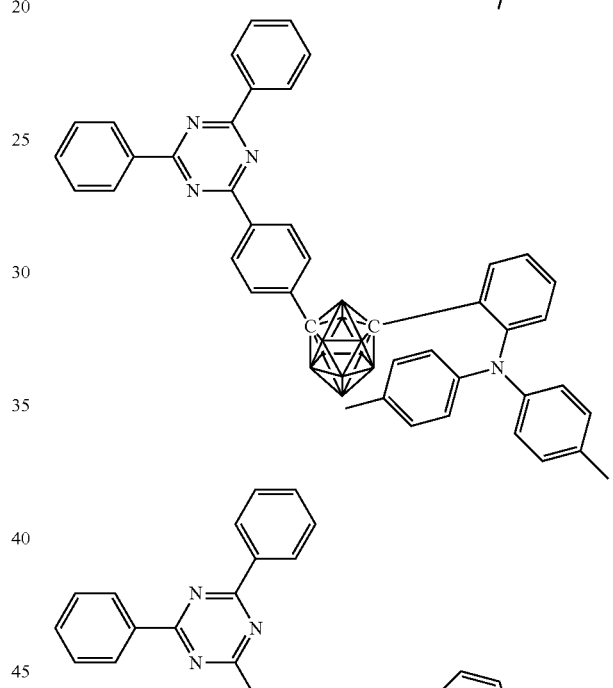
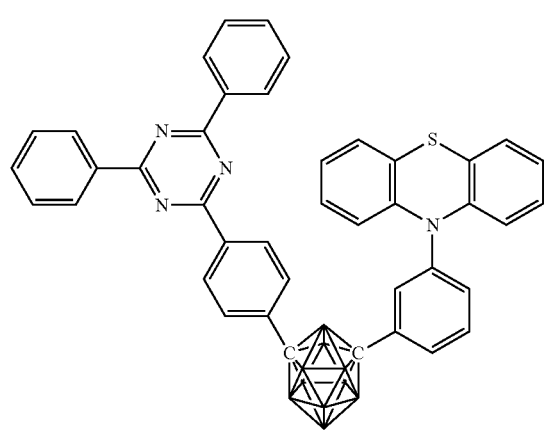
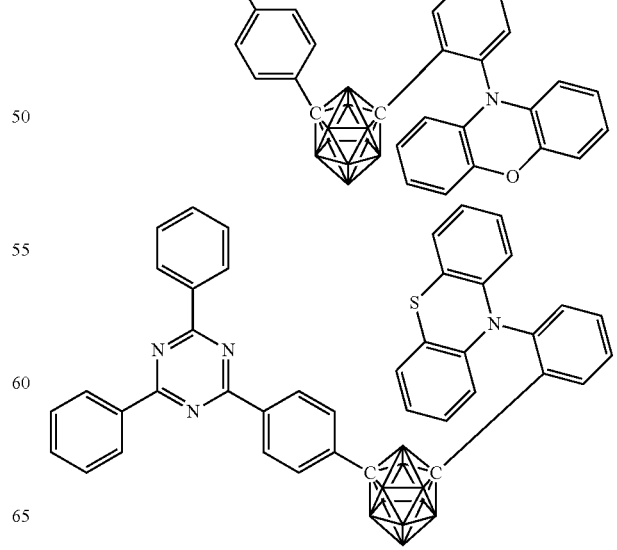

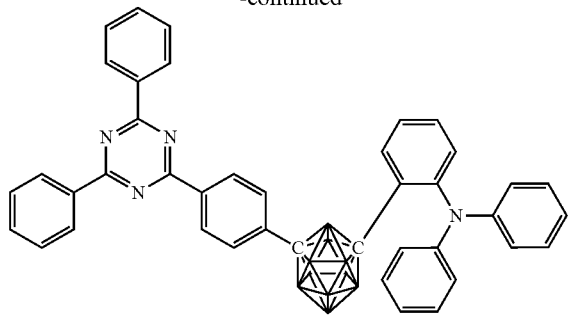

The molecular weight of the compound represented by the general formula (1) is preferably 1,500 or less, more preferably 1,200 or less, and further preferably 1,000 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a host material or a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $X^1$ to $X^{12}$, A, and D in the general formula (1) is prepared, and is homopolymerized or copolymerized with another monomer to prepare a polymer containing repeating units, and the polymer is used as a host material or a light-emitting material. In alternative, it may be considered that the compounds represented by the general formula (1) are reacted to form a dimer or a trimer, and the dimer or the trimer is used as a light-emitting material.

Examples of the polymer having the repeating unit containing the structure represented by the general formula (1) include a polymer containing a structure represented by the following general formula (4) or (5).

General Formula (4)

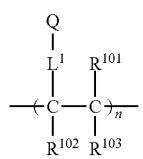

General Formula (5)

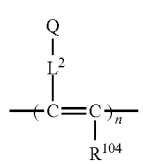

In the general formulae (4) and (5), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $—X^{101}-L^{11}-$, wherein $X^{101}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (4) and (5), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $X^1$ to $X^{12}$, A, and D of the structure of the general formula (1), any of $R^1$, $R^2$, and $Ar^1$ of the structure of the general formula (2), and any of Het and $Ar^2$ of the structure of the general formula (3), constituting Q. Two or more of the linking groups may be boded to one group represented by Q to form a crosslinked structure or a network structure.

Specific examples of the structure of the repeating unit include structures represented by the following formulae (6) to (9).

Formula (6)

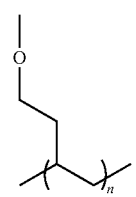

Formula (7)

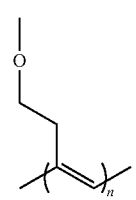

Formula (8)

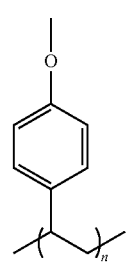

-continued

Formula (9)

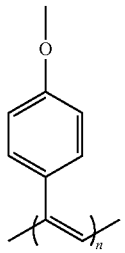

The polymer having the repeating unit containing the structure represented by any of the formulae (6) to (9) may be synthesized in such a manner that a hydroxy group is introduced to any of $X^1$ to $X^{12}$, A, and D in the structure represented by the general formula (1), and the hydroxy group as a linker is reacted with the following compound to introduce a polymerizable group thereto, followed by polymerizing the polymerizable group.

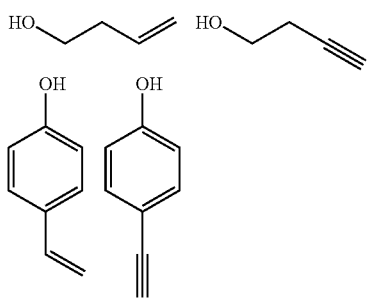

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound Represented by General Formula (1')

The compound represented by the general formula (1') is a novel compound.

General Formula (1')

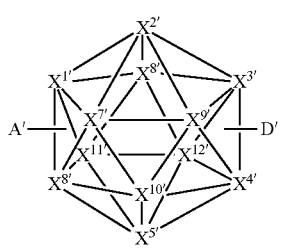

In the general formula (1'), $X^{1'}$ to $X^{12'}$ each independently represent C or BH constituting carborane, provided that among $X^{1'}$ to $X^{12'}$, the bonding positions to A' and D' each represent C, and the other thereof each represent BH; A' represents an acceptor bonded to the carborane through an aromatic ring or a heteroaromatic ring; and D' represents a donor bonded to the carborane through an aromatic ring or a heteroaromatic ring.

For the descriptions and the preferred ranges of $X^{1'}$ to $X^{12'}$, A', and D', reference may be made to the descriptions of the compound represented by the general formula (1).

Synthesis Method of Compound Represented by General Formula (1')

The compound represented by the general formula (1') may be synthesized by combining the known reactions. For example, a compound represented by the general formula (1'), in which $X^{1'}$ represents a group represented by the general formula (3), $X^{3'}$ represents a group represented by the general formula (2), and $Ar^1$ and $Ar^2$ each represent a phenylene group, can be synthesized by reacting the following two compounds.

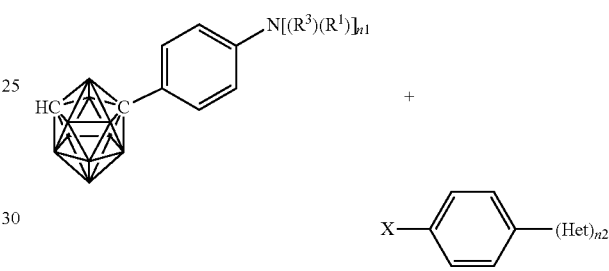

For the descriptions of $R^1$, $R^2$, Het, n1, and n2 in the aforementioned reaction scheme, reference may be made to the corresponding descriptions in the general formulae (2) and (3). X represents a halogen atom, examples of which include a fluorine atom, a chlorine atom, a bromine atom, and an iodine atom, and a chlorine atom, a bromine atom, and an iodine atom are preferred.

The reactions in the aforementioned scheme each are an application of the known reactions, and the known reaction conditions may be appropriately selected and used. For the details of the reactions, reference may be made to the synthesis examples described later. The compound represented by the general formula (1') may also be synthesized by combining the other known synthesis reactions.

Organic Light-Emitting Device

The compound represented by the general formula (1) of the invention is useful as a host material and/or a light-emitting material of an organic light-emitting device. Accordingly, the compound represented by the general formula (1) of the invention may be effectively used as a host material or a light-emitting material in a light-emitting layer of an organic light-emitting device. The compound represented by the general formula (1) includes a delayed fluorescent emitter emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a host material or a light-emitting material of a light-emitting layer may provide an excellent organic light-emitting device, such as an organic photoluminescent device (organic PL device) and an organic electroluminescent device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. In the case where the compound represented by the general formula (1) as a host material, one kind or two or more kinds selected from a group of compounds represented by the general formula (1) may be used. The light-emitting material may be a fluorescent light-emitting material or may be a phosphorescent light-emitting material, and in the case using a fluorescent light-emitting material, the light-emitting material is preferably one that emits delayed fluorescent light. A high light emission efficiency can be obtained thereby. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, the light-emitting material combined with the compound represented by the general formula (1) is preferably a compound that has excited singlet energy and excited triplet energy, at least one of which is higher than those of the compound represented by the general formula (1). As a result, the singlet excitons and the triplet excitons generated in the light-emitting material of the invention are capable of being confined in the molecules of the light-emitting material, thereby eliciting the light emission efficiency thereof sufficiently.

Examples of the light-emitting material combined with a host material containing the compound represented by the general formula (1) include a light-emitting material capable of emitting delayed fluorescent light. Preferred examples of the light-emitting material will be described below, but the light-emitting material capable of being used in the invention is not limited to the following examples.

Preferred examples of the light-emitting material include compounds represented by the following general formula (101). The entire description of WO 2013/154064 including the paragraphs 0008 to 0048 and 0095 to 0133 is incorporated herein by reference.

General Formula (101)

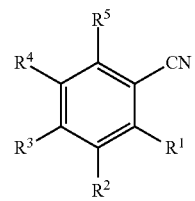

wherein in the general formula (101), at least one of $R^1$ to $R^5$ represents a cyano group, at least one of $R^1$ to $R^5$ represents a group represented by the following general formula (111), and the balance of $R^1$ to $R^5$ each represent a hydrogen atom or a substituent, General Formula (111)

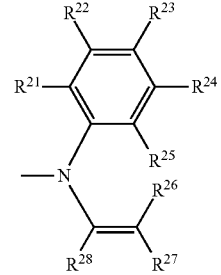

wherein in the general formula (111), $R^{21}$ to $R^{28}$ each independently represent a hydrogen atom or a substituent, provided that at least one of the following conditions (A) and (B) is satisfied:

(A) $R^{25}$ and $R^{26}$ together form a single bond, and (B) $R^{27}$ and $R^{28}$ together represent an atomic group that is necessary for forming a substituted or unsubstituted benzene ring.

In the general formula (101), at least one of $R^1$ to $R^5$ preferably represents a group represented by any one of the following general formulae (112) to (115).

General Formula (112)

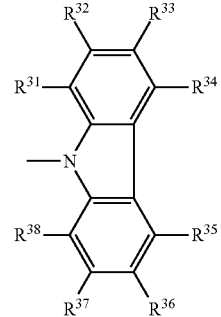

wherein in the general formula (112), $R^{31}$ to $R^{38}$ each independently represent a hydrogen atom or a substituent, General Formula (113)

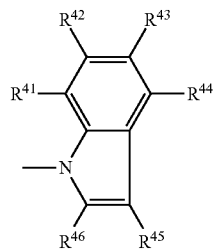

General Formula (113)

wherein in the general formula (113), $R^{41}$ to $R^{46}$ each independently represent a hydrogen atom or a substituent,

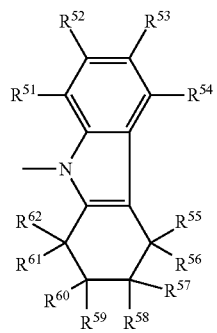

General Formula (114)

wherein in the general formula (114), $R^{51}$ to $R^{62}$ each independently represent a hydrogen atom or a substituent,

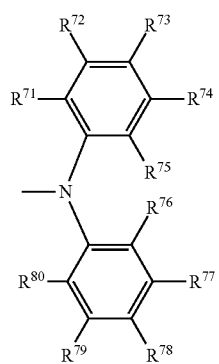

General Formula (115)

wherein in the general formula (115), $R^{71}$ to $R^{80}$ each independently represent a hydrogen atom or a substituent.

Specific examples of the compounds include the compounds shown in the following tables. In the case where two or more groups represented by any one of the general formulae (112) to (115) are present in the molecule of the following example compounds, all the groups have the same structure. The formulae (121) to (124) in the tables represent the following formulae, respectively, and n represents the number of the repeating units.

Formula (121)

Formula (122)

Formula (123)

Formula (124)

TABLE 1

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 1 | General formula (112) | General formula (112) | CN | General formula (112) | General formula (112) | H | H | H | H |
| 2 | General formula (112) | General formula (112) | CN | General formula (112) | General formula (112) | H | CH$_3$ | H | H |
| 3 | General formula (112) | General formula (112) | CN | General formula (112) | General formula (112) | H | CH$_3$O | H | H |

TABLE 1-continued

| Compound No. | R¹ | R² | R³ | R⁴ | R⁵ | R³¹, R³⁸ | R³², R³⁷ | R³³, R³⁶ | R³⁴, R³⁵ |
|---|---|---|---|---|---|---|---|---|---|
| 4 | General formula (112) | General formula (112) | CN | General formula (112) | General formula (112) | H | H | CH₃ | H |
| 5 | General formula (112) | General formula (112) | CN | General formula (112) | General formula (112) | H | H | CH₃O | H |
| 6 | General formula (112) | General formula (112) | CN | General formula (112) | General formula (112) | H | H | t-C₄H₉ | H |
| 7 | General formula (112) | General formula (112) | CN | General formula (112) | General formula (112) | H | H | Cl | H |
| 8 | General formula (112) | General formula (112) | CN | General formula (112) | General formula (112) | H | H | F | H |
| 9 | General formula (112) | General formula (112) | CN | General formula (112) | General formula (112) | H | H | H | CH₃ |
| 10 | General formula (112) | General formula (112) | CN | General formula (112) | General formula (112) | H | H | H | CH₃O |
| 11 | General formula (112) | General formula (112) | CN | General formula (112) | H | H | H | H | H |
| 12 | General formula (112) | General formula (112) | CN | General formula (112) | H | H | CH₃ | H | H |
| 13 | General formula (112) | General formula (112) | CN | General formula (112) | H | H | CH₃O | H | H |
| 14 | General formula (112) | General formula (112) | CN | General formula (112) | H | H | H | CH₃ | H |
| 15 | General formula (112) | General formula (112) | CN | General formula (112) | H | H | H | CH₃O | H |
| 16 | General formula (112) | General formula (112) | CN | General formula (112) | H | H | H | t-C₄H₉ | H |
| 17 | General formula (112) | General formula (112) | CN | General formula (112) | H | H | H | Cl | H |
| 18 | General formula (112) | General formula (112) | CN | General formula (112) | H | H | H | F | H |
| 19 | General formula (112) | General formula (112) | CN | General formula (112) | H | H | H | H | CH₃ |
| 20 | General formula (112) | General formula (112) | CN | General formula (112) | H | H | H | H | CH₃O |
| 21 | General formula (112) | General formula (112) | CN | H | H | H | H | H | H |
| 22 | General formula (112) | General formula (112) | CN | H | H | H | CH₃ | H | H |
| 23 | General formula (112) | General formula (112) | CN | H | H | H | CH₃O | H | H |
| 24 | General formula (112) | General formula (112) | CN | H | H | H | H | CH₃ | H |
| 25 | General formula (112) | General formula (112) | CN | H | H | H | H | CH₃O | H |
| 26 | General formula (112) | General formula (112) | CN | H | H | H | H | t-C₄H₉ | H |
| 27 | General formula (112) | General formula (112) | CN | H | H | H | H | Cl | H |
| 28 | General formula (112) | General formula (112) | CN | H | H | H | H | F | H |
| 29 | General formula (112) | General formula (112) | CN | H | H | H | H | H | CH₃ |
| 30 | General formula (112) | General formula (112) | CN | H | H | H | H | H | CH₃O |
| 31 | General formula (112) | H | CN | General formula (112) | H | H | H | H | H |
| 32 | General formula (112) | H | CN | General formula (112) | H | H | CH₃ | H | H |
| 33 | General formula (112) | H | CN | General formula (112) | H | H | CH₃O | H | H |
| 34 | General formula (112) | H | CN | General formula (112) | H | H | H | CH₃ | H |
| 35 | General formula (112) | H | CN | General formula (112) | H | H | H | CH₃O | H |
| 36 | General formula (112) | H | CN | General formula (112) | H | H | H | t-C₄H₉ | H |
| 37 | General formula (112) | H | CN | General formula (112) | H | H | H | Cl | H |
| 38 | General formula (112) | H | CN | General formula (112) | H | H | H | F | H |
| 39 | General formula (112) | H | CN | General formula (112) | H | H | H | H | CH₃ |
| 40 | General formula (112) | H | CN | General formula (112) | H | H | H | H | CH₃O |
| 41 | General formula (112) | H | CN | H | General formula (112) | H | H | H | H |

TABLE 1-continued

| Compound No. | General formula (1) | | | | | General formula (112) | | | |
| --- | --- | --- | --- | --- | --- | --- | --- | --- | --- |
| | R¹ | R² | R³ | R⁴ | R⁵ | R³¹, R³⁸ | R³², R³⁷ | R³³, R³⁶ | R³⁴, R³⁵ |
| 42 | General formula (112) | H | CN | H | General formula (112) | H | CH₃ | H | H |
| 43 | General formula (112) | H | CN | H | General formula (112) | H | CH₃O | H | H |
| 44 | General formula (112) | H | CN | H | General formula (112) | H | H | CH₃ | H |
| 45 | General formula (112) | H | CN | H | General formula (112) | H | H | CH₃O | H |
| 46 | General formula (112) | H | CN | H | General formula (112) | H | H | t-C₄H₉ | H |
| 47 | General formula (112) | H | CN | H | General formula (112) | H | H | Cl | H |
| 48 | General formula (112) | H | CN | H | General formula (112) | H | H | F | H |
| 49 | General formula (112) | H | CN | H | General formula (112) | H | H | H | CH₃ |
| 50 | General formula (112) | H | CN | H | General formula (112) | H | H | H | CH₃O |
| 51 | General formula (112) | H | CN | H | H | H | H | H | H |
| 52 | General formula (112) | H | CN | H | H | H | CH₃ | H | H |
| 53 | General formula (112) | H | CN | H | H | H | CH₃O | H | H |
| 54 | General formula (112) | H | CN | H | H | H | H | CH₃ | H |
| 55 | General formula (112) | H | CN | H | H | H | H | CH₃O | H |
| 56 | General formula (112) | H | CN | H | H | H | H | t-C₄H₉ | H |
| 57 | General formula (112) | H | CN | H | H | H | H | Cl | H |
| 58 | General formula (112) | H | CN | H | H | H | H | F | H |
| 59 | General formula (112) | H | CN | H | H | H | H | H | CH₃ |
| 60 | General formula (112) | H | CN | H | H | H | H | H | CH₃O |
| 61 | General formula (112) | General formula (112) | CN | General formula (112) | F | H | H | H | H |
| 62 | General formula (112) | General formula (112) | CN | General formula (112) | F | H | CH₃ | H | H |
| 63 | General formula (112) | General formula (112) | CN | General formula (112) | F | H | CH₃O | H | H |
| 64 | General formula (112) | General formula (112) | CN | General formula (112) | F | H | H | CH₃ | H |
| 65 | General formula (112) | General formula (112) | CN | General formula (112) | F | H | H | CH₃O | H |
| 66 | General formula (112) | General formula (112) | CN | General formula (112) | F | H | H | t-C₄H₉ | H |
| 67 | General formula (112) | General formula (112) | CN | General formula (112) | F | H | H | Cl | H |
| 68 | General formula (112) | General formula (112) | CN | General formula (112) | F | H | H | F | H |
| 69 | General formula (112) | General formula (112) | CN | General formula (112) | F | H | H | H | CH₃ |
| 70 | General formula (112) | General formula (112) | CN | General formula (112) | F | H | H | H | CH₃O |
| 71 | General formula (112) | General formula (112) | CN | F | F | H | H | H | H |
| 72 | General formula (112) | General formula (112) | CN | F | F | H | CH₃ | H | H |
| 73 | General formula (112) | General formula (112) | CN | F | F | H | CH₃O | H | H |
| 74 | General formula (112) | General formula (112) | CN | F | F | H | H | CH₃ | H |
| 75 | General formula (112) | General formula (112) | CN | F | F | H | H | CH₃O | H |
| 76 | General formula (112) | General formula (112) | CN | F | F | H | H | t-C₄H₉ | H |
| 77 | General formula (112) | General formula (112) | CN | F | F | H | H | Cl | H |
| 78 | General formula (112) | General formula (112) | CN | F | F | H | H | F | H |
| 79 | General formula (112) | General formula (112) | CN | F | F | H | H | H | CH₃ |

TABLE 1-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 80 | General formula (112) | General formula (112) | CN | F | F | H | H | H | $CH_3O$ |
| 81 | General formula (112) | F | CN | General formula (112) | F | H | H | H | H |
| 82 | General formula (112) | F | CN | General formula (112) | F | H | $CH_3$ | H | H |
| 83 | General formula (112) | F | CN | General formula (112) | F | H | $CH_3O$ | H | H |
| 84 | General formula (112) | F | CN | General formula (112) | F | H | H | $CH_3$ | H |
| 85 | General formula (112) | F | CN | General formula (112) | F | H | H | $CH_3O$ | H |
| 86 | General formula (112) | F | CN | General formula (112) | F | H | H | $t\text{-}C_4H_9$ | H |
| 87 | General formula (112) | F | CN | General formula (112) | F | H | H | Cl | H |
| 88 | General formula (112) | F | CN | General formula (112) | F | H | H | F | H |
| 89 | General formula (112) | F | CN | General formula (112) | F | H | H | H | $CH_3$ |
| 90 | General formula (112) | F | CN | General formula (112) | F | H | H | H | $CH_3O$ |
| 91 | General formula (112) | F | CN | F | General formula (112) | H | H | H | H |
| 92 | General formula (112) | F | CN | F | General formula (112) | H | $CH_3$ | H | H |
| 93 | General formula (112) | F | CN | F | General formula (112) | H | $CH_3O$ | H | H |
| 94 | General formula (112) | F | CN | F | General formula (112) | H | H | $CH_3$ | H |
| 95 | General formula (112) | F | CN | F | General formula (112) | H | H | $CH_3O$ | H |
| 96 | General formula (112) | F | CN | F | General formula (112) | H | H | $t\text{-}C_4H_9$ | H |
| 97 | General formula (112) | F | CN | F | General formula (112) | H | H | Cl | H |
| 98 | General formula (112) | F | CN | F | General formula (112) | H | H | F | H |
| 99 | General formula (112) | F | CN | F | General formula (112) | H | H | H | $CH_3$ |
| 100 | General formula (112) | F | CN | F | General formula (112) | H | H | H | $CH_3O$ |
| 101 | General formula (112) | F | CN | F | F | H | H | H | H |
| 102 | General formula (112) | F | CN | F | F | H | $CH_3$ | H | H |
| 103 | General formula (112) | F | CN | F | F | H | $CH_3O$ | H | H |
| 104 | General formula (112) | F | CN | F | F | H | H | $CH_3$ | H |
| 105 | General formula (112) | F | CN | F | F | H | H | $CH_3O$ | H |
| 106 | General formula (112) | F | CN | F | F | H | H | $t\text{-}C_4H_9$ | H |
| 107 | General formula (112) | F | CN | F | F | H | H | Cl | H |
| 108 | General formula (112) | F | CN | F | F | H | H | F | H |
| 109 | General formula (112) | F | CN | F | F | H | H | H | $CH_3$ |
| 110 | General formula (112) | F | CN | F | F | H | H | H | $CH_3O$ |
| 111 | General formula (112) | General formula (112) | CN | General formula (112) | OH | H | H | H | H |
| 112 | General formula (112) | General formula (112) | CN | General formula (112) | OH | H | $CH_3$ | H | H |
| 113 | General formula (112) | General formula (112) | CN | General formula (112) | OH | H | $CH_3O$ | H | H |
| 114 | General formula (112) | General formula (112) | CN | General formula (112) | OH | H | H | $CH_3$ | H |
| 115 | General formula (112) | General formula (112) | CN | General formula (112) | OH | H | H | $CH_3O$ | H |
| 116 | General formula (112) | General formula (112) | CN | General formula (112) | OH | H | H | $t\text{-}C_4H_9$ | H |
| 117 | General formula (112) | General formula (112) | CN | General formula (112) | OH | H | H | Cl | H |

TABLE 1-continued

| Compound No. | General formula (1) | | | | | General formula (112) | | | |
|---|---|---|---|---|---|---|---|---|---|
| | R¹ | R² | R³ | R⁴ | R⁵ | R³¹, R³⁸ | R³², R³⁷ | R³³, R³⁶ | R³⁴, R³⁵ |
| 118 | General formula (112) | General formula (112) | CN | General formula (112) | OH | H | H | F | H |
| 119 | General formula (112) | General formula (112) | CN | General formula (112) | OH | H | H | H | CH₃ |
| 120 | General formula (112) | General formula (112) | CN | General formula (112) | OH | H | H | H | CH₃O |
| 121 | General formula (112) | General formula (112) | CN | OH | OH | H | H | H | H |
| 122 | General formula (112) | General formula (112) | CN | OH | OH | H | CH₃ | H | H |
| 123 | General formula (112) | General formula (112) | CN | OH | OH | H | CH₃O | H | H |
| 124 | General formula (112) | General formula (112) | CN | OH | OH | H | H | CH₃ | H |
| 125 | General formula (112) | General formula (112) | CN | OH | OH | H | H | CH₃O | H |
| 126 | General formula (112) | General formula (112) | CN | OH | OH | H | H | t-C₄H₉ | H |
| 127 | General formula (112) | General formula (112) | CN | OH | OH | H | H | Cl | H |
| 128 | General formula (112) | General formula (112) | CN | OH | OH | H | H | F | H |
| 129 | General formula (112) | General formula (112) | CN | OH | OH | H | H | H | CH₃ |
| 130 | General formula (112) | General formula (112) | CN | OH | OH | H | H | H | CH₃O |
| 131 | General formula (112) | OH | CN | General formula (112) | OH | H | H | H | H |
| 132 | General formula (112) | OH | CN | General formula (112) | OH | H | CH₃ | H | H |
| 133 | General formula (112) | OH | CN | General formula (112) | OH | H | CH₃O | H | H |
| 134 | General formula (112) | OH | CN | General formula (112) | OH | H | H | CH₃ | H |
| 135 | General formula (112) | OH | CN | General formula (112) | OH | H | H | CH₃O | H |
| 136 | General formula (112) | OH | CN | General formula (112) | OH | H | H | t-C₄H₉ | H |
| 137 | General formula (112) | OH | CN | General formula (112) | OH | H | H | Cl | H |
| 138 | General formula (112) | OH | CN | General formula (112) | OH | H | H | F | H |
| 139 | General formula (112) | OH | CN | General formula (112) | OH | H | H | H | CH₃ |
| 140 | General formula (112) | OH | CN | General formula (112) | OH | H | H | H | CH₃O |
| 141 | General formula (112) | OH | CN | OH | General formula (112) | H | H | H | H |
| 142 | General formula (112) | OH | CN | OH | General formula (112) | H | CH₃ | H | H |
| 143 | General formula (112) | OH | CN | OH | General formula (112) | H | CH₃O | H | H |
| 144 | General formula (112) | OH | CN | OH | General formula (112) | H | H | CH₃ | H |
| 145 | General formula (112) | OH | CN | OH | General formula (112) | H | H | CH₃O | H |
| 146 | General formula (112) | OH | CN | OH | General formula (112) | H | H | t-C₄H₉ | H |
| 147 | General formula (112) | OH | CN | OH | General formula (112) | H | H | Cl | H |
| 148 | General formula (112) | OH | CN | OH | General formula (112) | H | H | F | H |
| 149 | General formula (112) | OH | CN | OH | General formula (112) | H | H | H | CH₃ |
| 150 | General formula (112) | OH | CN | OH | General formula (112) | H | H | H | CH₃O |
| 151 | General formula (112) | OH | CN | OH | OH | H | H | H | H |
| 152 | General formula (112) | OH | CN | OH | OH | H | CH₃ | H | H |
| 153 | General formula (112) | OH | CN | OH | OH | H | CH₃O | H | H |
| 154 | General formula (112) | OH | CN | OH | OH | H | H | CH₃ | H |
| 155 | General formula (112) | OH | CN | OH | OH | H | H | CH₃O | H |

TABLE 1-continued

| Compound No. | General formula (1) | | | | | General formula (112) | | | |
|---|---|---|---|---|---|---|---|---|---|
| | R¹ | R² | R³ | R⁴ | R⁵ | R³¹, R³⁸ | R³², R³⁷ | R³³, R³⁶ | R³⁴, R³⁵ |
| 156 | General formula (112) | OH | CN | OH | OH | H | H | t-C₄H₉ | H |
| 157 | General formula (112) | OH | CN | OH | OH | H | H | Cl | H |
| 158 | General formula (112) | OH | CN | OH | OH | H | H | F | H |
| 159 | General formula (112) | OH | CN | OH | OH | H | H | H | CH₃ |
| 160 | General formula (112) | OH | CN | OH | OH | H | H | H | CH₃O |
| 161 | General formula (112) | General formula (112) | CN | General formula (112) | Cl | H | H | H | H |
| 162 | General formula (112) | General formula (112) | CN | General formula (112) | Cl | H | CH₃ | H | H |
| 163 | General formula (112) | General formula (112) | CN | General formula (112) | Cl | H | CH₃O | H | H |
| 164 | General formula (112) | General formula (112) | CN | General formula (112) | Cl | H | H | CH₃ | H |
| 165 | General formula (112) | General formula (112) | CN | General formula (112) | Cl | H | H | CH₃O | H |
| 166 | General formula (112) | General formula (112) | CN | General formula (112) | Cl | H | H | t-C₄H₉ | H |
| 167 | General formula (112) | General formula (112) | CN | General formula (112) | Cl | H | H | Cl | H |
| 168 | General formula (112) | General formula (112) | CN | General formula (112) | Cl | H | H | F | H |
| 169 | General formula (112) | General formula (112) | CN | General formula (112) | Cl | H | H | H | CH₃ |
| 170 | General formula (112) | General formula (112) | CN | General formula (112) | Cl | H | H | H | CH₃O |
| 171 | General formula (112) | General formula (112) | CN | General formula (112) | F | H | H | H | H |
| 172 | General formula (112) | General formula (112) | CN | General formula (112) | F | H | CH₃ | H | H |
| 173 | General formula (112) | General formula (112) | CN | General formula (112) | F | H | CH₃O | H | H |
| 174 | General formula (112) | General formula (112) | CN | General formula (112) | F | H | H | CH₃ | H |
| 175 | General formula (112) | General formula (112) | CN | General formula (112) | F | H | H | CH₃O | H |
| 176 | General formula (112) | General formula (112) | CN | General formula (112) | F | H | H | t-C₄H₉ | H |
| 177 | General formula (112) | General formula (112) | CN | General formula (112) | F | H | H | Cl | H |
| 178 | General formula (112) | General formula (112) | CN | General formula (112) | F | H | H | F | H |
| 179 | General formula (112) | General formula (112) | CN | General formula (112) | F | H | H | H | CH₃ |
| 180 | General formula (112) | General formula (112) | CN | General formula (112) | F | H | H | H | CH₃O |
| 181 | General formula (112) | General formula (112) | CN | General formula (112) | CH₃O | H | H | H | H |
| 182 | General formula (112) | General formula (112) | CN | General formula (112) | CH₃O | H | CH₃ | H | H |
| 183 | General formula (112) | General formula (112) | CN | General formula (112) | CH₃O | H | CH₃O | H | H |
| 184 | General formula (112) | General formula (112) | CN | General formula (112) | CH₃O | H | H | CH₃ | H |
| 185 | General formula (112) | General formula (112) | CN | General formula (112) | CH₃O | H | H | CH₃O | H |
| 186 | General formula (112) | General formula (112) | CN | General formula (112) | CH₃O | H | H | t-C₄H₉ | H |
| 187 | General formula (112) | General formula (112) | CN | General formula (112) | CH₃O | H | H | Cl | H |
| 188 | General formula (112) | General formula (112) | CN | General formula (112) | CH₃O | H | H | F | H |
| 189 | General formula (112) | General formula (112) | CN | General formula (112) | C₂H₅O | H | H | H | CH₃ |
| 190 | General formula (112) | General formula (112) | CN | General formula (112) | C₂H₅O | H | H | H | CH₃O |
| 191 | General formula (112) | General formula (112) | CN | General formula (112) | C₂H₅O | H | H | H | H |
| 192 | General formula (112) | General formula (112) | CN | General formula (112) | C₂H₅O | H | CH₃ | H | H |
| 193 | General formula (112) | General formula (112) | CN | General formula (112) | C₂H₅O | H | CH₃O | H | H |

TABLE 1-continued

| Compound No. | General formula (1) | | | | | General formula (112) | | | |
|---|---|---|---|---|---|---|---|---|---|
| | R¹ | R² | R³ | R⁴ | R⁵ | R³¹, R³⁸ | R³², R³⁷ | R³³, R³⁶ | R³⁴, R³⁵ |
| 194 | General formula (112) | General formula (112) | CN | General formula (112) | C₂H₅O | H | H | CH₃ | H |
| 195 | General formula (112) | General formula (112) | CN | General formula (112) | C₂H₅O | H | H | CH₃O | H |
| 196 | General formula (112) | General formula (112) | CN | General formula (112) | C₂H₅O | H | H | t-C₄H₉ | H |
| 197 | General formula (112) | General formula (112) | CN | General formula (112) | C₂H₅O | H | H | Cl | H |
| 198 | General formula (112) | General formula (112) | CN | General formula (112) | C₂H₅O | H | H | F | H |
| 199 | General formula (112) | General formula (112) | CN | General formula (112) | C₂H₅O | H | H | H | CH₃ |
| 200 | General formula (112) | General formula (112) | CN | General formula (112) | C₂H₅O | H | H | H | CH₃O |
| 201 | General formula (112) | General formula (112) | CN | General formula (112) | C₆H₅O | H | H | H | H |
| 202 | General formula (112) | General formula (112) | CN | General formula (112) | C₆H₅O | H | CH₃ | H | H |
| 203 | General formula (112) | General formula (112) | CN | General formula (112) | C₆H₅O | H | CH₃O | H | H |
| 204 | General formula (112) | General formula (112) | CN | General formula (112) | C₆H₅O | H | H | CH₃ | H |
| 205 | General formula (112) | General formula (112) | CN | General formula (112) | C₆H₅O | H | H | CH₃O | H |
| 206 | General formula (112) | General formula (112) | CN | General formula (112) | C₆H₅O | H | H | t-C₄H₉ | H |
| 207 | General formula (112) | General formula (112) | CN | General formula (112) | C₆H₅O | H | H | Cl | H |
| 208 | General formula (112) | General formula (112) | CN | General formula (112) | C₆H₅O | H | H | F | H |
| 209 | General formula (112) | General formula (112) | CN | General formula (112) | C₆H₅O | H | H | H | CH₃ |
| 210 | General formula (112) | General formula (112) | CN | General formula (112) | C₆H₅O | H | H | H | CH₃O |
| 211 | General formula (112) | General formula (112) | CN | General formula (112) | Formula (121) | H | H | H | H |
| 212 | General formula (112) | General formula (112) | CN | General formula (112) | Formula (121) | H | CH₃ | H | H |
| 213 | General formula (112) | General formula (112) | CN | General formula (112) | Formula (121) | H | CH₃O | H | H |
| 214 | General formula (112) | General formula (112) | CN | General formula (112) | Formula (121) | H | H | CH₃ | H |
| 215 | General formula (112) | General formula (112) | CN | General formula (112) | Formula (121) | H | H | CH₃O | H |
| 216 | General formula (112) | General formula (112) | CN | General formula (112) | Formula (121) | H | H | t-C₄H₉ | H |
| 217 | General formula (112) | General formula (112) | CN | General formula (112) | Formula (121) | H | H | Cl | H |
| 218 | General formula (112) | General formula (112) | CN | General formula (112) | Formula (121) | H | H | F | H |
| 219 | General formula (112) | General formula (112) | CN | General formula (112) | Formula (121) | H | H | H | CH₃ |
| 220 | General formula (112) | General formula (112) | CN | General formula (112) | Formula (121) | H | H | H | CH₃O |
| 221 | General formula (112) | General formula (112) | CN | General formula (112) | Formula (122) | H | H | H | H |
| 222 | General formula (112) | General formula (112) | CN | General formula (112) | Formula (122) | H | CH₃ | H | H |
| 223 | General formula (112) | General formula (112) | CN | General formula (112) | Formula (122) | H | CH₃O | H | H |
| 224 | General formula (112) | General formula (112) | CN | General formula (112) | Formula (122) | H | H | CH₃ | H |
| 225 | General formula (112) | General formula (112) | CN | General formula (112) | Formula (122) | H | H | CH₃O | H |
| 226 | General formula (112) | General formula (112) | CN | General formula (112) | Formula (122) | H | H | t-C₄H₉ | H |
| 227 | General formula (112) | General formula (112) | CN | General formula (112) | Formula (122) | H | H | Cl | H |
| 228 | General formula (112) | General formula (112) | CN | General formula (112) | Formula (122) | H | H | F | H |
| 229 | General formula (112) | General formula (112) | CN | General formula (112) | Formula (122) | H | H | H | CH₃ |
| 230 | General formula (112) | General formula (112) | CN | General formula (112) | Formula (122) | H | H | H | CH₃O |
| 231 | General formula (112) | General formula (112) | CN | General formula (112) | Formula (123) | H | H | H | H |

TABLE 1-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 232 | General formula (112) | General formula (112) | CN | General formula (112) | Formula (123) | H | $CH_3$ | H | H |
| 233 | General formula (112) | General formula (112) | CN | General formula (112) | Formula (123) | H | $CH_3O$ | H | H |
| 234 | General formula (112) | General formula (112) | CN | General formula (112) | Formula (123) | H | H | $CH_3$ | H |
| 235 | General formula (112) | General formula (112) | CN | General formula (112) | Formula (123) | H | H | $CH_3O$ | H |
| 236 | General formula (112) | General formula (112) | CN | General formula (112) | Formula (123) | H | H | $t-C_4H_9$ | H |
| 237 | General formula (112) | General formula (112) | CN | General formula (112) | Formula (123) | H | H | Cl | H |
| 238 | General formula (112) | General formula (112) | CN | General formula (112) | Formula (123) | H | H | F | H |
| 239 | General formula (112) | General formula (112) | CN | General formula (112) | Formula (123) | H | H | H | $CH_3$ |
| 240 | General formula (112) | General formula (112) | CN | General formula (112) | Formula (123) | H | H | H | $CH_3O$ |
| 241 | General formula (112) | General formula (112) | CN | General formula (112) | Formula (124) | H | H | H | H |
| 242 | General formula (112) | General formula (112) | CN | General formula (112) | Formula (124) | H | $CH_3$ | H | H |
| 243 | General formula (112) | General formula (112) | CN | General formula (112) | Formula (124) | H | $CH_3O$ | H | H |
| 244 | General formula (112) | General formula (112) | CN | General formula (112) | Formula (124) | H | H | $CH_3$ | H |
| 245 | General formula (112) | General formula (112) | CN | General formula (112) | Formula (124) | H | H | $CH_3O$ | H |
| 246 | General formula (112) | General formula (112) | CN | General formula (112) | Formula (124) | H | H | $t-C_4H_9$ | H |
| 247 | General formula (112) | General formula (112) | CN | General formula (112) | Formula (124) | H | H | Cl | H |
| 248 | General formula (112) | General formula (112) | CN | General formula (112) | Formula (124) | H | H | F | H |
| 249 | General formula (112) | General formula (112) | CN | General formula (112) | Formula (124) | H | H | H | $CH_3$ |
| 250 | General formula (112) | General formula (112) | CN | General formula (112) | Formula (124) | H | H | H | $CH_3O$ |
| 251 | General formula (112) | General formula (112) | CN | General formula (112) | General formula (112) | H | $C_6H_5$ | H | H |
| 252 | General formula (112) | General formula (112) | CN | General formula (112) | General formula (112) | H | H | $C_5H_6$ | H |
| 253 | General formula (112) | General formula (112) | CN | General formula (112) | H | H | $C_6H_5$ | H | H |
| 254 | General formula (112) | General formula (112) | CN | General formula (112) | H | H | H | $C_5H_6$ | H |
| 255 | General formula (112) | General formula (112) | CN | H | H | H | $C_6H_5$ | H | H |
| 256 | General formula (112) | General formula (112) | CN | H | H | H | H | $C_6H_5$ | H |
| 257 | General formula (112) | H | CN | General formula (112) | H | H | $C_6H_5$ | H | H |
| 258 | General formula (112) | H | CN | General formula (112) | H | H | H | $C_6H_5$ | H |
| 259 | General formula (112) | H | CN | H | General formula (112) | H | $C_6H_5$ | H | H |
| 260 | General formula (112) | H | CN | H | General formula (112) | H | H | $C_6H_5$ | H |
| 261 | General formula (112) | H | CN | H | H | H | $C_6H_5$ | H | H |
| 262 | General formula (112) | H | CN | H | H | H | H | $C_6H_5$ | H |
| 263 | General formula (112) | General formula (112) | CN | General formula (112) | F | H | $C_6H_5$ | H | H |
| 264 | General formula (112) | General formula (112) | CN | General formula (112) | F | H | H | $C_6H_5$ | H |
| 265 | General formula (112) | General formula (112) | CN | F | F | H | $C_6H_5$ | H | H |
| 266 | General formula (112) | General formula (112) | CN | F | F | H | H | $C_6H_5$ | H |
| 267 | General formula (112) | F | CN | General formula (112) | F | H | $C_6H_5$ | H | H |
| 268 | General formula (112) | F | CN | General formula (112) | F | H | H | $C_6H_5$ | H |
| 269 | General formula (112) | F | CN | F | General formula (112) | H | $C_6H_5$ | H | H |

TABLE 1-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 270 | General formula (112) | F | CN | F | General formula (112) | H | H | $C_6H_5$ | H |
| 271 | General formula (112) | F | CN | F | F | H | $C_6H_5$ | H | H |
| 272 | General formula (112) | F | CN | F | F | H | H | $C_6H_5$ | H |
| 273 | General formula (112) | General formula (112) | CN | General formula (112) | OH | H | $C_6H_5$ | H | H |
| 274 | General formula (112) | General formula (112) | CN | General formula (112) | OH | H | H | $C_6H_5$ | H |
| 275 | General formula (112) | General formula (112) | CN | OH | OH | H | $C_6H_5$ | H | H |
| 276 | General formula (112) | General formula (112) | CN | OH | OH | H | H | $C_6H_5$ | H |
| 277 | General formula (112) | OH | CN | General formula (112) | OH | H | $C_6H_5$ | H | H |
| 278 | General formula (112) | OH | CN | General formula (112) | OH | H | H | $C_6H_5$ | H |
| 279 | General formula (112) | OH | CN | OH | General formula (112) | H | $C_6H_5$ | H | H |
| 280 | General formula (112) | OH | CN | OH | General formula (112) | H | H | $C_6H_5$ | H |
| 281 | General formula (112) | OH | CN | OH | OH | H | $C_6H_5$ | H | H |
| 282 | General formula (112) | OH | CN | OH | OH | H | H | $C_6H_5$ | H |
| 283 | General formula (112) | General formula (112) | CN | General formula (112) | Cl | H | $C_6H_5$ | H | H |
| 284 | General formula (112) | General formula (112) | CN | General formula (112) | Cl | H | H | $C_6H_5$ | H |
| 285 | General formula (112) | General formula (112) | CN | General formula (112) | F | H | $C_6H_5$ | H | H |
| 286 | General formula (112) | General formula (112) | CN | General formula (112) | F | H | H | $C_6H_5$ | H |
| 287 | General formula (112) | General formula (112) | CN | General formula (112) | $CH_3O$ | H | $C_6H_5$ | H | H |
| 288 | General formula (112) | General formula (112) | CN | General formula (112) | $CH_3O$ | H | H | $C_6H_5$ | H |
| 289 | General formula (112) | General formula (112) | CN | General formula (112) | $C_2H_5O$ | H | $C_6H_5$ | H | H |
| 290 | General formula (112) | General formula (112) | CN | General formula (112) | $C_2H_5O$ | H | H | $C_6H_5$ | H |
| 291 | General formula (112) | General formula (112) | CN | General formula (112) | $C_6H_5O$ | H | $C_6H_5$ | H | H |
| 292 | General formula (112) | General formula (112) | CN | General formula (112) | $C_6H_5O$ | H | H | $C_6H_5$ | H |
| 293 | General formula (112) | General formula (112) | CN | General formula (112) | Formula (121) | H | $C_6H_5$ | H | H |
| 294 | General formula (112) | General formula (112) | CN | General formula (112) | Formula (121) | H | H | $C_6H_5$ | H |
| 295 | General formula (112) | General formula (112) | CN | General formula (112) | Formula (122) | H | $C_6H_5$ | H | H |
| 296 | General formula (112) | General formula (112) | CN | General formula (112) | Formula (122) | H | H | $C_6H_5$ | H |
| 297 | General formula (112) | General formula (112) | CN | General formula (112) | Formula (123) | H | $C_6H_5$ | H | H |
| 298 | General formula (112) | General formula (112) | CN | General formula (112) | Formula (123) | H | H | $C_6H_5$ | H |
| 299 | General formula (112) | General formula (112) | CN | General formula (112) | Formula (124) | H | $C_6H_5$ | H | H |
| 300 | General formula (112) | General formula (112) | CN | General formula (112) | Formula (124) | H | H | $C_6H_5$ | H |

TABLE 2

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 301 | General formula (112) | CN | General formula (112) | General formula (112) | General formula (112) | H | H | H | H |
| 302 | General formula (112) | CN | General formula (112) | General formula (112) | General formula (112) | H | $CH_3$ | H | H |

TABLE 2-continued

| Compound No. | General formula (1) R¹ | R² | R³ | R⁴ | R⁵ | General formula (112) R³¹, R³⁸ | R³², R³⁷ | R³³, R³⁶ | R³⁴, R³⁵ |
|---|---|---|---|---|---|---|---|---|---|
| 303 | General formula (112) | CN | General formula (112) | General formula (112) | General formula (112) | H | CH₃O | H | H |
| 304 | General formula (112) | CN | General formula (112) | General formula (112) | General formula (112) | H | H | CH₃ | H |
| 305 | General formula (112) | CN | General formula (112) | General formula (112) | General formula (112) | H | H | CH₃O | H |
| 306 | General formula (112) | CN | General formula (112) | General formula (112) | General formula (112) | H | H | t-C₄H₉ | H |
| 307 | General formula (112) | CN | General formula (112) | General formula (112) | General formula (112) | H | H | Cl | H |
| 308 | General formula (112) | CN | General formula (112) | General formula (112) | General formula (112) | H | H | F | H |
| 309 | General formula (112) | CN | General formula (112) | General formula (112) | General formula (112) | H | H | H | CH₃ |
| 310 | General formula (112) | CN | General formula (112) | General formula (112) | General formula (112) | H | H | H | CH₃O |
| 311 | General formula (112) | CN | General formula (112) | General formula (112) | H | H | H | H | H |
| 312 | General formula (112) | CN | General formula (112) | General formula (112) | H | H | H | CH₃ | H |
| 313 | General formula (112) | CN | General formula (112) | General formula (112) | H | H | H | CH₃O | H |
| 314 | General formula (112) | CN | General formula (112) | H | General formula (112) | H | H | H | H |
| 315 | General formula (112) | CN | General formula (112) | H | General formula (112) | H | H | CH₃ | H |
| 316 | General formula (112) | CN | General formula (112) | H | General formula (112) | H | H | CH₃O | H |
| 317 | General formula (112) | CN | H | General formula (112) | General formula (112) | H | H | H | H |
| 318 | General formula (112) | CN | H | General formula (112) | General formula (112) | H | H | CH₃ | H |
| 319 | General formula (112) | CN | H | General formula (112) | General formula (112) | H | H | CH₃O | H |
| 320 | H | CN | General formula (112) | General formula (112) | General formula (112) | H | H | H | H |
| 321 | H | CN | General formula (112) | General formula (112) | General formula (112) | H | H | CH₃ | H |
| 322 | H | CN | General formula (112) | General formula (112) | General formula (112) | H | H | CH₃O | H |
| 323 | General formula (112) | CN | General formula (112) | H | H | H | H | H | H |
| 324 | General formula (112) | CN | General formula (112) | H | H | H | H | CH₃ | H |
| 325 | General formula (112) | CN | General formula (112) | H | H | H | H | CH₃O | H |
| 326 | General formula (112) | CN | H | General formula (112) | H | H | H | H | H |
| 327 | General formula (112) | CN | H | General formula (112) | H | H | H | CH₃ | H |
| 328 | General formula (112) | CN | H | General formula (112) | H | H | H | CH₃O | H |
| 329 | H | CN | General formula (112) | General formula (112) | H | H | H | H | H |
| 330 | H | CN | General formula (112) | General formula (112) | H | H | H | CH₃ | H |
| 331 | H | CN | General formula (112) | General formula (112) | H | H | H | CH₃O | H |
| 332 | General formula (112) | CN | H | H | General formula (112) | H | H | H | H |
| 333 | General formula (112) | CN | H | H | General formula (112) | H | H | CH₃ | H |
| 334 | General formula (112) | CN | H | H | General formula (112) | H | H | CH₃O | H |
| 335 | H | CN | General formula (112) | H | General formula (112) | H | H | H | H |
| 336 | H | CN | General formula (112) | H | General formula (112) | H | H | CH₃ | H |
| 337 | H | CN | General formula (112) | H | General formula (112) | H | H | CH₃O | H |
| 338 | H | CN | H | General formula (112) | General formula (112) | H | H | H | H |
| 339 | H | CN | H | General formula (112) | General formula (112) | H | H | CH₃ | H |
| 340 | H | CN | H | General formula (112) | General formula (112) | H | H | CH₃O | H |

TABLE 2-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 341 | General formula (112) | CN | H | H | H | H | H | H | H |
| 342 | General formula (112) | CN | H | H | H | H | H | $CH_3$ | H |
| 343 | General formula (112) | CN | H | H | H | H | H | $CH_3O$ | H |
| 344 | H | CN | General formula (112) | H | H | H | H | H | H |
| 345 | H | CN | General formula (112) | H | H | H | H | $CH_3$ | H |
| 346 | H | CN | General formula (112) | H | H | H | H | $CH_3O$ | H |
| 347 | H | CN | H | General formula (112) | H | H | H | H | H |
| 348 | H | CN | H | General formula (112) | H | H | H | $CH_3$ | H |
| 349 | H | CN | H | General formula (112) | H | H | H | $CH_3O$ | H |
| 350 | General formula (112) | CN | General formula (112) | F | H | H | H | H | H |
| 351 | General formula (112) | CN | General formula (112) | F | H | H | H | $CH_3$ | H |
| 352 | General formula (112) | CN | General formula (112) | F | H | H | H | $CH_3O$ | H |
| 353 | General formula (112) | CN | General formula (112) | F | General formula (112) | H | H | H | H |
| 354 | General formula (112) | CN | General formula (112) | F | General formula (112) | H | H | $CH_3$ | H |
| 355 | General formula (112) | CN | General formula (112) | F | General formula (112) | H | H | $CH_3O$ | H |
| 356 | General formula (112) | CN | F | General formula (112) | General formula (112) | H | H | H | H |
| 357 | General formula (112) | CN | F | General formula (112) | General formula (112) | H | H | $CH_3$ | H |
| 358 | General formula (112) | CN | F | General formula (112) | General formula (112) | H | H | $CH_3O$ | H |
| 359 | F | CN | General formula (112) | General formula (112) | General formula (112) | H | H | H | H |
| 360 | F | CN | General formula (112) | General formula (112) | General formula (112) | H | H | $CH_3$ | H |
| 361 | F | CN | General formula (112) | General formula (112) | General formula (112) | H | H | $CH_3O$ | H |
| 362 | General formula (112) | CN | General formula (112) | F | F | H | H | H | H |
| 363 | General formula (112) | CN | General formula (112) | F | F | H | H | $CH_3$ | H |
| 364 | General formula (112) | CN | General formula (112) | F | F | H | H | $CH_3O$ | H |
| 365 | General formula (112) | CN | F | General formula (112) | F | H | H | H | H |
| 366 | General formula (112) | CN | F | General formula (112) | F | H | H | $CH_3$ | H |
| 367 | General formula (112) | CN | F | General formula (112) | F | H | H | $CH_3O$ | H |
| 368 | F | CN | General formula (112) | General formula (112) | F | H | H | H | H |
| 369 | F | CN | General formula (112) | General formula (112) | F | H | H | $CH_3$ | H |
| 370 | F | CN | General formula (112) | General formula (112) | F | H | H | $CH_3O$ | H |
| 371 | General formula (112) | CN | F | F | General formula (112) | H | H | H | H |
| 372 | General formula (112) | CN | F | F | General formula (112) | H | H | $CH_3$ | H |
| 373 | General formula (112) | CN | F | F | General formula (112) | H | H | $CH_3O$ | H |
| 374 | F | CN | General formula (112) | F | General formula (112) | H | H | H | H |
| 375 | F | CN | General formula (112) | F | General formula (112) | H | H | $CH_3$ | H |
| 376 | F | CN | General formula (112) | F | General formula (112) | H | H | $CH_3O$ | H |
| 377 | F | CN | F | General formula (112) | General formula (112) | H | H | H | H |
| 378 | F | CN | F | General formula (112) | General formula (112) | H | H | $CH_3$ | H |

TABLE 2-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 379 | F | CN | F | General formula (112) | General formula (112) | H | H | $CH_3O$ | H |
| 380 | General formula (112) | CN | F | F | F | H | H | H | H |
| 381 | General formula (112) | CN | F | F | F | H | H | $CH_3$ | H |
| 382 | General formula (112) | CN | F | F | F | H | H | $CH_3O$ | H |
| 383 | F | CN | General formula (112) | F | F | H | H | H | H |
| 384 | F | CN | General formula (112) | F | F | H | H | $CH_3$ | H |
| 385 | F | CN | General formula (112) | F | F | H | H | $CH_3O$ | H |
| 386 | F | CN | F | General formula (112) | F | H | H | H | H |
| 387 | F | CN | F | General formula (112) | F | H | H | $CH_3$ | H |
| 388 | F | CN | F | General formula (112) | F | H | H | $CH_3O$ | H |
| 389 | General formula (112) | CN | General formula (112) | General formula (112) | OH | H | H | H | H |
| 390 | General formula (112) | CN | General formula (112) | General formula (112) | OH | H | H | $CH_3$ | H |
| 391 | General formula (112) | CN | General formula (112) | General formula (112) | OH | H | H | $CH_3O$ | H |
| 392 | General formula (112) | CN | General formula (112) | OH | General formula (112) | H | H | H | H |
| 393 | General formula (112) | CN | General formula (112) | OH | General formula (112) | H | H | $CH_3$ | H |
| 394 | General formula (112) | CN | General formula (112) | OH | General formula (112) | H | H | $CH_3O$ | H |
| 395 | General formula (112) | CN | General formula (112) | OH | General formula (112) | H | H | $t-C_4H_9$ | H |
| 396 | General formula (112) | CN | General formula (112) | OH | General formula (112) | H | H | Cl | H |
| 397 | General formula (112) | CN | General formula (112) | OH | General formula (112) | H | H | F | H |
| 398 | General formula (112) | CN | OH | General formula (112) | General formula (112) | H | H | H | H |
| 399 | General formula (112) | CN | OH | General formula (112) | General formula (112) | H | H | $CH_3$ | H |
| 400 | General formula (112) | CN | OH | General formula (112) | General formula (112) | H | H | $CH_3O$ | H |
| 401 | OH | CN | General formula (112) | General formula (112) | General formula (112) | H | H | H | H |
| 402 | OH | CN | General formula (112) | General formula (112) | General formula (112) | H | H | $CH_3$ | H |
| 403 | OH | CN | General formula (112) | General formula (112) | General formula (112) | H | H | $CH_3O$ | H |
| 404 | General formula (112) | CN | General formula (112) | OH | OH | H | H | H | H |
| 405 | General formula (112) | CN | General formula (112) | OH | OH | H | H | $CH_3$ | H |
| 406 | General formula (112) | CN | General formula (112) | OH | OH | H | H | $CH_3O$ | H |
| 407 | General formula (112) | CN | OH | General formula (112) | OH | H | H | H | H |
| 408 | General formula (112) | CN | OH | General formula (112) | OH | H | H | $CH_3$ | H |
| 409 | General formula (112) | CN | OH | General formula (112) | OH | H | H | $CH_3O$ | H |
| 410 | OH | CN | General formula (112) | General formula (112) | OH | H | H | H | H |
| 411 | OH | CN | General formula (112) | General formula (112) | OH | H | H | $CH_3$ | H |
| 412 | OH | CN | General formula (112) | General formula (112) | OH | H | H | $CH_3O$ | H |
| 413 | General formula (112) | CN | OH | OH | General formula (112) | H | H | H | H |
| 414 | General formula (112) | CN | OH | OH | General formula (112) | H | H | $CH_3$ | H |
| 415 | General formula (112) | CN | OH | OH | General formula (112) | H | H | $CH_3O$ | H |
| 416 | OH | CN | General formula (112) | OH | General formula (112) | H | H | H | H |

TABLE 2-continued

| Compound No. | General formula (1) | | | | | General formula (112) | | | |
| --- | --- | --- | --- | --- | --- | --- | --- | --- | --- |
| | R¹ | R² | R³ | R⁴ | R⁵ | R³¹, R³⁸ | R³², R³⁷ | R³³, R³⁶ | R³⁴, R³⁵ |
| 417 | OH | CN | General formula (112) | OH | General formula (112) | H | H | CH₃ | H |
| 418 | OH | CN | General formula (112) | OH | General formula (112) | H | H | CH₃O | H |
| 419 | OH | CN | OH | General formula (112) | General formula (112) | H | H | H | H |
| 420 | OH | CN | OH | General formula (112) | General formula (112) | H | H | CH₃ | H |
| 421 | OH | CN | OH | General formula (112) | General formula (112) | H | H | CH₃O | H |
| 422 | General formula (112) | CN | OH | OH | OH | H | H | H | H |
| 423 | General formula (112) | CN | OH | OH | OH | H | H | CH₃ | H |
| 424 | General formula (112) | CN | OH | OH | OH | H | H | CH₃O | H |
| 425 | OH | CN | General formula (112) | OH | OH | H | H | H | H |
| 426 | OH | CN | General formula (112) | OH | OH | H | H | CH₃ | H |
| 427 | OH | CN | General formula (112) | OH | OH | H | H | CH₃O | H |
| 428 | OH | CN | OH | General formula (112) | OH | H | H | H | H |
| 429 | OH | CN | OH | General formula (112) | OH | H | H | CH₃ | H |
| 430 | OH | CN | OH | General formula (112) | OH | H | H | CH₃O | H |
| 431 | OH | CN | OH | OH | General formula (112) | H | H | H | H |
| 432 | OH | CN | OH | OH | General formula (112) | H | H | CH₃ | H |
| 433 | OH | CN | OH | OH | General formula (112) | H | H | CH₃O | H |
| 434 | General formula (112) | CN | General formula (112) | Cl | General formula (112) | H | H | H | H |
| 435 | General formula (112) | CN | General formula (112) | Cl | General formula (112) | H | H | CH₃ | H |
| 436 | General formula (112) | CN | General formula (112) | Cl | General formula (112) | H | H | CH₃O | H |
| 437 | General formula (112) | CN | General formula (112) | Cl | General formula (112) | H | H | t-C₄H₉ | H |
| 438 | General formula (112) | CN | General formula (112) | Cl | General formula (112) | H | H | Cl | H |
| 439 | General formula (112) | CN | General formula (112) | Cl | General formula (112) | H | H | F | H |
| 440 | General formula (112) | CN | General formula (112) | F | General formula (112) | H | H | H | H |
| 441 | General formula (112) | CN | General formula (112) | F | General formula (112) | H | H | CH₃ | H |
| 442 | General formula (112) | CN | General formula (112) | F | General formula (112) | H | H | CH₃O | H |
| 443 | General formula (112) | CN | General formula (112) | F | General formula (112) | H | H | t-C₄H₉ | H |
| 444 | General formula (112) | CN | General formula (112) | F | General formula (112) | H | H | Cl | H |
| 445 | General formula (112) | CN | General formula (112) | F | General formula (112) | H | H | F | H |
| 446 | General formula (112) | CN | General formula (112) | CH₃O | General formula (112) | H | H | H | H |
| 447 | General formula (112) | CN | General formula (112) | CH₃O | General formula (112) | H | H | CH₃ | H |
| 448 | General formula (112) | CN | General formula (112) | CH₃O | General formula (112) | H | H | CH₃O | H |
| 449 | General formula (112) | CN | General formula (112) | CH₃O | General formula (112) | H | H | t-C₄H₉ | H |
| 450 | General formula (112) | CN | General formula (112) | CH₃O | General formula (112) | H | H | Cl | H |
| 451 | General formula (112) | CN | General formula (112) | CH₃O | General formula (112) | H | H | F | H |
| 452 | General formula (112) | CN | General formula (112) | C₂H₅O | General formula (112) | H | H | H | H |
| 453 | General formula (112) | CN | General formula (112) | C₂H₅O | General formula (112) | H | H | CH₃ | H |
| 454 | General formula (112) | CN | General formula (112) | C₂H₅O | General formula (112) | H | H | CH₃O | H |

TABLE 2-continued

| Compound No. | General formula (1) R¹ | R² | R³ | R⁴ | R⁵ | General formula (112) R³¹, R³⁸ | R³², R³⁷ | R³³, R³⁶ | R³⁴, R³⁵ |
|---|---|---|---|---|---|---|---|---|---|
| 455 | General formula (112) | CN | General formula (112) | C₂H₅O | General formula (112) | H | H | t-C₄H₉ | H |
| 456 | General formula (112) | CN | General formula (112) | C₂H₅O | General formula (112) | H | H | Cl | H |
| 457 | General formula (112) | CN | General formula (112) | C₂H₅O | General formula (112) | H | H | F | H |
| 458 | General formula (112) | CN | General formula (112) | C₆H₅O | General formula (112) | H | H | H | H |
| 459 | General formula (112) | CN | General formula (112) | C₆H₅O | General formula (112) | H | H | CH₃ | H |
| 460 | General formula (112) | CN | General formula (112) | C₆H₅O | General formula (112) | H | H | CH₃O | H |
| 461 | General formula (112) | CN | General formula (112) | C₆H₅O | General formula (112) | H | H | t-C₄H₉ | H |
| 462 | General formula (112) | CN | General formula (112) | C₆H₅O | General formula (112) | H | H | Cl | H |
| 463 | General formula (112) | CN | General formula (112) | C₆H₅O | General formula (112) | H | H | F | H |
| 464 | General formula (112) | CN | General formula (112) | Formula (121) | General formula (112) | H | H | H | H |
| 465 | General formula (112) | CN | General formula (112) | Formula (121) | General formula (112) | H | H | CH₃ | H |
| 466 | General formula (112) | CN | General formula (112) | Formula (121) | General formula (112) | H | H | CH₃O | H |
| 467 | General formula (112) | CN | General formula (112) | Formula (121) | General formula (112) | H | H | t-C₄H₉ | H |
| 468 | General formula (112) | CN | General formula (112) | Formula (121) | General formula (112) | H | H | Cl | H |
| 469 | General formula (112) | CN | General formula (112) | Formula (121) | General formula (112) | H | H | F | H |
| 470 | General formula (112) | CN | General formula (112) | Formula (122) | General formula (112) | H | H | H | H |
| 471 | General formula (112) | CN | General formula (112) | Formula (122) | General formula (112) | H | H | CH₃ | H |
| 472 | General formula (112) | CN | General formula (112) | Formula (122) | General formula (112) | H | H | CH₃O | H |
| 473 | General formula (112) | CN | General formula (112) | Formula (122) | General formula (112) | H | H | t-C₄H₉ | H |
| 474 | General formula (112) | CN | General formula (112) | Formula (122) | General formula (112) | H | H | Cl | H |
| 475 | General formula (112) | CN | General formula (112) | Formula (122) | General formula (112) | H | H | F | H |
| 476 | General formula (112) | CN | General formula (112) | Formula (123) | General formula (112) | H | H | H | H |
| 477 | General formula (112) | CN | General formula (112) | Formula (123) | General formula (112) | H | H | CH₃ | H |
| 478 | General formula (112) | CN | General formula (112) | Formula (123) | General formula (112) | H | H | CH₃O | H |
| 479 | General formula (112) | CN | General formula (112) | Formula (123) | General formula (112) | H | H | t-C₄H₉ | H |
| 480 | General formula (112) | CN | General formula (112) | Formula (123) | General formula (112) | H | H | Cl | H |
| 481 | General formula (112) | CN | General formula (112) | Formula (123) | General formula (112) | H | H | F | H |
| 482 | General formula (112) | CN | General formula (112) | Formula (124) | General formula (112) | H | H | H | H |
| 483 | General formula (112) | CN | General formula (112) | Formula (124) | General formula (112) | H | H | CH₃ | H |
| 484 | General formula (112) | CN | General formula (112) | Formula (124) | General formula (112) | H | H | CH₃O | H |
| 485 | General formula (112) | CN | General formula (112) | Formula (124) | General formula (112) | H | H | t-C₄H₉ | H |
| 486 | General formula (112) | CN | General formula (112) | Formula (124) | General formula (112) | H | H | Cl | H |
| 487 | General formula (112) | CN | General formula (112) | Formula (124) | General formula (112) | H | H | F | H |
| 488 | General formula (112) | CN | General formula (112) | General formula (112) | General formula (112) | H | C₆H₅ | H | H |
| 489 | General formula (112) | CN | General formula (112) | General formula (112) | General formula (112) | H | H | C₆H₅ | H |
| 490 | General formula (112) | CN | General formula (112) | General formula (112) | H | H | C₆H₅ | H | H |
| 491 | General formula (112) | CN | General formula (112) | General formula (112) | H | H | H | C₆H₅ | H |
| 492 | General formula (112) | CN | General formula (112) | H | General formula (112) | H | C₆H₅ | H | H |

TABLE 2-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}$, $R^{38}$ | $R^{32}$, $R^{37}$ | $R^{33}$, $R^{36}$ | $R^{34}$, $R^{35}$ |
| 493 | General formula (112) | CN | General formula (112) | H | General formula (112) | H | H | $C_6H_5$ | H |
| 494 | General formula (112) | CN | H | General formula (112) | General formula (112) | H | $C_6H_5$ | H | H |
| 495 | General formula (112) | CN | H | General formula (112) | General formula (112) | H | H | $C_6H_5$ | H |
| 496 | H | CN | General formula (112) | General formula (112) | General formula (112) | H | $C_6H_5$ | H | H |
| 497 | H | CN | General formula (112) | General formula (112) | General formula (112) | H | H | $C_6H_5$ | H |
| 498 | General formula (112) | CN | General formula (112) | H | H | H | $C_6H_5$ | H | H |
| 499 | General formula (112) | CN | General formula (112) | H | H | H | H | $C_6H_5$ | H |
| 500-1 | General formula (112) | CN | H | General formula (112) | H | H | $C_6H_5$ | H | H |
| 500-2 | General formula (112) | CN | H | General formula (112) | H | H | H | $C_6H_5$ | H |
| 500-3 | H | CN | General formula (112) | General formula (112) | H | H | $C_6H_5$ | H | H |
| 500-4 | H | CN | General formula (112) | General formula (112) | H | H | H | $C_6H_5$ | H |
| 500-5 | General formula (112) | CN | H | H | General formula (112) | H | $C_6H_5$ | H | H |
| 500-6 | General formula (112) | CN | H | H | General formula (112) | H | H | $C_6H_5$ | H |
| 500-7 | H | CN | General formula (112) | H | General formula (112) | H | $C_6H_5$ | H | H |
| 500-8 | H | CN | General formula (112) | H | General formula (112) | H | H | $C_6H_5$ | H |
| 500-9 | H | CN | H | General formula (112) | General formula (112) | H | $C_6H_5$ | H | H |
| 500-10 | H | CN | H | General formula (112) | General formula (112) | H | H | $C_6H_5$ | H |
| 500-11 | General formula (112) | CN | H | H | H | H | $C_6H_5$ | H | H |
| 500-12 | General formula (112) | CN | H | H | H | H | H | $C_6H_5$ | H |
| 500-13 | H | CN | General formula (112) | H | H | H | $C_6H_5$ | H | H |
| 500-14 | H | CN | General formula (112) | H | H | H | H | $C_6H_5$ | H |
| 500-15 | H | CN | H | General formula (112) | H | H | $C_6H_5$ | H | H |
| 500-16 | H | CN | H | General formula (112) | H | H | H | $C_6H_5$ | H |
| 500-17 | General formula (112) | CN | General formula (112) | General formula (112) | F | H | H | $C_6H_5$ | H |
| 500-18 | General formula (112) | CN | General formula (112) | F | General formula (112) | H | H | $C_6H_5$ | H |
| 500-19 | General formula (112) | CN | F | General formula (112) | General formula (112) | H | H | $C_6H_5$ | H |
| 500-20 | F | CN | General formula (112) | General formula (112) | General formula (112) | H | H | $C_6H_5$ | H |
| 500-21 | General formula (112) | CN | General formula (112) | F | F | H | H | $C_6H_5$ | H |
| 500-22 | General formula (112) | CN | F | General formula (112) | F | H | H | $C_6H_5$ | H |
| 500-23 | F | CN | General formula (112) | General formula (112) | F | H | H | $C_6H_5$ | H |
| 500-24 | General formula (112) | CN | F | F | General formula (112) | H | H | $C_6H_5$ | H |
| 500-25 | F | CN | General formula (112) | F | General formula (112) | H | H | $C_6H_5$ | H |
| 500-26 | F | CN | F | General formula (112) | General formula (112) | H | H | $C_6H_5$ | H |
| 500-27 | General formula (112) | CN | F | F | F | H | H | $C_6H_5$ | H |
| 500-28 | F | CN | General formula (112) | F | F | H | H | $C_6H_5$ | H |
| 500-29 | F | CN | F | General formula (112) | F | H | H | $C_6H_5$ | H |
| 500-30 | General formula (112) | CN | General formula (112) | General formula (112) | OH | H | H | $C_6H_5$ | H |
| 500-31 | General formula (112) | CN | General formula (112) | OH | General formula (112) | H | H | $C_6H_5$ | H |

TABLE 2-continued

| Compound | General formula (1) | | | | | General formula (112) | | | |
|---|---|---|---|---|---|---|---|---|---|
| No. | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 500-32 | General formula (112) | CN | OH | General formula (112) | General formula (112) | H | H | $C_6H_5$ | H |
| 500-33 | OH | CN | General formula (112) | General formula (112) | General formula (112) | H | H | $C_6H_5$ | H |
| 500-34 | General formula (112) | CN | General formula (112) | OH | OH | H | H | $C_6H_5$ | H |
| 500-35 | General formula (112) | CN | OH | General formula (112) | OH | H | H | $C_6H_5$ | H |
| 500-36 | OH | CN | General formula (112) | General formula (112) | OH | H | H | $C_6H_5$ | H |
| 500-37 | General formula (112) | CN | OH | OH | General formula (112) | H | H | $C_6H_5$ | H |
| 500-38 | OH | CN | General formula (112) | OH | General formula (112) | H | H | $C_6H_5$ | H |
| 500-39 | OH | CN | OH | General formula (112) | General formula (112) | H | H | $C_6H_5$ | H |
| 500-40 | General formula (112) | CN | OH | OH | OH | H | H | $C_6H_5$ | H |
| 500-41 | OH | CN | General formula (112) | OH | OH | H | H | $C_6H_5$ | H |
| 500-42 | OH | CN | OH | General formula (112) | OH | H | H | $C_6H_5$ | H |
| 500-43 | OH | CN | OH | OH | General formula (112) | H | H | $C_6H_5$ | H |
| 500-44 | General formula (112) | CN | General formula (112) | Cl | General formula (112) | H | H | $C_6H_5$ | H |
| 500-45 | General formula (112) | CN | General formula (112) | F | General formula (112) | H | H | $C_6H_5$ | H |
| 500-46 | General formula (112) | CN | General formula (112) | $CH_3O$ | General formula (112) | H | H | $C_6H_5$ | H |
| 500-47 | General formula (112) | CN | General formula (112) | $C_2H_5O$ | General formula (112) | H | H | $C_6H_5$ | H |
| 500-48 | General formula (112) | CN | General formula (112) | $C_6H_5O$ | General formula (112) | H | H | $C_6H_5$ | H |
| 500-49 | General formula (112) | CN | General formula (112) | Formula (121) | General formula (112) | H | H | $C_6H_5$ | H |
| 500-50 | General formula (112) | CN | General formula (112) | Formula (122) | General formula (112) | H | H | $C_6H_5$ | H |
| 500-51 | General formula (112) | CN | General formula (112) | Formula (123) | General formula (112) | H | H | $C_6H_5$ | H |
| 500-52 | General formula (112) | CN | General formula (112) | Formula (124) | General formula (112) | H | H | $C_6H_5$ | H |

TABLE 3

| Compound | General formula (1) | | | | | General formula (112) | | | |
|---|---|---|---|---|---|---|---|---|---|
| No. | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 501 | CN | General formula (112) | General formula (112) | General formula (112) | General formula (112) | H | H | H | H |
| 502 | CN | General formula (112) | General formula (112) | General formula (112) | General formula (112) | H | $CH_3$ | H | H |
| 503 | CN | General formula (112) | General formula (112) | General formula (112) | General formula (112) | H | $CH_3O$ | H | H |
| 504 | CN | General formula (112) | General formula (112) | General formula (112) | General formula (112) | H | H | $CH_3$ | H |
| 505 | CN | General formula (112) | General formula (112) | General formula (112) | General formula (112) | H | H | $CH_3O$ | H |
| 506 | CN | General formula (112) | General formula (112) | General formula (112) | General formula (112) | H | H | $t\text{-}C_4H_9$ | H |
| 507 | CN | General formula (112) | General formula (112) | General formula (112) | General formula (112) | H | H | Cl | H |
| 508 | CN | General formula (112) | General formula (112) | General formula (112) | General formula (112) | H | H | F | H |
| 509 | CN | General formula (112) | General formula (112) | General formula (112) | General formula (112) | H | H | H | $CH_3$ |
| 510 | CN | General formula (112) | General formula (112) | General formula (112) | General formula (112) | H | H | H | $CH_3O$ |
| 511 | CN | General formula (112) | General formula (112) | General formula (112) | H | H | H | H | H |
| 512 | CN | General formula (112) | General formula (112) | General formula (112) | H | H | H | $CH_3$ | H |
| 513 | CN | General formula (112) | General formula (112) | General formula (112) | H | H | H | $CH_3O$ | H |
| 514 | CN | General formula (112) | General formula (112) | H | General formula (112) | H | H | H | H |
| 515 | CN | General formula (112) | General formula (112) | H | General formula (112) | H | H | $CH_3$ | H |
| 516 | CN | General formula (112) | General formula (112) | H | General formula (112) | H | H | $CH_3O$ | H |
| 517 | CN | General formula (112) | General formula (112) | H | H | H | H | H | H |
| 518 | CN | General formula (112) | General formula (112) | H | H | H | H | $CH_3$ | H |
| 519 | CN | General formula (112) | General formula (112) | H | H | H | H | $CH_3O$ | H |
| 520 | CN | General formula (112) | H | General formula (112) | H | H | H | H | H |
| 521 | CN | General formula (112) | H | General formula (112) | H | H | H | $CH_3$ | H |
| 522 | CN | General formula (112) | H | General formula (112) | H | H | H | $CH_3O$ | H |
| 523 | CN | H | General formula (112) | General formula (112) | H | H | H | H | H |
| 524 | CN | H | General formula (112) | General formula (112) | H | H | H | $CH_3$ | H |

TABLE 3-continued

| Compound No. | R$^1$ | R$^2$ | R$^3$ | R$^4$ | R$^5$ | R$^{31}$, R$^{38}$ | R$^{32}$, R$^{37}$ | R$^{33}$, R$^{36}$ | R$^{34}$, R$^{35}$ |
|---|---|---|---|---|---|---|---|---|---|
| 525 | CN | H | General formula (112) | General formula (112) | H | H | H | CH$_3$O | H |
| 526 | CN | General formula (112) | H | H | General formula (112) | H | H | H | H |
| 527 | CN | General formula (112) | H | H | General formula (112) | H | H | CH$_3$ | H |
| 528 | CN | General formula (112) | H | H | General formula (112) | H | H | CH$_3$O | H |
| 529 | CN | General formula (112) | H | H | H | H | H | H | H |
| 530 | CN | General formula (112) | H | H | H | H | H | CH$_3$ | H |
| 531 | CN | General formula (112) | H | H | H | H | H | CH$_3$O | H |
| 532 | CN | H | General formula (112) | H | H | H | H | H | H |
| 533 | CN | H | General formula (112) | H | H | H | H | CH$_3$ | H |
| 534 | CN | H | General formula (112) | H | H | H | H | CH$_3$O | H |
| 535 | CN | General formula (112) | General formula (112) | General formula (112) | F | H | H | H | H |
| 536 | CN | General formula (112) | General formula (112) | General formula (112) | F | H | H | CH$_3$ | H |
| 537 | CN | General formula (112) | General formula (112) | General formula (112) | F | H | H | CH$_3$O | H |
| 538 | CN | General formula (112) | General formula (112) | F | General formula (112) | H | H | H | H |
| 539 | CN | General formula (112) | General formula (112) | F | General formula (112) | H | H | CH$_3$ | H |
| 540 | CN | General formula (112) | General formula (112) | F | General formula (112) | H | H | CH$_3$O | H |
| 541 | CN | General formula (112) | General formula (112) | F | F | H | H | H | H |
| 542 | CN | General formula (112) | General formula (112) | F | F | H | H | CH$_3$ | H |
| 543 | CN | General formula (112) | General formula (112) | F | F | H | H | CH$_3$O | H |
| 544 | CN | General formula (112) | F | General formula (112) | F | H | H | H | H |
| 545 | CN | General formula (112) | F | General formula (112) | F | H | H | CH$_3$ | H |
| 546 | CN | General formula (112) | F | General formula (112) | F | H | H | CH$_3$O | H |
| 547 | CN | F | General formula (112) | General formula (112) | F | H | H | H | H |
| 548 | CN | F | General formula (112) | General formula (112) | F | H | H | CH$_3$ | H |
| 549 | CN | F | General formula (112) | General formula (112) | F | H | H | CH$_3$O | H |
| 550 | CN | General formula (112) | F | F | General formula (112) | H | H | H | H |
| 551 | CN | General formula (112) | F | F | General formula (112) | H | H | CH$_3$ | H |
| 552 | CN | General formula (112) | F | F | General formula (112) | H | H | CH$_3$O | H |
| 553 | CN | General formula (112) | F | F | F | H | H | H | H |
| 554 | CN | General formula (112) | F | F | F | H | H | CH$_3$ | H |
| 555 | CN | General formula (112) | F | F | F | H | H | CH$_3$O | H |
| 556 | CN | F | General formula (112) | F | F | H | H | H | H |
| 557 | CN | F | General formula (112) | F | F | H | H | CH$_3$ | H |
| 558 | CN | F | General formula (112) | F | F | H | H | CH$_3$O | H |
| 559 | CN | General formula (112) | General formula (112) | General formula (112) | OH | H | H | H | H |
| 560 | CN | General formula (112) | General formula (112) | General formula (112) | OH | H | H | CH$_3$ | H |
| 561 | CN | General formula (112) | General formula (112) | General formula (112) | OH | H | H | CH$_3$O | H |
| 562 | CN | General formula (112) | General formula (112) | OH | General formula (112) | H | H | H | H |
| 563 | CN | General formula (112) | General formula (112) | OH | General formula (112) | H | H | CH$_3$ | H |
| 564 | CN | General formula (112) | General formula (112) | OH | General formula (112) | H | H | CH$_3$O | H |
| 565 | CN | General formula (112) | General formula (112) | OH | General formula (112) | H | H | Cl | H |
| 566 | CN | General formula (112) | General formula (112) | OH | General formula (112) | H | H | F | H |
| 567 | CN | General formula (112) | General formula (112) | OH | OH | H | H | H | H |
| 568 | CN | General formula (112) | General formula (112) | OH | OH | H | H | CH$_3$ | H |
| 569 | CN | General formula (112) | General formula (112) | OH | OH | H | H | CH$_3$O | H |
| 570 | CN | General formula (112) | OH | General formula (112) | OH | H | H | H | H |
| 571 | CN | General formula (112) | OH | General formula (112) | OH | H | H | CH$_3$ | H |
| 572 | CN | General formula (112) | OH | General formula (112) | OH | H | H | CH$_3$O | H |
| 573 | CN | OH | General formula (112) | General formula (112) | OH | H | H | H | H |
| 574 | CN | OH | General formula (112) | General formula (112) | OH | H | H | CH$_3$ | H |
| 575 | CN | OH | General formula (112) | General formula (112) | OH | H | H | CH$_3$O | H |
| 576 | CN | General formula (112) | OH | OH | General formula (112) | H | H | H | H |
| 577 | CN | General formula (112) | OH | OH | General formula (112) | H | H | CH$_3$ | H |
| 578 | CN | General formula (112) | OH | OH | General formula (112) | H | H | CH$_3$O | H |
| 579 | CN | General formula (112) | OH | OH | OH | H | H | H | H |
| 580 | CN | General formula (112) | OH | OH | OH | H | H | CH$_3$ | H |
| 581 | CN | General formula (112) | OH | OH | OH | H | H | CH$_3$O | H |
| 582 | CN | OH | General formula (112) | OH | OH | H | H | H | H |
| 583 | CN | OH | General formula (112) | OH | OH | H | H | CH$_3$ | H |
| 584 | CN | OH | General formula (112) | OH | OH | H | H | CH$_3$O | H |
| 585 | CN | General formula (112) | General formula (112) | Cl | General formula (112) | H | H | H | H |
| 586 | CN | General formula (112) | General formula (112) | Cl | General formula (112) | H | H | CH$_3$ | H |
| 587 | CN | General formula (112) | General formula (112) | Cl | General formula (112) | H | H | CH$_3$O | H |
| 588 | CN | General formula (112) | General formula (112) | Cl | General formula (112) | H | H | t-C$_4$H$_9$ | H |
| 589 | CN | General formula (112) | General formula (112) | Cl | General formula (112) | H | H | Cl | H |
| 590 | CN | General formula (112) | General formula (112) | Cl | General formula (112) | H | H | F | H |
| 591 | CN | General formula (112) | General formula (112) | F | General formula (112) | H | H | H | H |
| 592 | CN | General formula (112) | General formula (112) | F | General formula (112) | H | H | CH$_3$ | H |
| 593 | CN | General formula (112) | General formula (112) | F | General formula (112) | H | H | CH$_3$O | H |
| 594 | CN | General formula (112) | General formula (112) | F | General formula (112) | H | H | t-C$_4$H$_9$ | H |
| 595 | CN | General formula (112) | General formula (112) | F | General formula (112) | H | H | Cl | H |
| 596 | CN | General formula (112) | General formula (112) | F | General formula (112) | H | H | F | H |
| 597 | CN | General formula (112) | General formula (112) | CH$_3$O | General formula (112) | H | H | H | H |
| 598 | CN | General formula (112) | General formula (112) | CH$_3$O | General formula (112) | H | H | CH$_3$ | H |
| 599 | CN | General formula (112) | General formula (112) | CH$_3$O | General formula (112) | H | H | CH$_3$O | H |
| 600 | CN | General formula (112) | General formula (112) | CH$_3$O | General formula (112) | H | H | t-C$_4$H$_9$ | H |

TABLE 3-continued

| Compound No. | R¹ | R² | R³ | R⁴ | R⁵ | R³¹, R³⁸ | R³², R³⁷ | R³³, R³⁶ | R³⁴, R³⁵ |
|---|---|---|---|---|---|---|---|---|---|
| 601 | CN | General formula (112) | General formula (112) | CH₃O | General formula (112) | H | H | Cl | H |
| 602 | CN | General formula (112) | General formula (112) | CH₃O | General formula (112) | H | H | F | H |
| 603 | CN | General formula (112) | General formula (112) | C₂H₅O | General formula (112) | H | H | H | H |
| 604 | CN | General formula (112) | General formula (112) | C₂H₅O | General formula (112) | H | H | CH₃ | H |
| 605 | CN | General formula (112) | General formula (112) | C₂H₅O | General formula (112) | H | H | CH₃O | H |
| 606 | CN | General formula (112) | General formula (112) | C₃H₅O | General formula (112) | H | H | t-C₄H₉ | H |
| 607 | CN | General formula (112) | General formula (112) | C₂H₅O | General formula (112) | H | H | Cl | H |
| 608 | CN | General formula (112) | General formula (112) | C₂H₅O | General formula (112) | H | H | F | H |
| 609 | CN | General formula (112) | General formula (112) | C₆H₅O | General formula (112) | H | H | H | H |
| 610 | CN | General formula (112) | General formula (112) | C₆H₅O | General formula (112) | H | H | CH₃ | H |
| 611 | CN | General formula (112) | General formula (112) | C₆H₅O | General formula (112) | H | H | CH₃O | H |
| 612 | CN | General formula (112) | General formula (112) | C₆H₅O | General formula (112) | H | H | t-C₄H₉ | H |
| 613 | CN | General formula (112) | General formula (112) | C₆H₅O | General formula (112) | H | H | Cl | H |
| 614 | CN | General formula (112) | General formula (112) | C₆H₅O | General formula (112) | H | H | F | H |
| 615 | CN | General formula (112) | General formula (112) | Formula (121) | General formula (112) | H | H | H | H |
| 616 | CN | General formula (112) | General formula (112) | Formula (121) | General formula (112) | H | H | CH₃ | H |
| 617 | CN | General formula (112) | General formula (112) | Formula (121) | General formula (112) | H | H | CH₃O | H |
| 618 | CN | General formula (112) | General formula (112) | Formula (121) | General formula (112) | H | H | t-C₄H₉ | H |
| 619 | CN | General formula (112) | General formula (112) | Formula (121) | General formula (112) | H | H | Cl | H |
| 620 | CN | General formula (112) | General formula (112) | Formula (121) | General formula (112) | H | H | F | H |
| 621 | CN | General formula (112) | General formula (112) | Formula (122) | General formula (112) | H | H | H | H |
| 622 | CN | General formula (112) | General formula (112) | Formula (122) | General formula (112) | H | H | CH₃ | H |
| 623 | CN | General formula (112) | General formula (112) | Formula (122) | General formula (112) | H | H | CH₃O | H |
| 624 | CN | General formula (112) | General formula (112) | Formula (122) | General formula (112) | H | H | t-C₄H₉ | H |
| 625 | CN | General formula (112) | General formula (112) | Formula (122) | General formula (112) | H | H | Cl | H |
| 626 | CN | General formula (112) | General formula (112) | Formula (122) | General formula (112) | H | H | F | H |
| 627 | CN | General formula (112) | General formula (112) | Formula (123) | General formula (112) | H | H | H | H |
| 628 | CN | General formula (112) | General formula (112) | Formula (123) | General formula (112) | H | H | CH₃ | H |
| 629 | CN | General formula (112) | General formula (112) | Formula (123) | General formula (112) | H | H | CH₃O | H |
| 630 | CN | General formula (112) | General formula (112) | Formula (123) | General formula (112) | H | H | t-C₄H₉ | H |
| 631 | CN | General formula (112) | General formula (112) | Formula (123) | General formula (112) | H | H | Cl | H |
| 632 | CN | General formula (112) | General formula (112) | Formula (123) | General formula (112) | H | H | F | H |
| 633 | CN | General formula (112) | General formula (112) | Formula (124) | General formula (112) | H | H | H | H |
| 634 | CN | General formula (112) | General formula (112) | Formula (124) | General formula (112) | H | H | CH₃ | H |
| 635 | CN | General formula (112) | General formula (112) | Formula (124) | General formula (112) | H | H | CH₃O | H |
| 636 | CN | General formula (112) | General formula (112) | Formula (124) | General formula (112) | H | H | t-C₄H₉ | H |
| 637 | CN | General formula (112) | General formula (112) | Formula (124) | General formula (112) | H | H | Cl | H |
| 638 | CN | General formula (112) | General formula (112) | Formula (124) | General formula (112) | H | H | F | H |
| 639 | CN | General formula (112) | General formula (112) | General formula (112) | General formula (112) | H | C₆H₅ | H | H |
| 640 | CN | General formula (112) | General formula (112) | General formula (112) | General formula (112) | H | H | C₆H₅ | H |
| 641 | CN | General formula (112) | General formula (112) | General formula (112) | H | H | C₆H₅ | H | H |
| 642 | CN | General formula (112) | General formula (112) | General formula (112) | H | H | H | C₆H₅ | H |
| 643 | CN | General formula (112) | General formula (112) | H | General formula (112) | H | C₆H₅ | H | H |
| 644 | CN | General formula (112) | General formula (112) | H | General formula (112) | H | H | C₆H₅ | H |
| 645 | CN | General formula (112) | General formula (112) | H | H | H | C₆H₅ | H | H |
| 646 | CN | General formula (112) | General formula (112) | H | H | H | H | C₆H₅ | H |
| 647 | CN | General formula (112) | H | General formula (112) | H | H | C₆H₅ | H | H |
| 648 | CN | General formula (112) | H | General formula (112) | H | H | H | C₆H₅ | H |
| 649 | CN | H | General formula (112) | General formula (112) | H | H | C₆H₅ | H | H |
| 650 | CN | H | General formula (112) | General formula (112) | H | H | H | C₆H₅ | H |
| 651 | CN | H | H | General formula (112) | General formula (112) | H | C₆H₅ | H | H |
| 652 | CN | H | H | General formula (112) | General formula (112) | H | H | C₆H₅ | H |
| 653 | CN | General formula (112) | H | H | H | H | C₆H₅ | H | H |
| 654 | CN | General formula (112) | H | H | H | H | H | C₆H₅ | H |
| 655 | CN | H | General formula (112) | H | H | H | C₆H₅ | H | H |
| 656 | CN | H | General formula (112) | H | H | H | H | C₆H₅ | H |
| 657 | CN | General formula (112) | General formula (112) | General formula (112) | F | H | H | C₆H₅ | H |
| 658 | CN | General formula (112) | General formula (112) | F | General formula (112) | H | H | C₆H₅ | H |
| 659 | CN | General formula (112) | F | General formula (112) | F | H | H | C₆H₅ | H |
| 660 | CN | General formula (112) | F | General formula (112) | F | H | H | C₆H₅ | H |
| 661 | CN | F | General formula (112) | General formula (112) | F | H | H | C₆H₅ | H |
| 662 | CN | F | F | General formula (112) | General formula (112) | H | H | C₆H₅ | H |
| 663 | CN | General formula (112) | F | F | F | H | H | C₆H₅ | H |
| 664 | CN | F | F | F | F | H | H | C₆H₅ | H |
| 665 | CN | General formula (112) | General formula (112) | General formula (112) | OH | H | H | C₆H₅ | H |
| 666 | CN | General formula (112) | General formula (112) | OH | General formula (112) | H | H | C₆H₅ | H |
| 667 | CN | General formula (112) | General formula (112) | OH | OH | H | H | C₆H₅ | H |
| 668 | CN | General formula (112) | OH | General formula (112) | OH | H | H | C₆H₅ | H |
| 669 | CN | OH | General formula (112) | General formula (112) | OH | H | H | C₆H₅ | H |
| 670 | CN | OH | OH | General formula (112) | General formula (112) | H | H | C₆H₅ | H |
| 671 | CN | General formula (112) | OH | OH | OH | H | H | C₆H₅ | H |
| 672 | CN | OH | OH | OH | OH | H | H | C₆H₅ | H |
| 673 | CN | General formula (112) | General formula (112) | Cl | General formula (112) | H | H | C₆H₅ | H |
| 674 | CN | General formula (112) | General formula (112) | F | General formula (112) | H | H | C₆H₅ | H |
| 675 | CN | General formula (112) | General formula (112) | CH₃O | General formula (112) | H | H | C₆H₅ | H |
| 676 | CN | General formula (112) | General formula (112) | C₂H₅O | General formula (112) | H | H | C₆H₅ | H |

TABLE 3-continued

| Compound No. | General formula (1) | | | | | General formula (112) | | | |
|---|---|---|---|---|---|---|---|---|---|
| | $R^1$ | $R^2$ | $R^3$ | $R^4$ | $R^5$ | $R^{31}, R^{38}$ | $R^{32}, R^{37}$ | $R^{33}, R^{36}$ | $R^{34}, R^{35}$ |
| 677 | CN | General formula (112) | General formula (112) | $C_6H_5O$ | General formula (112) | H | H | $C_6H_5$ | H |
| 678 | CN | General formula (112) | General formula (112) | Formula (121) | General formula (112) | H | H | $C_6H_5$ | H |
| 679 | CN | General formula (112) | General formula (112) | Formula (122) | General formula (112) | H | H | $C_6H_5$ | H |
| 680 | CN | General formula (112) | General formula (112) | Formula (123) | General formula (112) | H | H | $C_6H_5$ | H |
| 681 | CN | General formula (112) | General formula (112) | Formula (124) | General formula (112) | H | H | $C_6H_5$ | H |

TABLE 4

| Compound No. | General formula (1) | | | | | General formula (113) | | | | | |
|---|---|---|---|---|---|---|---|---|---|---|---|
| | R¹ | R² | R³ | R⁴ | R⁵ | R⁴¹ | R⁴² | R⁴³ | R⁴⁴ | R⁴⁵ | R⁴⁶ |
| 701 | General formula (113) | General formula (113) | CN | General formula (113) | General formula (113) | H | H | H | H | H | H |
| 702 | General formula (113) | General formula (113) | CN | General formula (113) | General formula (113) | H | CH₃ | H | H | H | H |
| 703 | General formula (113) | General formula (113) | CN | General formula (113) | General formula (113) | H | CH₃O | H | H | H | H |
| 704 | General formula (113) | General formula (113) | CN | General formula (113) | General formula (113) | H | H | CH₃ | H | H | H |
| 705 | General formula (113) | General formula (113) | CN | General formula (113) | General formula (113) | H | H | CH₃O | H | H | H |
| 706 | General formula (113) | General formula (113) | CN | General formula (113) | General formula (113) | H | H | t-C₄H₉ | H | H | H |
| 707 | General formula (113) | General formula (113) | CN | General formula (113) | General formula (113) | H | H | Cl | H | H | H |
| 708 | General formula (113) | General formula (113) | CN | General formula (113) | General formula (113) | H | H | F | H | H | H |
| 709 | General formula (113) | General formula (113) | CN | General formula (113) | General formula (113) | H | H | H | CH₃ | H | H |
| 710 | General formula (113) | General formula (113) | CN | General formula (113) | General formula (113) | H | H | H | CH₃O | H | H |
| 711 | General formula (113) | General formula (113) | CN | General formula (113) | General formula (113) | H | H | H | H | CH₃ | H |
| 712 | General formula (113) | General formula (113) | CN | General formula (113) | General formula (113) | H | H | H | H | CH₃O | H |
| 713 | General formula (113) | General formula (113) | CN | General formula (113) | General formula (113) | H | H | H | H | t-C₄H₉ | H |
| 714 | General formula (113) | General formula (113) | CN | General formula (113) | General formula (113) | H | H | H | H | Cl | H |
| 715 | General formula (113) | General formula (113) | CN | General formula (113) | General formula (113) | H | H | H | H | F | H |
| 716 | General formula (113) | General formula (113) | CN | General formula (113) | General formula (113) | H | H | H | H | C₆H₅ | H |
| 717 | General formula (113) | General formula (113) | CN | General formula (113) | General formula (113) | H | H | H | H | p-CH₃C₆H₄ | H |
| 718 | General formula (113) | General formula (113) | CN | General formula (113) | General formula (113) | H | H | H | H | 2,4,6-(CH₃)₃C₆H₂ | H |
| 719 | General formula (113) | General formula (113) | CN | General formula (113) | General formula (113) | H | H | H | H | p-CH₃OC₆H₄ | H |
| 720 | General formula (113) | General formula (113) | CN | General formula (113) | General formula (113) | H | H | H | H | p-(CH₃)₂NC₆H₄ | H |
| 721 | General formula (113) | General formula (113) | CN | General formula (113) | General formula (113) | H | H | H | H | p-FC₆H₄ | H |
| 722 | General formula (113) | General formula (113) | CN | General formula (113) | General formula (113) | H | H | H | H | p-CNC₆H₄ | H |
| 723 | General formula (113) | General formula (113) | CN | General formula (113) | General formula (113) | H | H | H | H | H | CH₃ |
| 724 | General formula (113) | General formula (113) | CN | General formula (113) | General formula (113) | H | H | H | H | H | CH₃O |
| 725 | General formula (113) | General formula (113) | CN | General formula (113) | General formula (113) | H | H | H | H | H | t-C₄H₉ |
| 726 | General formula (113) | General formula (113) | CN | General formula (113) | General formula (113) | H | H | H | H | H | Cl |
| 727 | General formula (113) | General formula (113) | CN | General formula (113) | General formula (113) | H | H | H | H | H | F |
| 728 | General formula (113) | General formula (113) | CN | General formula (113) | General formula (113) | H | H | H | H | H | C₆H₅ |
| 729 | General formula (113) | General formula (113) | CN | General formula (113) | General formula (113) | H | H | H | H | H | p-CH₃C₆H₄ |
| 730 | General formula (113) | General formula (113) | CN | General formula (113) | General formula (113) | H | H | H | H | H | 2,4,6-(CH₃)₃C₆H₂ |
| 731 | General formula (113) | General formula (113) | CN | General formula (113) | General formula (113) | H | H | H | H | H | p-CH₃OC₆H₄ |
| 732 | General formula (113) | General formula (113) | CN | General formula (113) | General formula (113) | H | H | H | H | H | p-(CH₃)₂NC₆H₄ |
| 733 | General formula (113) | General formula (113) | CN | General formula (113) | General formula (113) | H | H | H | H | H | p-FC₆H₄ |
| 734 | General formula (113) | General formula (113) | CN | General formula (113) | General formula (113) | H | H | H | H | H | p-CNC₆H₄ |
| 735 | General formula (113) | General formula (113) | CN | General formula (113) | General formula (113) | H | H | H | H | H | H |
| 736 | General formula (113) | General formula (113) | CN | General formula (113) | General formula (113) | H | H | H | H | H | H |
| 737 | General formula (113) | General formula (113) | CN | H | H | H | H | H | H | H | H |
| 738 | General formula (113) | General formula (113) | CN | H | H | H | H | H | H | H | H |
| 739 | H | H | CN | H | H | H | H | H | H | H | H |
| 740 | General formula (113) | General formula (113) | CN | General formula (113) | H | H | H | H | H | H | H |
| 741 | General formula (113) | H | CN | General formula (113) | H | H | H | H | H | H | H |
| 742 | General formula (113) | H | CN | General formula (113) | F | H | H | H | H | H | H |
| 743 | General formula (113) | F | CN | F | F | H | H | H | H | H | H |
| 744 | F | General formula (113) | CN | General formula (113) | F | H | H | H | H | H | H |
| 745 | General formula (113) | F | CN | F | F | H | H | H | H | H | H |
| 746 | General formula (113) | F | CN | General formula (113) | F | H | H | H | H | H | H |
| 747 | General formula (113) | General formula (113) | CN | General formula (113) | OH | H | H | H | H | H | H |

TABLE 4-continued

| Compound No. | General formula (1) | | | | General formula (113) | | | | | |
|---|---|---|---|---|---|---|---|---|---|---|
| | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 748 | General formula (113) | General formula (113) | CN | OH | General formula (113) | H | H | H | H | H | H |
| 749 | General formula (113) | General formula (113) | CN | OH | OH | H | H | H | H | H | H |
| 750 | General formula (113) | OH | CN | General formula (113) | OH | H | H | H | H | H | H |
| 751 | OH | General formula (113) | CN | General formula (113) | OH | H | H | H | H | H | H |
| 752 | General formula (113) | OH | CN | OH | OH | H | H | H | H | H | H |
| 753 | General formula (113) | General formula (113) | CN | Cl | General formula (113) | H | H | H | H | H | H |
| 754 | General formula (113) | General formula (113) | CN | Cl | General formula (113) | H | H | $CH_3$ | H | H | H |
| 755 | General formula (113) | General formula (113) | CN | Cl | General formula (113) | H | H | $CH_3O$ | H | H | H |
| 756 | General formula (113) | General formula (113) | CN | Cl | General formula (113) | H | H | $t-C_4H_9$ | H | H | H |
| 757 | General formula (113) | General formula (113) | CN | Cl | General formula (113) | H | H | Cl | H | H | H |
| 758 | General formula (113) | General formula (113) | CN | F | General formula (113) | H | H | F | H | H | H |
| 759 | General formula (113) | General formula (113) | CN | F | General formula (113) | H | H | H | H | H | H |
| 760 | General formula (113) | General formula (113) | CN | F | General formula (113) | H | H | $CH_3$ | H | H | H |
| 761 | General formula (113) | General formula (113) | CN | F | General formula (113) | H | H | $CH_3O$ | H | H | H |
| 762 | General formula (113) | General formula (113) | CN | F | General formula (113) | H | H | $t-C_4H_9$ | H | H | H |
| 763 | General formula (113) | General formula (113) | CN | F | General formula (113) | H | H | Cl | H | H | H |
| 764 | General formula (113) | General formula (113) | CN | F | General formula (113) | H | H | F | H | H | H |
| 765 | General formula (113) | General formula (113) | CN | $CH_3O$ | General formula (113) | H | H | H | H | H | H |
| 766 | General formula (113) | General formula (113) | CN | $CH_3O$ | General formula (113) | H | H | $CH_3$ | H | H | H |
| 767 | General formula (113) | General formula (113) | CN | $CH_3O$ | General formula (113) | H | H | $CH_3O$ | H | H | H |
| 768 | General formula (113) | General formula (113) | CN | $CH_3O$ | General formula (113) | H | H | $t-C_4H_9$ | H | H | H |
| 769 | General formula (113) | General formula (113) | CN | $CH_3O$ | General formula (113) | H | H | Cl | H | H | H |
| 770 | General formula (113) | General formula (113) | CN | $CH_3O$ | General formula (113) | H | H | F | H | H | H |
| 771 | General formula (113) | General formula (113) | CN | $C_2H_5O$ | General formula (113) | H | H | H | H | H | H |
| 772 | General formula (113) | General formula (113) | CN | $C_2H_5O$ | General formula (113) | H | H | $CH_3$ | H | H | H |
| 773 | General formula (113) | General formula (113) | CN | $C_2H_5O$ | General formula (113) | H | H | $CH_3O$ | H | H | H |
| 774 | General formula (113) | General formula (113) | CN | $C_2H_5O$ | General formula (113) | H | H | $t-C_4H_9$ | H | H | H |
| 775 | General formula (113) | General formula (113) | CN | $C_2H_5O$ | General formula (113) | H | H | Cl | H | H | H |
| 776 | General formula (113) | General formula (113) | CN | $C_2H_5O$ | General formula (113) | H | H | F | H | H | H |
| 777 | General formula (113) | General formula (113) | CN | $C_6H_5O$ | General formula (113) | H | H | H | H | H | H |
| 778 | General formula (113) | General formula (113) | CN | $C_6H_5O$ | General formula (113) | H | H | $CH_3$ | H | H | H |
| 779 | General formula (113) | General formula (113) | CN | $C_6H_5O$ | General formula (113) | H | H | $CH_3O$ | H | H | H |
| 780 | General formula (113) | General formula (113) | CN | $C_6H_5O$ | General formula (113) | H | H | $t-C_4H_9$ | H | H | H |
| 781 | General formula (113) | General formula (113) | CN | $C_6H_5O$ | General formula (113) | H | H | Cl | H | H | H |
| 782 | General formula (113) | General formula (113) | CN | $C_6H_5O$ | General formula (113) | H | H | F | H | H | H |
| 783 | General formula (113) | General formula (113) | CN | Formula (121) | General formula (113) | H | H | H | H | H | H |
| 784 | General formula (113) | General formula (113) | CN | Formula (121) | General formula (113) | H | H | $CH_3$ | H | H | H |
| 785 | General formula (113) | General formula (113) | CN | Formula (121) | General formula (113) | H | H | $CH_3O$ | H | H | H |
| 786 | General formula (113) | General formula (113) | CN | Formula (121) | General formula (113) | H | H | $t-C_4H_9$ | H | H | H |
| 787 | General formula (113) | General formula (113) | CN | Formula (121) | General formula (113) | H | H | Cl | H | H | H |
| 788 | General formula (113) | General formula (113) | CN | Formula (121) | General formula (113) | H | H | F | H | H | H |
| 789 | General formula (113) | General formula (113) | CN | Formula (122) | General formula (113) | H | H | H | H | H | H |
| 790 | General formula (113) | General formula (113) | CN | Formula (122) | General formula (113) | H | H | $CH_3$ | H | H | H |
| 791 | General formula (113) | General formula (113) | CN | Formula (122) | General formula (113) | H | H | $CH_3O$ | H | H | H |
| 792 | General formula (113) | General formula (113) | CN | Formula (122) | General formula (113) | H | H | $t-C_4H_9$ | H | H | H |
| 793 | General formula (113) | General formula (113) | CN | Formula (122) | General formula (113) | H | H | Cl | H | H | H |
| 794 | General formula (113) | General formula (113) | CN | Formula (122) | General formula (113) | H | H | F | H | H | H |
| 795 | General formula (113) | General formula (113) | CN | Formula (123) | General formula (113) | H | H | H | H | H | H |
| 796 | General formula (113) | General formula (113) | CN | Formula (123) | General formula (113) | H | H | $CH_3$ | H | H | H |

TABLE 4-continued

| | General formula (1) | | | | General formula (113) | | | | | | |
|---|---|---|---|---|---|---|---|---|---|---|---|
| Compound No. | $R^1$ | $R^2$ | $R^3$ | $R^4$ | $R^5$ | $R^{41}$ | $R^{42}$ | $R^{43}$ | $R^{44}$ | $R^{45}$ | $R^{46}$ |
| 797 | General formula (113) | General formula (113) | CN | Formula (123) | General formula (113) | H | H | CH$_3$O | H | H | H |
| 798 | General formula (113) | General formula (113) | CN | Formula (123) | General formula (113) | H | H | t-C$_4$H$_9$ | H | H | H |
| 799 | General formula (113) | General formula (113) | CN | Formula (123) | General formula (113) | H | H | Cl | H | H | H |
| 800 | General formula (113) | General formula (113) | CN | Formula (123) | General formula (113) | H | H | F | H | H | H |
| 801 | General formula (113) | General formula (113) | CN | Formula (124) | General formula (113) | H | H | H | H | H | H |
| 802 | General formula (113) | General formula (113) | CN | Formula (124) | General formula (113) | H | H | CH$_3$ | H | H | H |
| 803 | General formula (113) | General formula (113) | CN | Formula (124) | General formula (113) | H | H | CH$_3$O | H | H | H |
| 804 | General formula (113) | General formula (113) | CN | Formula (124) | General formula (113) | H | H | t-C$_4$H$_9$ | H | H | H |
| 805 | General formula (113) | General formula (113) | CN | Formula (124) | General formula (113) | H | H | Cl | H | H | H |
| 806 | General formula (113) | General formula (113) | CN | Formula (124) | General formula (113) | H | H | F | H | H | H |

TABLE 5

| Compound No. | General formula (1) | | | | | General formula (114) | | | | | | | | | | |
|---|---|---|---|---|---|---|---|---|---|---|---|---|---|---|---|---|
| | $R^1$ | $R^2$ | $R^3$ | $R^4$ | $R^5$ | $R^{52}$ | $R^{53}$ | $R^{54}$ | $R^{55}$ | $R^{57}$ | $R^{59}$ | $R^{61}$ | $R^{51}, R^{56}, R^{58}, R^{60}, R^{62}$ |
| 901 | General formula (114) | General formula (114) | CN | General formula (114) | General formula (114) | H | H | H | H | H | H | H | H |
| 902 | General formula (114) | General formula (114) | CN | General formula (114) | General formula (114) | $CH_3$ | H | H | H | H | H | H | H |
| 903 | General formula (114) | General formula (114) | CN | General formula (114) | General formula (114) | $CH_3O$ | H | H | H | H | H | H | H |
| 904 | General formula (114) | General formula (114) | CN | General formula (114) | General formula (114) | H | $CH_3$ | H | H | H | H | H | H |
| 905 | General formula (114) | General formula (114) | CN | General formula (114) | General formula (114) | H | $CH_3O$ | H | H | H | H | H | H |
| 906 | General formula (114) | General formula (114) | CN | General formula (114) | General formula (114) | H | $t-C_4H_9$ | H | H | H | H | H | H |
| 907 | General formula (114) | General formula (114) | CN | General formula (114) | General formula (114) | H | Cl | H | H | H | H | H | H |
| 908 | General formula (114) | General formula (114) | CN | General formula (114) | General formula (114) | H | F | H | H | H | H | H | H |
| 909 | General formula (114) | General formula (114) | CN | General formula (114) | General formula (114) | H | H | $CH_3$ | H | H | H | H | H |
| 910 | General formula (114) | General formula (114) | CN | General formula (114) | General formula (114) | H | H | $CH_3O$ | H | H | H | H | H |
| 911 | General formula (114) | General formula (114) | CN | General formula (114) | General formula (114) | H | H | H | $CH_3$ | H | H | H | H |
| 912 | General formula (114) | General formula (114) | CN | General formula (114) | General formula (114) | H | H | H | $CH_3O$ | H | H | H | H |
| 913 | General formula (114) | General formula (114) | CN | General formula (114) | General formula (114) | H | H | H | H | $CH_3$ | H | H | H |
| 914 | General formula (114) | General formula (114) | CN | General formula (114) | General formula (114) | H | H | H | H | $CH_3O$ | H | H | H |
| 915 | General formula (114) | General formula (114) | CN | General formula (114) | General formula (114) | H | H | H | H | H | $CH_3$ | H | H |
| 916 | General formula (114) | General formula (114) | CN | General formula (114) | General formula (114) | H | H | H | H | H | $CH_3O$ | H | H |
| 917 | General formula (114) | General formula (114) | CN | General formula (114) | General formula (114) | H | H | H | H | H | H | $CH_3$ | H |
| 918 | General formula (114) | General formula (114) | CN | General formula (114) | General formula (114) | H | H | H | H | H | H | $CH_3O$ | H |
| 919 | General formula (114) | General formula (114) | CN | H | H | H | H | H | H | H | H | H | H |
| 920 | General formula (114) | General formula (114) | CN | H | General formula (114) | H | H | H | H | H | H | H | H |
| 921 | H | General formula (114) | CN | General formula (114) | H | H | H | H | H | H | H | H | H |
| 922 | General formula (114) | H | CN | General formula (114) | H | H | H | H | H | H | H | H | H |
| 923 | H | H | CN | H | H | H | H | H | H | H | H | H | H |
| 924 | General formula (114) | General formula (114) | CN | H | H | H | H | H | H | H | H | H | H |
| 925 | General formula (114) | General formula (114) | CN | F | F | H | H | H | H | H | H | H | H |
| 926 | General formula (114) | F | CN | F | General formula (114) | H | H | H | H | H | H | H | H |
| 927 | General formula (114) | F | CN | F | F | H | H | H | H | H | H | H | H |
| 928 | F | General formula (114) | CN | F | F | H | H | H | H | H | H | H | H |
| 929 | F | General formula (114) | CN | F | F | H | H | H | H | H | H | H | H |
| 930 | General formula (114) | General formula (114) | CN | OH | OH | H | H | H | H | H | H | H | H |
| 931 | General formula (114) | General formula (114) | CN | OH | General formula (114) | H | H | H | H | H | H | H | H |
| 932 | General formula (114) | OH | CN | OH | OH | H | H | H | H | H | H | H | H |
| 933 | General formula (114) | OH | CN | OH | OH | H | H | H | H | H | H | H | H |
| 934 | OH | General formula (114) | CN | OH | OH | H | H | H | H | H | H | H | H |
| 935 | OH | General formula (114) | CN | OH | OH | H | H | H | H | H | H | H | H |
| 936 | General formula (114) | OH | CN | OH | OH | H | H | H | H | H | H | H | H |
| 937 | General formula (114) | General formula (114) | CN | Cl | General formula (114) | H | H | H | H | H | H | H | H |
| 938 | General formula (114) | General formula (114) | CN | Cl | General formula (114) | H | $CH_3$ | H | H | H | H | H | H |
| 939 | General formula (114) | General formula (114) | CN | Cl | General formula (114) | H | $CH_3O$ | H | H | H | H | H | H |
| 940 | General formula (114) | General formula (114) | CN | Cl | General formula (114) | H | $t-C_4H_9$ | H | H | H | H | H | H |
| 941 | General formula (114) | General formula (114) | CN | Cl | General formula (114) | H | Cl | H | H | H | H | H | H |

TABLE 5-continued

| Compound No. | General formula (1) | | | | General formula (114) | | | | | | | | | |
|---|---|---|---|---|---|---|---|---|---|---|---|---|---|---|
| | $R^1$ | $R^2$ | $R^3$ | $R^4$ | $R^5$ | $R^{52}$ | $R^{53}$ | $R^{54}$ | $R^{55}$ | $R^{57}$ | $R^{59}$ | $R^{61}$ | $R^{51}, R^{56}, R^{58}, R^{60}, R^{62}$ |
| 942 | General formula (114) | General formula (114) | CN | Cl | General formula (114) | H | F | H | H | H | H | H | H |
| 943 | General formula (114) | General formula (114) | CN | F | General formula (114) | H | H | H | H | H | H | H | H |
| 944 | General formula (114) | General formula (114) | CN | F | General formula (114) | H | $CH_3$ | H | H | H | H | H | H |
| 945 | General formula (114) | General formula (114) | CN | F | General formula (114) | H | $CH_3O$ | H | H | H | H | H | H |
| 946 | General formula (114) | General formula (114) | CN | F | General formula (114) | H | $t-C_4H_9$ | H | H | H | H | H | H |
| 947 | General formula (114) | General formula (114) | CN | F | General formula (114) | H | Cl | H | H | H | H | H | H |
| 948 | General formula (114) | General formula (114) | CN | F | General formula (114) | H | F | H | H | H | H | H | H |
| 949 | General formula (114) | General formula (114) | CN | $CH_3O$ | General formula (114) | H | H | H | H | H | H | H | H |
| 950 | General formula (114) | General formula (114) | CN | $CH_3O$ | General formula (114) | H | $CH_3$ | H | H | H | H | H | H |
| 951 | General formula (114) | General formula (114) | CN | $CH_3O$ | General formula (114) | H | $CH_3O$ | H | H | H | H | H | H |
| 952 | General formula (114) | General formula (114) | CN | $CH_3O$ | General formula (114) | H | $t-C_4H_9$ | H | H | H | H | H | H |
| 953 | General formula (114) | General formula (114) | CN | $CH_3O$ | General formula (114) | H | Cl | H | H | H | H | H | H |
| 954 | General formula (114) | General formula (114) | CN | $CH_3O$ | General formula (114) | H | F | H | H | H | H | H | H |
| 955 | General formula (114) | General formula (114) | CN | $C_2H_5O$ | General formula (114) | H | H | H | H | H | H | H | H |
| 956 | General formula (114) | General formula (114) | CN | $C_2H_5O$ | General formula (114) | H | $CH_3$ | H | H | H | H | H | H |
| 957 | General formula (114) | General formula (114) | CN | $C_2H_5O$ | General formula (114) | H | $CH_3O$ | H | H | H | H | H | H |
| 958 | General formula (114) | General formula (114) | CN | $C_2H_5O$ | General formula (114) | H | $t-C_4H_9$ | H | H | H | H | H | H |
| 959 | General formula (114) | General formula (114) | CN | $C_2H_5O$ | General formula (114) | H | Cl | H | H | H | H | H | H |
| 960 | General formula (114) | General formula (114) | CN | $C_2H_5O$ | General formula (114) | H | F | H | H | H | H | H | H |
| 961 | General formula (114) | General formula (114) | CN | $C_6H_5O$ | General formula (114) | H | H | H | H | H | H | H | H |
| 962 | General formula (114) | General formula (114) | CN | $C_6H_5O$ | General formula (114) | H | $CH_3$ | H | H | H | H | H | H |
| 963 | General formula (114) | General formula (114) | CN | $C_6H_5O$ | General formula (114) | H | $CH_3O$ | H | H | H | H | H | H |
| 964 | General formula (114) | General formula (114) | CN | $C_6H_5O$ | General formula (114) | H | $t-C_4H_9$ | H | H | H | H | H | H |
| 965 | General formula (114) | General formula (114) | CN | $C_6H_5O$ | General formula (114) | H | Cl | H | H | H | H | H | H |
| 966 | General formula (114) | General formula (114) | CN | $C_6H_5O$ | General formula (114) | H | F | H | H | H | H | H | H |
| 967 | General formula (114) | General formula (114) | CN | Formula (121) | General formula (114) | H | H | H | H | H | H | H | H |
| 968 | General formula (114) | General formula (114) | CN | Formula (121) | General formula (114) | H | $CH_3$ | H | H | H | H | H | H |
| 969 | General formula (114) | General formula (114) | CN | Formula (121) | General formula (114) | H | $CH_3O$ | H | H | H | H | H | H |
| 970 | General formula (114) | General formula (114) | CN | Formula (121) | General formula (114) | H | $t-C_4H_9$ | H | H | H | H | H | H |
| 971 | General formula (114) | General formula (114) | CN | Formula (121) | General formula (114) | H | Cl | H | H | H | H | H | H |
| 972 | General formula (114) | General formula (114) | CN | Formula (121) | General formula (114) | H | F | H | H | H | H | H | H |
| 973 | General formula (114) | General formula (114) | CN | Formula (122) | General formula (114) | H | H | H | H | H | H | H | H |
| 974 | General formula (114) | General formula (114) | CN | Formula (122) | General formula (114) | H | $CH_3$ | H | H | H | H | H | H |
| 975 | General formula (114) | General formula (114) | CN | Formula (122) | General formula (114) | H | $CH_3O$ | H | H | H | H | H | H |
| 976 | General formula (114) | General formula (114) | CN | Formula (122) | General formula (114) | H | $t-C_4H_9$ | H | H | H | H | H | H |
| 977 | General formula (114) | General formula (114) | CN | Formula (122) | General formula (114) | H | Cl | H | H | H | H | H | H |
| 978 | General formula (114) | General formula (114) | CN | Formula (122) | General formula (114) | H | F | H | H | H | H | H | H |
| 989 | General formula (114) | General formula (114) | CN | Formula (123) | General formula (114) | H | H | H | H | H | H | H | H |
| 980 | General formula (114) | General formula (114) | CN | Formula (123) | General formula (114) | H | $CH_3$ | H | H | H | H | H | H |
| 981 | General formula (114) | General formula (114) | CN | Formula (123) | General formula (114) | H | $CH_3O$ | H | H | H | H | H | H |
| 982 | General formula (114) | General formula (114) | CN | Formula (123) | General formula (114) | H | $t-C_4H_9$ | H | H | H | H | H | H |
| 983 | General formula (114) | General formula (114) | CN | Formula (123) | General formula (114) | H | Cl | H | H | H | H | H | H |
| 984 | General formula (114) | General formula (114) | CN | Formula (123) | General formula (114) | H | F | H | H | H | H | H | H |

TABLE 5-continued

| Compound | General formula (1) | | | | | General formula (114) | | | | | | | |
|---|---|---|---|---|---|---|---|---|---|---|---|---|---|
| No. | R¹ | R² | R³ | R⁴ | R⁵ | R⁵² | R⁵³ | R⁵⁴ | R⁵⁵ | R⁵⁷ | R⁵⁹ | R⁶¹ | R⁵¹, R⁵⁶, R⁵⁸, R⁶⁰, R⁶² |
| 985 | General formula (114) | General formula (114) | CN | Formula (124) | General formula (114) | H | H | H | H | H | H | H | H |
| 986 | General formula (114) | General formula (114) | CN | Formula (124) | General formula (114) | H | CH₃ | H | H | H | H | H | H |
| 987 | General formula (114) | General formula (114) | CN | Formula (124) | General formula (114) | H | CH₃O | H | H | H | H | H | H |
| 988 | General formula (114) | General formula (114) | CN | Formula (124) | General formula (114) | H | t-C₄H₉ | H | H | H | H | H | H |
| 989 | General formula (114) | General formula (114) | CN | Formula (124) | General formula (114) | H | Cl | H | H | H | H | H | H |
| 990 | General formula (114) | General formula (114) | CN | Formula (124) | General formula (114) | H | F | H | H | H | H | H | H |

TABLE 6

| Compound No. | General formula (1) | | | | | General formula (115) | | | | |
|---|---|---|---|---|---|---|---|---|---|---|
| | $R^1$ | $R^2$ | $R^3$ | $R^4$ | $R^5$ | $R^{71}, R^{80}$ | $R^{72}, R^{79}$ | $R^{73}, R^{78}$ | $R^{74}, R^{77}$ | $R^{75}, R^{76}$ |
| 1001 | General formula (115) | General formula (115) | CN | General formula (115) | General formula (115) | H | H | H | H | H |
| 1002 | General formula (115) | General formula (115) | CN | General formula (115) | General formula (115) | H | $CH_3$ | H | H | H |
| 1003 | General formula (115) | General formula (115) | CN | General formula (115) | General formula (115) | H | $CH_3O$ | H | H | H |
| 1004 | General formula (115) | General formula (115) | CN | General formula (115) | General formula (115) | H | $C_6H_5$ | H | H | H |
| 1005 | General formula (115) | General formula (115) | CN | General formula (115) | General formula (115) | H | $CH_3$ | H | $CH_3$ | H |
| 1006 | General formula (115) | General formula (115) | CN | General formula (115) | General formula (115) | H | $CH_3O$ | H | $CH_3O$ | H |
| 1007 | General formula (115) | General formula (115) | CN | General formula (115) | General formula (115) | H | $C_6H_5$ | H | $C_6H_5$ | H |
| 1008 | General formula (115) | General formula (115) | CN | General formula (115) | General formula (115) | H | H | $CH_3$ | H | H |
| 1009 | General formula (115) | General formula (115) | CN | General formula (115) | General formula (115) | H | H | $CH_3O$ | H | H |
| 1010 | General formula (115) | General formula (115) | CN | General formula (115) | General formula (115) | H | H | $t\text{-}C_4H_9$ | H | H |
| 1011 | General formula (115) | General formula (115) | CN | General formula (115) | General formula (115) | H | H | Cl | H | H |
| 1012 | General formula (115) | General formula (115) | CN | General formula (115) | General formula (115) | H | H | F | H | H |
| 1013 | General formula (115) | General formula (115) | CN | General formula (115) | General formula (115) | H | H | $C_6H_5$ | H | H |
| 1014 | General formula (115) | General formula (115) | CN | General formula (115) | General formula (115) | H | H | $p\text{-}C_6H_5\text{—}C_6H_4$ | H | H |
| 1015 | General formula (115) | General formula (115) | CN | General formula (115) | H | H | H | H | H | H |
| 1016 | General formula (115) | General formula (115) | CN | H | General formula (115) | H | H | H | H | H |
| 1017 | General formula (115) | General formula (115) | CN | H | H | H | H | H | H | H |
| 1018 | General formula (115) | H | CN | General formula (115) | H | H | H | H | H | H |
| 1019 | H | General formula (115) | CN | General formula (115) | H | H | H | H | H | H |
| 1020 | General formula (115) | H | CN | H | H | H | H | H | H | H |
| 1021 | General formula (115) | General formula (115) | CN | General formula (115) | F | H | H | H | H | H |
| 1022 | General formula (115) | General formula (115) | CN | F | General formula (115) | H | H | H | H | H |
| 1023 | General formula (115) | General formula (115) | CN | F | F | H | H | H | H | H |
| 1024 | General formula (115) | F | CN | General formula (115) | F | H | H | H | H | H |
| 1025 | F | General formula (115) | CN | General formula (115) | F | H | H | H | H | H |
| 1026 | General formula (115) | F | CN | F | F | H | H | H | H | H |
| 1027 | General formula (115) | General formula (115) | CN | General formula (115) | OH | H | H | H | H | H |
| 1028 | General formula (115) | General formula (115) | CN | OH | General formula (115) | H | H | H | H | H |
| 1029 | General formula (115) | General formula (115) | CN | OH | OH | H | H | H | H | H |
| 1030 | General formula (115) | OH | CN | General formula (115) | OH | H | H | H | H | H |
| 1031 | OH | General formula (115) | CN | General formula (115) | OH | H | H | H | H | H |
| 1032 | General formula (115) | OH | CN | OH | OH | H | H | H | H | H |
| 1033 | General formula (115) | General formula (115) | CN | Cl | General formula (115) | H | H | H | H | H |
| 1034 | General formula (115) | General formula (115) | CN | Cl | General formula (115) | H | H | $CH_3$ | H | H |
| 1035 | General formula (115) | General formula (115) | CN | Cl | General formula (115) | H | H | $CH_3O$ | H | H |
| 1036 | General formula (115) | General formula (115) | CN | Cl | General formula (115) | H | H | $t\text{-}C_4H_9$ | H | H |
| 1037 | General formula (115) | General formula (115) | CN | Cl | General formula (115) | H | H | Cl | H | H |
| 1038 | General formula (115) | General formula (115) | CN | Cl | General formula (115) | H | H | F | H | H |
| 1039 | General formula (115) | General formula (115) | CN | F | General formula (115) | H | H | H | H | H |
| 1040 | General formula (115) | General formula (115) | CN | F | General formula (115) | H | H | $CH_3$ | H | H |
| 1041 | General formula (115) | General formula (115) | CN | F | General formula (115) | H | H | $CH_3O$ | H | H |
| 1042 | General formula (115) | General formula (115) | CN | F | General formula (115) | H | H | $t\text{-}C_4H_9$ | H | H |
| 1043 | General formula (115) | General formula (115) | CN | F | General formula (115) | H | H | Cl | H | H |
| 1044 | General formula (115) | General formula (115) | CN | F | General formula (115) | H | H | F | H | H |
| 1045 | General formula (115) | General formula (115) | CN | $CH_3O$ | General formula (115) | H | H | H | H | H |
| 1046 | General formula (115) | General formula (115) | CN | $CH_3O$ | General formula (115) | H | H | $CH_3$ | H | H |
| 1047 | General formula (115) | General formula (115) | CN | $CH_3O$ | General formula (115) | H | H | $CH_3O$ | H | H |
| 1048 | General formula (115) | General formula (115) | CN | $CH_3O$ | General formula (115) | H | H | $t\text{-}C_4H_9$ | H | H |
| 1049 | General formula (115) | General formula (115) | CN | $CH_3O$ | General formula (115) | H | H | Cl | H | H |
| 1050 | General formula (115) | General formula (115) | CN | $CH_3O$ | General formula (115) | H | H | F | H | H |
| 1051 | General formula (115) | General formula (115) | CN | $C_2H_5O$ | General formula (115) | H | H | H | H | H |
| 1052 | General formula (115) | General formula (115) | CN | $C_2H_5O$ | General formula (115) | H | H | $CH_3$ | H | H |
| 1053 | General formula (115) | General formula (115) | CN | $C_2H_5O$ | General formula (115) | H | H | $CH_3O$ | H | H |
| 1054 | General formula (115) | General formula (115) | CN | $C_2H_5O$ | General formula (115) | H | H | $t\text{-}C_4H_9$ | H | H |
| 1055 | General formula (115) | General formula (115) | CN | $C_2H_5O$ | General formula (115) | H | H | Cl | H | H |
| 1056 | General formula (115) | General formula (115) | CN | $C_2H_5O$ | General formula (115) | H | H | F | H | H |
| 1057 | General formula (115) | General formula (115) | CN | $C_6H_5O$ | General formula (115) | H | H | H | H | H |
| 1058 | General formula (115) | General formula (115) | CN | $C_6H_5O$ | General formula (115) | H | H | $CH_3$ | H | H |
| 1059 | General formula (115) | General formula (115) | CN | $C_6H_5O$ | General formula (115) | H | H | $CH_3O$ | H | H |
| 1060 | General formula (115) | General formula (115) | CN | $C_6H_5O$ | General formula (115) | H | H | $t\text{-}C_4H_9$ | H | H |
| 1061 | General formula (115) | General formula (115) | CN | $C_6H_5O$ | General formula (115) | H | H | Cl | H | H |
| 1062 | General formula (115) | General formula (115) | CN | $C_6H_5O$ | General formula (115) | H | H | F | H | H |
| 1063 | General formula (115) | General formula (115) | CN | Formula (121) | General formula (115) | H | H | H | H | H |
| 1064 | General formula (115) | General formula (115) | CN | Formula (121) | General formula (115) | H | H | $CH_3$ | H | H |
| 1065 | General formula (115) | General formula (115) | CN | Formula (121) | General formula (115) | H | H | $CH_3O$ | H | H |
| 1066 | General formula (115) | General formula (115) | CN | Formula (121) | General formula (115) | H | H | $t\text{-}C_4H_9$ | H | H |
| 1067 | General formula (115) | General formula (115) | CN | Formula (121) | General formula (115) | H | H | Cl | H | H |
| 1068 | General formula (115) | General formula (115) | CN | Formula (121) | General formula (115) | H | H | F | H | H |
| 1069 | General formula (115) | General formula (115) | CN | Formula (122) | General formula (115) | H | H | H | H | H |
| 1070 | General formula (115) | General formula (115) | CN | Formula (122) | General formula (115) | H | H | $CH_3$ | H | H |
| 1071 | General formula (115) | General formula (115) | CN | Formula (122) | General formula (115) | H | H | $CH_3O$ | H | H |
| 1072 | General formula (115) | General formula (115) | CN | Formula (122) | General formula (115) | H | H | $t\text{-}C_4H_9$ | H | H |
| 1073 | General formula (115) | General formula (115) | CN | Formula (122) | General formula (115) | H | H | Cl | H | H |

TABLE 6-continued

| Compound No. | General formula (1) | | | | | General formula (115) | | | | |
|---|---|---|---|---|---|---|---|---|---|---|
| | $R^1$ | $R^2$ | $R^3$ | $R^4$ | $R^5$ | $R^{71}$, $R^{80}$ | $R^{72}$, $R^{79}$ | $R^{73}$, $R^{78}$ | $R^{74}$, $R^{77}$ | $R^{75}$, $R^{76}$ |
| 1074 | General formula (115) | General formula (115) | CN | Formula (122) | General formula (115) | H | H | F | H | H |
| 1075 | General formula (115) | General formula (115) | CN | Formula (123) | General formula (115) | H | H | H | H | H |
| 1076 | General formula (115) | General formula (115) | CN | Formula (123) | General formula (115) | H | H | $CH_3$ | H | H |
| 1077 | General formula (115) | General formula (115) | CN | Formula (123) | General formula (115) | H | H | $CH_3O$ | H | H |
| 1078 | General formula (115) | General formula (115) | CN | Formula (123) | General formula (115) | H | H | $t-C_4H_9$ | H | H |
| 1079 | General formula (115) | General formula (115) | CN | Formula (123) | General formula (115) | H | H | Cl | H | H |
| 1080 | General formula (115) | General formula (115) | CN | Formula (123) | General formula (115) | H | H | F | H | H |
| 1081 | General formula (115) | General formula (115) | CN | Formula (124) | General formula (115) | H | H | H | H | H |
| 1082 | General formula (115) | General formula (115) | CN | Formula (124) | General formula (115) | H | H | $CH_3$ | H | H |
| 1083 | General formula (115) | General formula (115) | CN | Formula (124) | General formula (115) | H | H | $CH_3O$ | H | H |
| 1084 | General formula (115) | General formula (115) | CN | Formula (124) | General formula (115) | H | H | $t-C_4H_9$ | H | H |
| 1085 | General formula (115) | General formula (115) | CN | Formula (124) | General formula (115) | H | H | Cl | H | H |
| 1086 | General formula (115) | General formula (115) | CN | Formula (124) | General formula (115) | H | H | F | H | H |

Examples of the preferred light-emitting material include the following compounds.

(1) A compound represented by the following general formula (131):

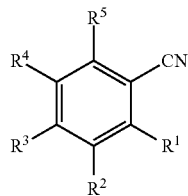

General Formula (131)

wherein in the general formula (131), from 0 to 1 of $R^1$ to $R^5$ represents a cyano group, from 1 to 5 of $R^1$ to $R^5$ each represent a group represented by the following general formula (132), and the balance of $R^1$ to $R^5$ each represent a hydrogen atom or a substituent other than the above,

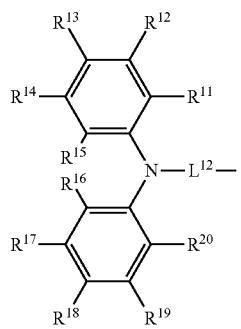

General Formula (132)

wherein in the general formula (132), $R^{11}$ to $R^{20}$ each independently represent a hydrogen atom or a substituent, in which $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure; and $L^{12}$ represents a substituted or unsubstituted arylene group or a substituted or unsubstituted heteroarylene group.

(2) The compound according to the item (1), wherein the group represented by the general formula (132) is a group represented by any one of the following general formulae (133) to (138):

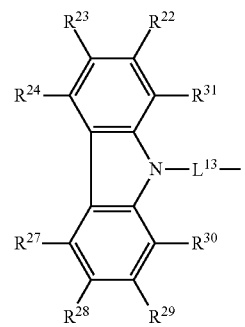

General Formula (133)

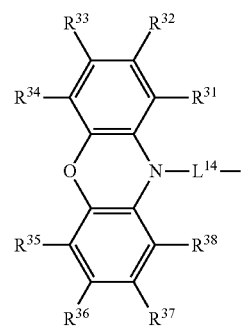

General Formula (134)

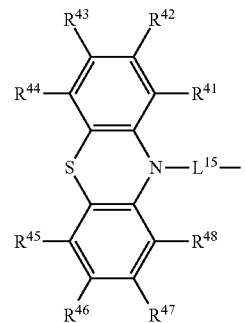

General Formula (135)

-continued

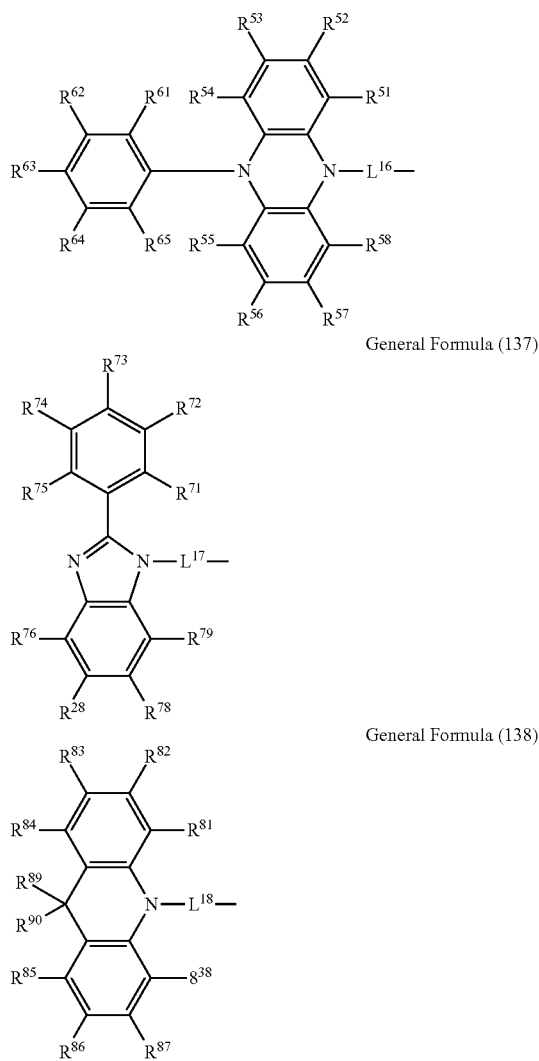

General Formula (136)

General Formula (137)

General Formula (138)

wherein in the general formulae (133) to (138), $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, $R^{81}$ to $R^{90}$ each independently represent a hydrogen atom or a substituent, in which $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$, $R^{81}$ and $R^{82}$, $R^{82}$ and $R^{83}$, $R^{83}$ and $R^{84}$, $R^{85}$ and $R^{86}$, $R^{86}$ and $R^{87}$, $R^{87}$ and $R^{88}$, and $R^{89}$ and $R^{90}$ each may be bonded to each other to form a cyclic structure; and $L^{13}$ to $L^{18}$ each independently represent a substituted or unsubstituted arylene group or a substituted or unsubstituted heteroarylene group.

(3) The compound according to the item (1) or (2), wherein in the general formula (131), $R^3$ represents a cyano group.

(4) The compound according to any one of the items (1) to (3), wherein in the general formula (131), $R^1$ and $R^4$ each represent a group represented by the general formula (132).

(5) The compound according to any one of the items (1) to (4), wherein in the general formula (132), $L^{12}$ represents a phenylene group.

(6) The compound according to any one of the items (1) to (5), wherein the group represented by the general formula (132) is a group represented by the general formula (133).

(7) The compound according to the item (6), wherein in the general formula (133), $L^{13}$ represents a 1,3-phenylene group.

(8) The compound according to any one of the items (1) to (5), wherein the group represented by the general formula (132) is a group represented by the general formula (134).

(9) The compound according to the item (8), wherein in the general formula (134), $L^{14}$ represents a 1,4-phenylene group.

(10) The compound according to any one of the items (1) to (5), wherein the group represented by the general formula (132) is a group represented by the general formula (138).

(11) The compound according to the item (10), wherein in the general formula (138), $L^{18}$ represents a 1,4-phenylene group.

Examples of the compound include the following compounds.

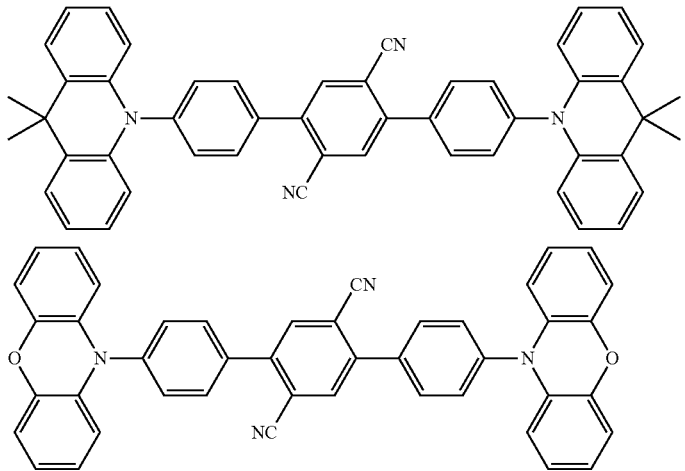

-continued
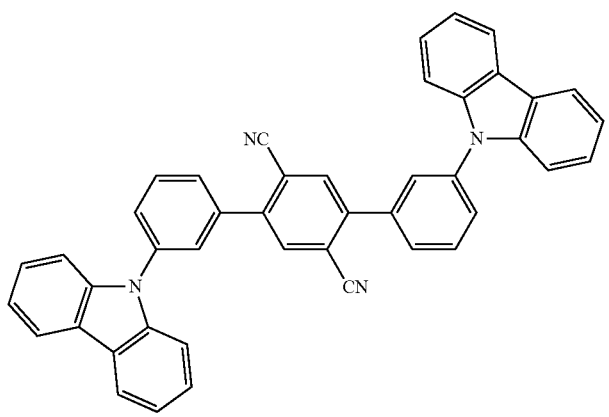
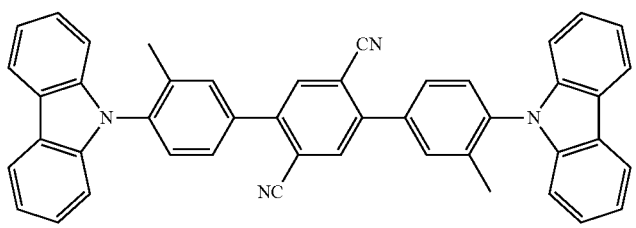
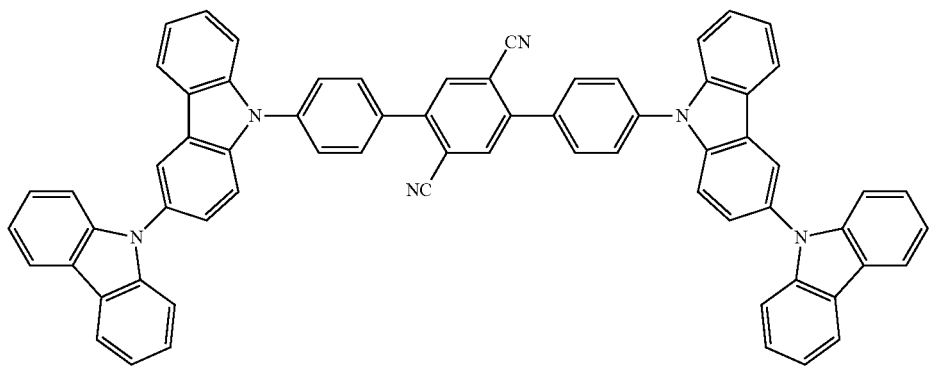
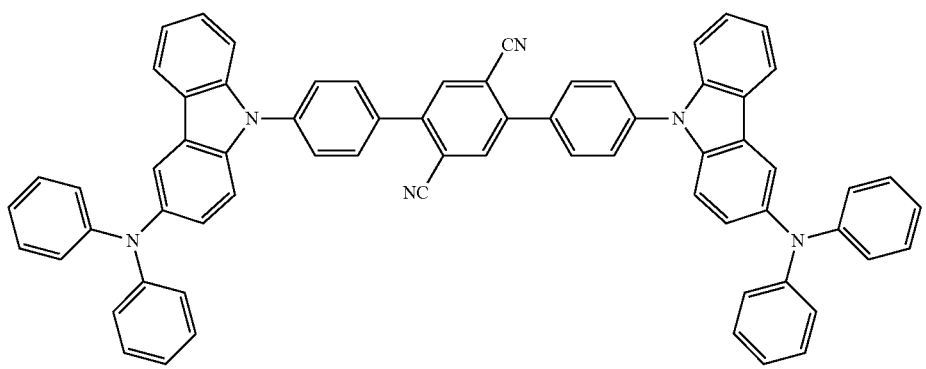

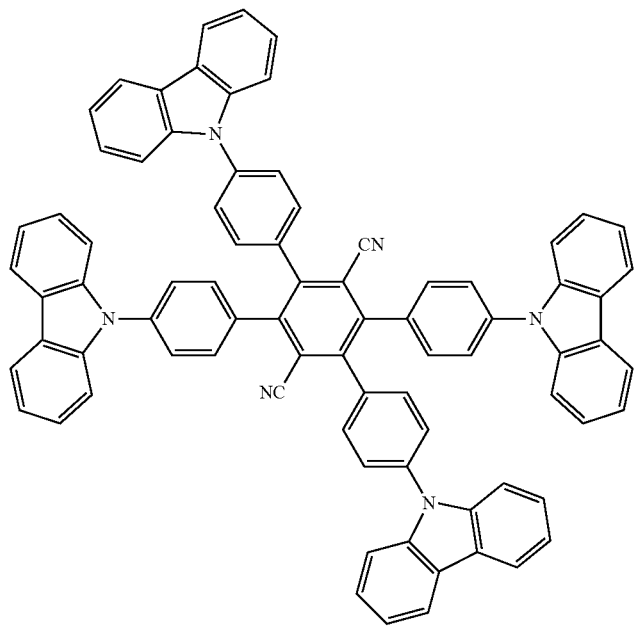
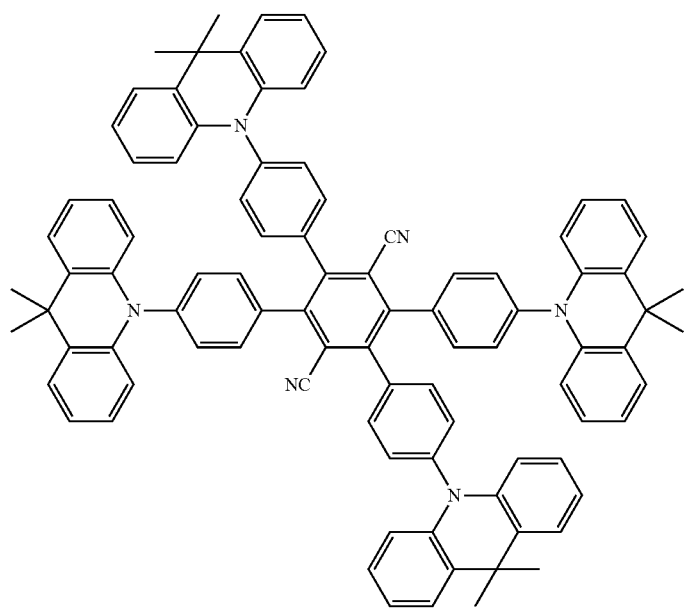

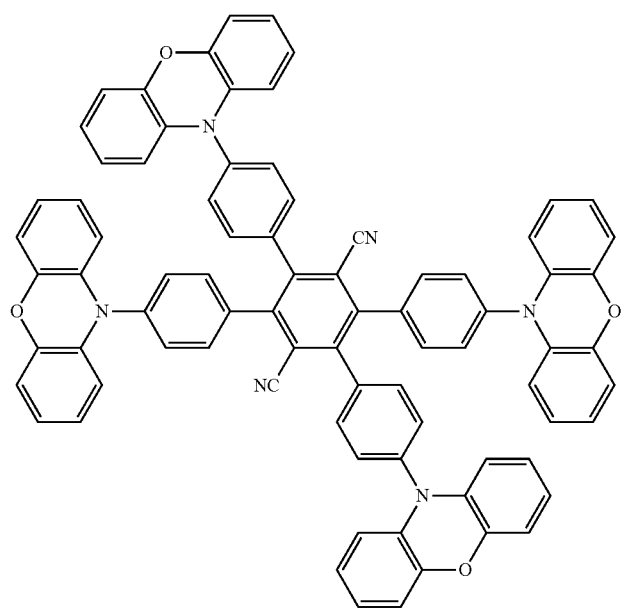
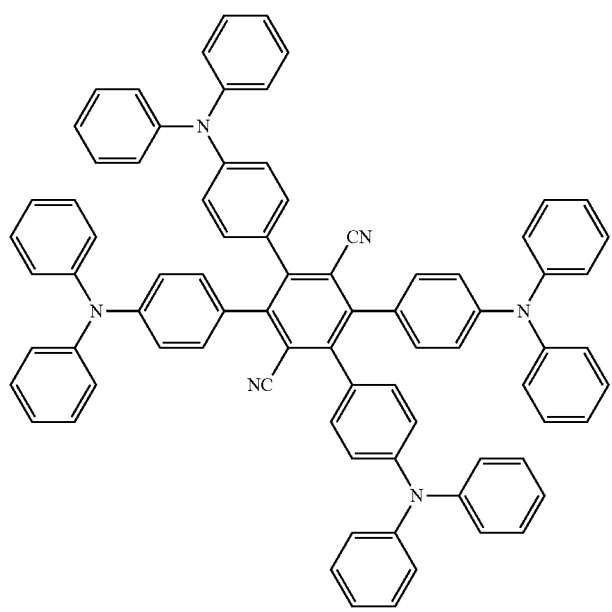
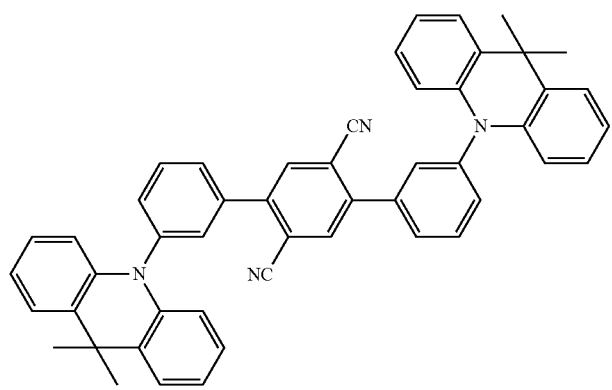

-continued
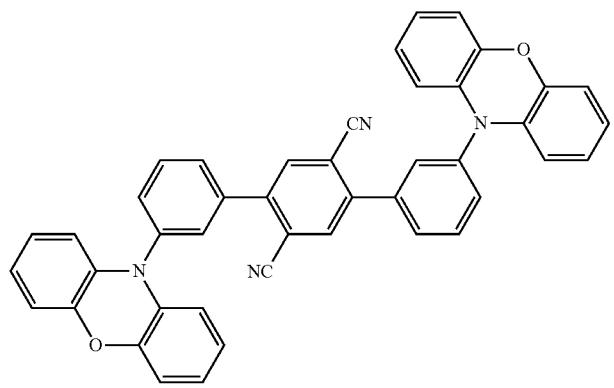
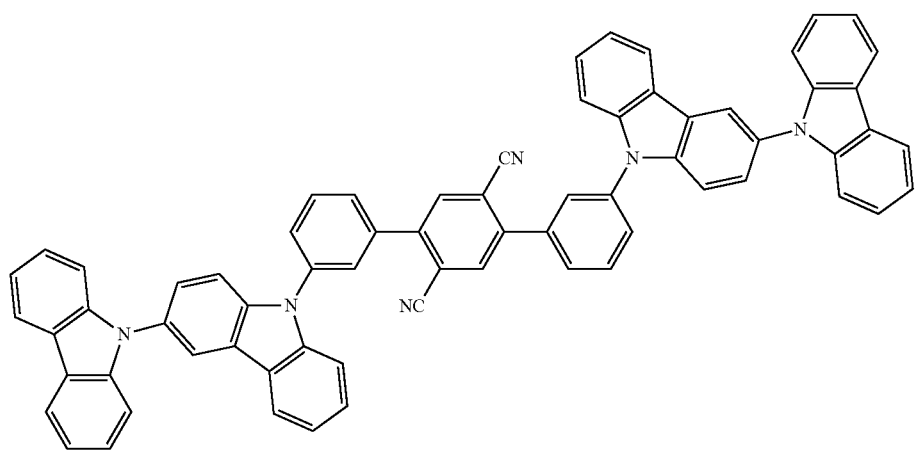
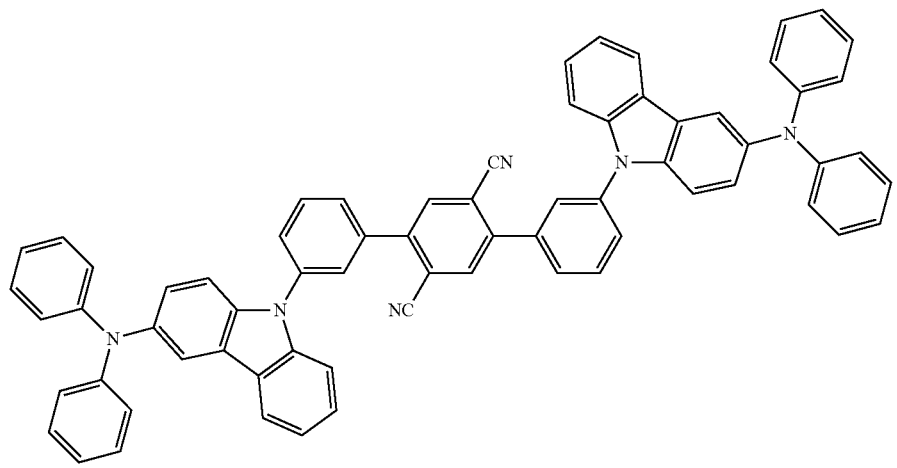
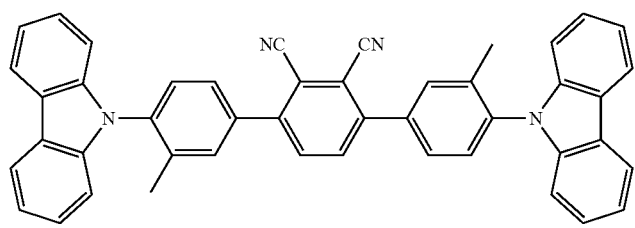

121
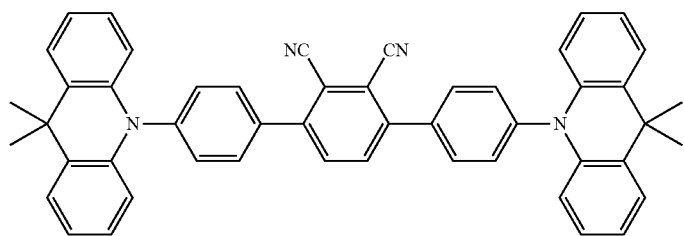
122
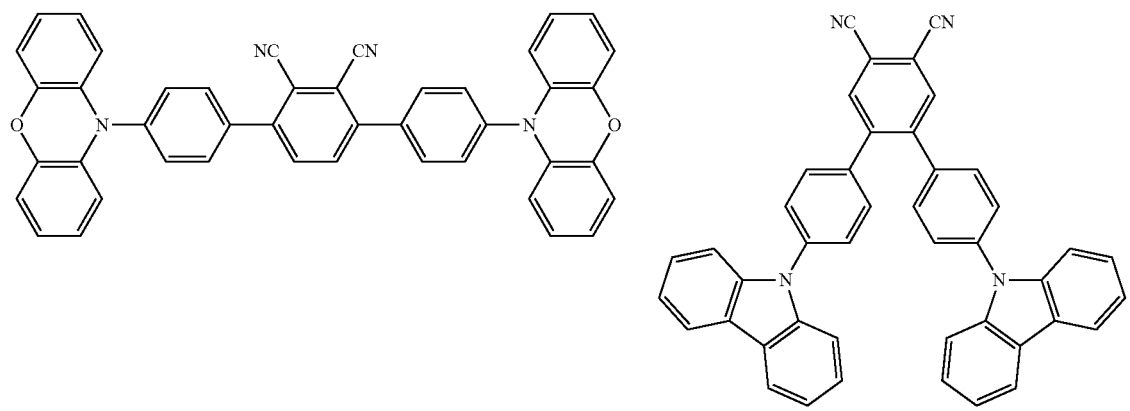
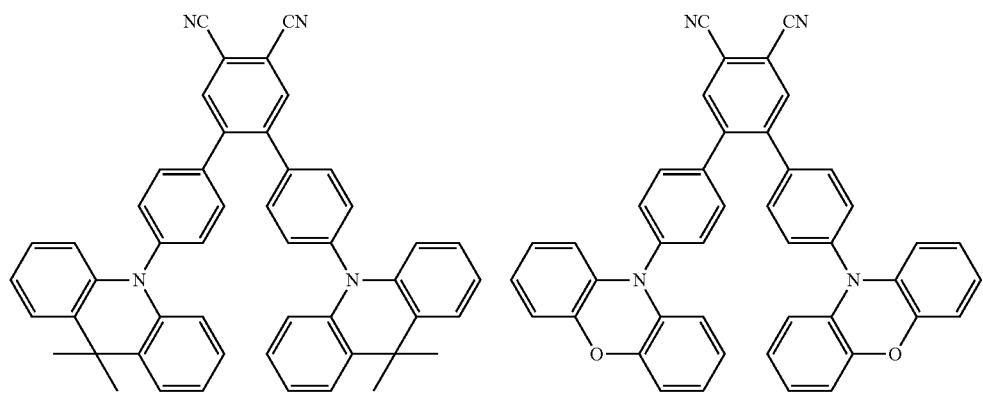
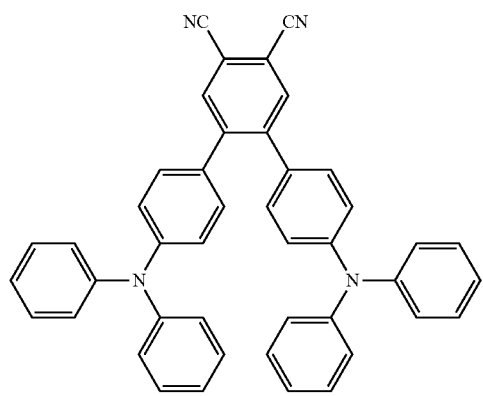

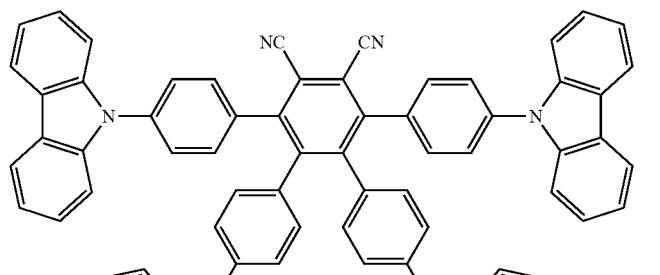
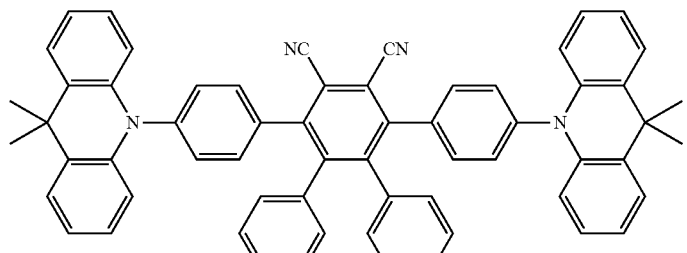
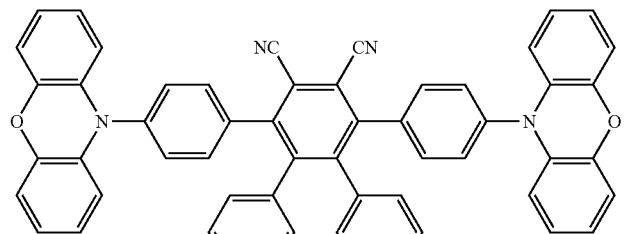
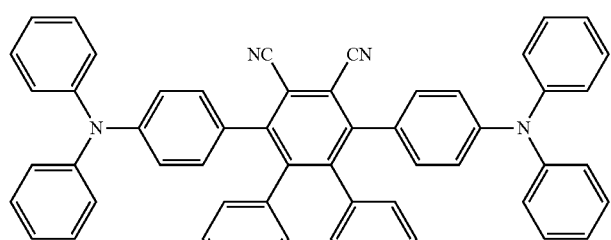

-continued
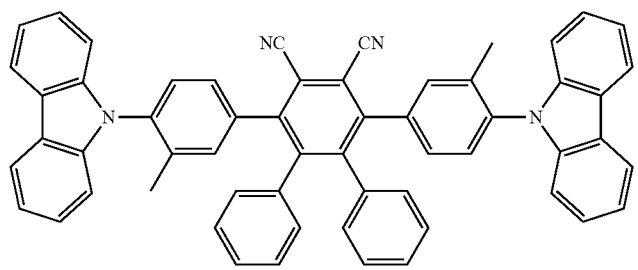
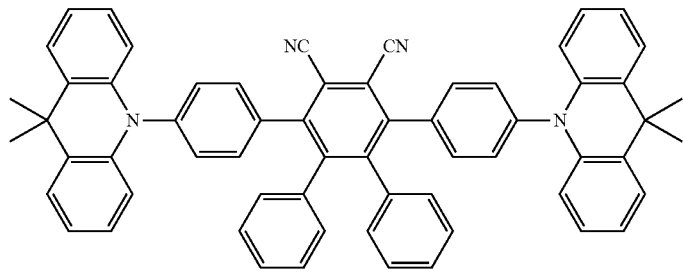
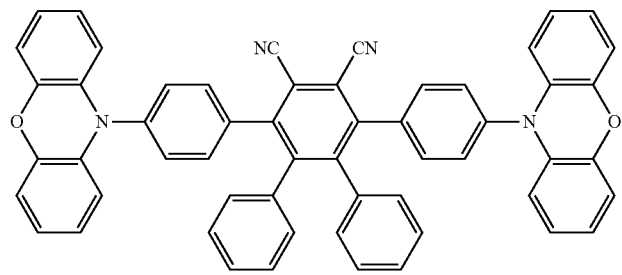
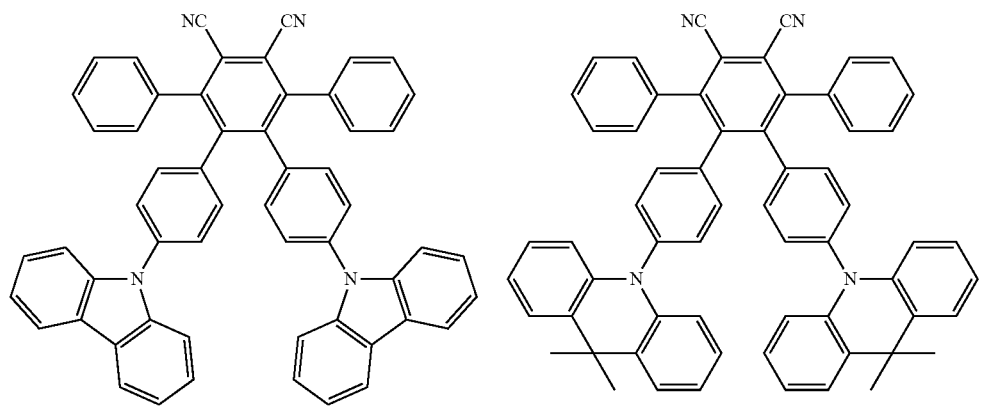
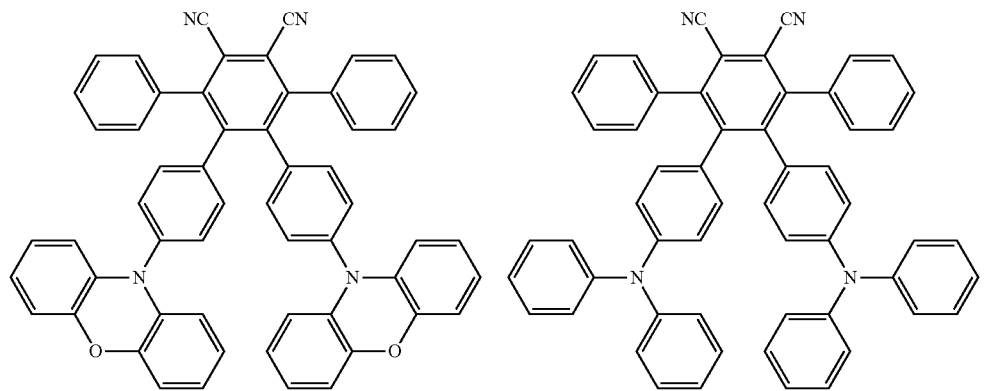

Examples of the preferred light-emitting material include compounds represented by the following general formula (141). The entire description of WO 2013/011954 including the paragraphs 0007 to 0047 and 0073 to 0085 is incorporated herein by reference.

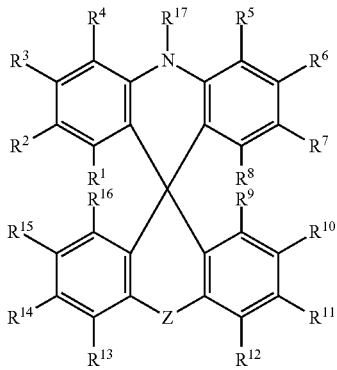

Genenal Formula (141)

wherein in the general formula (141), $R^1$, $R^2$, $R^3$, $R^4$, $R^5$, $R^6$, $R^7$, $R^8$ and $R^{17}$ each independently represent a hydrogen atom or an electron donating group, provided that at least one thereof represents an electron donating group; $R^9$, $R^{10}$, $R^{11}$, $R^{12}$, $R^{13}$, $R^{14}$, $R^{15}$ and $R^{16}$ each independently represent a hydrogen atom or an electron withdrawing group having no unshared electron pair at the α-position; and Z represents a single bond or >C=Y, wherein Y represents O, S, C(CN)$_2$ or C(COOH)$_2$, provided that when Z represents a single bond, at least one of $R^9$, $R^{10}$, $R^{11}$, $R^{12}$, $R^{13}$, $R^{14}$, $R^{15}$ and $R^{16}$ represents an electron withdrawing group having no unshared electron pair at the α-position.

Specific examples of the compounds include the compounds shown in the following tables. In the tables, D1 to D3 represent the following aryl groups substituted with an electron donating group, respectively; A1 to A5 represent the following electron withdrawing groups, respectively; H represents a hydrogen atom; and Ph represents a phenyl group.

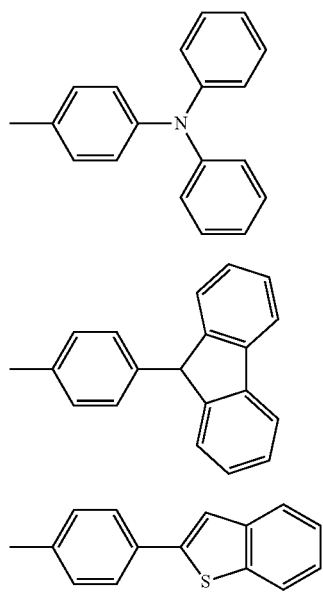

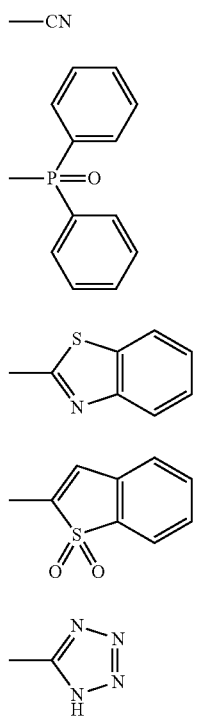

TABLE 7

| Compound No. | $R^2$ | $R^7$ | $R^{10}$ | $R^{15}$ | $R^{17}$ | Z | Other Rs |
|---|---|---|---|---|---|---|---|
| 2001 | H | H | A1 | A1 | Ph | single bond | H |
| 2002 | H | D1 | A1 | A1 | Ph | single bond | H |
| 2003 | H | D2 | A1 | A1 | Ph | single bond | H |
| 2004 | H | D3 | A1 | A1 | Ph | single bond | H |
| 2005 | H | H | A2 | A2 | Ph | single bond | H |
| 2006 | H | D1 | A2 | A2 | Ph | single bond | H |
| 2007 | H | D2 | A2 | A2 | Ph | single bond | H |
| 2008 | H | D3 | A2 | A2 | Ph | single bond | H |
| 2009 | H | H | A3 | A3 | Ph | single bond | H |
| 2010 | H | D1 | A3 | A3 | Ph | single bond | H |
| 2011 | H | D2 | A3 | A3 | Ph | single bond | H |
| 2012 | H | D3 | A3 | A3 | Ph | single bond | H |
| 2013 | H | H | A4 | A4 | Ph | single bond | H |
| 2014 | H | D1 | A4 | A4 | Ph | single bond | H |
| 2015 | H | D2 | A4 | A4 | Ph | single bond | H |
| 2016 | H | D3 | A4 | A4 | Ph | single bond | H |
| 2017 | H | H | A5 | A5 | Ph | single bond | H |
| 2018 | H | D1 | A5 | A5 | Ph | single bond | H |
| 2019 | H | D2 | A5 | A5 | Ph | single bond | H |
| 2020 | H | D3 | A5 | A5 | Ph | single bond | H |
| 2021 | D1 | D1 | A1 | A1 | Ph | single bond | H |
| 2022 | D2 | D2 | A1 | A1 | Ph | single bond | H |
| 2023 | D3 | D3 | A1 | A1 | Ph | single bond | H |
| 2024 | D1 | D1 | A2 | A2 | Ph | single bond | H |
| 2025 | D2 | D2 | A2 | A2 | Ph | single bond | H |
| 2026 | D3 | D3 | A2 | A2 | Ph | single bond | H |
| 2027 | D1 | D1 | A3 | A3 | Ph | single bond | H |
| 2028 | D2 | D2 | A3 | A3 | Ph | single bond | H |
| 2029 | D3 | D3 | A3 | A3 | Ph | single bond | H |
| 2030 | D1 | D1 | A4 | A4 | Ph | single bond | H |
| 2031 | D2 | D2 | A4 | A4 | Ph | single bond | H |
| 2032 | D3 | D3 | A4 | A4 | Ph | single bond | H |
| 3033 | D1 | D1 | A5 | A5 | Ph | single bond | H |
| 2034 | D2 | D2 | A5 | A5 | Ph | single bond | H |
| 2035 | D3 | D3 | A5 | A5 | Ph | single bond | H |

TABLE 8

| Compound No. | R³ | R⁶ | R¹¹ | R¹⁴ | R¹⁷ | Z | Other Rs |
|---|---|---|---|---|---|---|---|
| 2036 | H | H | H | A1 | Ph | single bond | H |
| 2037 | H | D1 | H | A1 | Ph | single bond | H |
| 2038 | H | D2 | H | A1 | Ph | single bond | H |
| 2039 | H | D3 | H | A1 | Ph | single bond | H |
| 2040 | H | H | H | A2 | Ph | single bond | H |
| 2041 | H | D1 | H | A2 | Ph | single bond | H |
| 2042 | H | D2 | H | A2 | Ph | single bond | H |
| 2043 | H | D3 | H | A2 | Ph | single bond | H |
| 2044 | H | H | H | A3 | Ph | single bond | H |
| 2045 | H | D1 | H | A3 | Ph | single bond | H |
| 2046 | H | D2 | H | A3 | Ph | single bond | H |
| 2047 | H | D3 | H | A3 | Ph | single bond | H |
| 2048 | H | H | H | A4 | Ph | single bond | H |
| 2049 | H | D1 | H | A4 | Ph | single bond | H |
| 2050 | H | D2 | H | A4 | Ph | single bond | H |
| 2051 | H | D3 | H | A4 | Ph | single bond | H |
| 2052 | H | H | H | A5 | Ph | single bond | H |
| 2053 | H | D1 | H | A5 | Ph | single bond | H |
| 2054 | H | D2 | H | A5 | Ph | single bond | H |
| 2055 | H | D3 | H | A5 | Ph | single bond | H |
| 2056 | D1 | D1 | H | A1 | Ph | single bond | H |
| 2057 | D2 | D2 | H | A1 | Ph | single bond | H |
| 2058 | D3 | D3 | H | A1 | Ph | single bond | H |
| 2059 | D1 | D1 | H | A2 | Ph | single bond | H |
| 2060 | D2 | D2 | H | A2 | Ph | single bond | H |
| 2061 | D3 | D3 | H | A2 | Ph | single bond | H |
| 2062 | D1 | D1 | H | A3 | Ph | single bond | H |
| 2063 | D2 | D2 | H | A3 | Ph | single bond | H |
| 2064 | D3 | D3 | H | A3 | Ph | single bond | H |
| 2065 | D1 | D1 | H | A4 | Ph | single bond | H |
| 2066 | D2 | D2 | H | A4 | Ph | single bond | H |
| 2067 | D3 | D3 | H | A4 | Ph | single bond | H |
| 2068 | D1 | D1 | H | A5 | Ph | single bond | H |
| 2069 | D2 | D2 | H | A5 | Ph | single bond | H |
| 2070 | D3 | D3 | H | A5 | Ph | single bond | H |

TABLE 9

| Compound No. | R² | R⁷ | R¹⁰ | R¹⁵ | R¹⁷ | Z | Other Rs |
|---|---|---|---|---|---|---|---|
| 2071 | H | H | A1 | A1 | Ph | C=O | H |
| 2072 | H | D1 | A1 | A1 | Ph | C=O | H |
| 2073 | H | D2 | A1 | A1 | Ph | C=O | H |
| 2074 | H | D3 | A1 | A1 | Ph | C=O | H |
| 2075 | H | H | A2 | A2 | Ph | C=O | H |
| 2076 | H | D1 | A2 | A2 | Ph | C=O | H |
| 2077 | H | D2 | A2 | A2 | Ph | C=O | H |
| 2078 | H | D3 | A2 | A2 | Ph | C=O | H |
| 2079 | H | H | A3 | A3 | Ph | C=O | H |
| 2080 | H | D1 | A3 | A3 | Ph | C=O | H |
| 2081 | H | D2 | A3 | A3 | Ph | C=O | H |
| 2082 | H | D3 | A3 | A3 | Ph | C=O | H |
| 2083 | H | H | A4 | A4 | Ph | C=O | H |
| 2084 | H | D1 | A4 | A4 | Ph | C=O | H |
| 2085 | H | D2 | A4 | A4 | Ph | C=O | H |
| 2086 | H | D3 | A4 | A4 | Ph | C=O | H |
| 2087 | H | H | A5 | A5 | Ph | C=O | H |
| 2088 | H | D1 | A5 | A5 | Ph | C=O | H |
| 2089 | H | D2 | A5 | A5 | Ph | C=O | H |
| 2090 | H | D3 | A5 | A5 | Ph | C=O | H |
| 2091 | D1 | D1 | A1 | A1 | Ph | C=O | H |
| 2092 | D2 | D2 | A1 | A1 | Ph | C=O | H |
| 2093 | D3 | D3 | A1 | A1 | Ph | C=O | H |
| 2094 | D1 | D1 | A2 | A2 | Ph | C=O | H |
| 2095 | D2 | D2 | A2 | A2 | Ph | C=O | H |
| 2096 | D3 | D3 | A2 | A2 | Ph | C=O | H |
| 2097 | D1 | D1 | A3 | A3 | Ph | C=O | H |
| 2098 | D2 | D2 | A3 | A3 | Ph | C=O | H |
| 2099 | D3 | D3 | A3 | A3 | Ph | C=O | H |
| 2100 | D1 | D1 | A4 | A4 | Ph | C=O | H |
| 2101 | D2 | D2 | A4 | A4 | Ph | C=O | H |
| 2102 | D3 | D3 | A4 | A4 | Ph | C=O | H |
| 2103 | D1 | D1 | A5 | A5 | Ph | C=O | H |
| 2104 | D2 | D2 | A5 | A5 | Ph | C=O | H |
| 2105 | D3 | D3 | A5 | A5 | Ph | C=O | H |

TABLE 10

| Compound No. | R³ | R⁶ | R¹¹ | R¹⁴ | R¹⁷ | Z | Other Rs |
|---|---|---|---|---|---|---|---|
| 2106 | H | H | H | A1 | Ph | C=O | H |
| 2107 | H | D1 | H | A1 | Ph | C=O | H |
| 2108 | H | D2 | H | A1 | Ph | C=O | H |
| 2109 | H | D3 | H | A1 | Ph | C=O | H |
| 2110 | H | H | H | A2 | Ph | C=O | H |
| 2111 | H | D1 | H | A2 | Ph | C=O | H |
| 2112 | H | D2 | H | A2 | Ph | C=O | H |
| 2113 | H | D3 | H | A2 | Ph | C=O | H |
| 2114 | H | H | H | A3 | Ph | C=O | H |
| 2115 | H | D1 | H | A3 | Ph | C=O | H |
| 2116 | H | D2 | H | A3 | Ph | C=O | H |
| 2117 | H | D3 | H | A3 | Ph | C=O | H |
| 2118 | H | H | H | A4 | Ph | C=O | H |
| 2119 | H | D1 | H | A4 | Ph | C=O | H |
| 2120 | H | D2 | H | A4 | Ph | C=O | H |
| 2121 | H | D3 | H | A4 | Ph | C=O | H |
| 2122 | H | H | H | A5 | Ph | C=O | H |
| 2123 | H | D1 | H | A5 | Ph | C=O | H |
| 2124 | H | D2 | H | A5 | Ph | C=O | H |
| 2125 | H | D3 | H | A5 | Ph | C=O | H |
| 2126 | D1 | D1 | H | A1 | Ph | C=O | H |
| 2127 | D2 | D2 | H | A1 | Ph | C=O | H |
| 2128 | D3 | D3 | H | A1 | Ph | C=O | H |
| 2129 | D1 | D1 | H | A2 | Ph | C=O | H |
| 2130 | D2 | D2 | H | A2 | Ph | C=O | H |
| 2131 | D3 | D3 | H | A2 | Ph | C=O | H |
| 2132 | D1 | D1 | H | A3 | Ph | C=O | H |
| 2133 | D2 | D2 | H | A3 | Ph | C=O | H |
| 2134 | D3 | D3 | H | A3 | Ph | C=O | H |
| 2135 | D1 | D1 | H | A4 | Ph | C=O | H |
| 2136 | D2 | D2 | H | A4 | Ph | C=O | H |
| 2137 | D3 | D3 | H | A4 | Ph | C=O | H |
| 2138 | D1 | D1 | H | A5 | Ph | C=O | H |
| 2139 | D2 | D2 | H | A5 | Ph | C=O | H |
| 2140 | D3 | D3 | H | A5 | Ph | C=O | H |
| 2141 | H | H | H | H | Ph | C=O | H |

TABLE 11

| Compound No. | R² | R⁷ | R¹⁰ | R¹⁵ | R¹⁷ | Z | Other Rs |
|---|---|---|---|---|---|---|---|
| 2142 | H | H | A1 | A1 | Ph | C=S | H |
| 2143 | H | D1 | A1 | A1 | Ph | C=S | H |
| 2144 | H | D2 | A1 | A1 | Ph | C=S | H |
| 2145 | H | D3 | A1 | A1 | Ph | C=S | H |
| 2146 | H | H | A2 | A2 | Ph | C=S | H |
| 2147 | H | D1 | A2 | A2 | Ph | C=S | H |
| 2148 | H | D2 | A2 | A2 | Ph | C=S | H |
| 2149 | H | D3 | A2 | A2 | Ph | C=S | H |
| 2150 | H | H | A3 | A3 | Ph | C=S | H |
| 2151 | H | D1 | A3 | A3 | Ph | C=S | H |
| 2152 | H | D2 | A3 | A3 | Ph | C=S | H |
| 2153 | H | D3 | A3 | A3 | Ph | C=S | H |
| 2154 | H | H | A4 | A4 | Ph | C=S | H |
| 2155 | H | D1 | A4 | A4 | Ph | C=S | H |
| 2156 | H | D2 | A4 | A4 | Ph | C=S | H |
| 2157 | H | D3 | A4 | A4 | Ph | C=S | H |
| 2158 | H | H | A5 | A5 | Ph | C=S | H |
| 2159 | H | D1 | A5 | A5 | Ph | C=S | H |
| 2160 | H | D2 | A5 | A5 | Ph | C=S | H |
| 2161 | H | D3 | A5 | A5 | Ph | C=S | H |
| 2162 | D1 | D1 | A1 | A1 | Ph | C=S | H |
| 2163 | D2 | D2 | A1 | A1 | Ph | C=S | H |
| 2164 | D3 | D3 | A1 | A1 | Ph | C=S | H |
| 2165 | D1 | D1 | A2 | A2 | Ph | C=S | H |

TABLE 11-continued

| Compound No. | R² | R⁷ | R¹⁰ | R¹⁵ | R¹⁷ | Z | Other Rs |
|---|---|---|---|---|---|---|---|
| 2166 | D2 | D2 | A2 | A2 | Ph | C=S | H |
| 2167 | D3 | D3 | A2 | A2 | Ph | C=S | H |
| 2168 | D1 | D1 | A3 | A3 | Ph | C=S | H |
| 2169 | D2 | D2 | A3 | A3 | Ph | C=S | H |
| 2170 | D3 | D3 | A3 | A3 | Ph | C=S | H |
| 2171 | D1 | D1 | A4 | A4 | Ph | C=S | H |
| 2172 | D2 | D2 | A4 | A4 | Ph | C=S | H |
| 2173 | D3 | D3 | A4 | A4 | Ph | C=S | H |
| 2174 | D1 | D1 | A5 | A5 | Ph | C=S | H |
| 2175 | D2 | D2 | A5 | A5 | Ph | C=S | H |
| 2176 | D3 | D3 | A5 | A5 | Ph | C=S | H |

TABLE 12

| Compound No. | R³ | R⁶ | R¹¹ | R¹⁴ | R¹⁷ | Z | Other Rs |
|---|---|---|---|---|---|---|---|
| 2177 | H | H | H | A1 | Ph | C=S | H |
| 2178 | H | D1 | H | A1 | Ph | C=S | H |
| 2179 | H | D2 | H | A1 | Ph | C=S | H |
| 2180 | H | D3 | H | A1 | Ph | C=S | H |
| 2181 | H | H | H | A2 | Ph | C=S | H |
| 2182 | H | D1 | H | A2 | Ph | C=S | H |
| 2183 | H | D2 | H | A2 | Ph | C=S | H |
| 2184 | H | D3 | H | A2 | Ph | C=S | H |
| 2185 | H | H | H | A3 | Ph | C=S | H |
| 2186 | H | D1 | H | A3 | Ph | C=S | H |
| 2187 | H | D2 | H | A3 | Ph | C=S | H |
| 2188 | H | D3 | H | A3 | Ph | C=S | H |
| 2189 | H | H | H | A4 | Ph | C=S | H |
| 2190 | H | D1 | H | A4 | Ph | C=S | H |
| 2191 | H | D2 | H | A4 | Ph | C=S | H |
| 2192 | H | D3 | H | A4 | Ph | C=S | H |
| 2193 | H | H | H | A5 | Ph | C=S | H |
| 2194 | H | D1 | H | A5 | Ph | C=S | H |
| 2195 | H | D2 | H | A5 | Ph | C=S | H |
| 2196 | H | D3 | H | A5 | Ph | C=S | H |
| 2197 | D1 | D1 | H | A1 | Ph | C=S | H |
| 2198 | D2 | D2 | H | A1 | Ph | C=S | H |
| 2199 | D3 | D3 | H | A1 | Ph | C=S | H |
| 2200 | D1 | D1 | H | A2 | Ph | C=S | H |
| 2201 | D2 | D2 | H | A2 | Ph | C=S | H |
| 2202 | D3 | D3 | H | A2 | Ph | C=S | H |
| 2203 | D1 | D1 | H | A3 | Ph | C=S | H |
| 2204 | D2 | D2 | H | A3 | Ph | C=S | H |
| 2205 | D3 | D3 | H | A3 | Ph | C=S | H |
| 2206 | D1 | D1 | H | A4 | Ph | C=S | H |
| 2207 | D2 | D2 | H | A4 | Ph | C=S | H |
| 2208 | D3 | D3 | H | A4 | Ph | C=S | H |
| 2209 | D1 | D1 | H | A5 | Ph | C=S | H |
| 2210 | D2 | D2 | H | A5 | Ph | C=S | H |
| 2211 | D3 | D3 | H | A5 | Ph | C=S | H |
| 2212 | H | H | H | H | Ph | C=S | H |

TABLE 13

| Compound No. | R² | R⁷ | R¹⁰ | R¹⁵ | R¹⁷ | Z | Other Rs |
|---|---|---|---|---|---|---|---|
| 2213 | H | H | A1 | A1 | Ph | C=C(CN)₂ | H |
| 2214 | H | D1 | A1 | A1 | Ph | C=C(CN)₂ | H |
| 2215 | H | D2 | A1 | A1 | Ph | C=C(CN)₂ | H |
| 2216 | H | D3 | A1 | A1 | Ph | C=C(CN)₂ | H |
| 2217 | H | H | A2 | A2 | Ph | C=C(CN)₂ | H |
| 2218 | H | D1 | A2 | A2 | Ph | C=C(CN)₂ | H |
| 2219 | H | D2 | A2 | A2 | Ph | C=C(CN)₂ | H |
| 2220 | H | D3 | A2 | A2 | Ph | C=C(CN)₂ | H |
| 2221 | H | H | A3 | A3 | Ph | C=C(CN)₂ | H |
| 2222 | H | D1 | A3 | A3 | Ph | C=C(CN)₂ | H |
| 2223 | H | D2 | A3 | A3 | Ph | C=C(CN)₂ | H |
| 2224 | H | D3 | A3 | A3 | Ph | C=C(CN)₂ | H |
| 2225 | H | H | A4 | A4 | Ph | C=C(CN)₂ | H |
| 2226 | H | D1 | A4 | A4 | Ph | C=C(CN)₂ | H |
| 2227 | H | D2 | A4 | A4 | Ph | C=C(CN)₂ | H |
| 2228 | H | D3 | A4 | A4 | Ph | C=C(CN)₂ | H |

TABLE 13-continued

| Compound No. | R² | R⁷ | R¹⁰ | R¹⁵ | R¹⁷ | Z | Other Rs |
|---|---|---|---|---|---|---|---|
| 2229 | H | H | A5 | A5 | Ph | C=C(CN)₂ | H |
| 2230 | H | D1 | A5 | A5 | Ph | C=C(CN)₂ | H |
| 2231 | H | D2 | A5 | A5 | Ph | C=C(CN)₂ | H |
| 2232 | H | D3 | A5 | A5 | Ph | C=C(CN)₂ | H |
| 2233 | D1 | D1 | A1 | A1 | Ph | C=C(CN)₂ | H |
| 2234 | D2 | D2 | A1 | A1 | Ph | C=C(CN)₂ | H |
| 2235 | D3 | D3 | A1 | A1 | Ph | C=C(CN)₂ | H |
| 2236 | D1 | D1 | A2 | A2 | Ph | C=C(CN)₂ | H |
| 2237 | D2 | D2 | A2 | A2 | Ph | C=C(CN)₂ | H |
| 2238 | D3 | D3 | A2 | A2 | Ph | C=C(CN)₂ | H |
| 2239 | D1 | D1 | A3 | A3 | Ph | C=C(CN)₂ | H |
| 2240 | D2 | D2 | A3 | A3 | Ph | C=C(CN)₂ | H |
| 2241 | D3 | D3 | A3 | A3 | Ph | C=C(CN)₂ | H |
| 2242 | D1 | D1 | A4 | A4 | Ph | C=C(CN)₂ | H |
| 2243 | D2 | D2 | A4 | A4 | Ph | C=C(CN)₂ | H |
| 2244 | D3 | D3 | A4 | A4 | Ph | C=C(CN)₂ | H |
| 2245 | D1 | D1 | A5 | A5 | Ph | C=C(CN)₂ | H |
| 2246 | D2 | D2 | A5 | A5 | Ph | C=C(CN)₂ | H |
| 2247 | D3 | D3 | A5 | A5 | Ph | C=C(CN)₂ | H |

TABLE 14

| Compound No. | R³ | R⁶ | R¹¹ | R¹⁴ | R¹⁷ | Z | Other Rs |
|---|---|---|---|---|---|---|---|
| 2248 | H | H | H | A1 | Ph | C=C(CN)₂ | H |
| 2249 | H | D1 | H | A1 | Ph | C=C(CN)₂ | H |
| 2250 | H | D2 | H | A1 | Ph | C=C(CN)₂ | H |
| 2251 | H | D3 | H | A1 | Ph | C=C(CN)₂ | H |
| 2252 | H | H | H | A2 | Ph | C=C(CN)₂ | H |
| 2253 | H | D1 | H | A2 | Ph | C=C(CN)₂ | H |
| 2254 | H | D2 | H | A2 | Ph | C=C(CN)₂ | H |
| 2255 | H | D3 | H | A2 | Ph | C=C(CN)₂ | H |
| 2256 | H | H | H | A3 | Ph | C=C(CN)₂ | H |
| 2257 | H | D1 | H | A3 | Ph | C=C(CN)₂ | H |
| 2258 | H | D2 | H | A3 | Ph | C=C(CN)₂ | H |
| 2259 | H | D3 | H | A3 | Ph | C=C(CN)₂ | H |
| 2260 | H | H | H | A4 | Ph | C=C(CN)₂ | H |
| 2261 | H | D1 | H | A4 | Ph | C=C(CN)₂ | H |
| 2262 | H | D2 | H | A4 | Ph | C=C(CN)₂ | H |
| 2263 | H | D3 | H | A4 | Ph | C=C(CN)₂ | H |
| 2264 | H | H | H | A5 | Ph | C=C(CN)₂ | H |
| 2265 | H | D1 | H | A5 | Ph | C=C(CN)₂ | H |
| 2266 | H | D2 | H | A5 | Ph | C=C(CN)₂ | H |
| 2267 | H | D3 | H | A5 | Ph | C=C(CN)₂ | H |
| 2268 | D1 | D1 | H | A1 | Ph | C=C(CN)₂ | H |
| 2269 | D2 | D2 | H | A1 | Ph | C=C(CN)₂ | H |
| 2270 | D3 | D3 | H | A1 | Ph | C=C(CN)₂ | H |
| 2271 | D1 | D1 | H | A2 | Ph | C=C(CN)₂ | H |
| 2272 | D2 | D2 | H | A2 | Ph | C=C(CN)₂ | H |
| 2273 | D3 | D3 | H | A2 | Ph | C=C(CN)₂ | H |
| 2274 | D1 | D1 | H | A3 | Ph | C=C(CN)₂ | H |
| 2275 | D2 | D2 | H | A3 | Ph | C=C(CN)₂ | H |
| 2276 | D3 | D3 | H | A3 | Ph | C=C(CN)₂ | H |
| 2277 | D1 | D1 | H | A4 | Ph | C=C(CN)₂ | H |
| 2278 | D2 | D2 | H | A4 | Ph | C=C(CN)₂ | H |
| 2279 | D3 | D3 | H | A4 | Ph | C=C(CN)₂ | H |
| 2280 | D1 | D1 | H | A5 | Ph | C=C(CN)₂ | H |
| 2281 | D2 | D2 | H | A5 | Ph | C=C(CN)₂ | H |
| 2282 | D3 | D3 | H | A5 | Ph | C=C(CN)₂ | H |
| 2283 | H | H | H | H | Ph | C=C(CN)₂ | H |

TABLE 15

| Compound No. | R² | R⁷ | R¹⁰ | R¹⁵ | R¹⁷ | Z | Other Rs |
|---|---|---|---|---|---|---|---|
| 2284 | H | H | A1 | A1 | Ph | C=C(COOH)₂ | H |
| 2285 | H | D1 | A1 | A1 | Ph | C=C(COOH)₂ | H |
| 2286 | H | D2 | A1 | A1 | Ph | C=C(COOH)₂ | H |
| 2287 | H | D3 | A1 | A1 | Ph | C=C(COOH)₂ | H |
| 2288 | H | H | A2 | A2 | Ph | C=C(COOH)₂ | H |
| 2289 | H | D1 | A2 | A2 | Ph | C=C(COOH)₂ | H |
| 2290 | H | D2 | A2 | A2 | Ph | C=C(COOH)₂ | H |
| 2291 | H | D3 | A2 | A2 | Ph | C=C(COOH)₂ | H |

TABLE 15-continued

| Compound No. | $R^2$ | $R^7$ | $R^{10}$ | $R^{15}$ | $R^{17}$ | Z | Other Rs |
|---|---|---|---|---|---|---|---|
| 2292 | H | H | A3 | A3 | Ph | C=C(COOH)$_2$ | H |
| 2293 | H | D1 | A3 | A3 | Ph | C=C(COOH)$_2$ | H |
| 2294 | H | D2 | A3 | A3 | Ph | C=C(COOH)$_2$ | H |
| 2295 | H | D3 | A3 | A3 | Ph | C=C(COOH)$_2$ | H |
| 2296 | H | H | A4 | A4 | Ph | C=C(COOH)$_2$ | H |
| 2297 | H | D1 | A4 | A4 | Ph | C=C(COOH)$_2$ | H |
| 2298 | H | D2 | A4 | A4 | Ph | C=C(COOH)$_2$ | H |
| 2299 | H | D3 | A4 | A4 | Ph | C=C(COOH)$_2$ | H |
| 2300 | H | H | A5 | A5 | Ph | C=C(COOH)$_2$ | H |
| 2301 | H | D1 | A5 | A5 | Ph | C=C(COOH)$_2$ | H |
| 2302 | H | D2 | A5 | A5 | Ph | C=C(COOH)$_2$ | H |
| 2303 | H | D3 | A5 | A5 | Ph | C=C(COOH)$_2$ | H |
| 2304 | D1 | D1 | A1 | A1 | Ph | C=C(COOH)$_2$ | H |
| 2305 | D2 | D2 | A1 | A1 | Ph | C=C(COOH)$_2$ | H |
| 2306 | D3 | D3 | A1 | A1 | Ph | C=C(COOH)$_2$ | H |
| 2307 | D1 | D1 | A2 | A2 | Ph | C=C(COOH)$_2$ | H |
| 2308 | D2 | D2 | A2 | A2 | Ph | C=C(COOH)$_2$ | H |
| 2309 | D3 | D3 | A2 | A2 | Ph | C=C(COOH)$_2$ | H |
| 2310 | D1 | D1 | A3 | A3 | Ph | C=C(COOH)$_2$ | H |
| 2311 | D2 | D2 | A3 | A3 | Ph | C=C(COOH)$_2$ | H |
| 2312 | D3 | D3 | A3 | A3 | Ph | C=C(COOH)$_2$ | H |
| 2313 | D1 | D1 | A4 | A4 | Ph | C=C(COOH)$_2$ | H |
| 2314 | D2 | D2 | A4 | A4 | Ph | C=C(COOH)$_2$ | H |
| 2315 | D3 | D3 | A4 | A4 | Ph | C=C(COOH)$_2$ | H |
| 2316 | D1 | D1 | A5 | A5 | Ph | C=C(COOH)$_2$ | H |
| 2317 | D2 | D2 | A5 | A5 | Ph | C=C(COOH)$_2$ | H |
| 2318 | D3 | D3 | A5 | A5 | Ph | C=C(COOH)$_2$ | H |

TABLE 16

| Compound No. | $R^3$ | $R^6$ | $R^{11}$ | $R^{14}$ | $R^{17}$ | Z | Other Rs |
|---|---|---|---|---|---|---|---|
| 2319 | H | H | H | A1 | Ph | C=C(COOH)$_2$ | H |
| 2320 | H | D1 | H | A1 | Ph | C=C(COOH)$_2$ | H |
| 2321 | H | D2 | H | A1 | Ph | C=C(COOH)$_2$ | H |
| 2322 | H | D3 | H | A1 | Ph | C=C(COOH)$_2$ | H |
| 2323 | H | H | H | A2 | Ph | C=C(COOH)$_2$ | H |
| 2324 | H | D1 | H | A2 | Ph | C=C(COOH)$_2$ | H |
| 2325 | H | D2 | H | A2 | Ph | C=C(COOH)$_2$ | H |
| 2326 | H | D3 | H | A2 | Ph | C=C(COOH)$_2$ | H |
| 2327 | H | H | H | A3 | Ph | C=C(COOH)$_2$ | H |
| 2328 | H | D1 | H | A3 | Ph | C=C(COOH)$_2$ | H |
| 2329 | H | D2 | H | A3 | Ph | C=C(COOH)$_2$ | H |
| 2330 | H | D3 | H | A3 | Ph | C=C(COOH)$_2$ | H |
| 2331 | H | H | H | A4 | Ph | C=C(COOH)$_2$ | H |
| 2332 | H | D1 | H | A4 | Ph | C=C(COOH)$_2$ | H |
| 2333 | H | D2 | H | A4 | Ph | C=C(COOH)$_2$ | H |
| 2334 | H | D3 | H | A4 | Ph | C=C(COOH)$_2$ | H |
| 2335 | H | H | H | A5 | Ph | C=C(COOH)$_2$ | H |
| 2336 | H | D1 | H | A5 | Ph | C=C(COOH)$_2$ | H |
| 2337 | H | D2 | H | A5 | Ph | C=C(COOH)$_2$ | H |
| 2338 | H | D3 | H | A5 | Ph | C=C(COOH)$_2$ | H |
| 2339 | D1 | D1 | H | A1 | Ph | C=C(COOH)$_2$ | H |
| 2340 | D2 | D2 | H | A1 | Ph | C=C(COOH)$_2$ | H |
| 2341 | D3 | D3 | H | A1 | Ph | C=C(COOH)$_2$ | H |
| 2342 | D1 | D1 | H | A2 | Ph | C=C(COOH)$_2$ | H |
| 2343 | D2 | D2 | H | A2 | Ph | C=C(COOH)$_2$ | H |
| 2344 | D3 | D3 | H | A2 | Ph | C=C(COOH)$_2$ | H |
| 2345 | D1 | D1 | H | A3 | Ph | C=C(COOH)$_2$ | H |
| 2346 | D2 | D2 | H | A3 | Ph | C=C(COOH)$_2$ | H |
| 2347 | D3 | D3 | H | A3 | Ph | C=C(COOH)$_2$ | H |
| 2348 | D1 | D1 | H | A4 | Ph | C=C(COOH)$_2$ | H |
| 2349 | D2 | D2 | H | A4 | Ph | C=C(COOH)$_2$ | H |
| 2350 | D3 | D3 | H | A4 | Ph | C=C(COOH)$_2$ | H |
| 2351 | D1 | D1 | H | A5 | Ph | C=C(COOH)$_2$ | H |
| 2352 | D2 | D2 | H | A5 | Ph | C=C(COOH)$_2$ | H |
| 2353 | D3 | D3 | H | A5 | Ph | C=C(COOH)$_2$ | H |
| 2354 | H | H | H | H | Ph | C=C(COOH)$_2$ | H |

Examples of the preferred light-emitting material include compounds represented by the following general formula (151). The entire description of WO 2013/011955 including the paragraphs 0007 to 0033 and 0059 to 0066 is incorporated herein by reference.

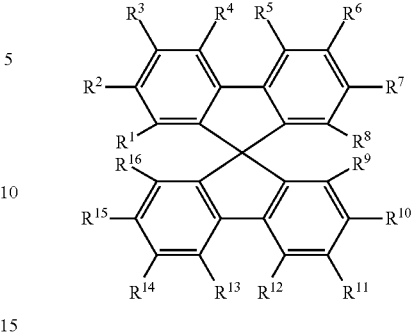

General Formula (151)

wherein in the general formula (151), $R^1$, $R^2$, $R^3$, $R^4$, $R^5$, $R^6$, $R^7$ and $R^8$ each independently represent a hydrogen atom or an electron donating group, provided that at least one thereof represents an electron donating group; $R^9$, $R^{10}$, $R^{11}$, $R^{12}$, $R^{13}$, $R^{14}$, $R^{15}$ and $R^{16}$ each independently represent a hydrogen atom or an electron withdrawing group, provided that at least one thereof represents an electron withdrawing group.

Specific examples of the compounds include the compounds shown in the following tables. In the tables, D1 to D10 represent the unsubstituted electron donating groups having the following structures, respectively.

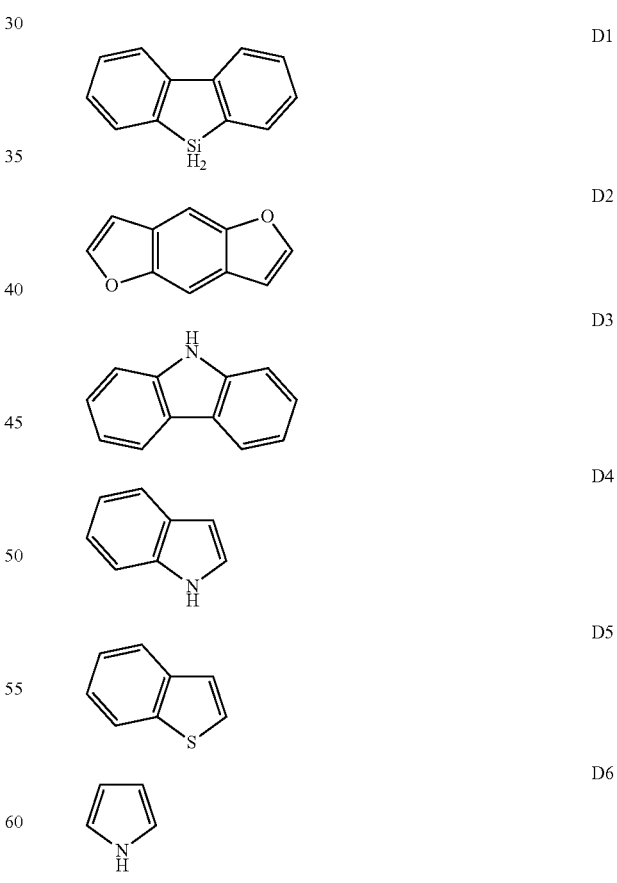

-continued

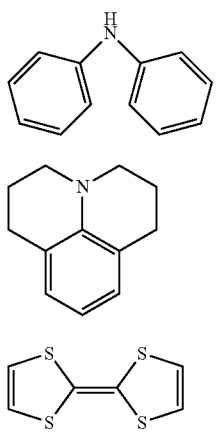

TABLE 17

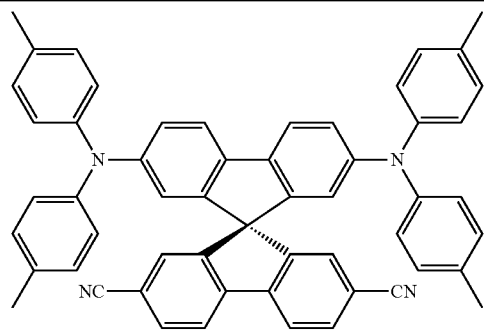

Compound 3001

| Compound No. | $R^2$ | $R^7$ | $R^{10}$ | $R^{15}$ | Other Rs |
|---|---|---|---|---|---|
| 3002 | D1 | D1 | CN | CN | H |
| 3003 | D2 | D2 | CN | CN | H |
| 3004 | D3 | D3 | CN | CN | H |
| 3005 | D4 | D4 | CN | CN | H |
| 3006 | D5 | D5 | CN | CN | H |
| 3007 | D6 | D6 | CN | CN | H |
| 3008 | D7 | D7 | CN | CN | H |
| 3009 | D8 | D8 | CN | CN | H |
| 3010 | D9 | D9 | CN | CN | H |
| 3011 | D10 | D10 | CN | CN | H |
| 3012 | H | D1 | H | CN | H |
| 3013 | H | D2 | H | CN | H |

TABLE 17-continued

Compound 3001

| Compound No. | $R^2$ | $R^7$ | $R^{10}$ | $R^{15}$ | Other Rs |
|---|---|---|---|---|---|
| 3014 | H | D3 | H | CN | H |
| 3015 | H | D4 | H | CN | H |
| 3016 | H | D5 | H | CN | H |
| 3017 | H | D6 | H | CN | H |
| 3018 | H | D7 | H | CN | H |
| 3019 | H | D8 | H | CN | H |
| 3020 | H | D9 | H | CN | H |
| 3021 | H | D10 | H | CN | H |

TABLE 18

| Compound No. | $R^3$ | $R^6$ | $R^{11}$ | $R^{14}$ | Other Rs |
|---|---|---|---|---|---|
| 3022 | D1 | D1 | CN | CN | H |
| 3023 | D2 | D2 | CN | CN | H |
| 3024 | D3 | D3 | CN | CN | H |
| 3025 | D4 | D4 | CN | CN | H |
| 3026 | D5 | D5 | CN | CN | H |
| 3027 | D6 | D6 | CN | CN | H |
| 3028 | D7 | D7 | CN | CN | H |
| 3029 | D8 | D8 | CN | CN | H |
| 3030 | D9 | D9 | CN | CN | H |
| 3031 | D10 | D10 | CN | CN | H |
| 3032 | H | D1 | H | CN | H |
| 3033 | H | D2 | H | CN | H |
| 3034 | H | D3 | H | CN | H |
| 3035 | H | D4 | H | CN | H |
| 3036 | H | D5 | H | CN | H |
| 3037 | H | D6 | H | CN | H |
| 3038 | H | D7 | H | CN | H |
| 3039 | H | D8 | H | CN | H |
| 3040 | H | D9 | H | CN | H |
| 3041 | H | D10 | H | CN | H |

TABLE 19

| Compound No. | $R^2, R^7$ | $R^3, R^6, R^{10}, R^{15}$ | $R^{11}, R^{14}$ | Other Rs |
|---|---|---|---|---|
| 3042 | diphenylamino group | H | CN | H |
| 3043 | bis (2-methylphenyl) amino group | H | CN | H |
| 3044 | bis (3-methylphenyl) amino group | H | CN | H |
| 3045 | bis (2,4-dimethylphenyl) amino group | H | CN | H |
| 3046 | bis (2,6-dimethylphenyl) amino group | H | CN | H |
| 3047 | bis (3,5-dimethylphenyl) amino group | H | CN | H |
| 3048 | bis (2,4,6-trimethylphenyl) amino group | H | CN | H |
| 3049 | bis (4-ethylphenyl) amino group | H | CN | H |
| 3050 | bis (4-propylphenyl) amino group | H | CN | H |
| 3051 | diphenylamino group | H | H | CN | H |
| 3052 | bis (2-methylphenyl) amino group | H | H | CN | H |
| 3053 | bis (3-methylphenyl) amino group | H | H | CN | H |
| 3054 | bis (4-methylphenyl) amino group | H | H | CN | H |
| 3055 | bis (2,4-dimethylphenyl) amino group | H | H | CN | H |

TABLE 19-continued

| Compound No. | $R^2, R^7$ | $R^3, R^6$ | $R^{10}, R^{15}$ | $R^{11}, R^{14}$ | Other Rs |
|---|---|---|---|---|---|
| 3056 | bis (2,6-dimethylphenyl) amino group | H | H | CN | H |
| 3057 | bis (3,5-dimethylphenyl) amino group | H | H | CN | H |
| 3058 | bis (2,4,6-trimethylphenyl) amino group | H | H | CN | H |
| 3059 | bis (4-ethylphenyl) amino group | H | H | CN | H |
| 3060 | bis (4-propylphenyl) amino group | H | H | CN | H |

TABLE 20

| Compound No. | $R^2, R^7$ | $R^3, R^6$ | $R^{10}, R^{15}$ | $R^{11}, R^{14}$ | Other Rs |
|---|---|---|---|---|---|
| 3061 | H | diphenylamino group | CN | H | H |
| 3062 | H | bis (2-methylphenyl) amino group | CN | H | H |
| 3063 | H | bis (3-methylphenyl) amino group | CN | H | H |
| 3064 | H | bis (4-methylphenyl) amino group | CN | H | H |
| 3065 | H | bis (2,4-dimethylphenyl) amino group | CN | H | H |
| 3066 | H | bis (2,6-dimethylphenyl) amino group | CN | H | H |
| 3067 | H | bis (3,5-dimethylphenyl) amino group | CN | H | H |
| 3068 | H | bis (2,4,6-trimethylphenyl) amino group | CN | H | H |
| 3069 | H | bis (4-ethylphenyl) amino group | CN | H | H |
| 3070 | H | bis (4-propylphenyl) amino group | CN | H | H |
| 3071 | H | diphenylamino group | H | CN | H |
| 3072 | H | bis (2-methylphenyl) amino group | H | CN | H |
| 3073 | H | bis (3-methylphenyl) amino group | H | CN | H |
| 3074 | H | bis (4-methylphenyl) amino group | H | CN | H |
| 3075 | H | bis (2,4-dimethylphenyl) amino group | H | CN | H |
| 3076 | H | bis (2,6-dimethylphenyl) amino group | H | CN | H |
| 3077 | H | bis (3,5-dimethylphenyl) amino group | H | CN | H |
| 3078 | H | bis (2,4,6-trimethylphenyl) amino group | H | CN | H |
| 3079 | H | bis (4-ethylphenyl) amino group | H | CN | H |
| 3080 | H | bis (4-propylphenyl) amino group | H | CN | H |

Examples of the preferred light-emitting material include compounds represented by the following general formula (161). The entire description of WO 2013/081088 including the paragraphs 0008 to 0071 and 0118 to 0133 is incorporated herein by reference.

General Formula (161)

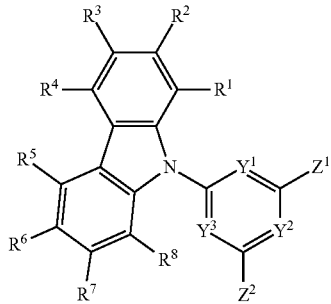

wherein in the general formula (161), any two or $Y^1$, $Y^2$ and $Y^3$ each represent a nitrogen atom, and the balance thereof represents a methine group, or all $Y^1$, $Y^2$ and $Y^3$ each represent a nitrogen atom; $Z^1$ and $Z^2$ each independently represent a hydrogen atom or a substituent; and $R^1$ to $R^8$ each independently represent a hydrogen atom or a substituent, provided that at least one of $R^1$ to $R^8$ represents a substituted or unsubstituted diarylamino group or a substituted or unsubstituted carbazolyl group. The compound represented by the general formula (161) has at least two carbazole structures in the molecule thereof.

Examples of the compound include the following compounds.

1

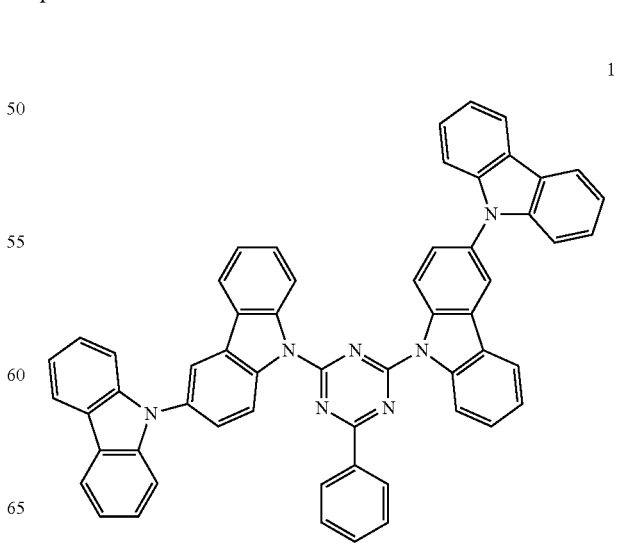

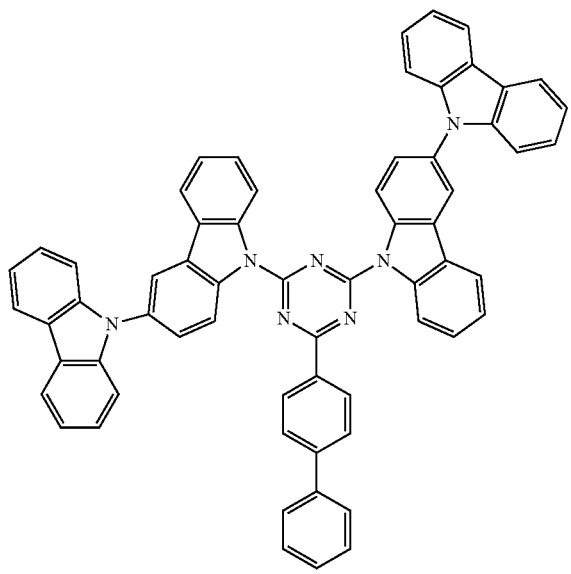
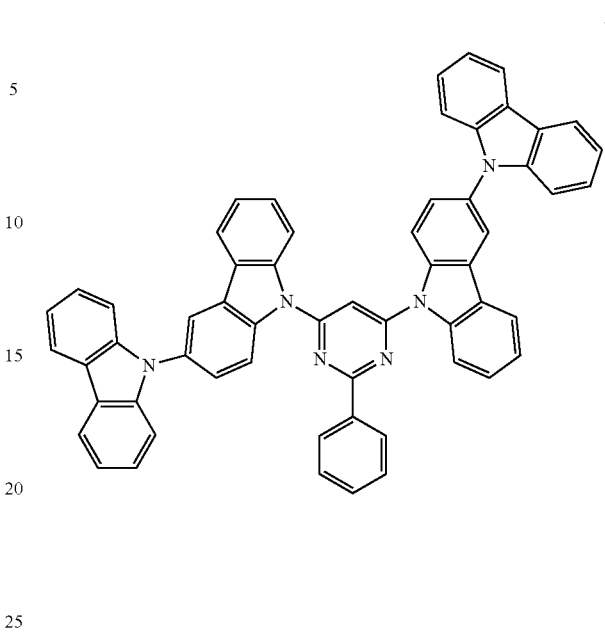
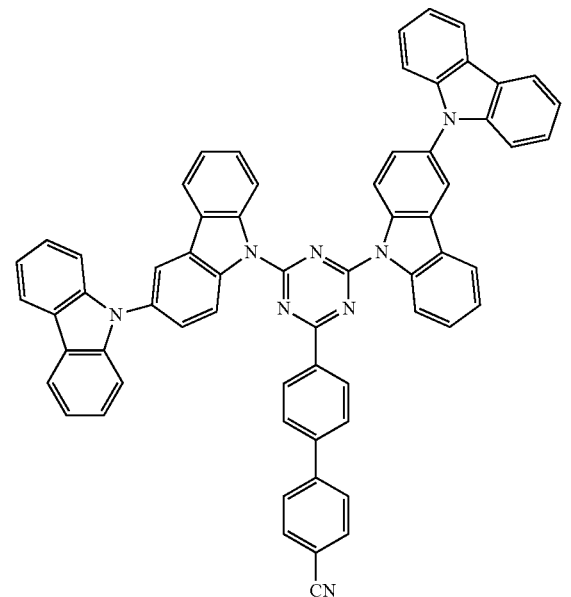
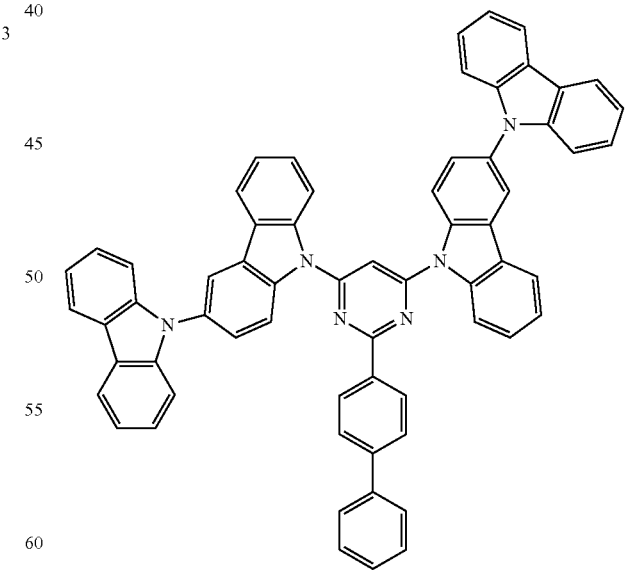

-continued
6
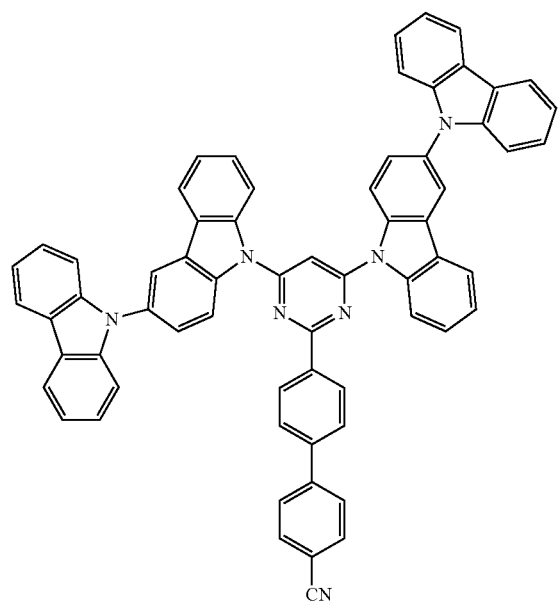
7
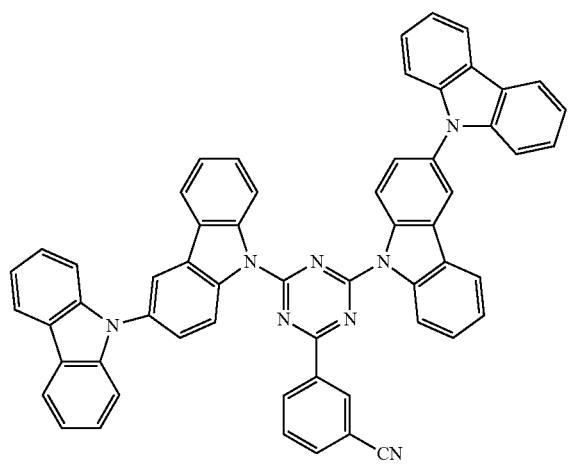
8
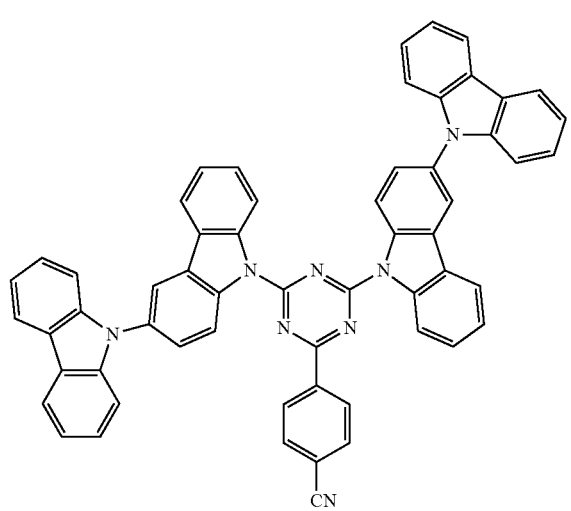
-continued
9
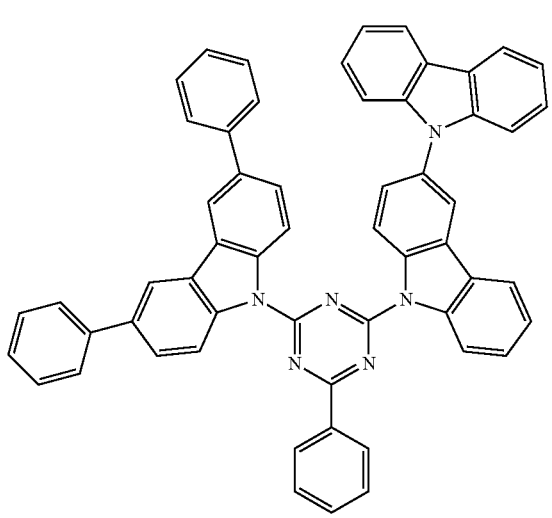
10
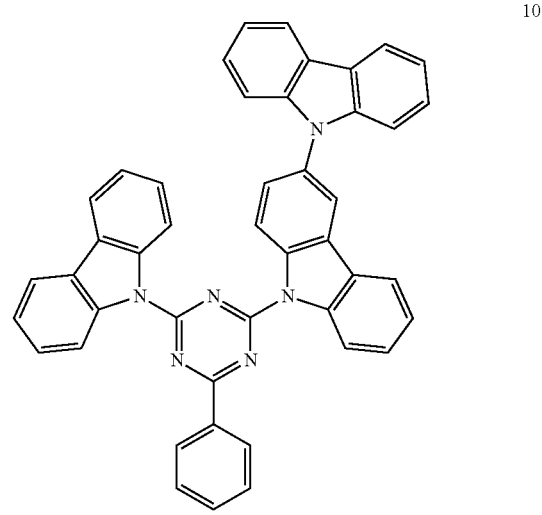
11
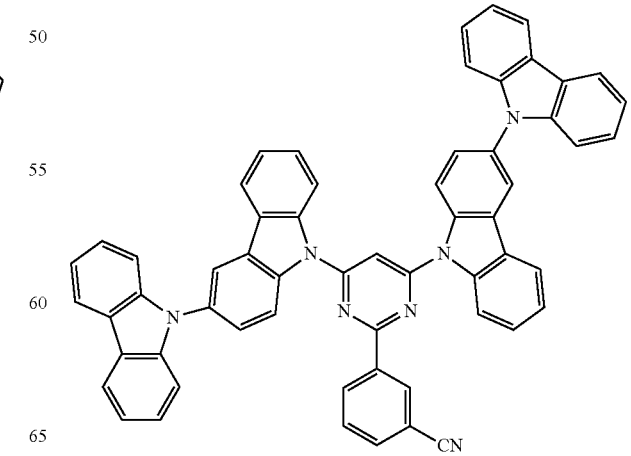

12
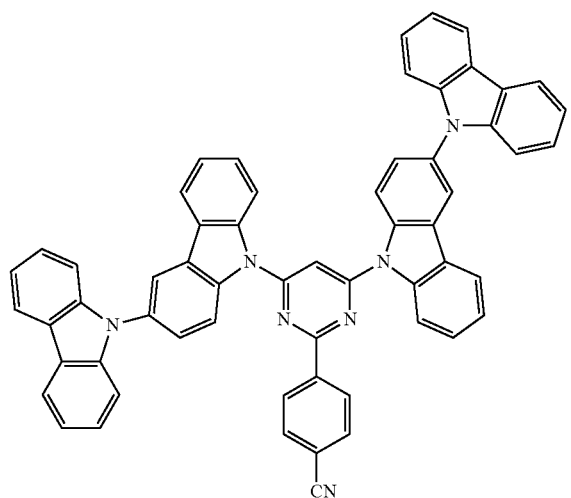
13
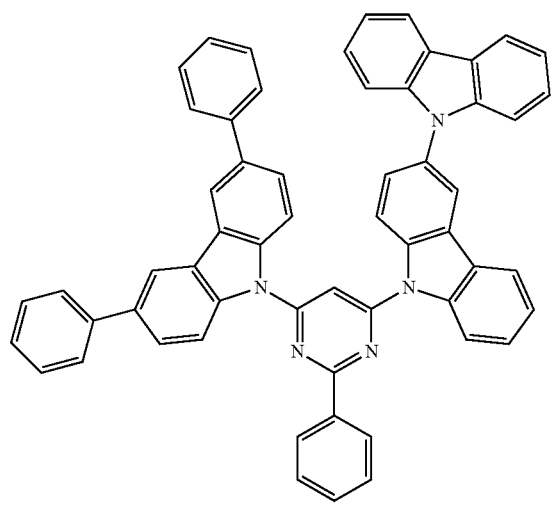
14
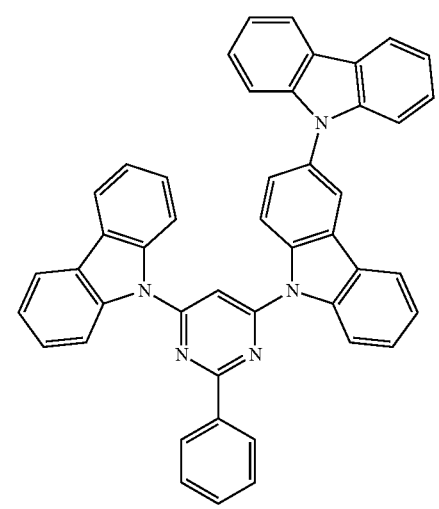
15
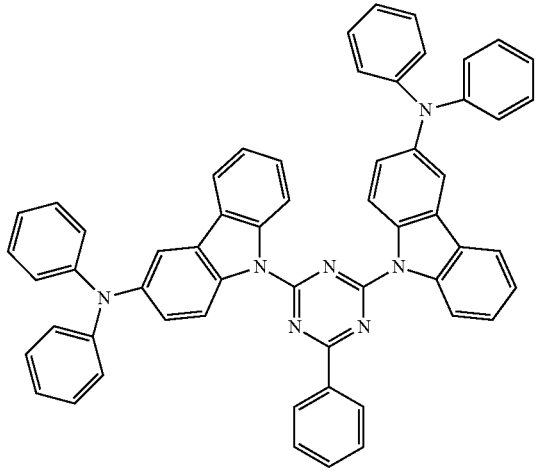
16
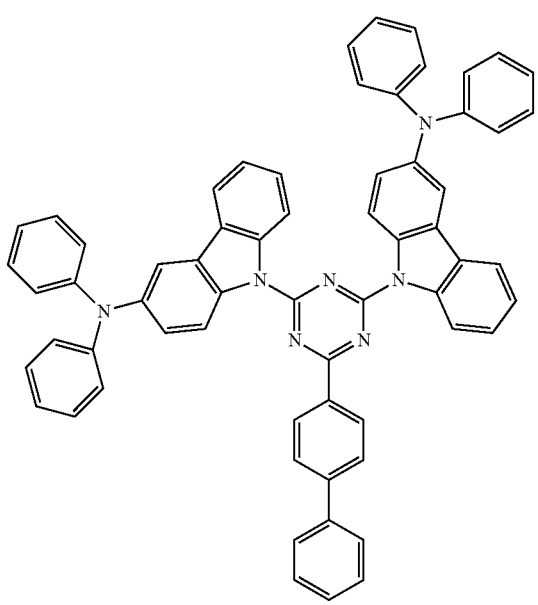
17
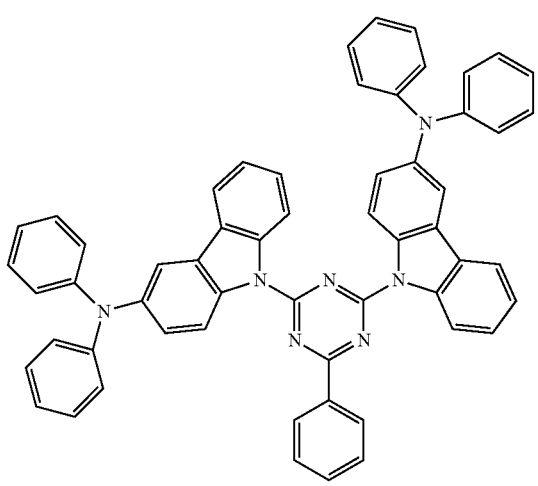

18
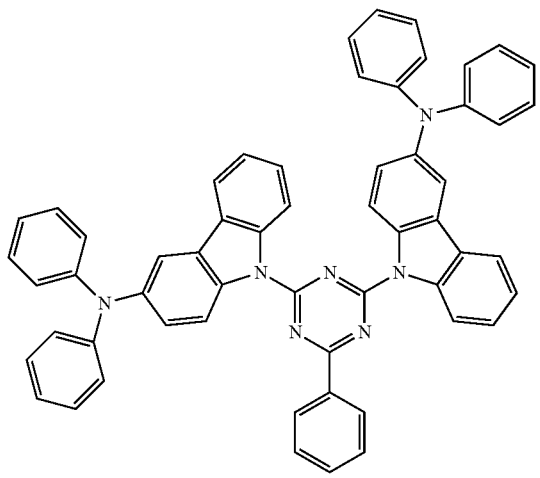
19
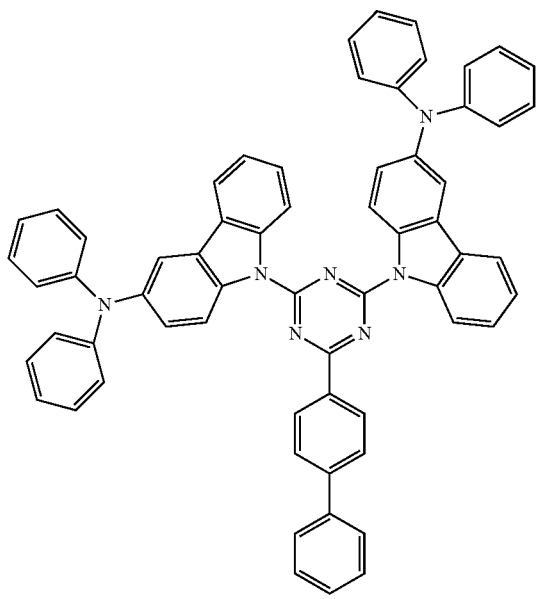
20
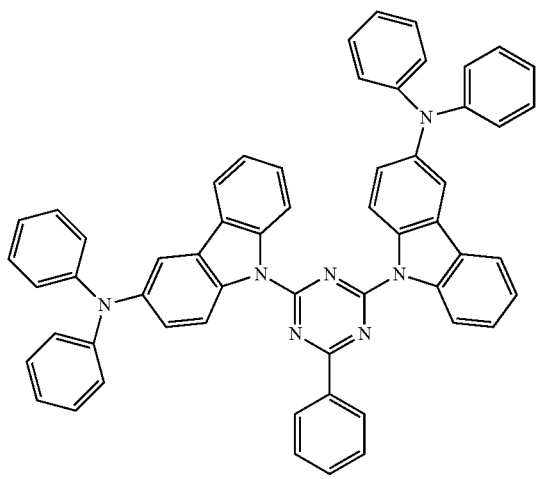
21
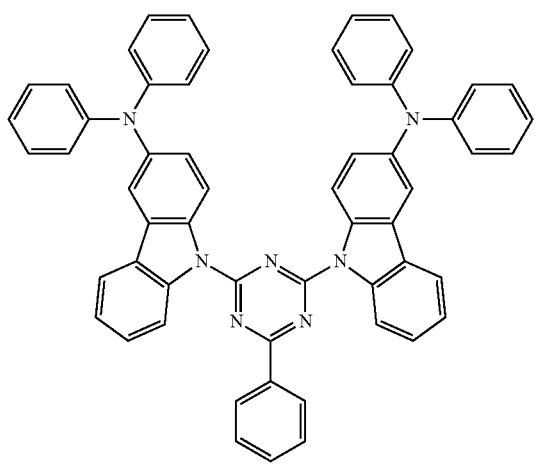
22
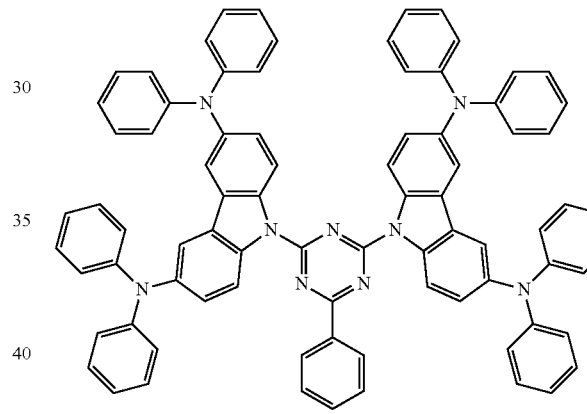
23
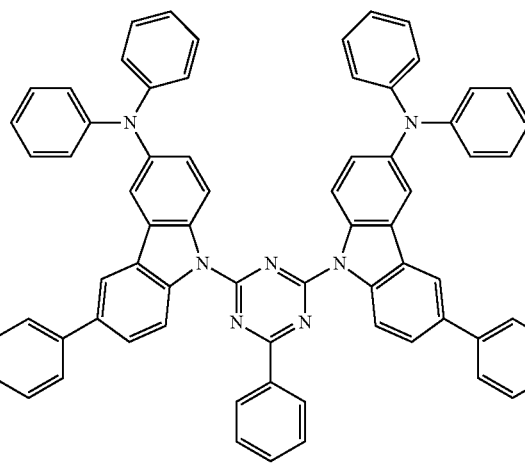

24
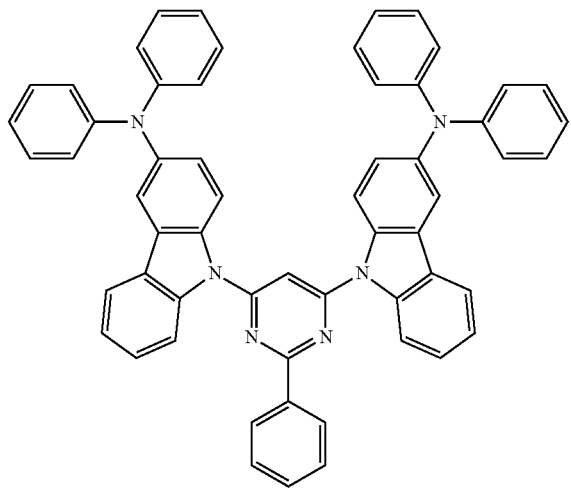
25
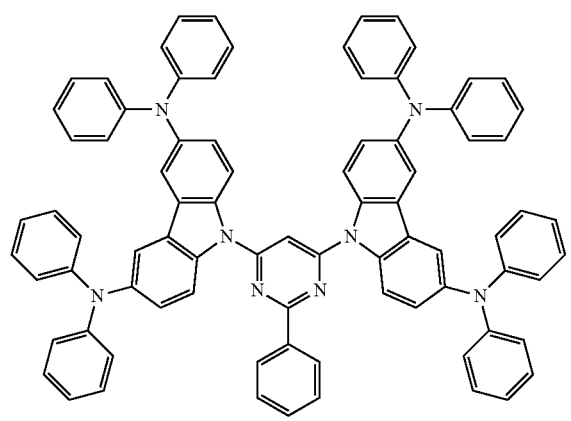
26
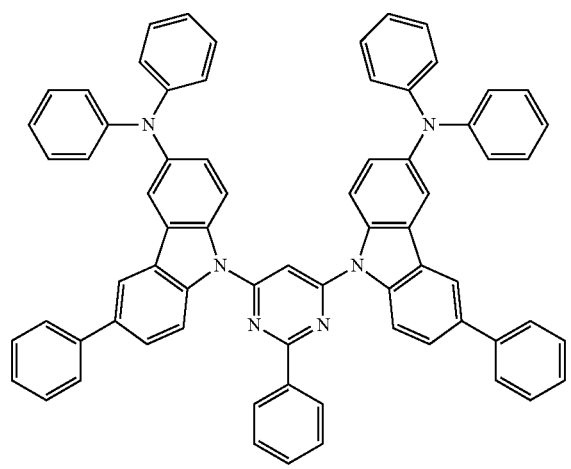
27
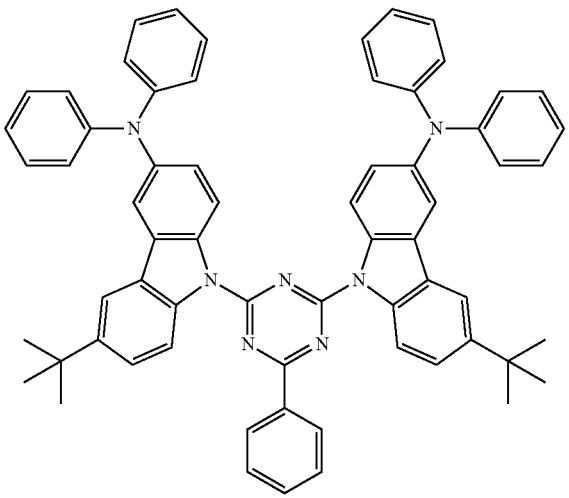
28
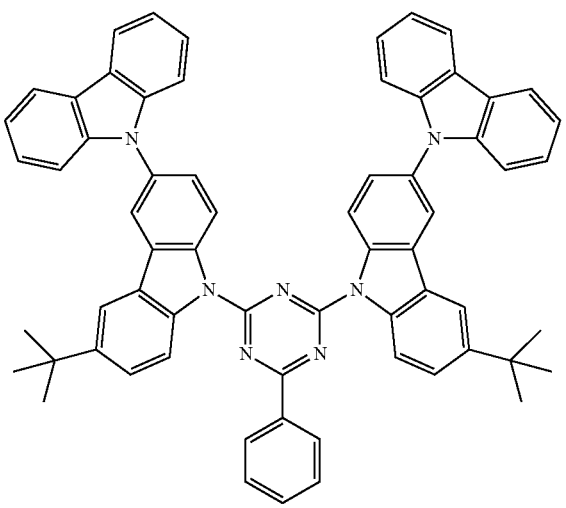
29
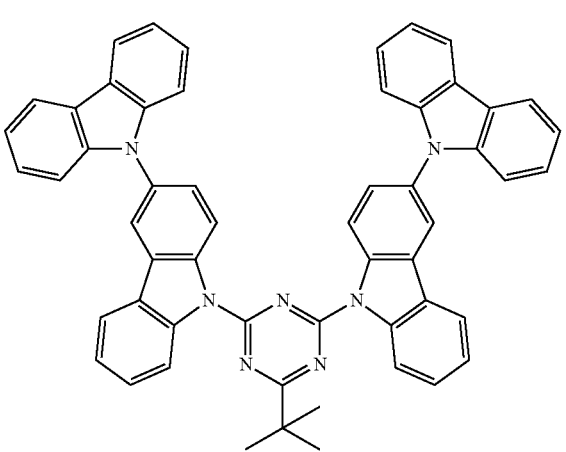

30
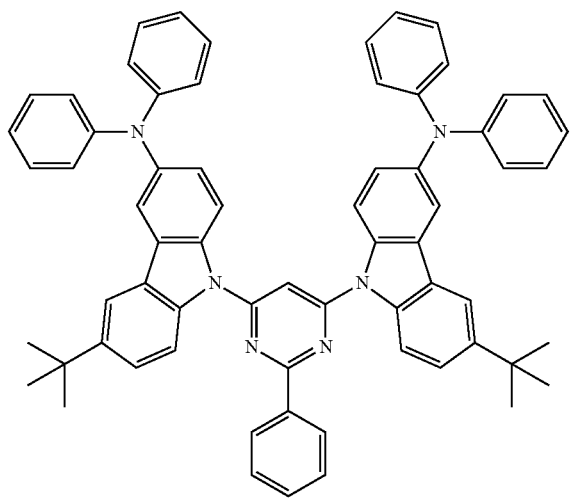
31
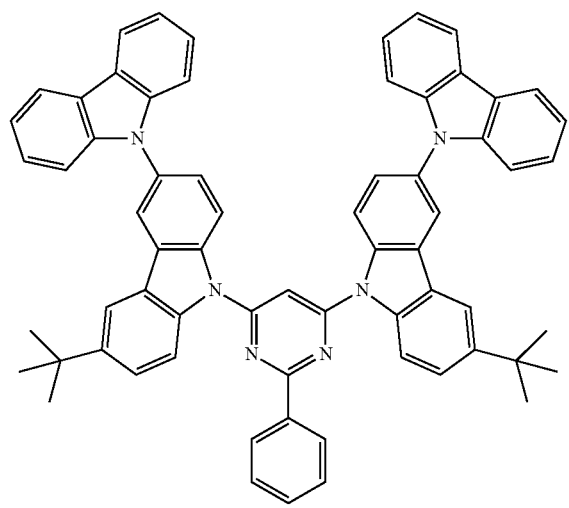
32
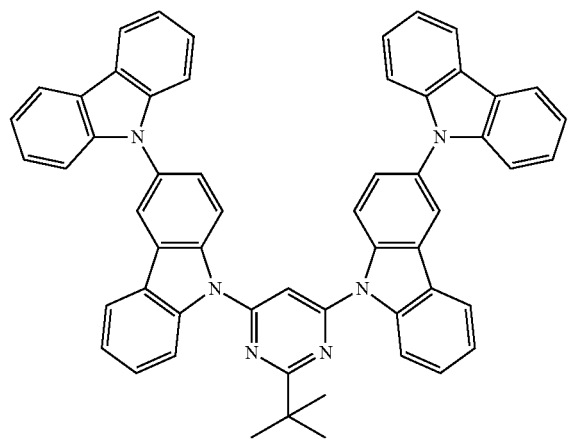
33
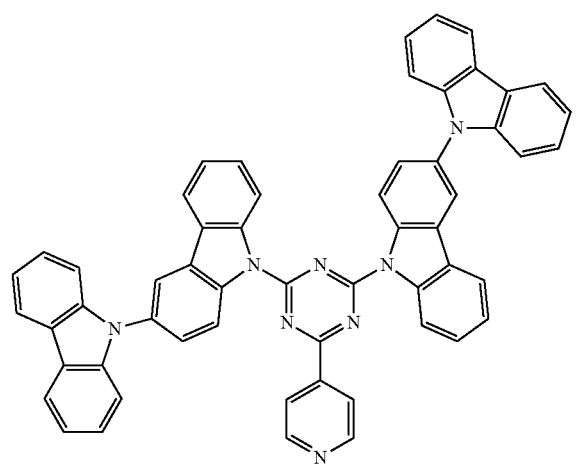
34
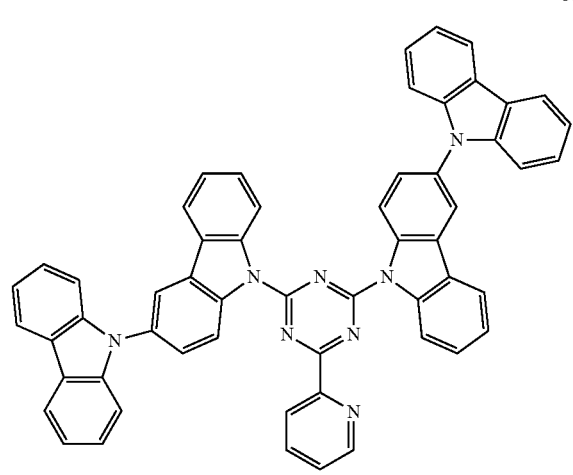
35

36
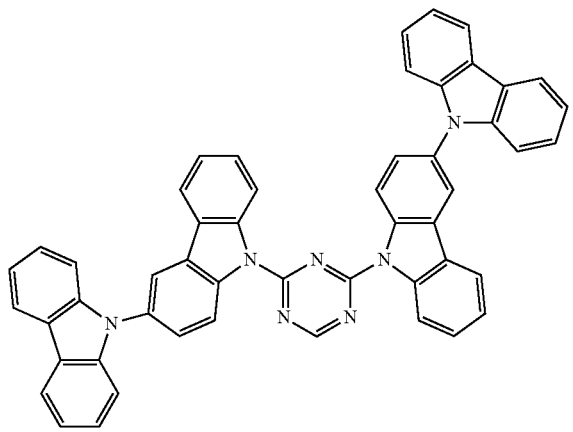
37
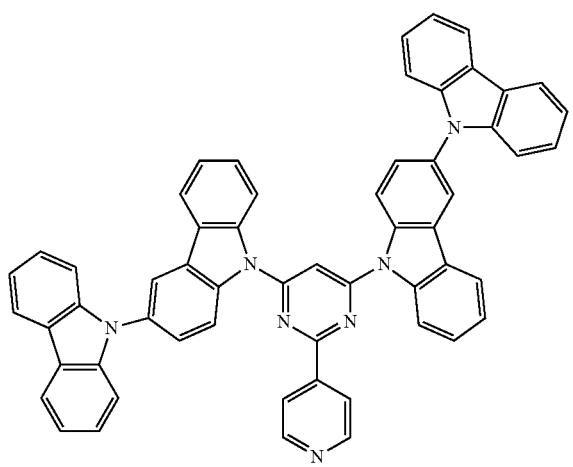
38
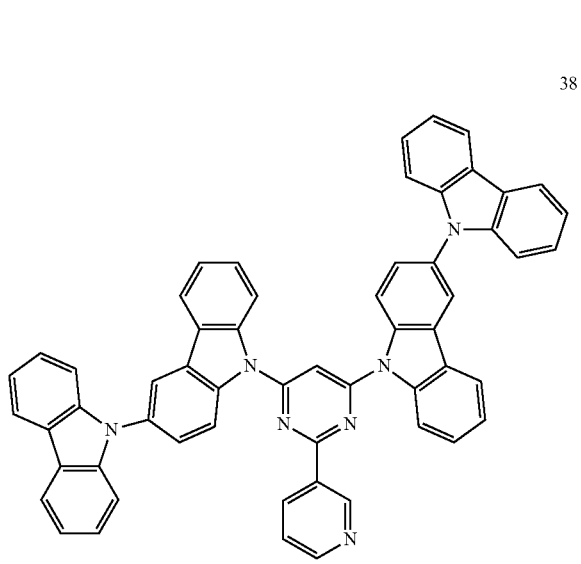
39
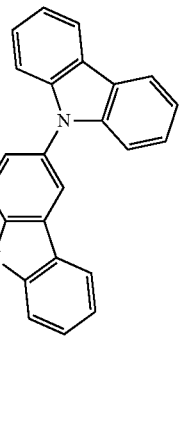
40
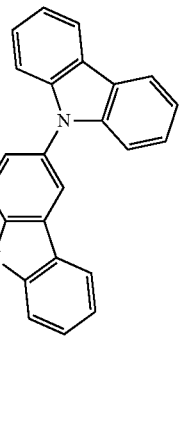
41
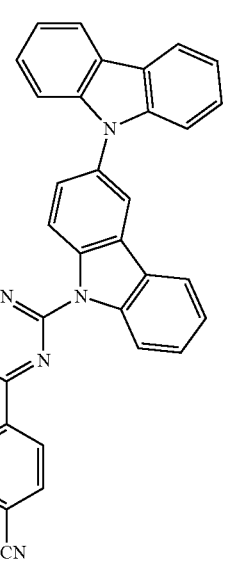

-continued
42
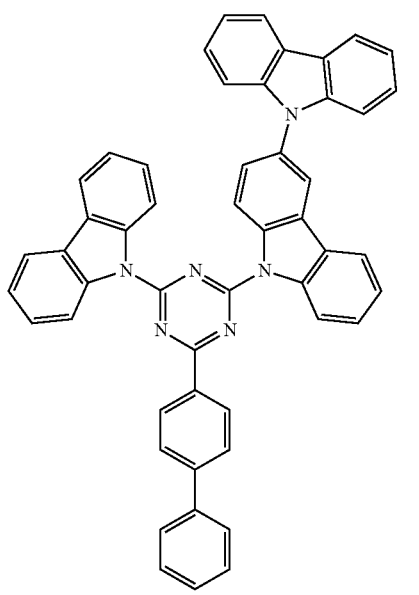
43
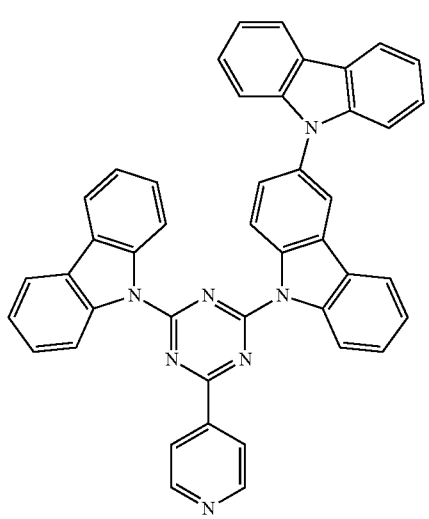
44
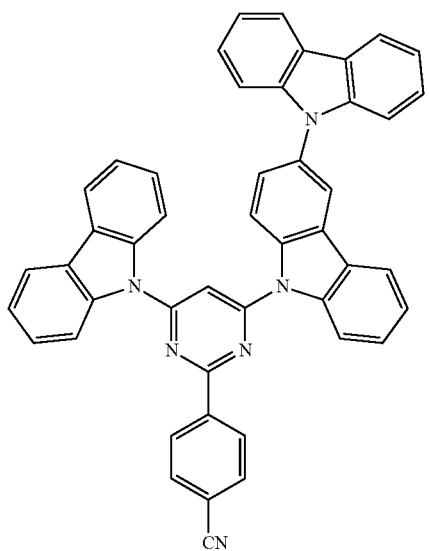
-continued
45
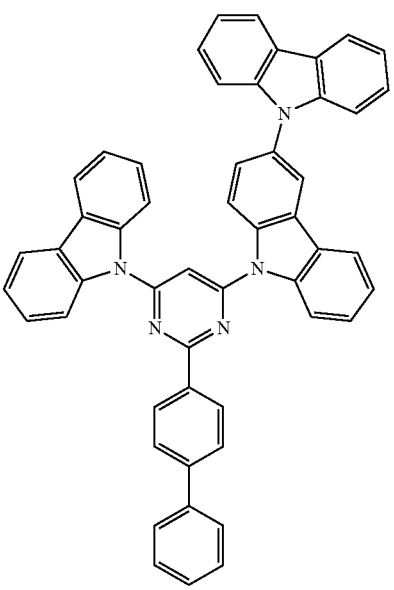
46
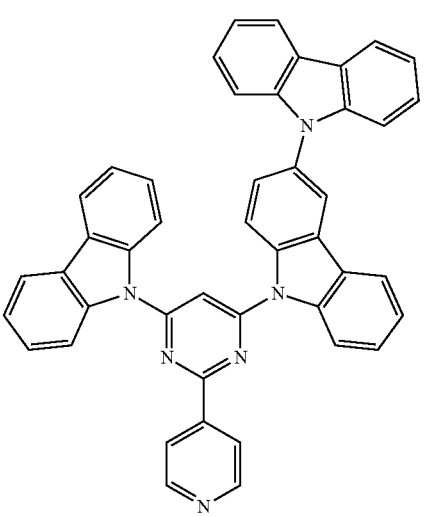
47
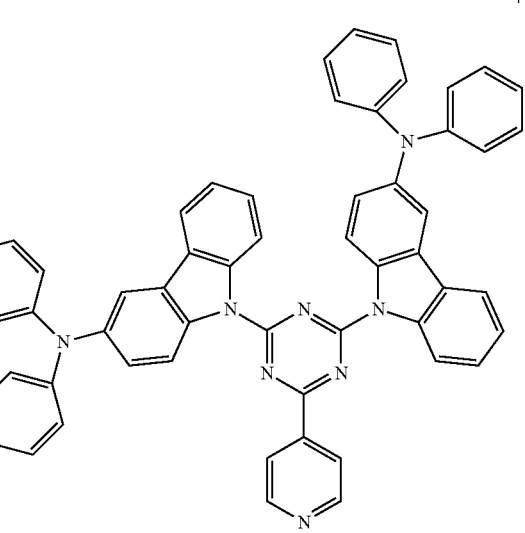

48
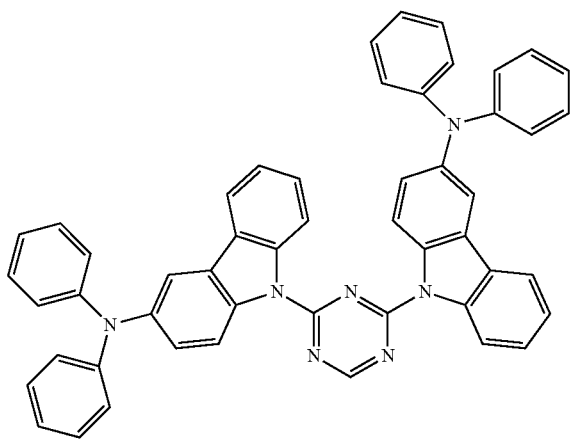
49
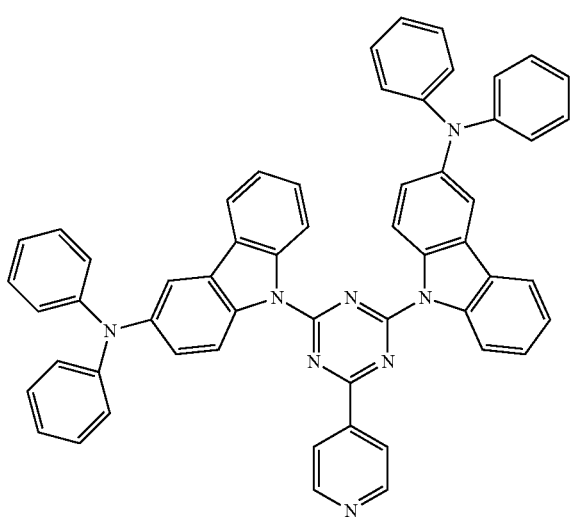
50
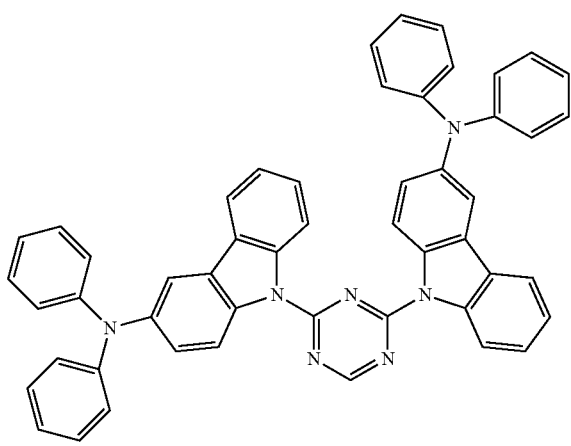
51
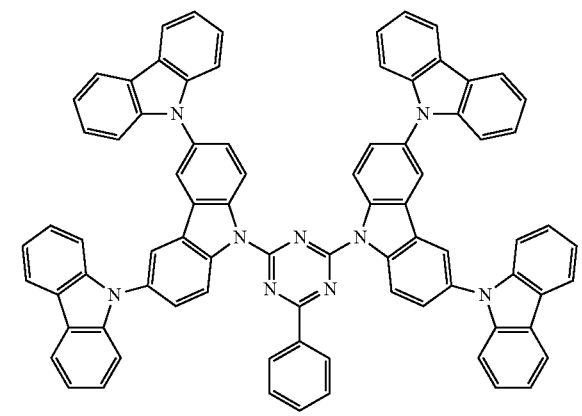
52
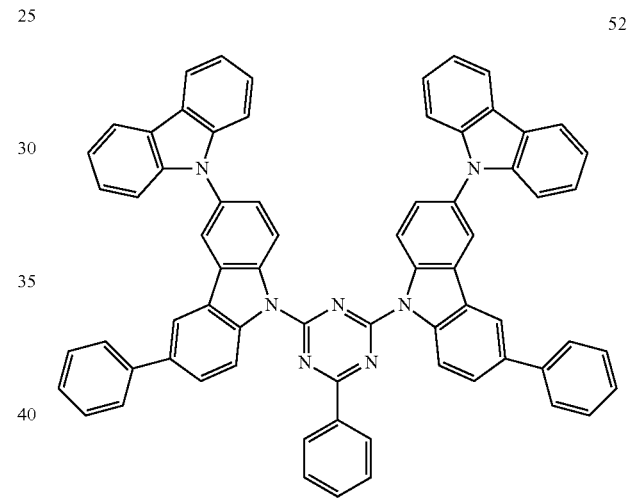
53
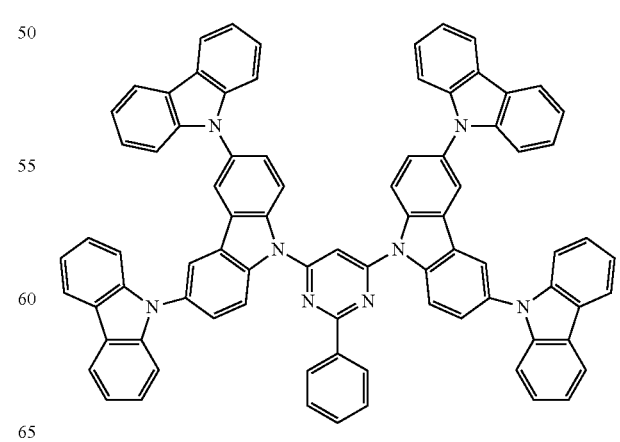

54
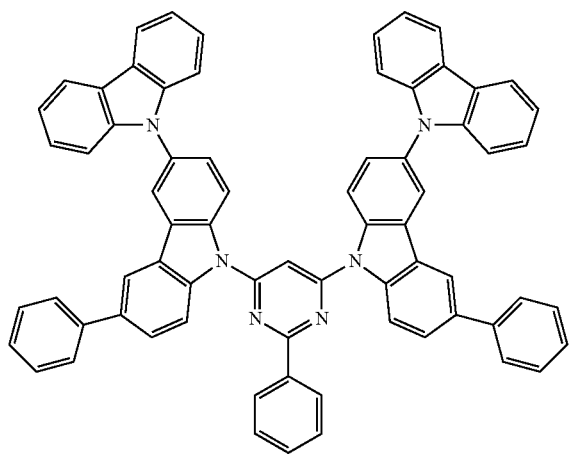
55
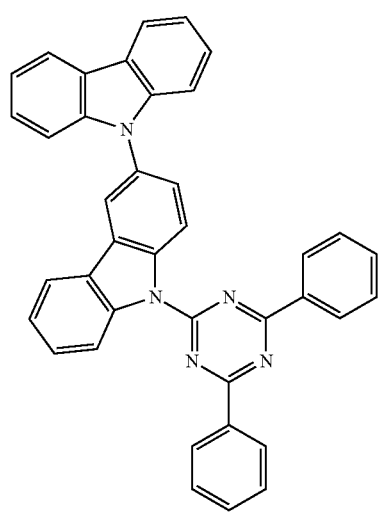
56
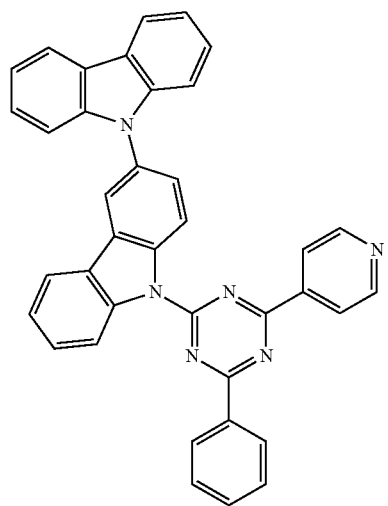
57
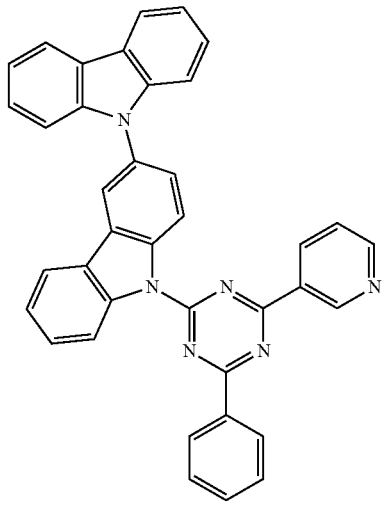
58
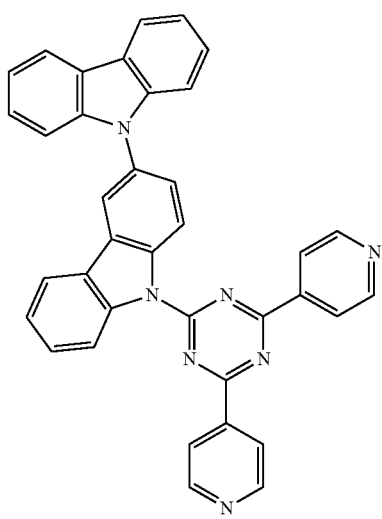
59
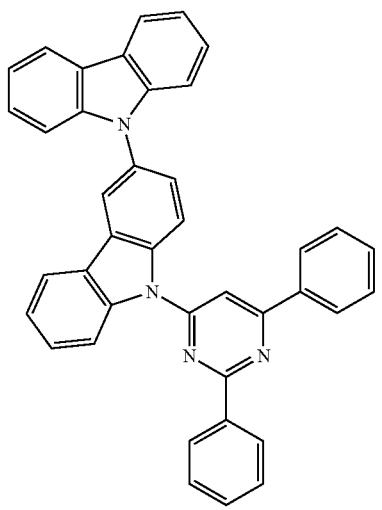

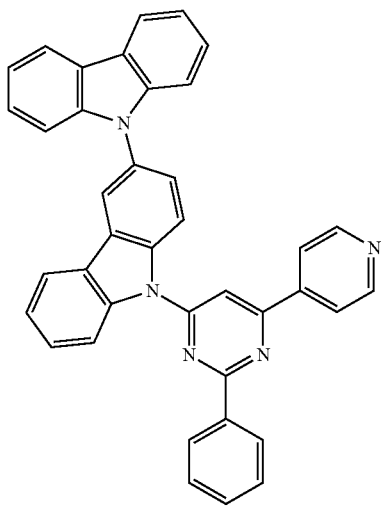
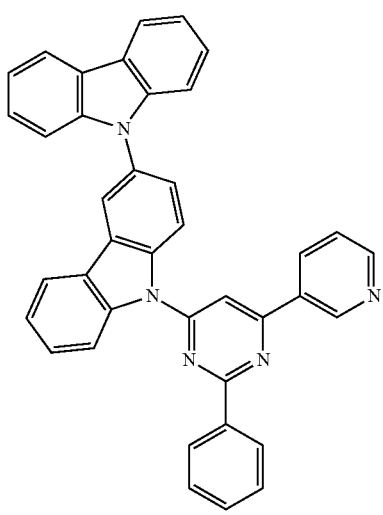
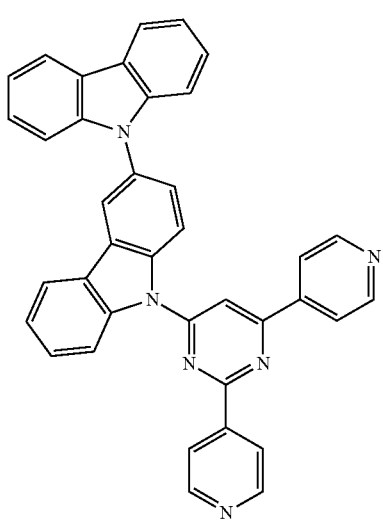
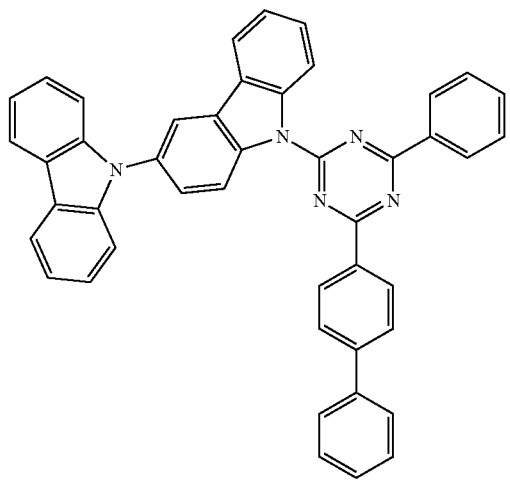
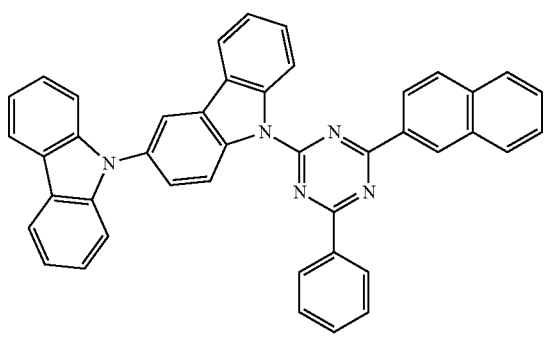

66
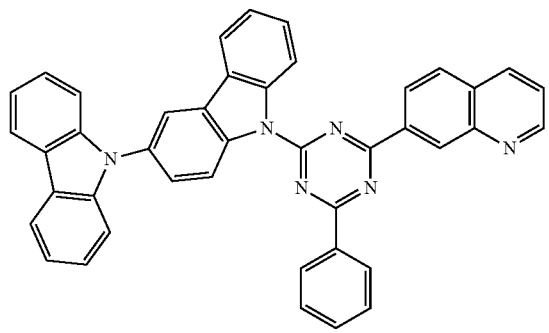
67
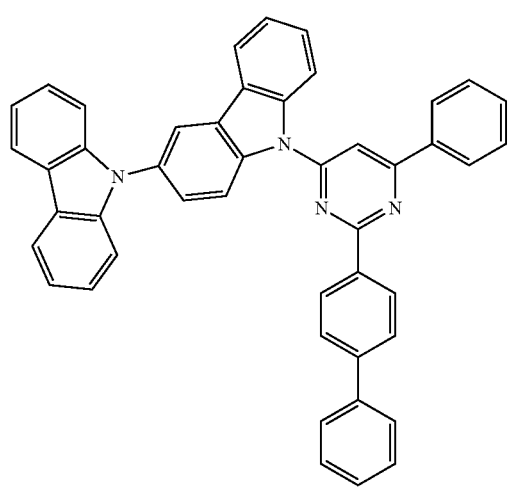
68
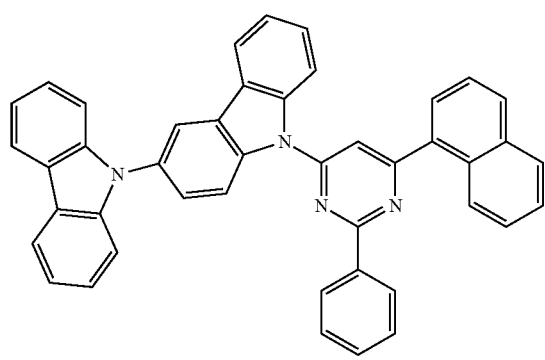
69
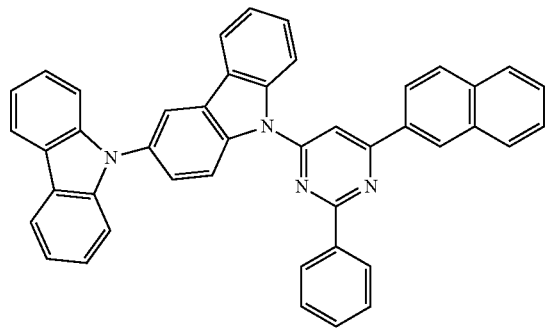
70
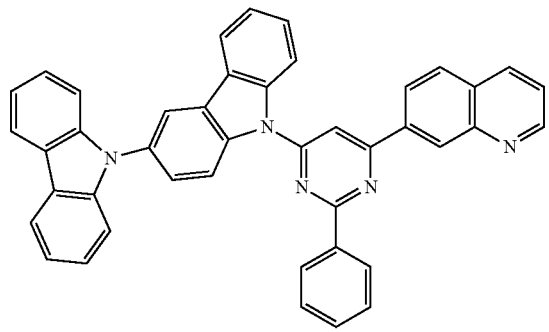
71
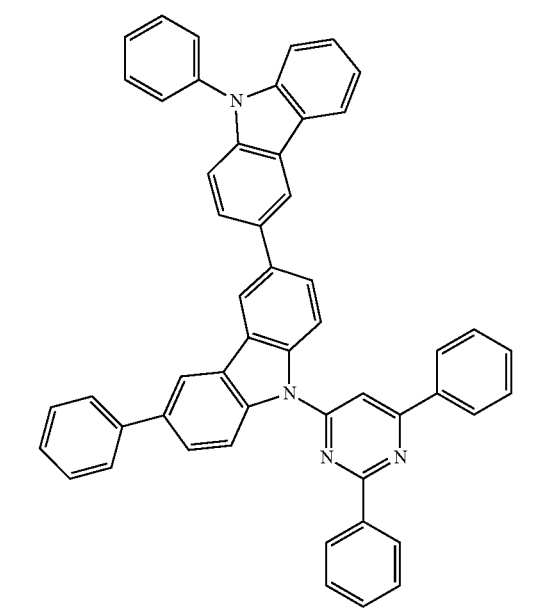

72
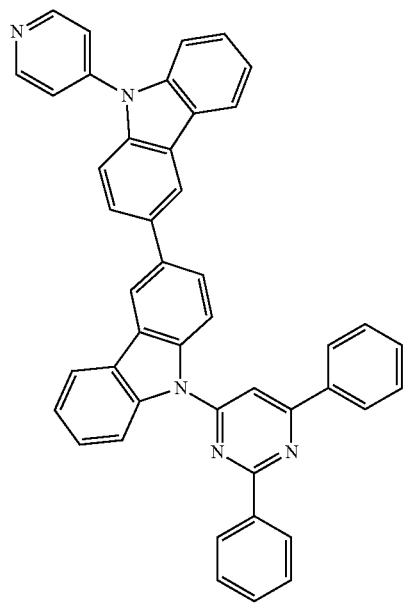
73
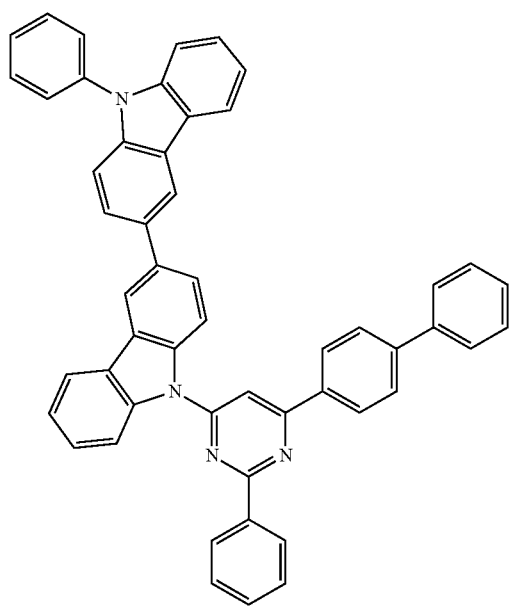
74
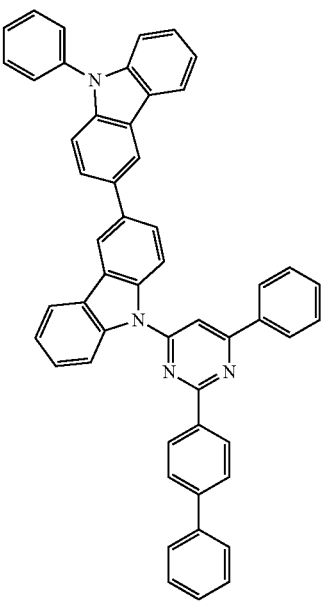
75
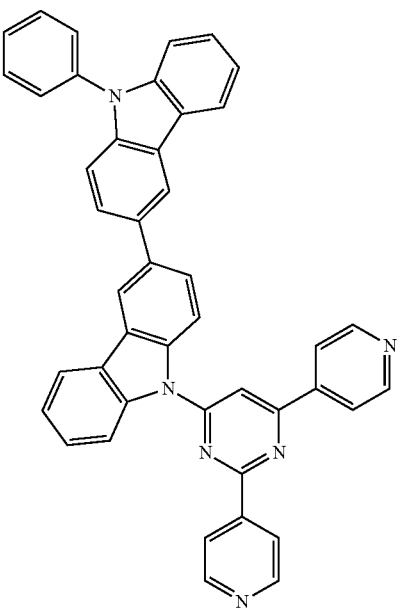

76
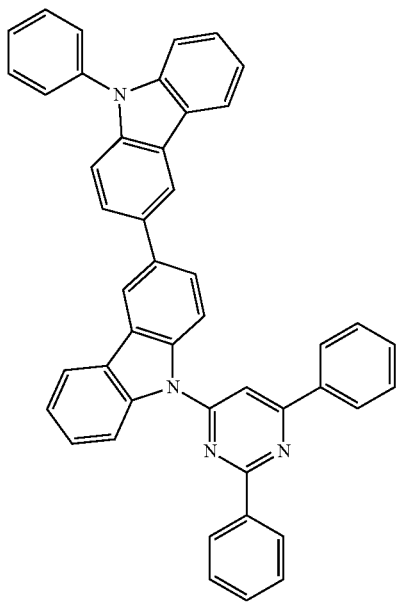
77
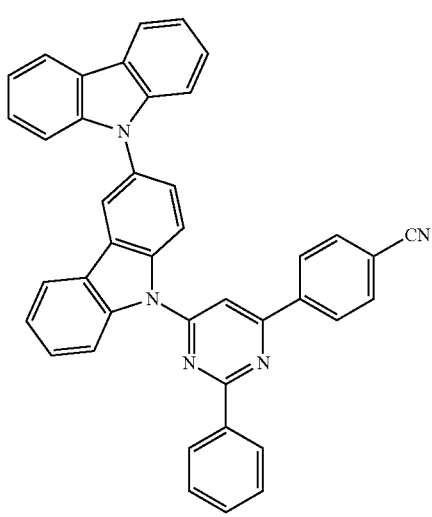
78
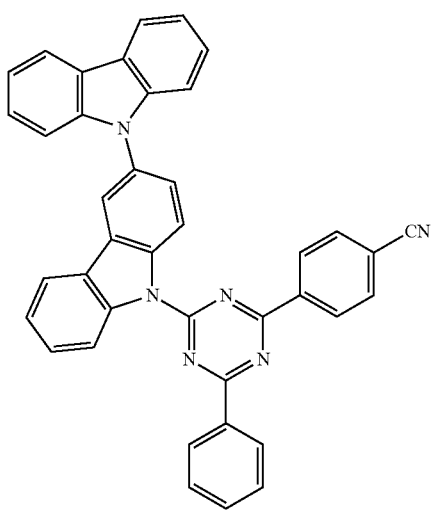
79
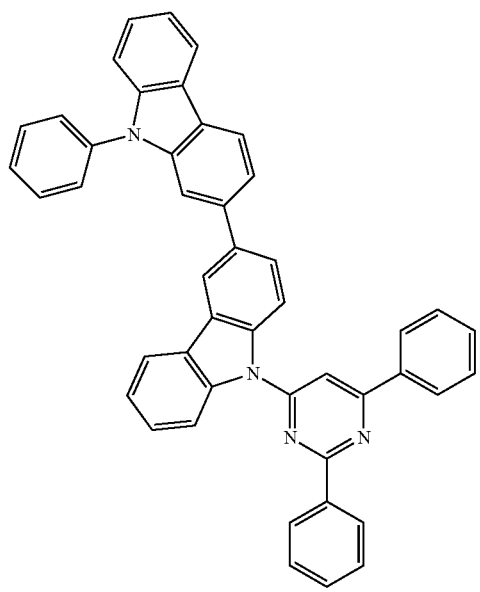
80
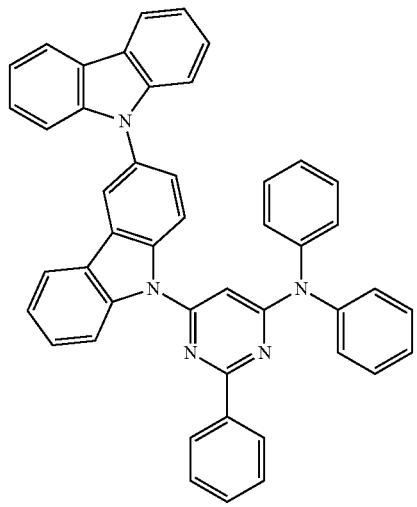
81
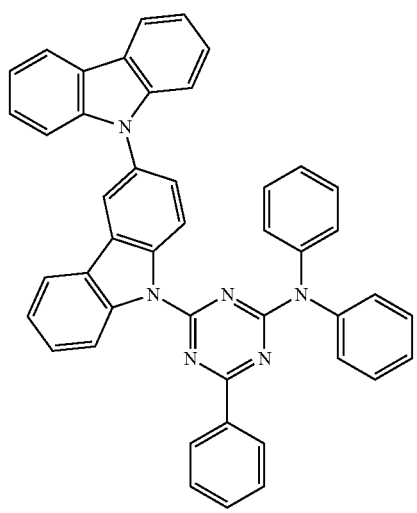

82
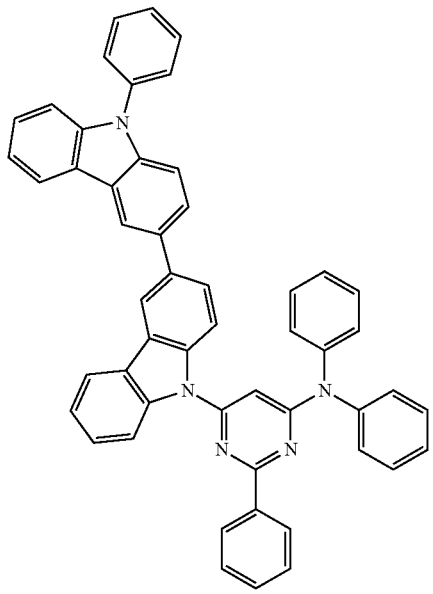
83
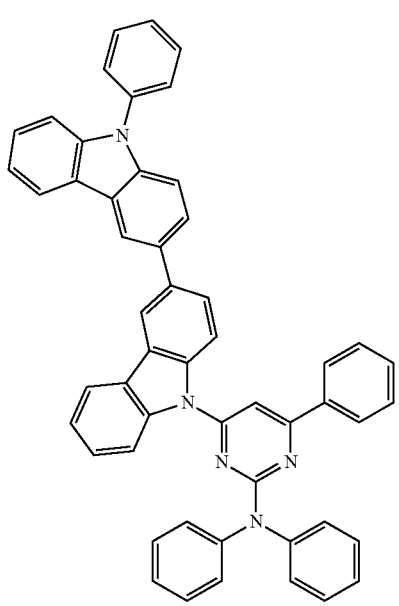
84
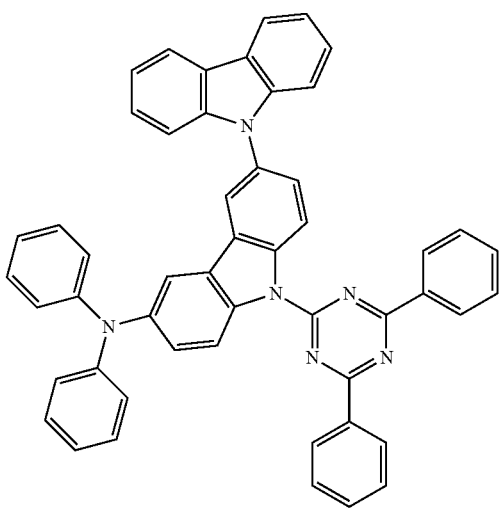
85
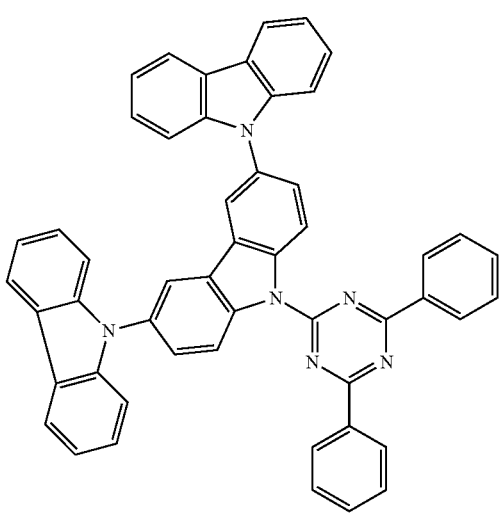
86
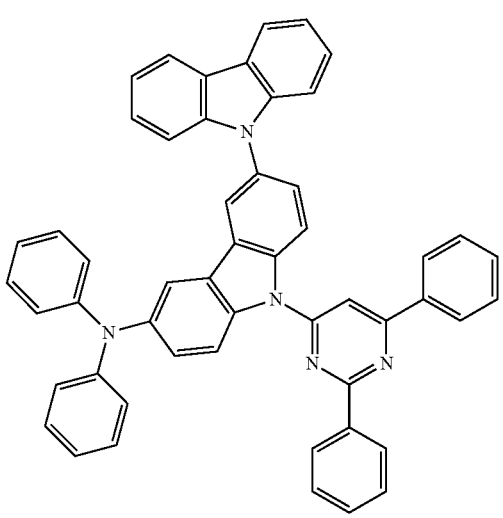

87

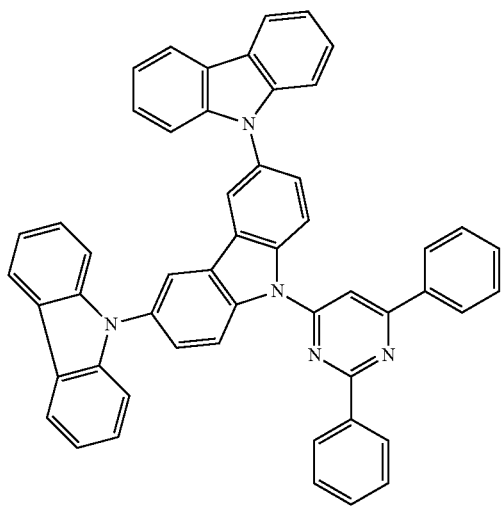

88

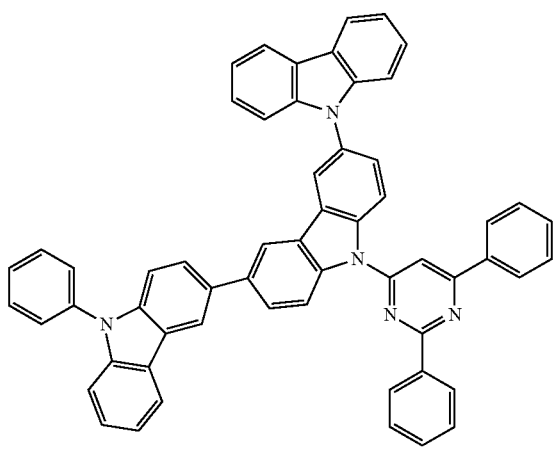

89

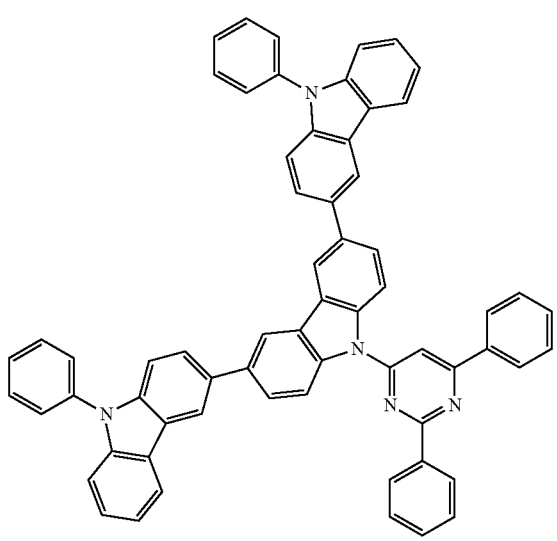

Examples of the preferred light-emitting material include compounds represented by the following general formula (171). The entire description of JP-A-2013-256490 including the paragraphs 0009 to 0046 and 0093 to 0134 is incorporated herein by reference.

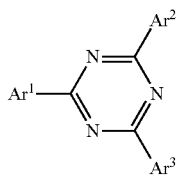

General Formula (171)

wherein in the general formula (171), $Ar^1$ to $Ar^3$ each independently represent a substituted or unsubstituted aryl group, provided that at least one thereof represents an aryl group substituted with a group represented by the following general formula (172).

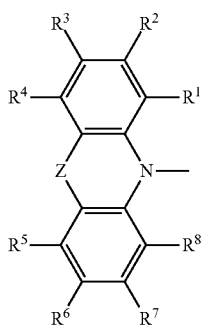

General Formula (172)

wherein in the general formula (172), $R^1$ to $R^8$ each independently represent a hydrogen atom or a substituent; Z represents O, S, O=C, or $Ar^4$—N; and $Ar^4$ represents a substituted or unsubstituted aryl group, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

Examples of the compound include the following compounds.

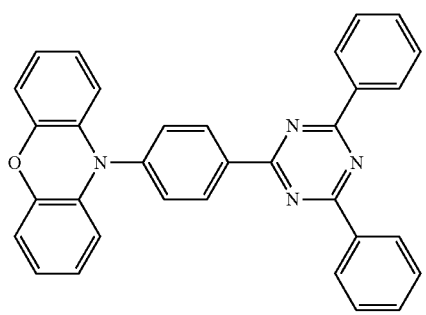

-continued
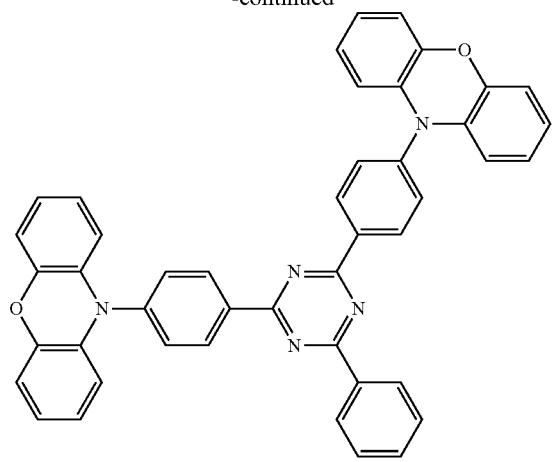
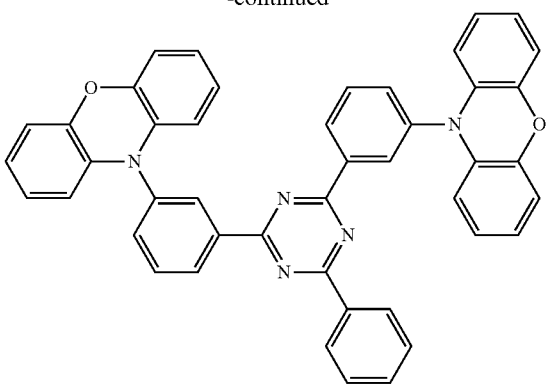
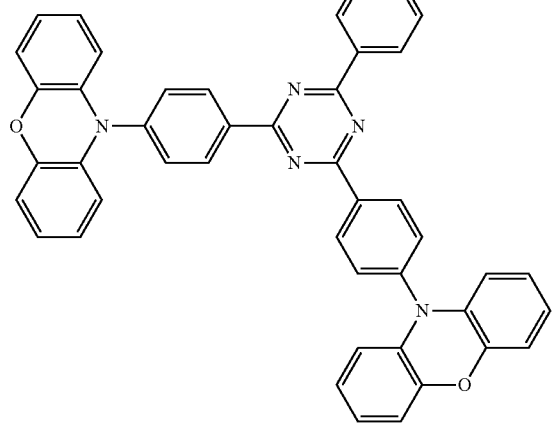
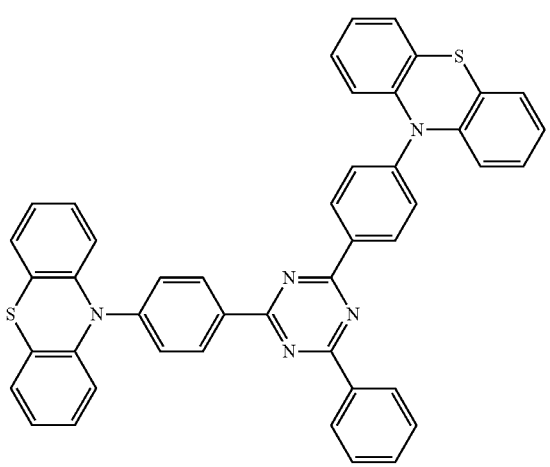

173
-continued
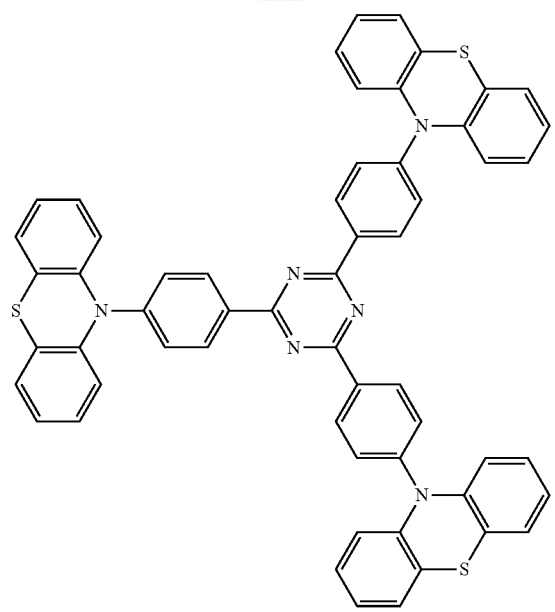
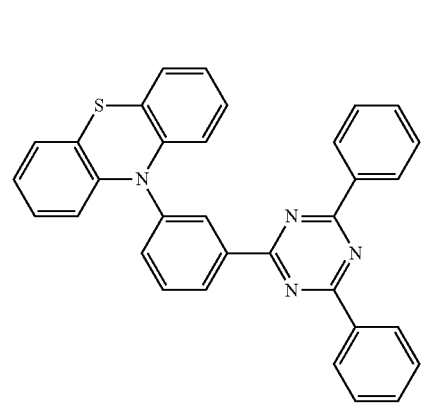
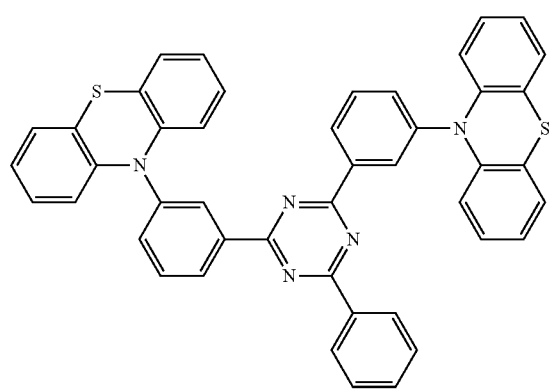
174
-continued
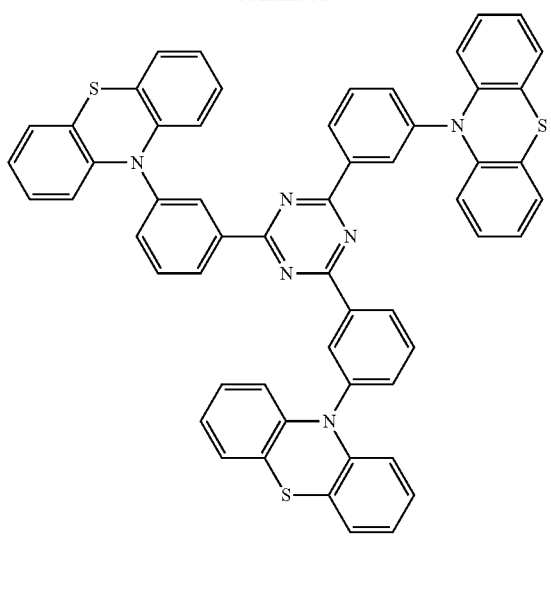
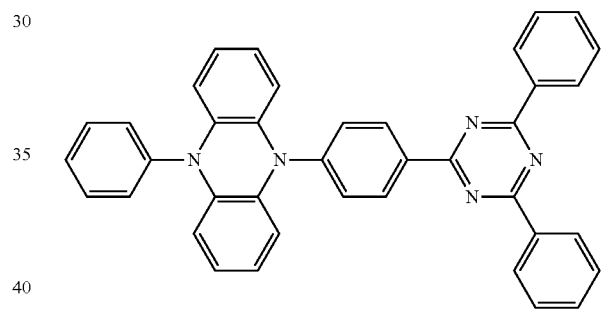
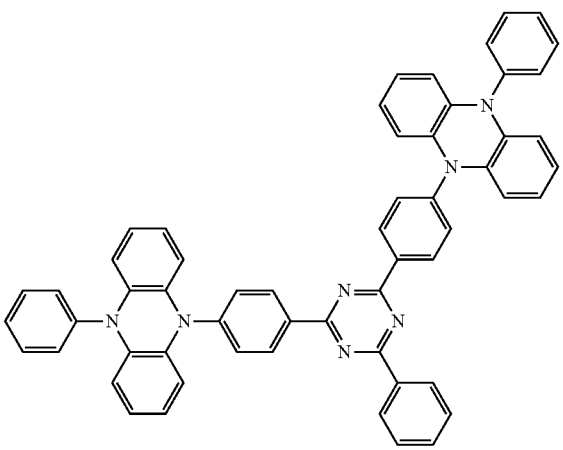

-continued
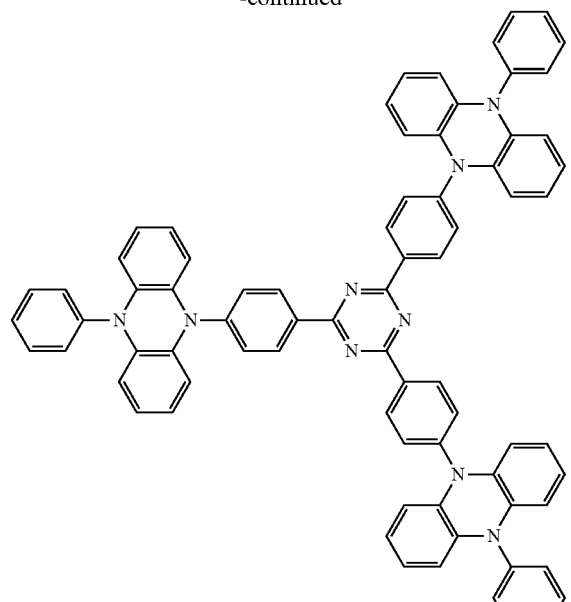
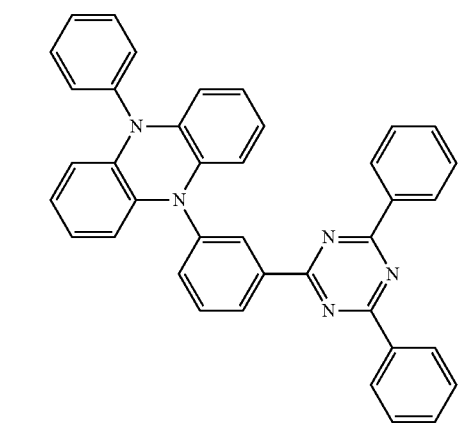
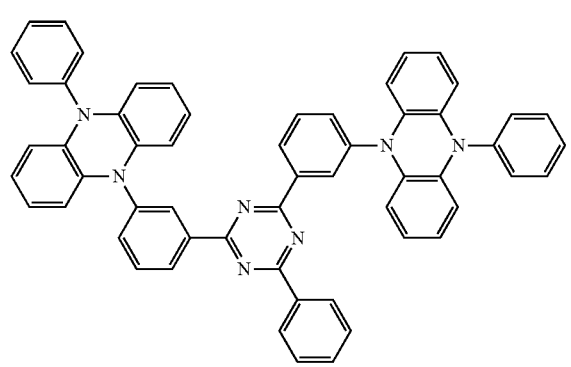
-continued
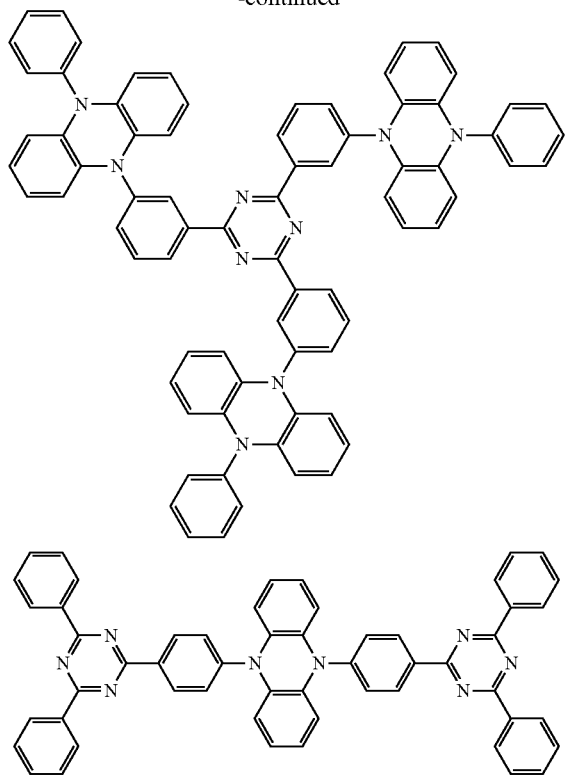
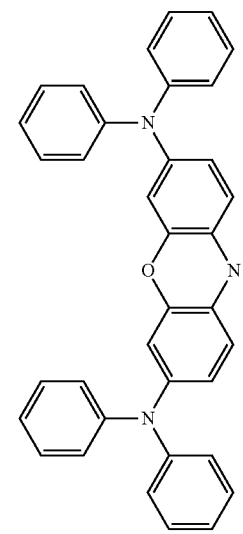
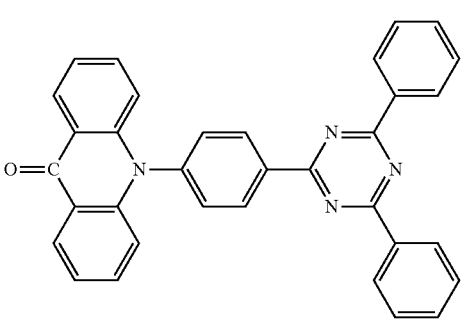

-continued

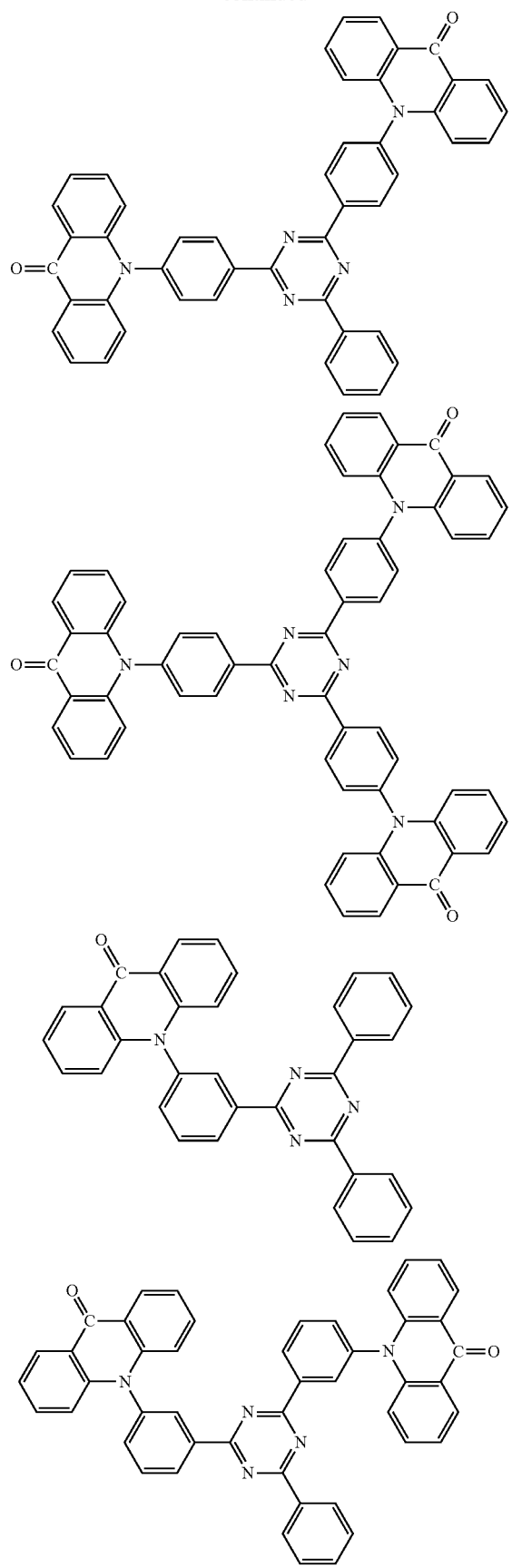

-continued

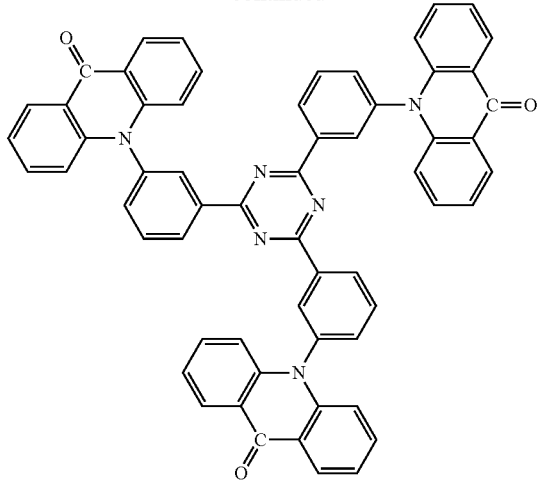

Examples of the preferred light-emitting material include compounds represented by the following general formula (181). The entire description of JP-A-2013-116975 including the paragraphs 0008 to 0020 and 0038 to 0040 is incorporated herein by reference.

General Formula (181)

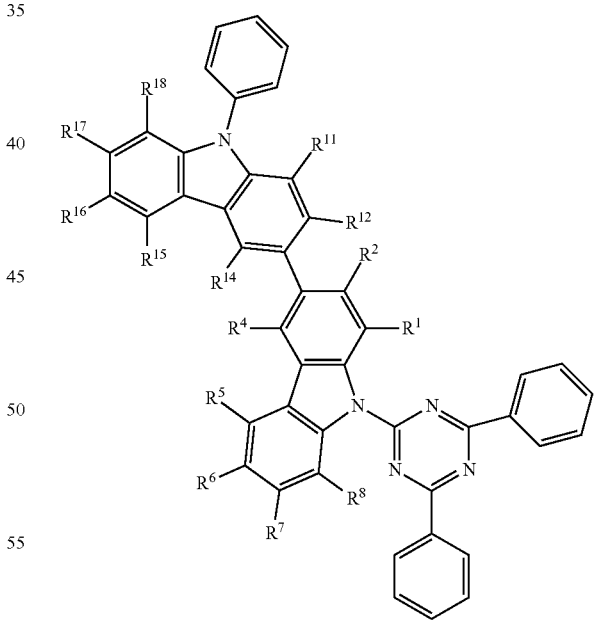

wherein in the general formula (181), $R^1$, $R^2$, $R^4$ to $R^8$, $R^{11}$, $R^{12}$ and $R^{14}$ to $R^{18}$ each independently represent a hydrogen atom or a substituent.

Examples of the compound include the following compound.

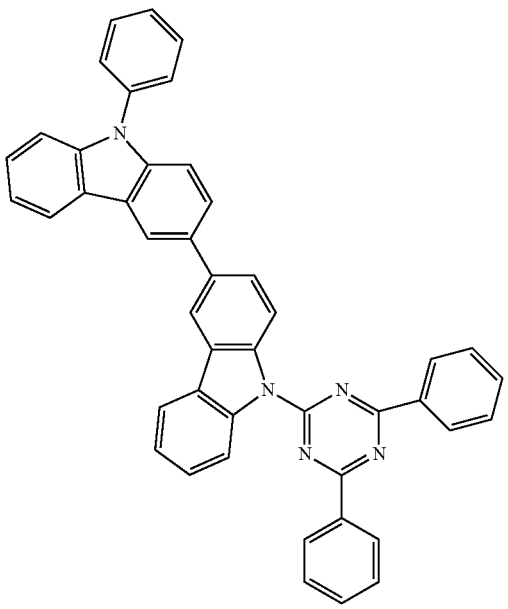 [SMILES: c1ccc(-c2nc(-c3ccccc3)nc(-n3c4ccccc4c4cc(-c5ccc6c(c5)c5ccccc5n6-c5ccccc5)ccc43)n2)cc1]

Examples of the preferred light-emitting material include the following compounds.

(1) A compound represented by the following general formula (191):

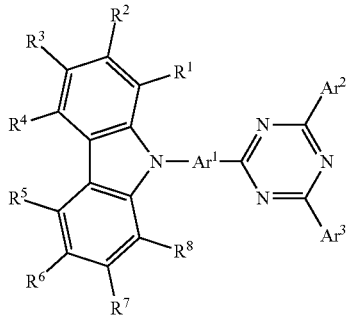

General Formula (191)

wherein in the general formula (191), $Ar^1$ represents a substituted or unsubstituted arylene group; $Ar^2$ and $Ar^3$ each independently represent a substituted or unsubstituted aryl group; and $R^1$ to $R^8$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(2) The compound according to the item (1), wherein in the general formula (191), at least one of $R^1$ to $R^4$ represents a substituted or unsubstituted diarylamino group, and at least one of $R^5$ to $R^8$ represents a substituted or unsubstituted diarylamino group.

(3) The compound according to the item (2), wherein in the general formula (191), $R^3$ and $R^6$ each represent a substituted or unsubstituted diarylamino group.

(4) The compound according to any one of the items (1) to (3), wherein in the general formula (191), at least one of $R^1$ to $R^8$ represents a substituted or unsubstituted diphenylamino group.

(5) The compound according to any one of the items (1) to (4), wherein in the general formula (191), $Ar^2$ and $Ar^3$ each independently represent a substituted or unsubstituted phenyl group.

(6) The compound according to any one of the items (1) to (5), wherein in the general formula (191), $Ar^1$ represents a substituted or unsubstituted phenylene group, a substituted or unsubstituted naphthylene group or a substituted or unsubstituted anthracenylene group.

(7) The compound according to the item (1), wherein the compound has a structure represented by the following general formula (192):

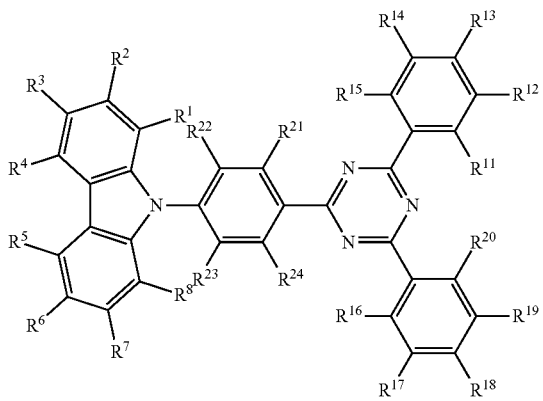

General Formula (192)

wherein in the general formula (192), $R^1$ to $R^8$ and $R^{11}$ to $R^{24}$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, and $R^{23}$ and $R^{24}$ each may be bonded to each other to form a cyclic structure.

(8) The compound according to the item (7), wherein in the general formula (192), at least one of $R^1$ to $R^4$ represents a substituted or unsubstituted diarylamino group, and at least one of $R^5$ to $R^8$ represents a substituted or unsubstituted diarylamino group.

(9) The compound according to the item (8), wherein in the general formula (192), $R^3$ and $R^6$ each represent a substituted or unsubstituted diarylamino group.

Specific examples of the compound include the following compounds. Ph represents a phenyl group.

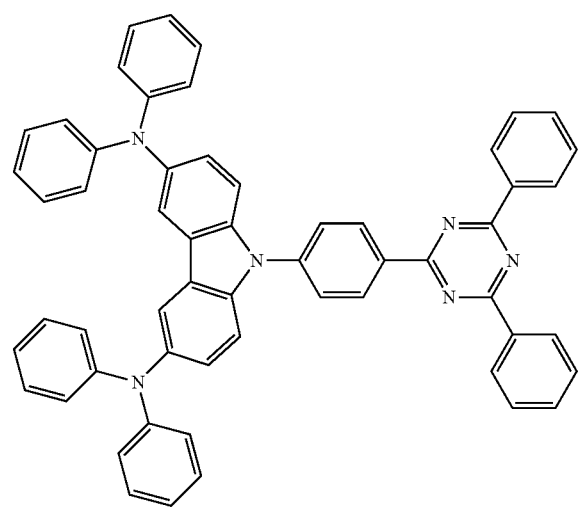
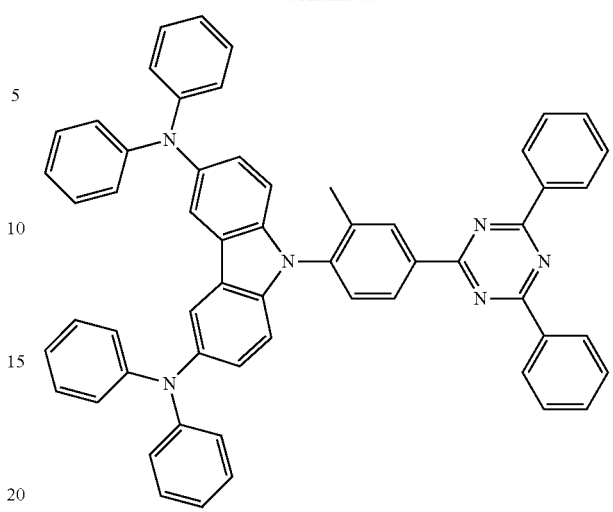
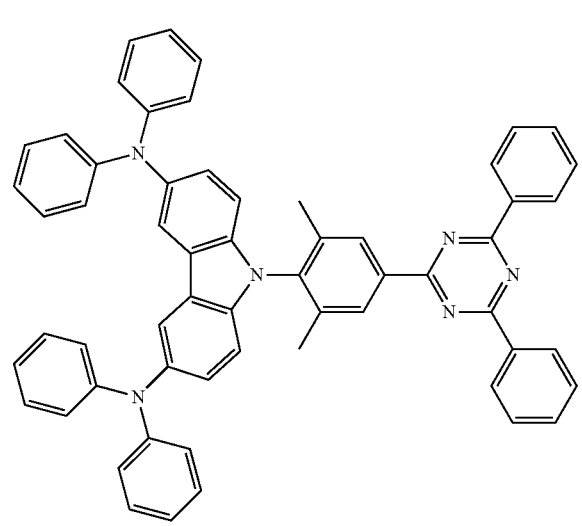
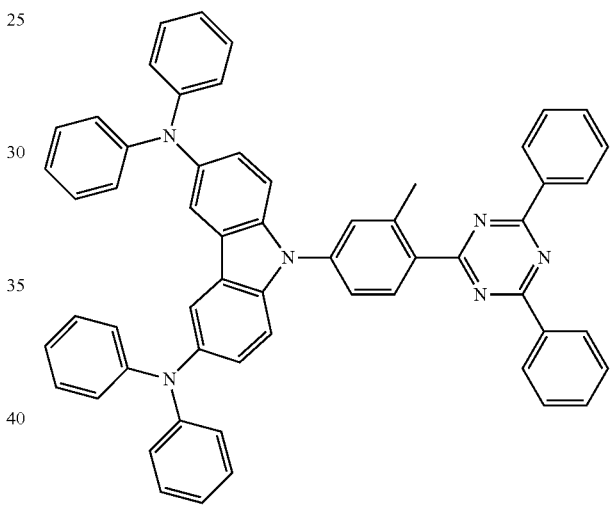
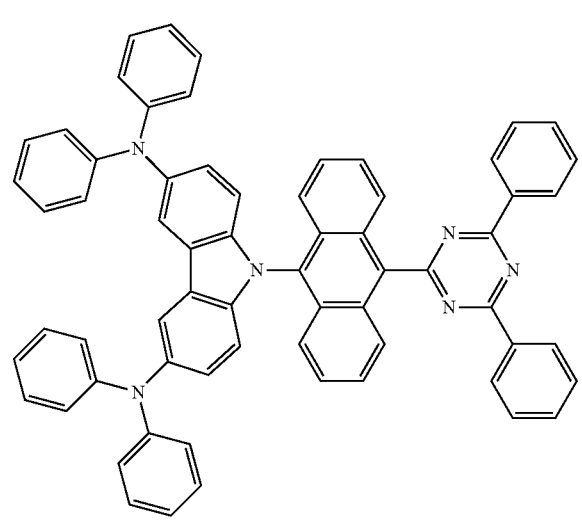
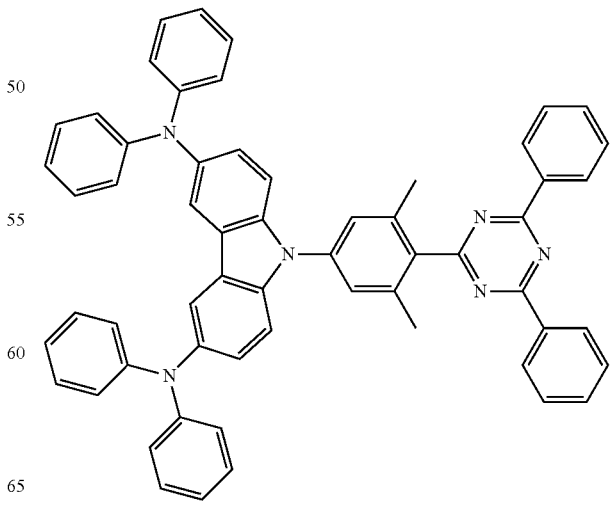

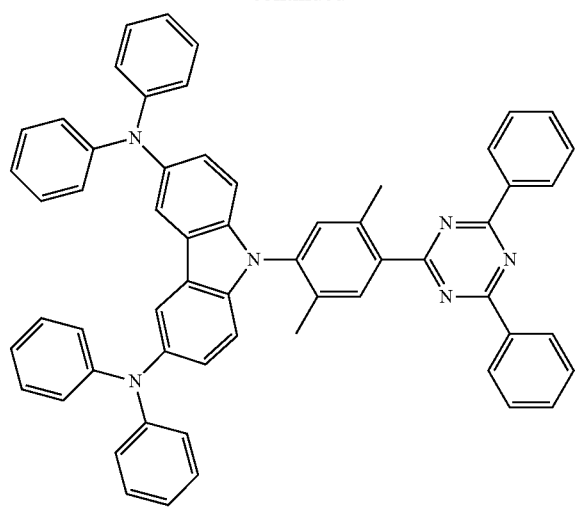
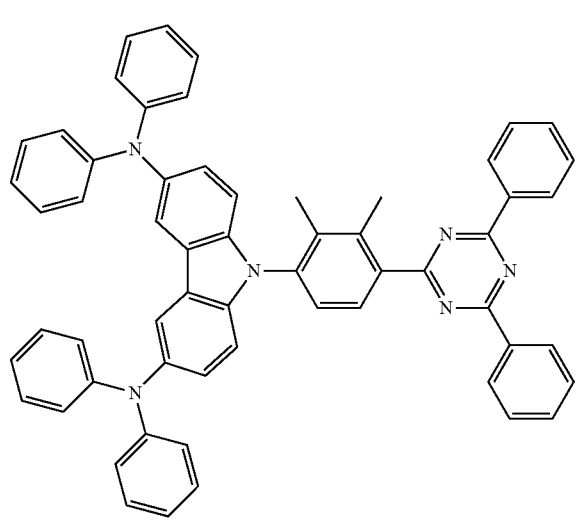
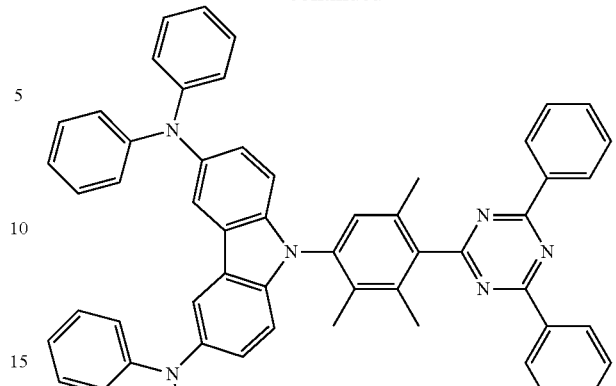
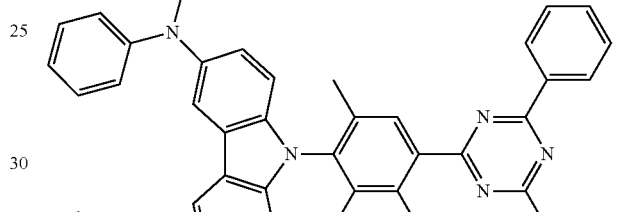
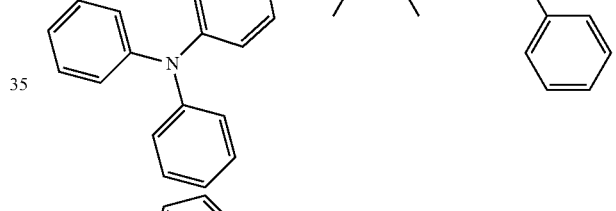
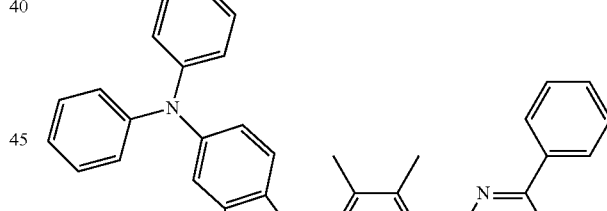
Examples of the preferred light-emitting material include the following compounds.
(1) A compound represented by the following general formula (201):

General Formula (201)

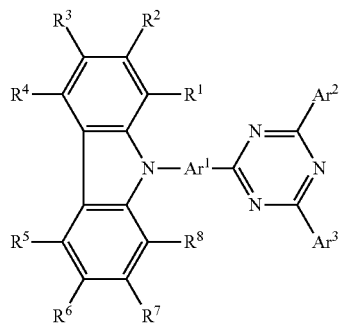

wherein in the general formula (201), R¹ to R⁸ each independently represent a hydrogen atom or a substituent, provided that at least one of R¹ to R⁸ represents a substituted or unsubstituted carbazolyl group; and Ar¹ to Ar³ each independently represent a substituted or unsubstituted aromatic ring or a heteroaromatic ring.

(2) The compound according to the item (1), wherein in the general formula (201), at least one of R³ and R⁶ represents a substituted or unsubstituted carbazolyl group.

(3) The compound according to the item (1) or (2), wherein the carbazolyl group is a 1-carbazolyl group, a 2-carbazolyl group, a 3-carbazolyl group or a 4-carbazolyl group.

(4) The compound according to any one of the items (1) to (3), wherein the carbazolyl group has a substituent on the nitrogen atom in the carbazole ring structure.

(5) The compound according to any one of the items (1) to (4), wherein in the general formula (201), at least one of Ar¹, Ar² and Ar³ represents a benzene ring or a naphthalene ring.

(6) The compound according to any one of the items (1) to (5), wherein in the general formula (201), Ar¹, Ar² and Ar³ each represent the same aromatic ring or the same heteroaromatic ring.

(7) The compound according to any one of the items (1) to (6), wherein in the general formula (201), Ar¹, Ar² and Ar³ each represent a benzene ring.

Specific examples of the compound include the following compounds.

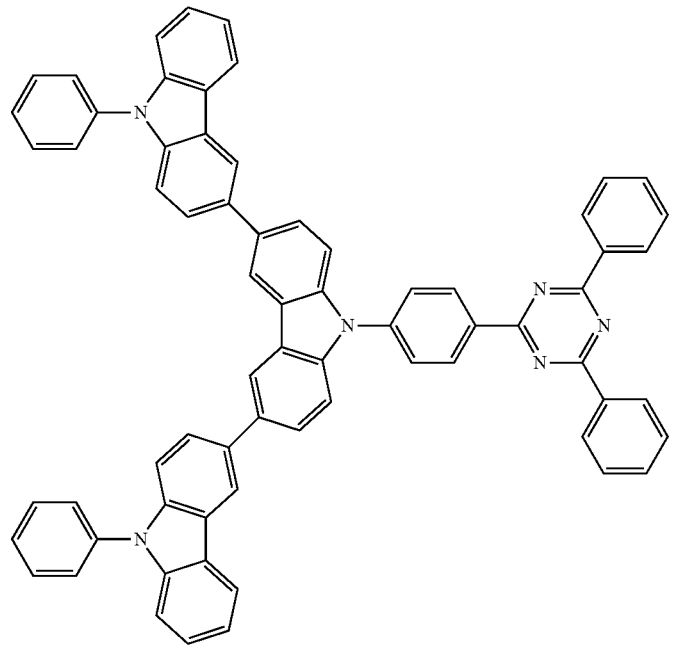

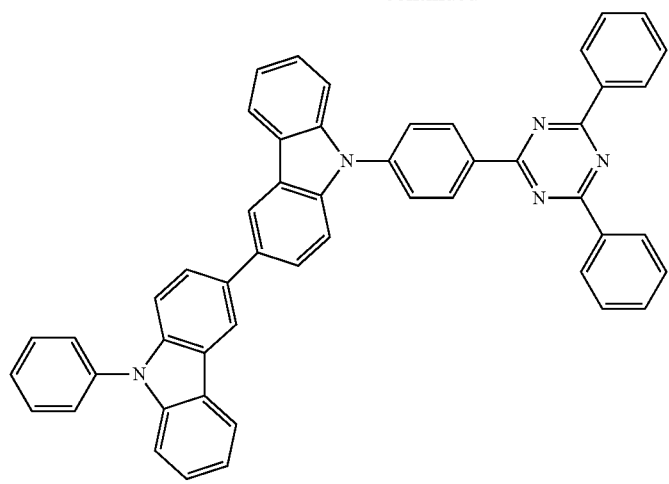
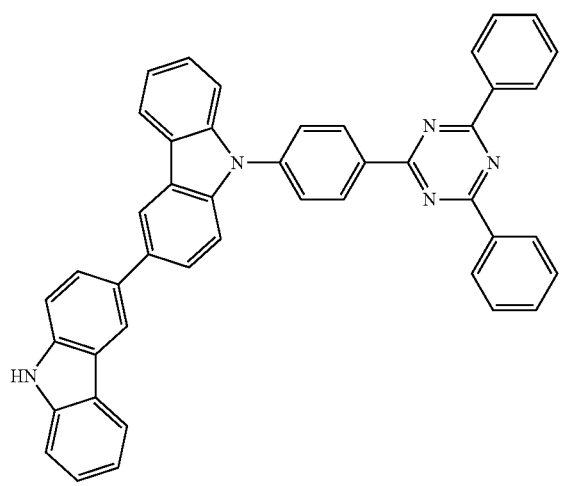
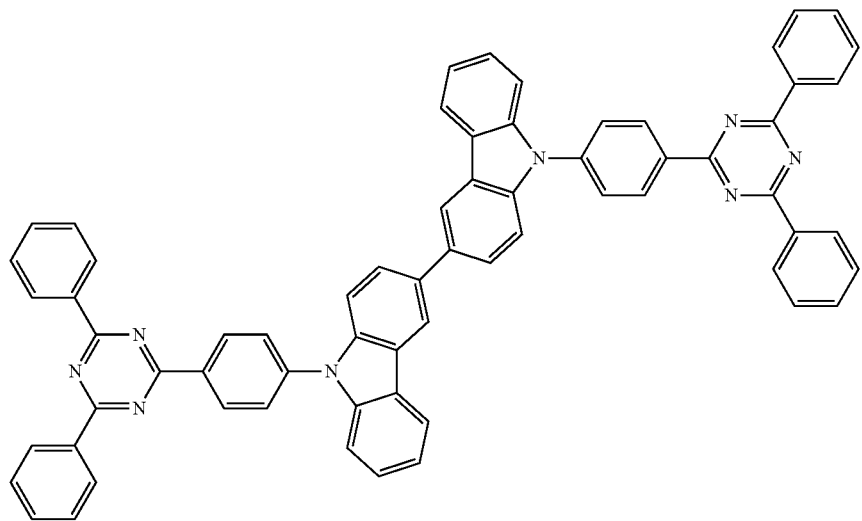

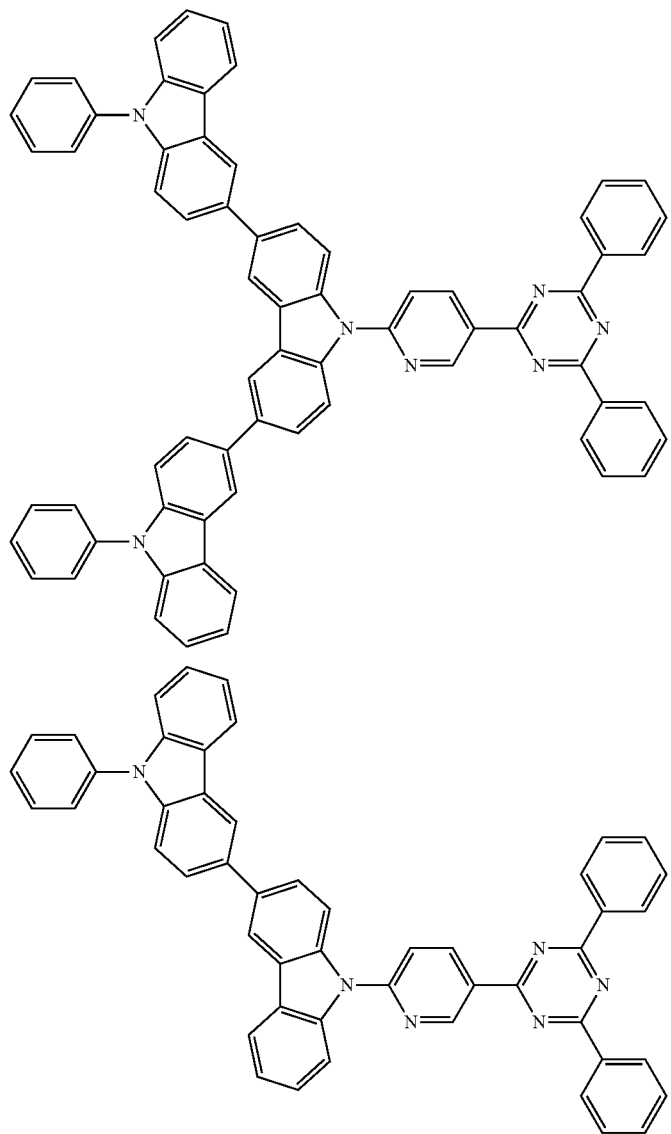
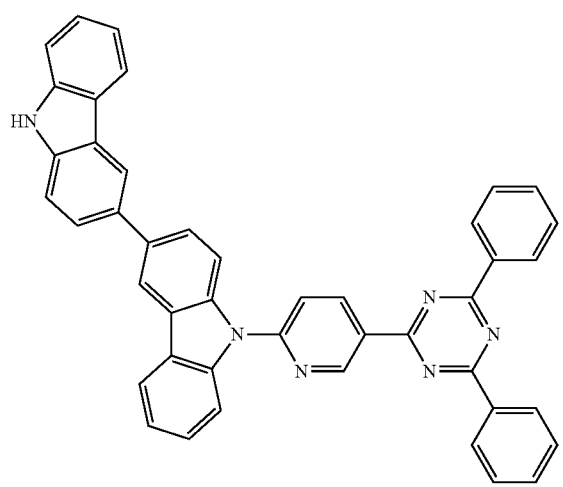

-continued
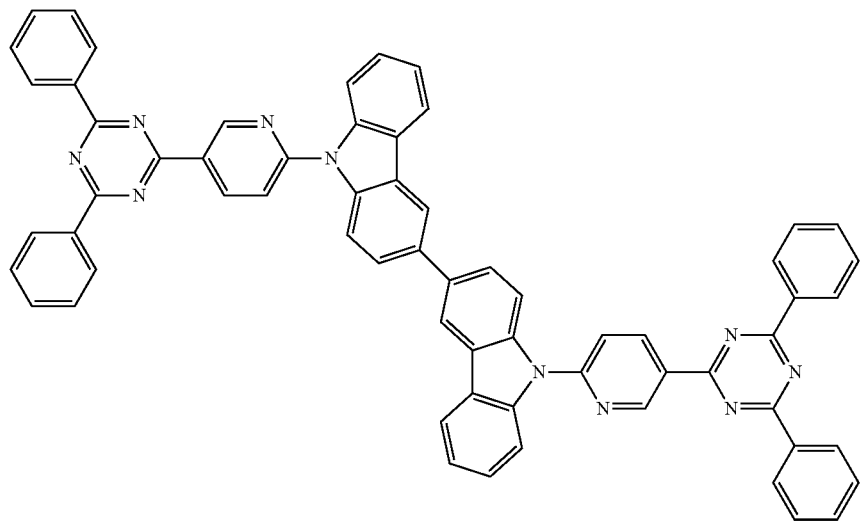
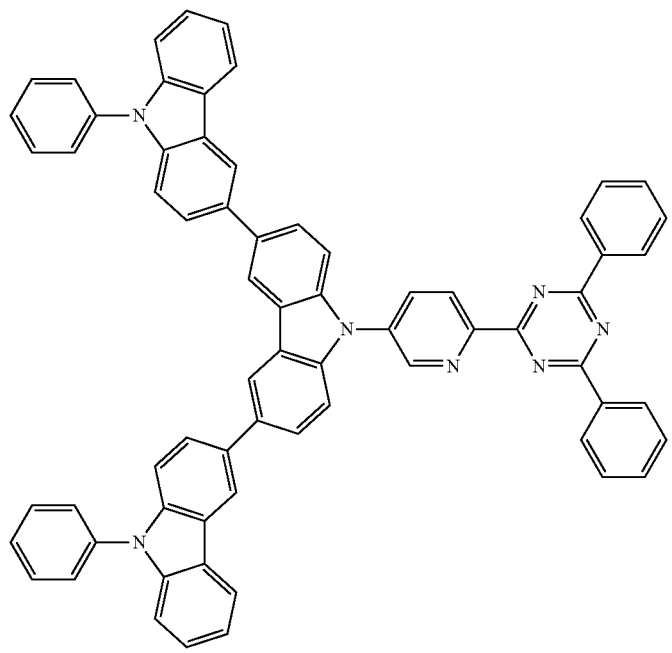
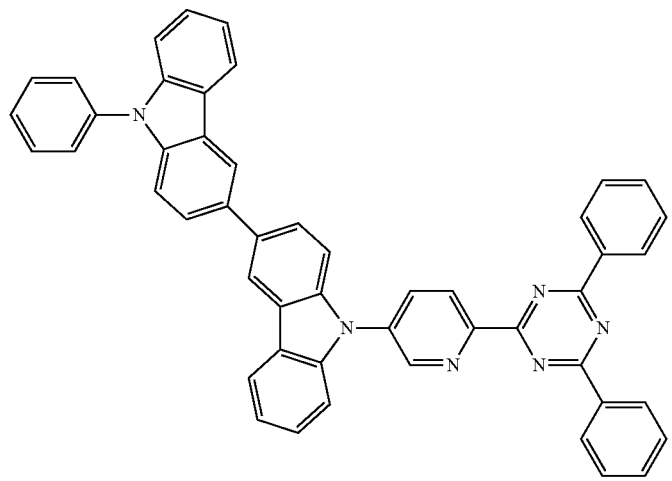

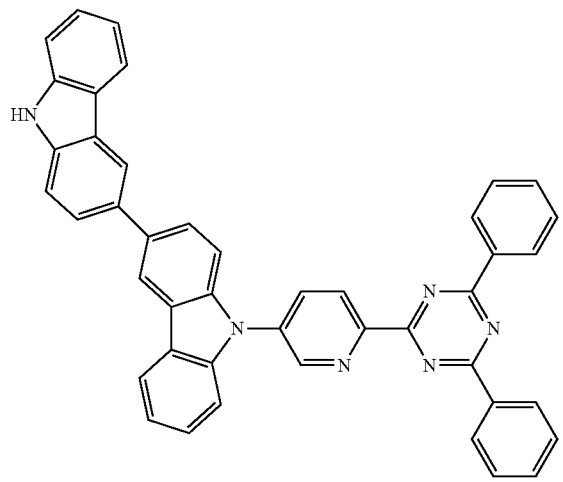
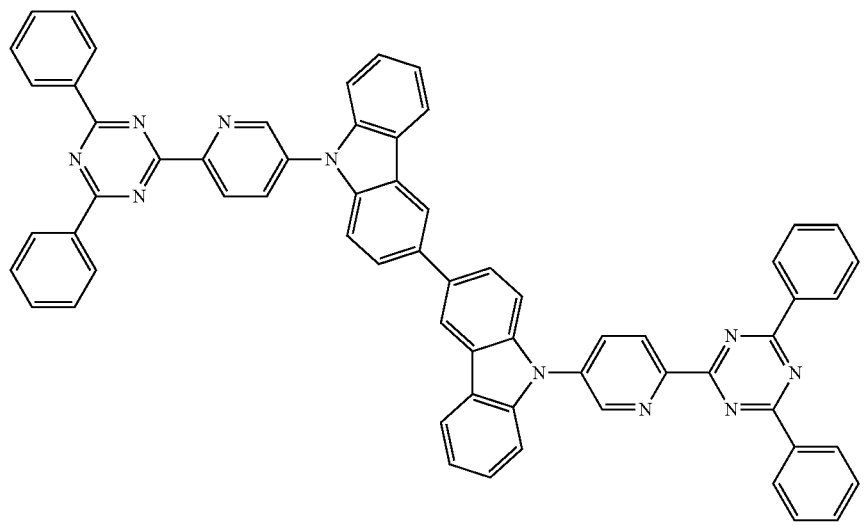
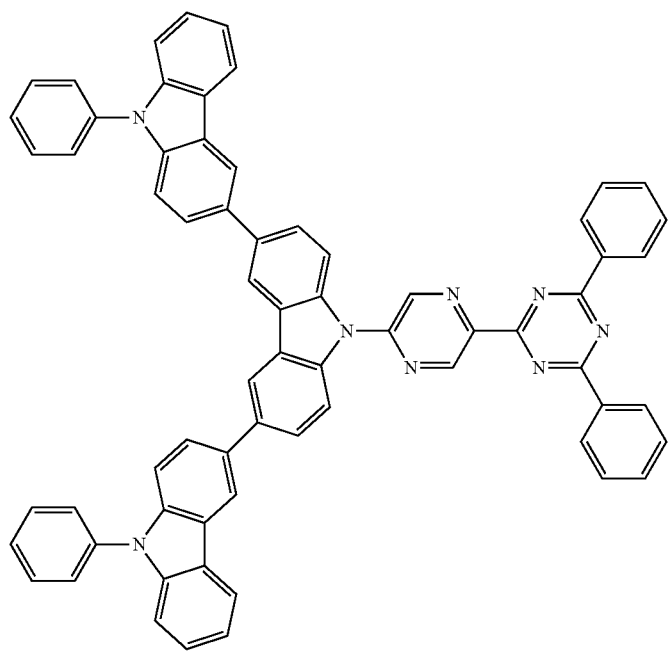

-continued
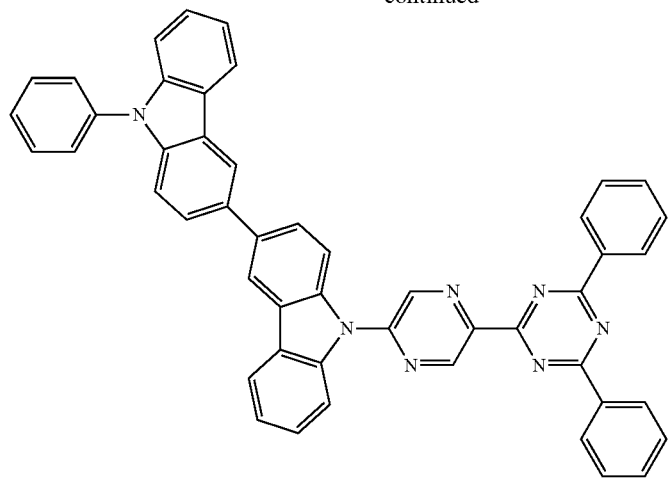
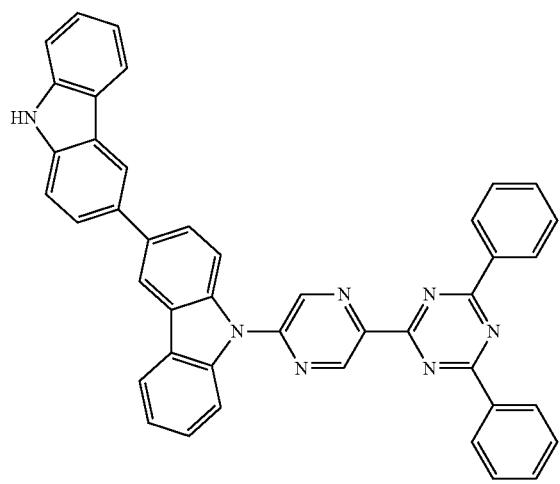
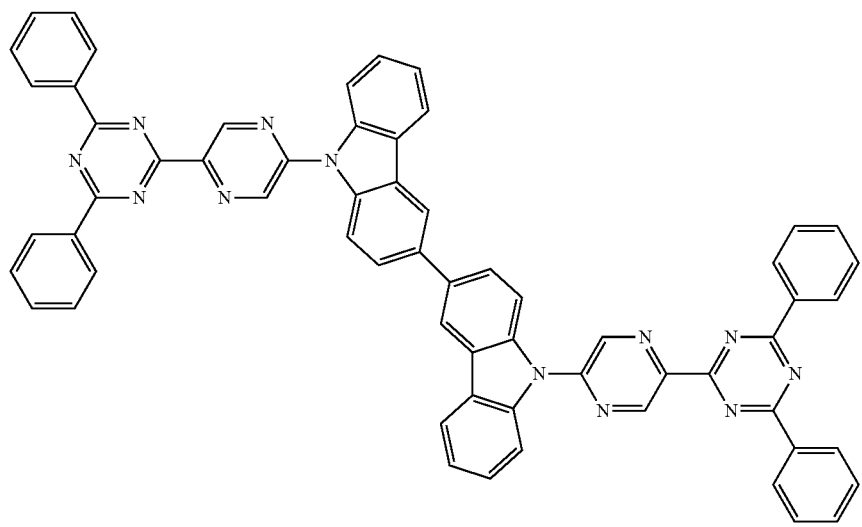

-continued
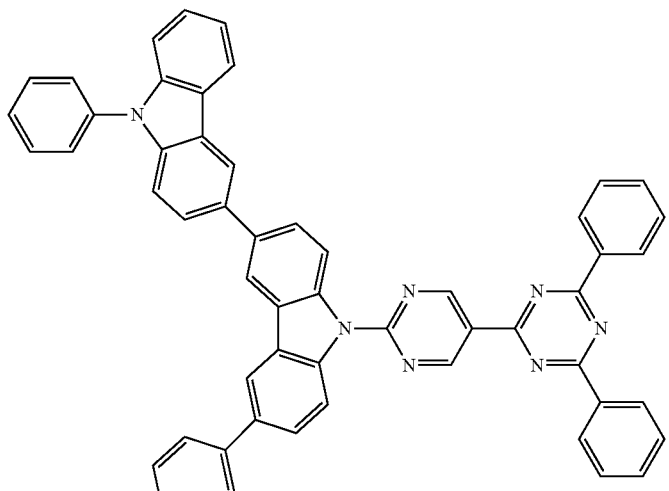
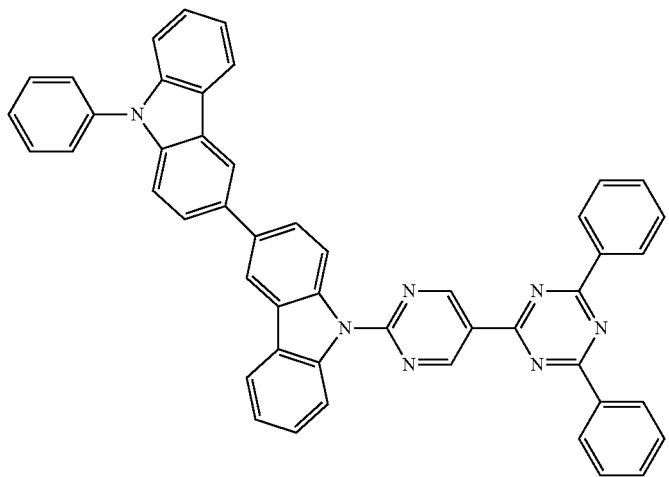
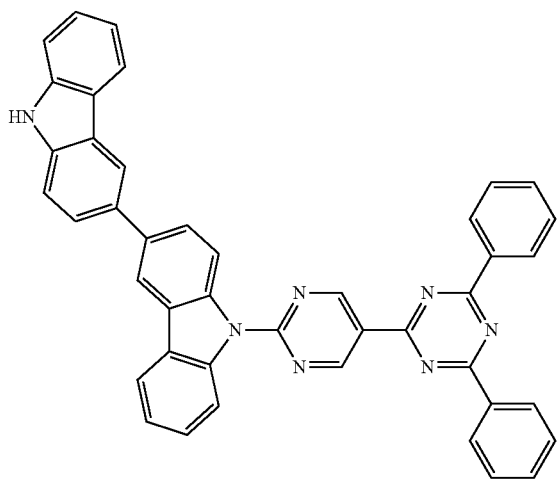

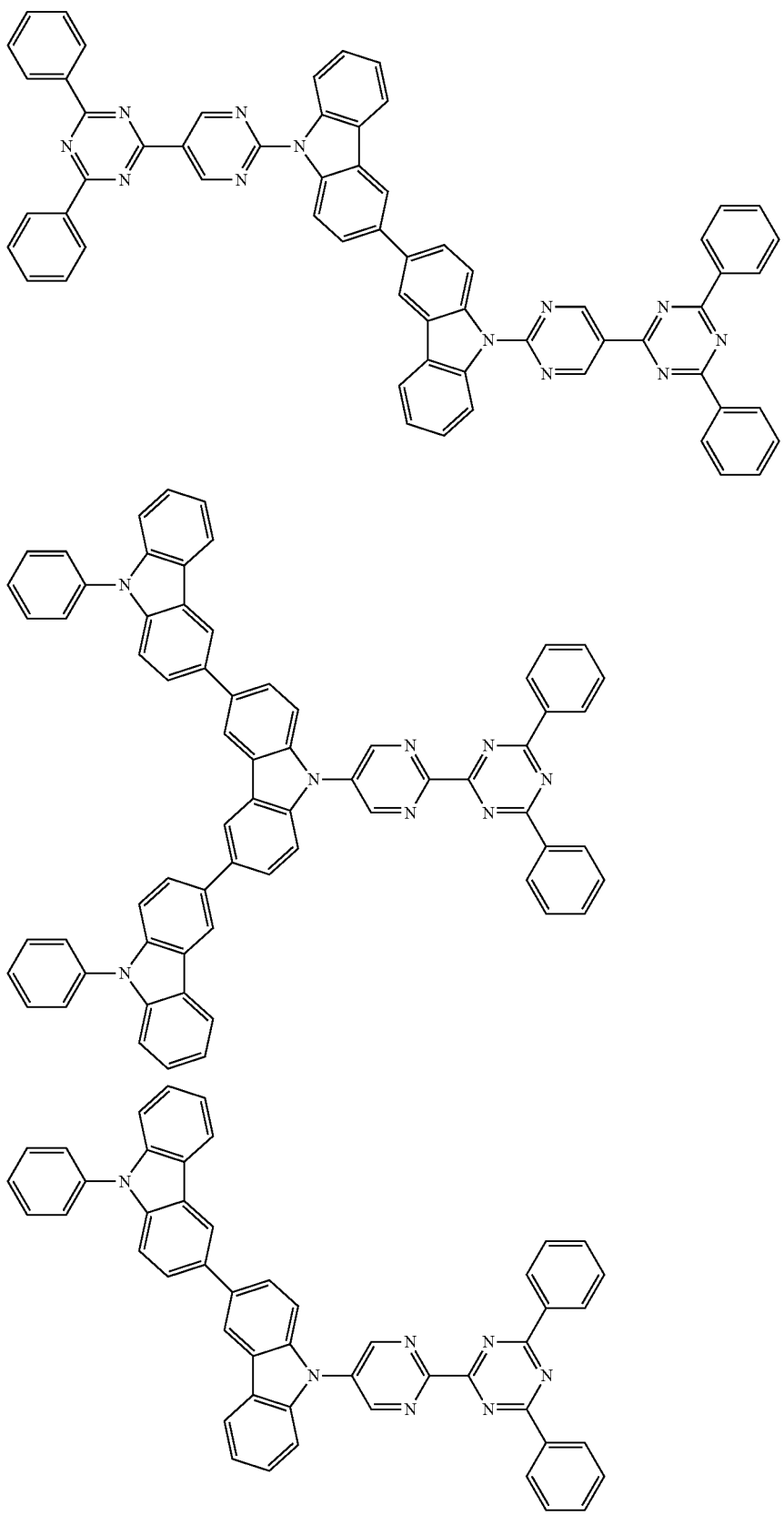

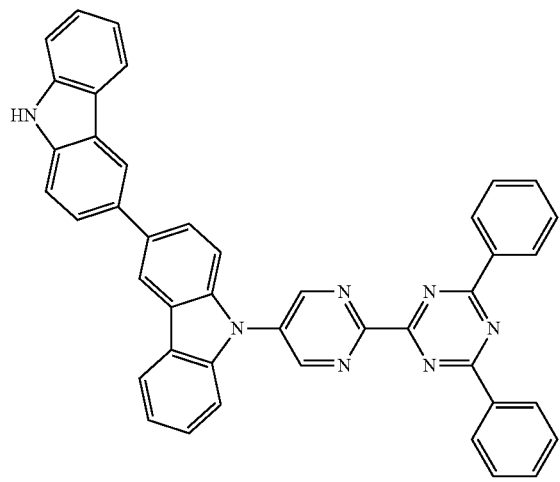
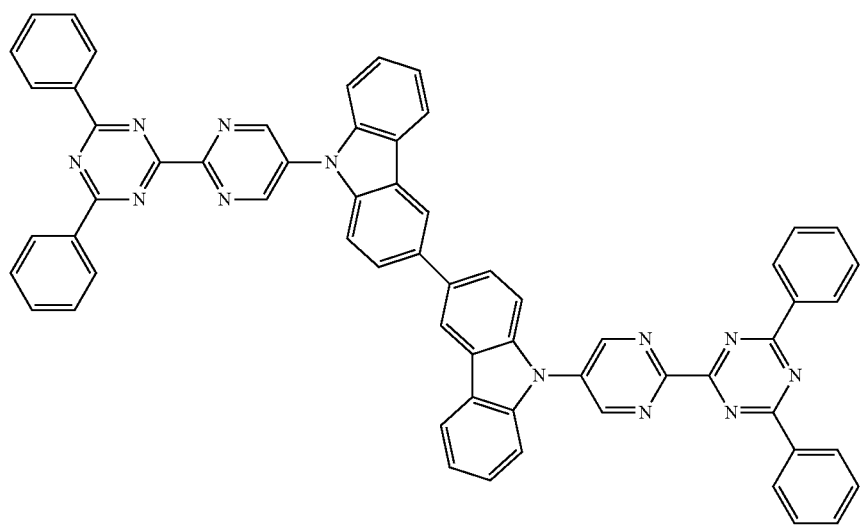
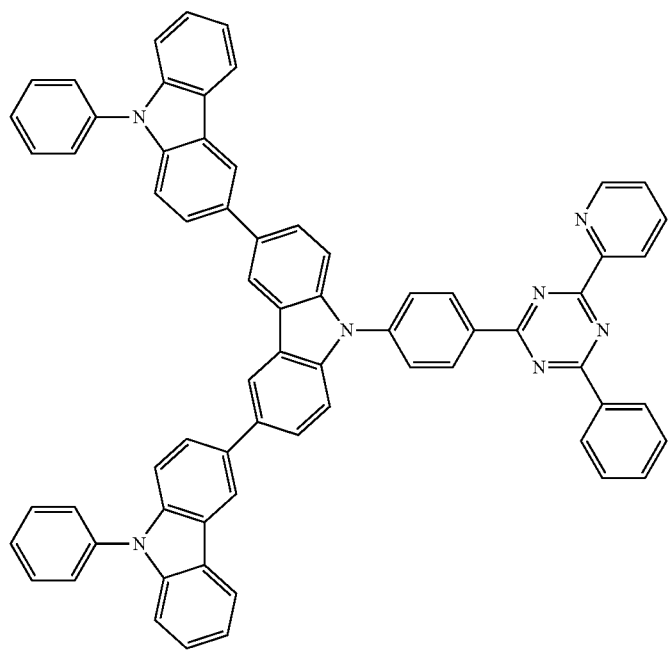

-continued
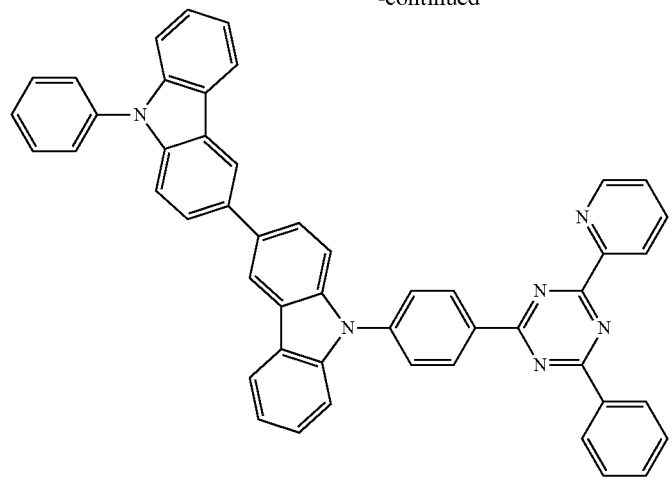
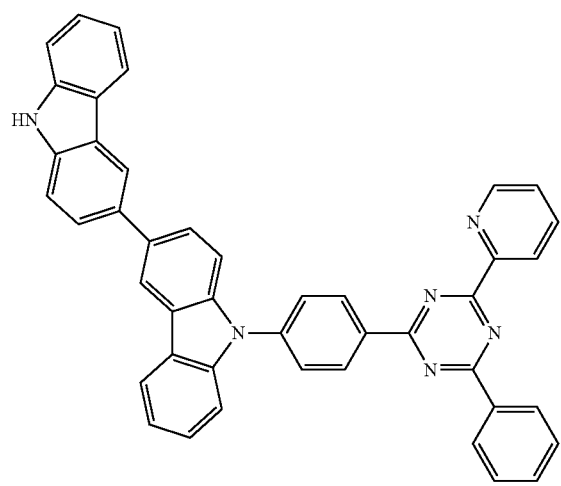
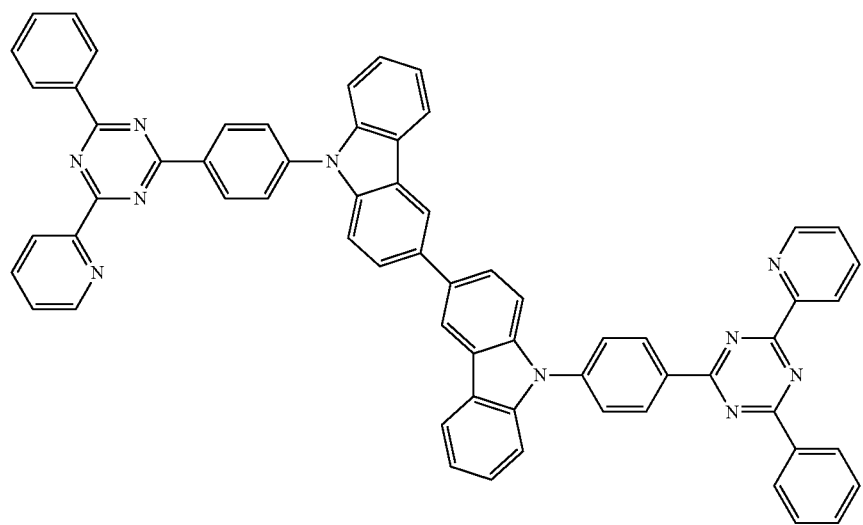

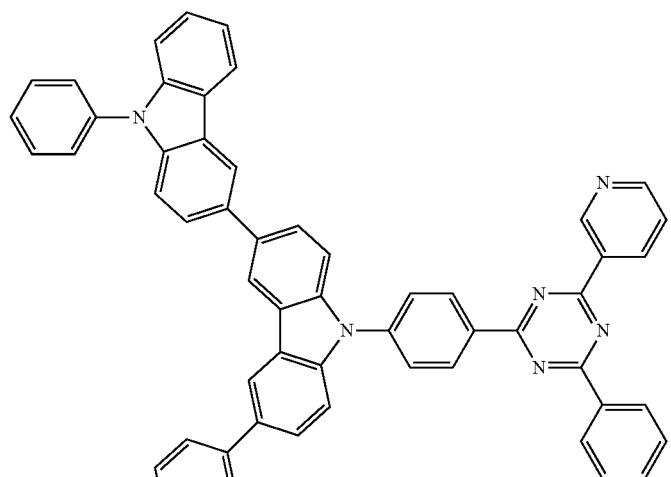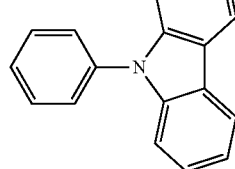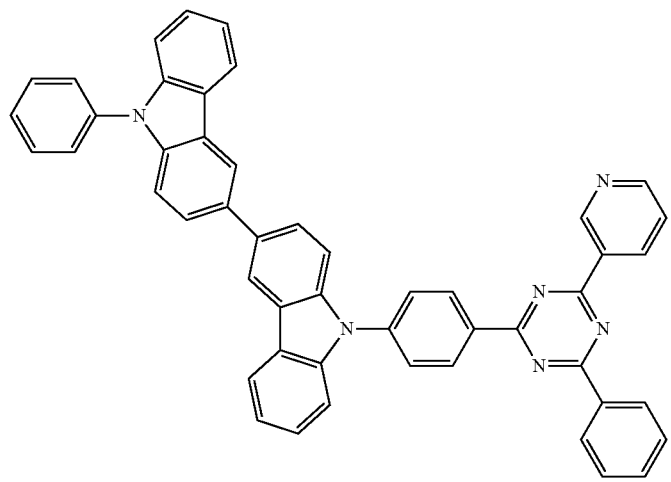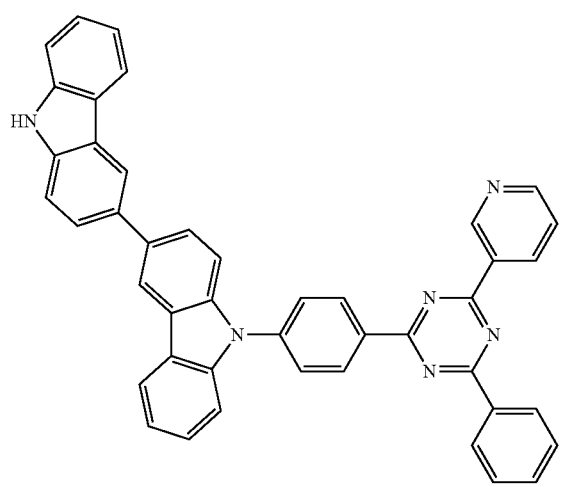

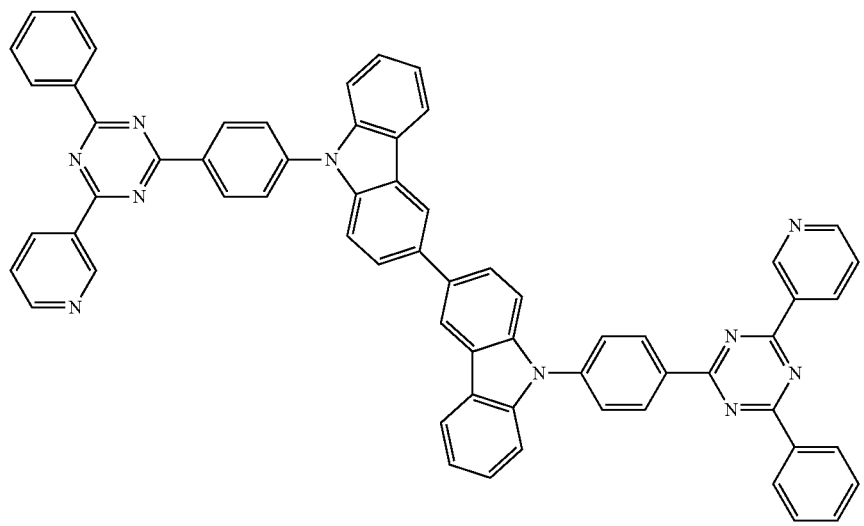
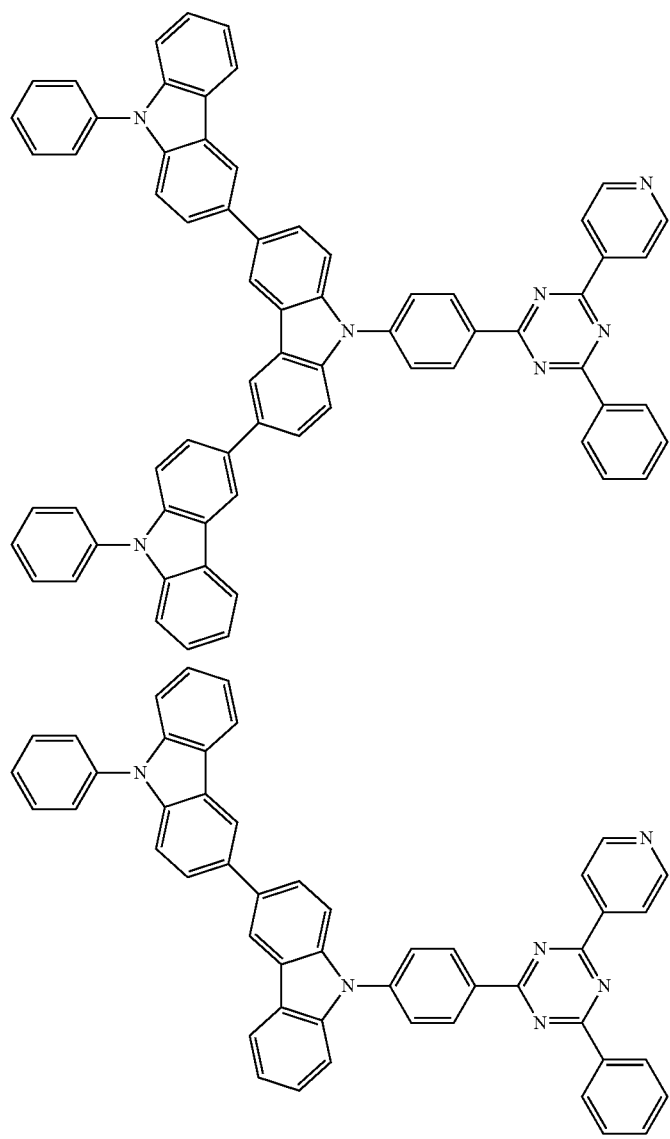

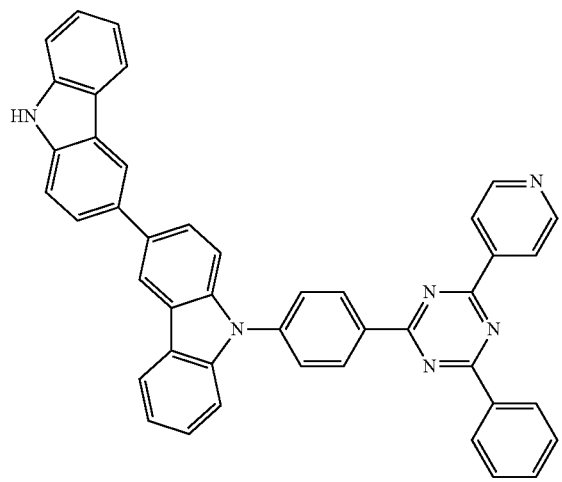
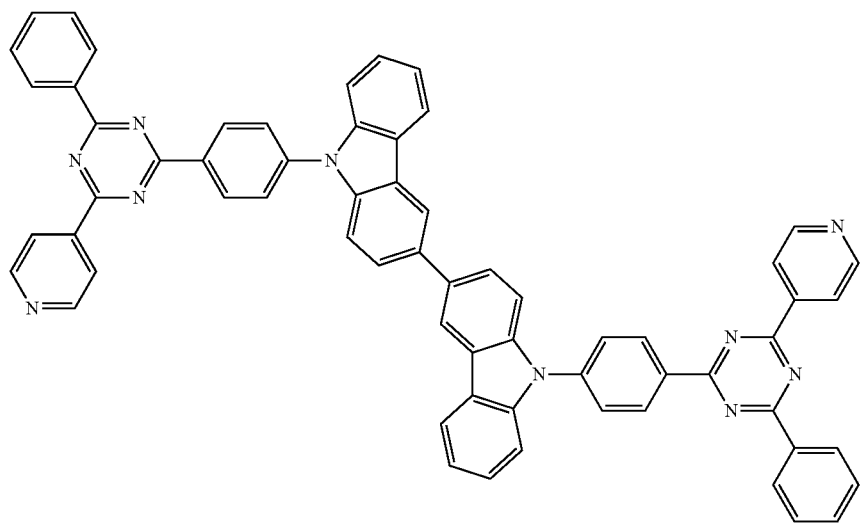 [SMILES: c1ccc(-c2nc(-c3ccncc3)nc(-c3ccc(-n4c5ccccc5c5cc(-c6ccc7c(c6)c6ccccc6n7-c6ccc(-c7nc(-c8ccccc8)nc(-c8ccncc8)n7)cc6)ccc54)cc3)n2)cc1]
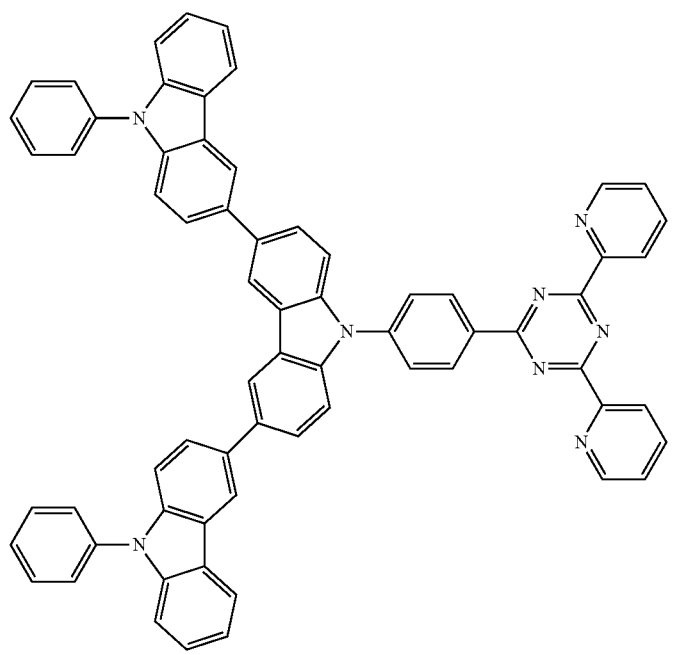

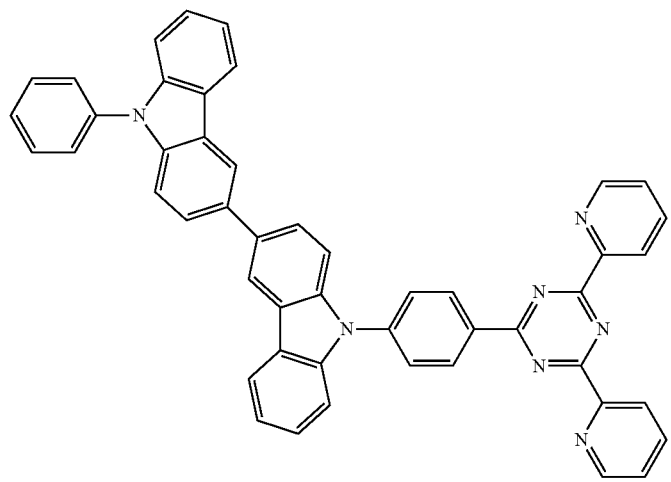
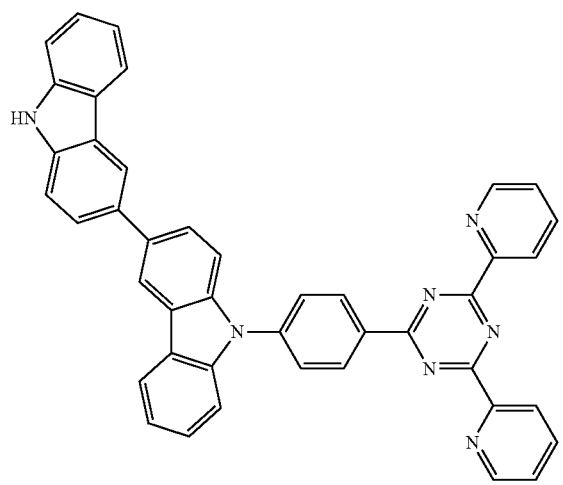
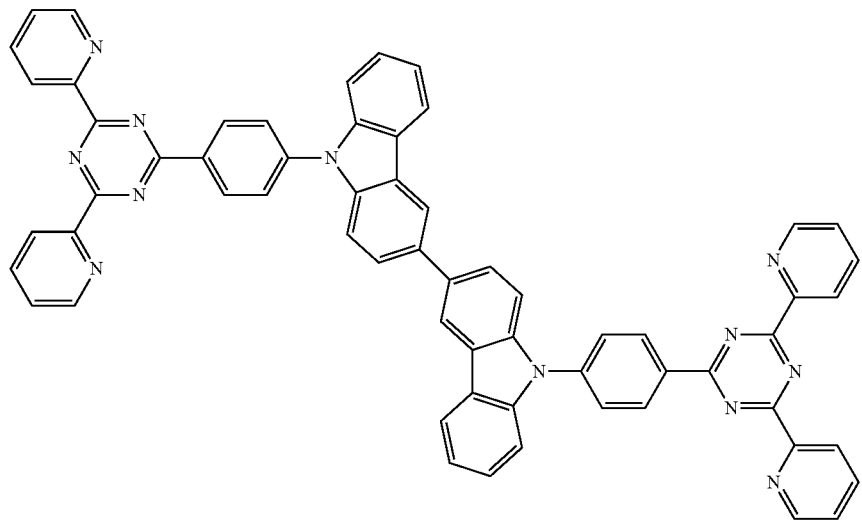 [SMILES: c1ccc(-c2nc(-c3ccc(-n4c5ccccc5c5cc(-c6ccc7c(c6)c6ccccc6n7-c6ccc(-c7nc(-c8ccccn8)nc(-c8ccccn8)n7)cc6)ccc54)cc3)nc(-c3ccccn3)n2)nc1]

-continued
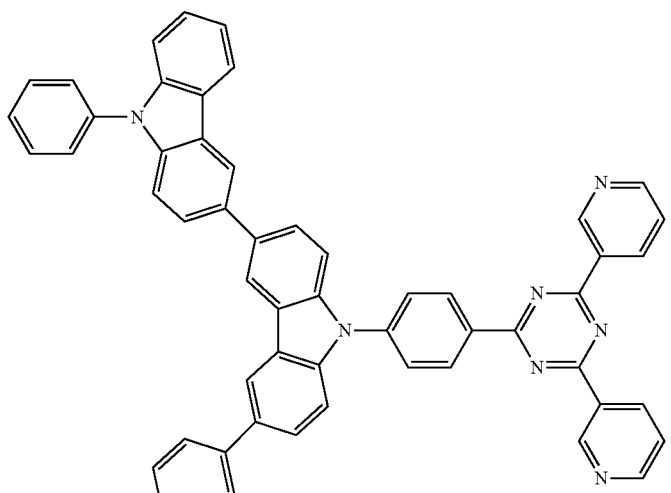
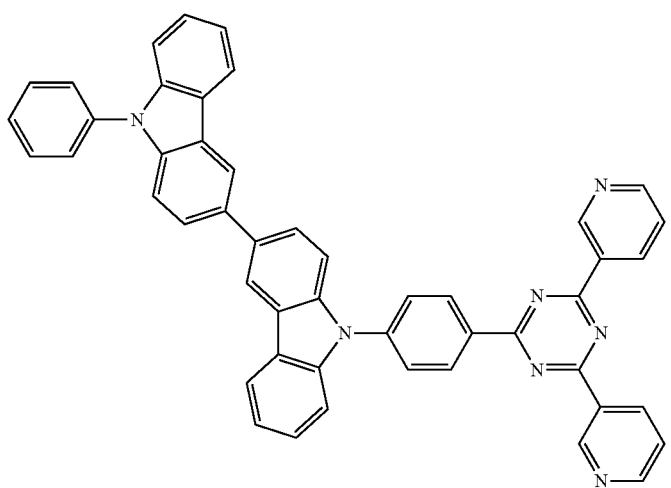
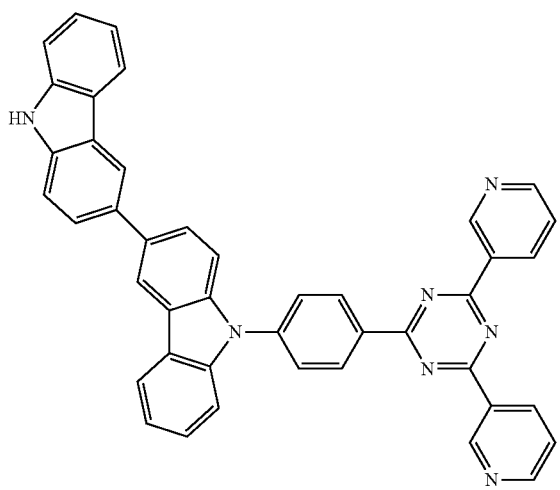

-continued
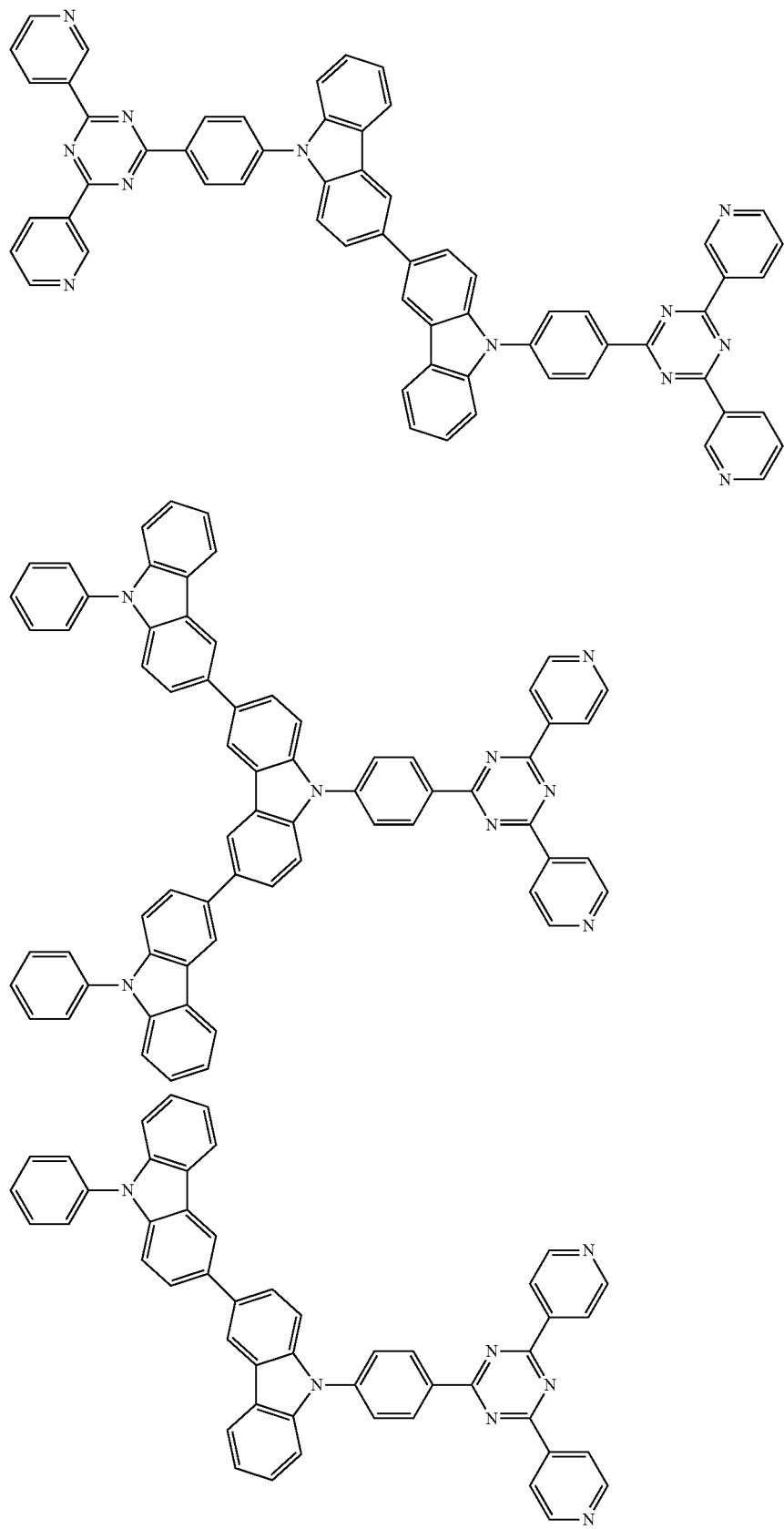

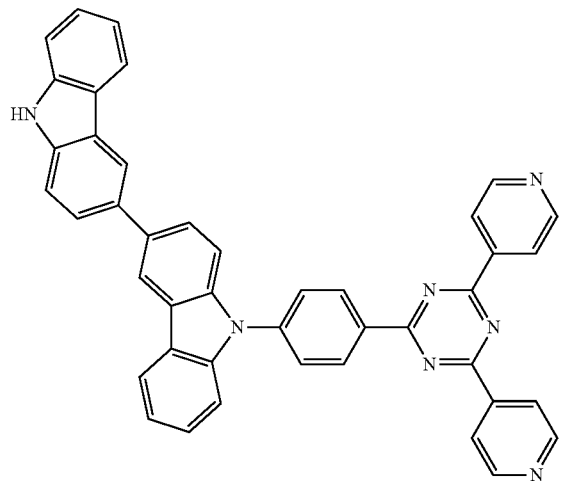
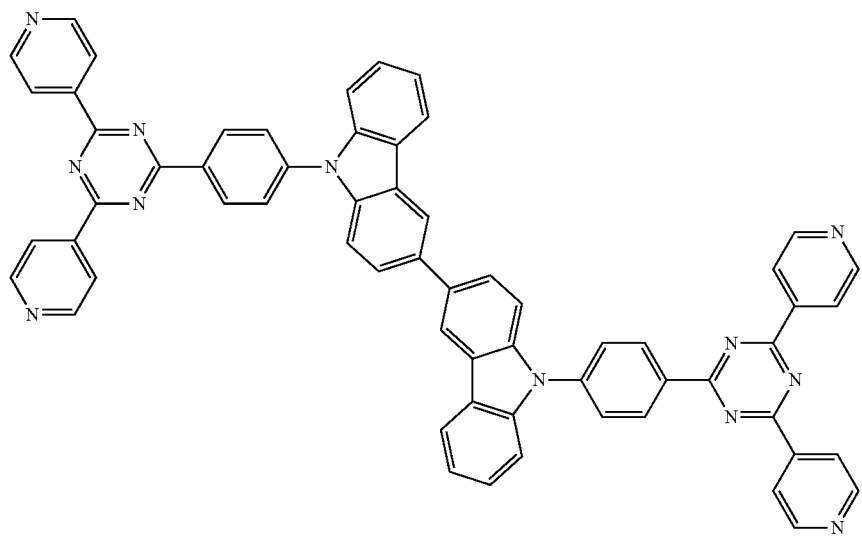 [SMILES: c1ccc2c(c1)c1cc(-c3ccc4c(c3)c3ccccc3n4-c3ccc(-c4nc(-c5ccncc5)nc(-c5ccncc5)n4)cc3)ccc1n2-c1ccc(-c2nc(-c3ccncc3)nc(-c3ccncc3)n2)cc1]
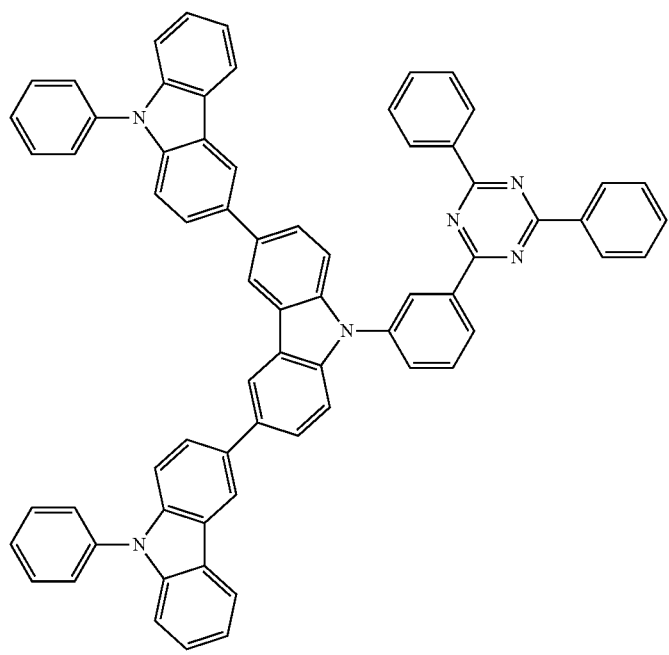

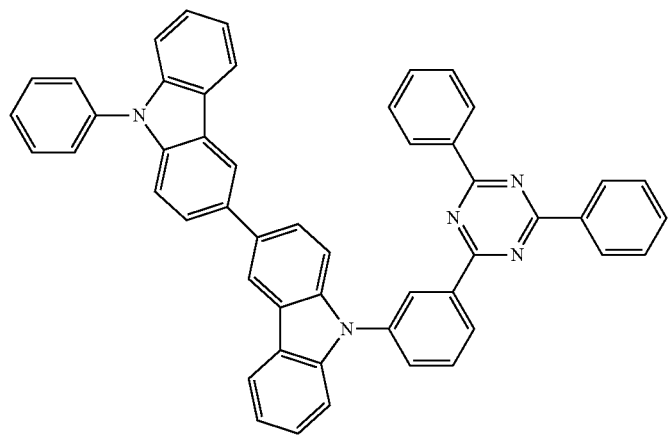
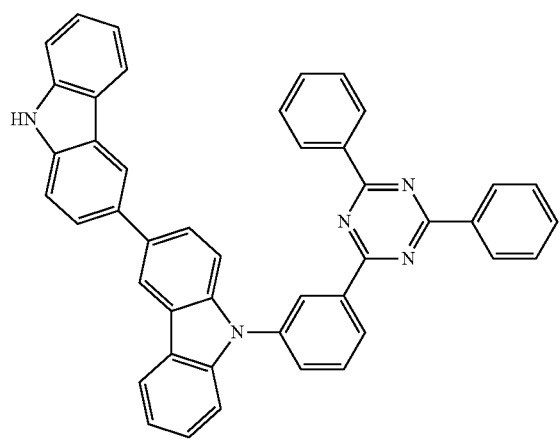
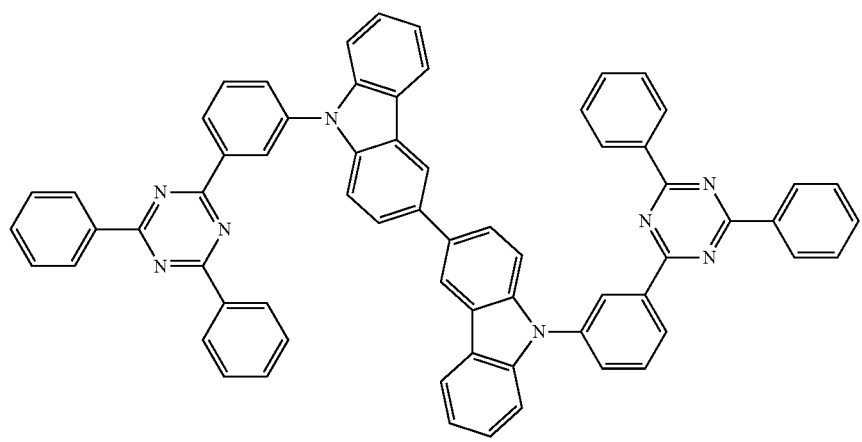

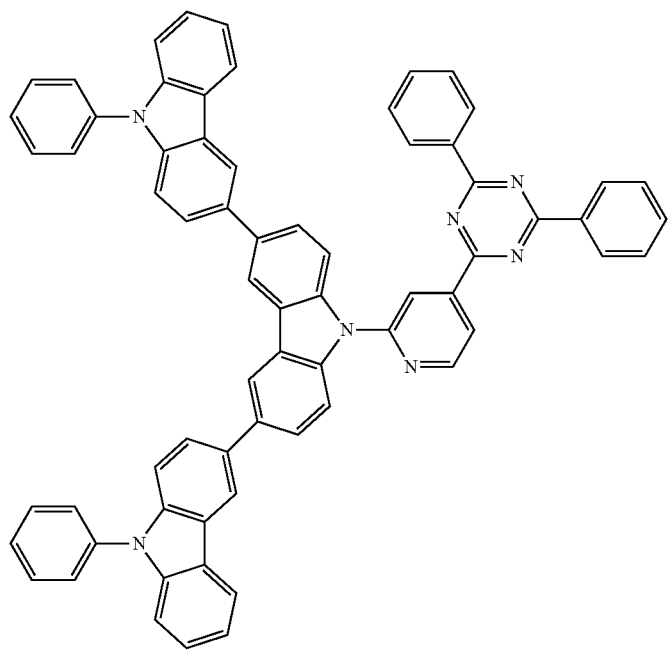
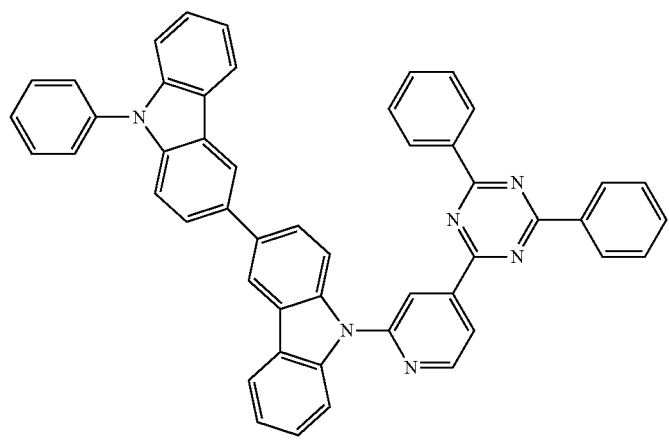
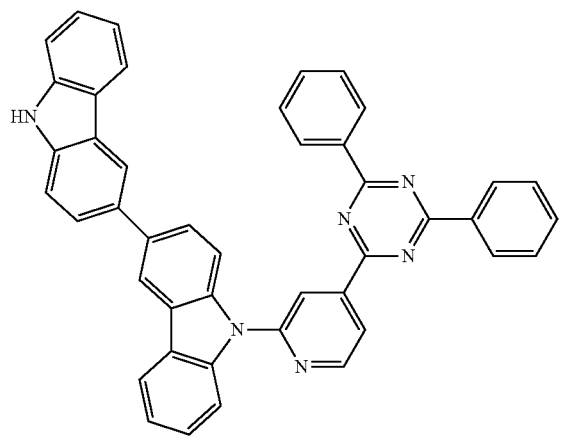

-continued
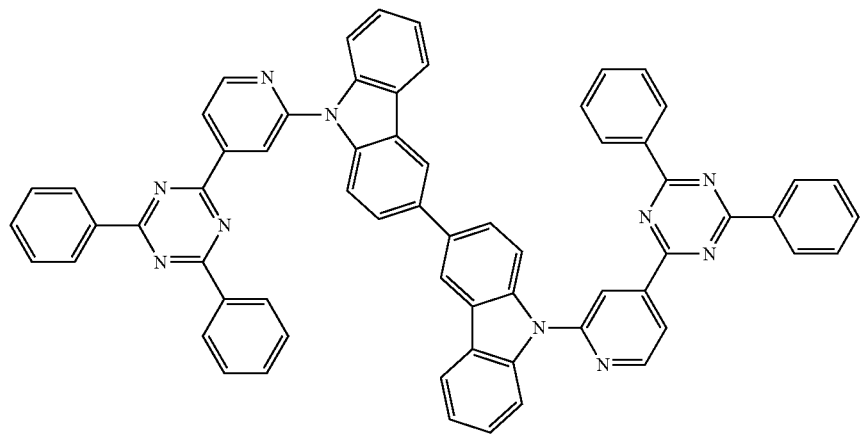 [SMILES: c1ccc(-c2nc(-c3ccccc3)nc(-c3ccnc(-n4c5ccccc5c5cc(-c6ccc7c(c6)c6ccccc6n7-c6cc(-c7nc(-c8ccccc8)nc(-c8ccccc8)n7)ccn6)ccc54)c3)n2)cc1]
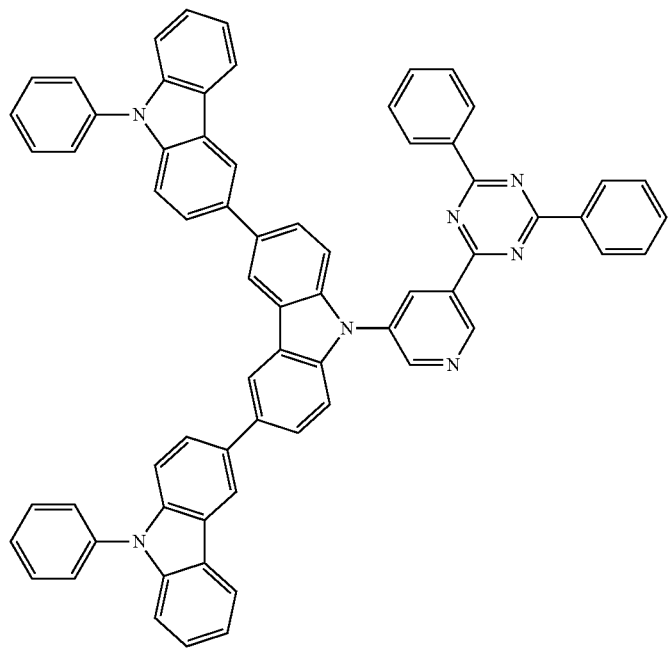
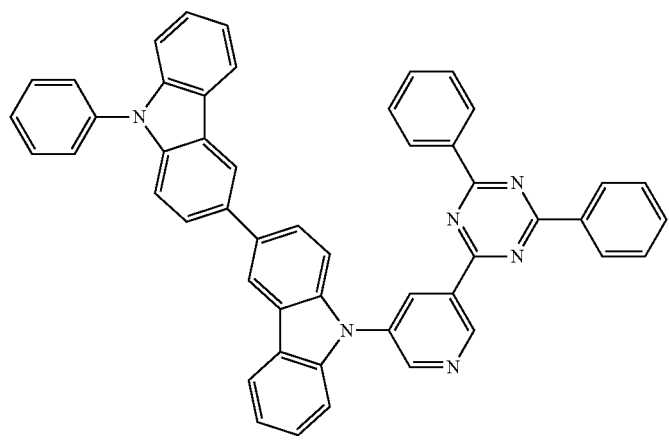

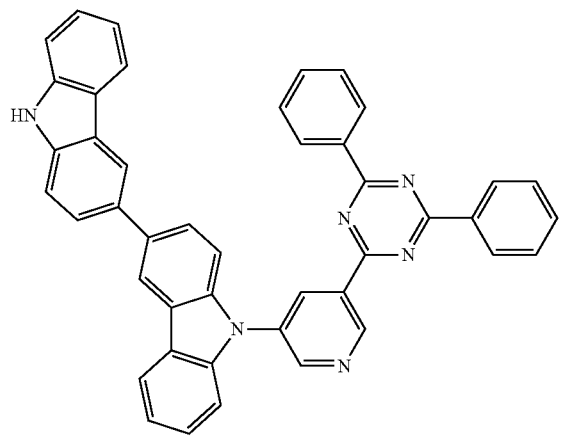
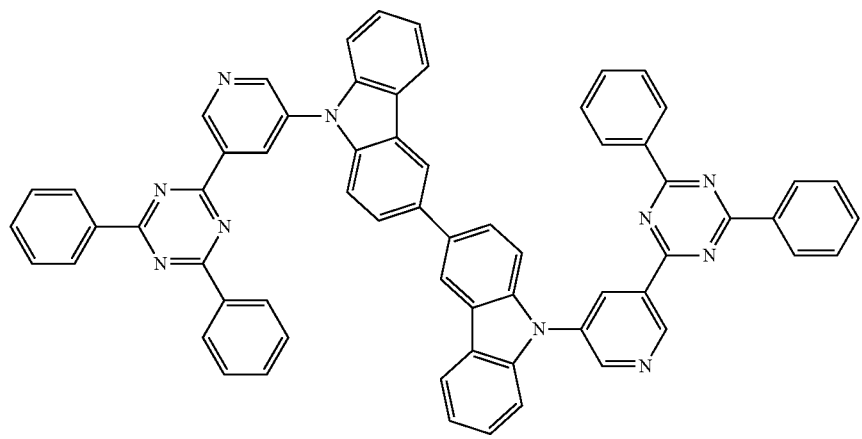 [SMILES: c1ccc(-c2nc(-c3ccccc3)nc(-c3cncc(-n4c5ccccc5c5cc(-c6ccc7c(c6)c6ccccc6n7-c6cncc(-c7nc(-c8ccccc8)nc(-c8ccccc8)n7)c6)ccc54)c3)n2)cc1]
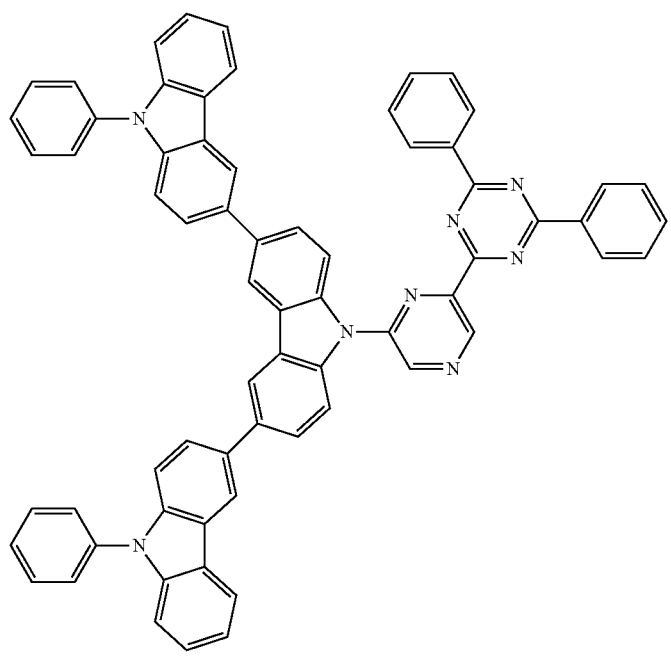

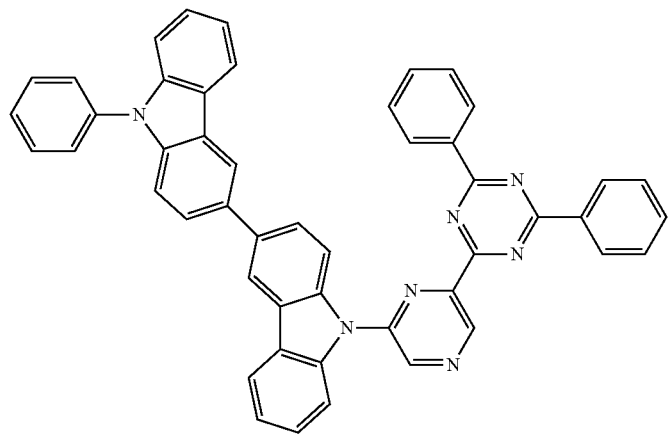
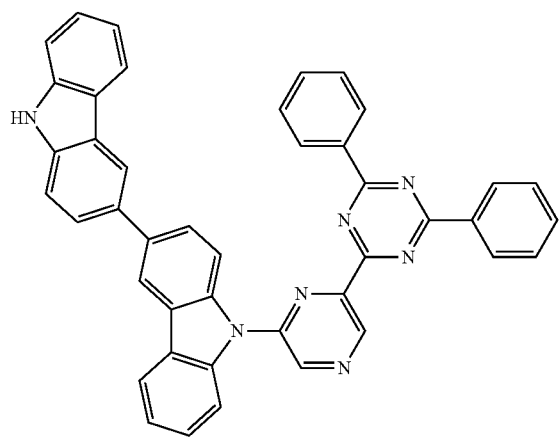
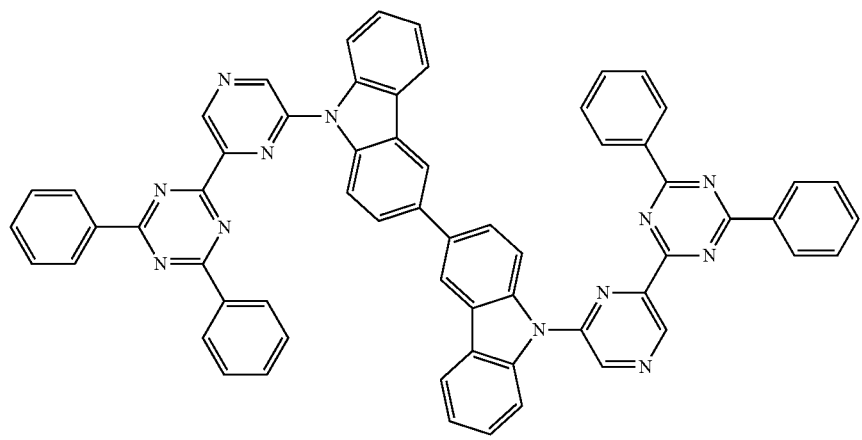 [SMILES: c1ccc(-c2nc(-c3ccccc3)nc(-c3cncc(-n4c5ccccc5c5cc(-c6ccc7c(c6)c6ccccc6n7-c6cncc(-c7nc(-c8ccccc8)nc(-c8ccccc8)n7)n6)ccc54)n3)n2)cc1]

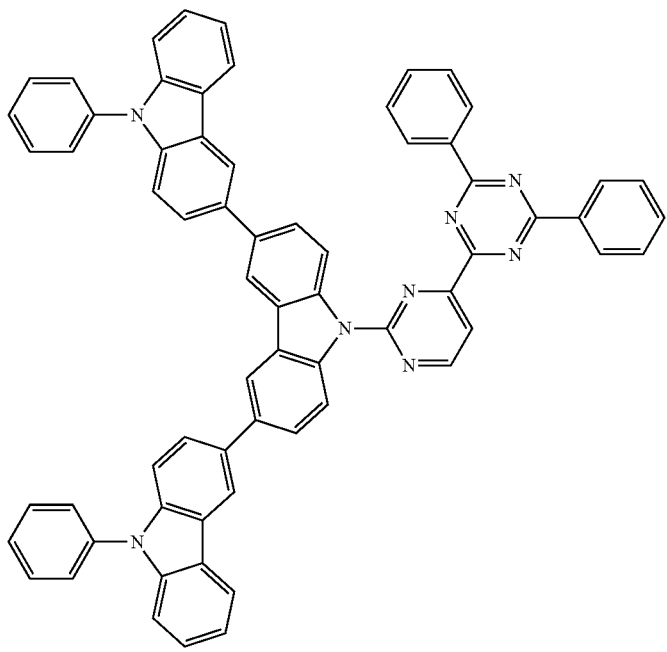
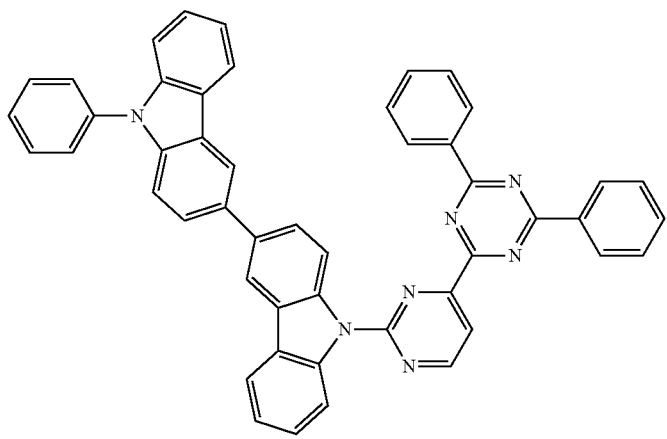
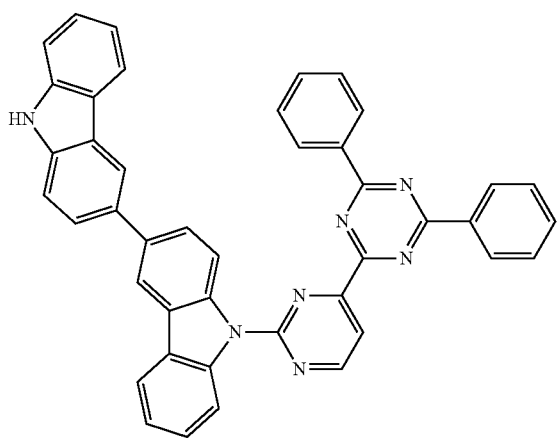

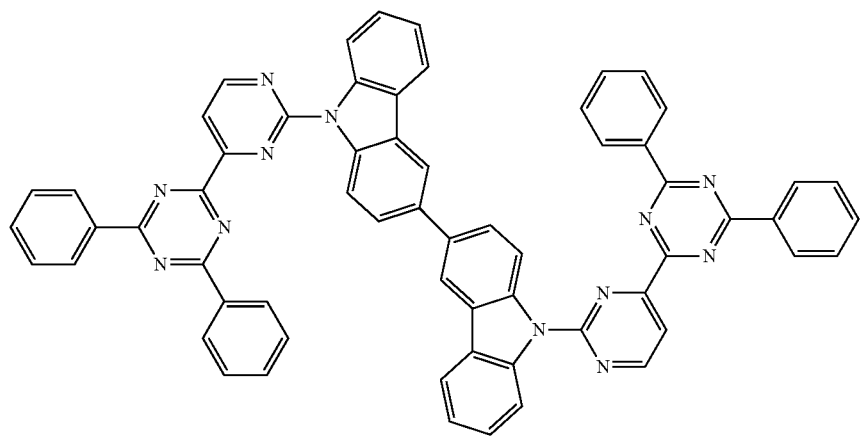 [SMILES: c1ccc(-c2nc(-c3ccccc3)nc(-c3ccnc(-n4c5ccccc5c5cc(-c6ccc7c(c6)c6ccccc6n7-c6nccc(-c7nc(-c8ccccc8)nc(-c8ccccc8)n7)n6)ccc54)n3)n2)cc1]
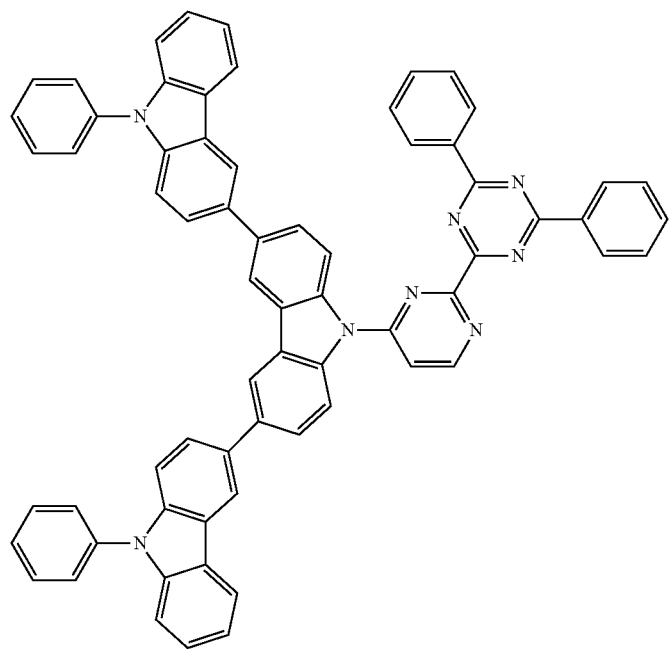
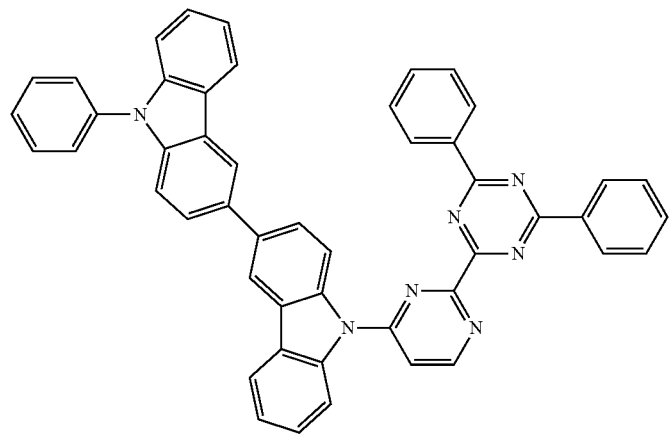

-continued
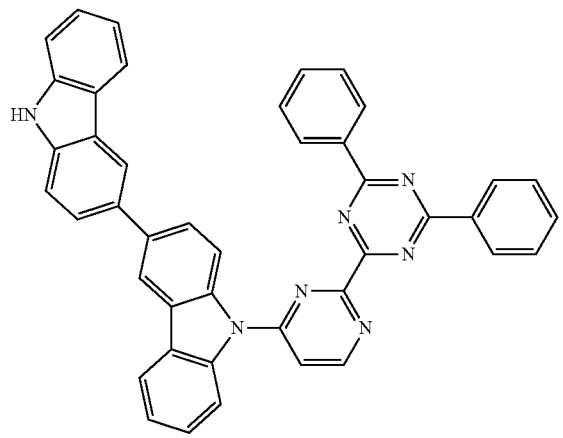
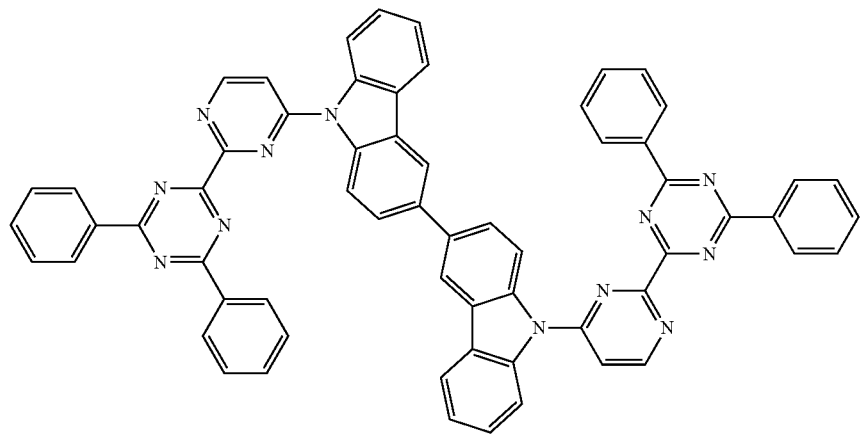
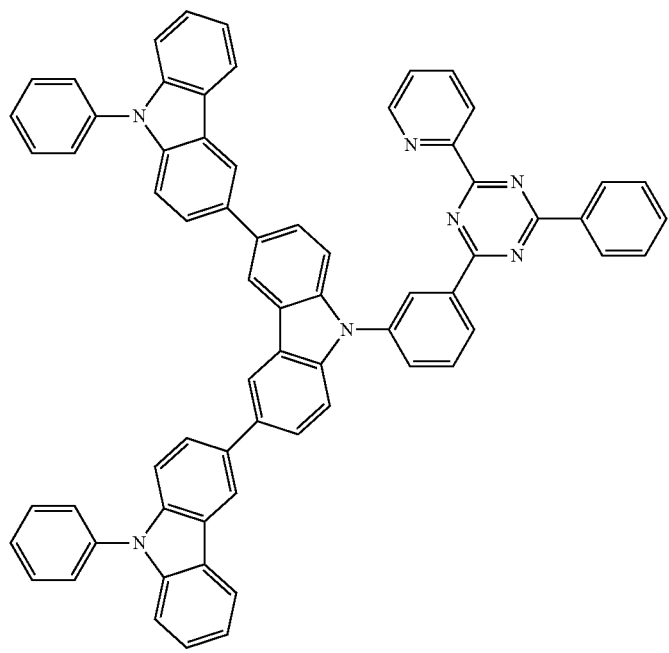

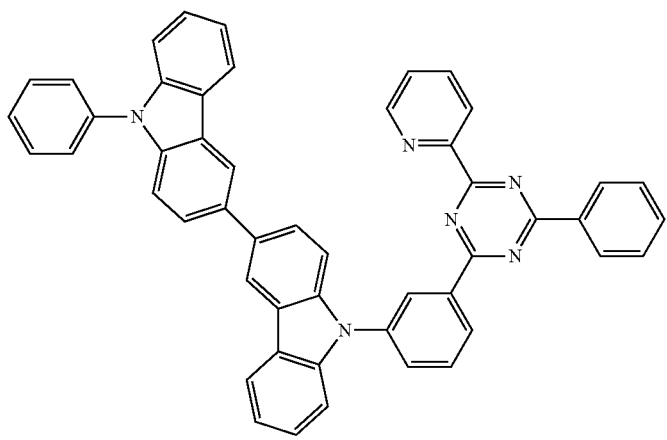
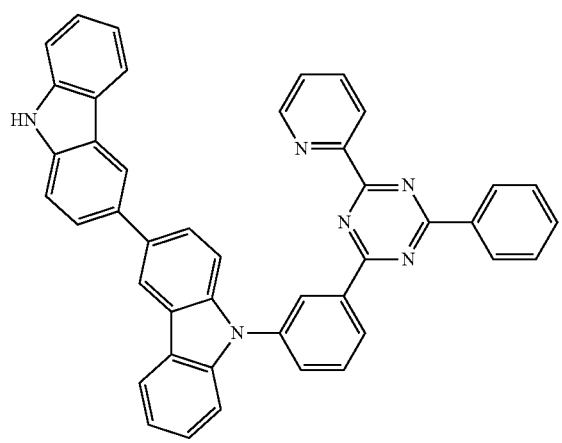
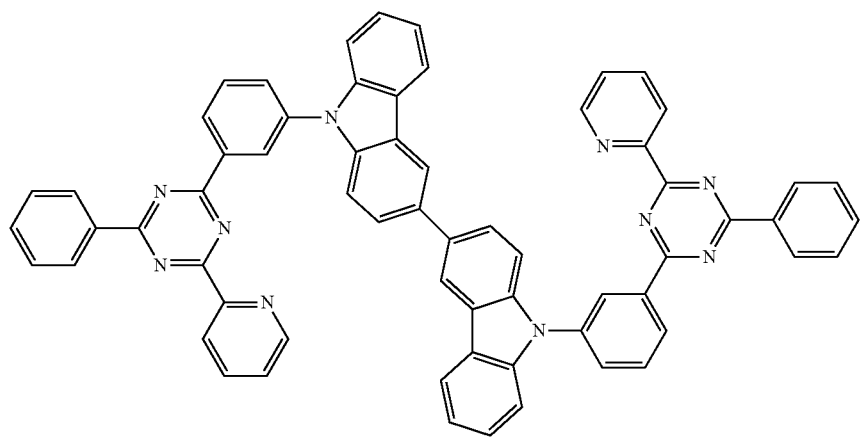 [SMILES: c1ccc(-c2nc(-c3cccc(-n4c5ccccc5c5cc(-c6ccc7c(c6)c6ccccc6n7-c6cccc(-c7nc(-c8ccccc8)nc(-c8ccccn8)n7)c6)ccc54)c3)nc(-c3ccccn3)n2)cc1]

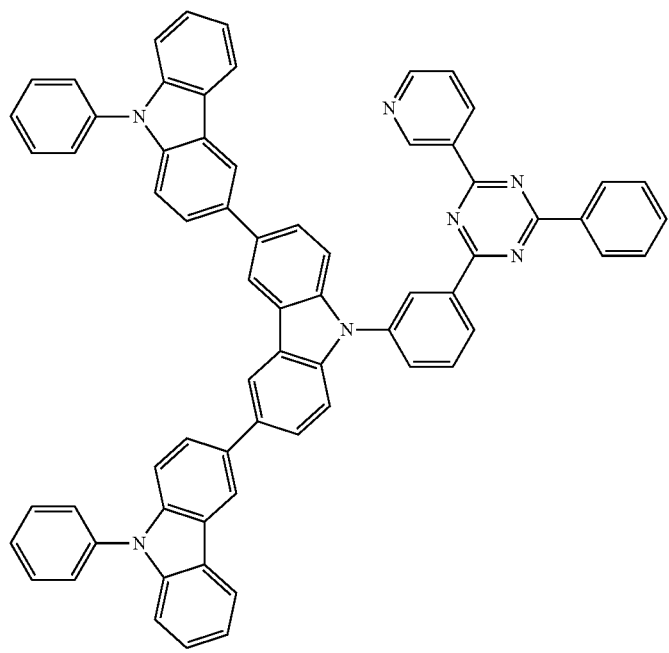
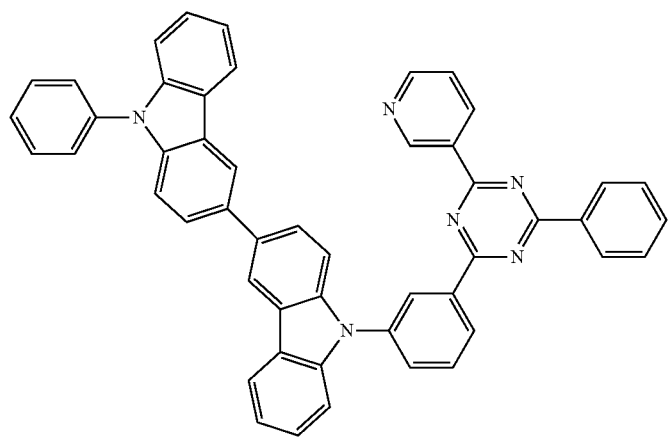
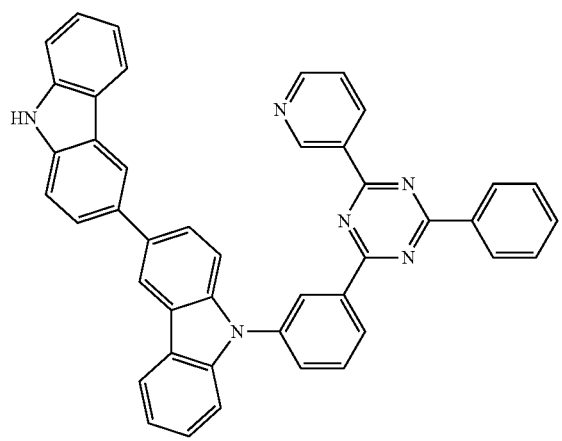

-continued
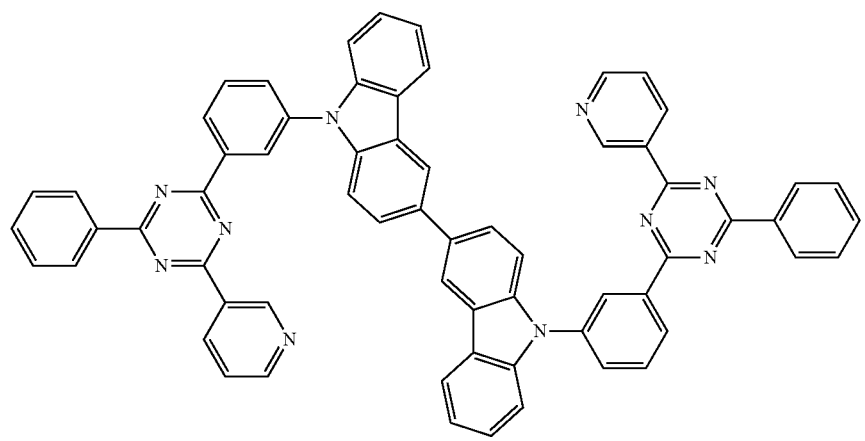
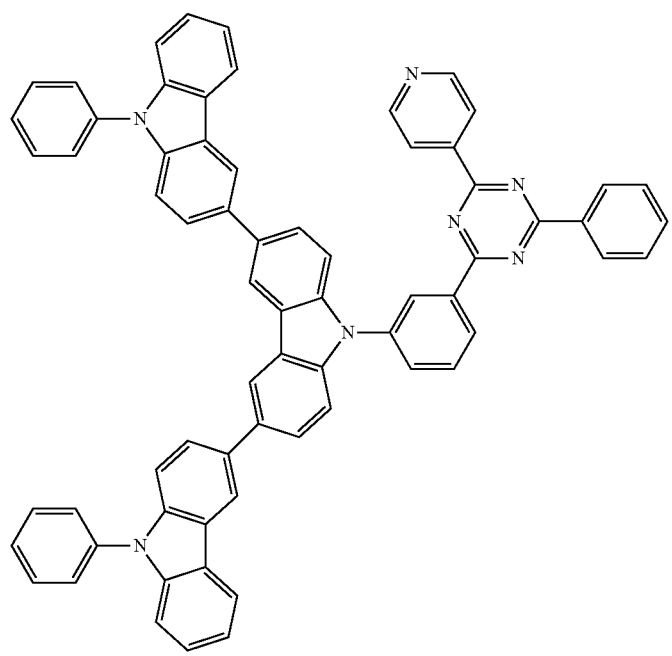
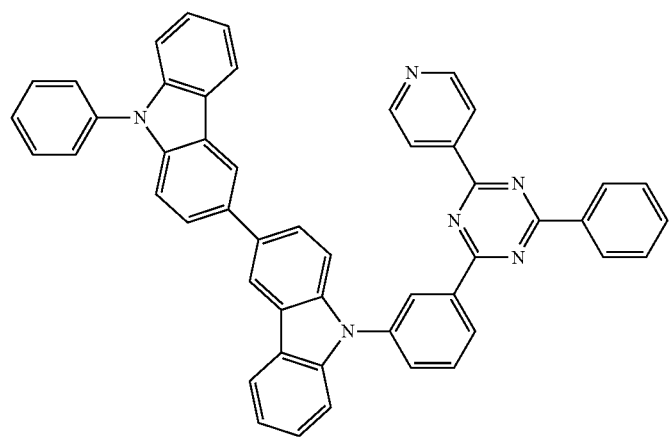

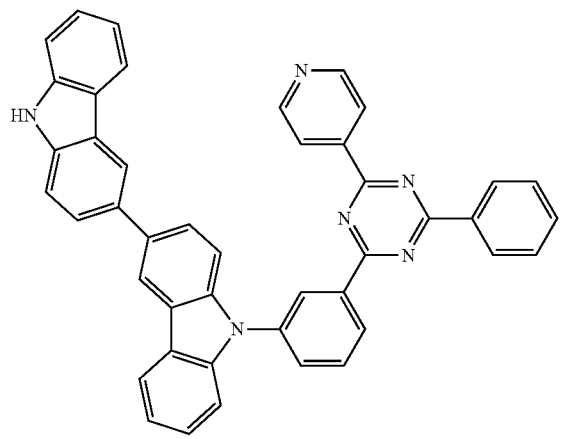
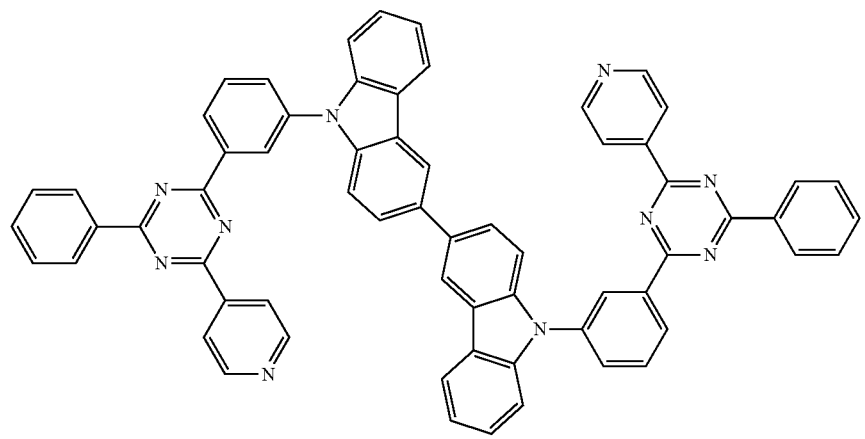 [SMILES: c1ccc(-c2nc(-c3ccncc3)nc(-c3cccc(-n4c5ccccc5c5cc(-c6ccc7c(c6)c6ccccc6n7-c6cccc(-c7nc(-c8ccccc8)nc(-c8ccncc8)n7)c6)ccc54)c3)n2)cc1]
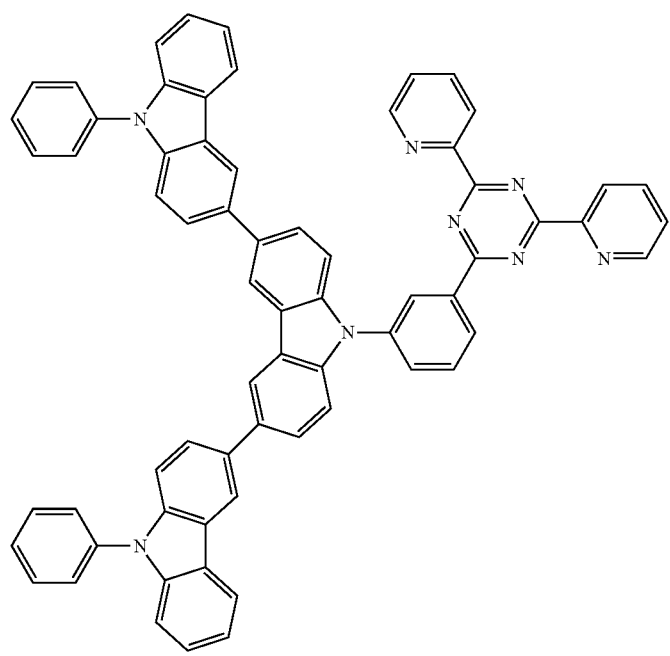

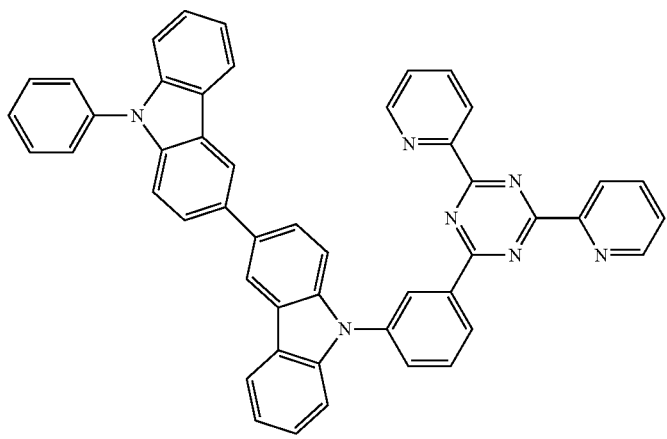
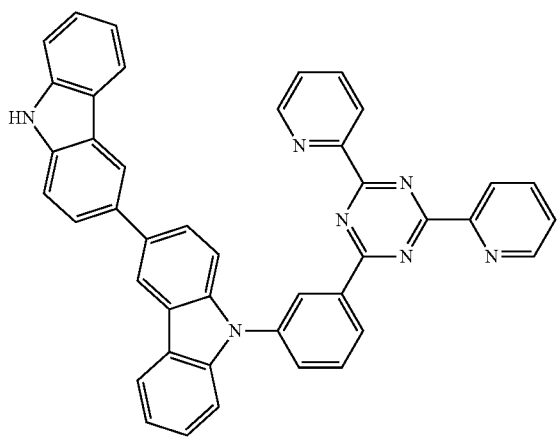
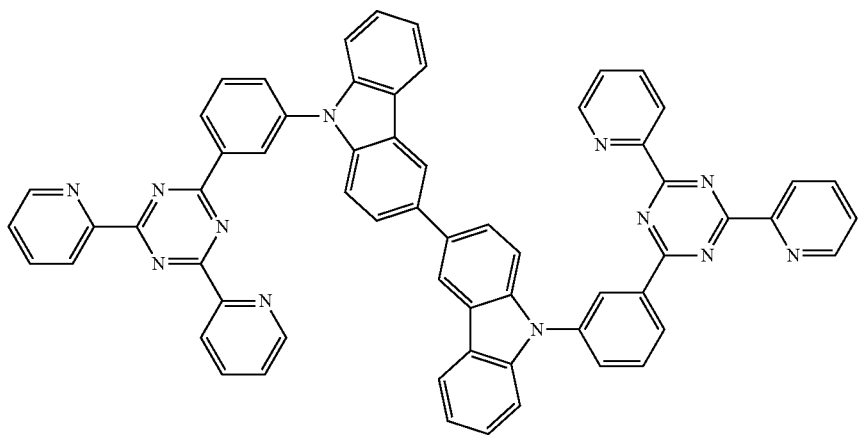 [SMILES: c1ccc(-c2nc(-c3cccc(-n4c5ccccc5c5cc(-c6ccc7c(c6)c6ccccc6n7-c6cccc(-c7nc(-c8ccccn8)nc(-c8ccccn8)n7)c6)ccc54)c3)nc(-c3ccccn3)n2)nc1]

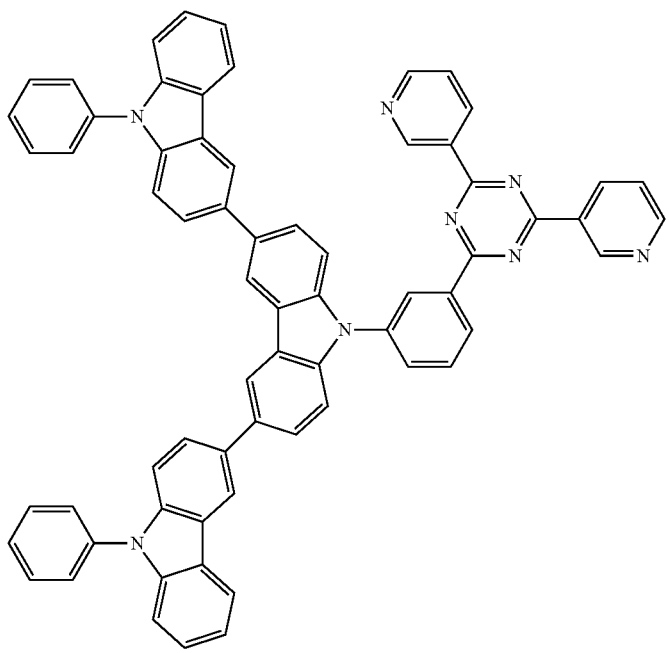
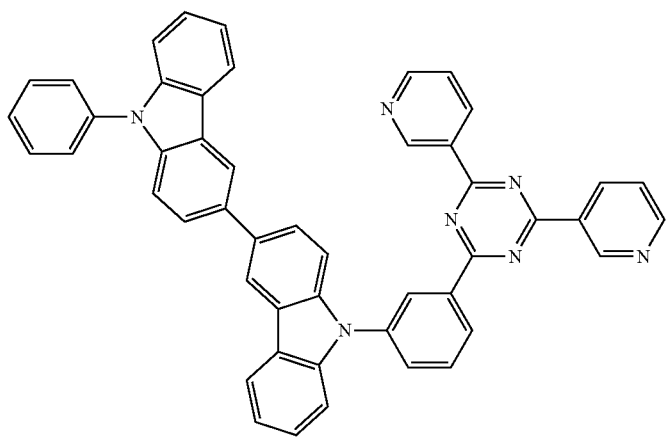
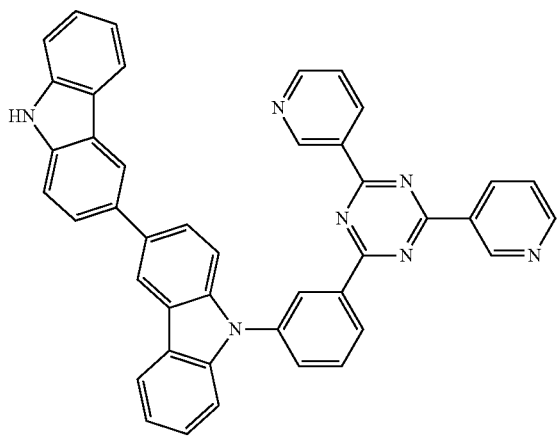

-continued
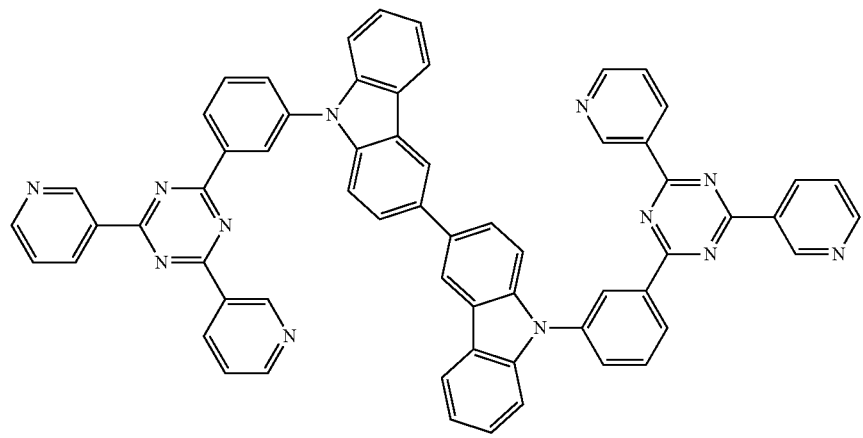
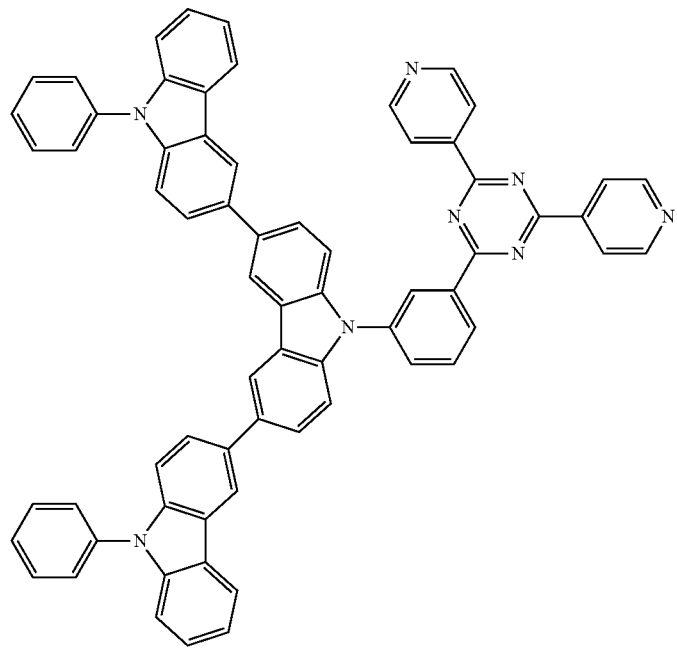
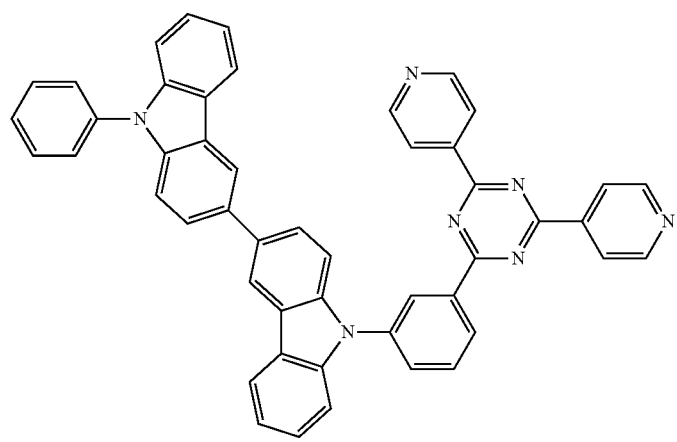

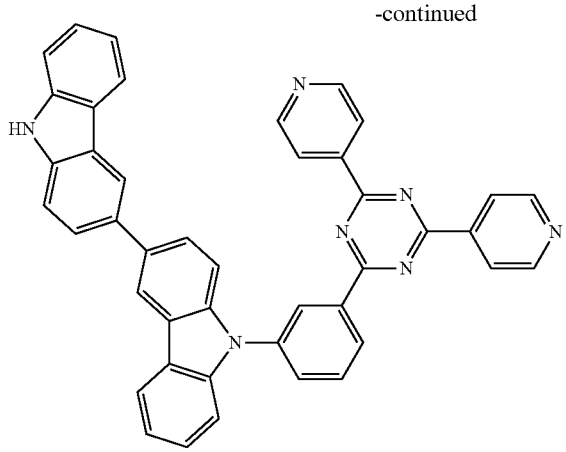

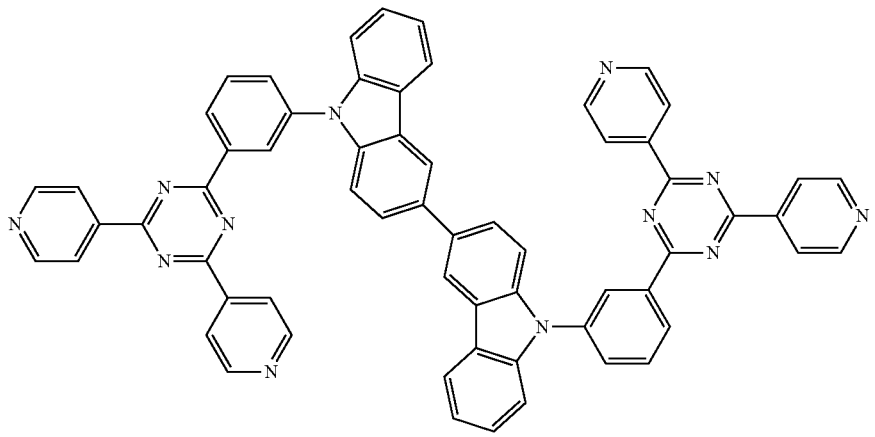 [SMILES: c1cc(-c2nc(-c3ccncc3)nc(-c3ccncc3)n2)cc(-n2c3ccccc3c3cc(-c4ccc5c(c4)c4ccccc4n5-c4cccc(-c5nc(-c6ccncc6)nc(-c6ccncc6)n5)c4)ccc32)c1]

Examples of the preferred light-emitting material include compounds represented by the following general formulae (211) and (212). The entire description of WO 2013/133359 including the paragraphs 0007 to 0032 and 0079 to 0084 is incorporated herein by reference.

General Formula (211)

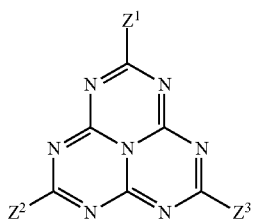

wherein in the general formula (211), $Z^1$, $Z^2$ and $Z^3$ each independently represent a substituent.

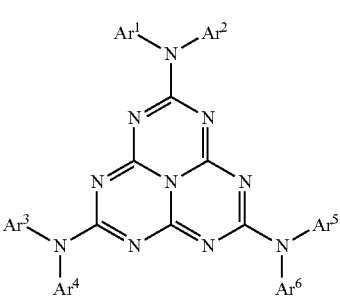

wherein in the general formula (212), $Ar^1$, $Ar^2$, $Ar^3$, $Ar^4$, $Ar^5$ and $Ar^6$ each independently represent a substituted or unsubstituted aryl group.

Specific examples of the compound represented by the general formula (212) include the compound represented by the following structural formula.

Compound 4001

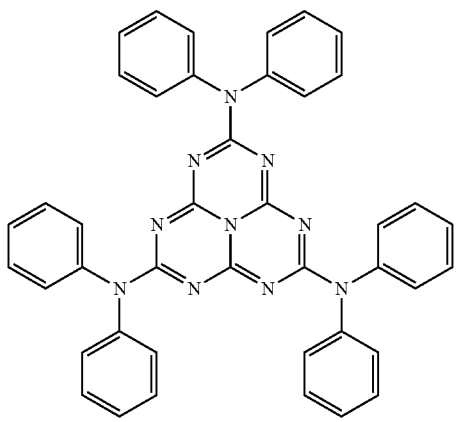

Specific examples of the compound represented by the general formula (212) include the compounds shown in the following table. In the compounds shown in the table, $Ar^1$, $Ar^2$, $Ar^3$, $Ar^4$, $Ar^5$ and $Ar^6$ are the same as each other, and are expressed by Ar.

TABLE 21

| Compound No. | Ar |
| --- | --- |
| 4002 | 4-fluorophenyl |
| 4003 | 3-fluorophenyl |
| 4004 | 2-fluorophenyl |
| 4005 | 3,5-difluorophenyl |
| 4006 | 2,4,6-trifluorophenyl |
| 4007 | 4-methylphenyl |
| 4008 | 3-methylphenyl |
| 4009 | 2-methylphenyl |
| 4010 | 3,5-dimethylphenyl |
| 4011 | 2,4,6-trimethylphenyl |
| 4012 | 4-ethylphenyl |
| 4013 | 3-ethylphenyl |

TABLE 21-continued

| Compound No. | Ar |
| --- | --- |
| 4014 | 2-ethylphenyl |
| 4015 | 3,5-diethylphenyl |
| 4016 | 4-propylphenyl |
| 4017 | 3-propylphenyl |
| 4018 | 3,5-dipropylphenyl |
| 4019 | 4-tert-butylphenyl |
| 4020 | 3-tert-butylphenyl |
| 4021 | 3,5-di-tert-butylphenyl |
| 4022 | 1-naphthyl |
| 4023 | 2-naphthyl |

Examples of the preferred light-emitting material include compounds represented by the following general formula (221). The entire description of WO 2013/161437 including the paragraphs 0008 to 0054 and 0101 to 0121 is incorporated herein by reference.

General Formula (221)

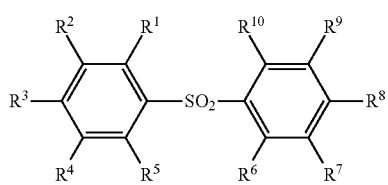

wherein in the general formula (221), $R^1$ to $R^{10}$ each independently represent a hydrogen atom or a substituent, provided that at least one of $R^1$ to $R^{10}$ represents a substituted or unsubstituted aryl group, a substituted or unsubstituted diarylamino group or a substituted or unsubstituted 9-carbazolyl group, and $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^8$ and $R^9$, and $R^9$ and $R^{10}$ each may be bonded to each other to form a cyclic structure.

Specific examples of the compound include the following compounds.

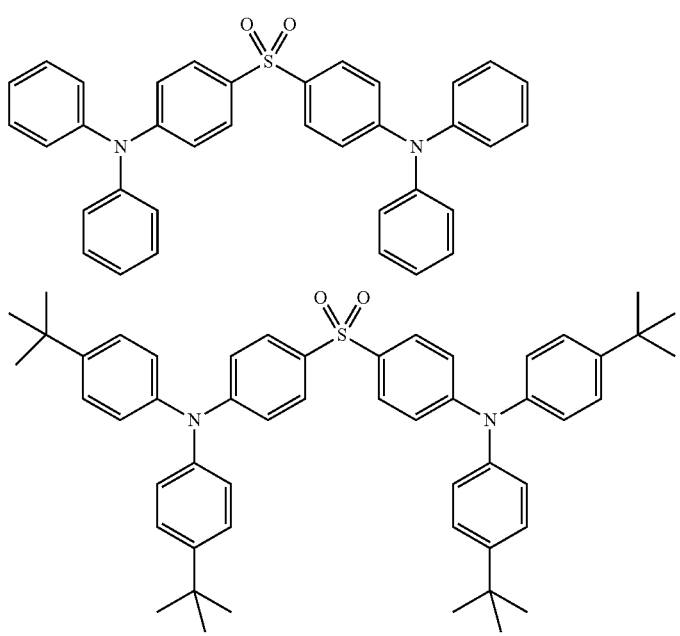

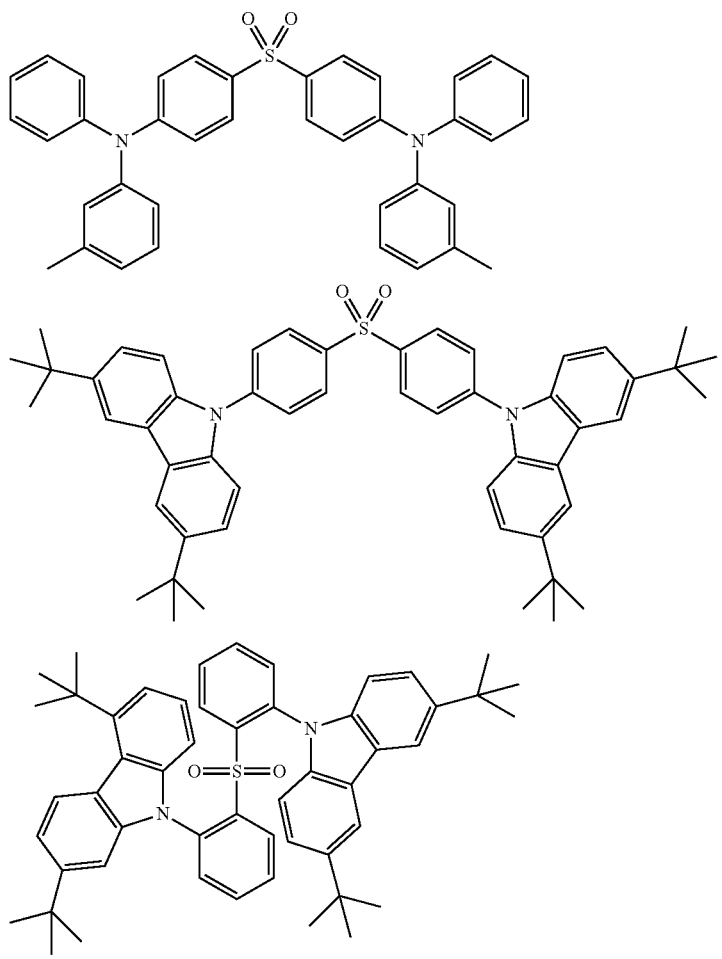
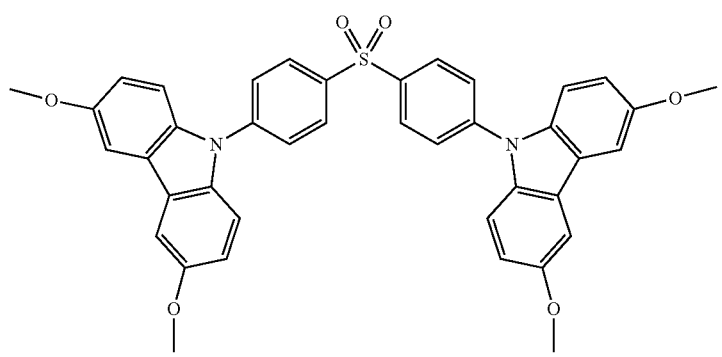
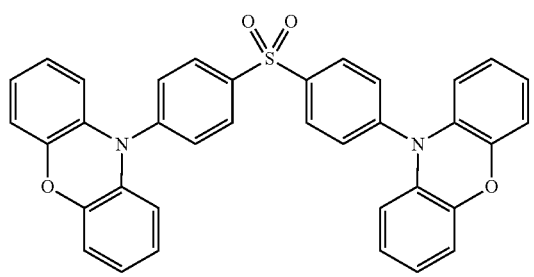

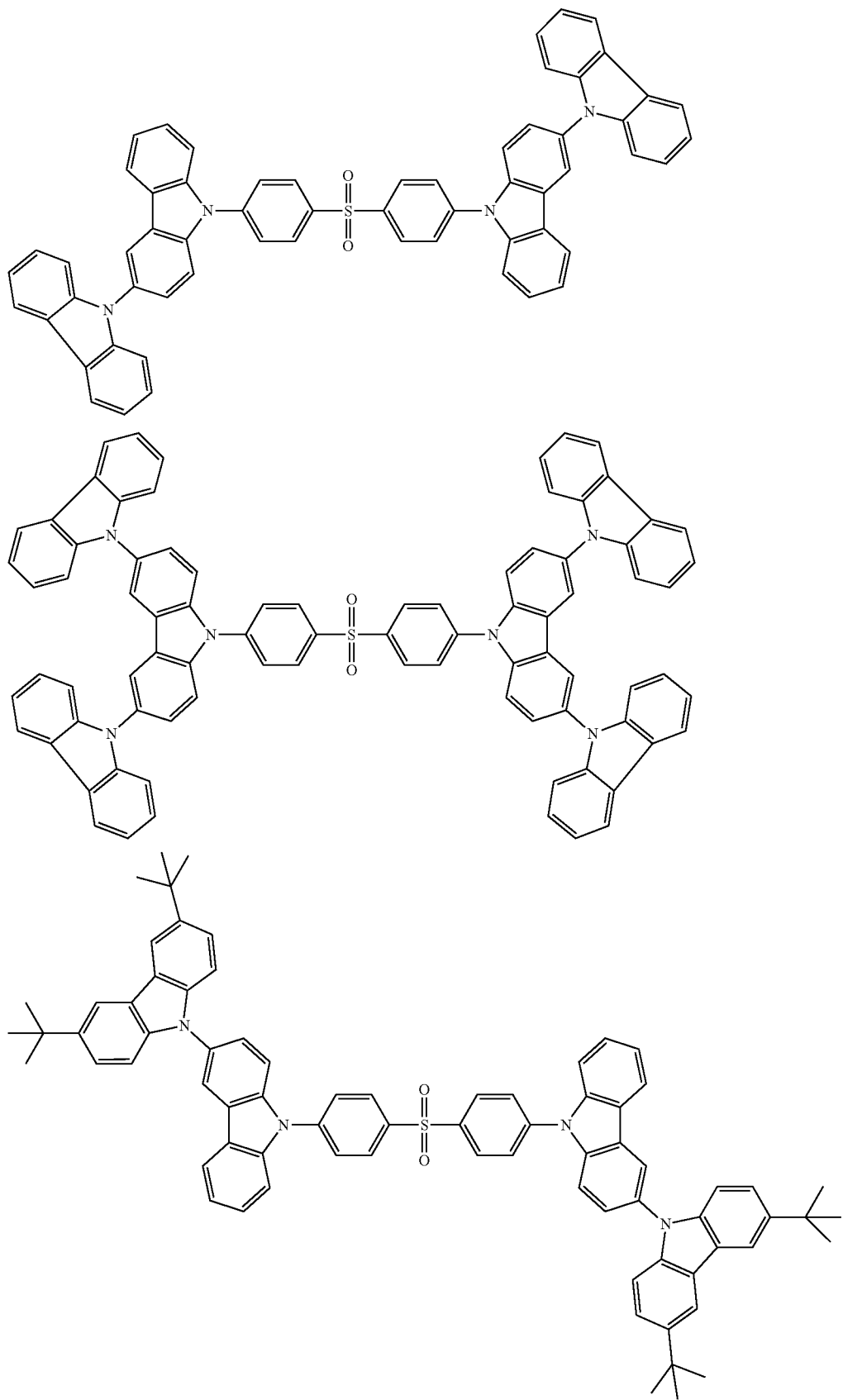

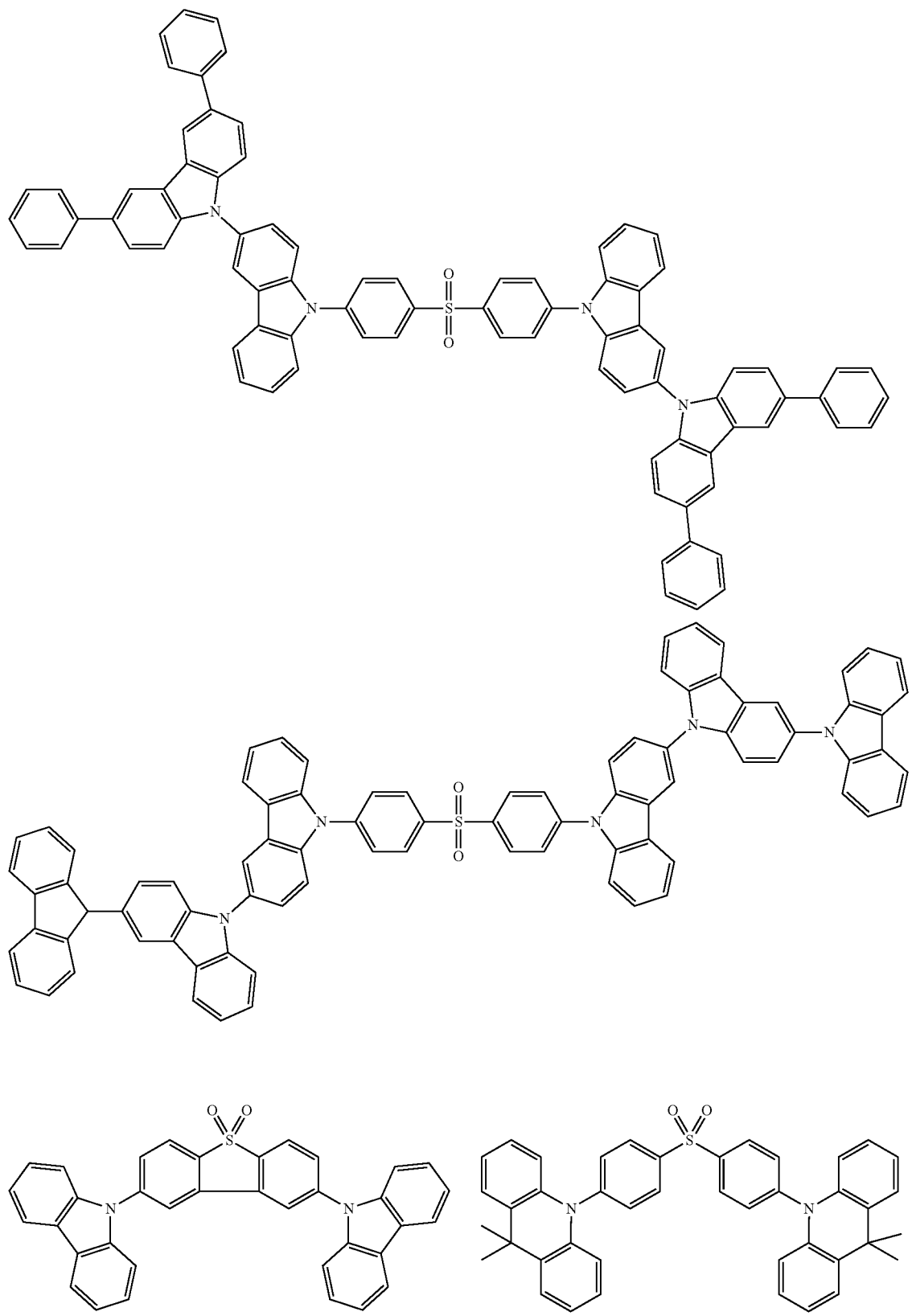

Examples of the preferred light-emitting material include compounds represented by the following general formula (231). The entire description of JP-A-2014-9352 including the paragraphs 0007 to 0041 and 0060 to 0069 is incorporated herein by reference.

General Formula (231)

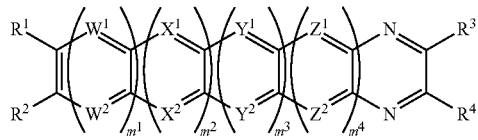

wherein in the general formula (231), $R^1$ to $R^4$ each independently represent a hydrogen atom or a substituted or unsubstituted (N,N-diarylamino)aryl group, provided that at least one of $R^1$ to $R^4$ represents a substituted or unsubstituted (N,N-diarylamino)aryl group, and two aryl groups constituting the diarylamino moiety of the (N,N-diarylamino)aryl group may be bonded to each other; $W^1$, $W^2$, $X^1$, $X^2$, $Y^1$, $Y^2$, $Z^1$ and $Z^2$ each independently represent a carbon atom or a nitrogen atom; and $m^1$ to $m^4$ each independently represent 0, 1 or 2.

Specific examples of the compound include the following compounds.

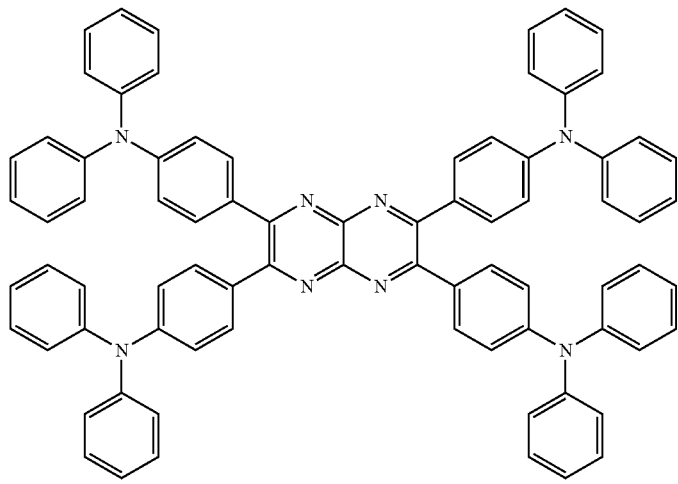

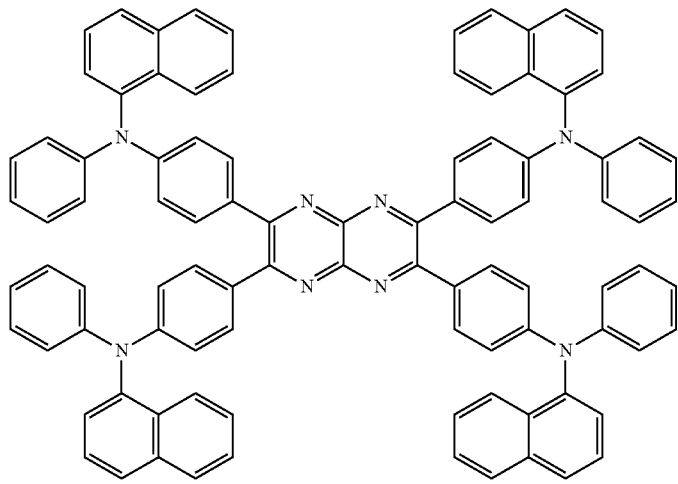

-continued
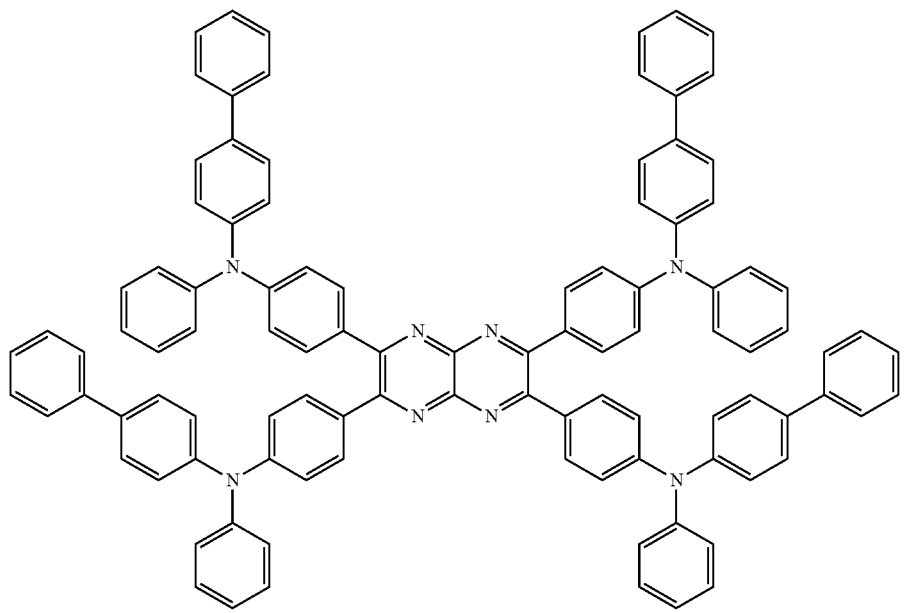
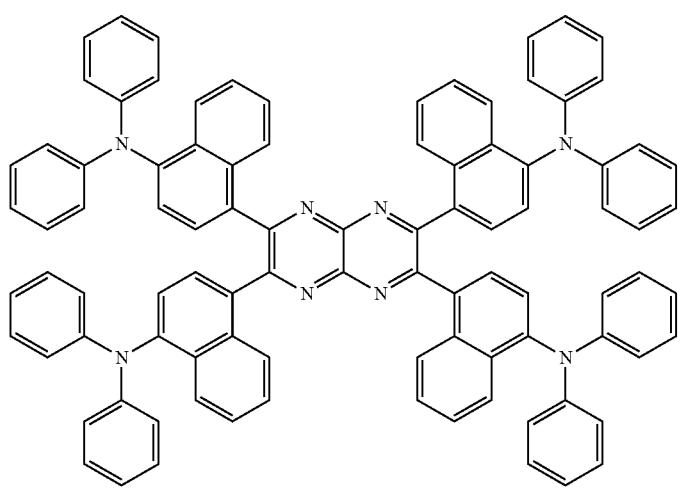
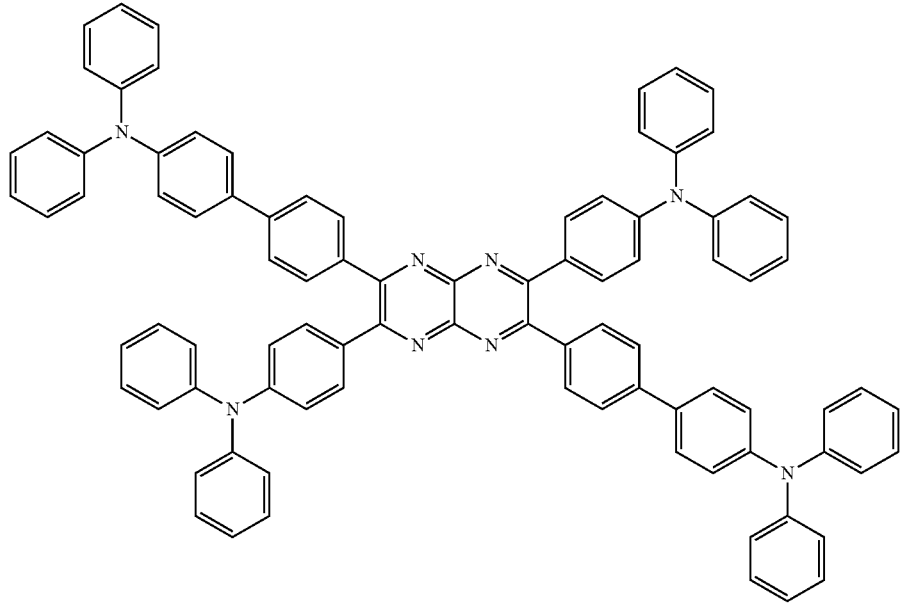

-continued
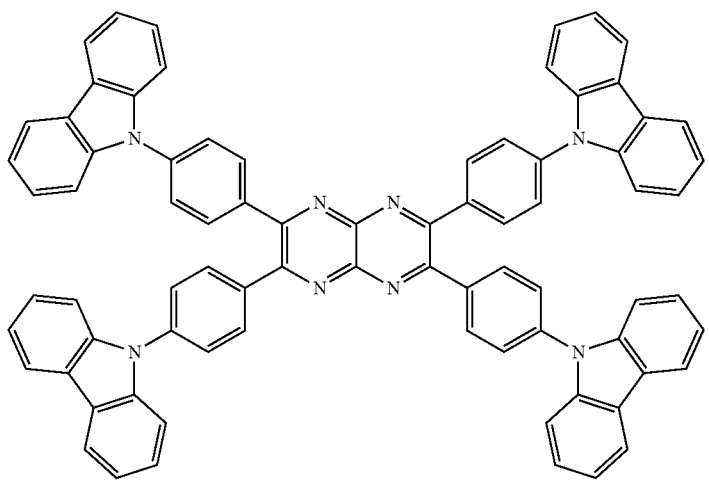
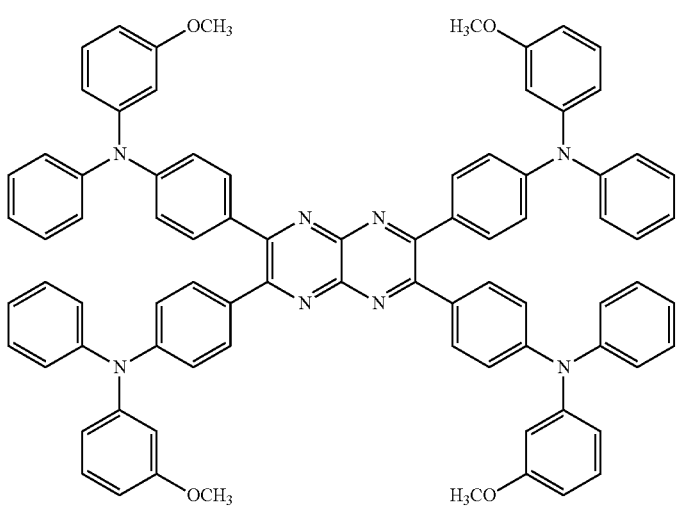
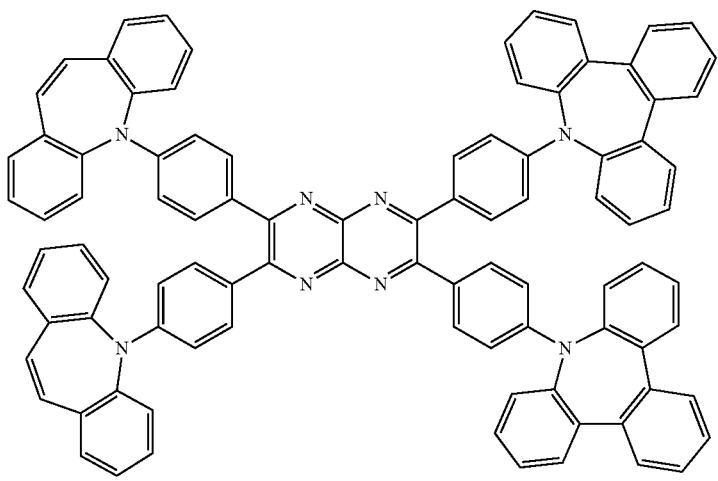

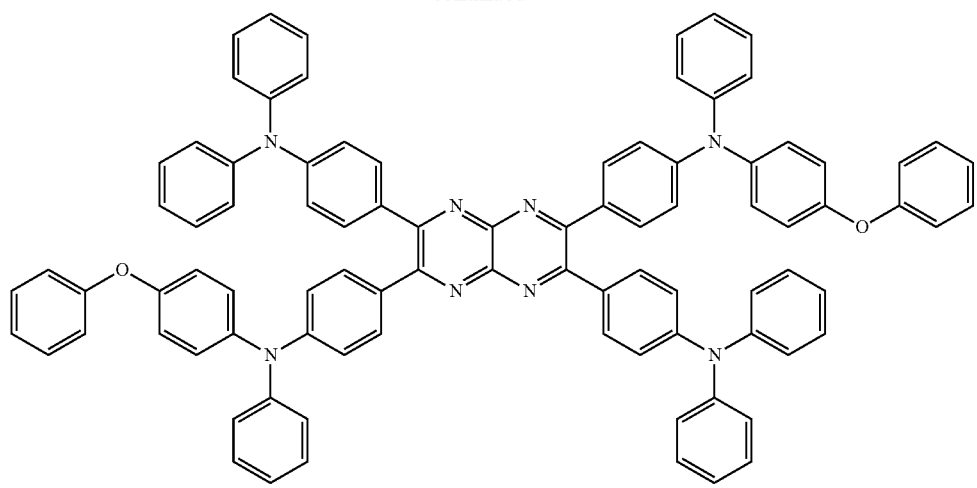
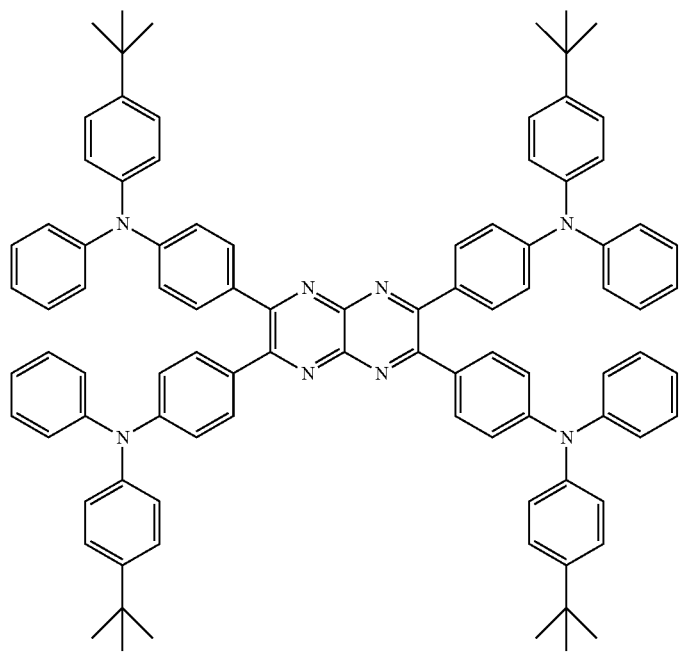
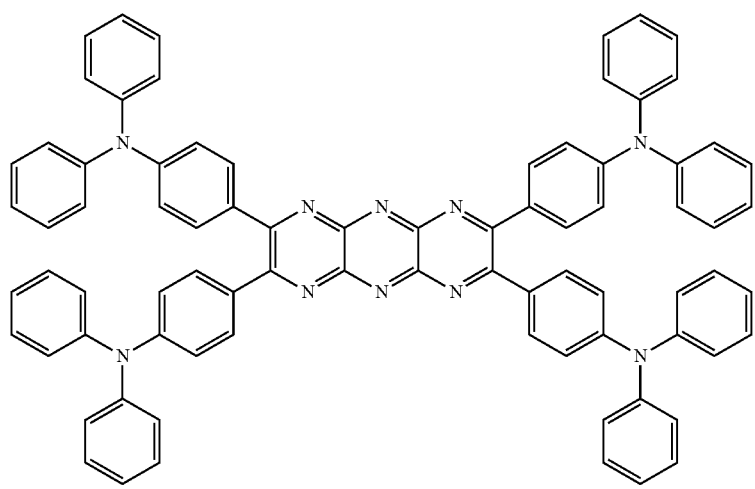

-continued
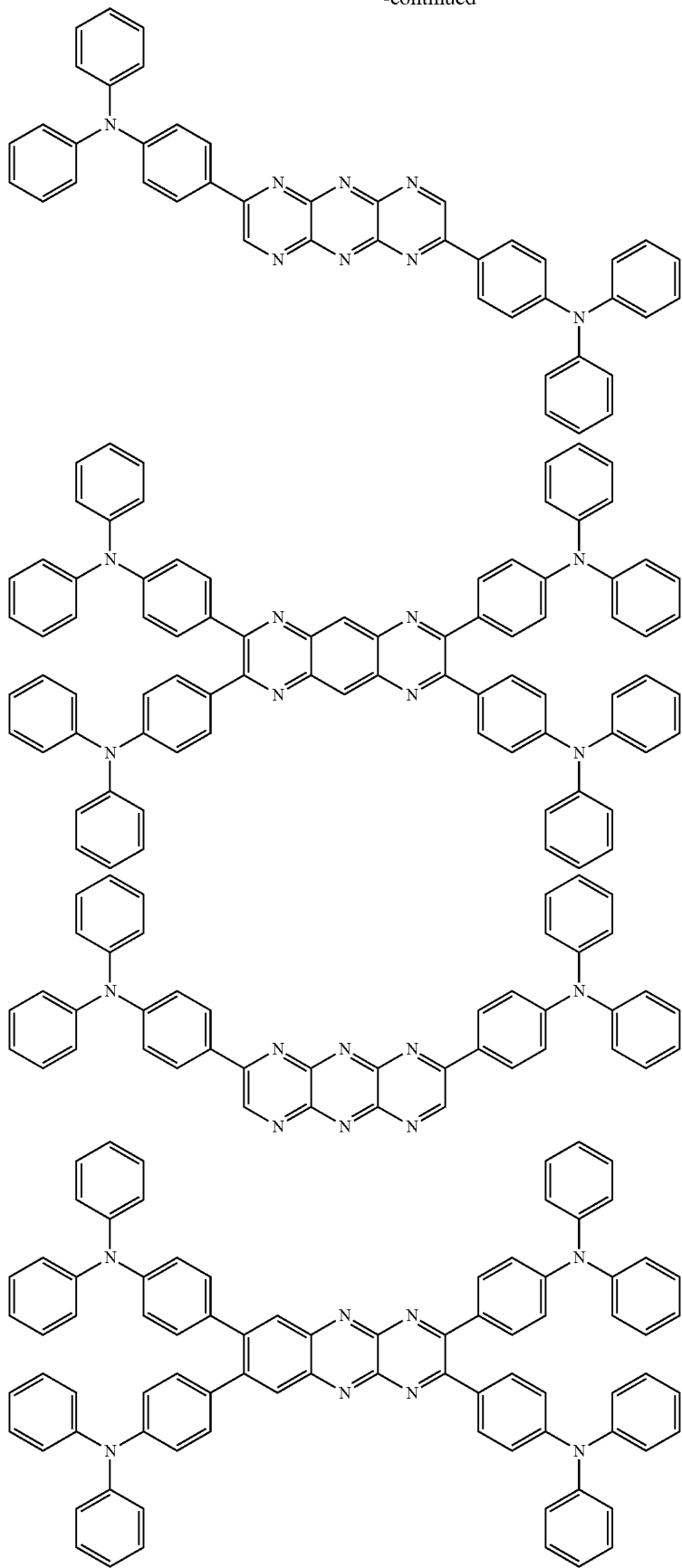

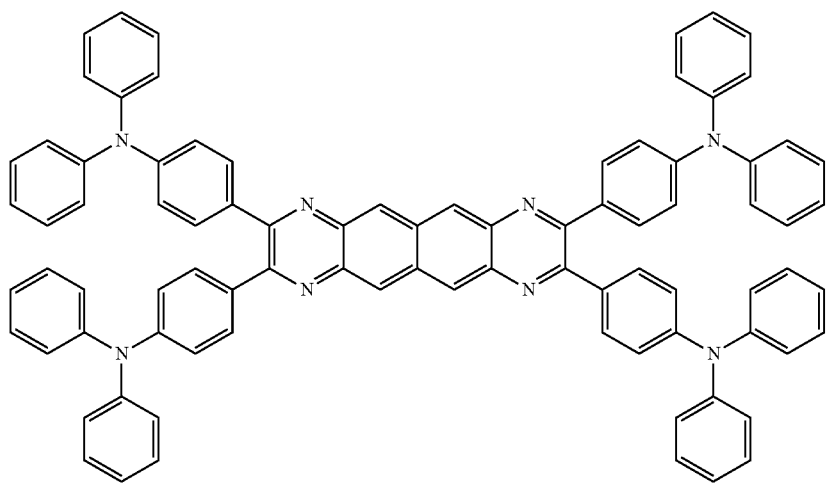
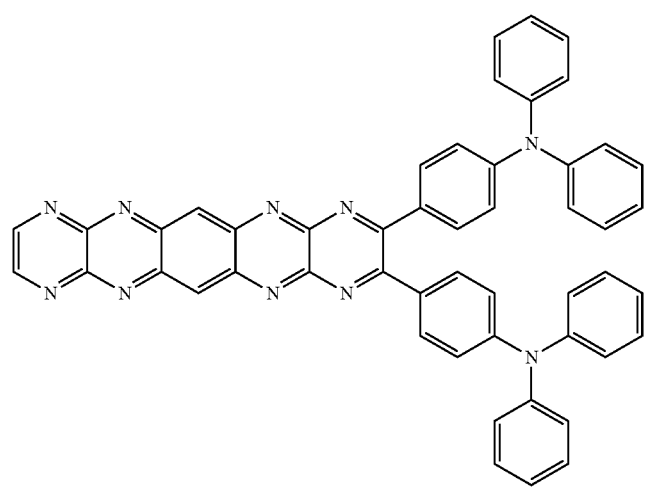
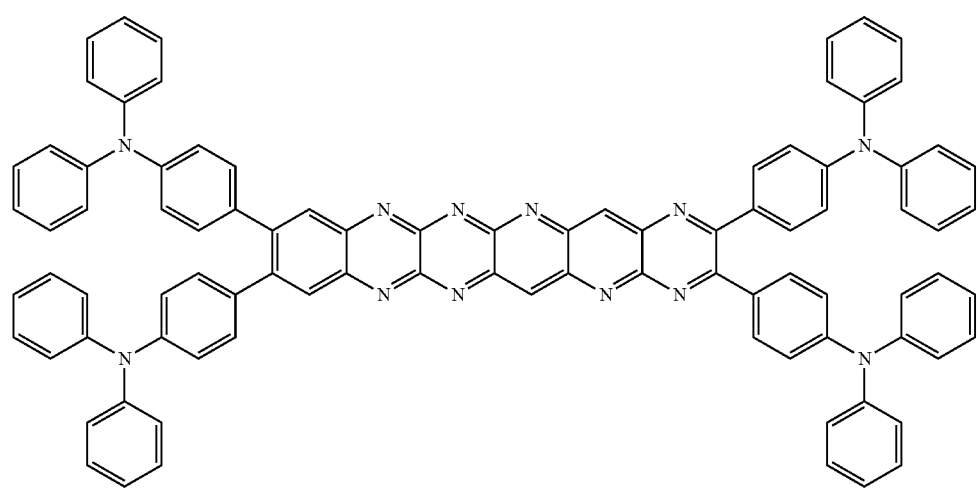

-continued
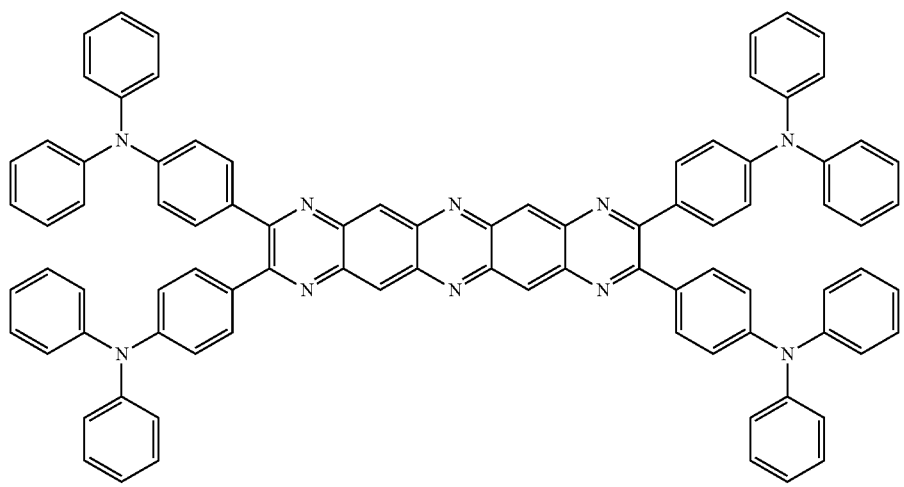
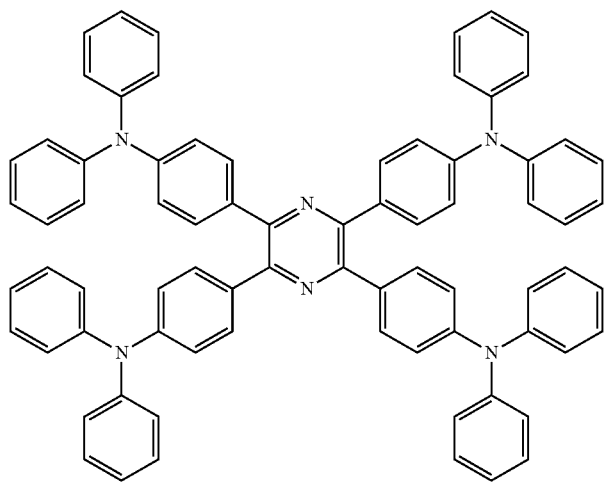

Examples of the preferred light-emitting material include compounds represented by the following general formula (241). The entire description of JP-A-2014-9224 including the by reference.

General Formula (241)

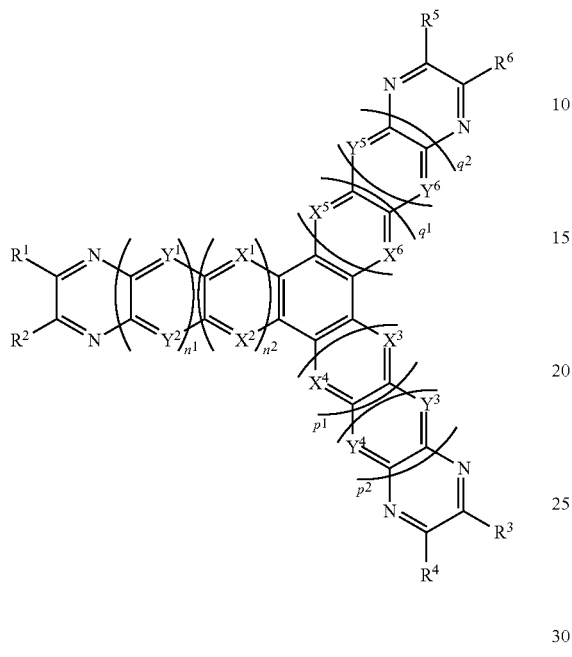

wherein in the general formula (241), $R^1$ to $R^6$ each independently represent a hydrogen atom or a substituent, provided that at least one of $R^1$ to $R^6$ represents a substituted or unsubstituted (N, N-diarylamino)aryl group, and two aryl groups constituting the diarylamino moiety of the (N,N-diarylamino)aryl group may be bonded to each other; $X^1$ to $X^6$ and $Y^1$ to $Y^6$ each independently represent a carbon atom or a nitrogen atom; and $n^1$, $n^2$, $p^1$, $p^2$, $q^1$ and $q^2$ each independently represent 0, 1 or 2.

Specific examples of the compound include the following compounds.

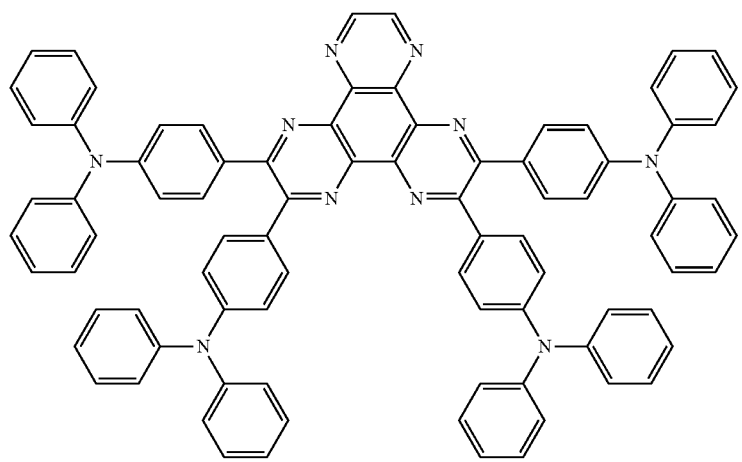

-continued
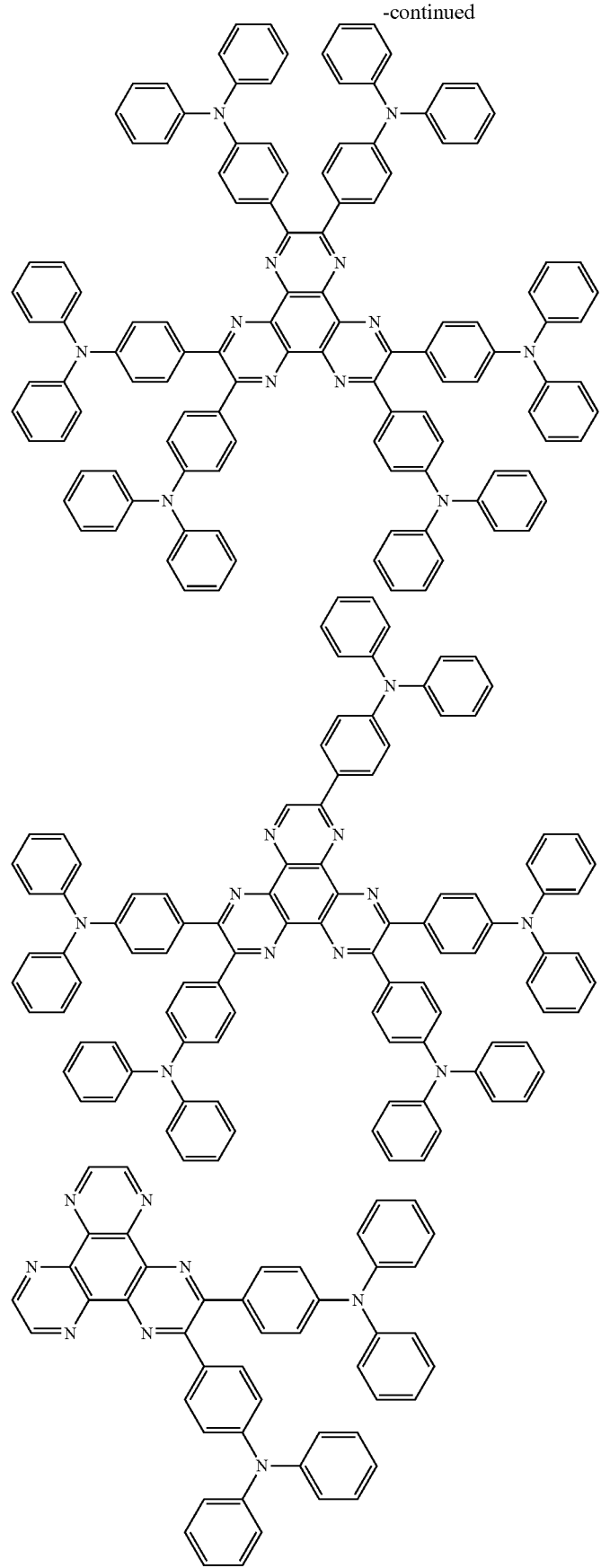

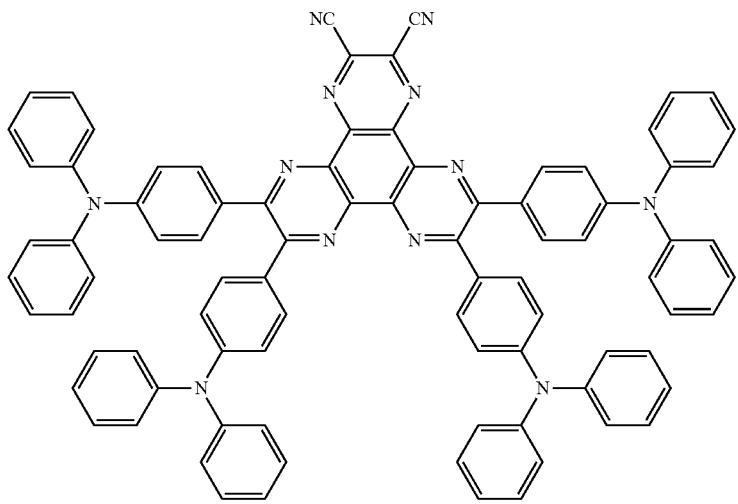
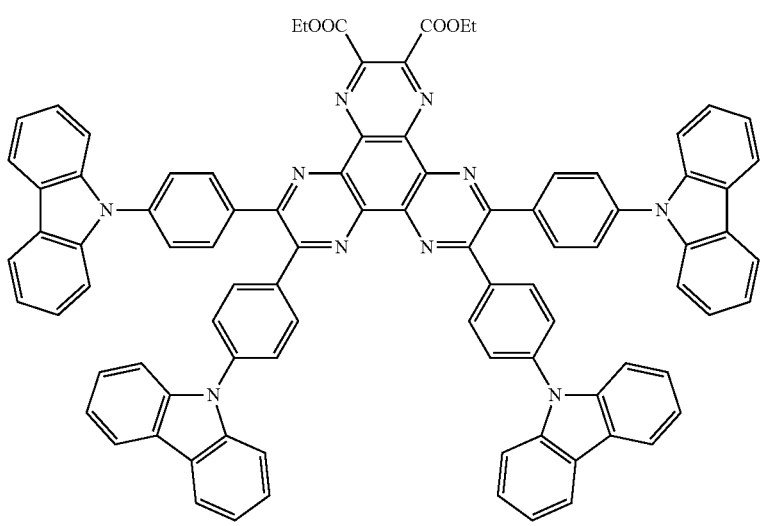
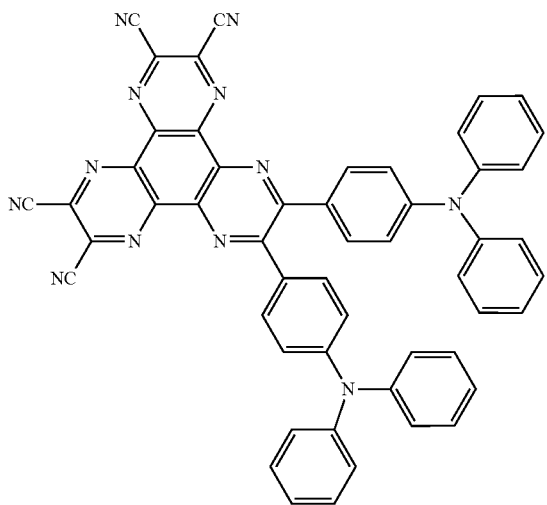

-continued
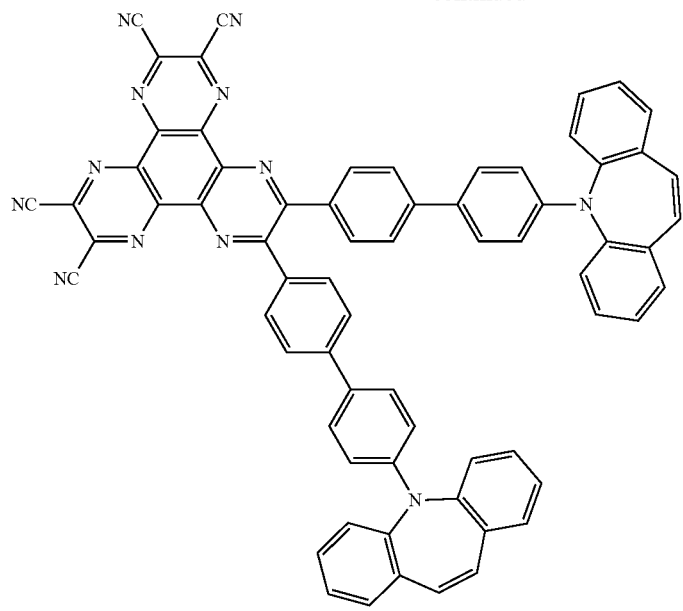
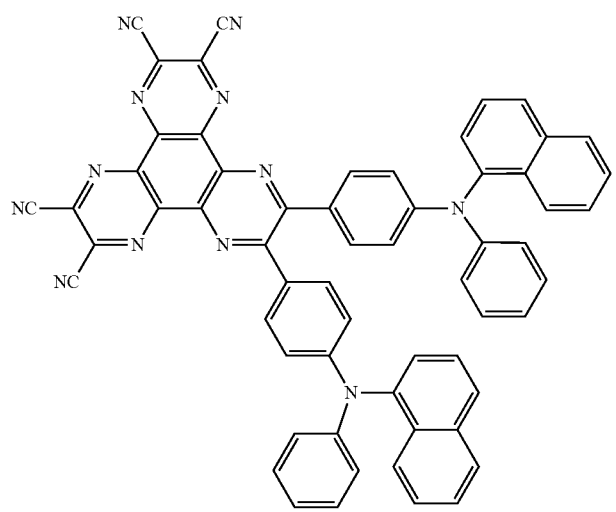
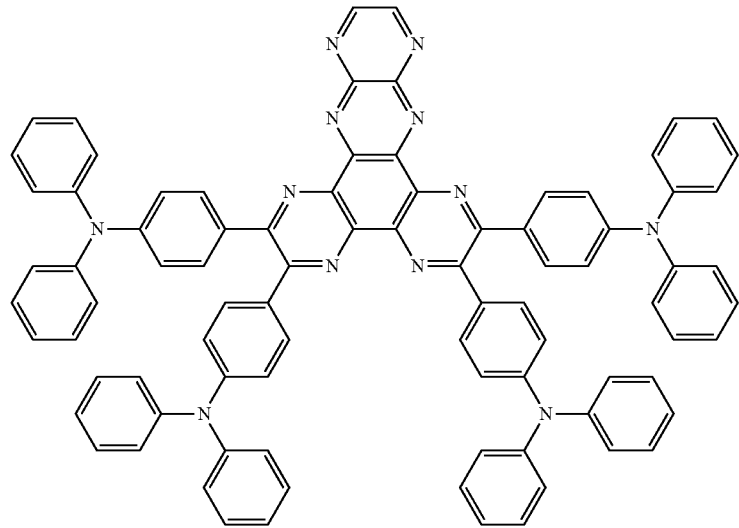

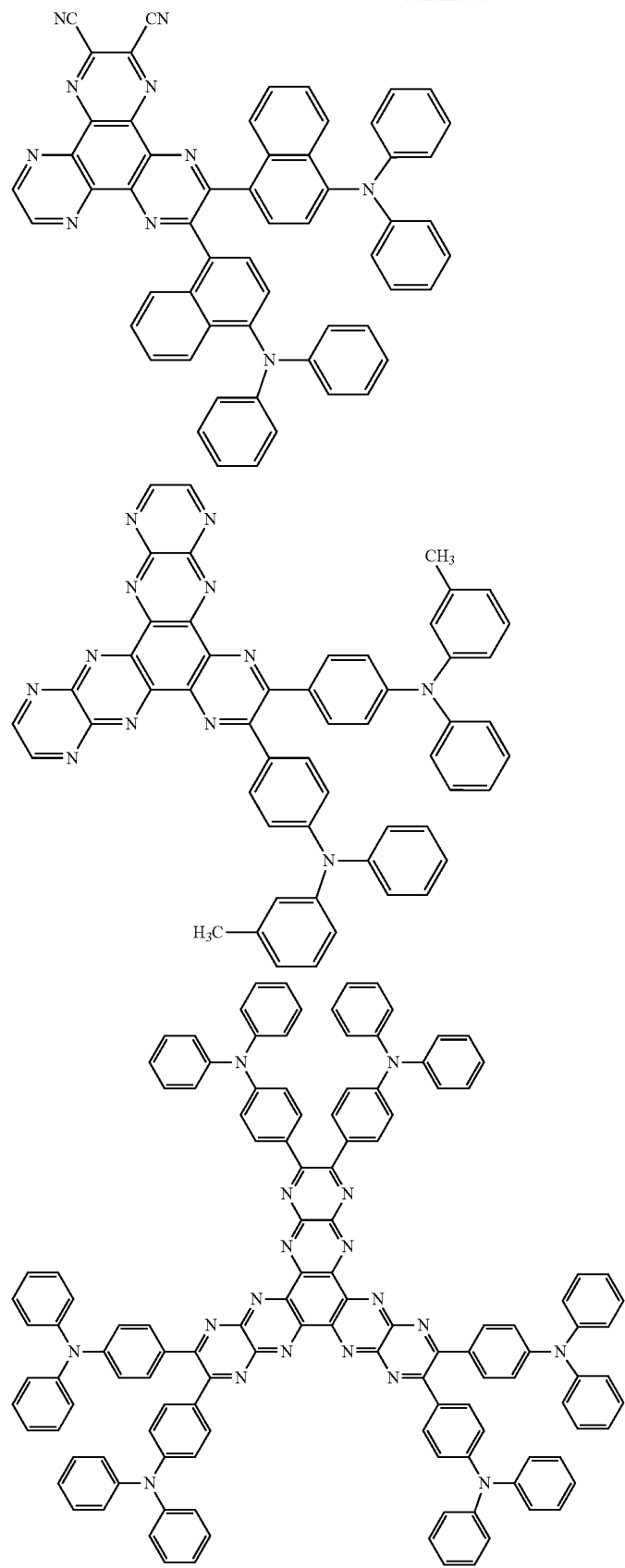

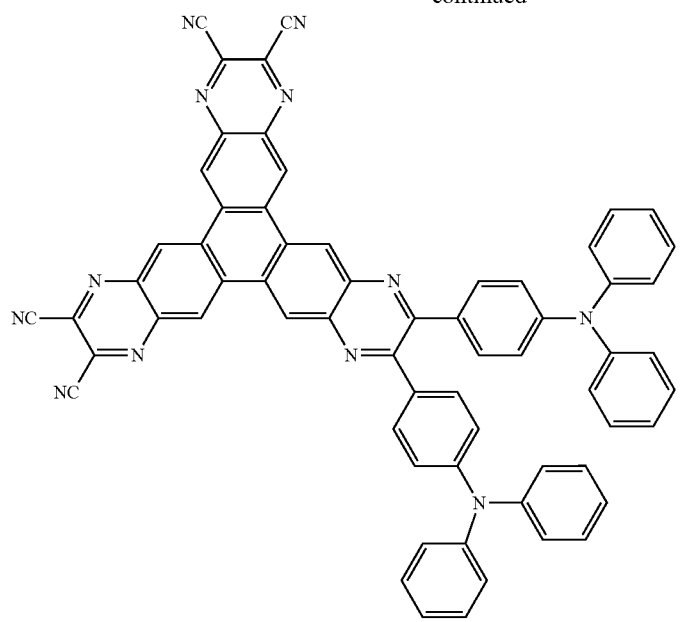
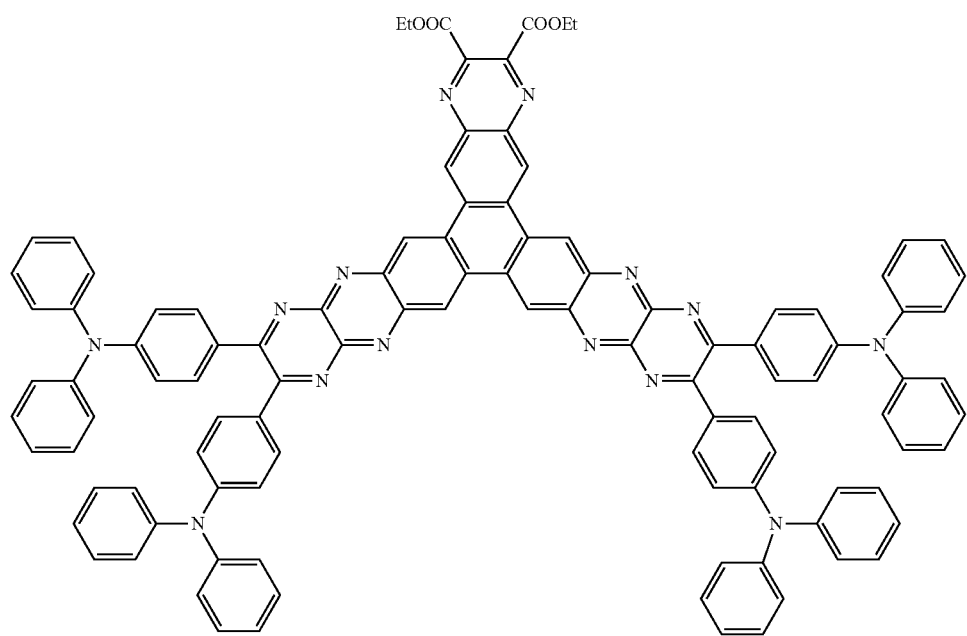

-continued

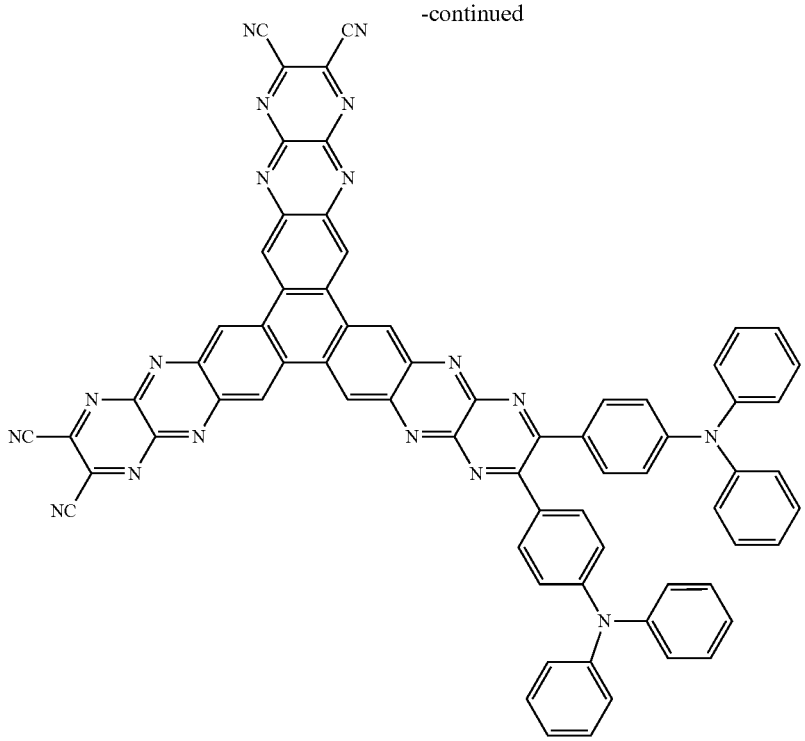

Examples of the preferred light-emitting material include the following compounds.

(1) A compound represented by the following general formula (251):

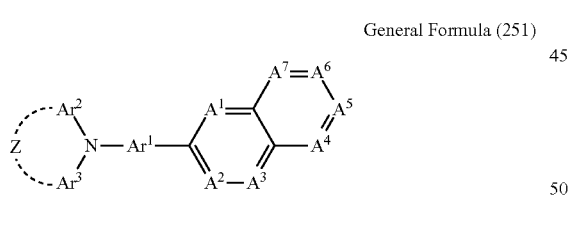

General Formula (251)

wherein in the general formula (251), one of $A^1$ to $A^7$ represents N, and the balance each independently represent C—R; R represents a non-aromatic group; $Ar^1$ to $Ar^3$ each independently represent a substituted or unsubstituted arylene group; and Z represents a single bond or a linking group.

(2) The compound according to the item (1), wherein the compound represented by the general formula (251) has a structure represented by the following general formula (252):

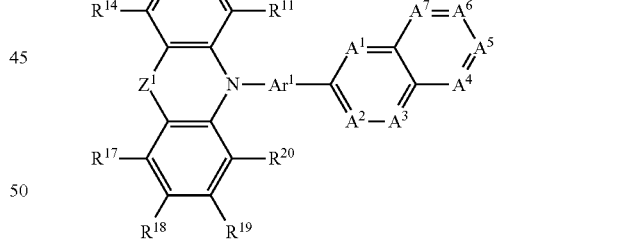

General Formula (252)

wherein in the general formula (252), one of $A^1$ to $A^7$ represents N, and the balance each independently represent C—R; R represents a non-aromatic group; $Ar^1$ represents a substituted or unsubstituted arylene group; $R^{11}$ to $R^{14}$ and $R^{17}$ to $R^{20}$ each independently represent a hydrogen atom or a substituent, in which $R^{11}$ and $R^{12}$, $R^{12}$ and $R^{13}$, $R^{13}$ and $R^{14}$, $R^{17}$ and $R^{18}$, $R^{18}$ and $R^{19}$, and $R^{19}$ and $R^{20}$ each may be bonded to each other to form a cyclic structure; and $Z^1$ represents a single bond or a linking group having 1 or 2 linking chain atoms.

(3) The compound according to the item (1), wherein the compound represented by the general formula (251) has a structure represented by the following general formula (253):

General Formula (253)

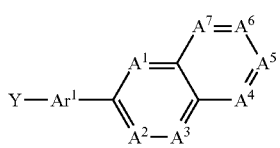

wherein in the general formula (253), from 2 to 4 of $A^1$ to $A^7$ represent N, and the balance represent C—R; R represents a non-aromatic group; $Ar^1$ represents a substituted or unsubstituted arylene group; and Y represents a substituted or unsubstituted carbazol-9-yl group, a substituted or unsubstituted 10H-phenoxazin-10-yl group, a substituted or unsubstituted 10H-phenothiazin-10-yl group, or a substituted or unsubstituted 10H-phenazin-5-yl group.

(4) The compound according to the item (3), wherein in the general formula (253), Y represents a group represented by any one of the following general formulae (254) to (257):

General Formula (254)

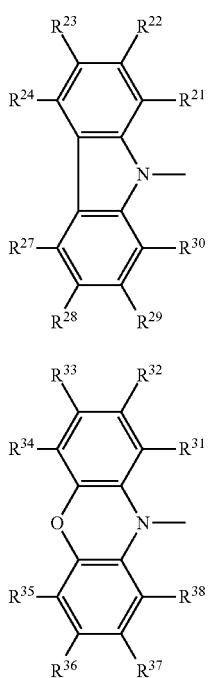

General Formula (255)

General Formula (256)

General Formula (257)

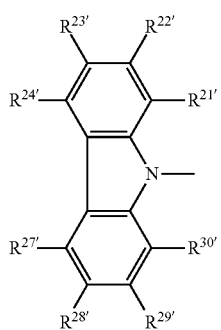

wherein in the general formulae (254) to (257), $R^{21}$ to $R^{24}$, $R^{27}$ to $R^{38}$, $R^{41}$ to $R^{48}$, $R^{51}$ to $R^{58}$, and $R^{61}$ to $R^{65}$ each independently represent a hydrogen atom or a substituent, in which $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, and $R^{55}$ and $R^{65}$ each may be bonded to each other to form a cyclic structure.

(5) The compound according to the item (3), wherein in the general formula (253), Y represents a group represented by the following general formula (258):

General Formula (258)

R^{23'}  R^{22'}
R^{24'}         R^{21'}
         N—
R^{27'}         R^{30'}
R^{28'}  R^{29'} wherein in the general formula (258), $R^{21'}$ to $R^{24'}$ and $R^{27'}$ to $R^{30'}$ each independently represent a hydrogen atom or a substituent, provided that at least one of $R^{23'}$ and $R^{28'}$ represents a substituent, and $R^{21'}$ and $R^{22'}$, $R^{22'}$ and $R^{23'}$, $R^{23'}$ and $R^{24'}$, $R^{27'}$ and $R^{28'}$, $R^{28'}$ and $R^{29'}$, and $R^{29'}$ and $R^{30'}$ each may be bonded to each other to form a cyclic structure.

(6) The compound according to the item (5), wherein in the general formula (258), at least one of $R^{23'}$ and $R^{28'}$ represents a substituted or unsubstituted diarylamino group or a substituted or unsubstituted carbazol-9-yl group.

(7) The compound according to the item (4), wherein in the general formula (253), Y represents a group represented by the general formula (255).

Examples of the compound include the following compounds.

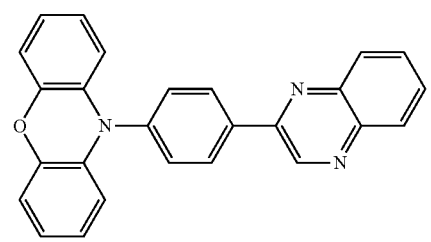
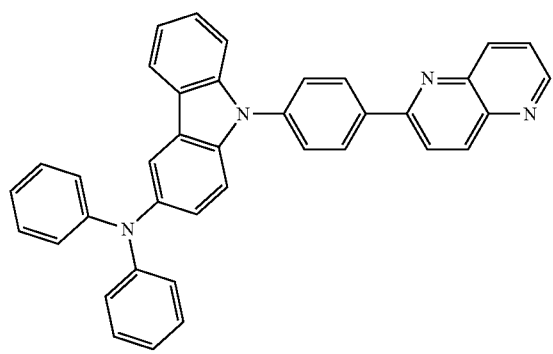
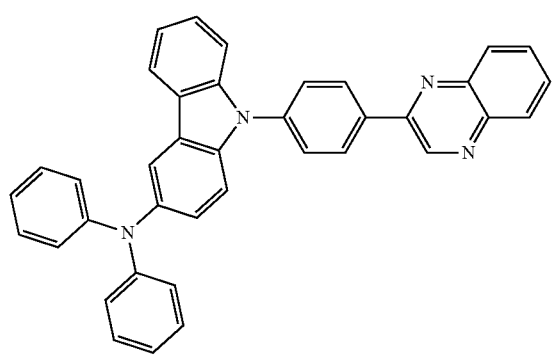
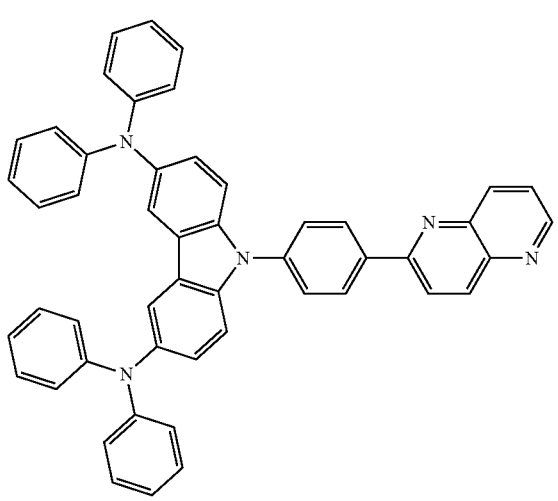
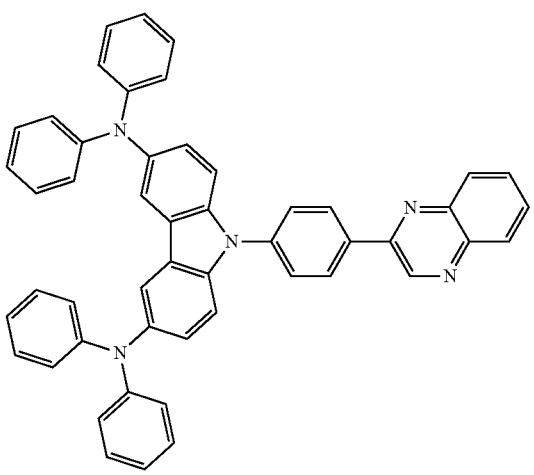
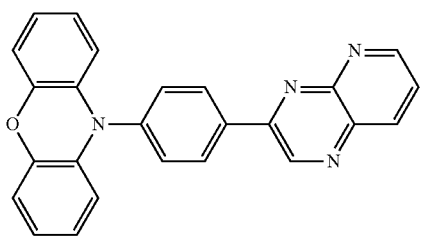
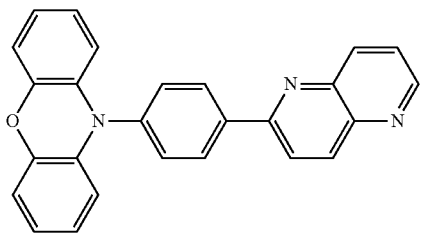
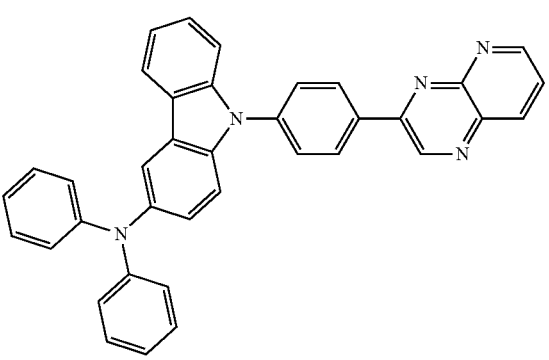

291
-continued
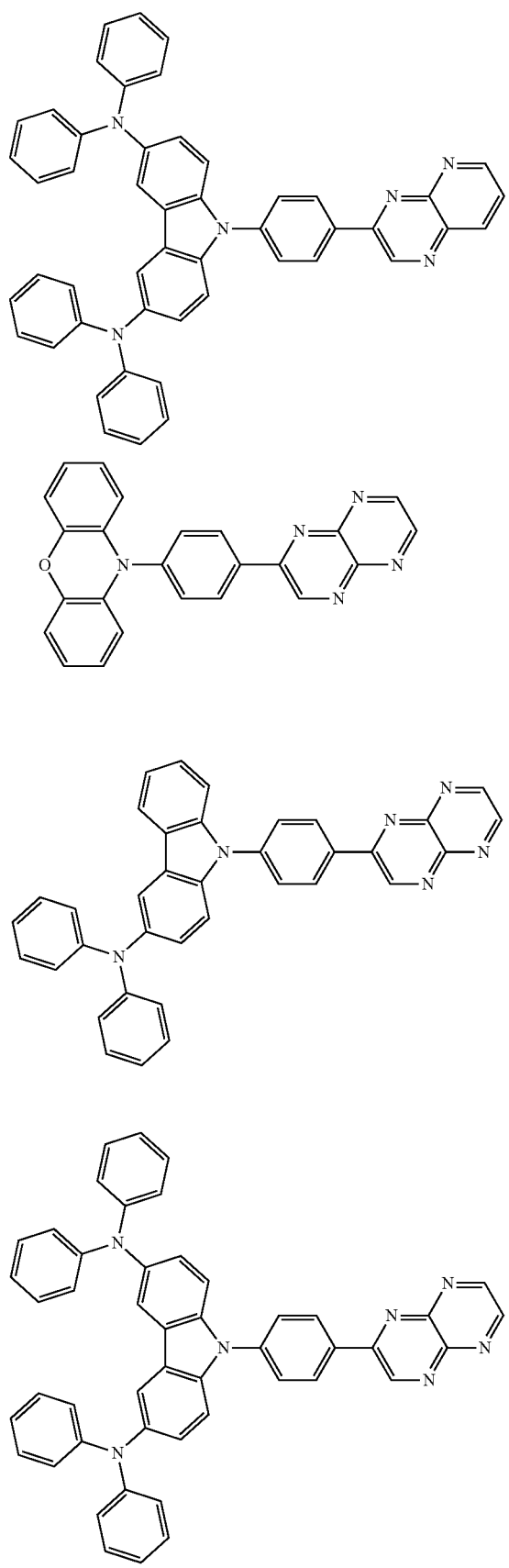
292
-continued
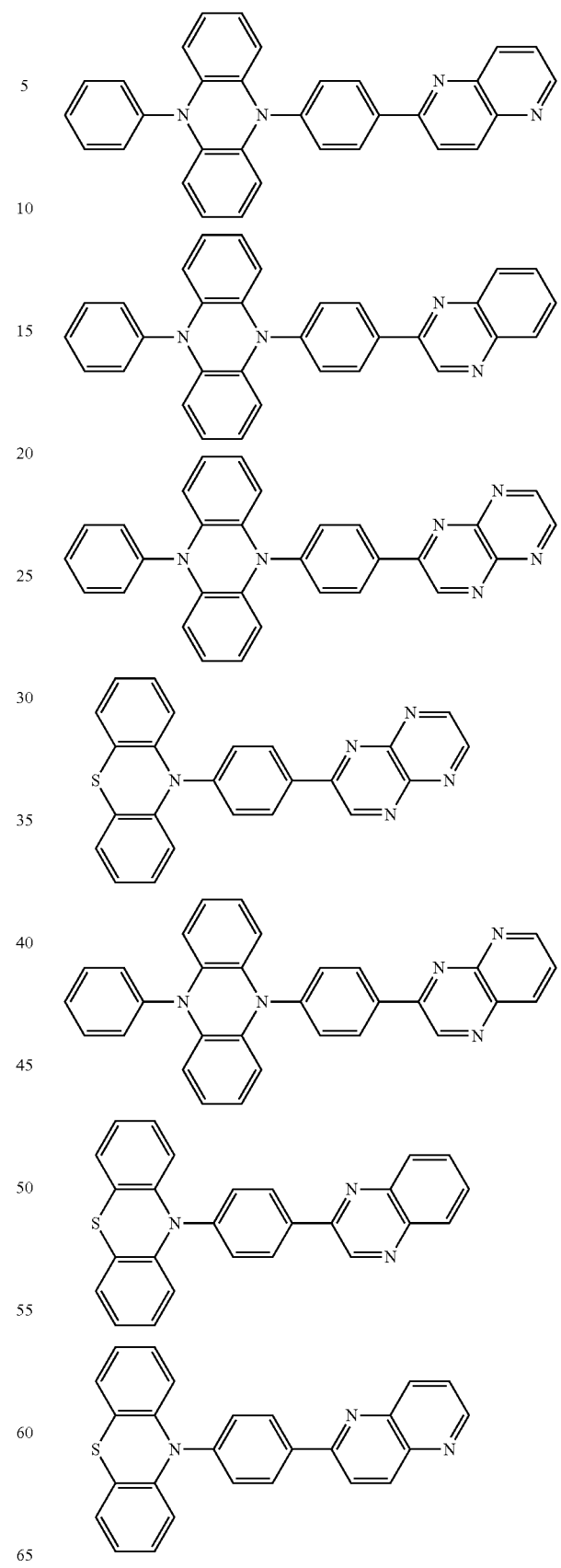

-continued

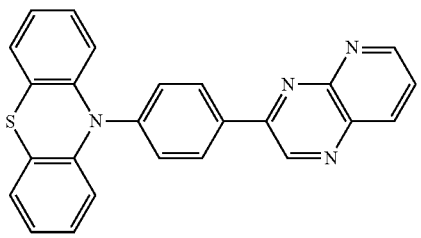

Examples of the preferred light-emitting material include the following compounds.

(1) A compound represented by the following general formula (261):

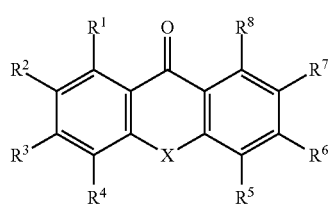

General Formula (261)

wherein in the general formula (261), X represents an oxygen atom or a sulfur atom; and R1 to R8 each independently represent a hydrogen atom or a substituent, provided that at least one of R1 to R8 each independently represent a group represented by any of the following formulae (262) to (266), and $R^1$ and $R^2$, $R^2$ and $R^3$, $R^3$ and $R^4$, $R^5$ and $R^6$, $R^6$ and $R^7$, $R^7$ and $R^8$ each may be bonded to each other to form a cyclic structure.

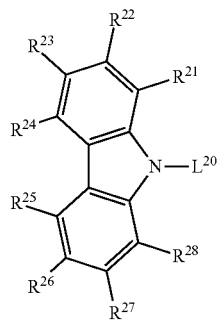

General Formula (262)

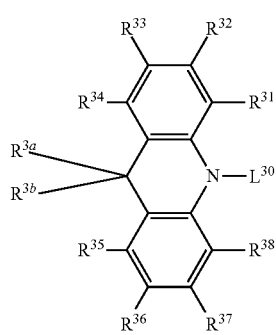

General Formula (263)

-continued

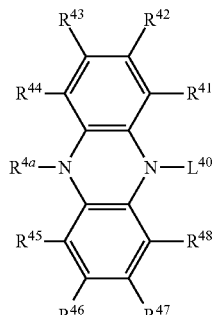

General Formula (264)

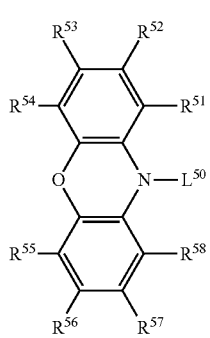

General Formula (265)

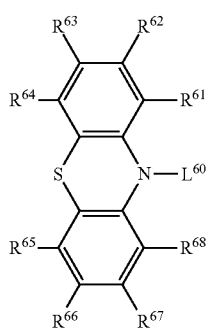

General Formula (266)

wherein in the general formulae (262) to (266), $L^{20}$, $L^{30}$, $L^{40}$, $L^{50}$, and $L^{60}$ each independently represent a single bond or a divalent linking group, and the group is bonded to the cyclic structure of the general formula (261) through $L^{20}$, $L^{30}$, $L^{40}$, $L^{50}$, and $L^{60}$; and $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, and $R^{61}$ to $R^{68}$ each independently represent a hydrogen atom or a substituent, provided that $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, and $R^6$ and $R^{68}$ each may be bonded to each other to form a cyclic structure.

(2) The compound according to the item (1), wherein in the general formula (261), at least one of $R^3$ and $R^6$ represents a group represented by any of the general formulae (262) to (266).

(3) The compound according to the item (2), wherein in the general formula (261), $R^3$ and $R^6$ each represent a group represented by any of the general formulae (262) to (266).

(4) The compound according to the item (2), wherein in the general formula (261), at least one of $R^3$ and $R^6$ represents a group represented by the general formula (263).

(5) The compound according to the item (2), wherein in the general formula (261), at least one of $R^3$ and $R^6$ represents a group represented by the general formula (262).

(6) The compound according to any one of the items (1) to (5), wherein in the general formulae (262) to (266), at least one of $R^{21}$ to $R^{28}$, $R^{31}$ to $R^{38}$, $R^{41}$ to $R^{48}$, $R^{51}$ to $R^{58}$, and $R^{61}$ to $R^{68}$ represents a substituent.

(7) The compound according to the item (6), wherein in the general formulae (262) to (266), at least one of $R^{23}$, $R^{26}$, $R^{33}$, $R^{36}$, $R^{43}$, $R^{46}$, $R^{53}$, $R^{56}$, $R^{63}$, and $R^{66}$ represents a substituent.

(8) The compound according to the item (7), wherein the substituent is a group represented by any of general formulae (262) to (266).

(9) The compound according to any one of the items (1) to (8), wherein in the general formulae (262) to (266), L represents a single bond.

(10) The compound according to any one of the items (1) to (9), wherein in the general formula (261), X represents an oxygen atom.

Examples of the compound include the following compounds.

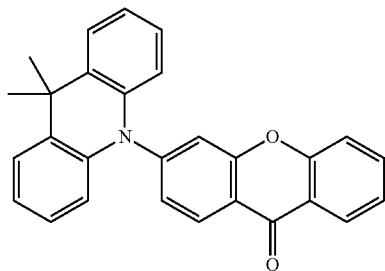
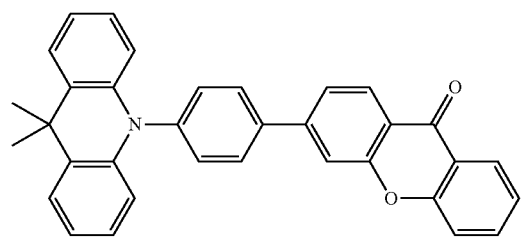
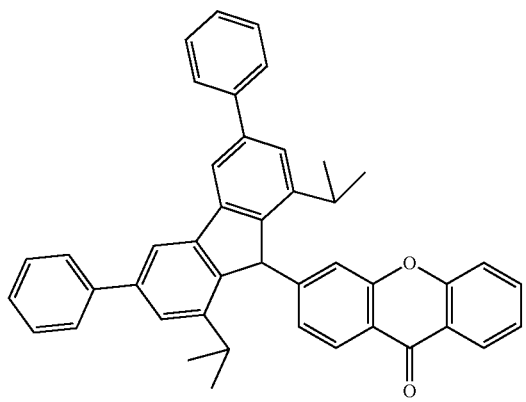
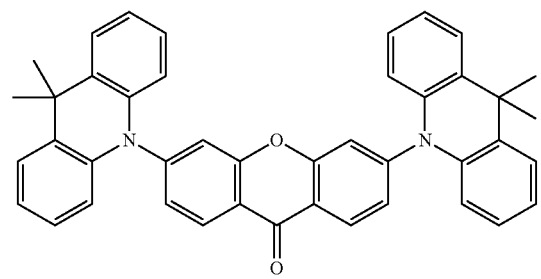
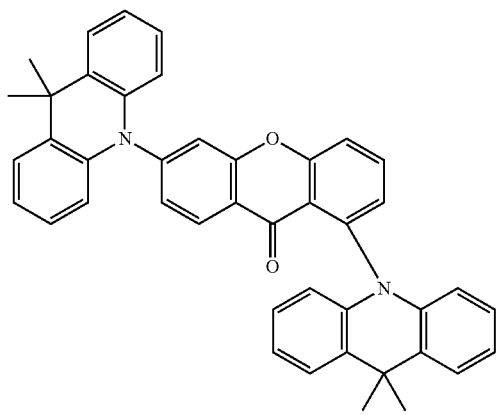

297
-continued
298
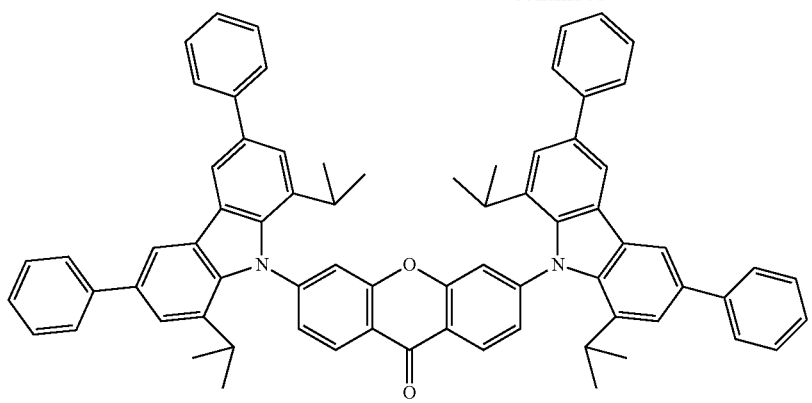
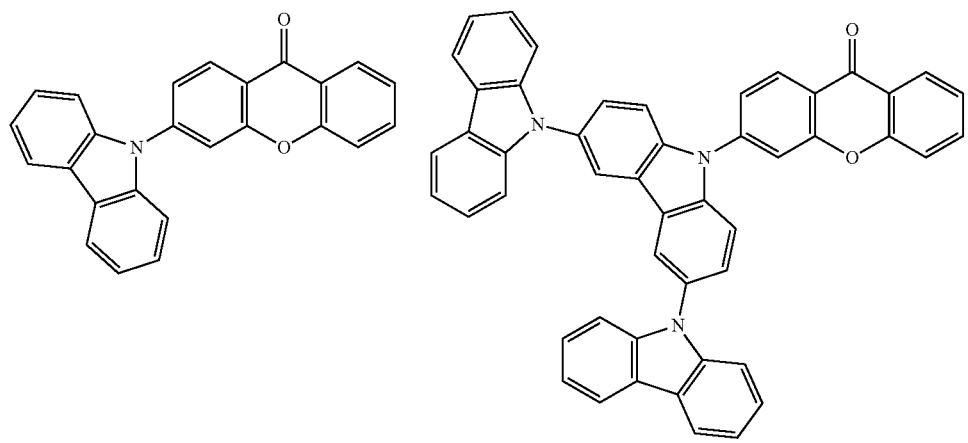
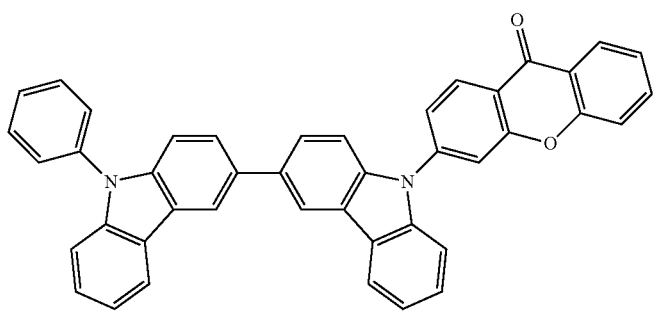
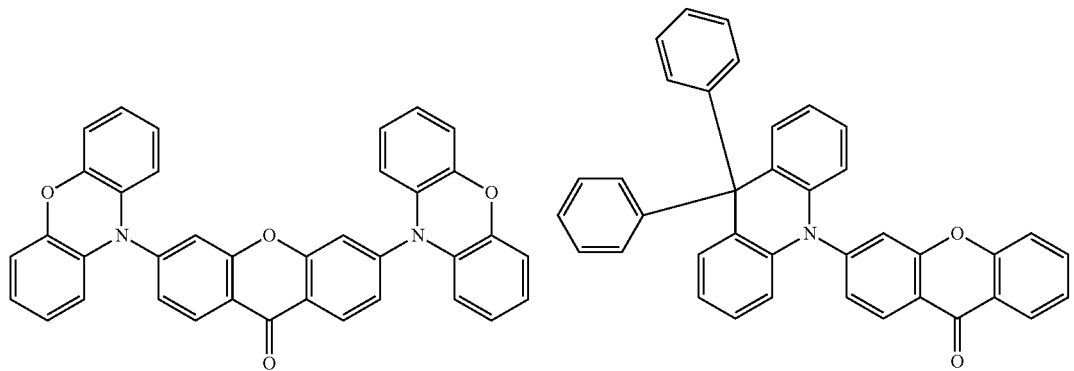

-continued
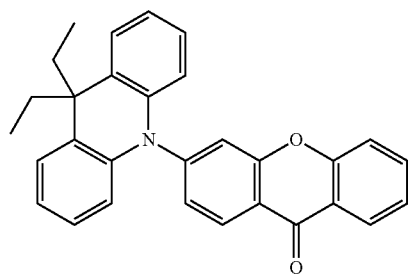
299
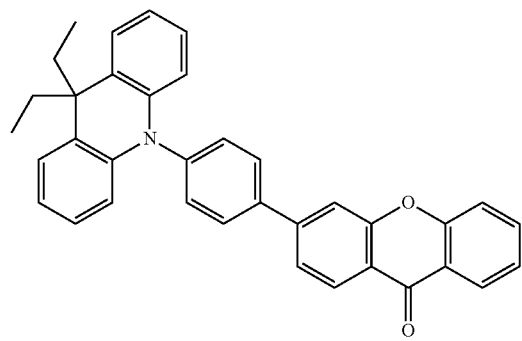
300
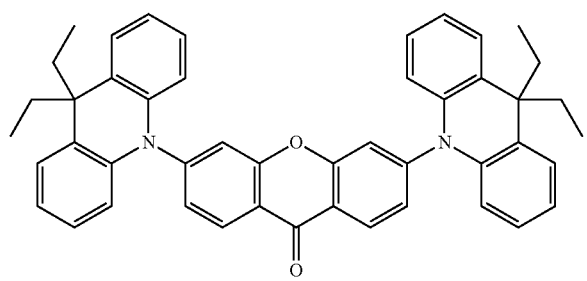
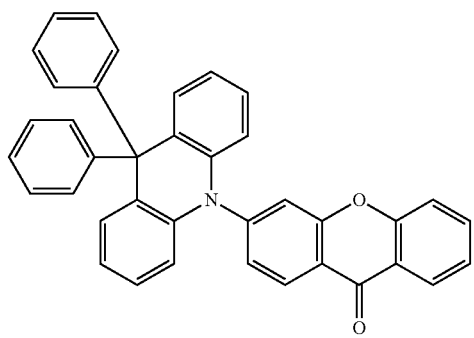
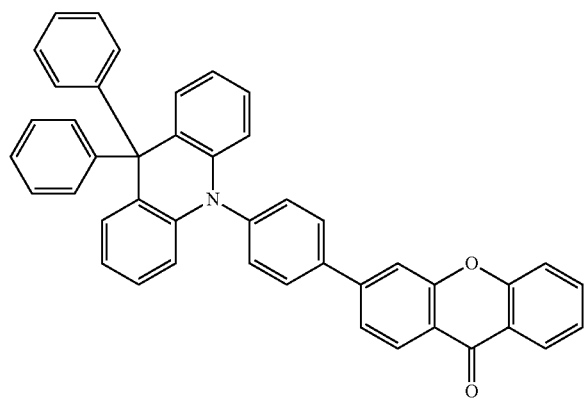
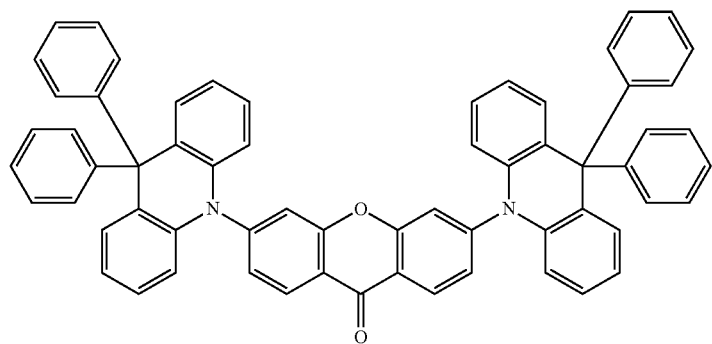

301
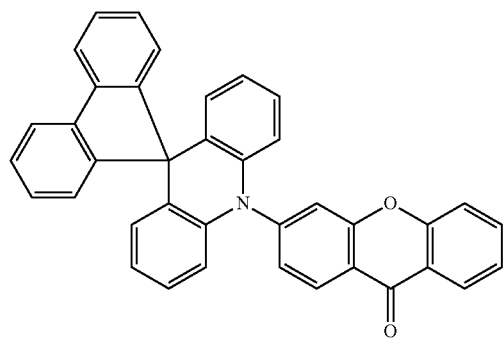
302
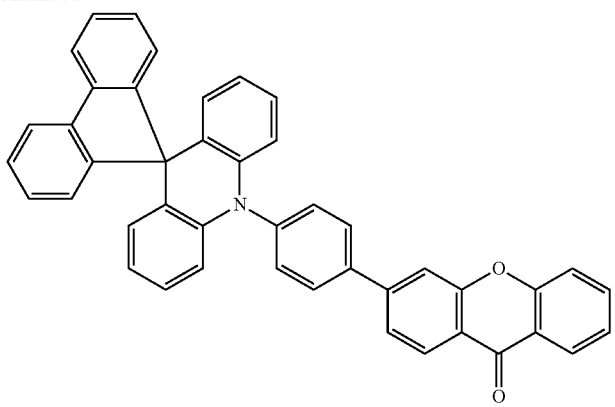
-continued
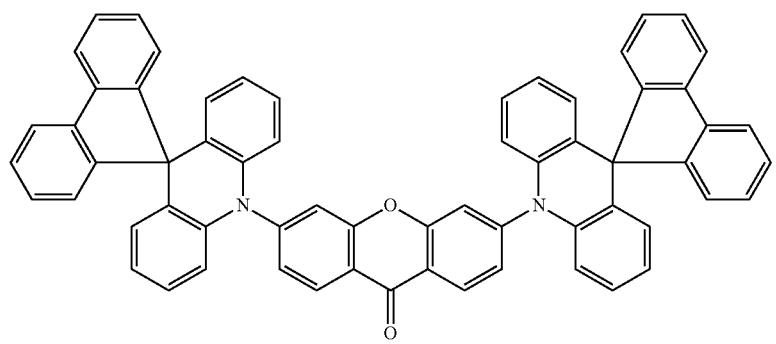
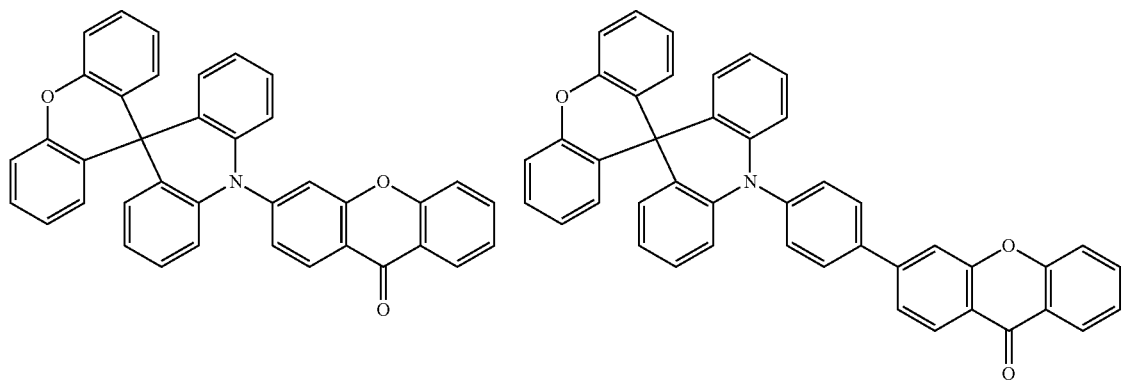
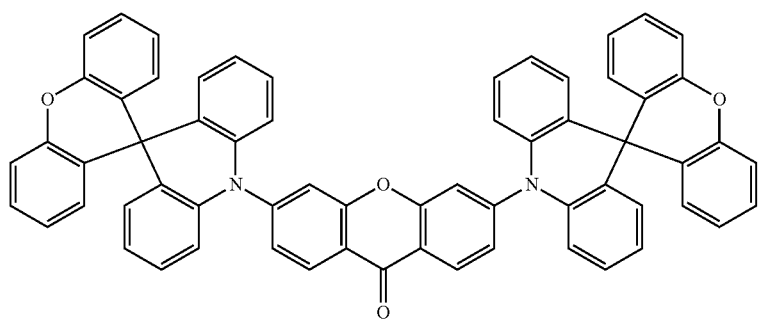

303
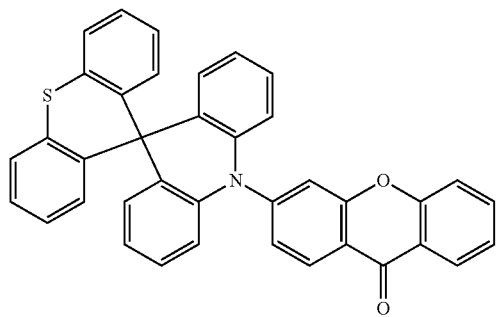
304
-continued
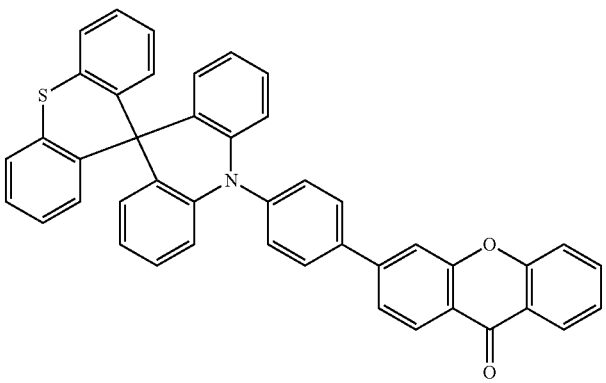
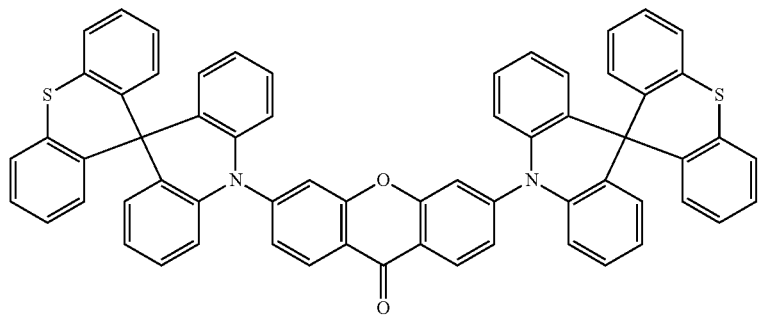
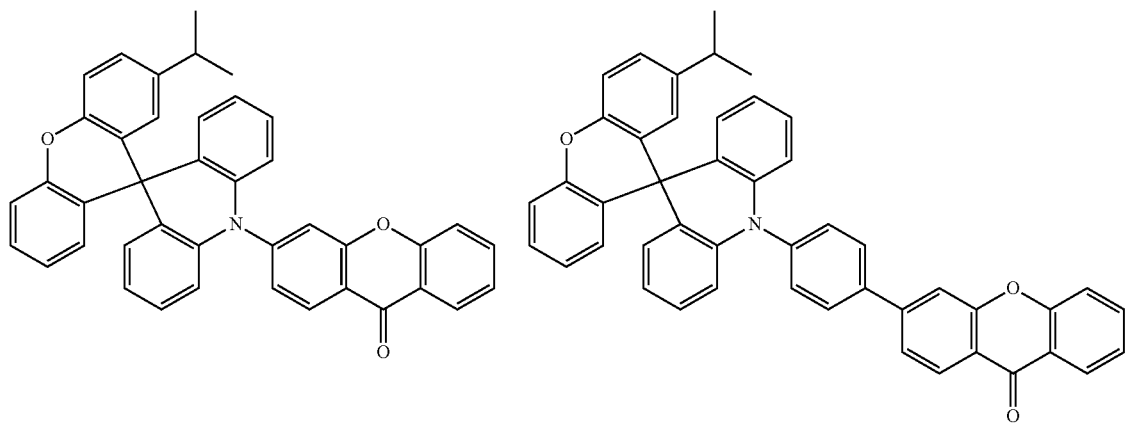
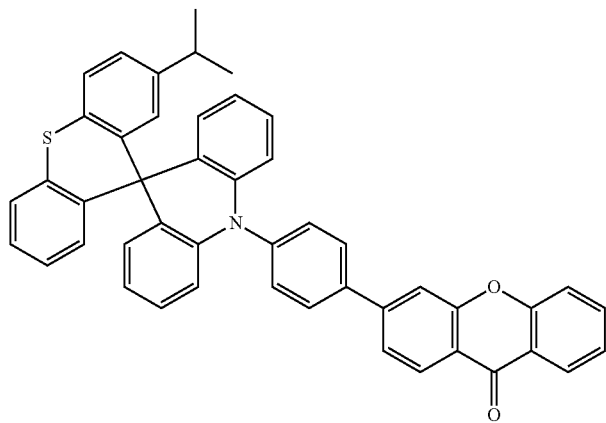

-continued
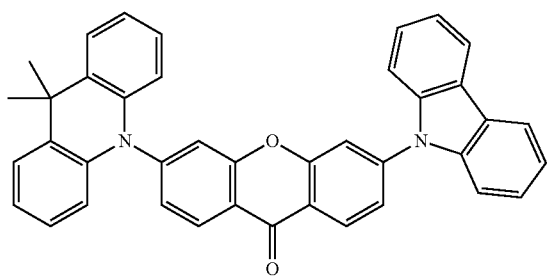
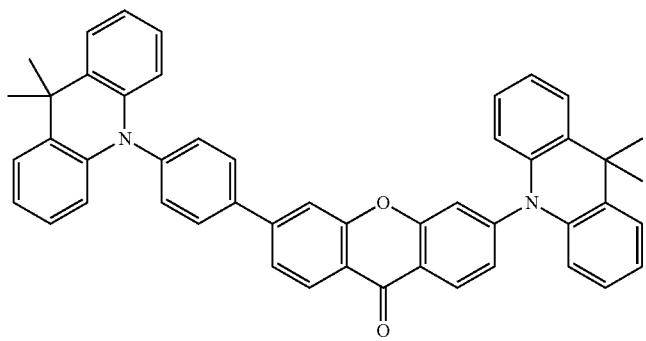
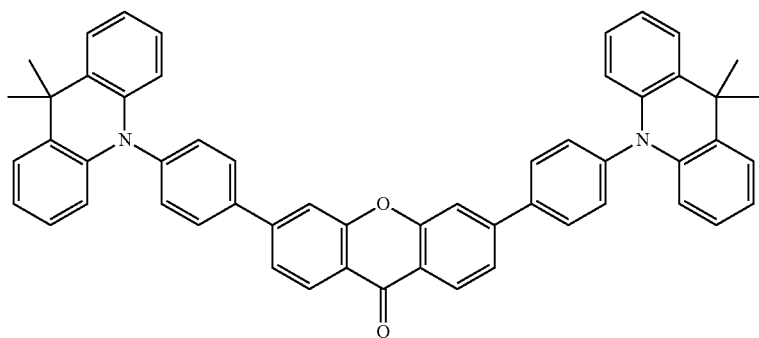
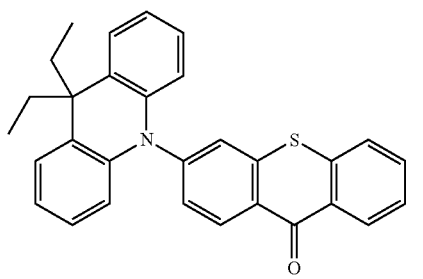
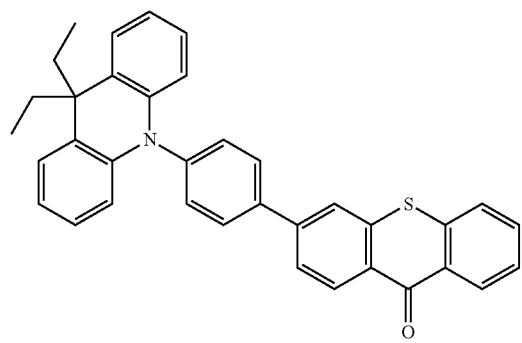
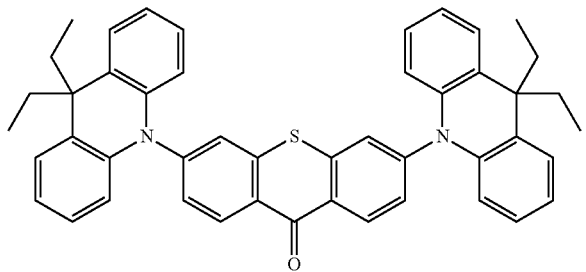
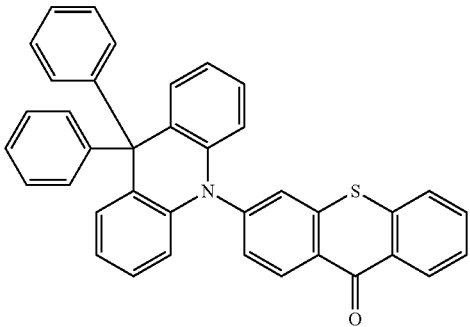

-continued
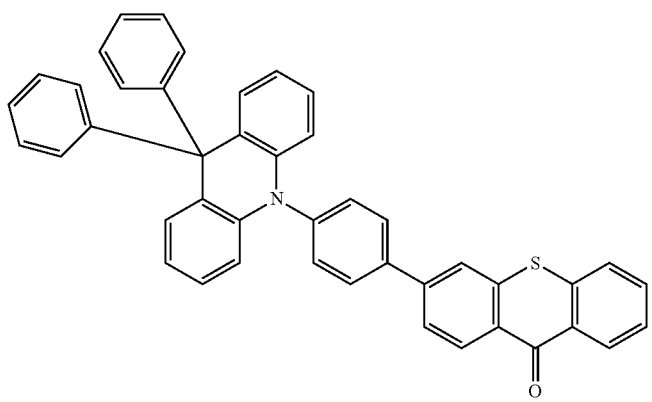
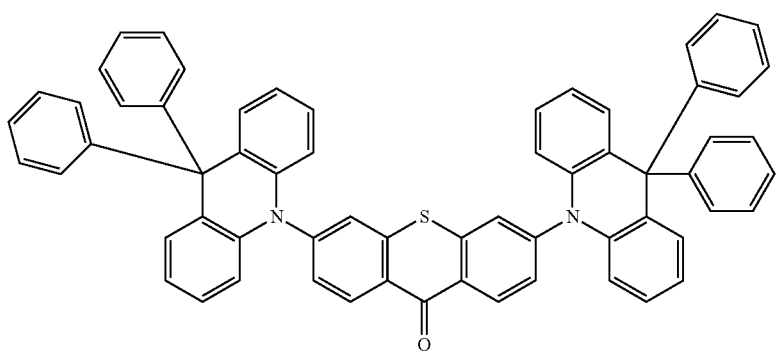
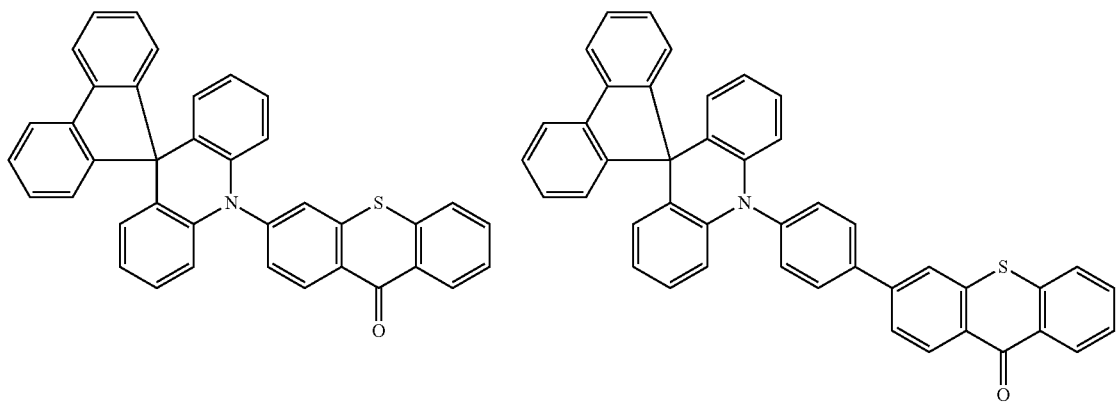
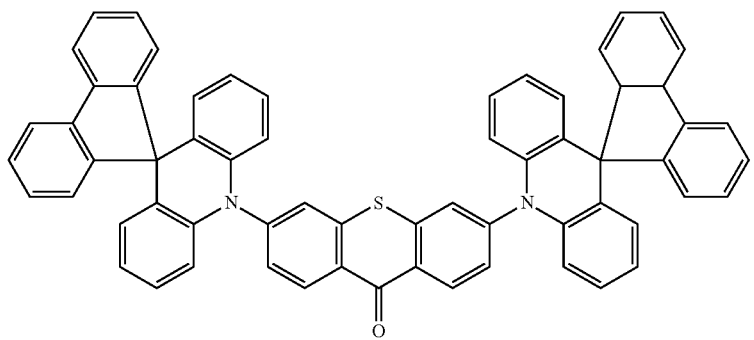

-continued
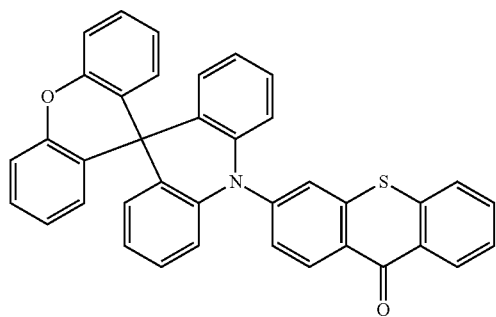
309
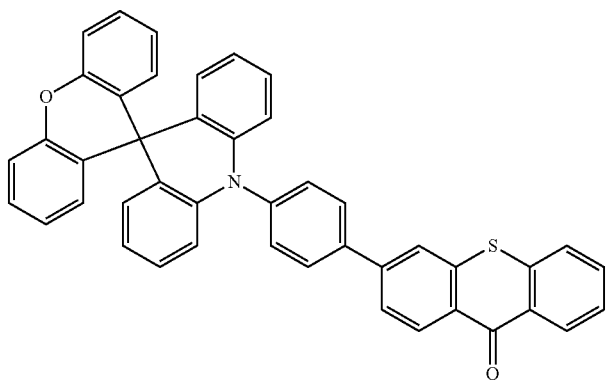
310
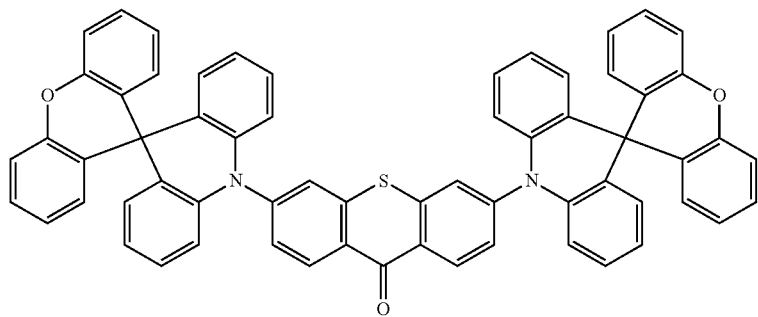
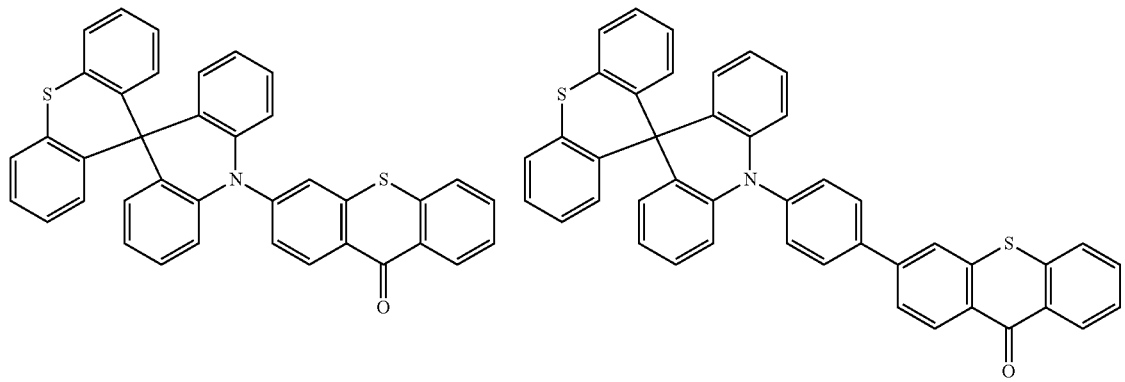
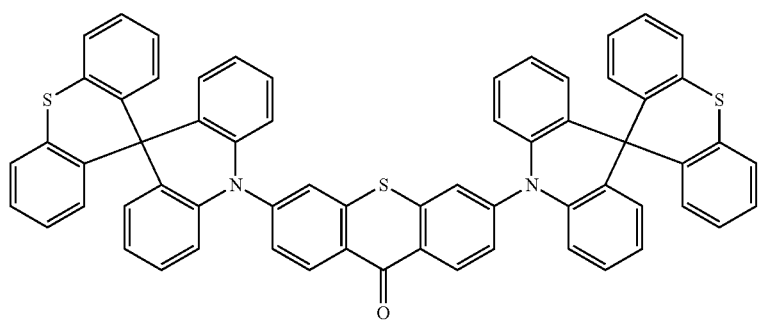

-continued
| 311 | 312 |
|---|---|
| 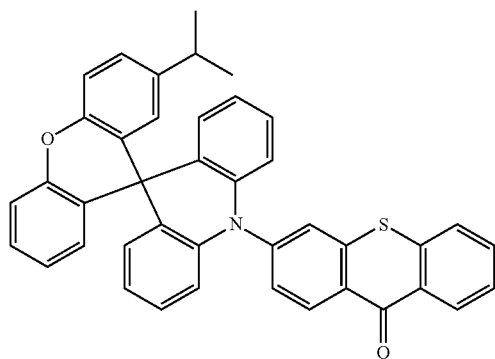 | 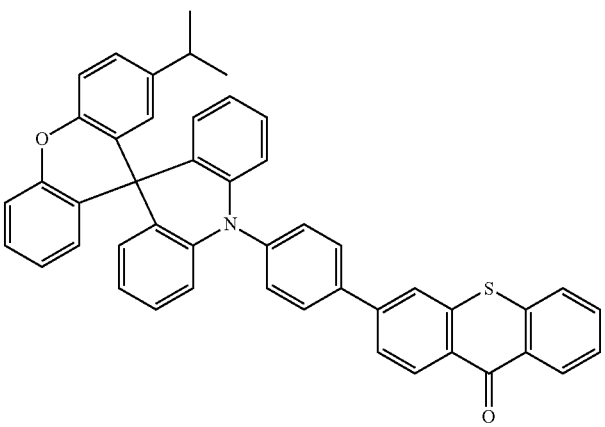 |
| 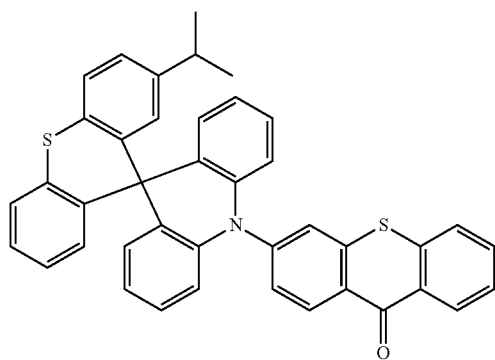 | 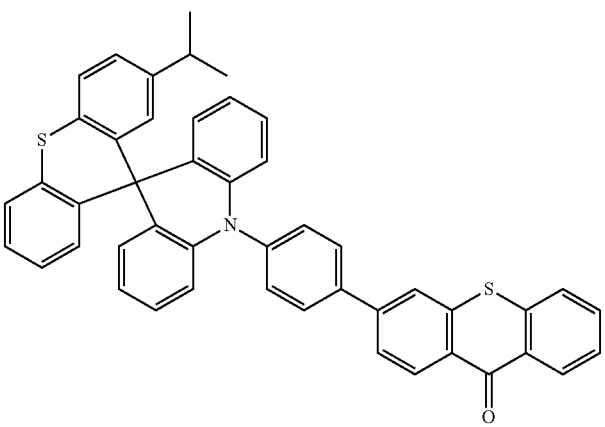 |
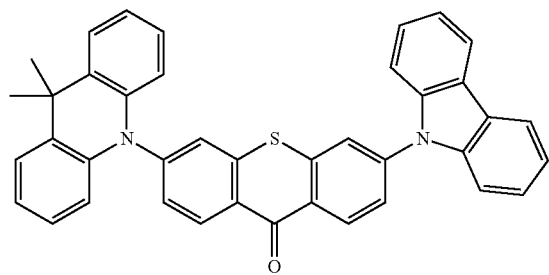
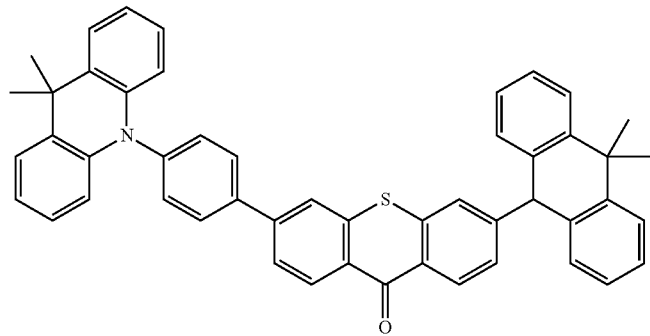

-continued

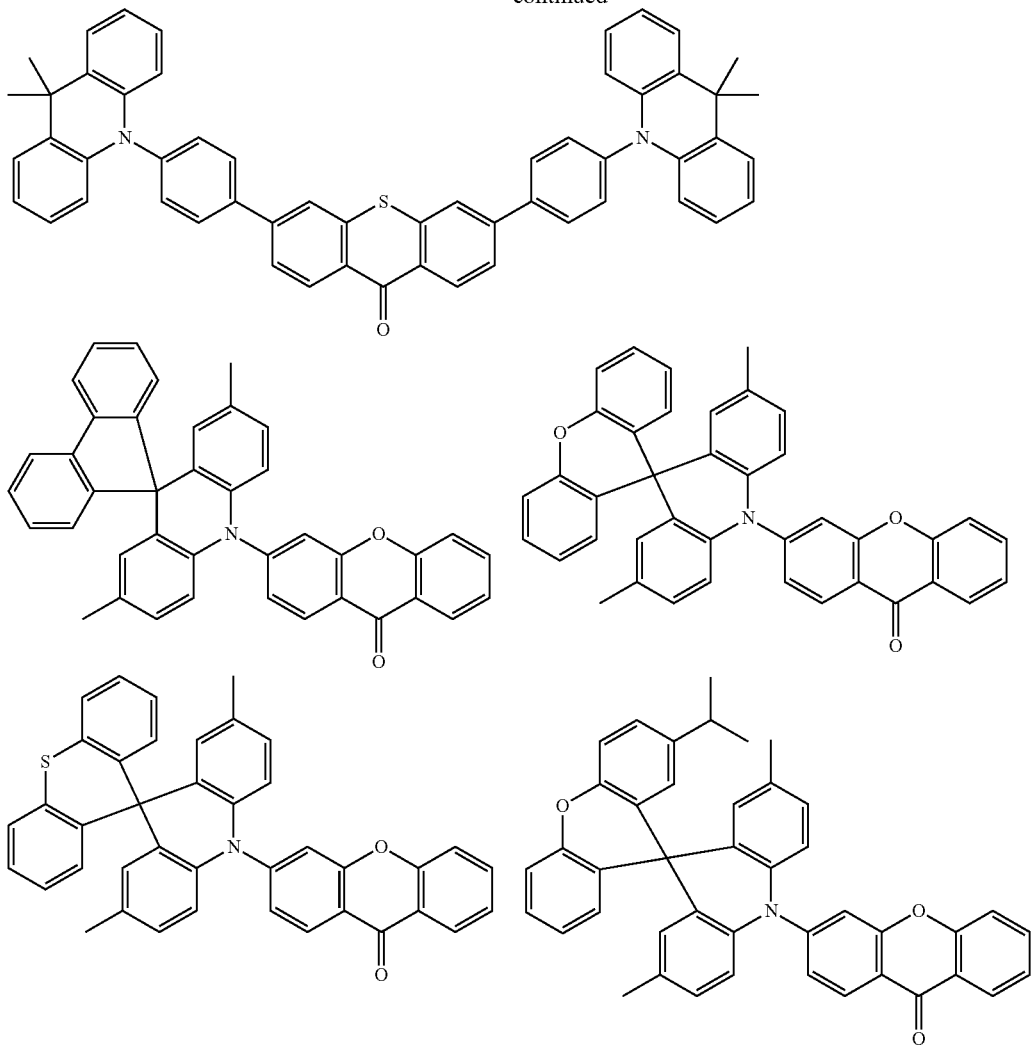

Examples of the preferred light-emitting material include the following compounds.

(1) A compound represented by the following general formula (271):

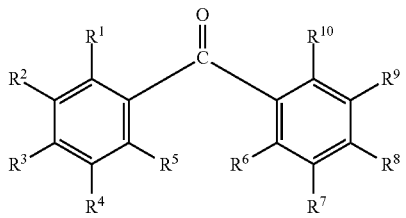
General Formula (271)

wherein in the general formula (271), $R^1$ to $R^{10}$ each independently represent a hydrogen atom or a substituent, provided that at least one of $R^1$ to $R^{10}$ each independently represent a group represented by the following general formula (272), and $R^1$ and $R^2$, $R^2$ and $R^3$, $R^3$ and $R^4$, $R^4$ and $R^5$, $R^6$ and $R^7$, $R^7$ and $R^8$, $R^8$ and $R^9$, and $R^9$ and $R^{10}$ each may be bonded to each other to form a cyclic structure:

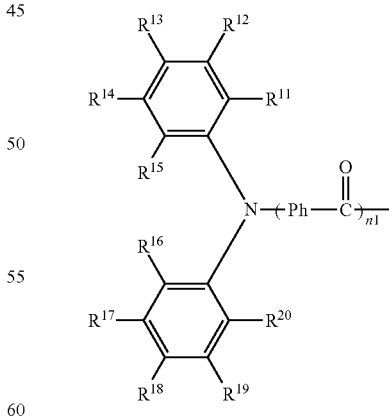
General Formula (272)

wherein in the general formula (272), $R^{11}$ to $R^{20}$ each independently represent a hydrogen atom or a substituent, in which $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure; Ph represents a substituted or unsubstituted phenylene group; and n1 represents 0 or 1.

(2) The compound according to the item (1), wherein the group represented by the general formula (272) is a group represented by any one of the following general formulae (273) to (278):

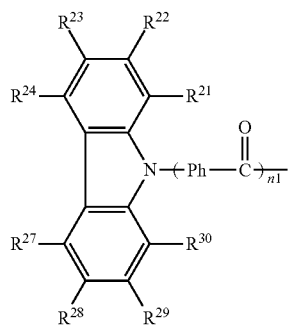

General Formula (273)

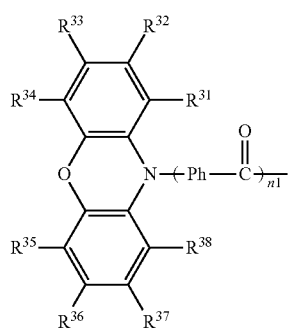

General Formula (274)

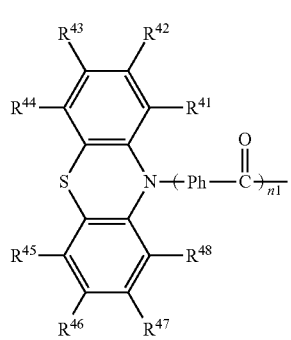

General Formula (275)

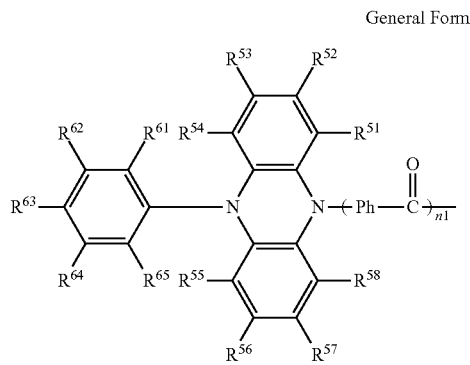

General Formula (276)

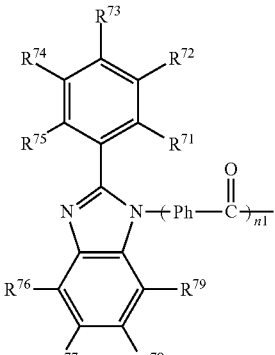

General Formula (277)

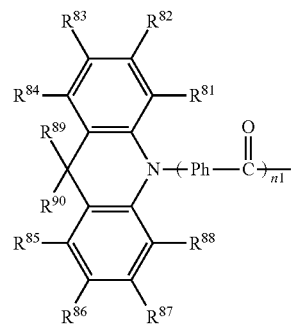

General Formula (278)

wherein in the general formulae (273) to (278), $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, and $R^{81}$ to $R^{90}$ each independently represent a hydrogen atom or a substituent, in which $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$, $R^{81}$ and $R^{82}$, $R^{82}$ and $R^{83}$, $R^{83}$ and $R^{84}$, $R^{85}$ and $R^{86}$, $R^{86}$ and $R^{87}$, $R^{87}$ and $R^{88}$, and $R^{89}$ and $R^{90}$ each may be bonded to each other to form a cyclic structure; Ph represents a substituted or unsubstituted phenylene group; and n1 represents 0 or 1.

(3) The compound according to the item (1) or (2), wherein in the general formula (271), at least one of $R^1$ to $R^5$ and at least one of $R^6$ to $R^{10}$ each represent a group represented by the general formula (272).

(4) The compound according to the item (3), wherein in the general formula (271), $R^3$ and $R^8$ each represent a group represented by the general formula (272).

(5) The compound according to any one of the items (1) to (4), wherein the group represented by the general formula (272) is a group represented by the general formula (274).

(6) The compound according to any one of the items (1) to (4), wherein the group represented by the general formula (272) is a group represented by the general formula (273).

(7) The compound according to the item (6), wherein in the general formula (273), at least one of $R^{21}$ to $R^{24}$ and $R^{27}$ to $R^{30}$ represents a substituent.

(8) The compound according to the item (7), wherein the substituent is a group represented by any one of the general formulae (273) to (278).

(9) The compound according to the item (8), wherein in the general formula (273), at least one of $R^{23}$ and $R^{28}$ represents the substituent.

Examples of the compound include the following compounds.

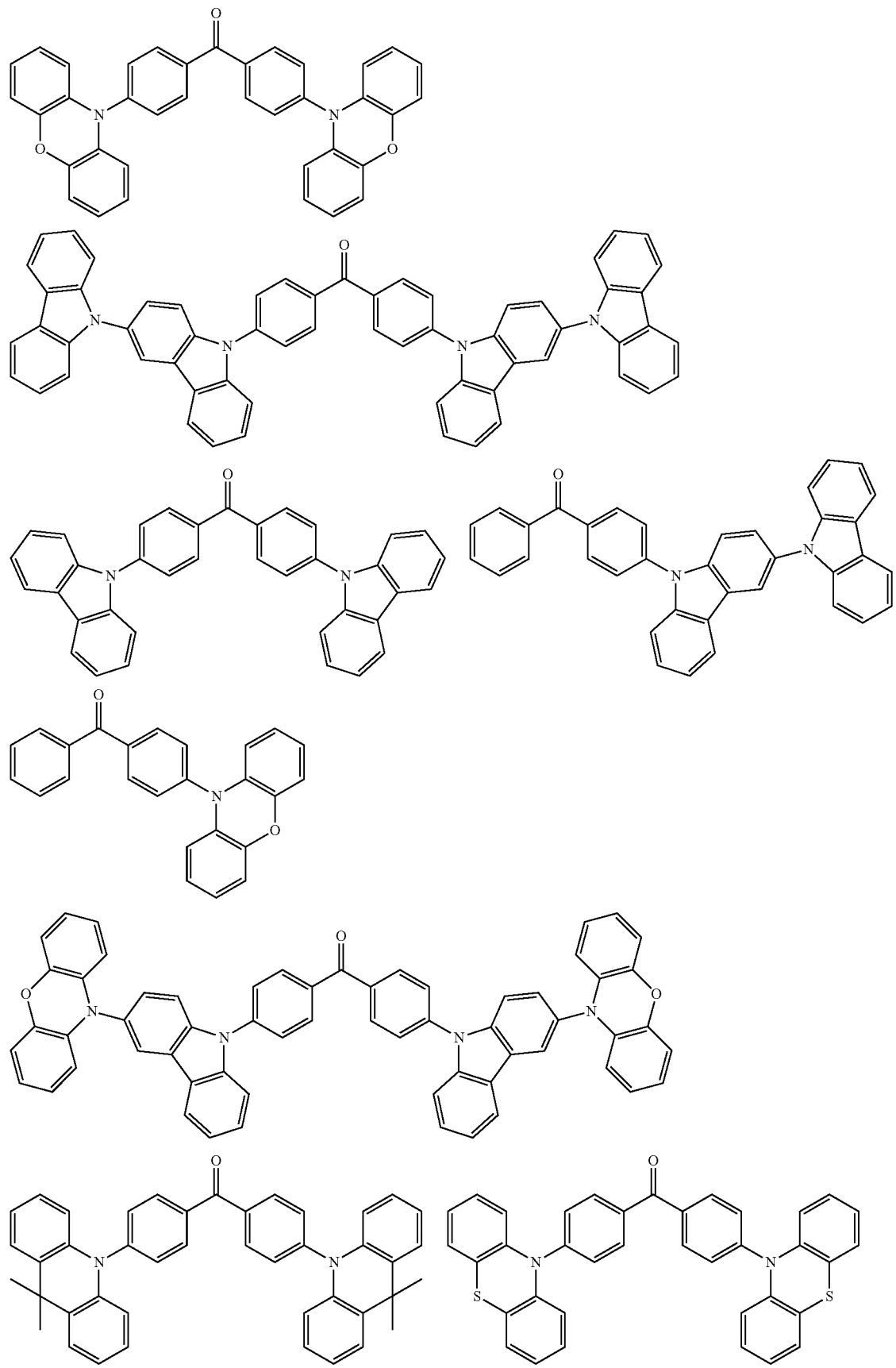

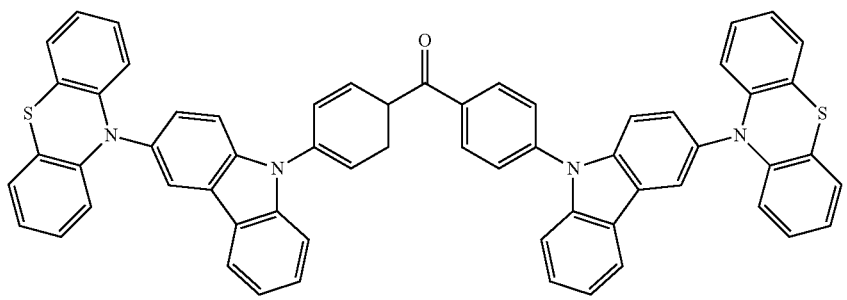
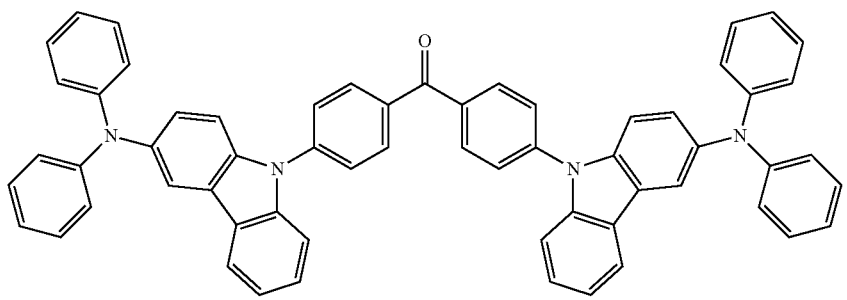
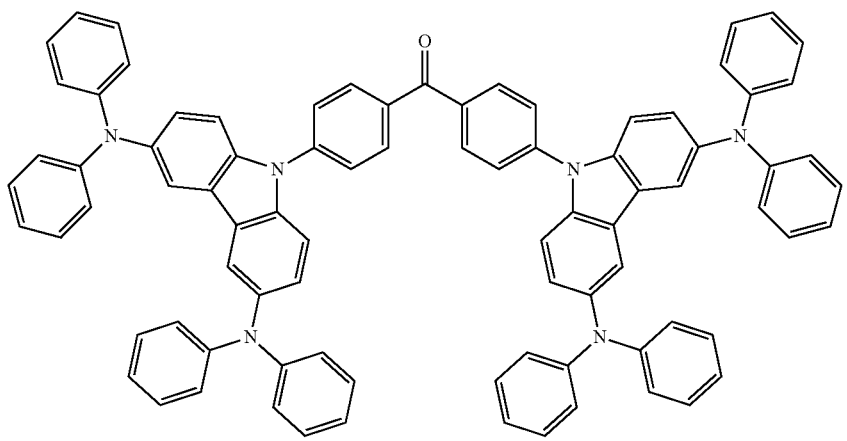
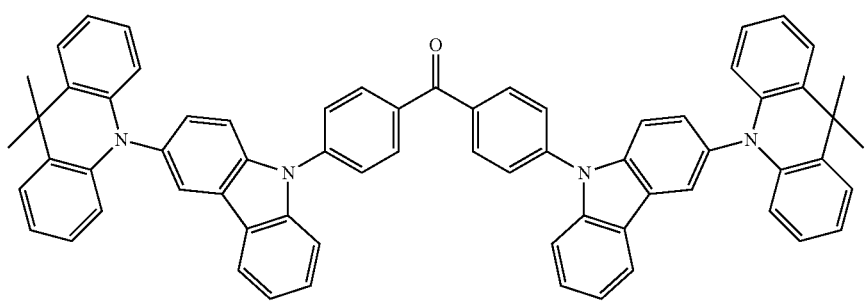

-continued
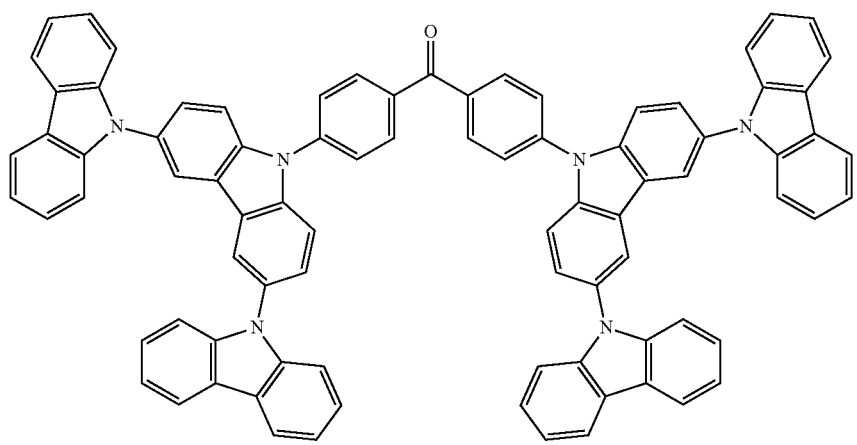
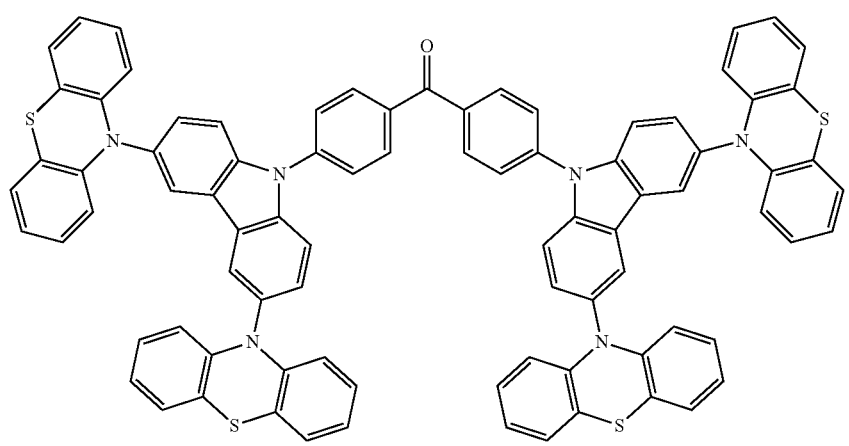
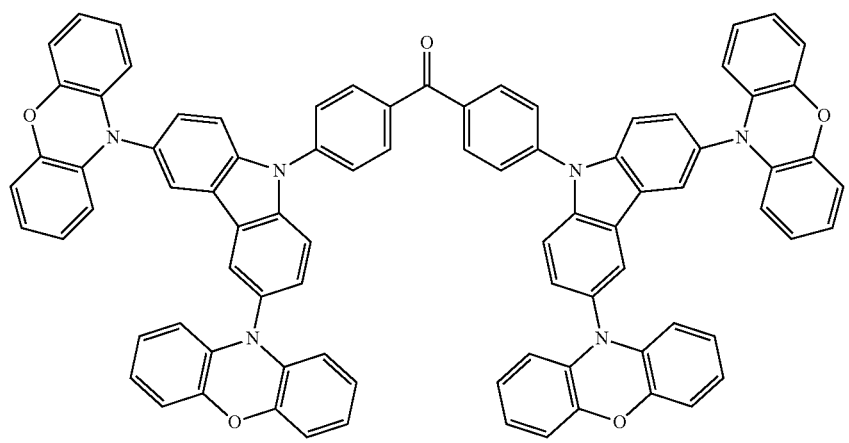

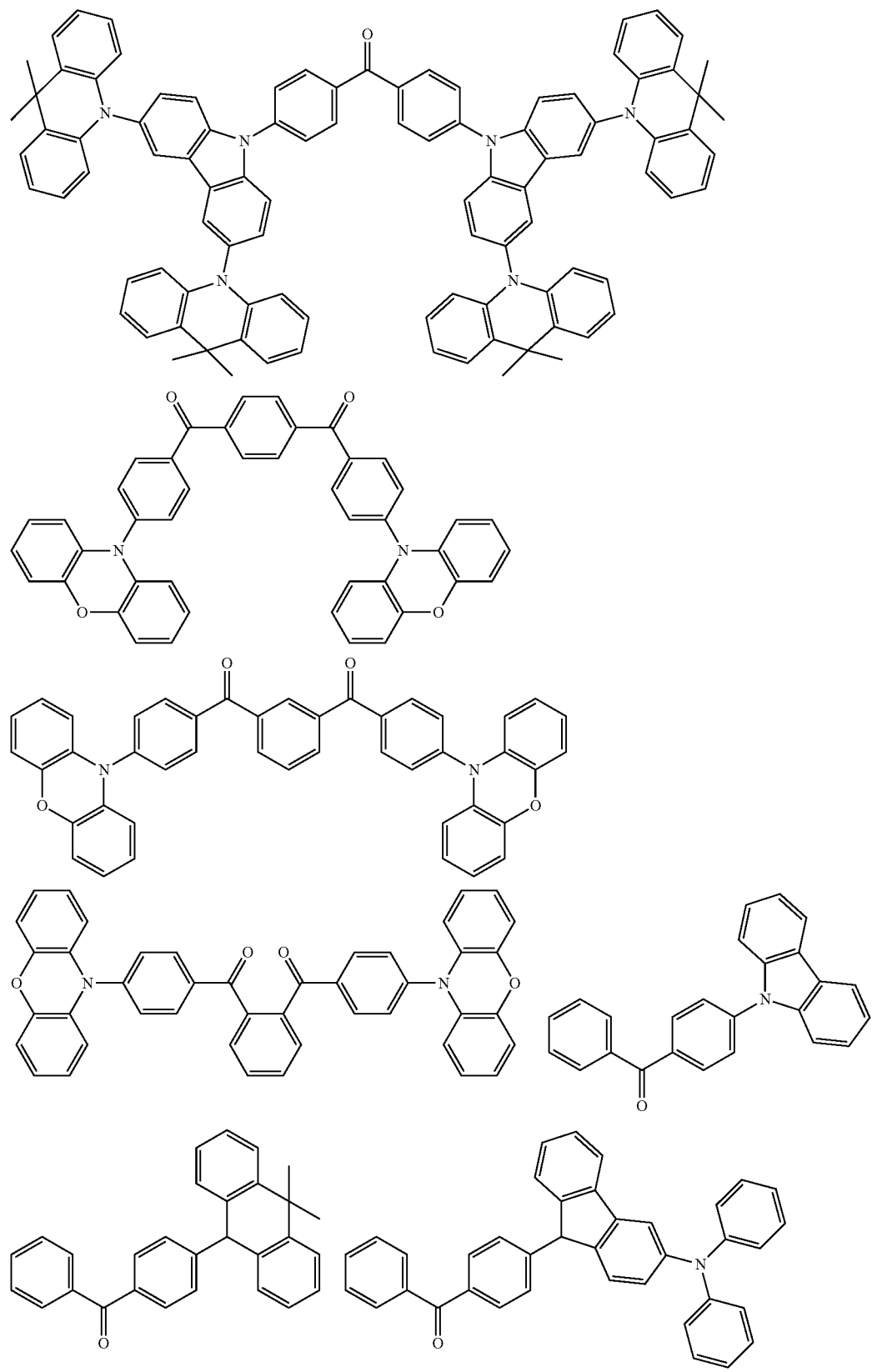

-continued
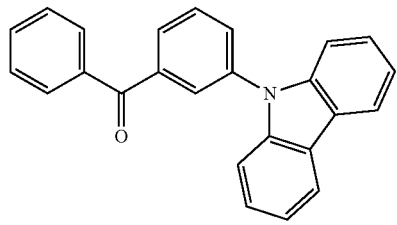
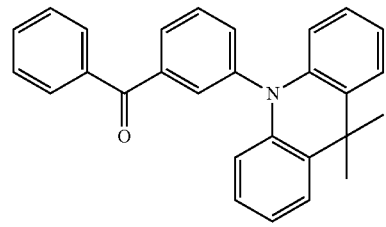
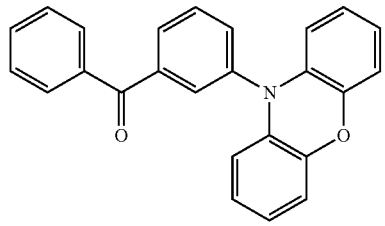
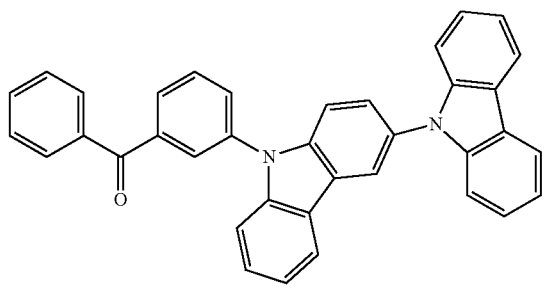
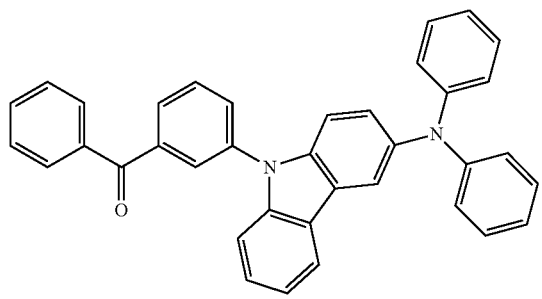
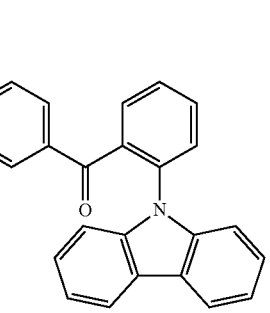
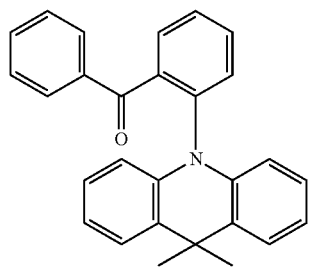
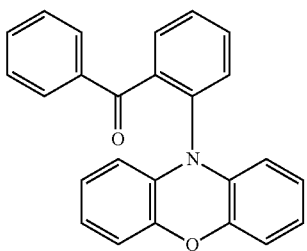
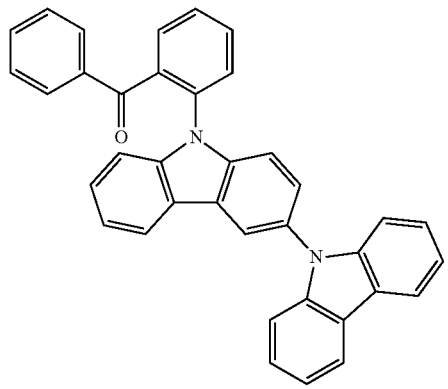
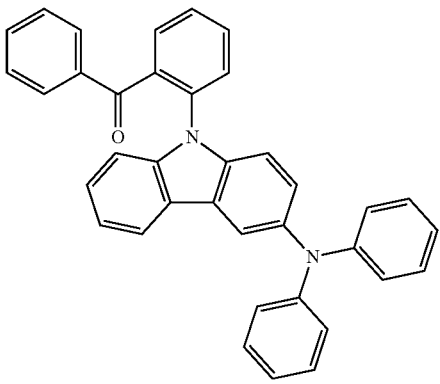
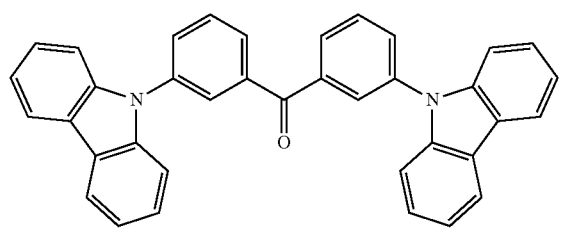
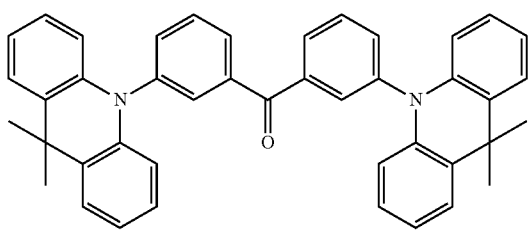

327 328
-continued
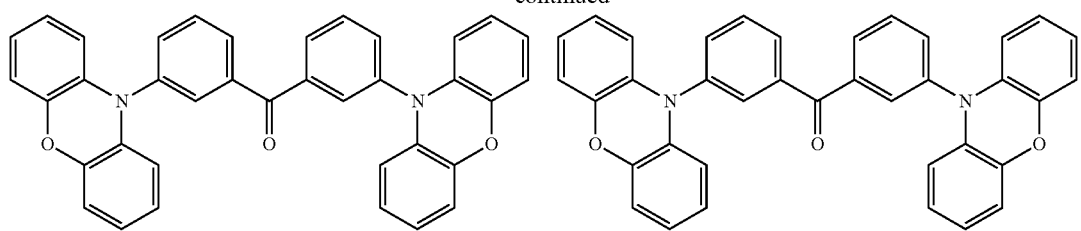

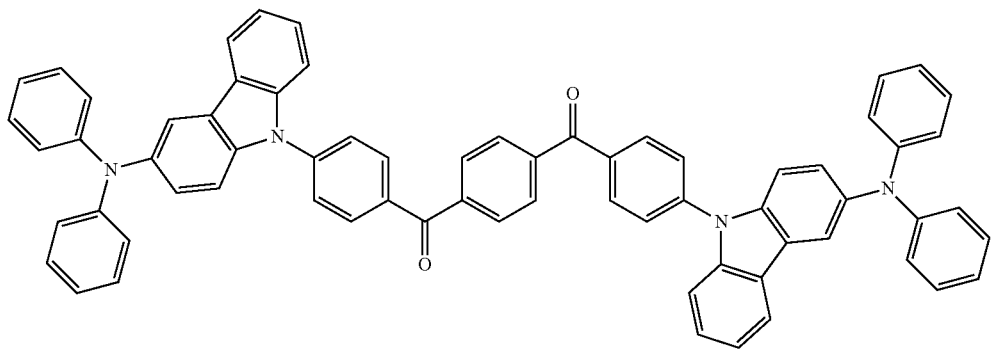
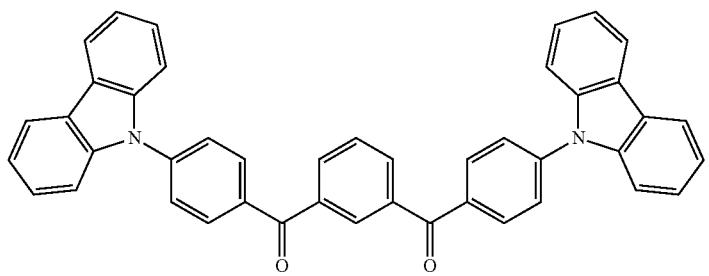
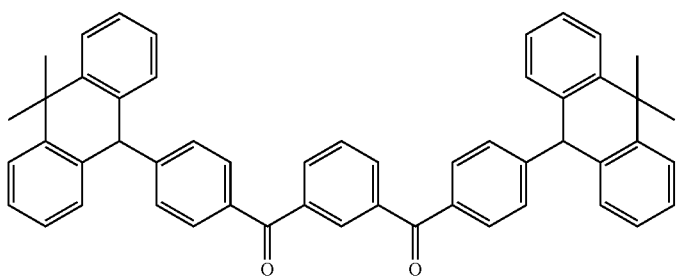
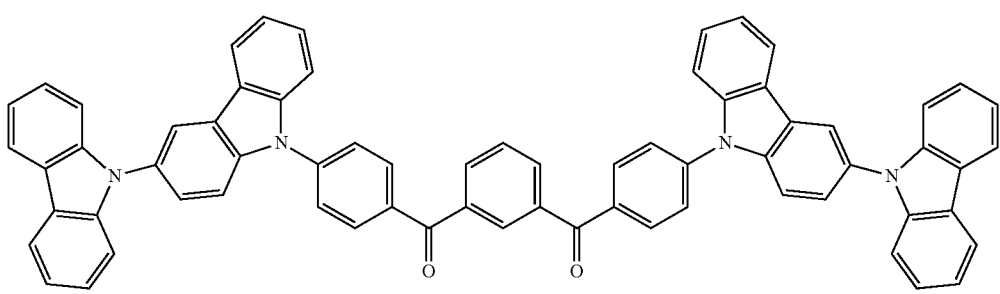
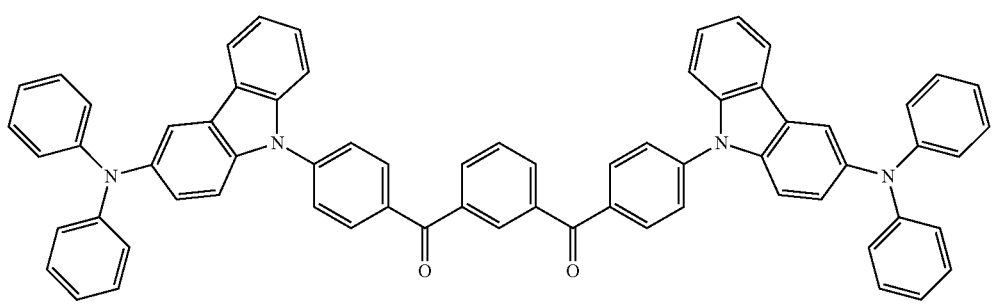

-continued
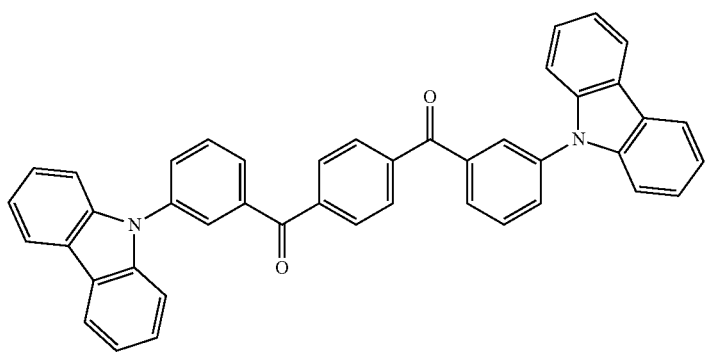
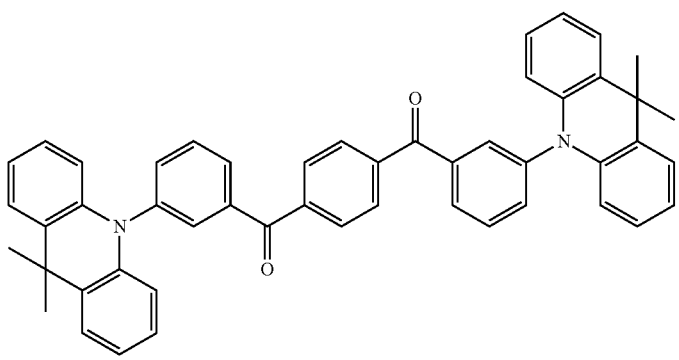
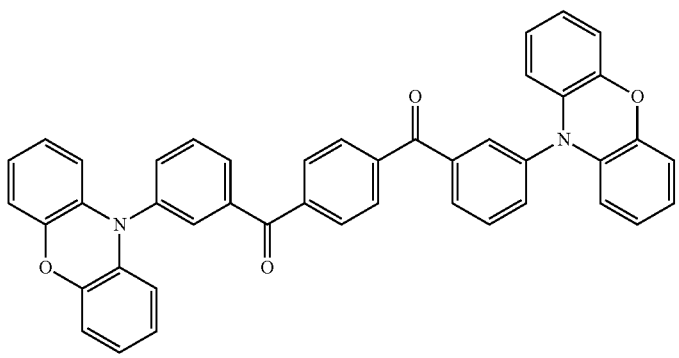
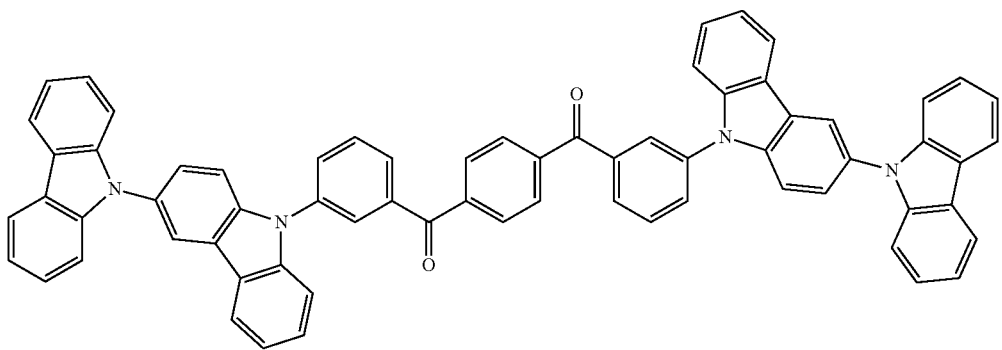

-continued
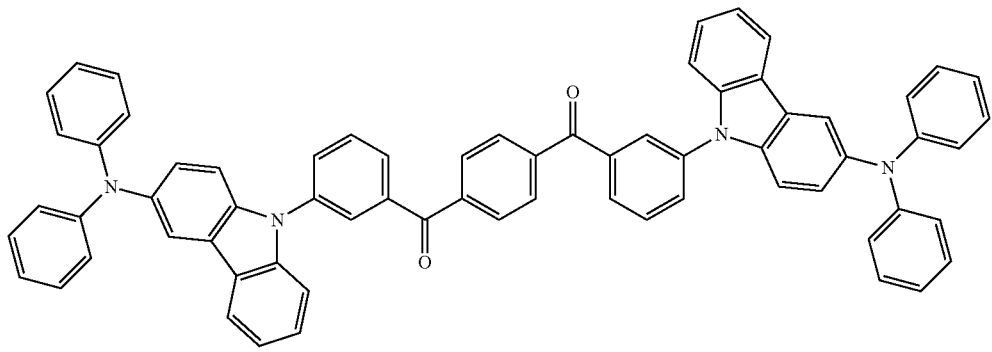
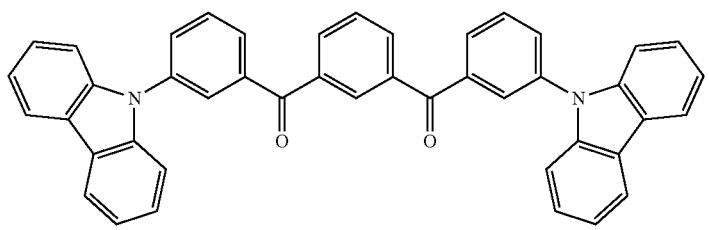
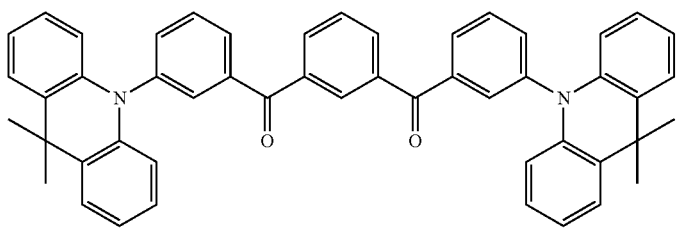
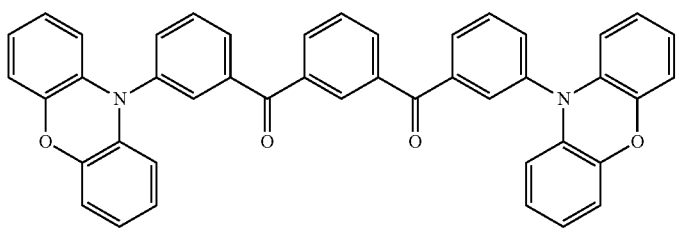
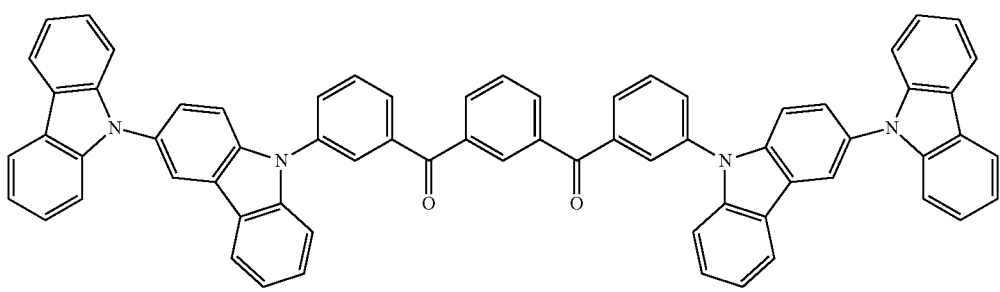
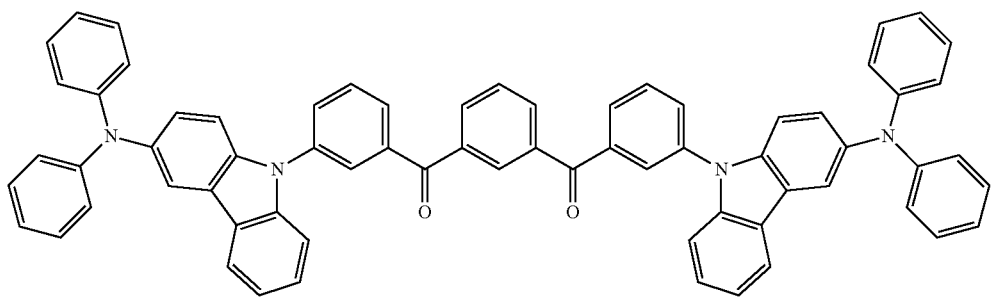

-continued
335
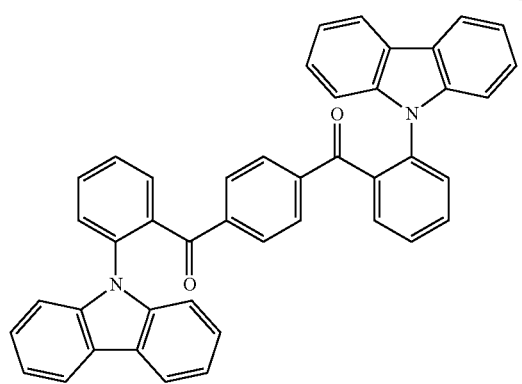
336
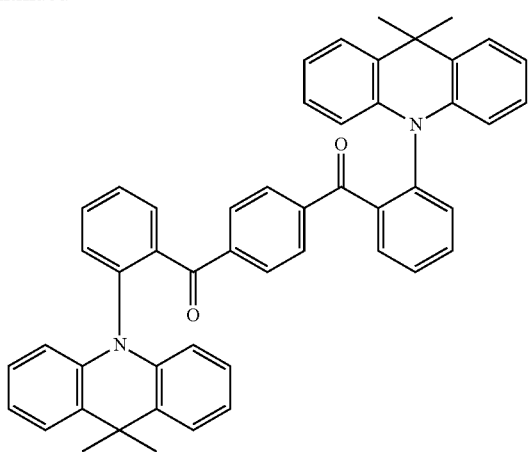
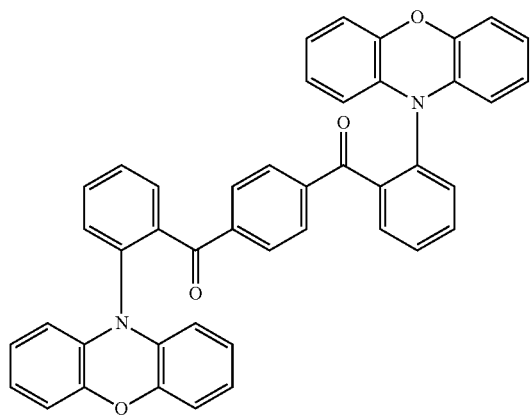
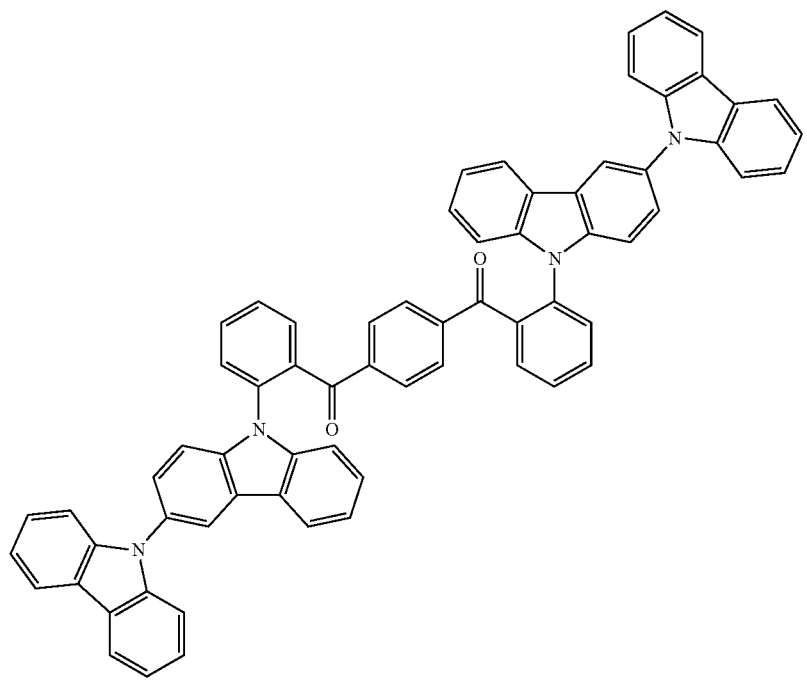

-continued
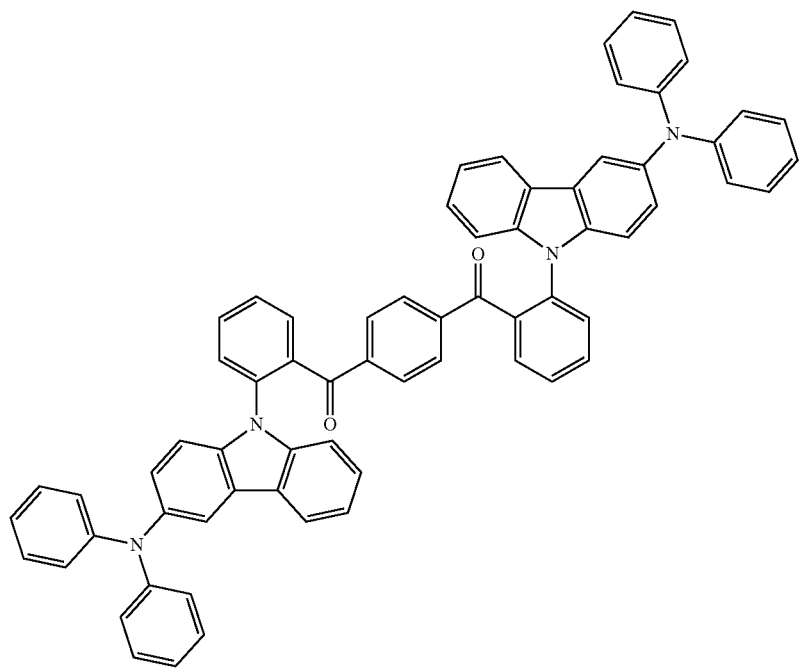
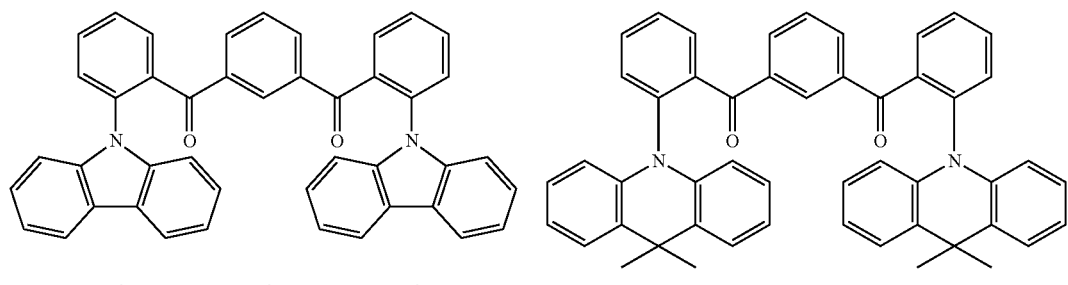
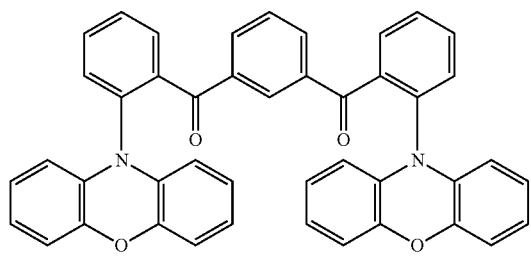
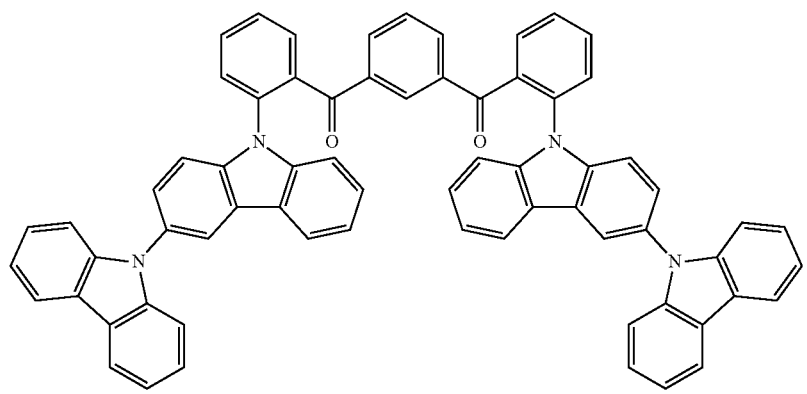

-continued
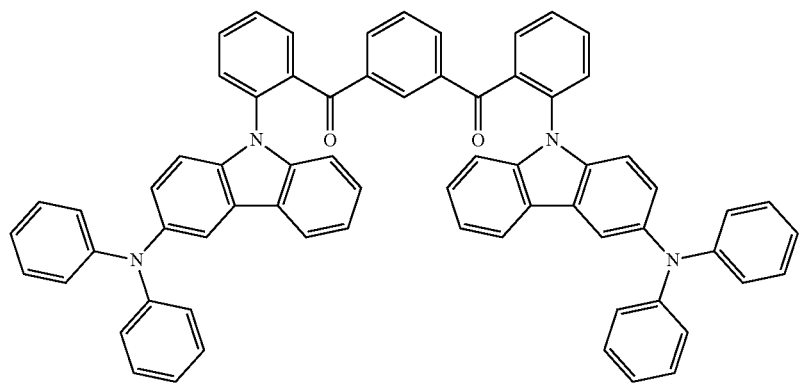
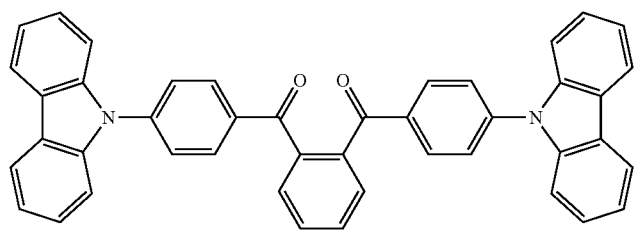
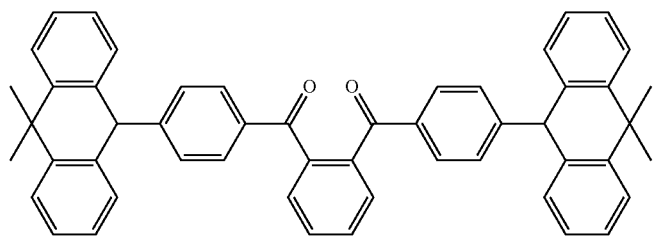
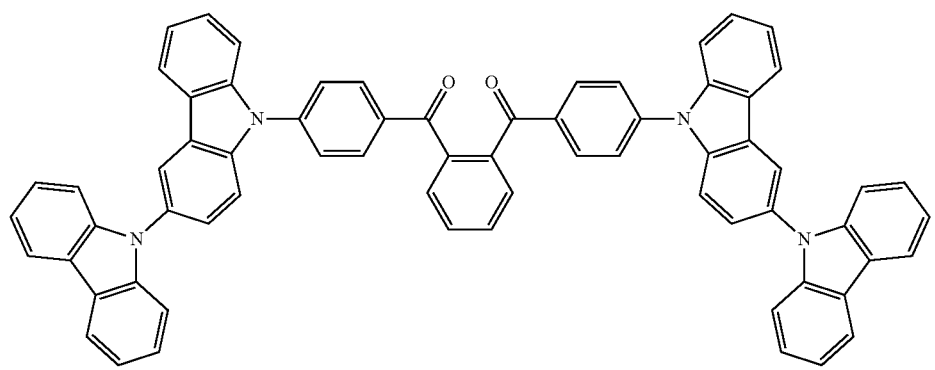
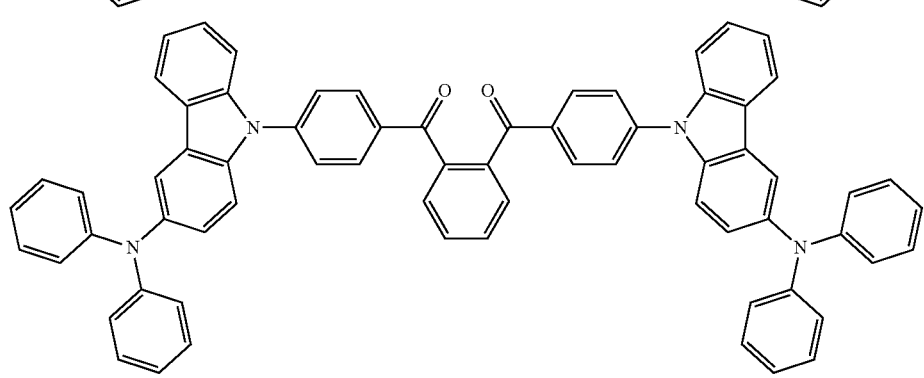

-continued
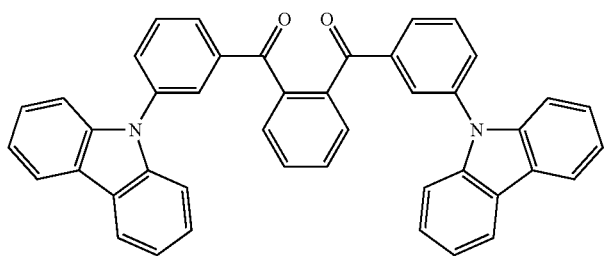
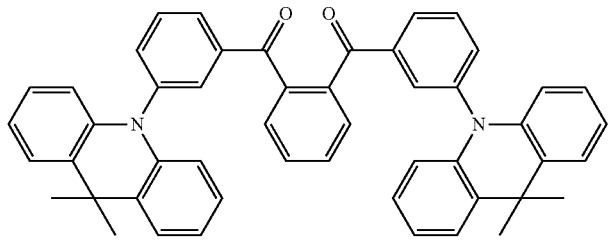
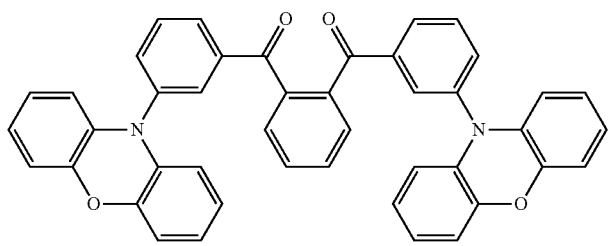
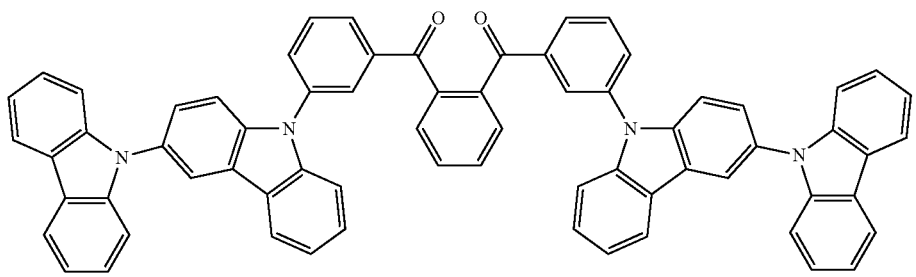
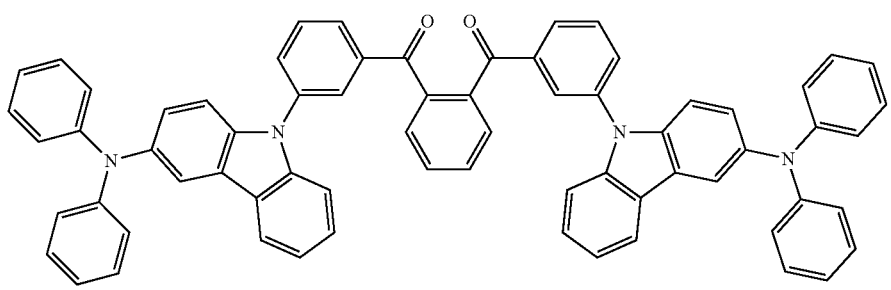

-continued
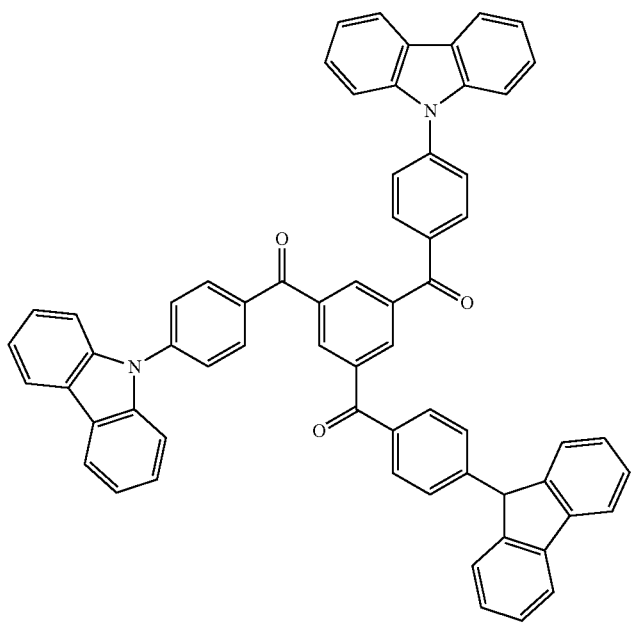
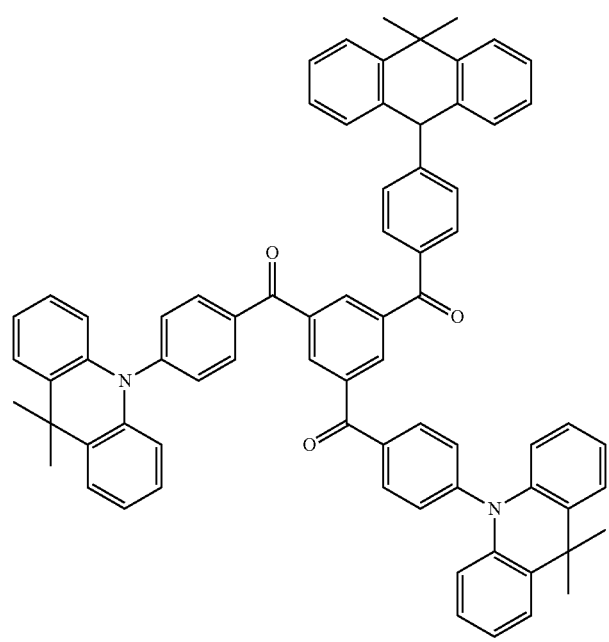

345
-continued
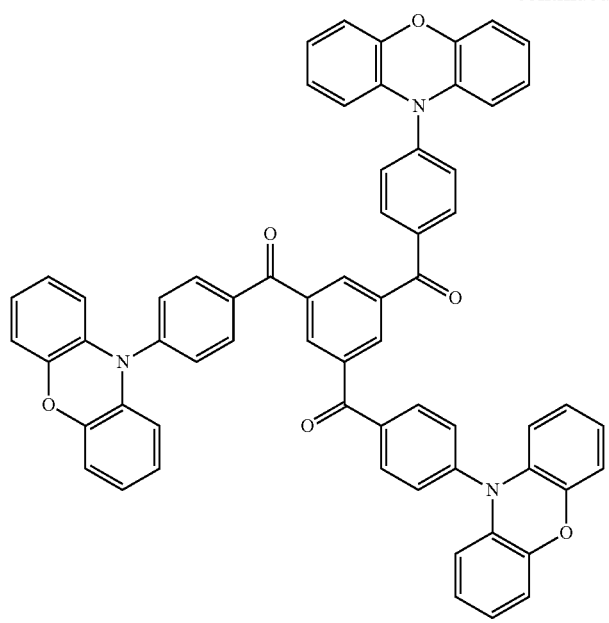
346
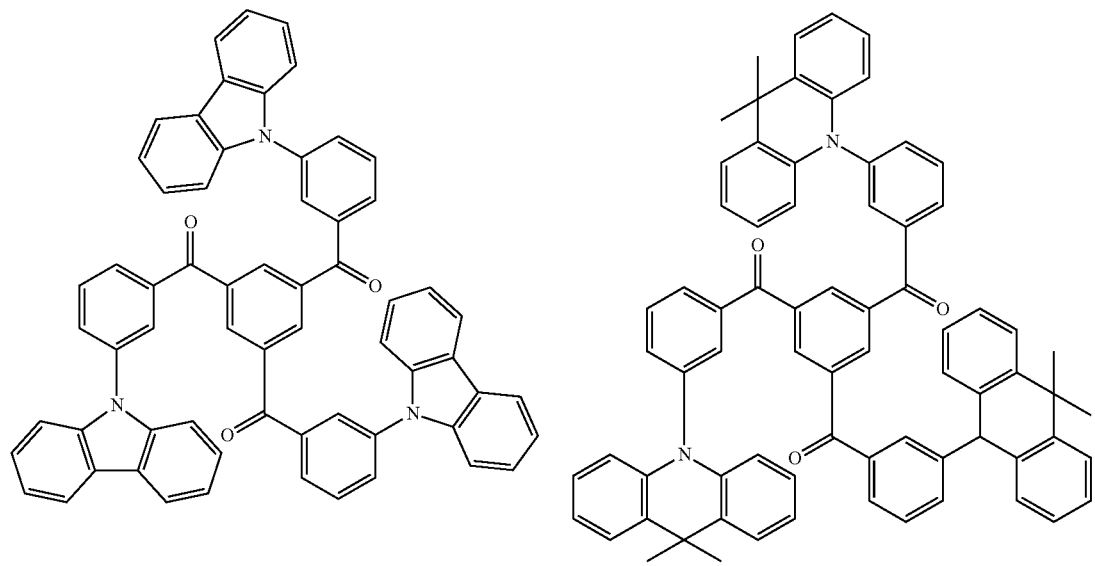

347
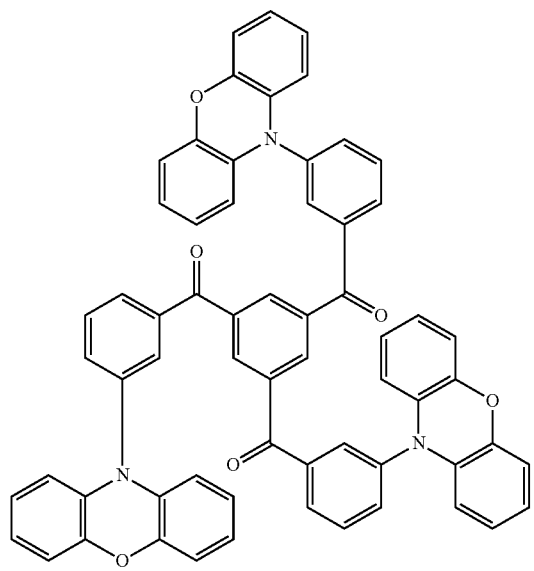
348
-continued
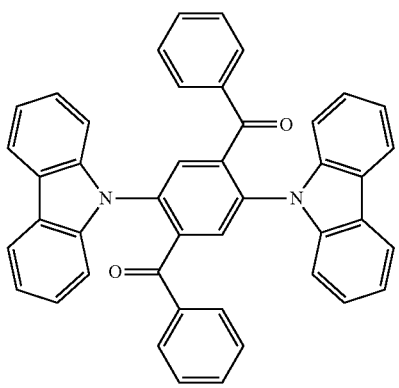
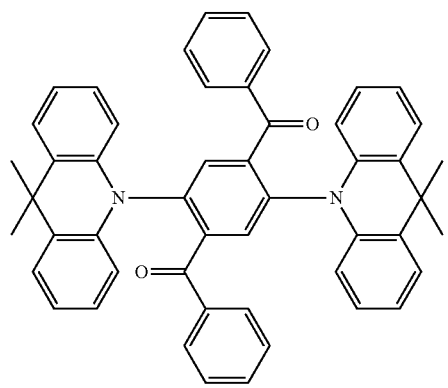 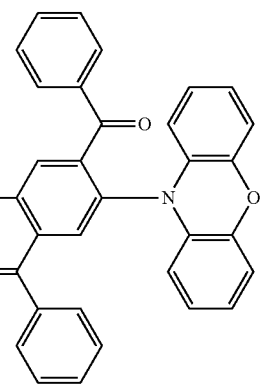
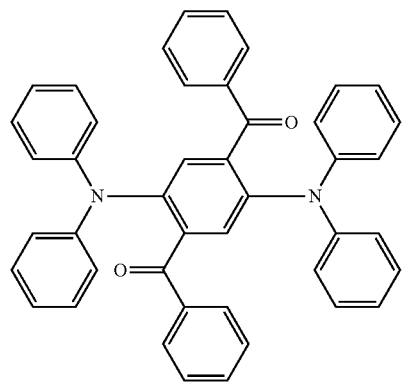 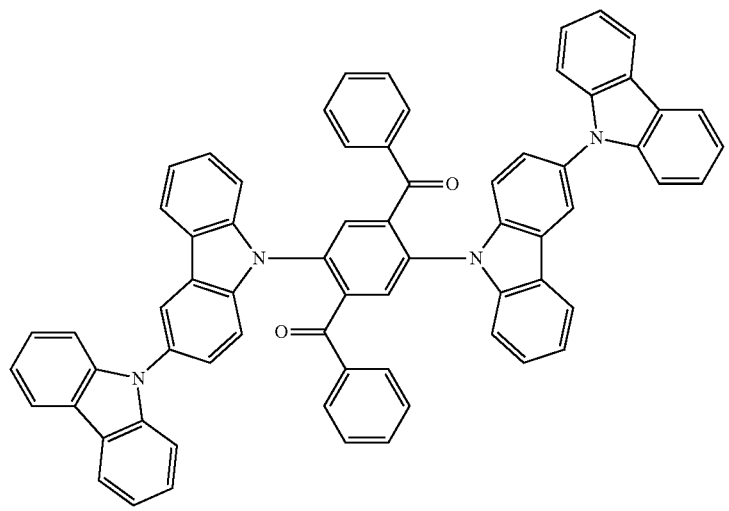

-continued
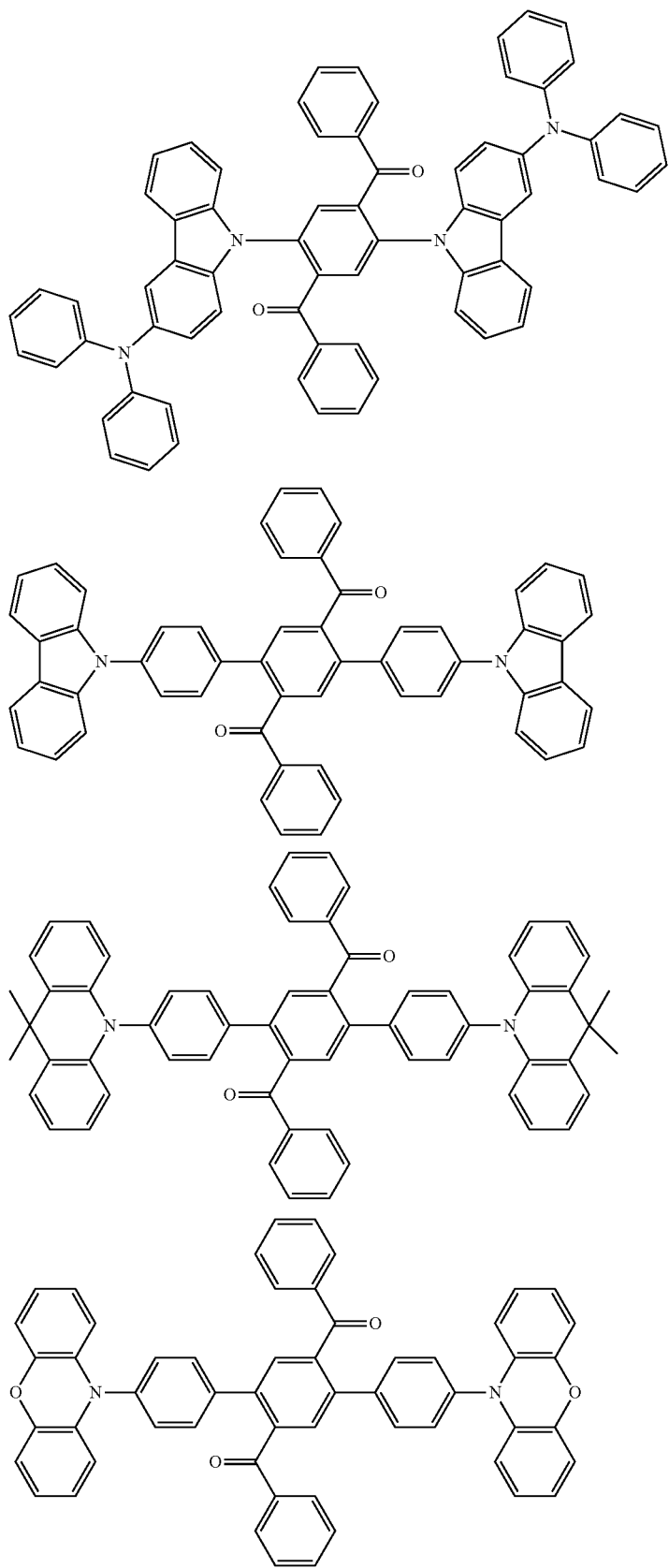

-continued

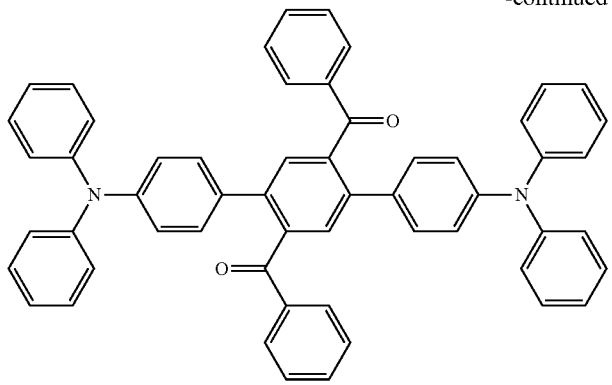

Examples of the preferred light-emitting material include the following compounds.

(1) A compound represented by the following general formula (281):

General Formula (281)

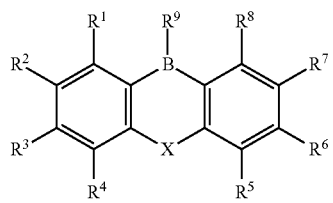

wherein in the general formula (281), X represents an oxygen atom or a sulfur atom; $R^1$ to $R^8$ each independently represent a hydrogen atom or a substituent, provided that at least one of $R^1$ to $R^8$ represents a group represented by any one of the following general formulae (282) to (287), and $R^1$ and $R^2$, $R^2$ and $R^3$, $R^3$ and $R^4$, $R^5$ and $R^6$, $R^6$ and $R^7$, $R^7$ and $R^8$, $R^8$ and $R^9$, and $R^9$ and $R^1$ may be bonded to each other to form a cyclic structure; and $R^9$ represents a substituent, provided that when $R^9$ contains an atom that contains a lone electron pair without forming a single bond to the boron atom, the atom may form a cyclic structure through a coordination bond with the boron atom:

General Formula (282)

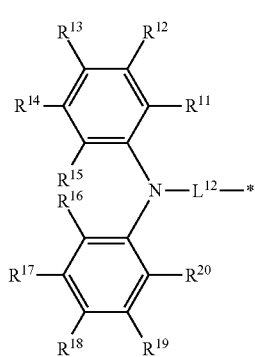

General Formula (283)

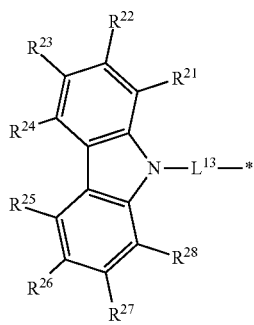

General Formula (284)

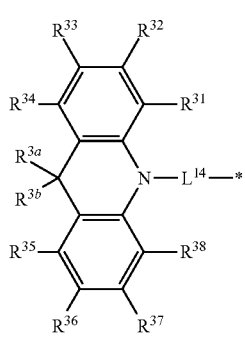

General Formula (285)

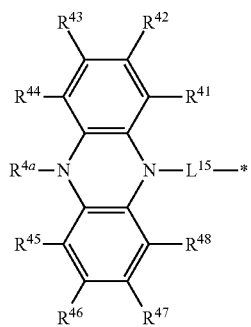

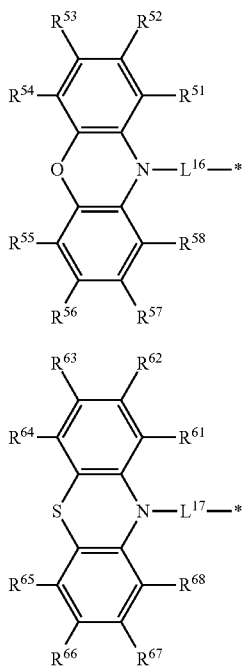

General Formula (286)

General Formula (287)

wherein in the general formulae (282) to (287), $L^{12}$ to $L^{17}$ each independently represent a single bond or a divalent linking group; * represents the position bonded to the benzene ring in the general formula (281); and $R^{11}$ to $R^{20}$, $R^{21}$ to $R^{28}$, $R^{31}$ to $R^3$, $R^{3a}$, $R^{3b}$, $R^{41}$ to $R^{48}$, $R^{4a}$, $R^{51}$ to $R^{58}$, $R^{61}$ to $R^{68}$ each independently represent a hydrogen atom or a substituent, in which $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, and $R^{67}$ and $R^{68}$ each may be bonded to each other to form a cyclic structure.

(2) The compound according to the item (1), wherein in the general formula (281), at least one of $R^1$ to $R^8$ represents a group represented by any one of the general formulae (283) to (287).

(3) The compound according to the item (1) or (2), wherein in the case where at least one of $R^1$ to $R^8$ in the general formula (281) represents a group represented by the general formula (283), at least one of $R^{21}$ to $R^{28}$ in the general formula (283) represents a substituent.

(4) The compound according to any one of the items (1) to (3), wherein in the general formula (281), at least one of $R^2$, $R^3$, $R^6$, and $R^7$ represents a group represented by any one of the general formulae (282) to (287).

(5) The compound according to the item (4), wherein in the general formula (281), at least one of $R^3$ and $R^6$ represents a group represented by any one of the general formulae (282) to (287).

(6) The compound according to the item (5), wherein in the general formula (281), $R^3$ and $R^6$ each independently represent a group represented by any one of the general formulae (282) to (287).

(7) The compound according to any one of the items (1) to (6), wherein at least one of $R^{11}$ to $R^{20}$ in the general formula (282), at least one of $R^{21}$ to $R^{28}$ in the general formula (283), at least one of $R^{31}$ to $R^{38}$ and at least one of $R^{3a}$ and $R^{3b}$ in the general formula (284), at least one of $R^{41}$ to $R^{48}$ in the general formula (285), at least one of $R^{51}$ to $R^{5s}$ in the general formula (286), and at least one of $R^{61}$ to $R^{68}$ in the general formula (287) each represent a substituent.

(8) The compound according to the item (7), wherein at least one of $R^{13}$ and $R^{18}$ in the general formula (282), at least one of $R^{23}$ and $R^{26}$ in the general formula (283), at least one of $R^{33}$ and $R^{36}$ and at least one of $R^{3a}$ and $R^{3b}$ in the general formula (284), at least one of $R^{43}$ and $R^{46}$ in the general formula (285), at least one of $R^{53}$ and $R^{56}$ in the general formula (286), and at least one of $R^{63}$ and $R^{66}$ in the general formula (287) each represent a substituent.

(9) The compound according to the item (8), wherein at least one of $R^{13}$ and $R^{18}$ in the general formula (282), at least one of $R^{23}$ and $R^{26}$ in the general formula (283), at least one of $R^{33}$ and $R^{36}$ and at least one of $R^{3a}$ and $R^{3b}$ in the general formula (284), at least one of $R^{43}$ and $R^{46}$ in the general formula (285), at least one of $R^{53}$ and $R^{56}$ in the general formula (286), and at least one of $R^{63}$ and $R^{66}$ in the general formula (287) each represent a group represented by any one of the general formulae (282) to (287).

(10) The compound according to any one of the items (1) to (9), wherein in the general formulae (282) to (287), $L^{12}$ to $L^{17}$ each represent a single bond.

(11) The compound according to any one of the items (1) to (10), wherein in the general formula (281), X represents an oxygen atom.

(12) The compound according to any one of the items (1) to (11), wherein in the general formula (281), $R^9$ represents a group represented by the following general formula (a):

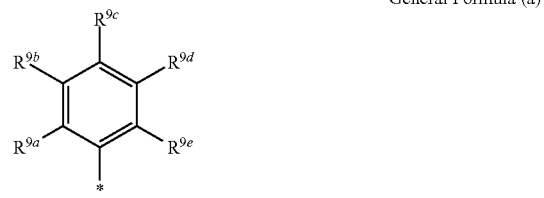

General Formula (a)

wherein in the general formula (a), * represents the position bonded to the boron atom in the general formula (281); and $R^{9a}$, $R^{9b}$, $R^{9c}$, $R^{9d}$, and $R^{9e}$ each independently represent a hydrogen atom or a substituent, in which $R^{9a}$ and $R^{9b}$, $R^{9b}$ and $R^{9c}$, $R^{9c}$ and $R^{9d}$, and $R^{9d}$ and $R^{9e}$ may be bonded to each other to form a cyclic structure.

(13) The compound according to the item (12), wherein in the general formula (a), $R^{9a}$ and $R^{9e}$ each represent a substituent.

(14) The compound according to any one of the items (1) to (13), wherein in the general formula (281), at least one of $R^1$ to $R^8$ represents a group represented by the general formula (284).

(15) The compound according to any one of the items (1) to (4), and (7) to (14), wherein in the general formula (281), $R^3$ and $R^6$, or $R^2$ and $R^7$ each represent a group represented by the general formula (284).

(16) The compound according to the item (14) or (15), wherein in the general formula (284), $R^{3a}$ and $R^{3b}$ each represent a substituent.

(17) The compound according to any one of the items (14) to (16), wherein the substituent is an alkyl group having from 1 to 15 carbon atoms or a phenyl group.

(18) The compound according to any one of the items (14) to (16), wherein in the general formula (284), $R^{3a}$ and $R^{3b}$ are bonded to each other to form a cyclic structure.

Examples of the compound include the following compounds.
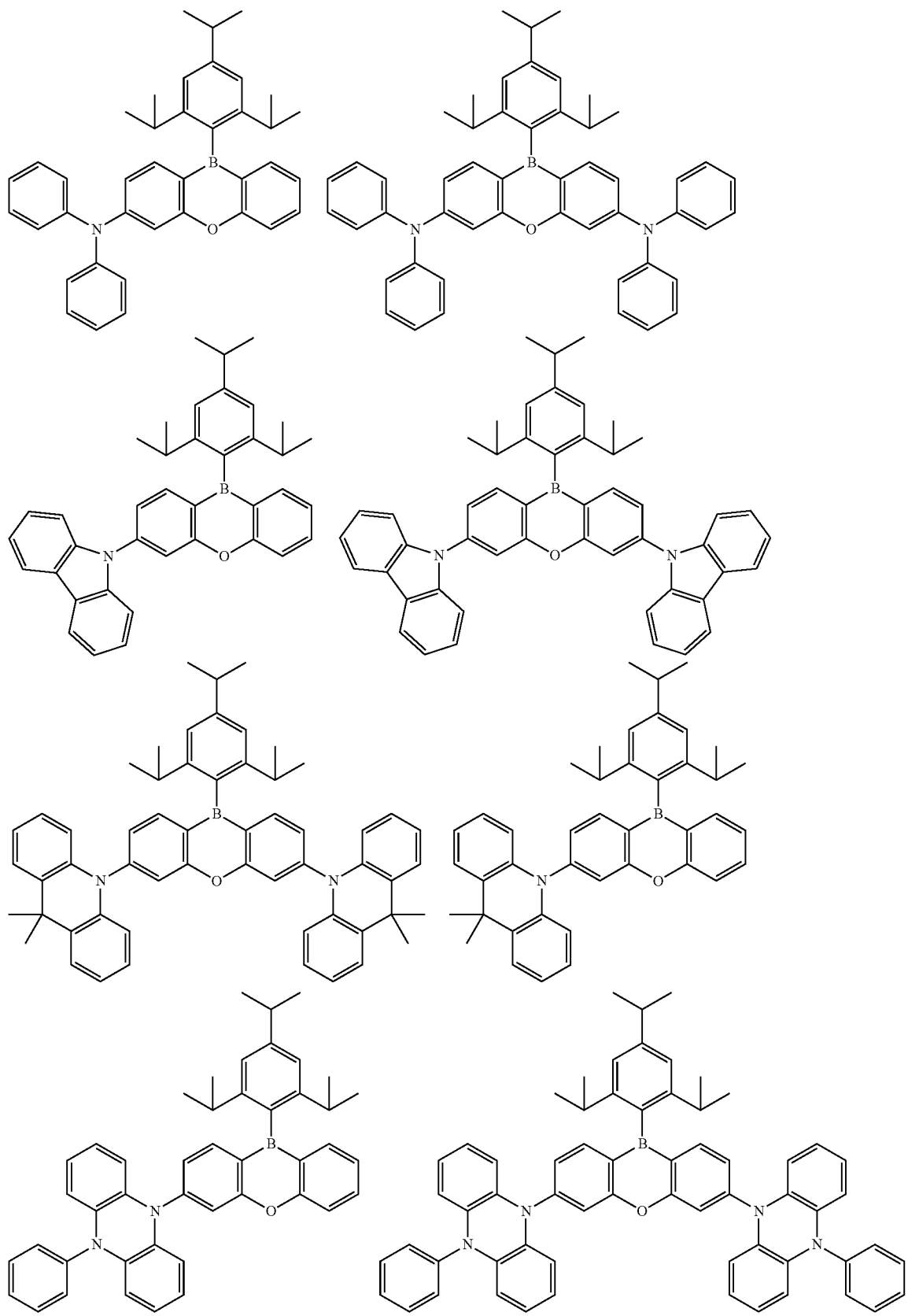

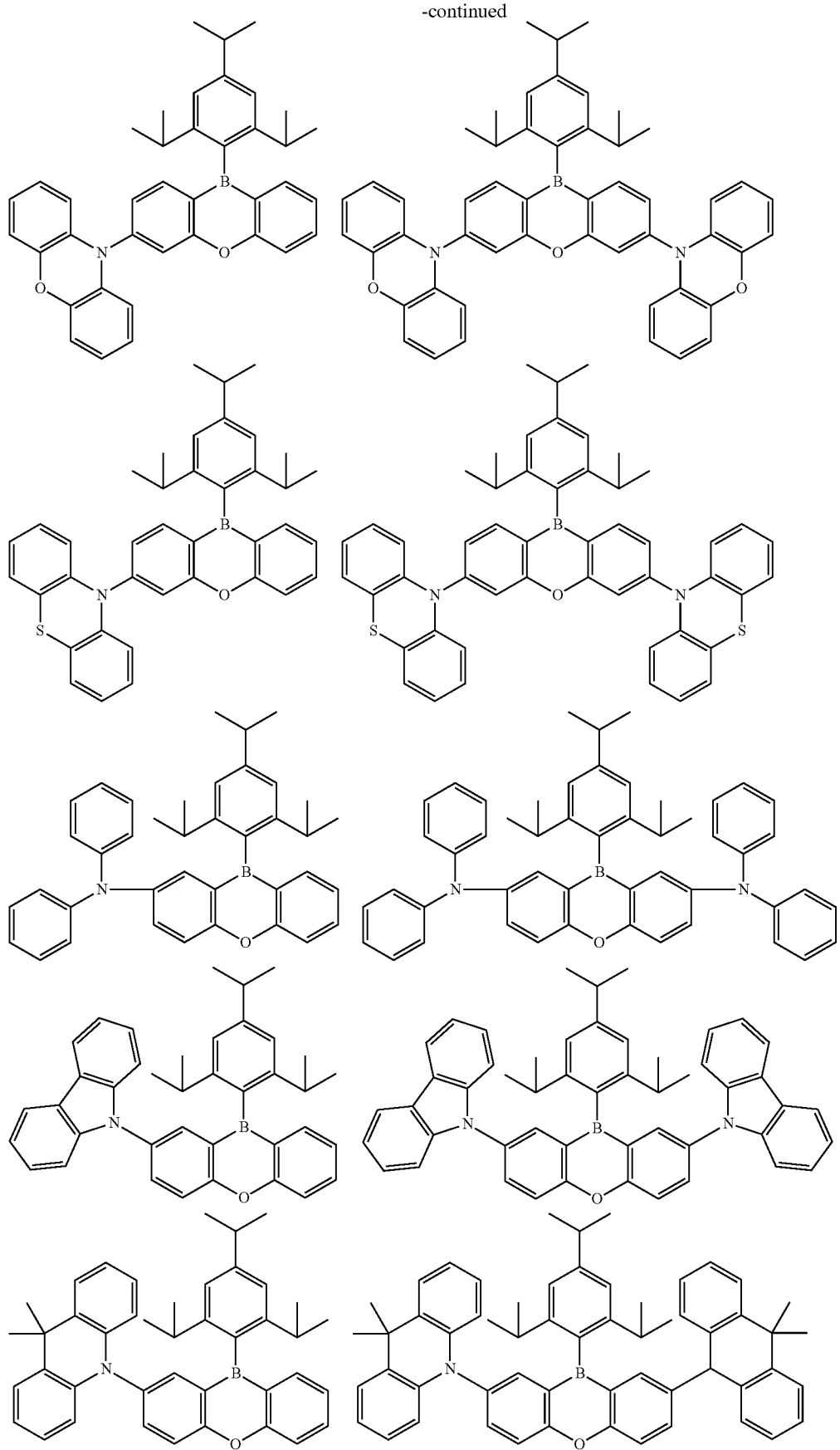

-continued
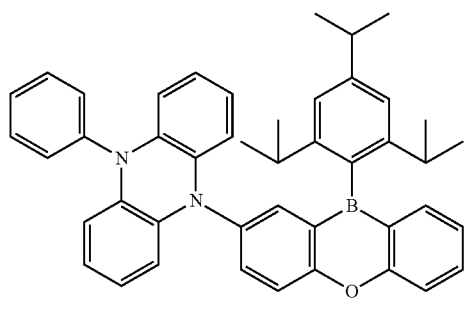
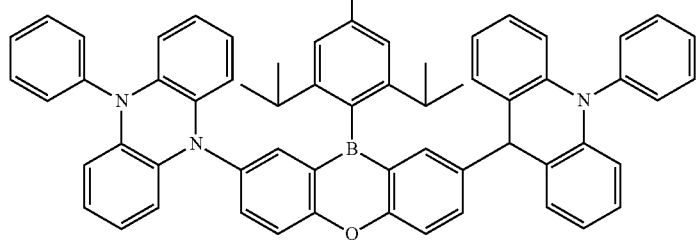
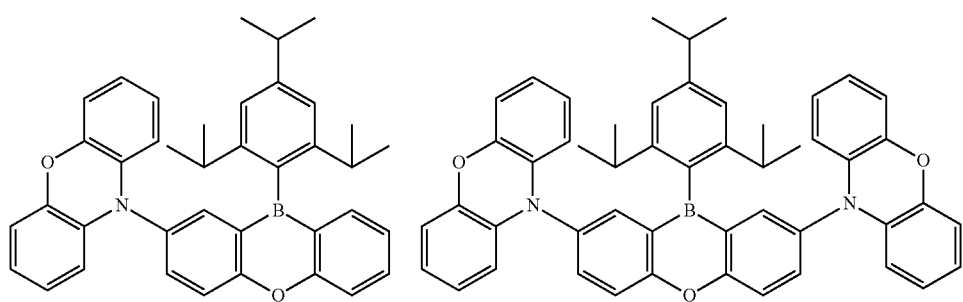
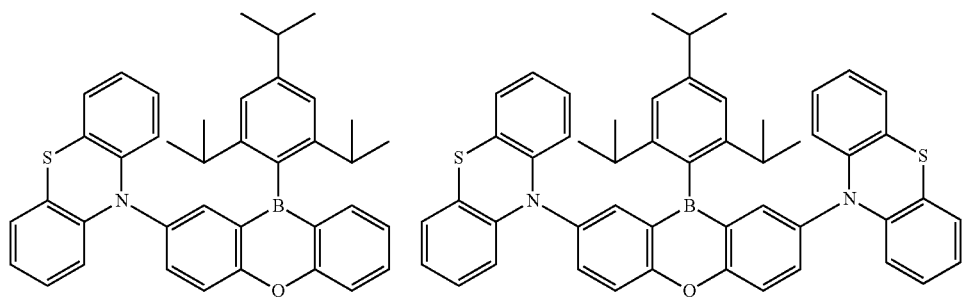
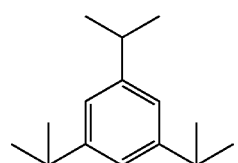
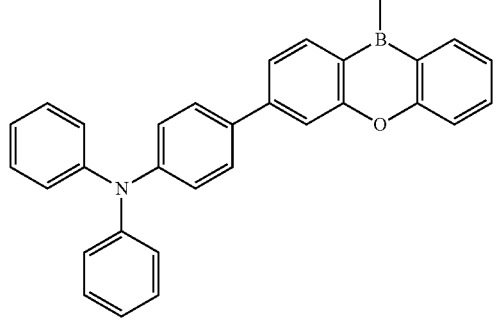

-continued
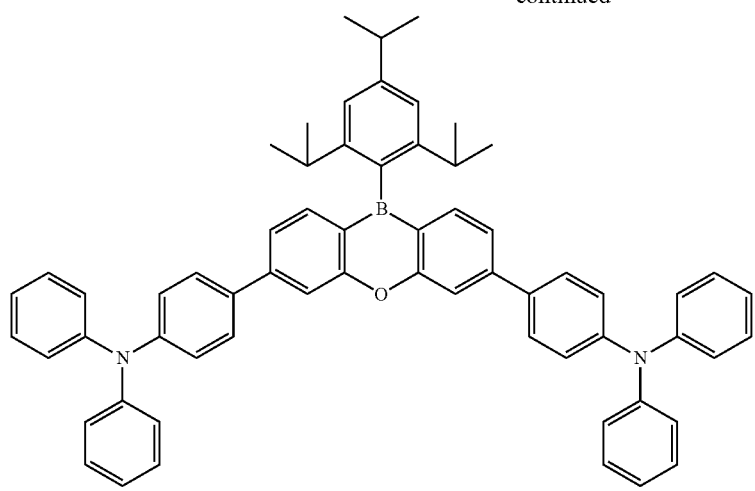
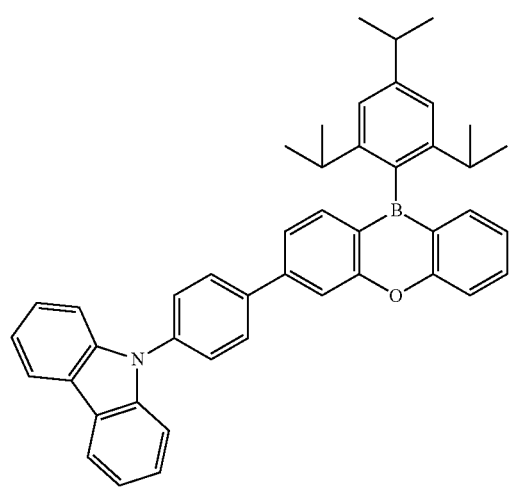
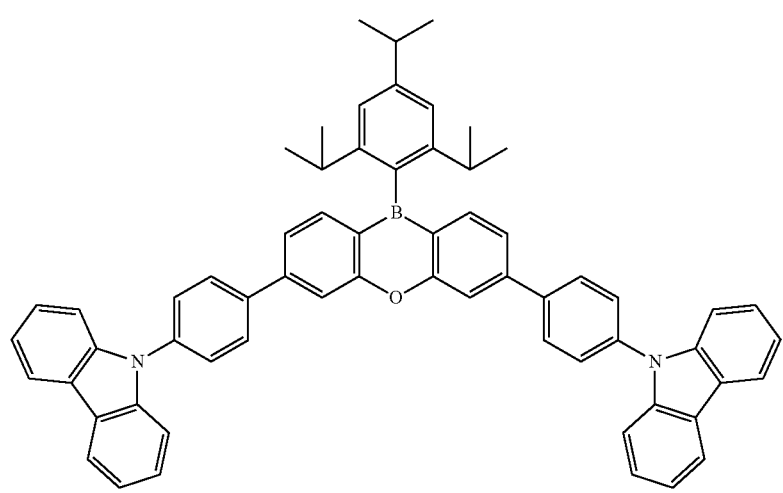

-continued
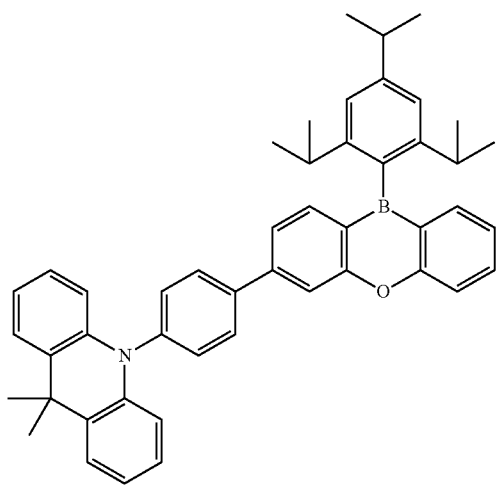
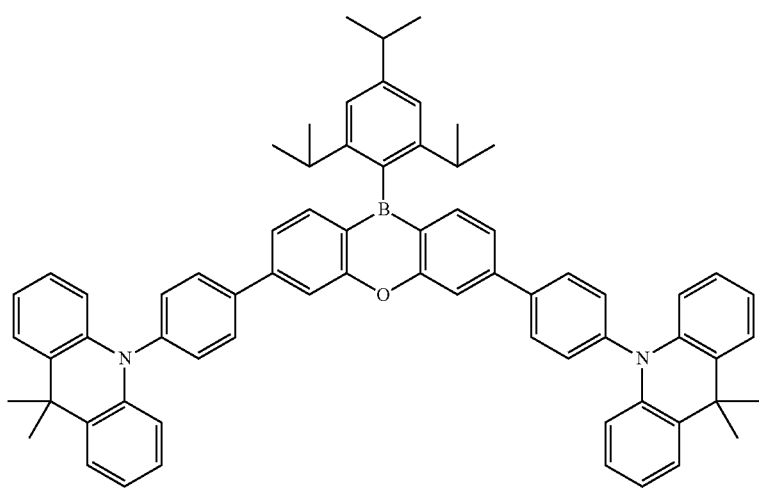
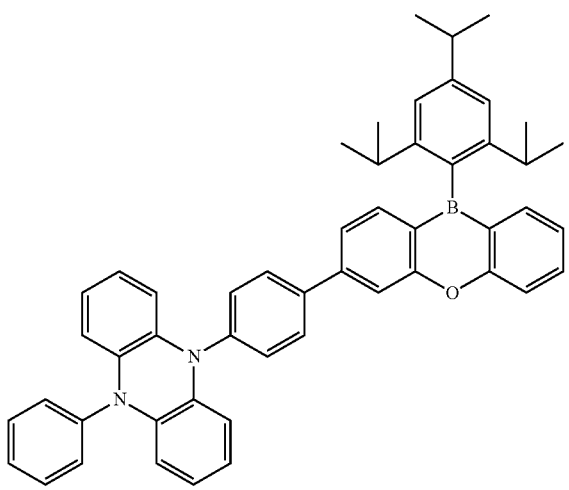

-continued
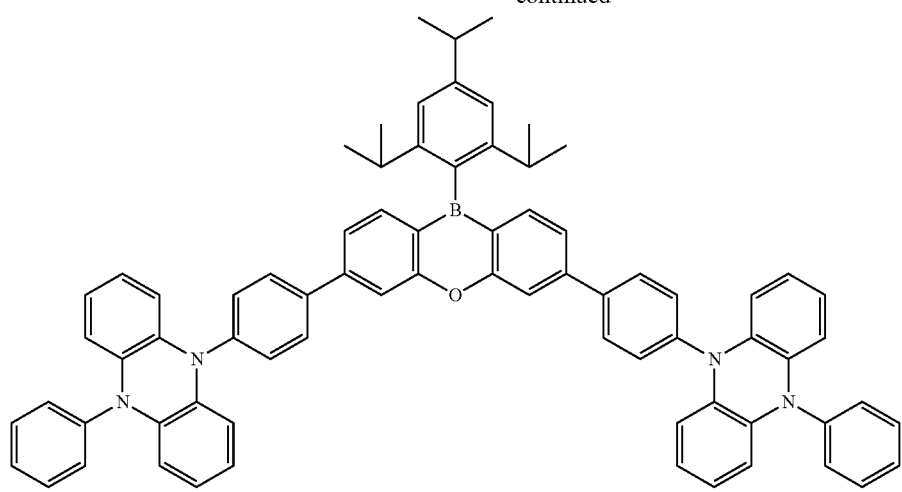
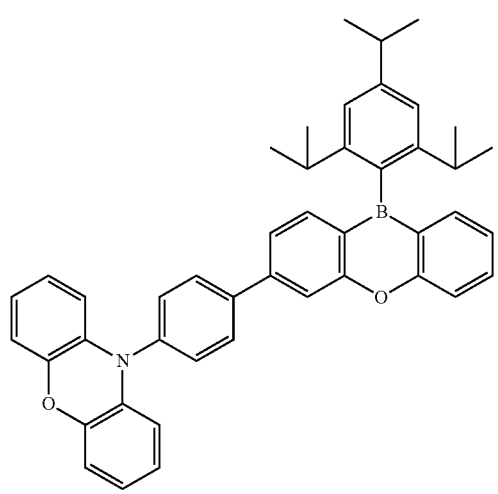
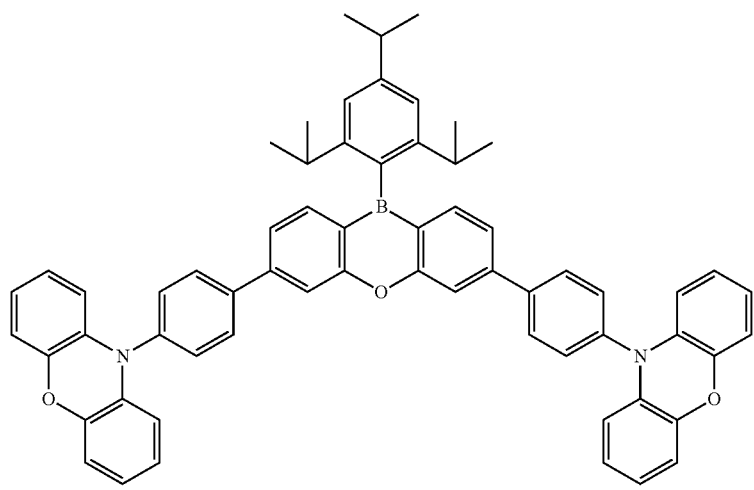

-continued
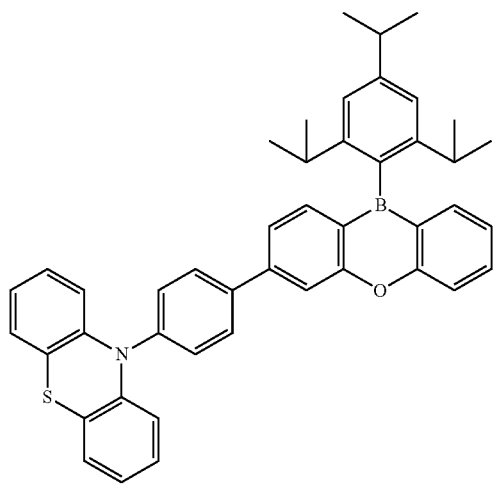
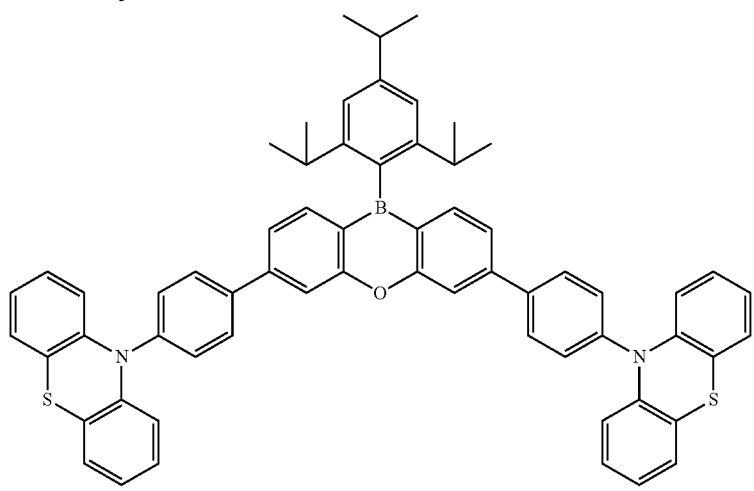
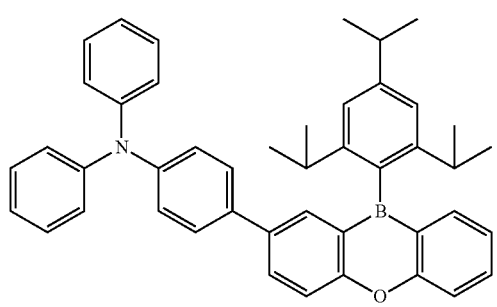
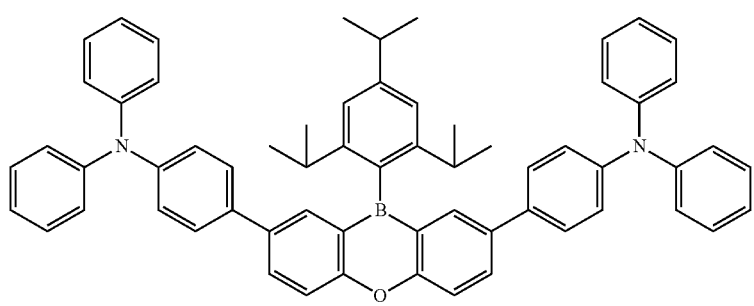

-continued
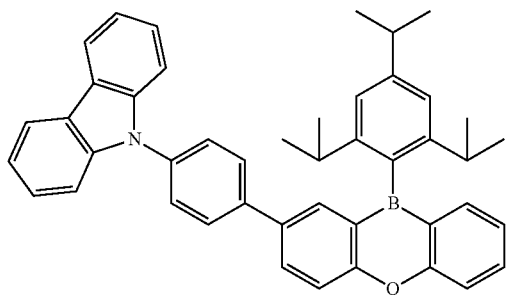
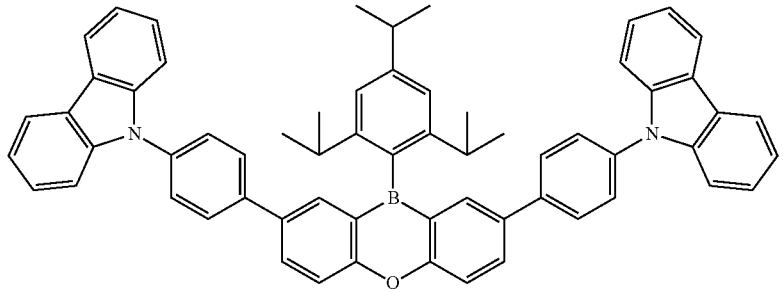
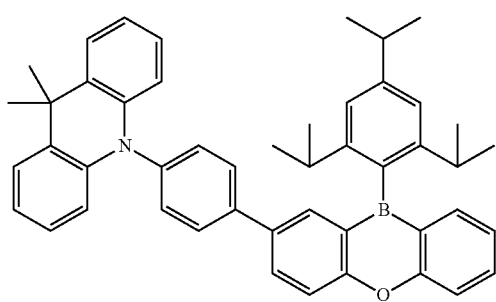
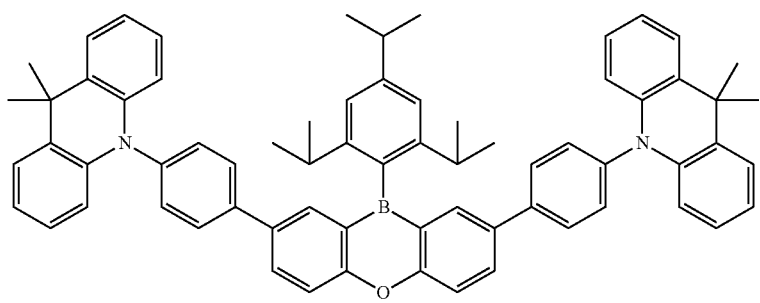
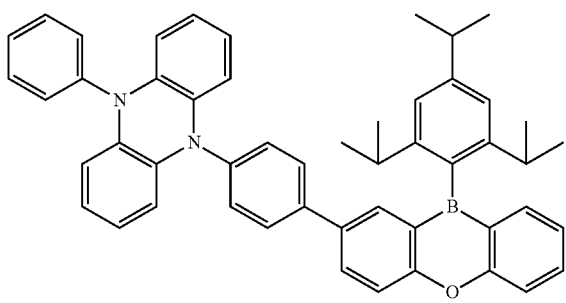

-continued
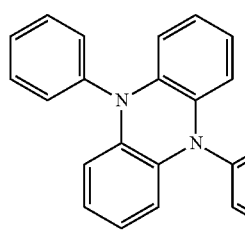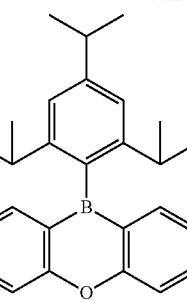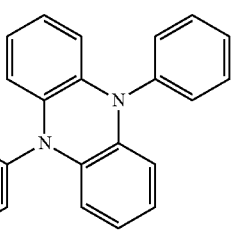
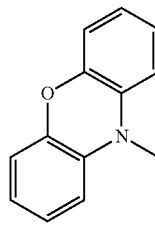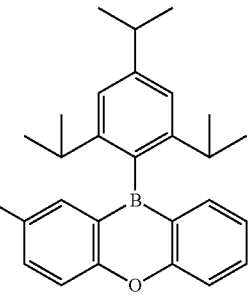
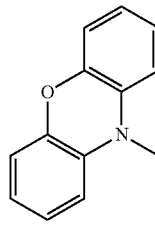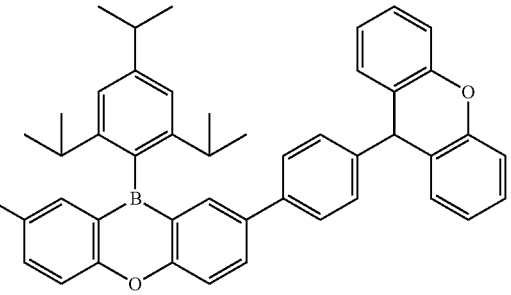
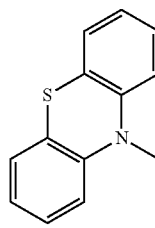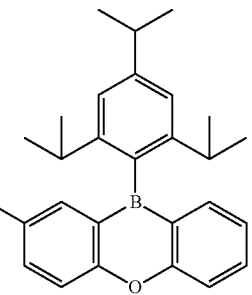
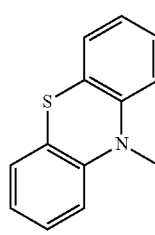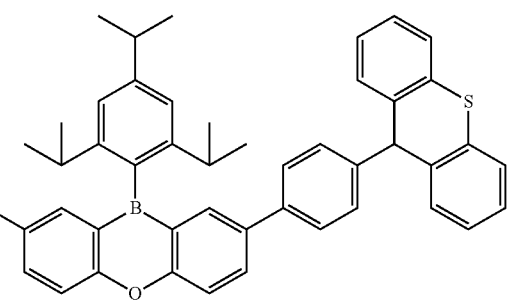

373
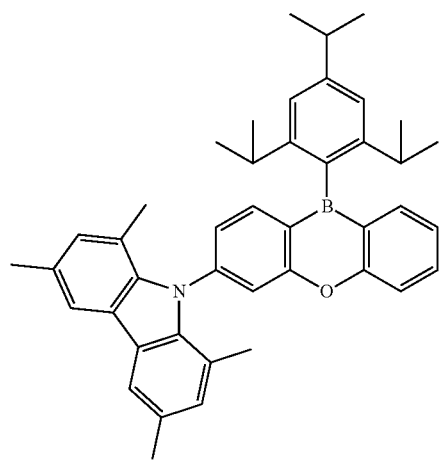
374
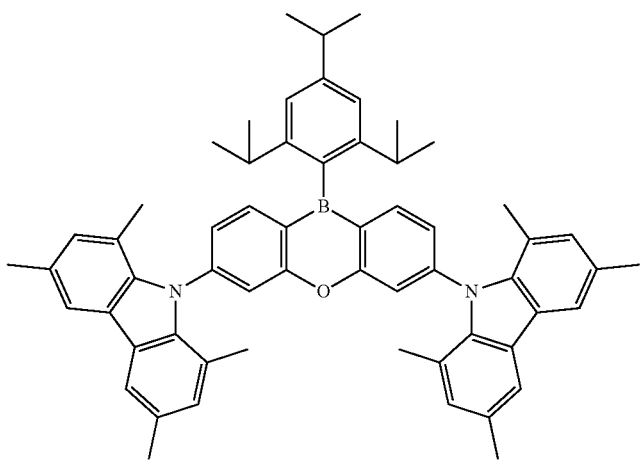
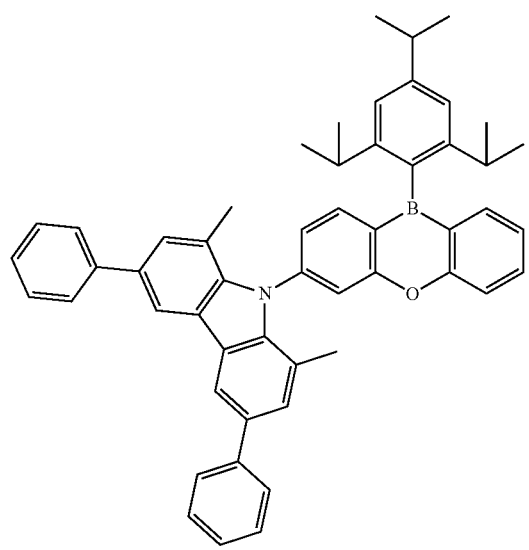
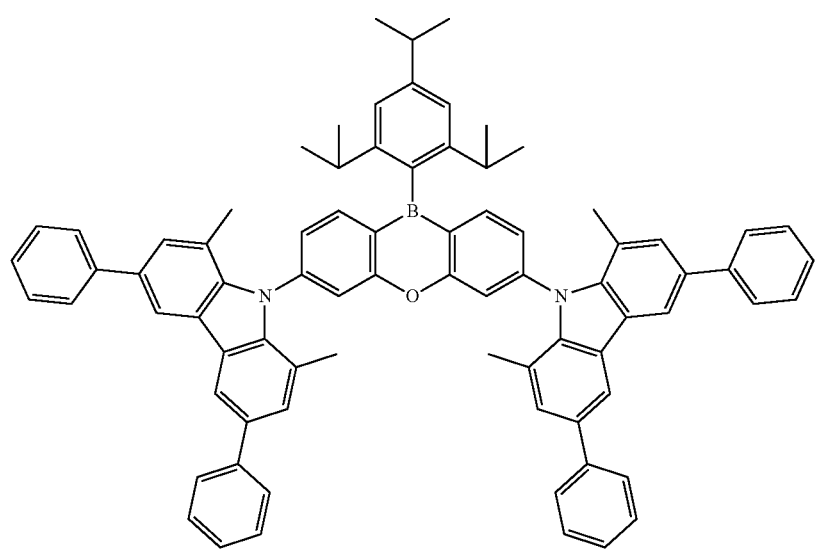

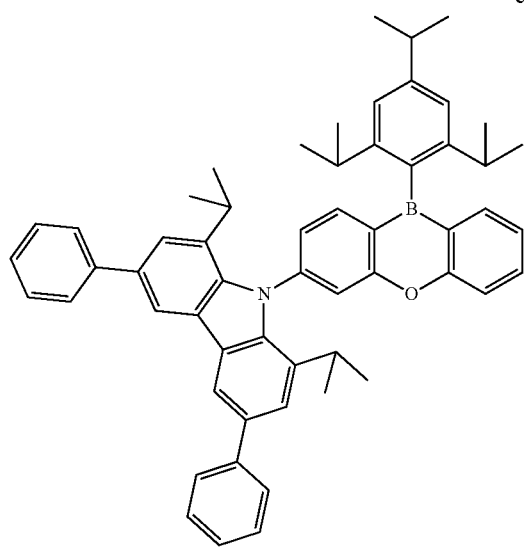
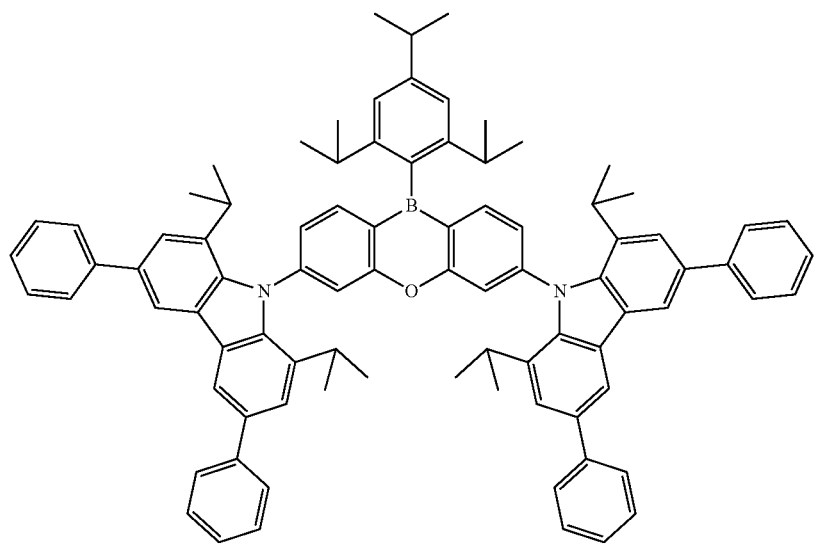
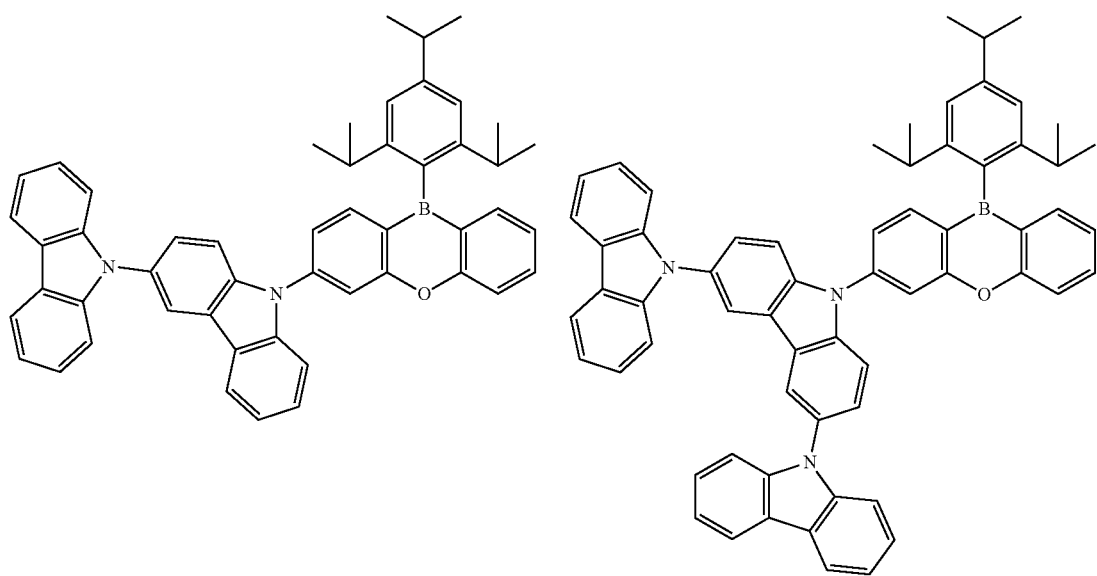

-continued
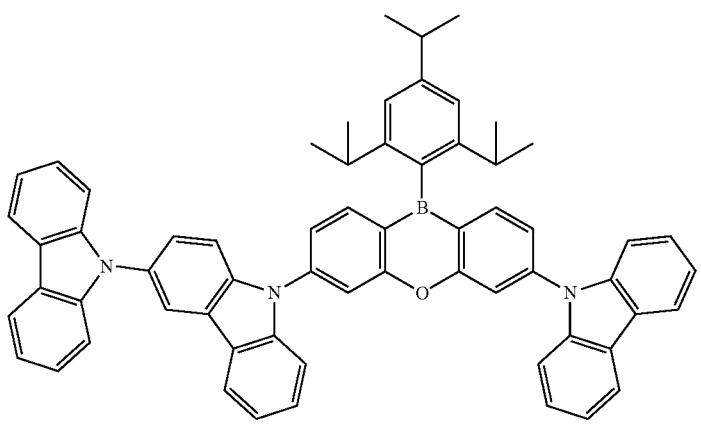
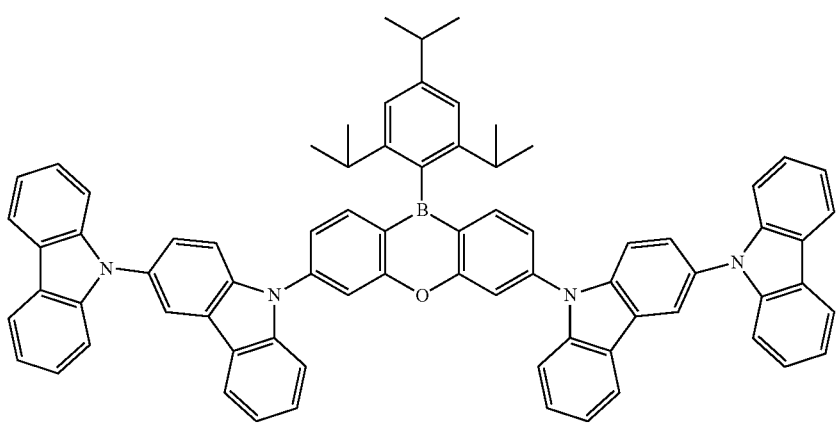
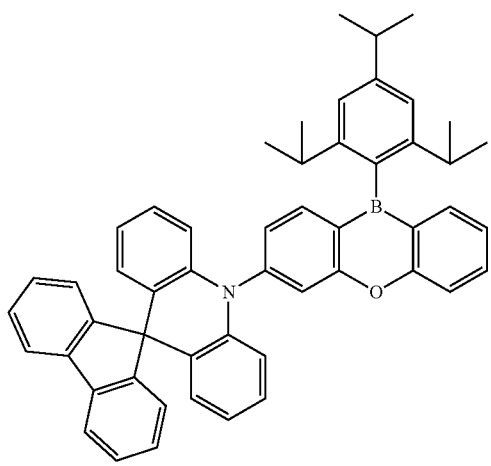

-continued
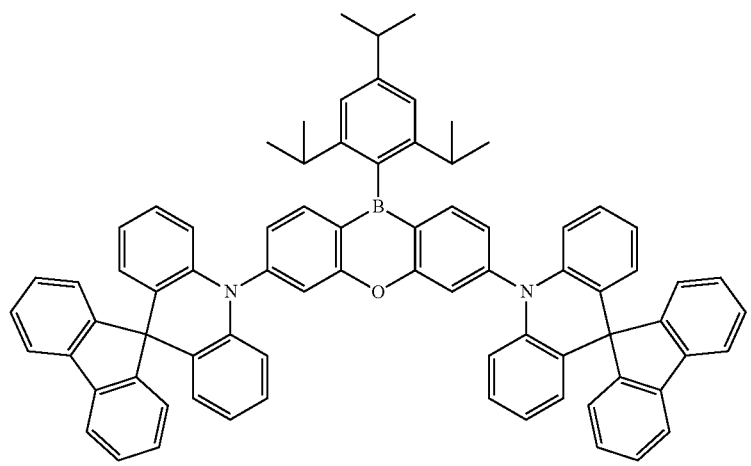
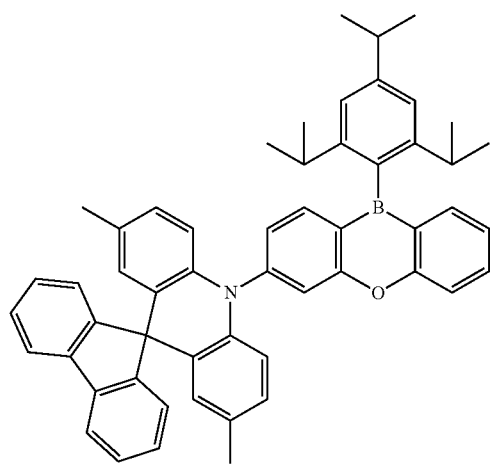
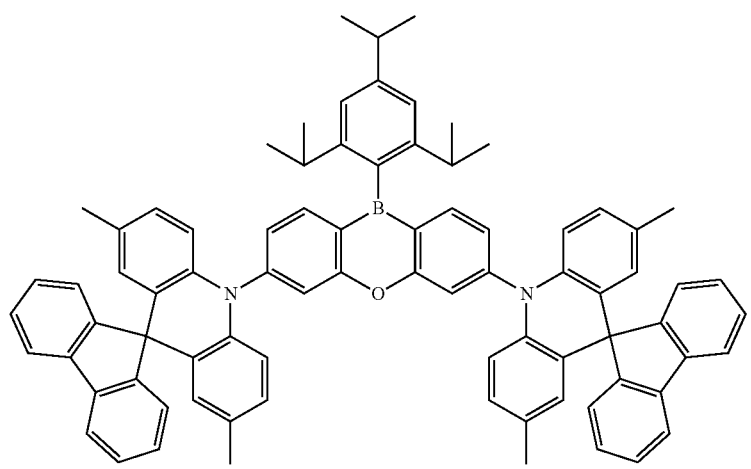

-continued
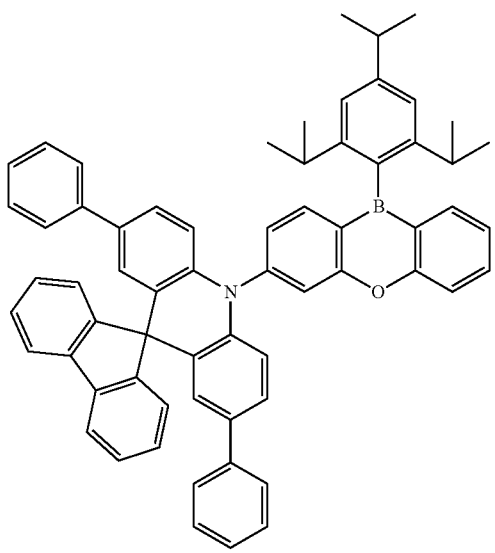
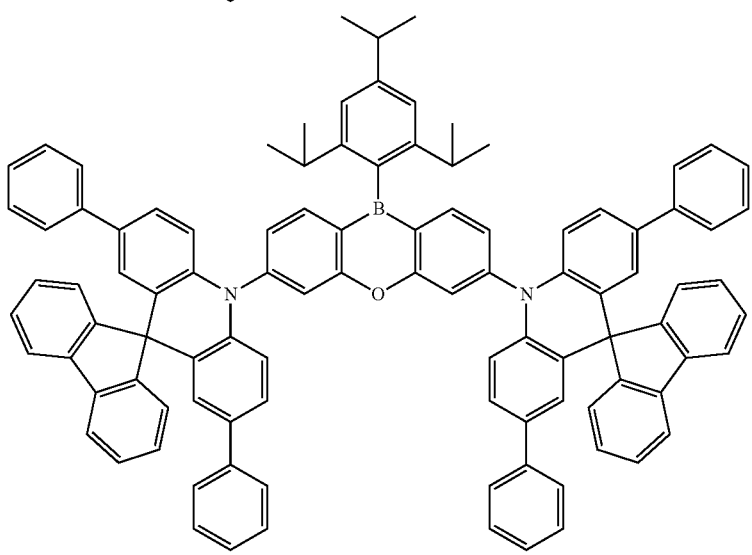
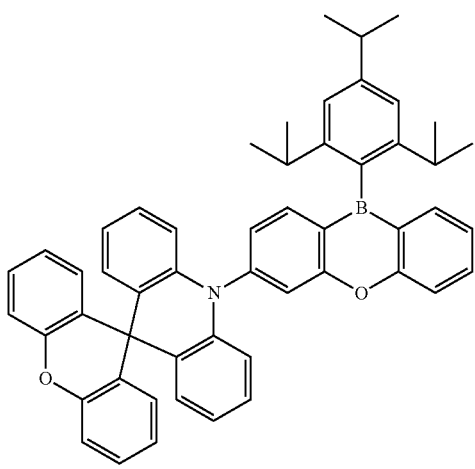

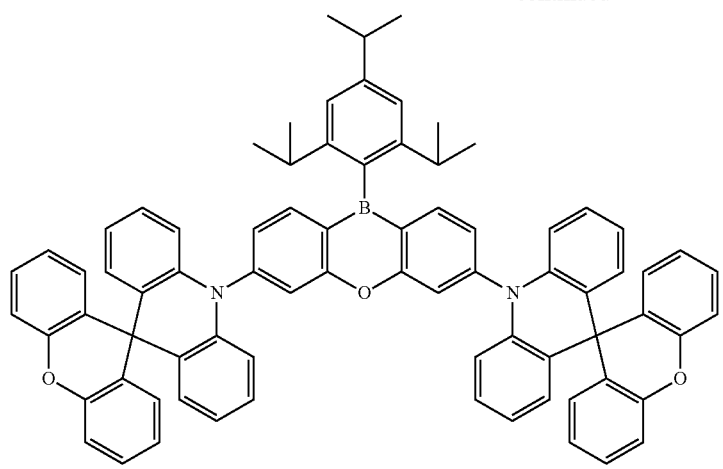
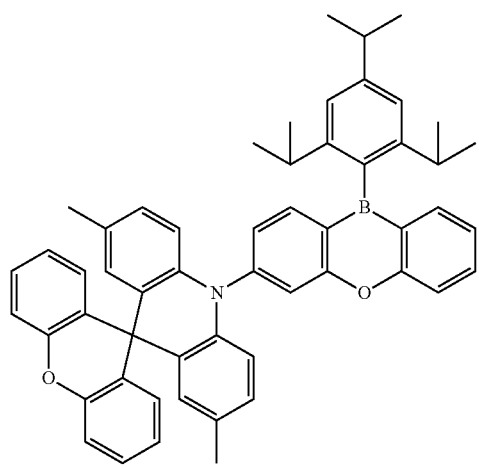
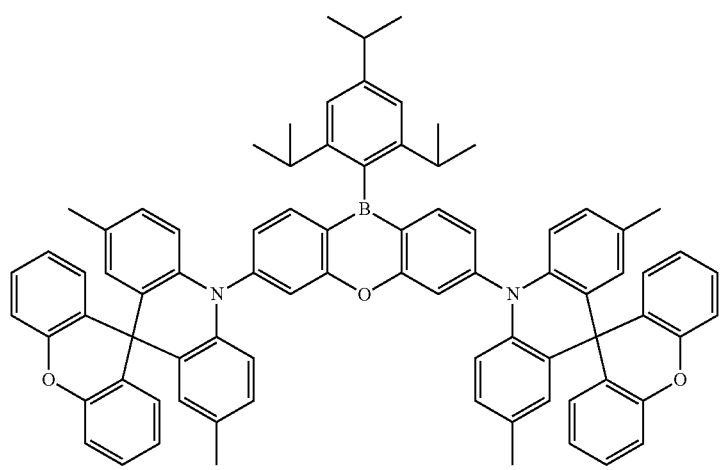

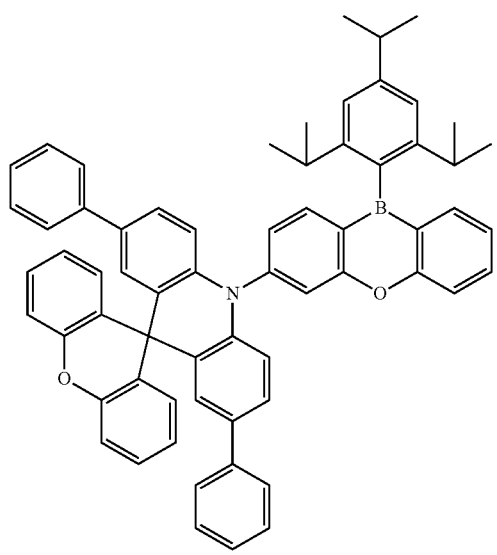
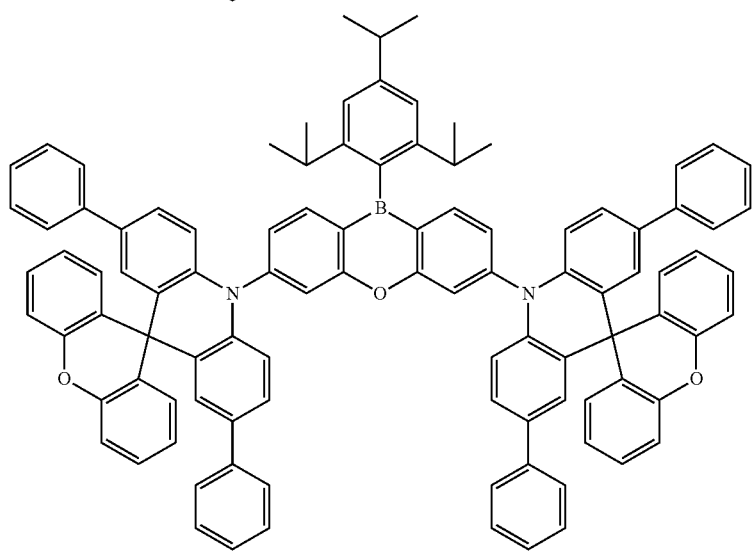
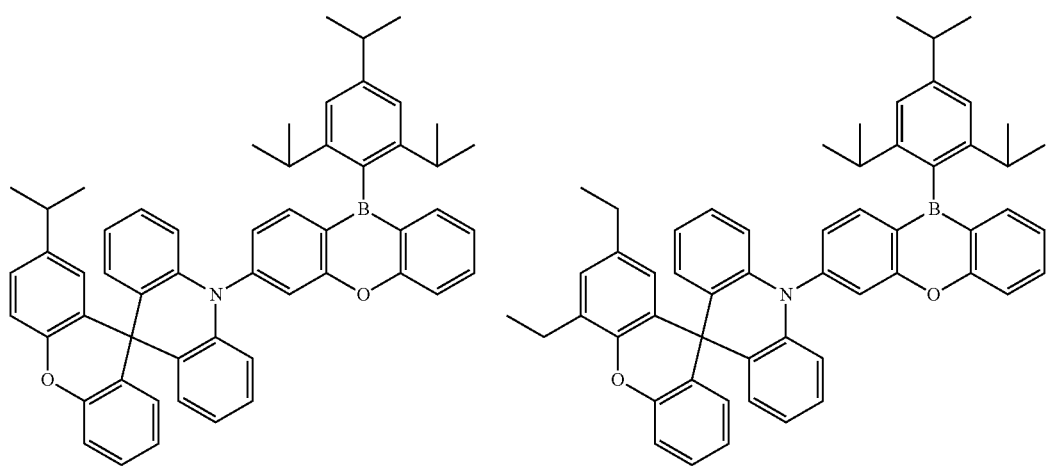

-continued
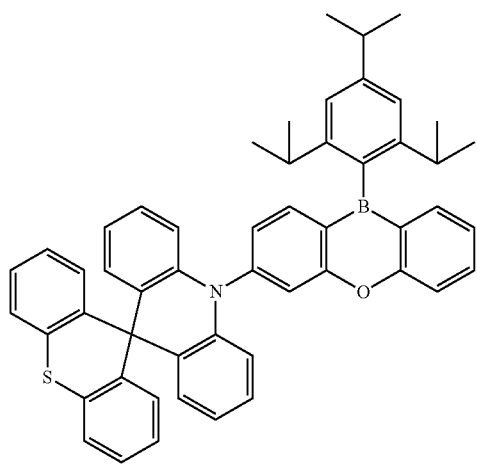
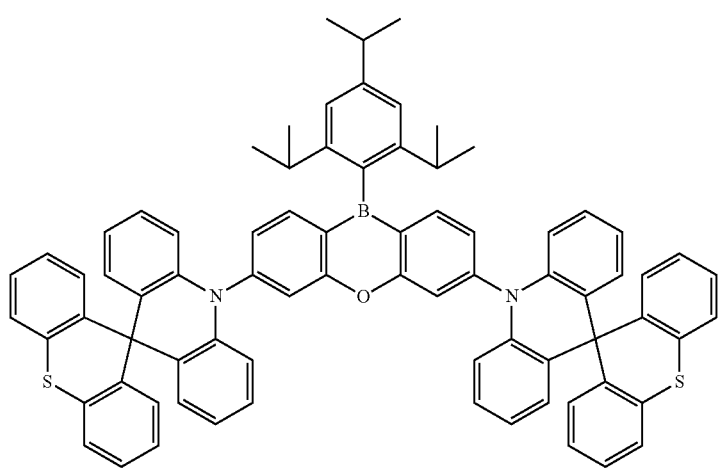
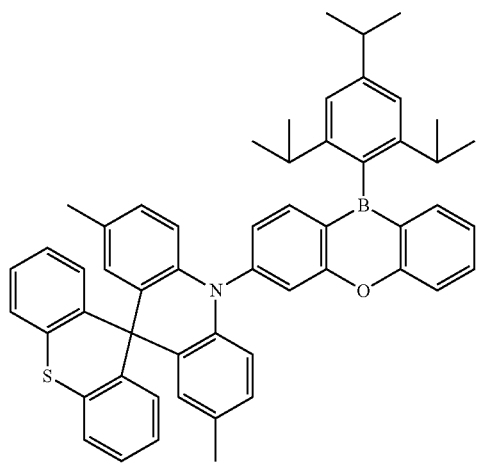

-continued
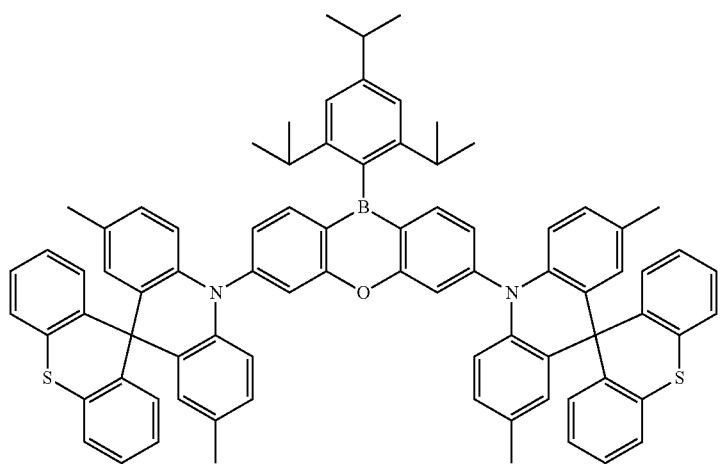
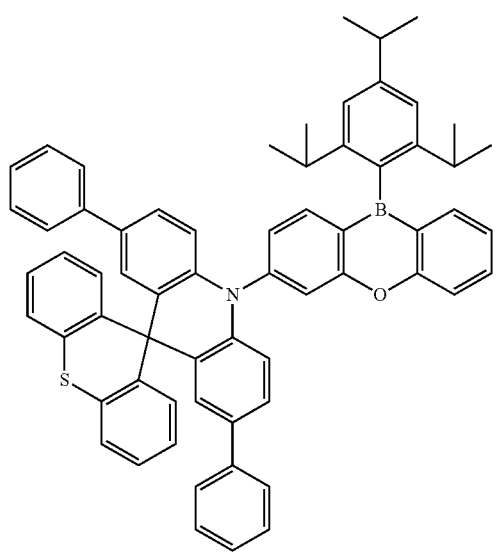
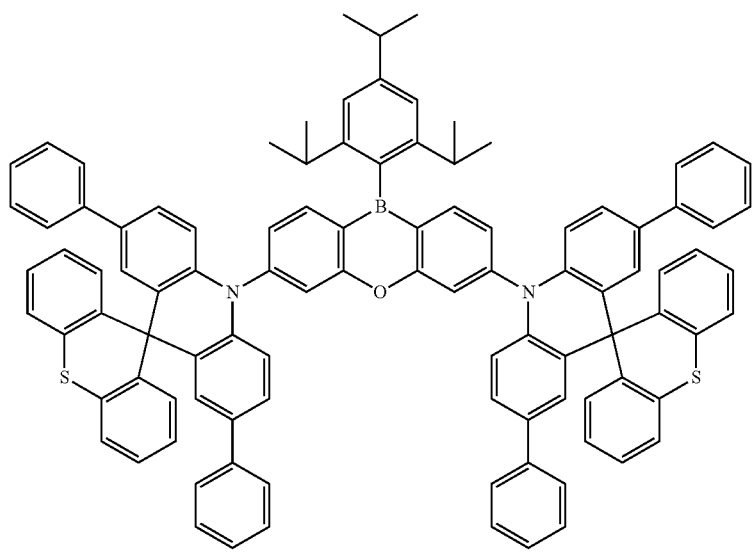

391 392
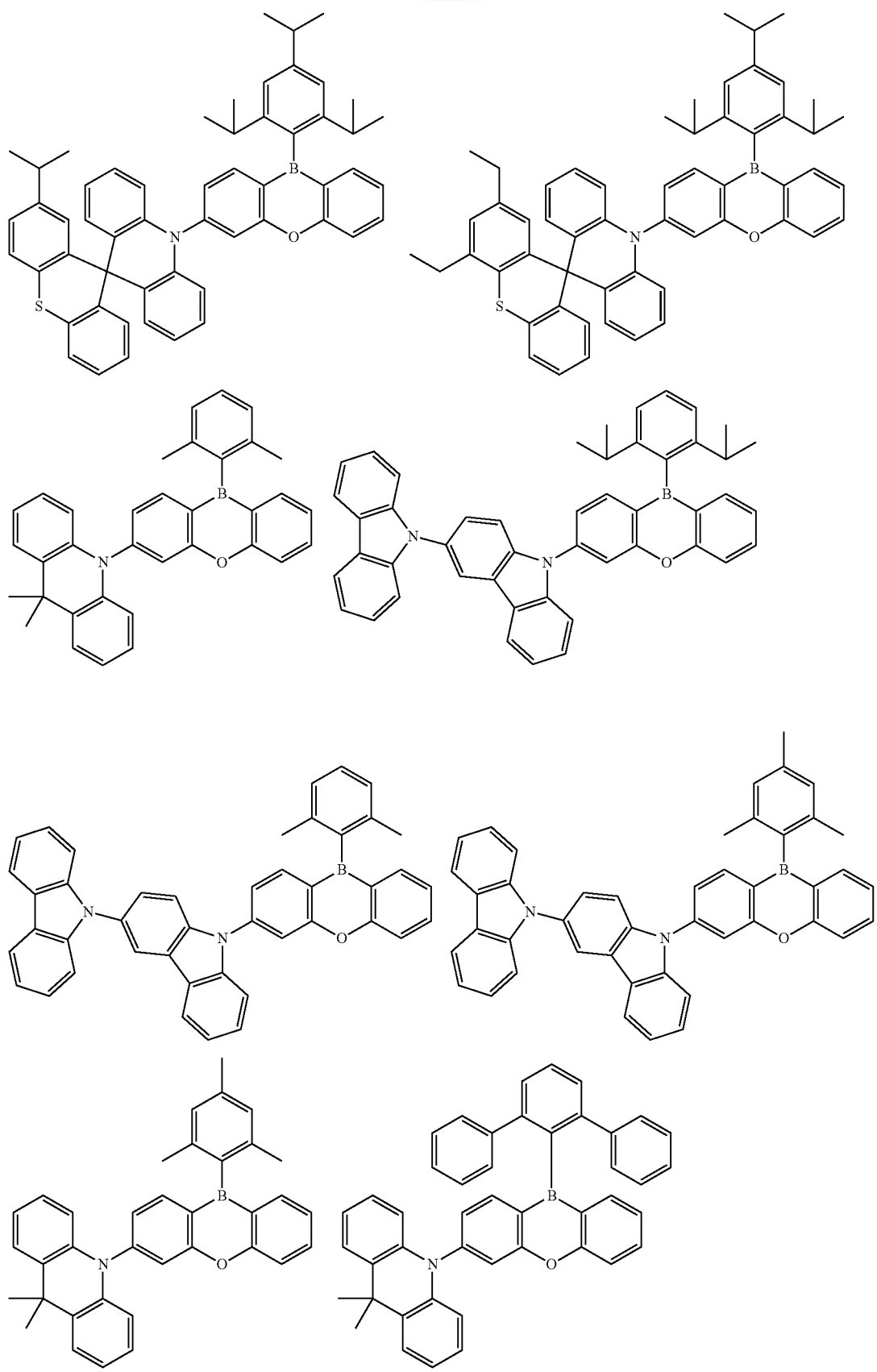
-continued 393
394
-continued
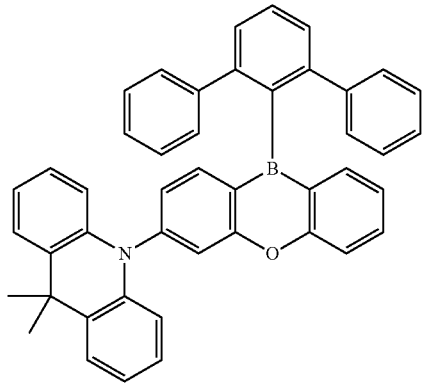
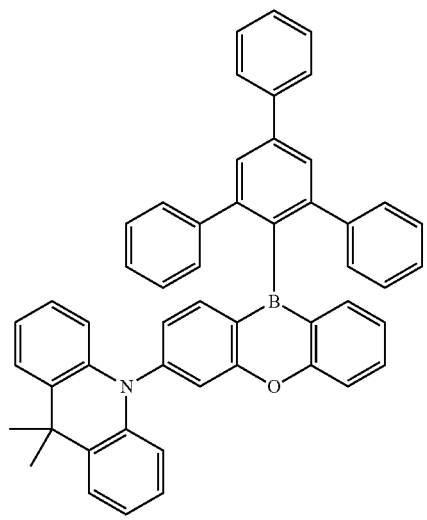
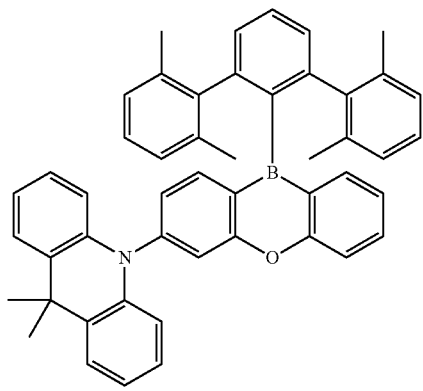
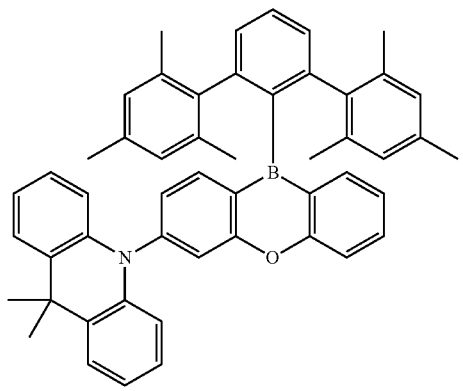
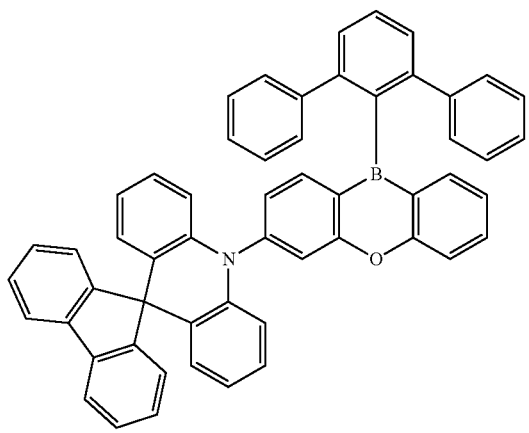
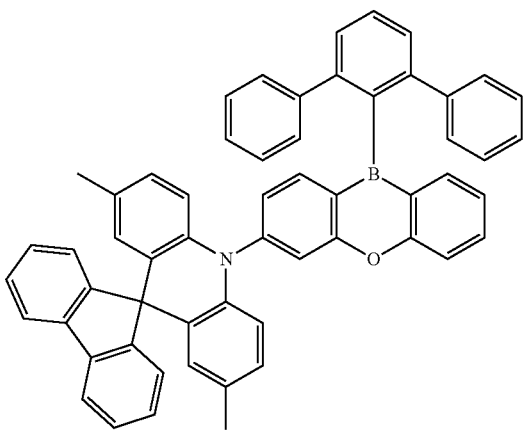

-continued
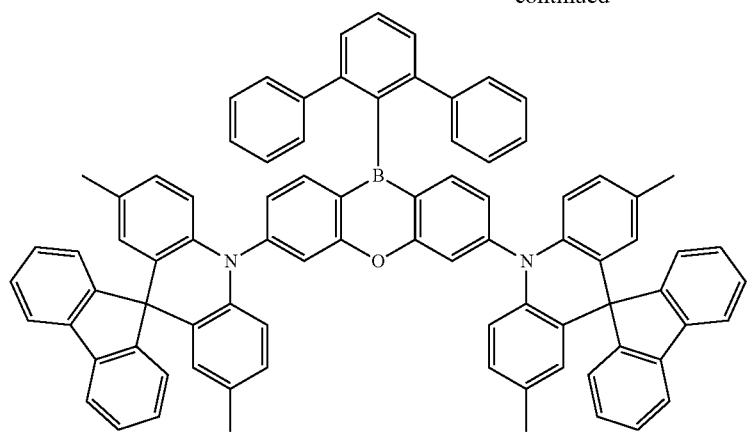
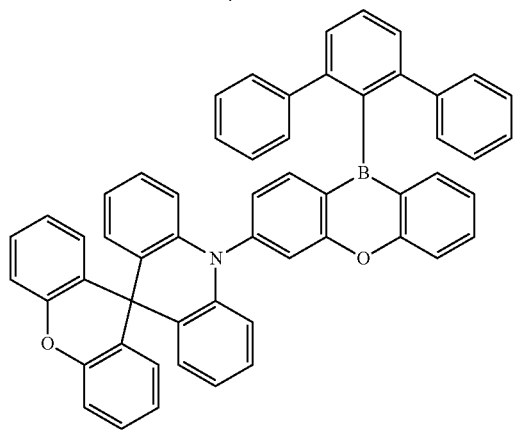
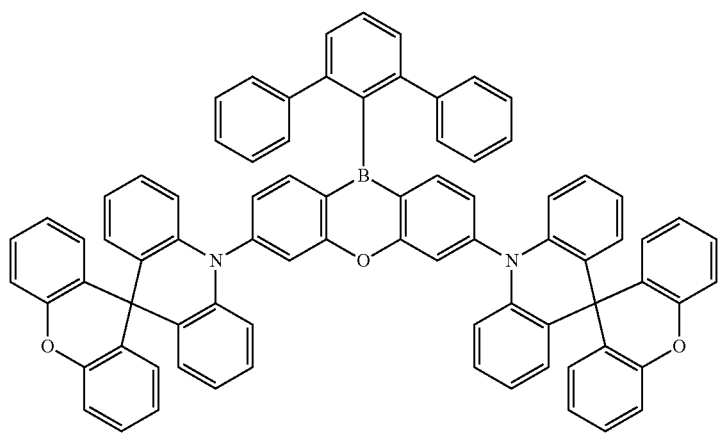
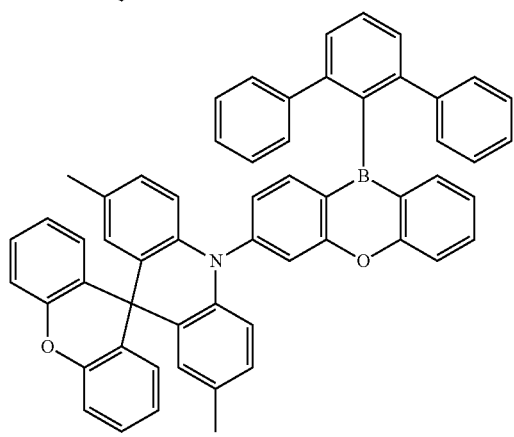

-continued
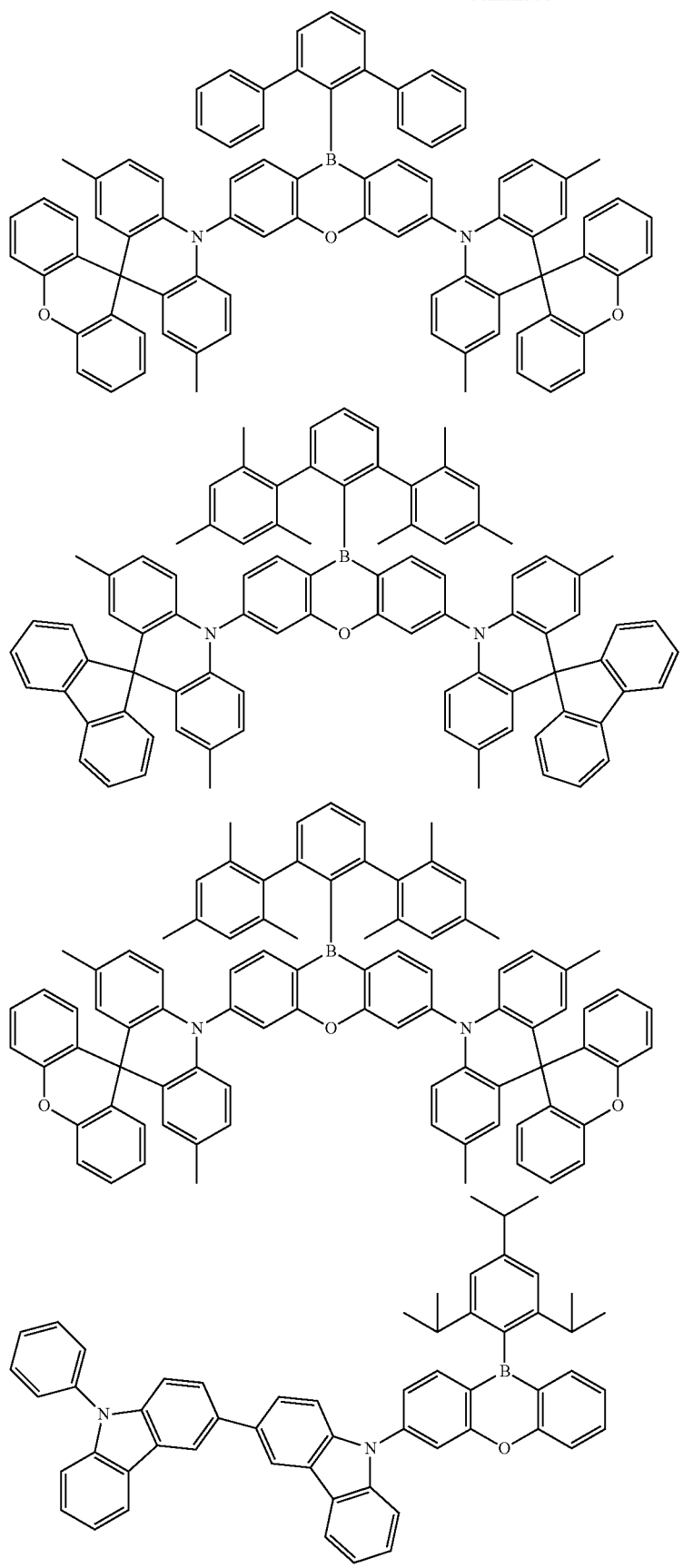

399 400
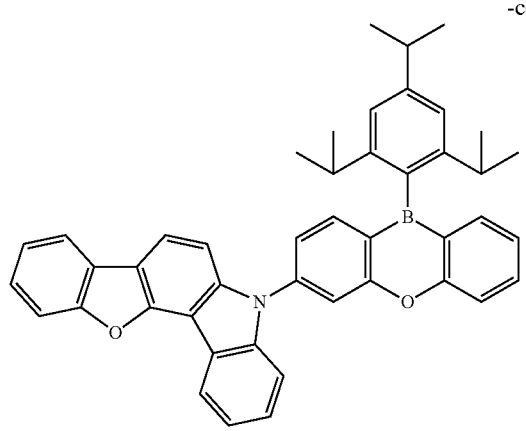 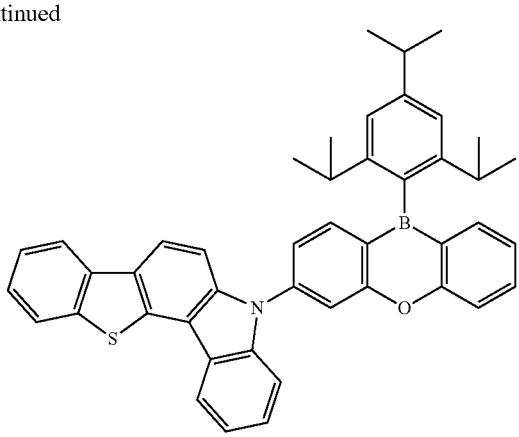
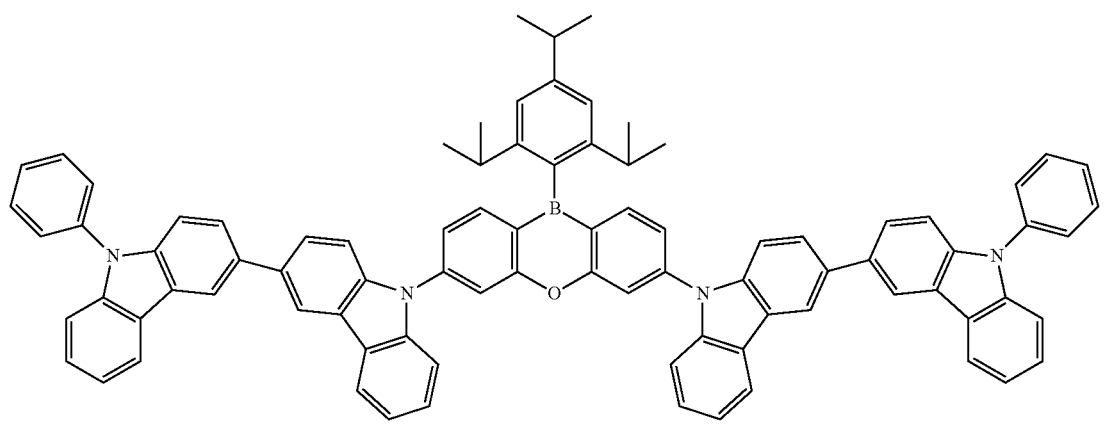
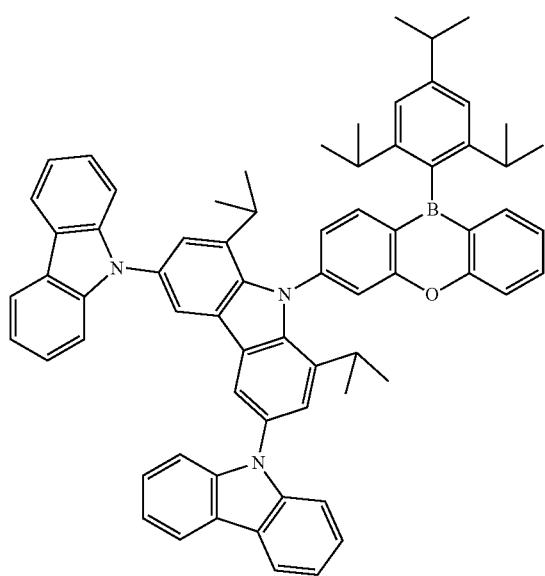

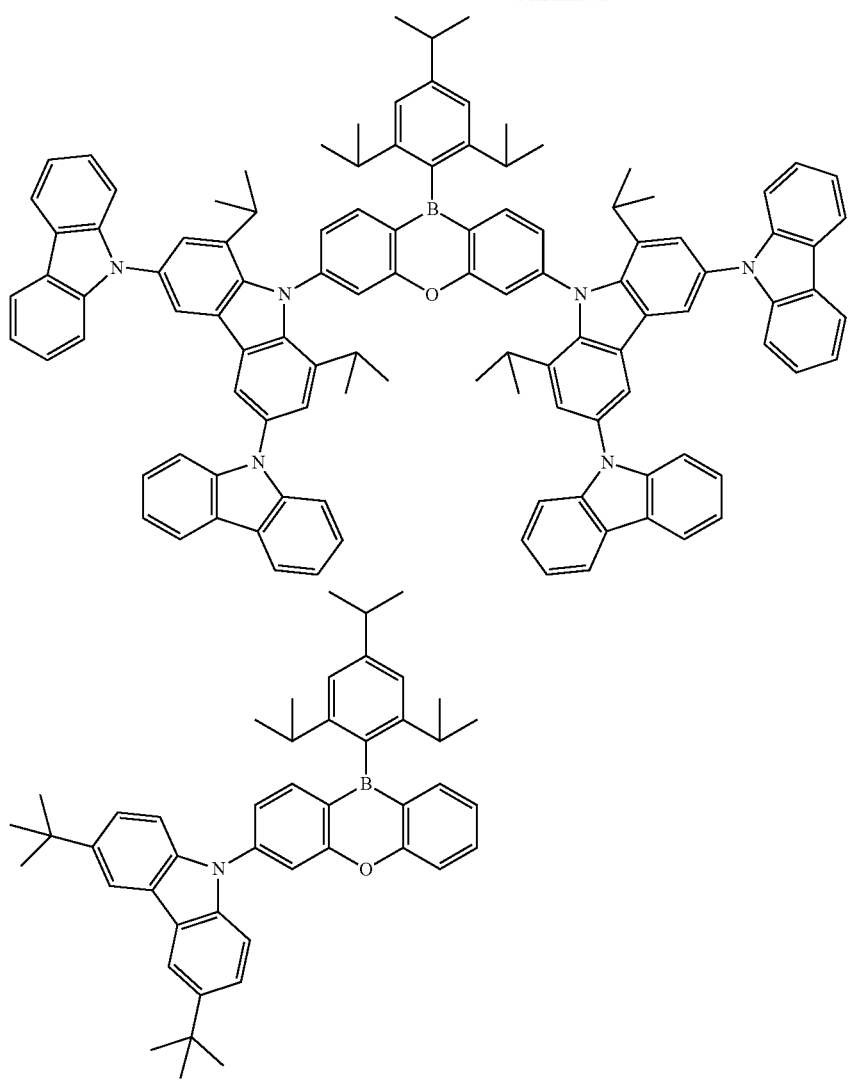
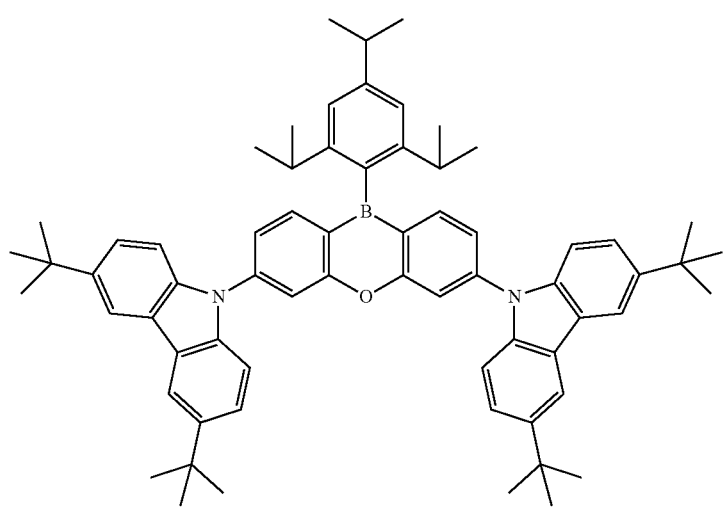

-continued
403
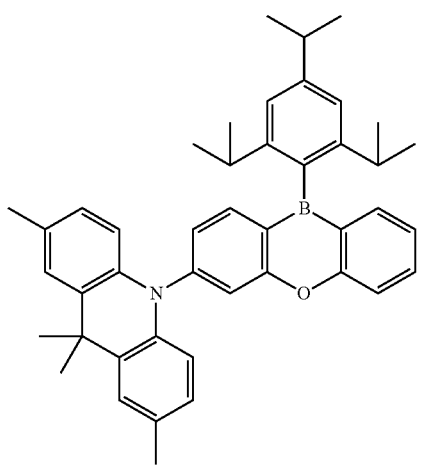
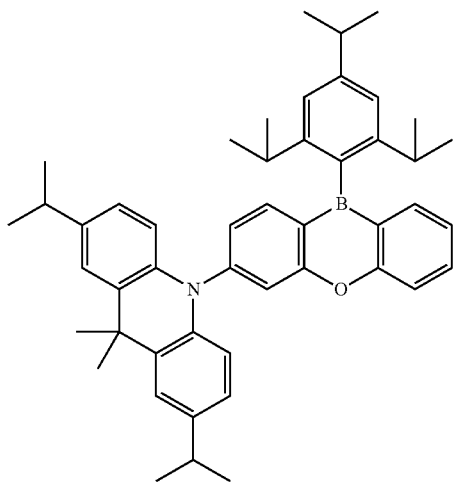
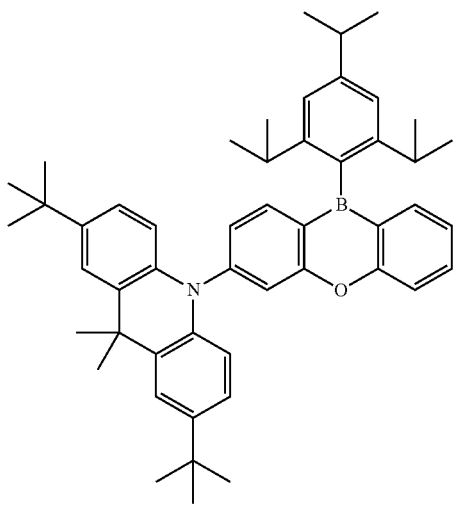
404
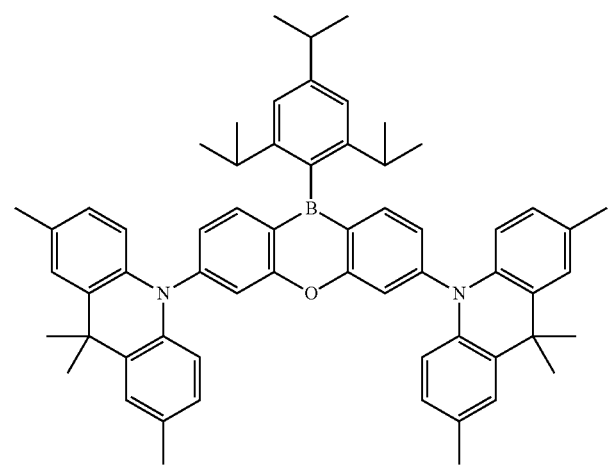
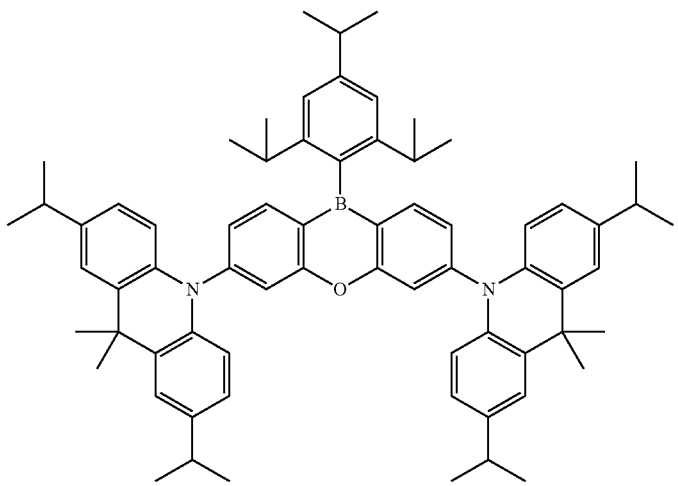
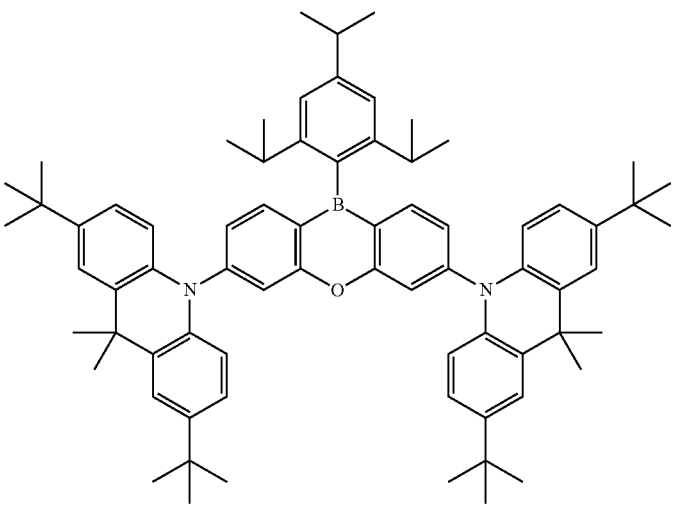

405
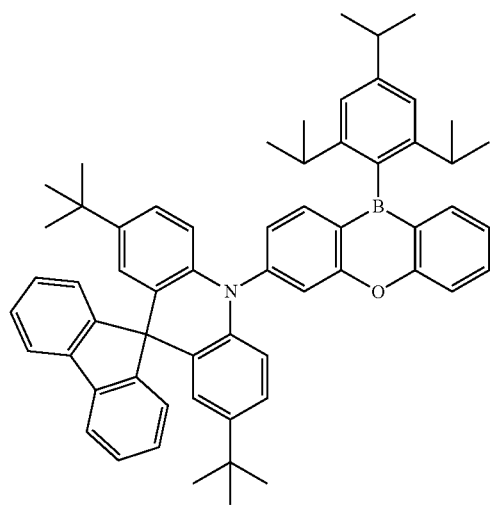
406
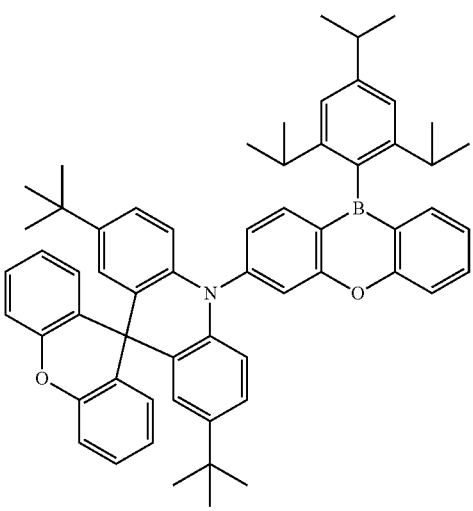
-continued
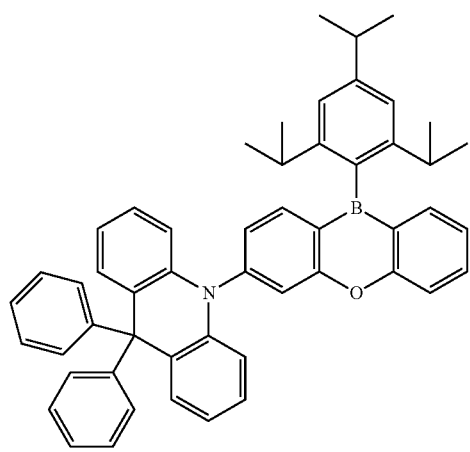
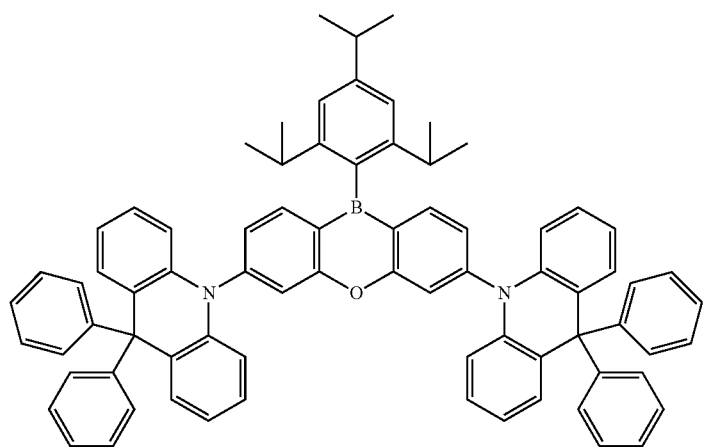

-continued
407
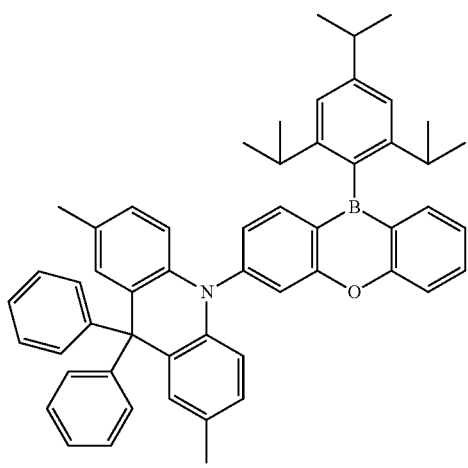
408
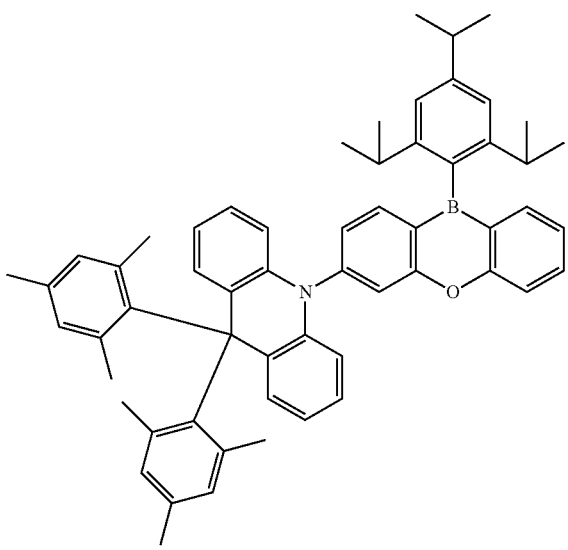
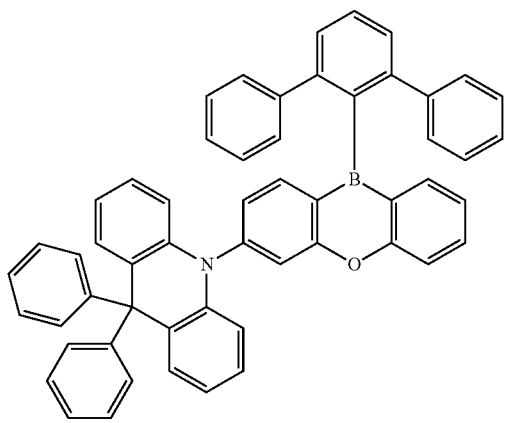
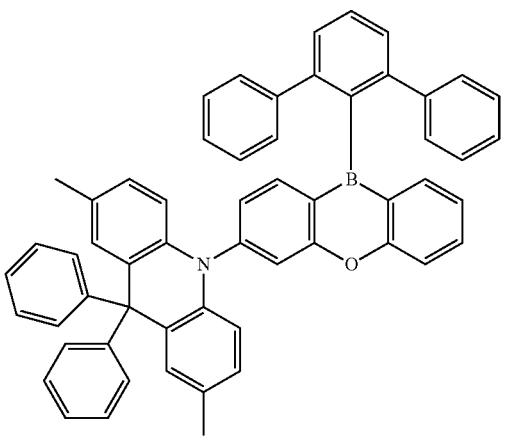
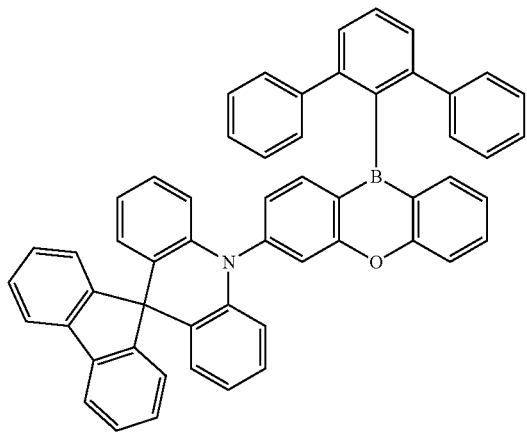
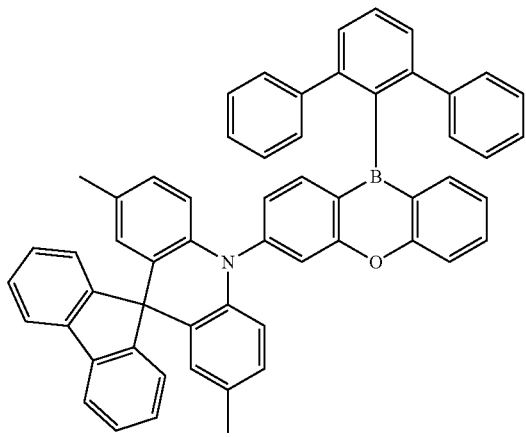

-continued
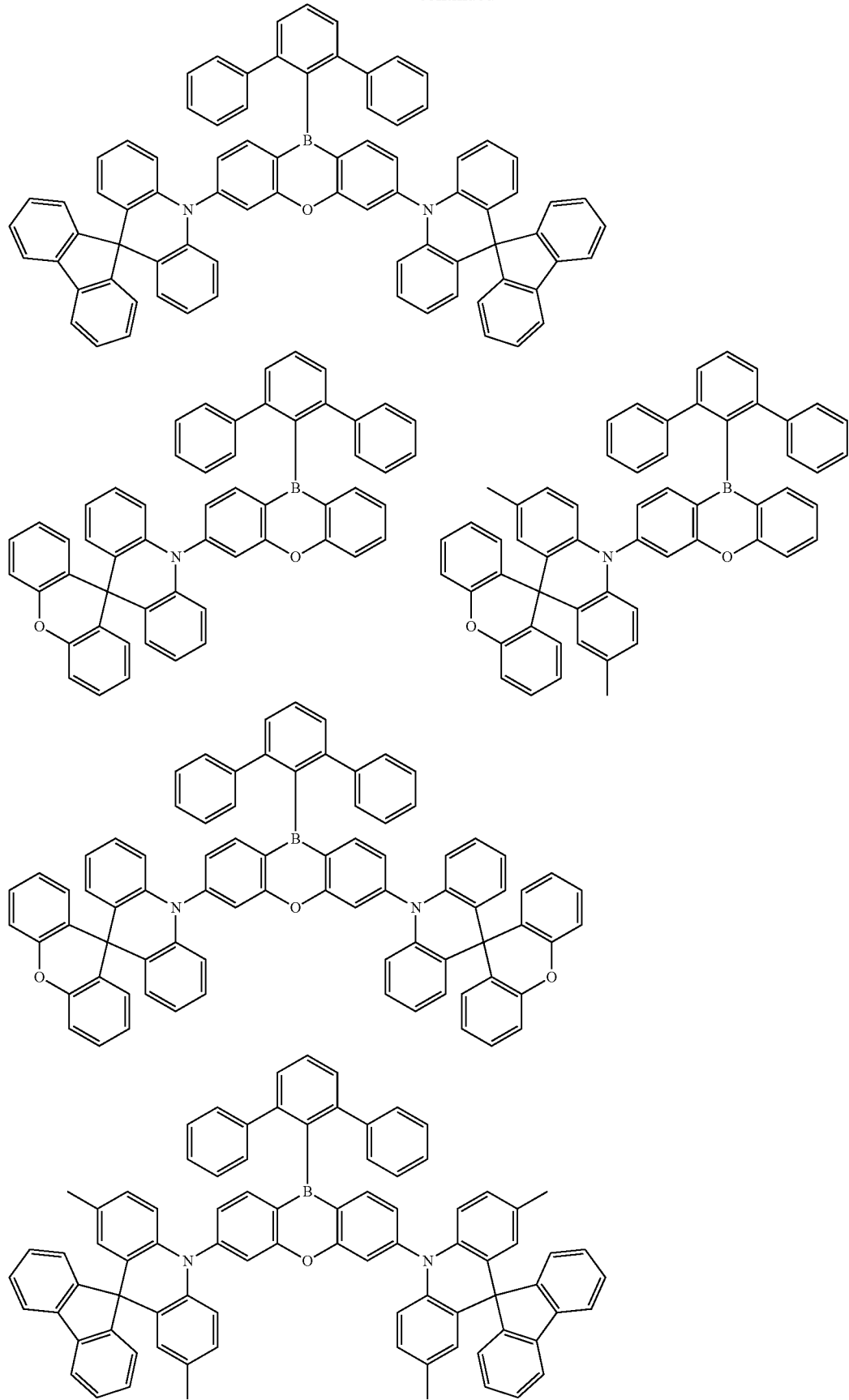

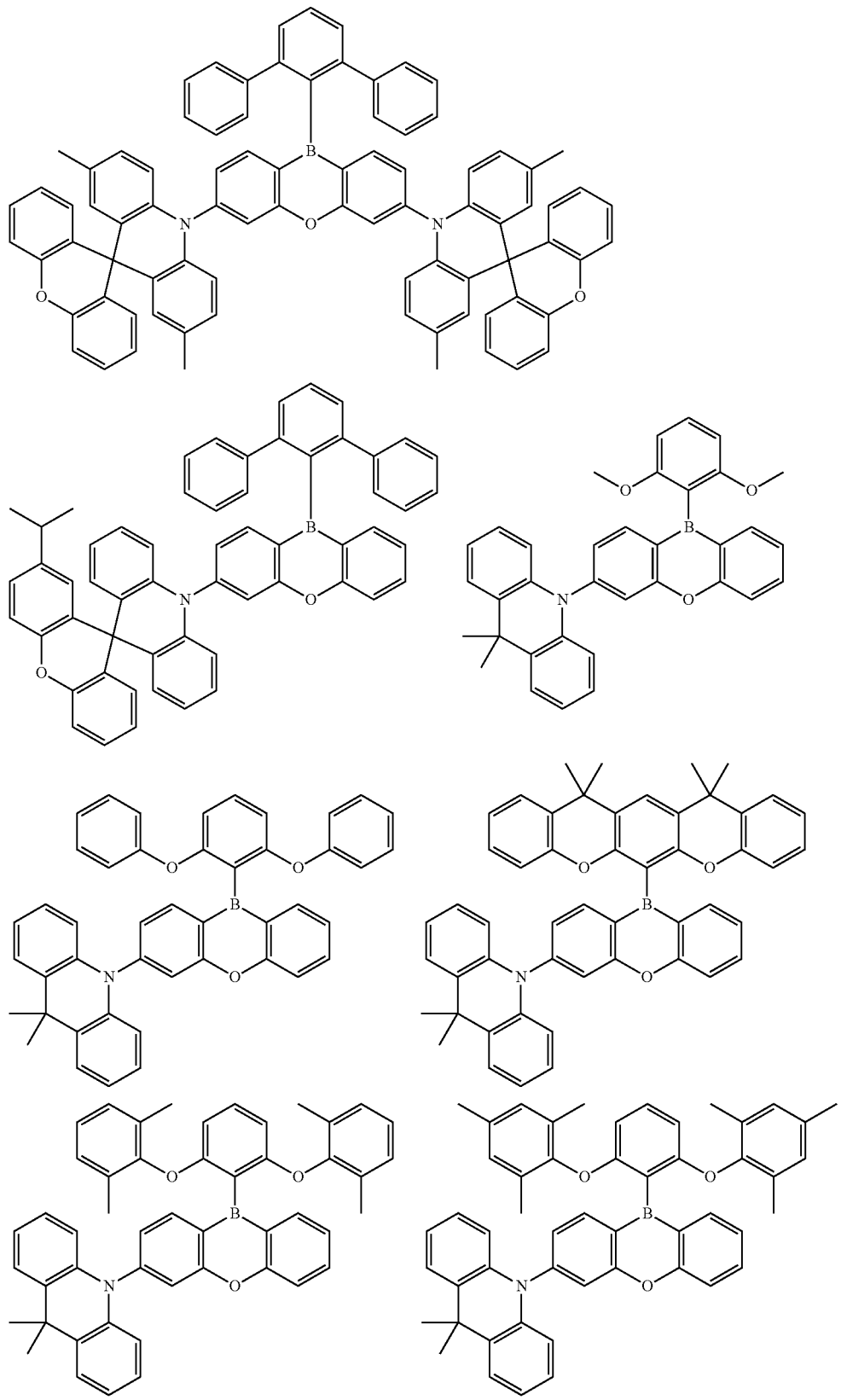

413 414
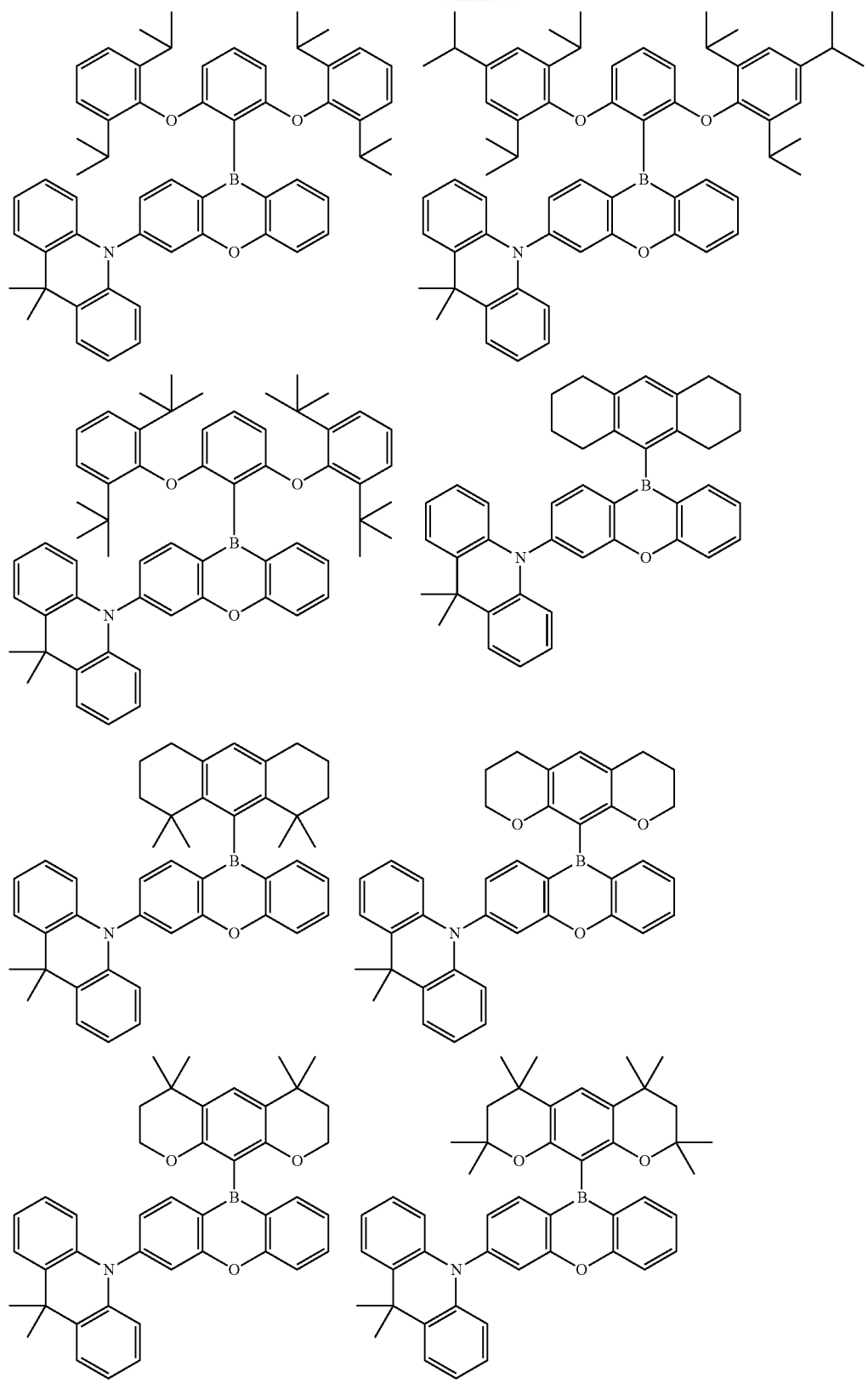
-continued 415
416
-continued
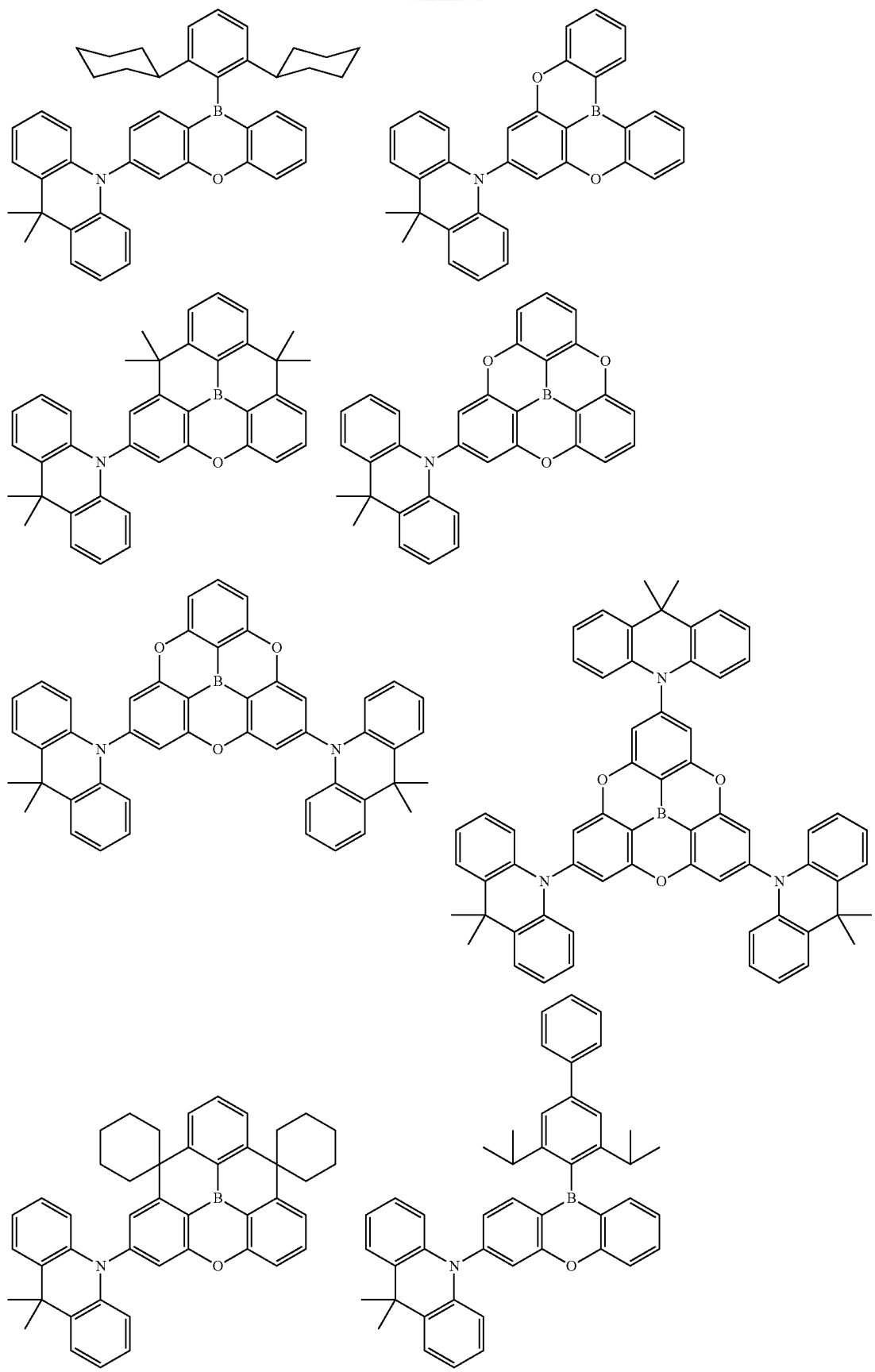

417    418
-continued
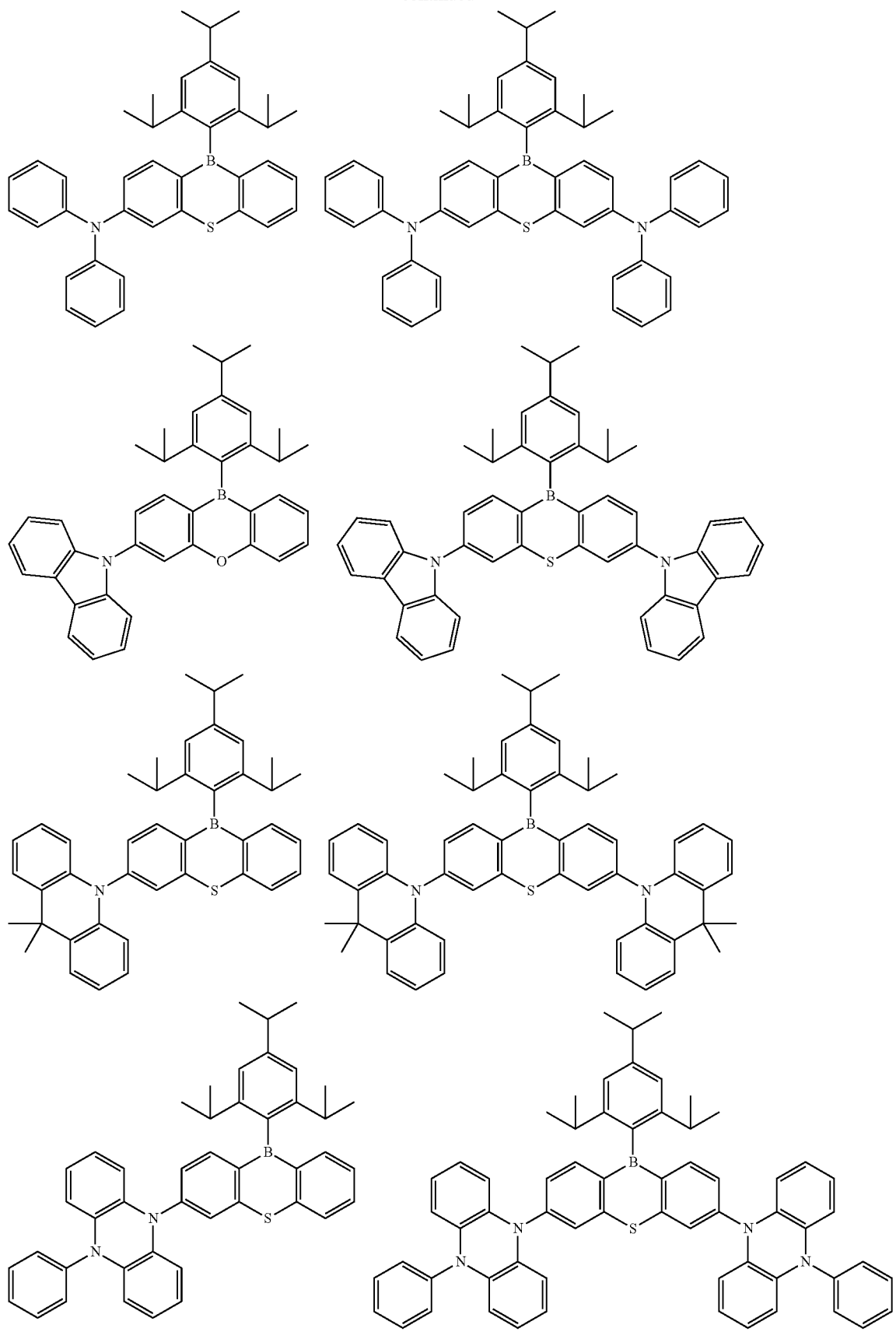

419
420
-continued
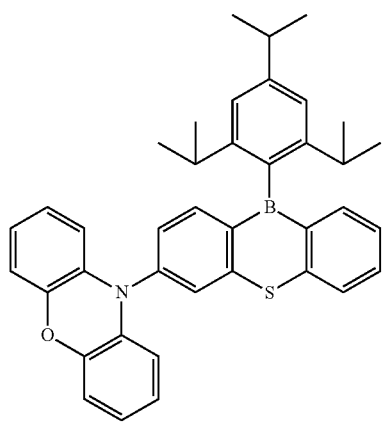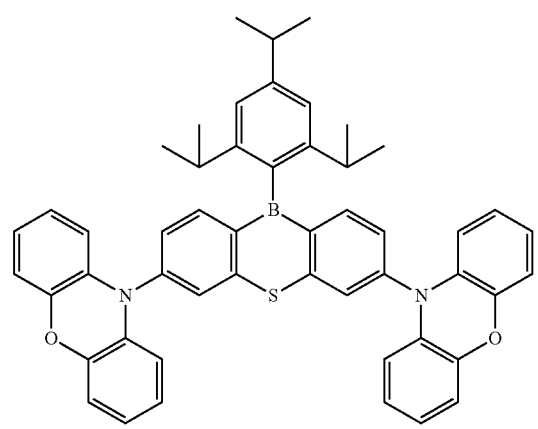
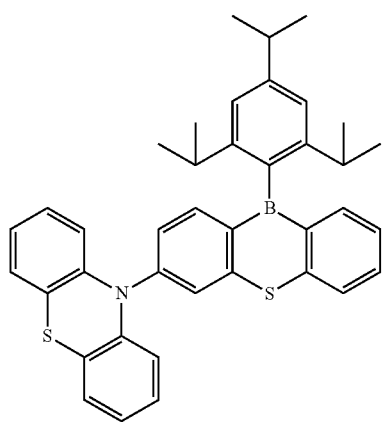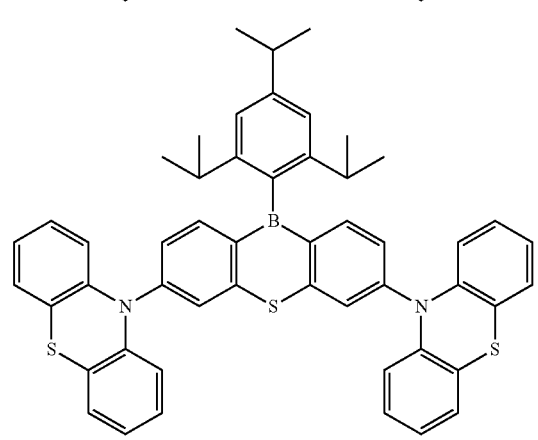
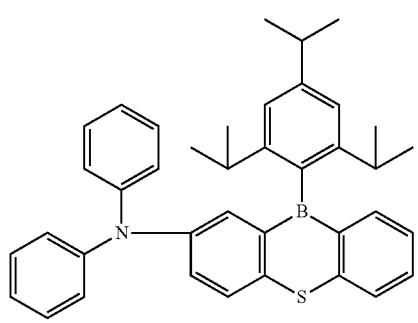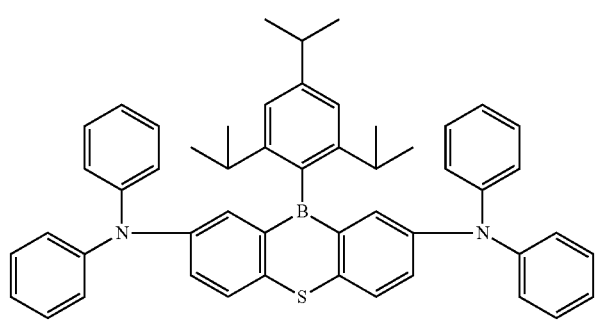
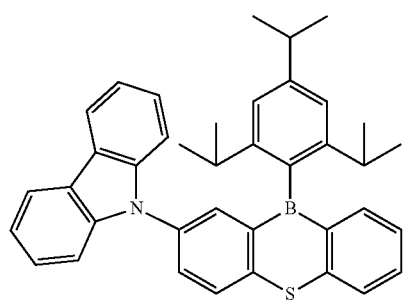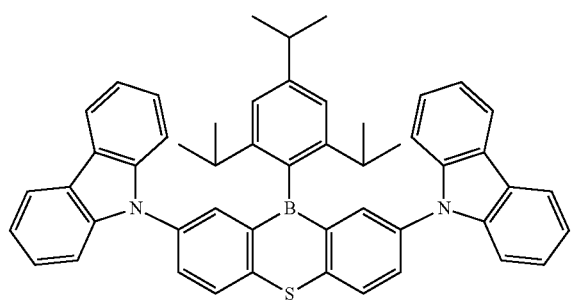

-continued
| 421 | 422 |
|---|---|
| 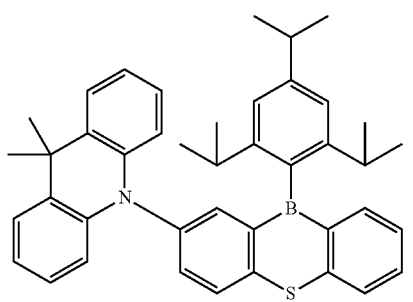 | 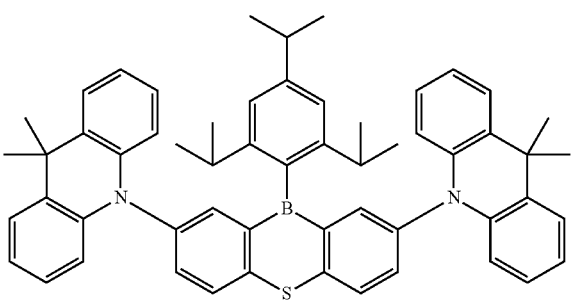 |
| 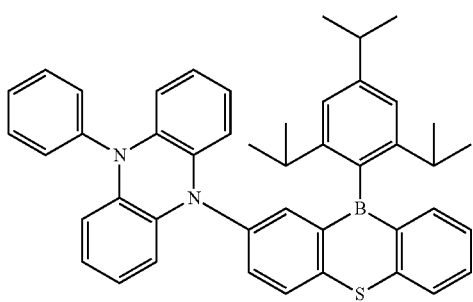 | |
| 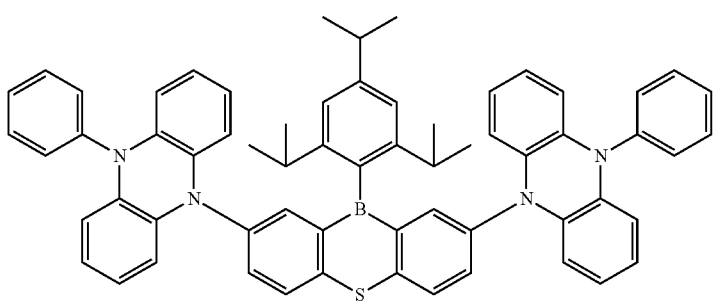 | |
| 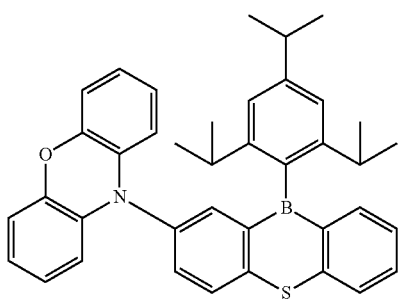 | 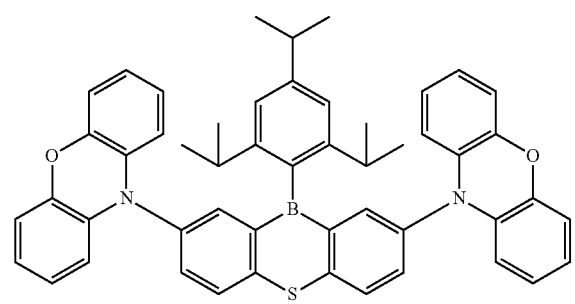 |
| 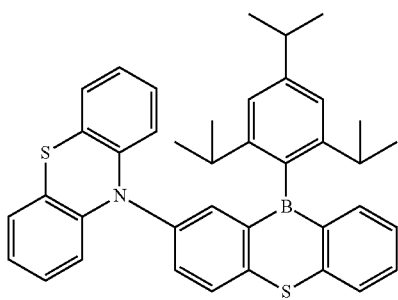 | 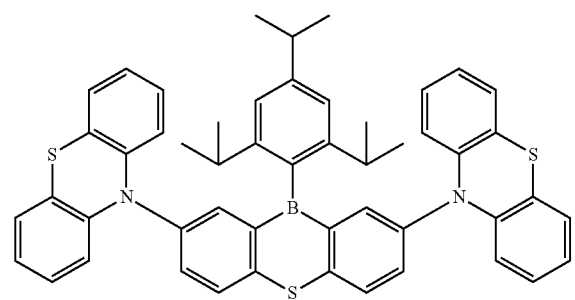 |

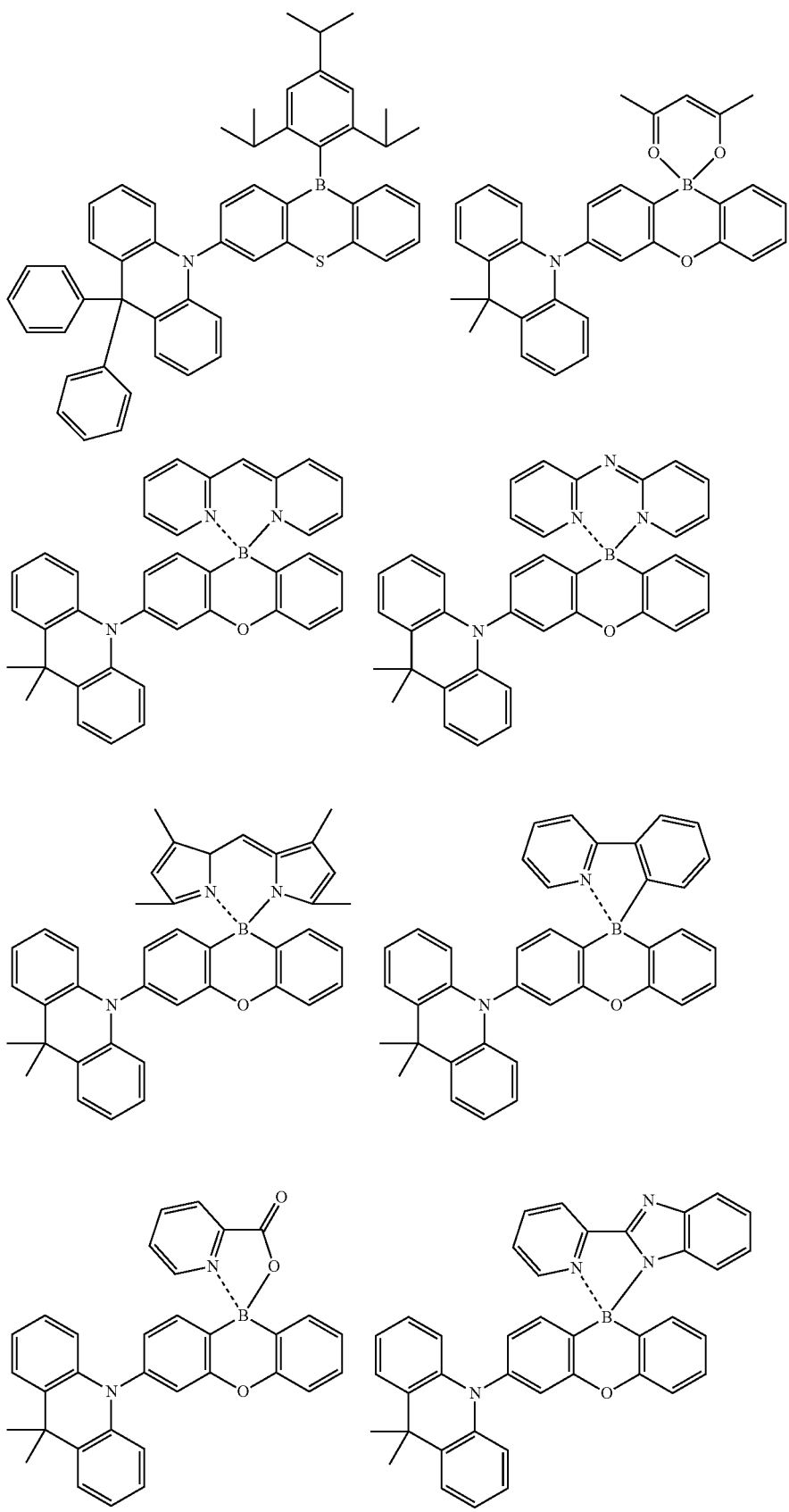

-continued
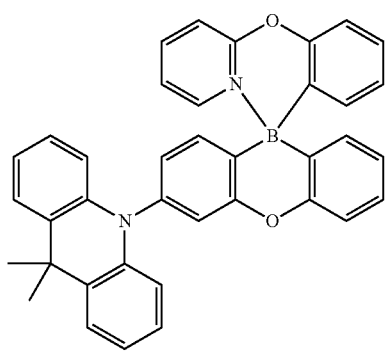
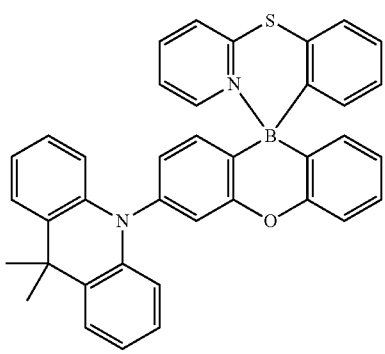
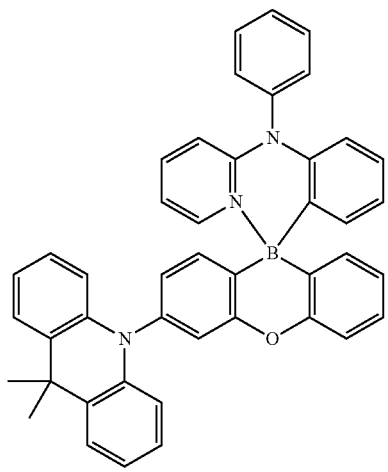
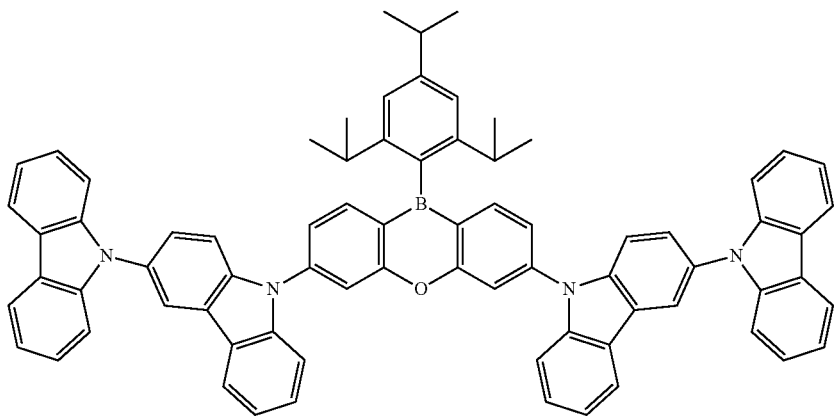
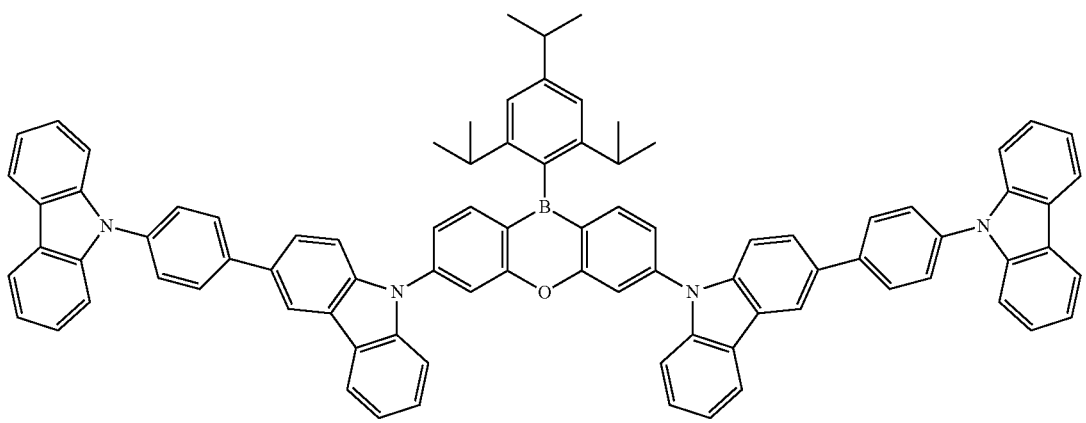

-continued
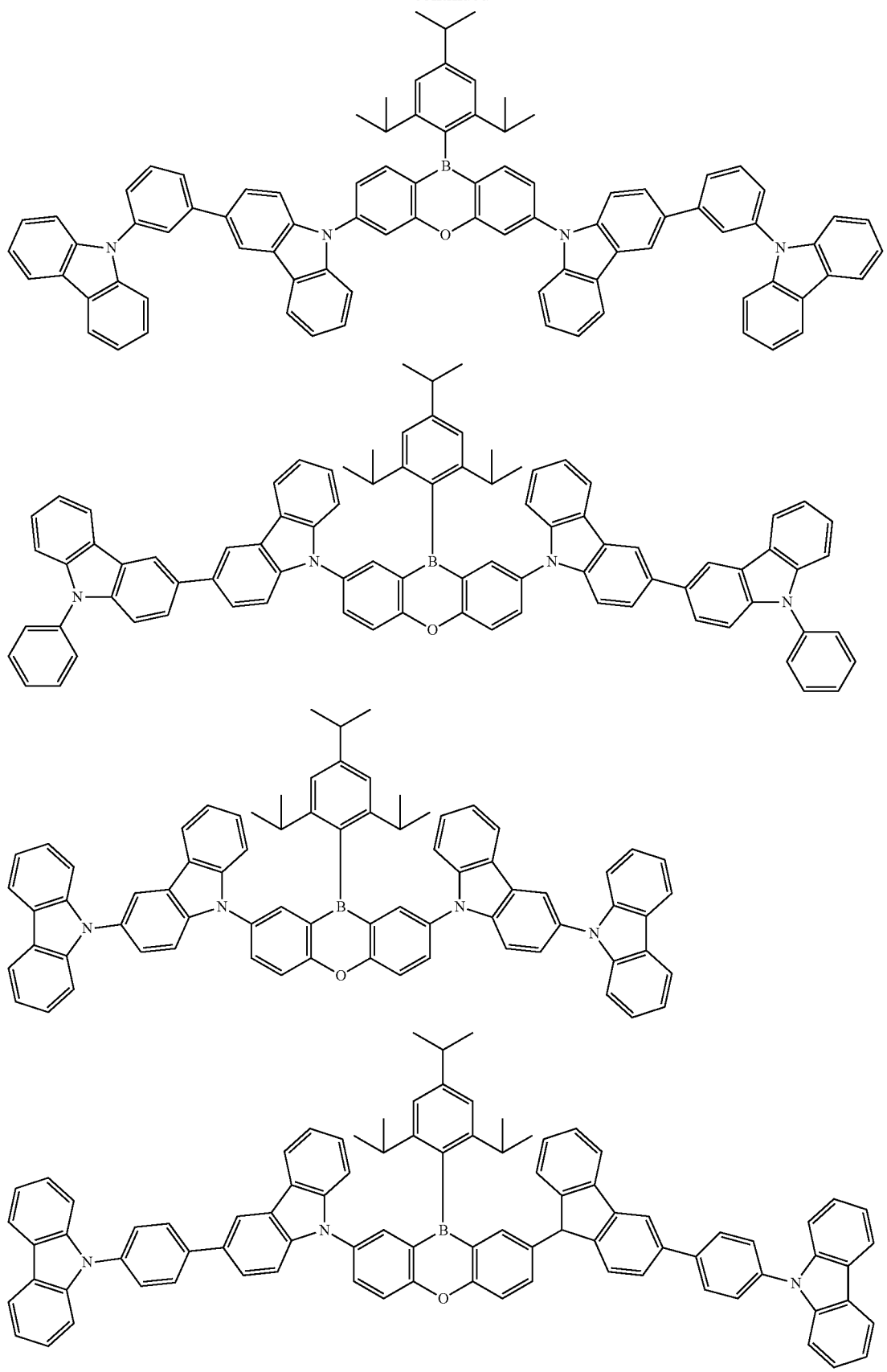

-continued

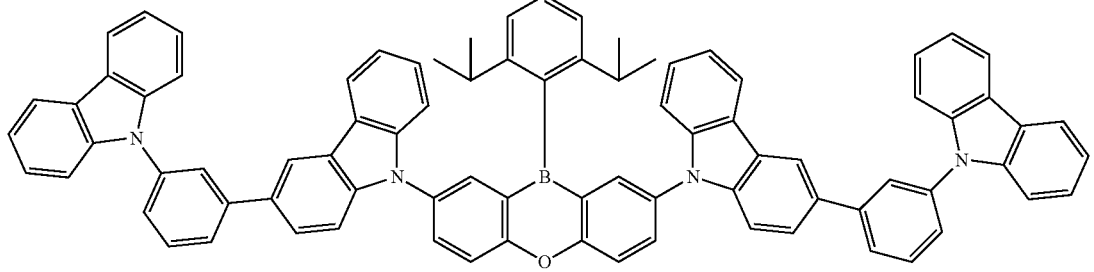

Examples of the preferred light-emitting material include the following compounds.

(1) A compound represented by the following general formula (291):

General Formula (291)

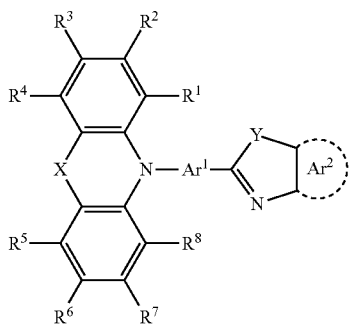

wherein in the general formula (291), X represents O, S, N—$R^{11}$, C=O, C($R^{12}$) ($R^{13}$), or Si($R^{14}$)($R^{15}$); Y represents O, S, or N—$R^{16}$; $Ar^1$ represents a substituted or unsubstituted arylene group; $Ar^2$ represents an aromatic ring or a heteroaromatic ring; and $R^1$ to $R^8$ and $R^{11}$ to $R^{16}$ each independently represent a hydrogen atom or a substituent, in which $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(2) The compound according to the item (1), wherein the compound represented by the general formula (291) is a compound represented by the following general formula (292):

General Formula (292)

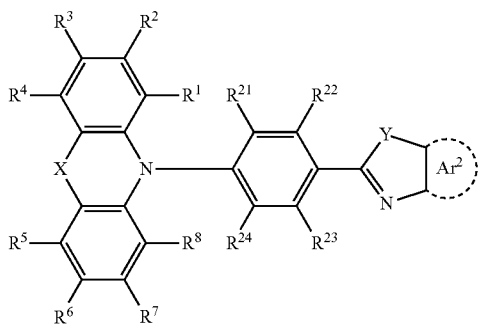

wherein in the general formula (292), X represents O, S, N—$R^{11}$, C=O, C($R^{12}$) ($R^{13}$), or Si($R^{14}$) ($R^{15}$); Y represents O, S, or N—$R^{16}$; $Ar^2$ represents an aromatic ring or a heteroaromatic ring; and $R^1$ to $R^8$, $R^{11}$ to $R^{16}$, and $R^{21}$ to $R^{24}$ each independently represent a hydrogen atom or a substituent, in which $R^1$ and $R^2$, $R^2$ and $R^3$, $R^3$ and $R^4$, $R^5$ and $R^6$, $R^6$ and $R^7$, $R^7$ and $R^8$, $R^{21}$ and $R^{22}$, and $R^{23}$ and $R^{24}$ each may be bonded to each other to form a cyclic structure.

(3) The compound according to the item (1), wherein the compound represented by the general formula (291) is a compound represented by the following general formula (293):

General Formula (293)

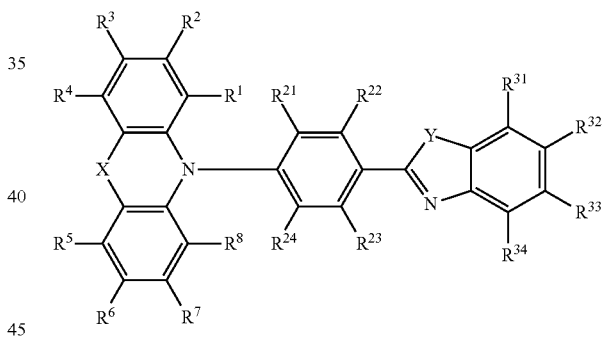

wherein in the general formula (293), X represents O, S, N—$R^{11}$, C=O, C($R^{12}$) ($R^{13}$), or Si($R^{14}$) ($R^{15}$); Y represents O, S, or N—$R^{16}$; and $R^1$ to $R^8$, $R^{11}$ to $R^{16}$, $R^{21}$ to $R^{24}$, and $R^{31}$ to $R^{34}$ each independently represent a hydrogen atom or a substituent, in which $R^1$ and $R^2$, $R^2$ and $R^3$, $R^3$ and $R^4$, $R^5$ and $R^6$, $R^6$ and $R^7$, $R^7$ and $R^8$, $R^{21}$ and $R^{22}$, $R^{23}$ and $R^{24}$, $R^{31}$ and $R^{32}$, $R^{32}$ and $R^{33}$, and $R^{33}$ and $R^{34}$ each may be bonded to each other to form a cyclic structure.

(4) The compound according to any one of the items (1) to (3), wherein X represents O or S.

(5) The compound according to any one of the items (1) to (4), wherein Y represents O, S, or N—$R^{16}$, and $R^{16}$ represents a substituted or unsubstituted aryl group.

(6) The compound according to any one of the items (1) to (5), wherein $R^1$ to $R^8$ each independently represent a hydrogen atom, a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted diarylamino group having from 12 to 40 carbon atoms, a substituted or unsubstituted aryl group having from 6 to 15 carbon atoms, a substituted or unsubstituted heteroaryl group having from 3 to 12 carbon atoms.
Examples of the compound include the following compounds.
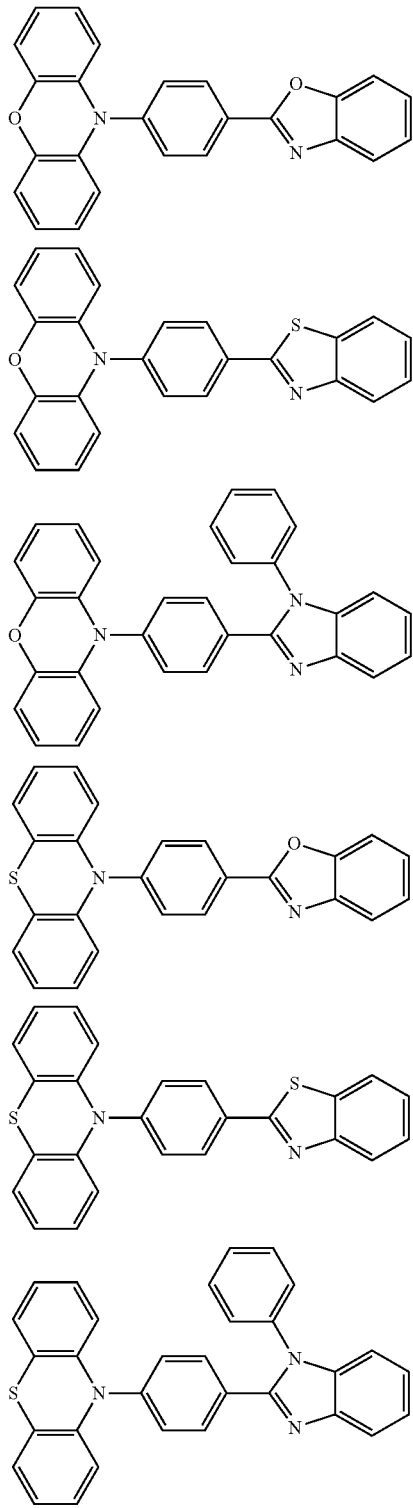
-continued
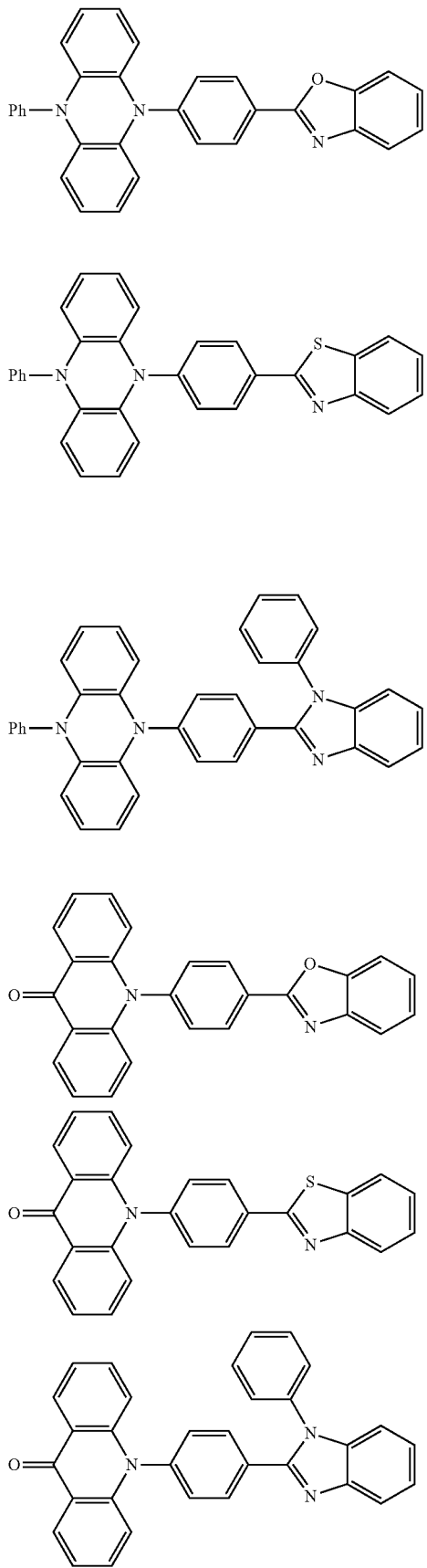

-continued

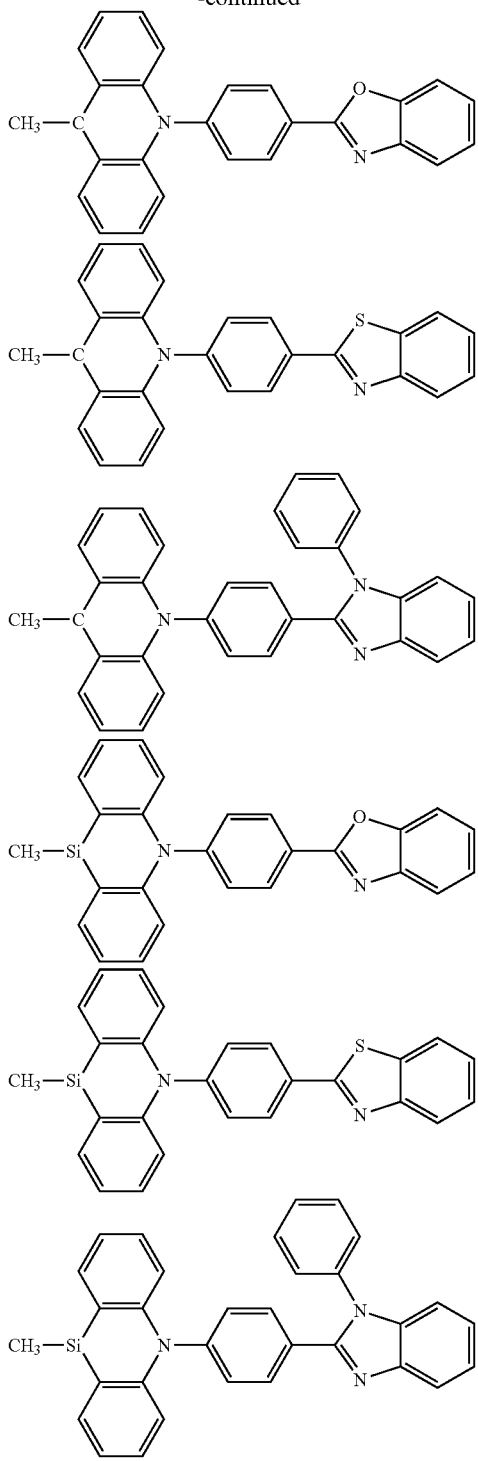

Examples of the preferred light-emitting material include the following compounds.

(1) A compound represented by the following general formula (301):

$(D)_n\text{-A}$          General Formula (301)

wherein in the general formula (301), D represents a group represented by the following general formula (302); A represents an n-valent group containing a structure represented by the following general formula (303); and n represents an integer of from 1 to 8:

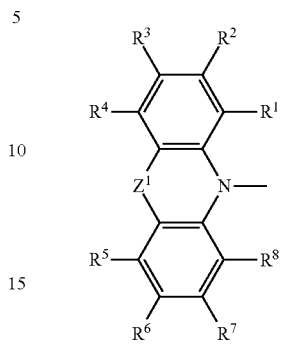

General Formula (302)

wherein in t e genera formula (302), $Z^1$ represents O, S, C=O, C($R^{21}$) ($R^{22}$), Si($R^{23}$) ($R^{24}$), N—$Ar^3$, or a single bond; $R^{21}$ to $R^{24}$ each independently represent an alkyl group having from 1 to 8 carbon atoms; $Ar^3$ represents a substituted or unsubstituted aryl group; and $R^1$ to $R^8$ each independently represent a hydrogen atom or a substituent, in which $R^1$ and $R^2$, $R^2$ and $R^3$, $R^3$ and $R^4$, $R^5$ and $R^6$, $R^6$ and $R^7$, and $R^7$ and $R^8$ may be bonded to each other to form a cyclic structure, and when $Z^1$ represents a single bond, at least one of $R^1$ to $R^8$ represents a substituted or unsubstituted diarylamino group:

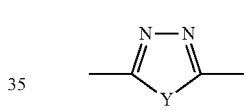

General Formula (303)

wherein in the general formula (303), Y represents O, S, or N—$Ar^4$; and $Ar^4$ represents a substituted or unsubstituted aryl group.

(2) The compound according to the item (1), wherein in the general formula (302), $Z^1$ represents O, S, C=O, C($R^{21}$) ($R^{22}$), Si($R^{23}$) ($R^{24}$), or a single bond.

(3) The compound according to the item (1), wherein in the general formula (302), $Z^1$ represents N—$Ar^3$.

(4) The compound according to any one of the items (1) to (3), wherein in the general formula (301), A has a structure represented by the following general formula (304):

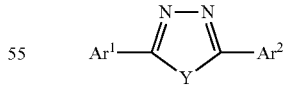

General Formula (304)

wherein in the general formula (304), Y represents O, S, or N—$Ar^4$; and $Ar^1$ and $Ar^2$ each independently represent a substituted or unsubstituted aromatic group.

(5) The compound according to any one of the items (1) to (4), wherein in the general formula (301), n represents an integer of from 1 to 4.

(6) The compound according to any one of the items (1) to (3), wherein the compound is represented by the following general formula (305):

General Formula (305)

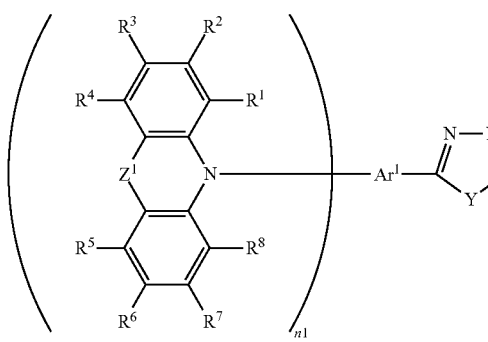
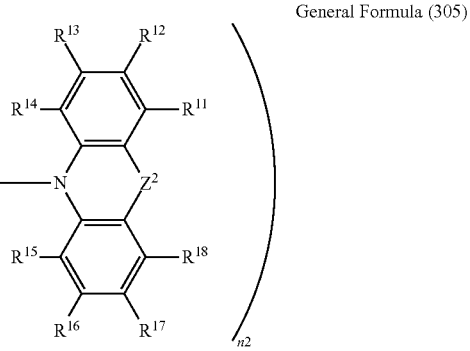

wherein in the general formula (305), $Z^1$ and $Z^2$ each independently represent O, S, C=O, C($R^{21}$) ($R^{22}$), Si($R^{23}$) ($R^{24}$), N—$Ar^3$, or a single bond; $R^{21}$ to $R^{24}$ each independently represent an alkyl group having from 1 to 8 carbon atoms; $Ar^3$ represents a substituted or unsubstituted aryl group; $Ar^1$ and $Ar^2$ each independently represent a substituted or unsubstituted aromatic group; Y represents O, S, or N—$Ar^4$; $Ar^4$ represents a substituted or unsubstituted aryl group; $R^1$ to $R^8$ and $R^{11}$ to $R^{18}$ each independently represent a hydrogen atom or a substituent, in which $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ each may be bonded to each other to form a cyclic structure, provided that when $Z^1$ represents a single bond, at least one of $R^1$ to $R^8$ represents a substituted or unsubstituted diarylamino group, and when $Z^2$ represents a single bond, at least one of $R^{11}$ to $R^{18}$ represents a substituted or unsubstituted diarylamino group; and n1 and n2 each independently represent an integer of from 0 to 8, provided that the sum of n1 and n2 is from 1 to 8.

(7) The compound according to the item (6), wherein in the general formula (305), $Z^1$ and $Z^2$ each independently represent O, S, N—$Ar^3$, or a single bond.

(8) The compound according to the item (6) or (7), wherein in the general formula (305), Y represents O or N—$Ar^4$.

(9) The compound according to any one of the items (1) to (3), wherein the compound is represented by the following general formula (306):

General Formula (306)

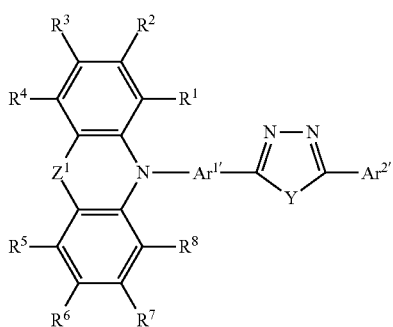

wherein in the general formula (306), $Z^1$ represents O, S, C=O, C($R^{21}$) ($R^{22}$), Si($R^{23}$) ($R^{24}$), N—$Ar^3$, or a single bond; $R^{21}$ to $R^{24}$ each independently represent an alkyl group having from 1 to 8 carbon atoms; $Ar^3$ represents a substituted or unsubstituted aryl group; $Ar^{1'}$ represents a substituted or unsubstituted arylene group; $Ar^{2'}$ represents a substituted or unsubstituted aryl group; Y represents O, S, or N—$Ar^4$; $Ar^4$ represents a substituted or unsubstituted aryl group; and $R^1$ to $R^8$ each independently represent a hydrogen atom or a substituent, in which $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure, provided that when $Z^1$ represents a single bond, at least one of $R^1$ to $R^8$ represents a substituted or unsubstituted diarylamino group.

(10) The compound according to any one of the items (1) to (3), wherein the compound is represented by the following general formula (307):

General Formula (307)

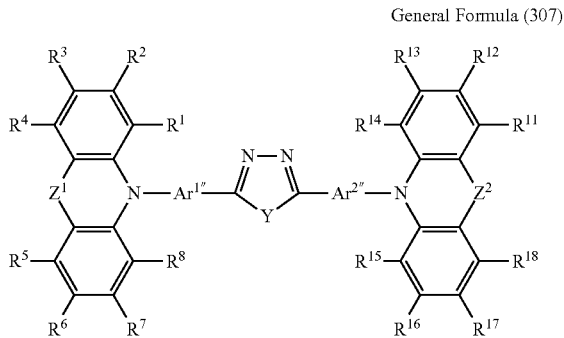

wherein in the general formula (307), $Z^1$ and $Z^2$ each independently represent O, S, C=O, C($R^{21}$) ($R^{22}$), Si($R^{23}$) ($R^{24}$), N—$Ar^3$, or a single bond; $R^{21}$ to $R^{24}$ each independently represent an alkyl group having from 1 to 8 carbon atoms; $Ar^3$ represents a substituted or unsubstituted aryl group; $Ar^{1''}$ and $Ar^{2''}$ each independently represent a substituted or unsubstituted arylene group; Y represents O, S, or N—$Ar^4$; $Ar^4$ represents a substituted or unsubstituted aryl group; and $R^1$ to $R^8$ and $R^{11}$ to $R^{18}$ each independently represent a hydrogen atom or a substituent, in which $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ each may be bonded to each other to form a cyclic structure, provided that when $Z^1$ represents a single bond, at least one of $R^1$ to $R^8$ represents a substituted or unsubstituted diarylamino group, and when $Z^2$ represents a single bond, at least one of $R^{11}$ to $R^{18}$ represents a substituted or unsubstituted diarylamino group.

(11) The compound according to the item (10), wherein in the general formula (307), $Z^1$ and $Z^2$ are the same as each other, $Ar^{1'''}$ and $Ar^{2''}$ are the same as each other, $R^1$ and $R^{14}$ are the same as each other, $R^2$ and $R^{13}$ are the same as each other, $R^3$ and $R^{12}$ are the same as each other, $R^4$ and $R^{11}$ are the same as each other, $R^5$ and $R^{18}$ are the same as each other, $R^6$ and $R^{17}$ are the same as each other, $R^7$ and $R^{16}$ are the same as each other, and $R^8$ and $R^{15}$ are the same as each other.

(12) The compound according to the item (10) or (11), wherein in the general formula (307), $Z^1$ and $Z^2$ each independently represent O, S, or N—$Ar^3$.

Examples of the compound include the following compounds.

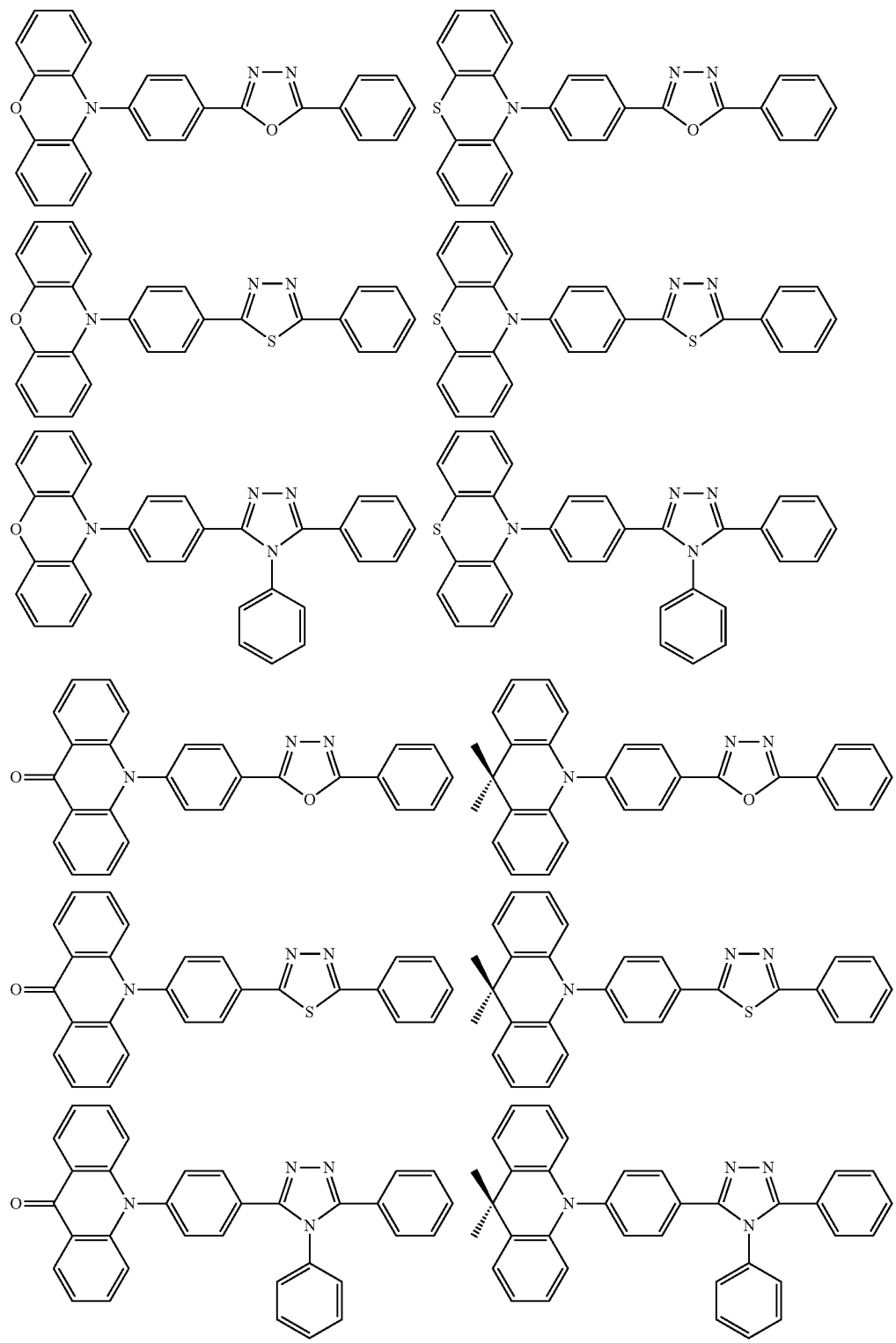

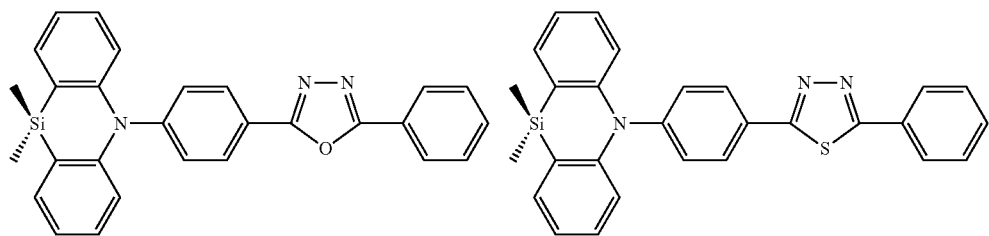
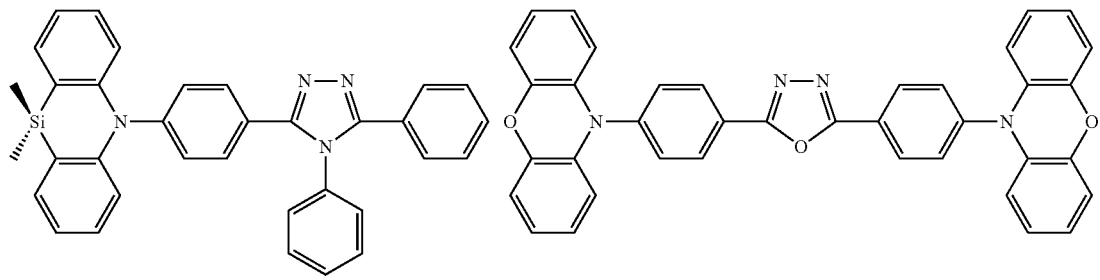
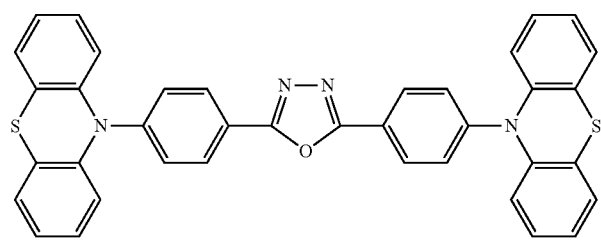
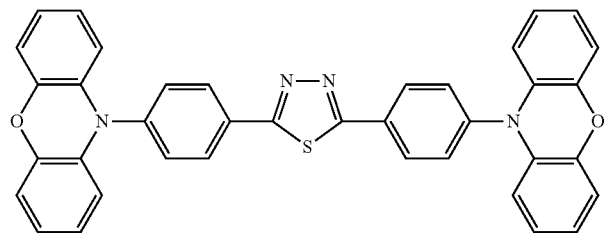
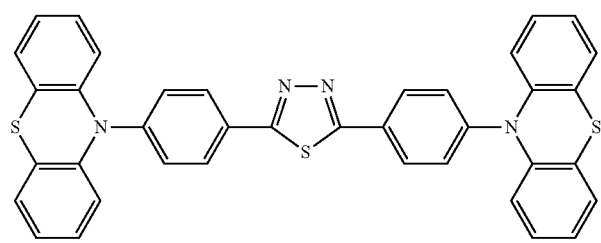
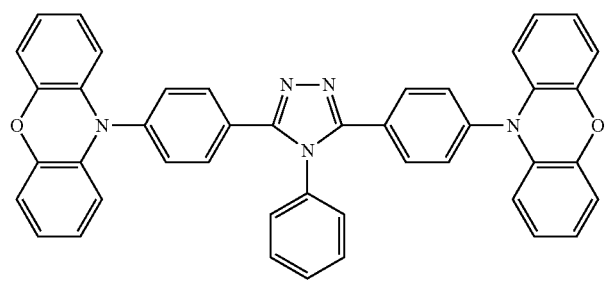

-continued
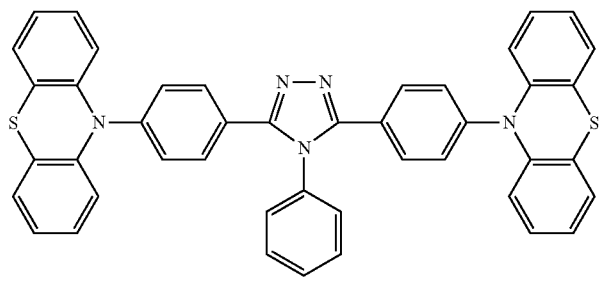
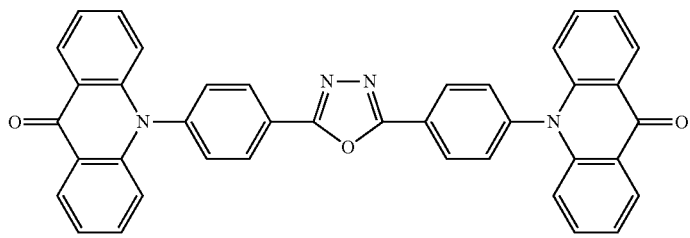
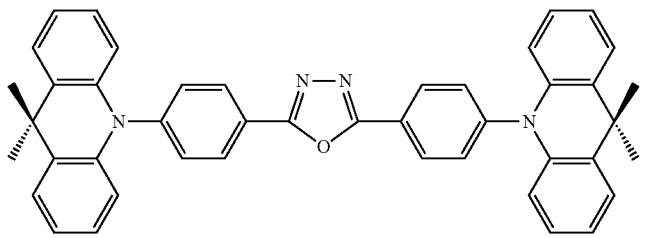
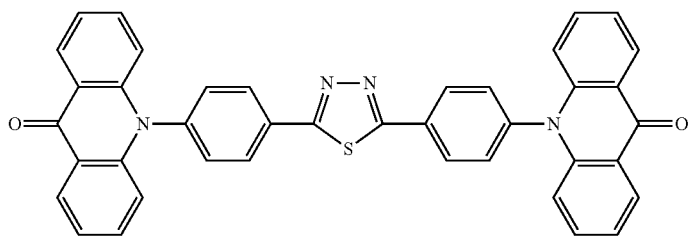
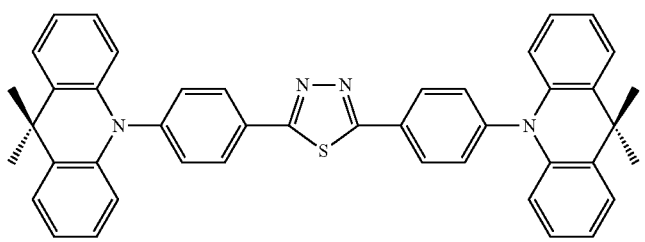
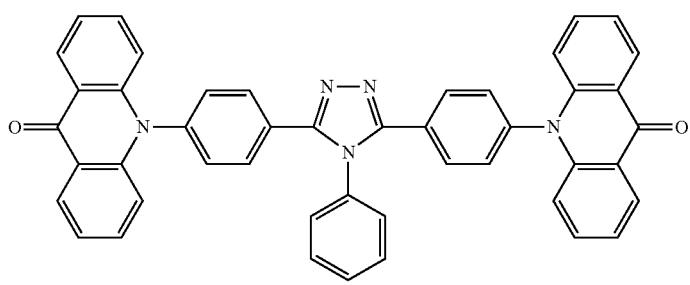

-continued
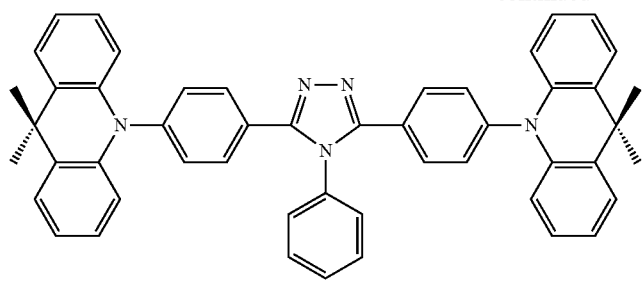
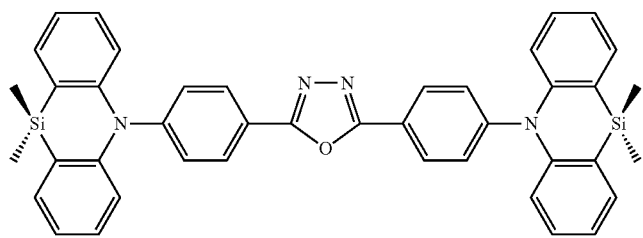
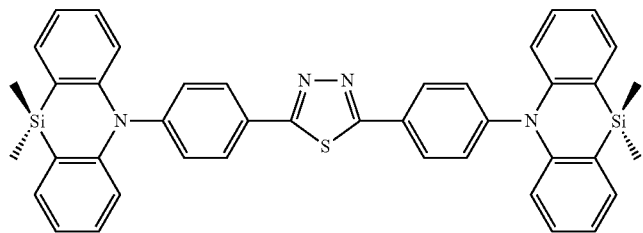
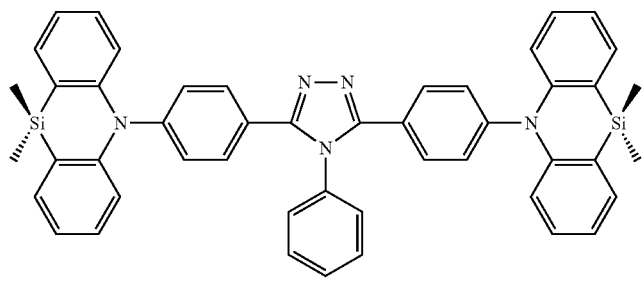
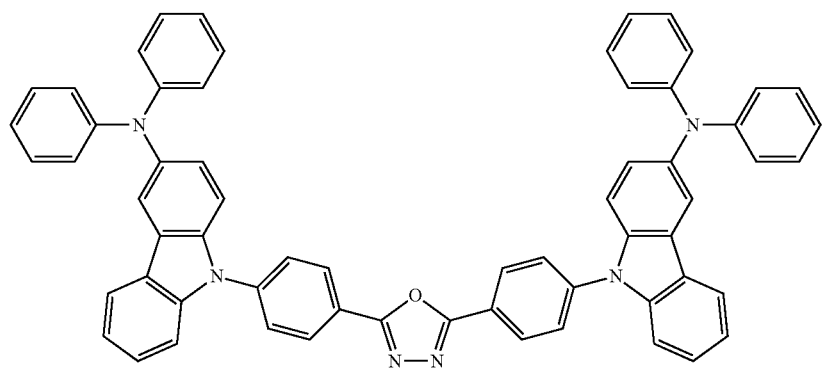

-continued
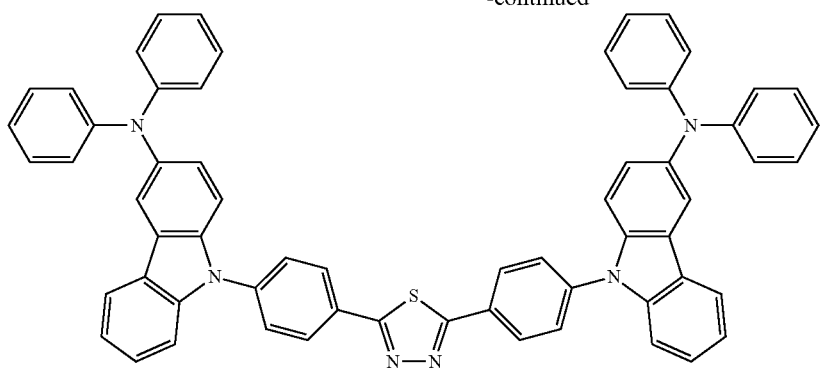
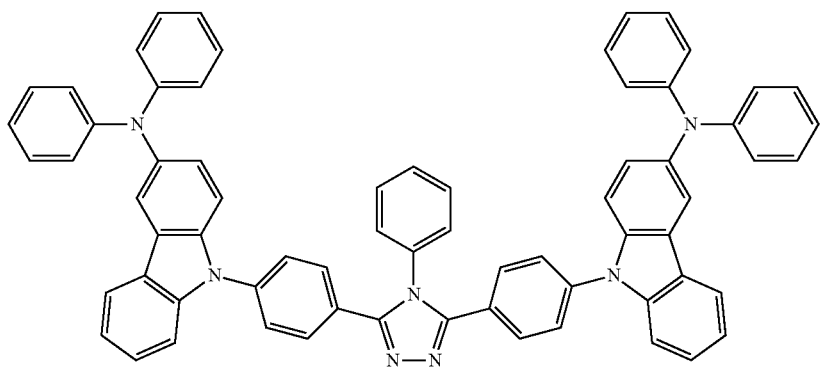
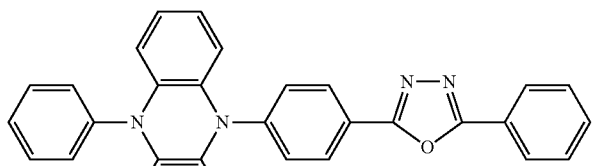
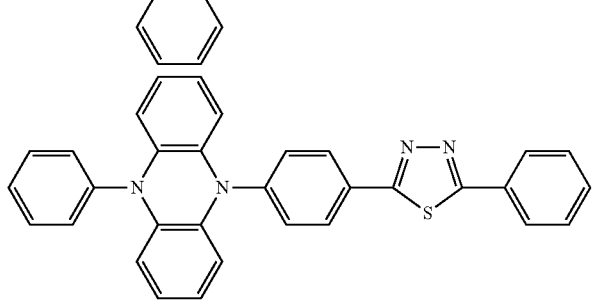
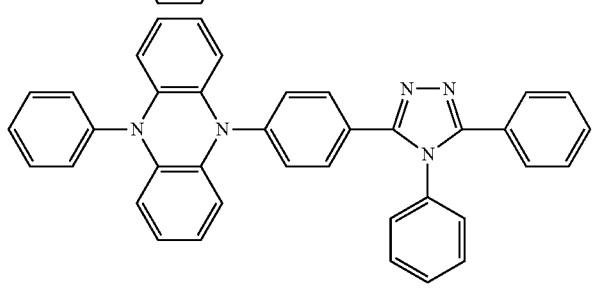
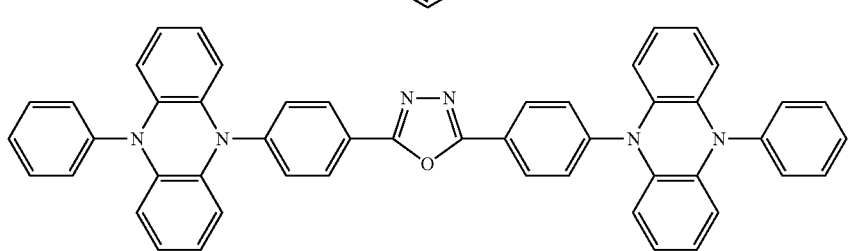

-continued

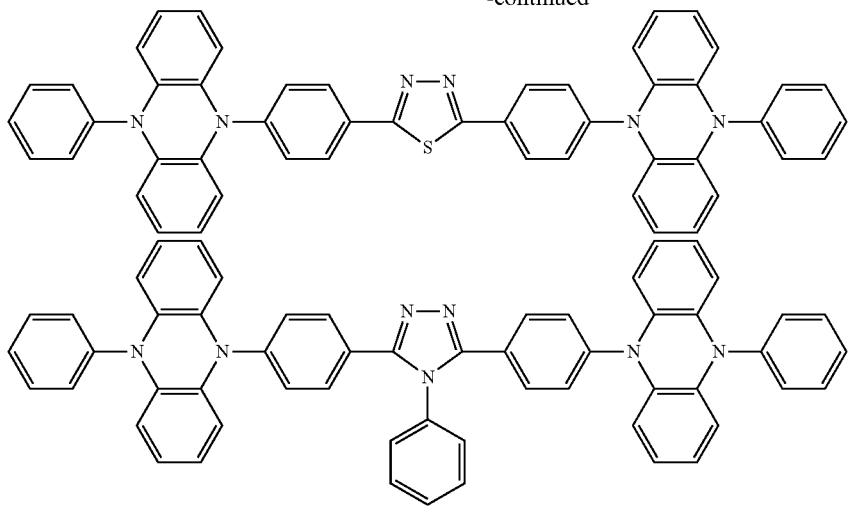

In the case where the compound represented by the general formula (1) is used as a light-emitting material, on the other hand, one kind or two or more kinds selected from the group of compounds represented by the general formula (1) of the invention may be used therefor. As described above, from the standpoint that the singlet excitons and the triplet excitons generated in the light-emitting material are confined in the light-emitting material, a host material is preferably used in addition to the light-emitting material in the light-emitting layer. The host material used may be an organic compound that has excited singlet energy and excited triplet energy, at least one of which is higher than those of the light-emitting material of the invention. Even though the singlet excitons and the triplet excitons are not confined sufficiently, however, a high light emission efficiency may be obtained in some cases, and thus a host material that is capable of achieving a high light emission efficiency may be used in the invention without any particular limitation.

In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less. The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in abroad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron withdrawing group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.

In the case where the compound represented by the general formula (1) is used as a light-emitting material, preferred examples of a compound that may also be used as the host material of the light-emitting layer are shown below.

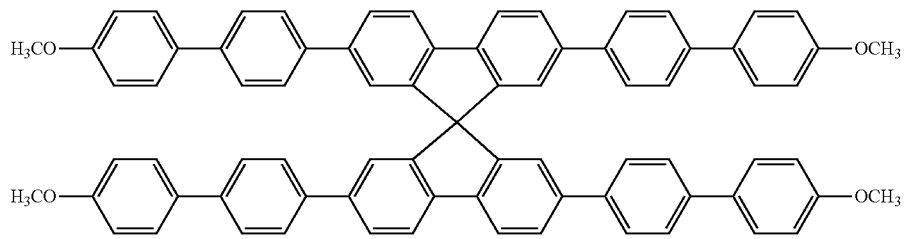

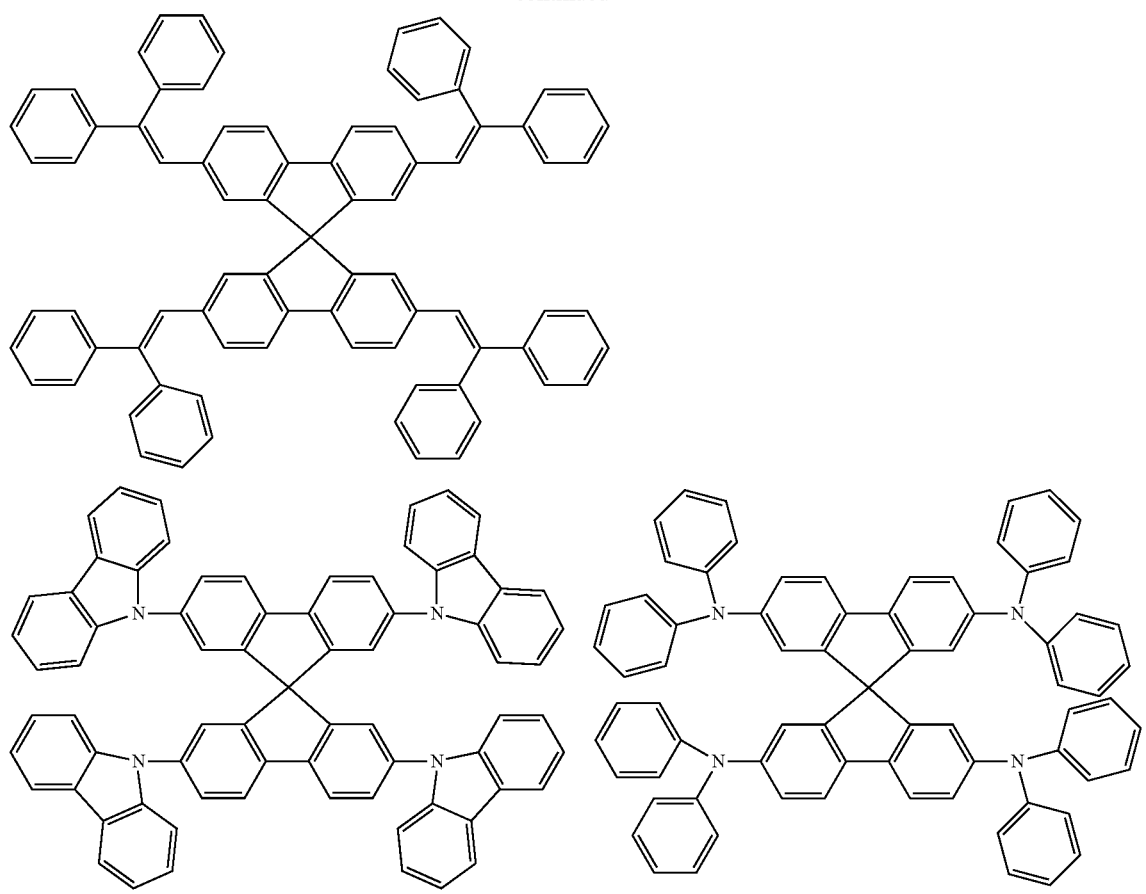
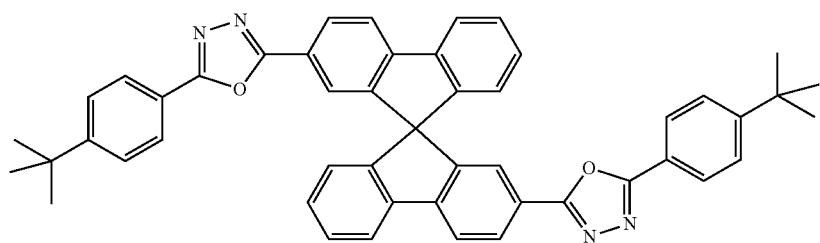
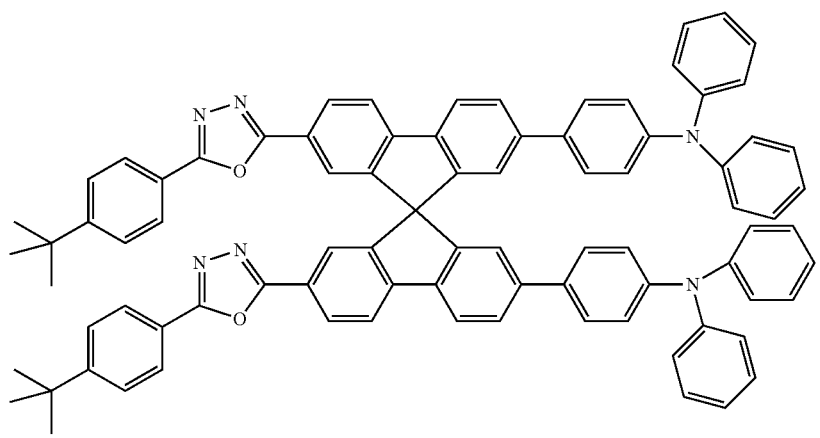

453
454
-continued
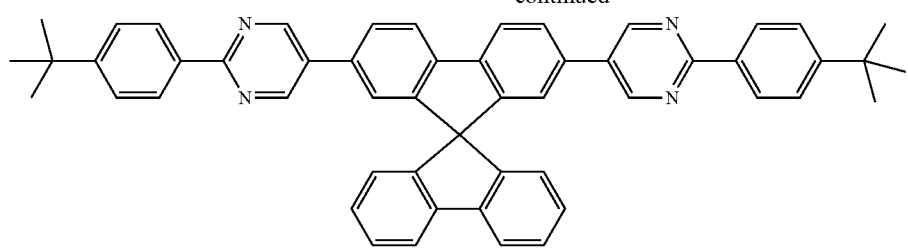
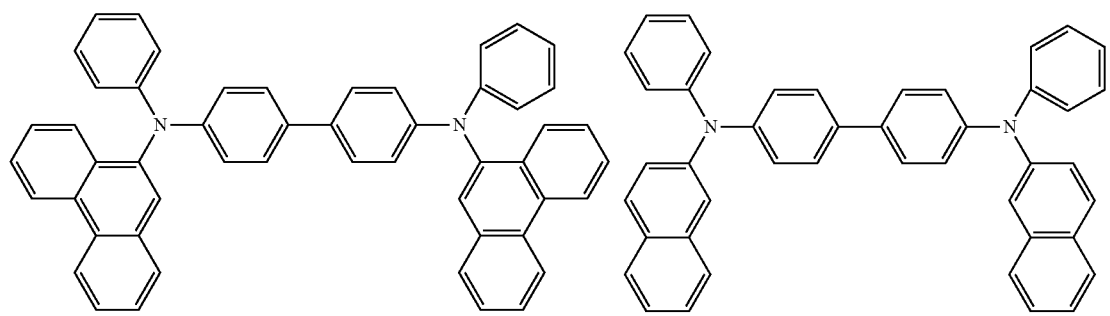
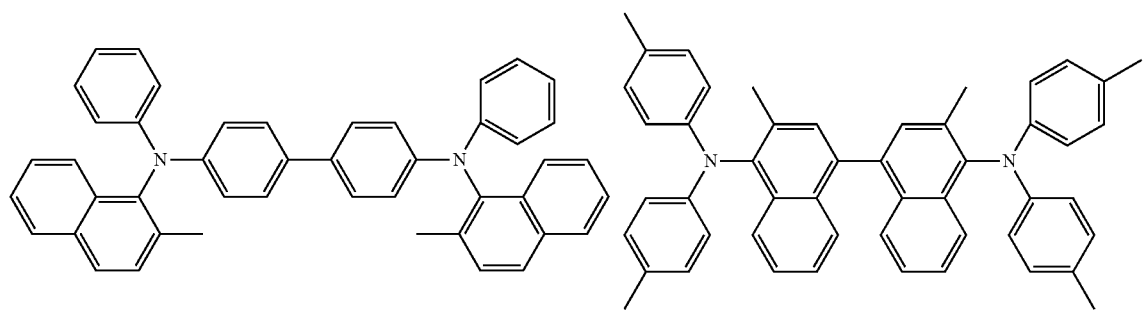
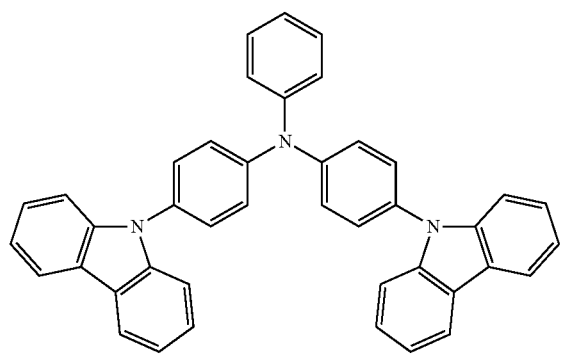

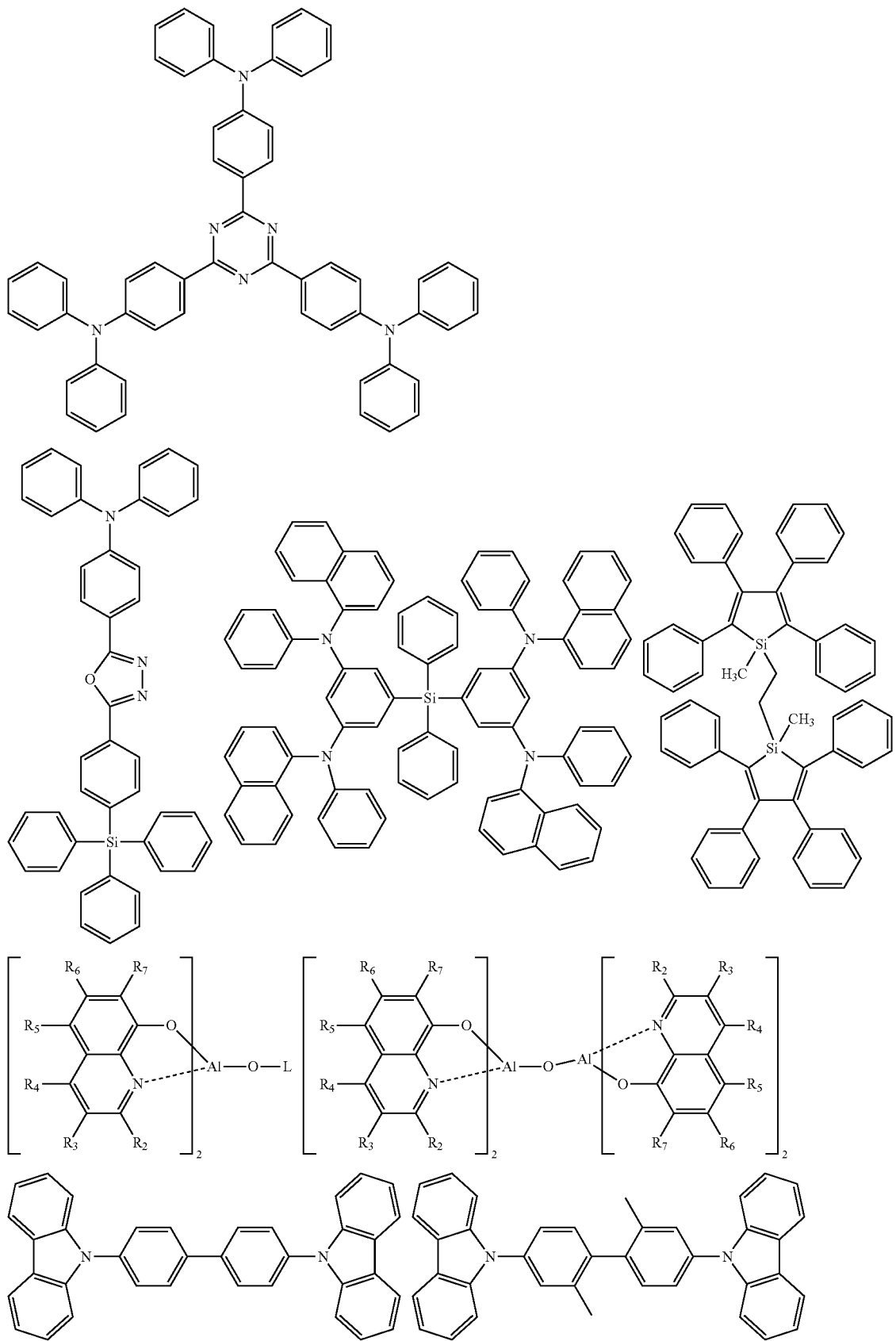

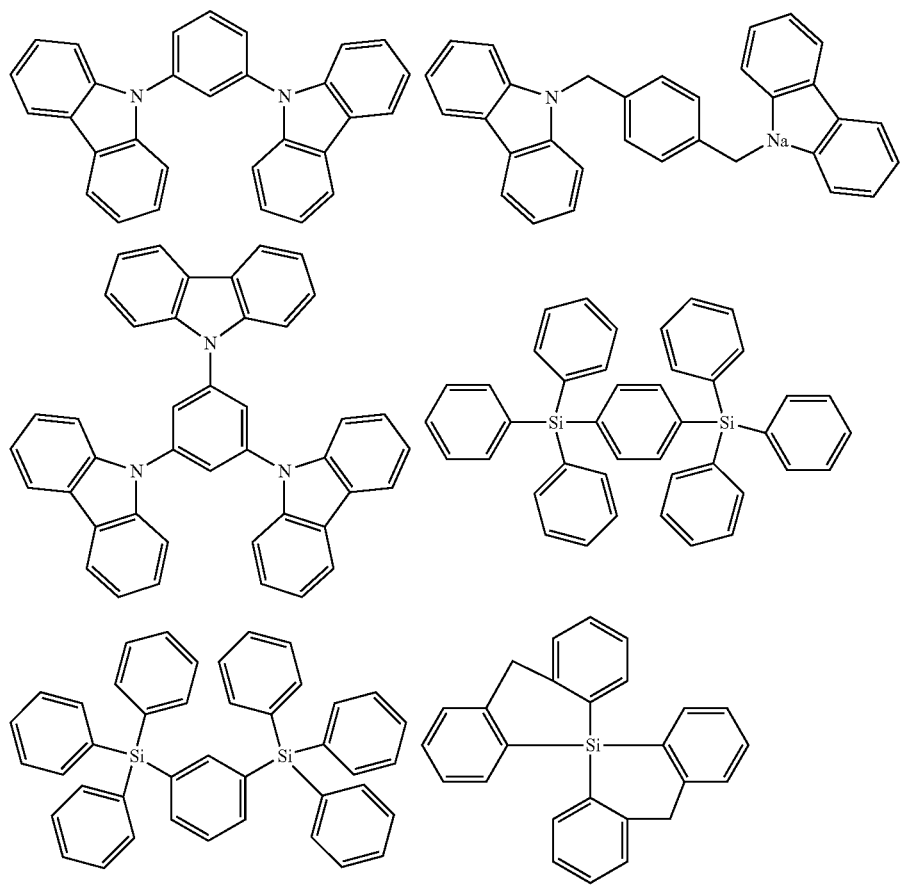
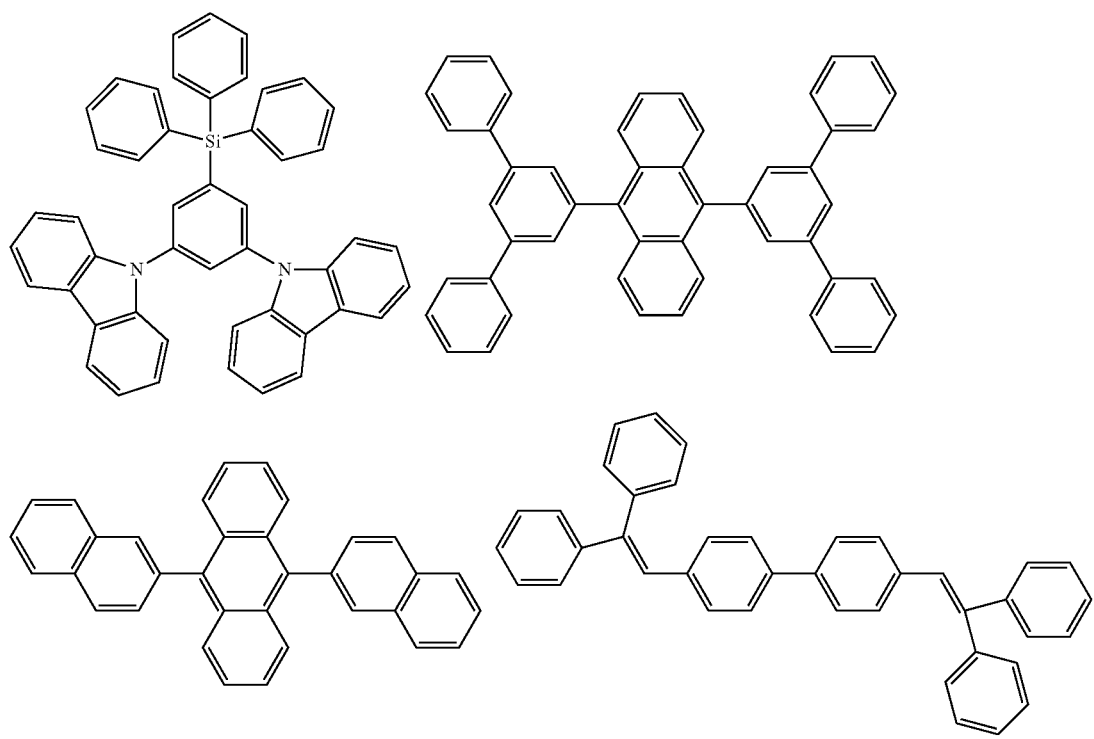

459
460
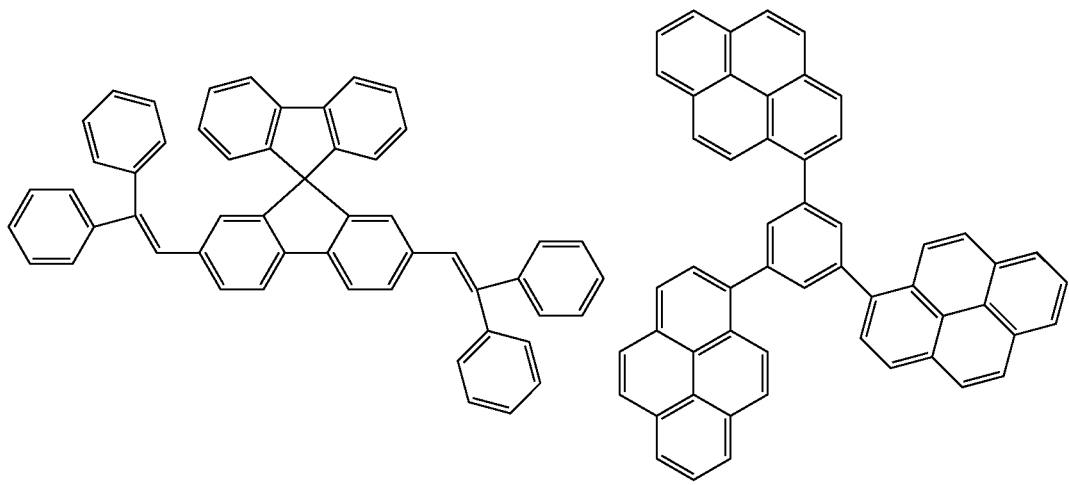
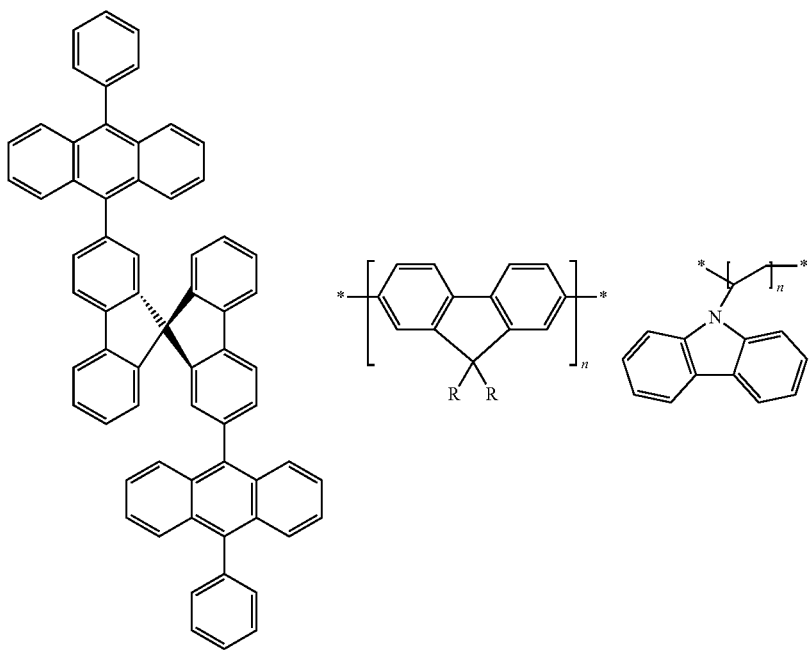
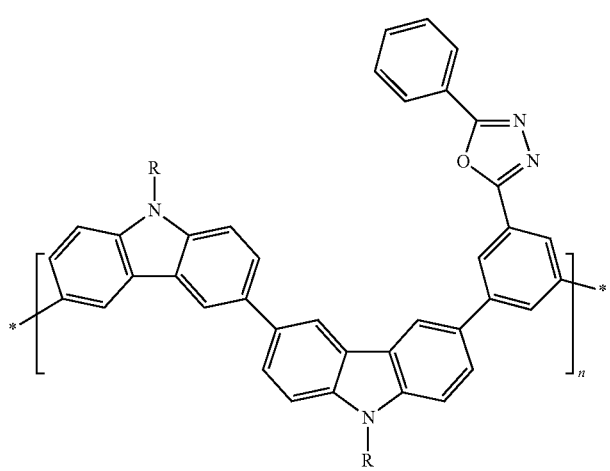

-continued
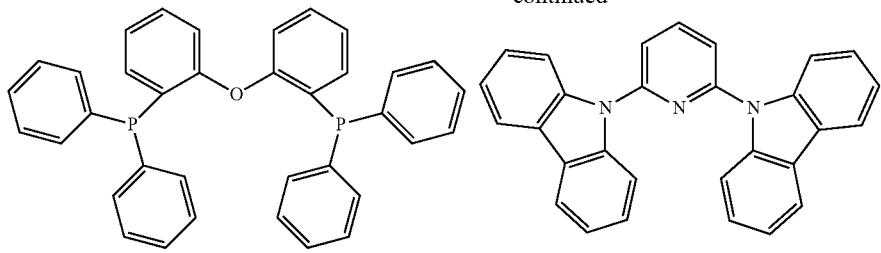
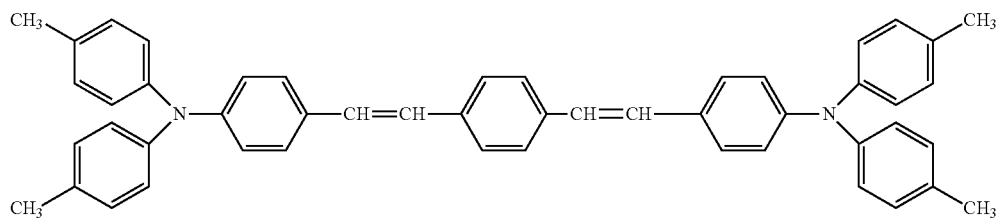
Preferred examples of a compound that may be used as the hole injection material are shown below.
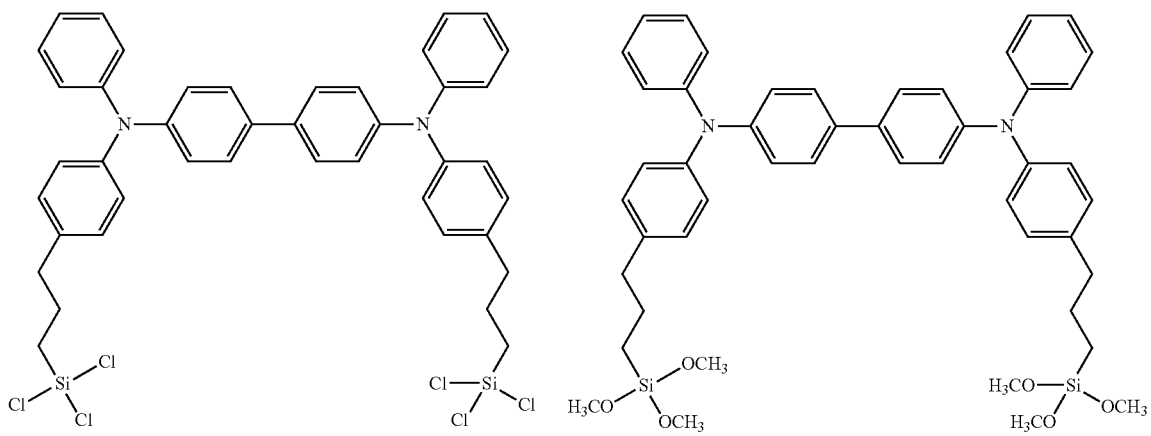
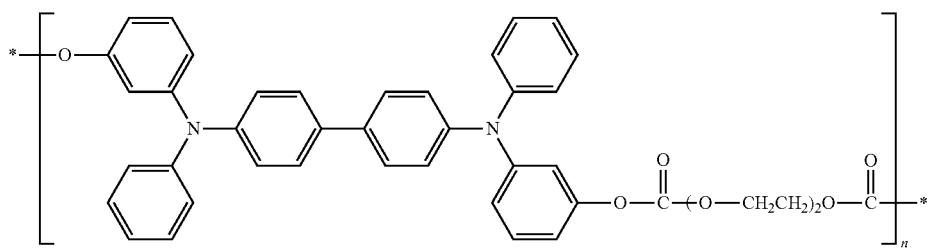

463
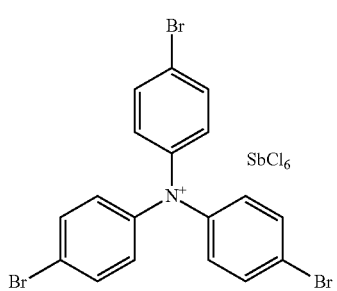
-continued
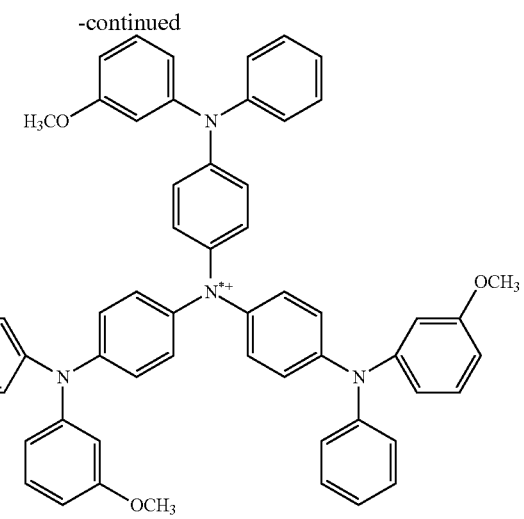
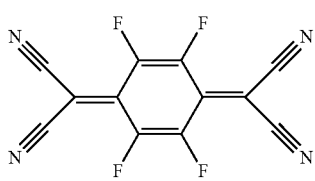
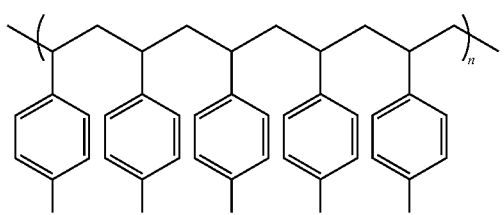
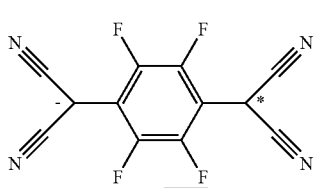
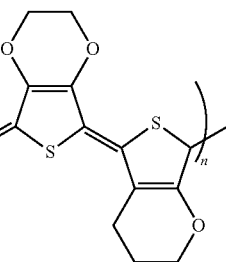
Preferred examples of a compound that may be used as the hole transporting material are shown below.
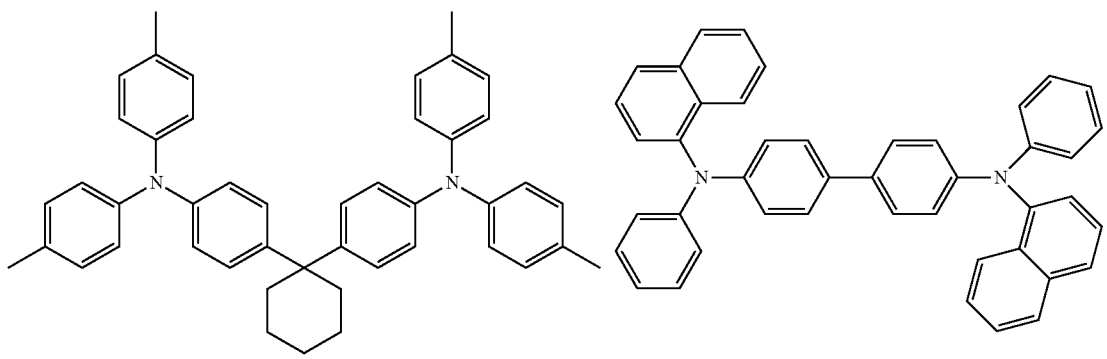

-continued
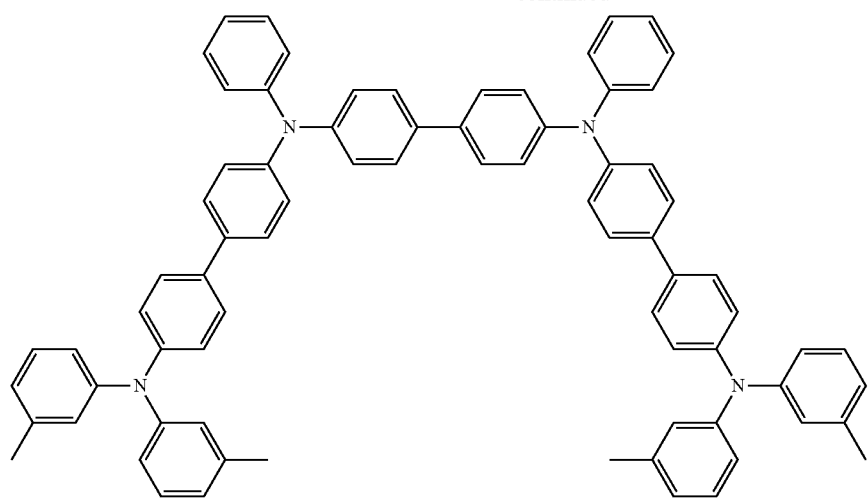
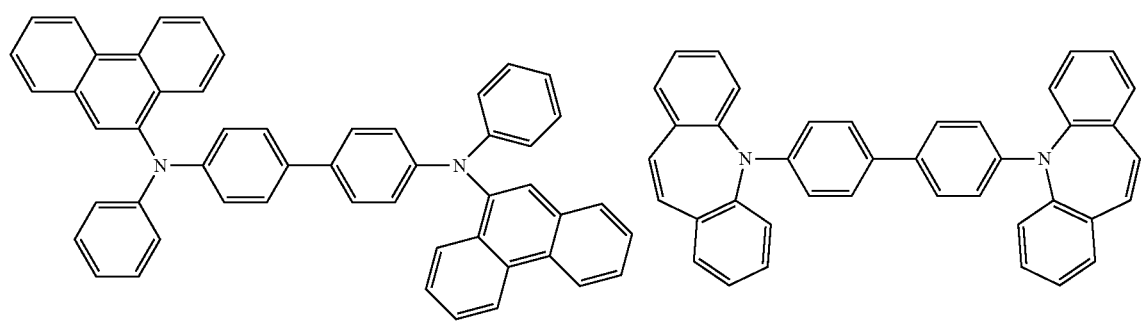
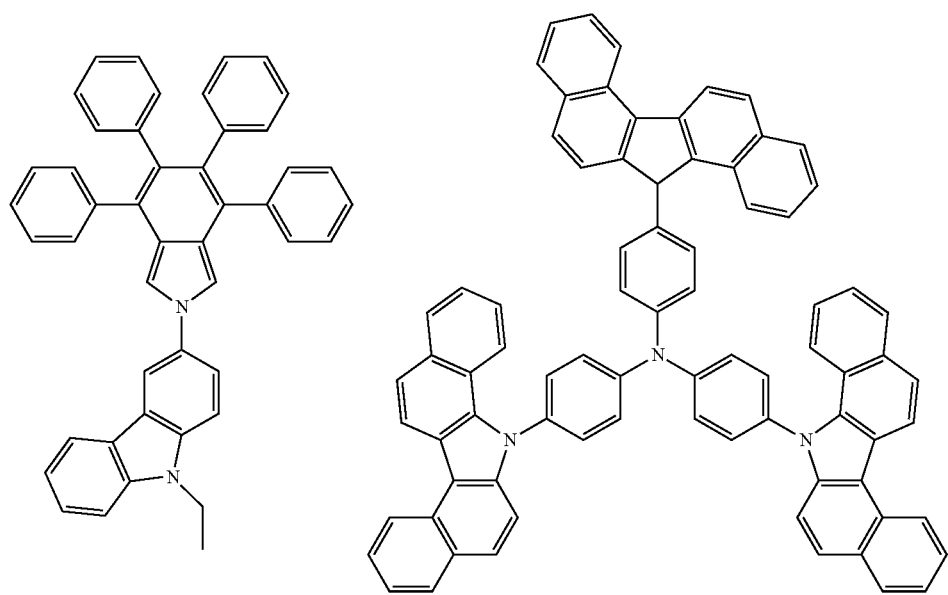

-continued
467  468
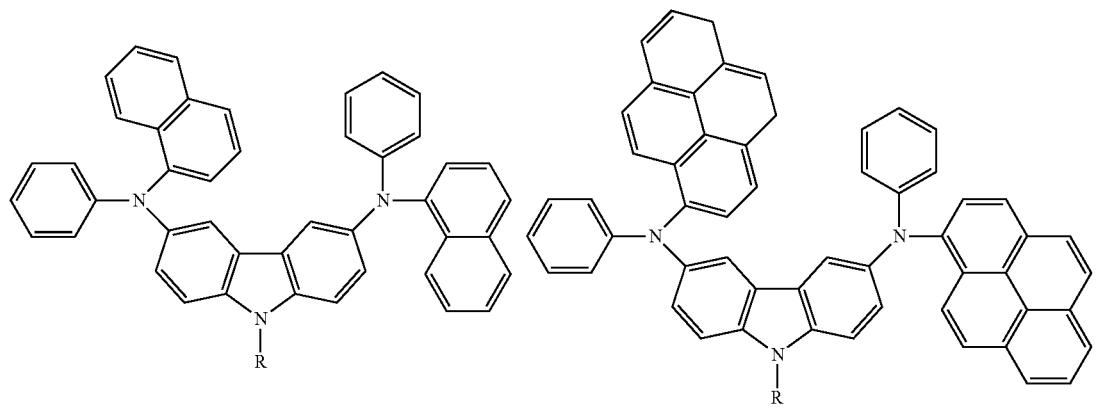
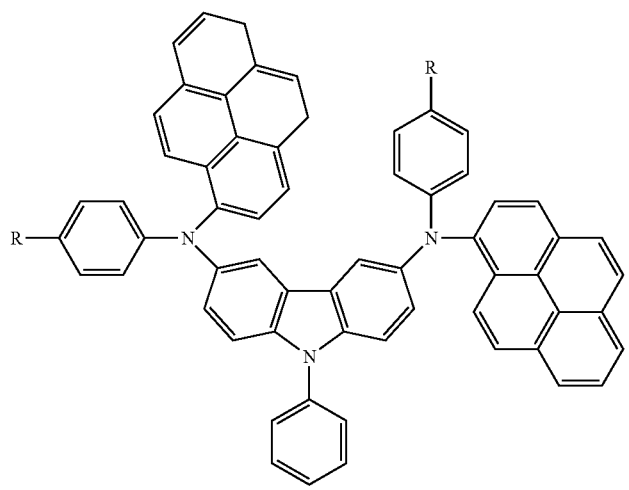
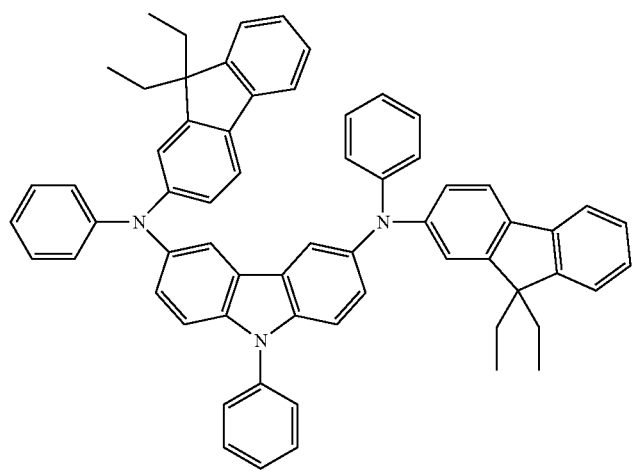

469
-continued
470
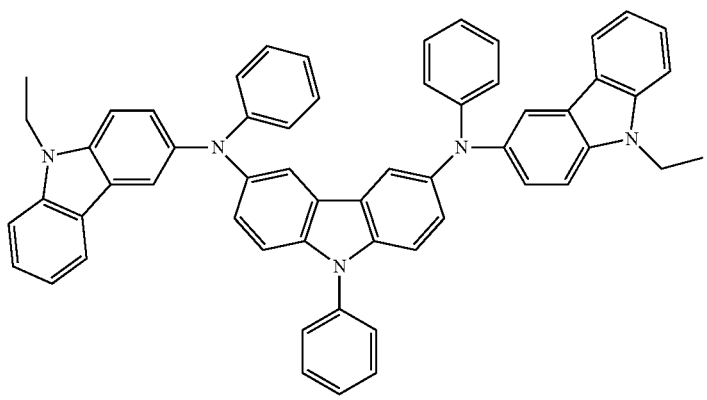
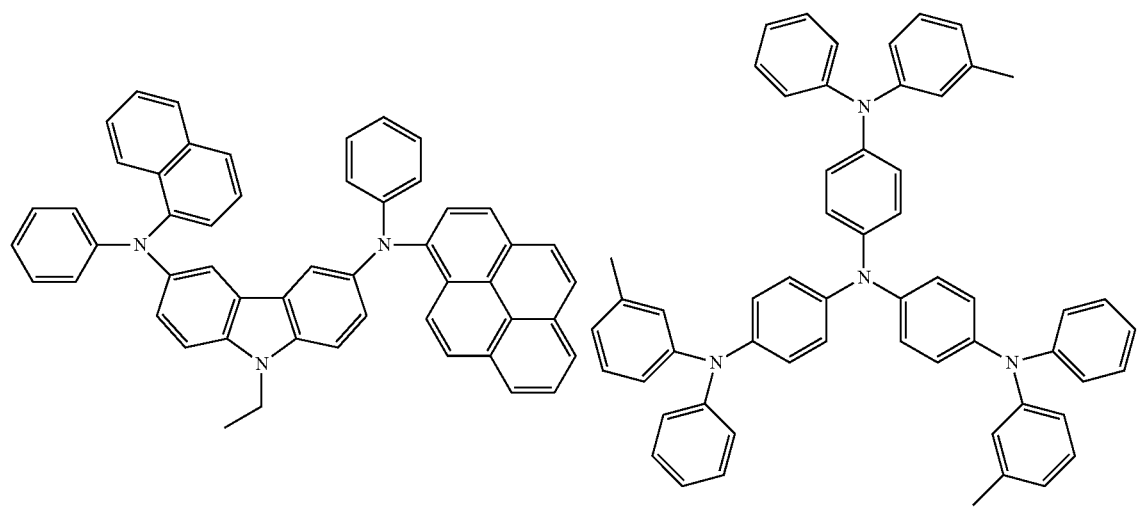
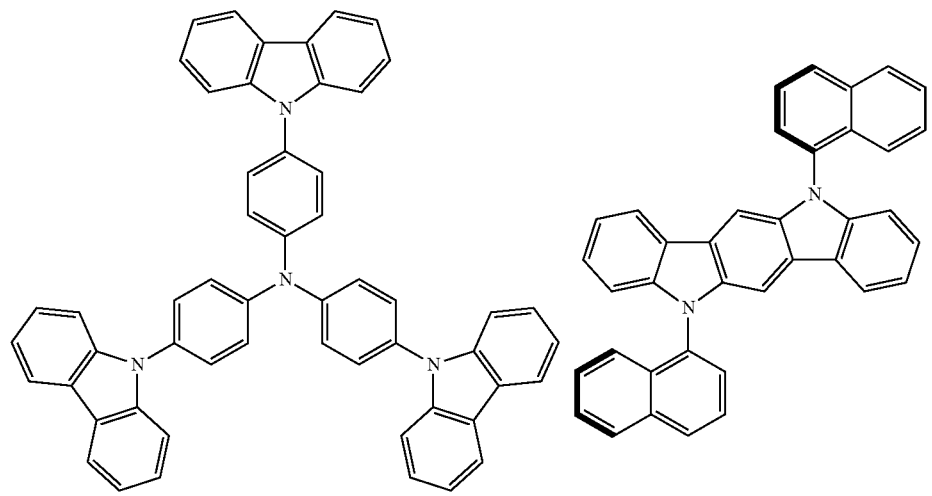

471
472
-continued
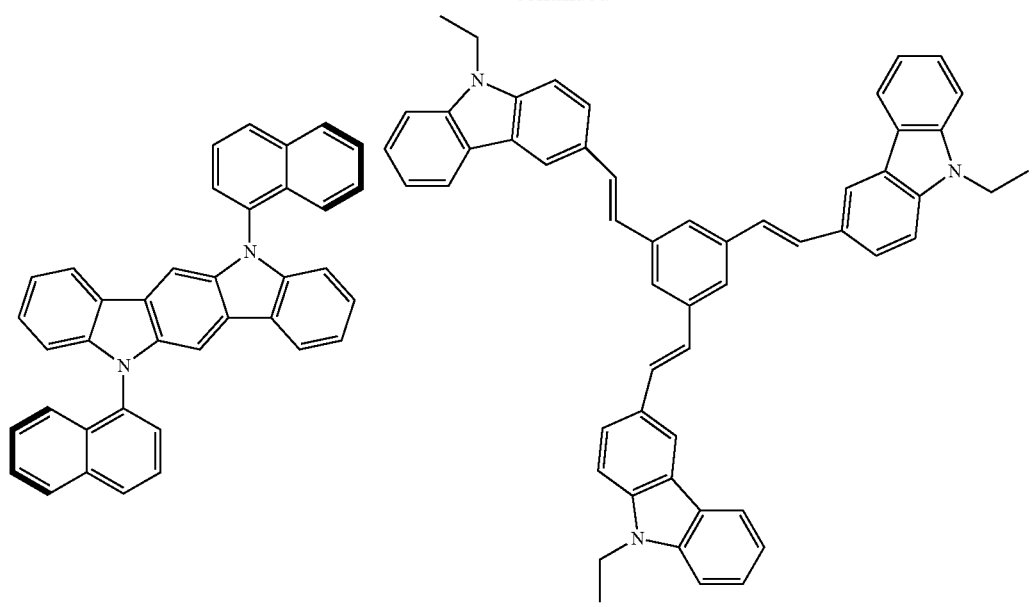
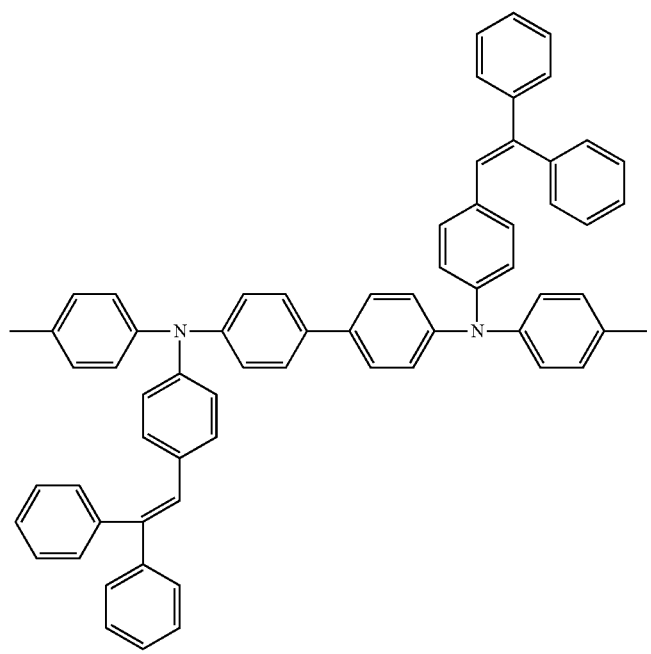
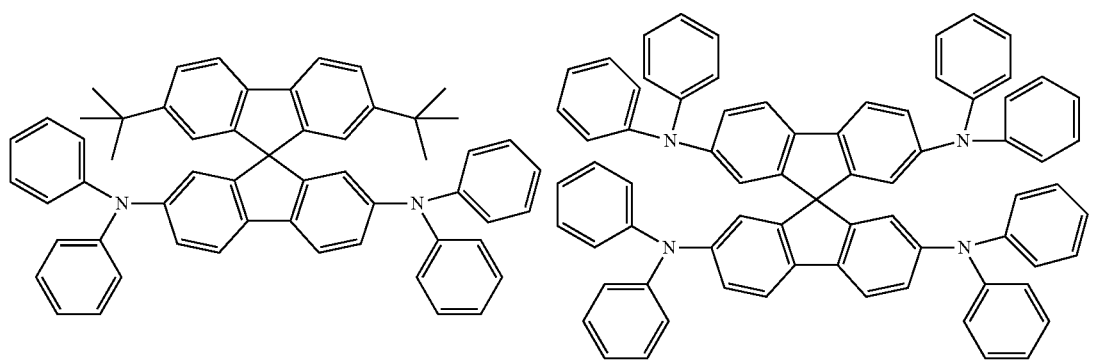

-continued
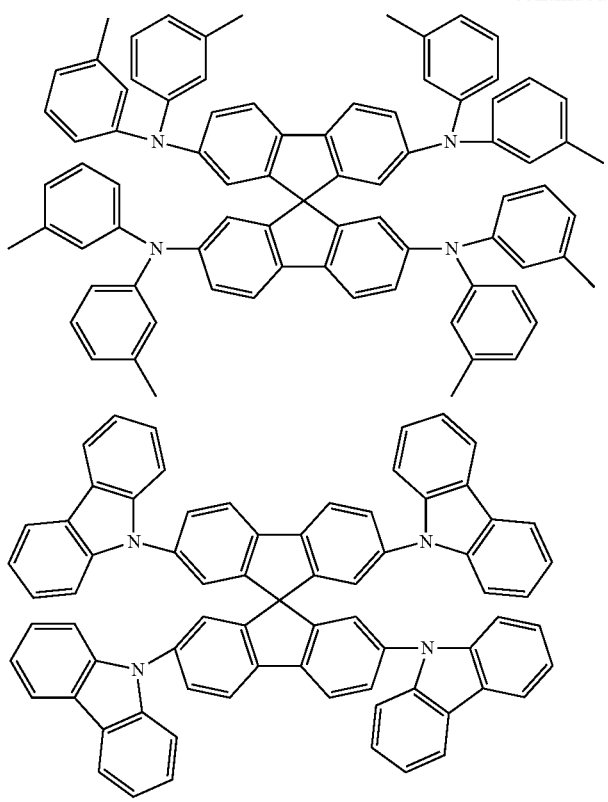
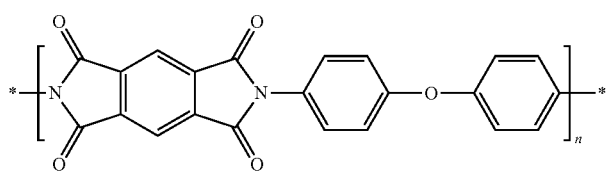
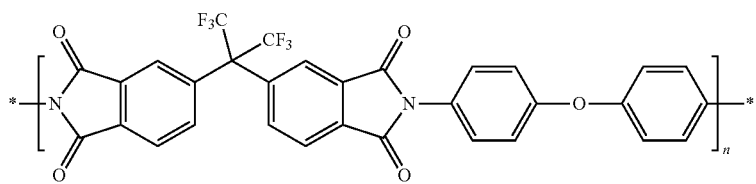
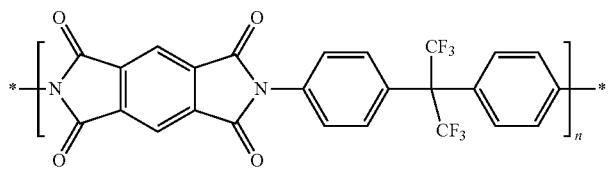
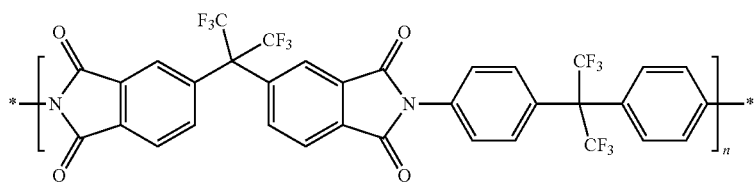

475
476
-continued
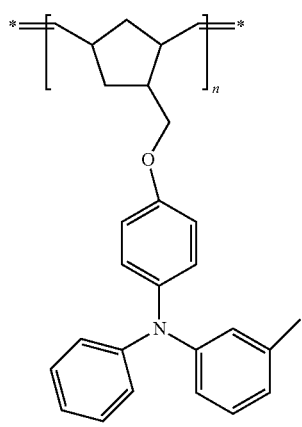
R =
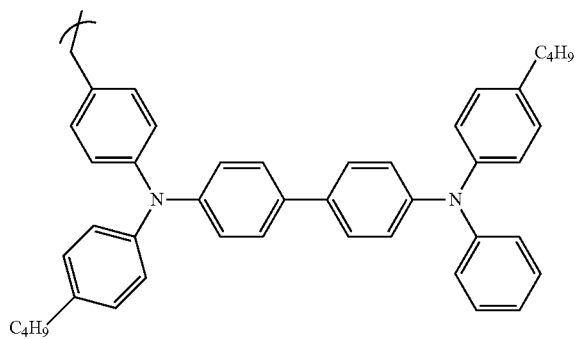
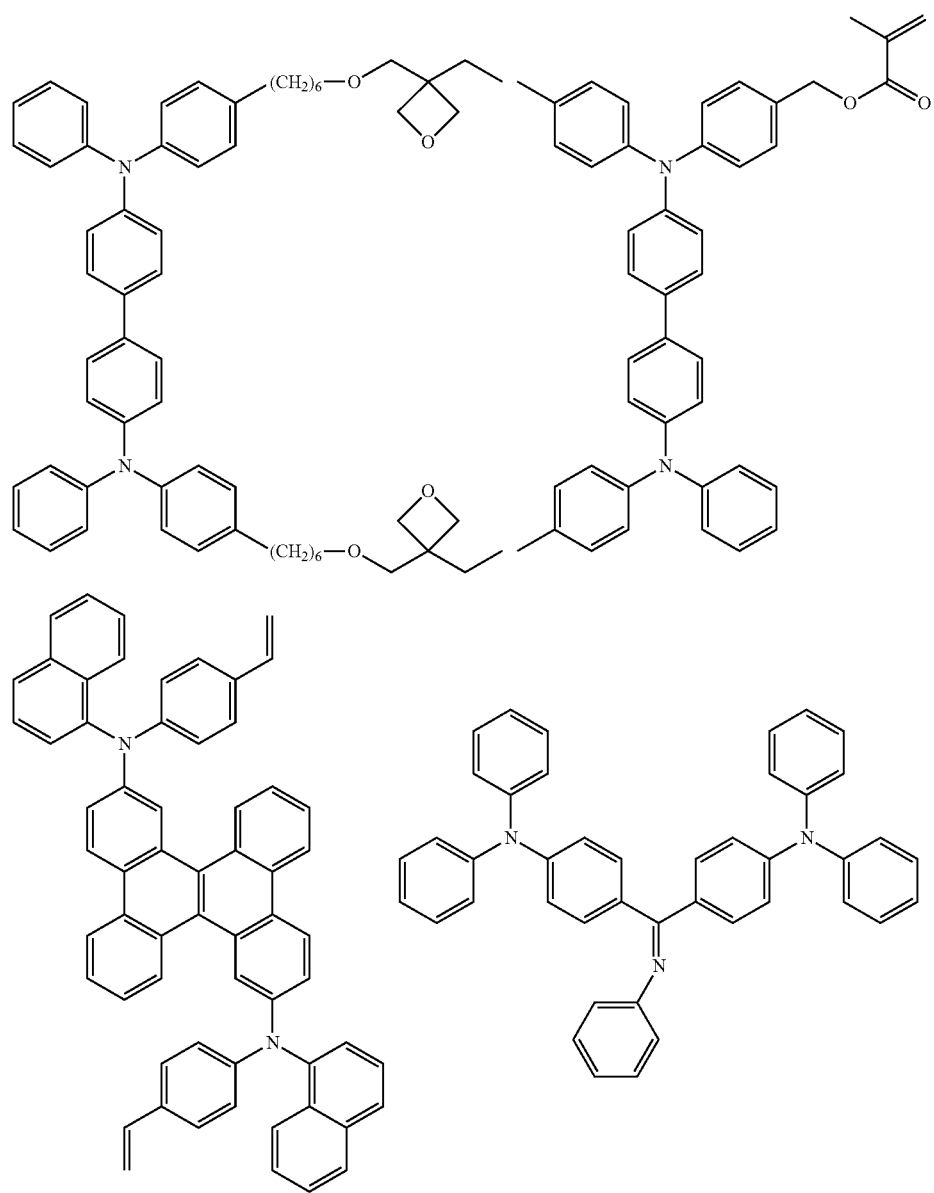

-continued
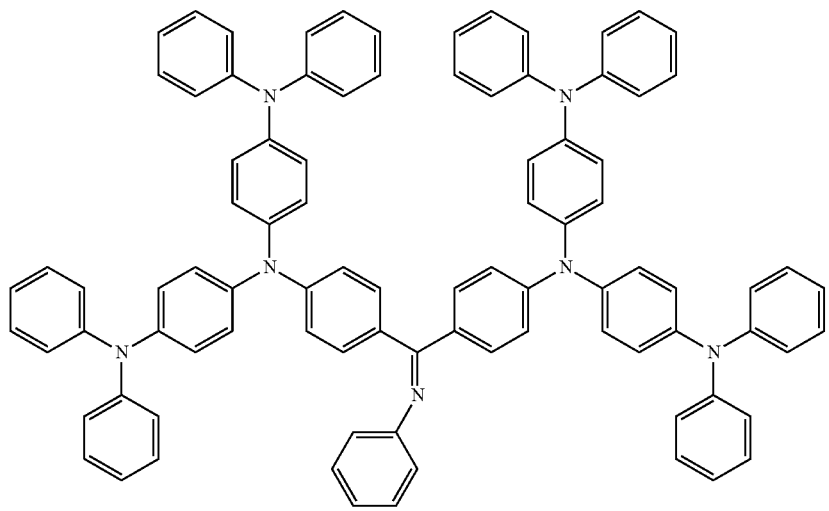
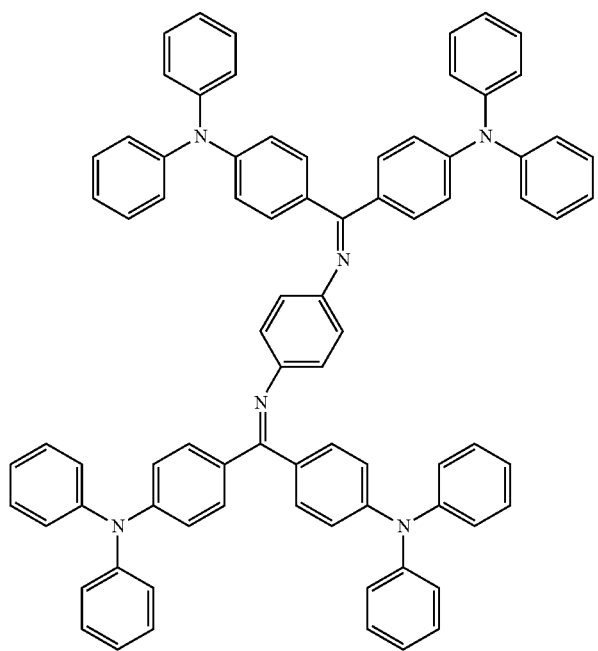

-continued
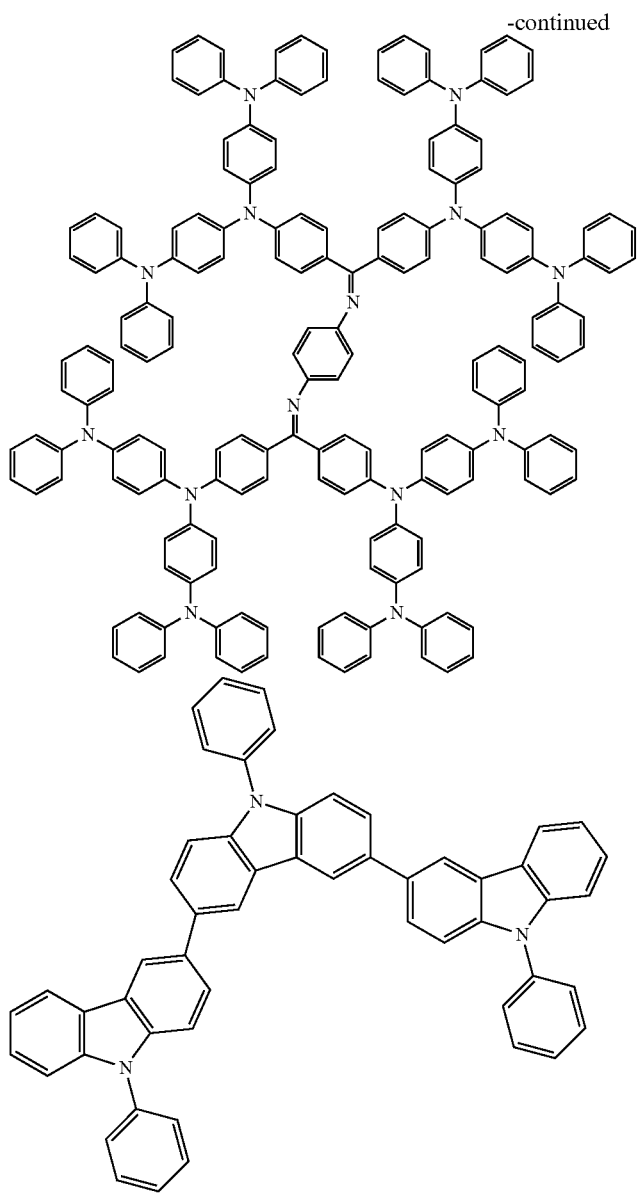
Preferred examples of a compound that may be used as the electron barrier material are shown below.
-continued
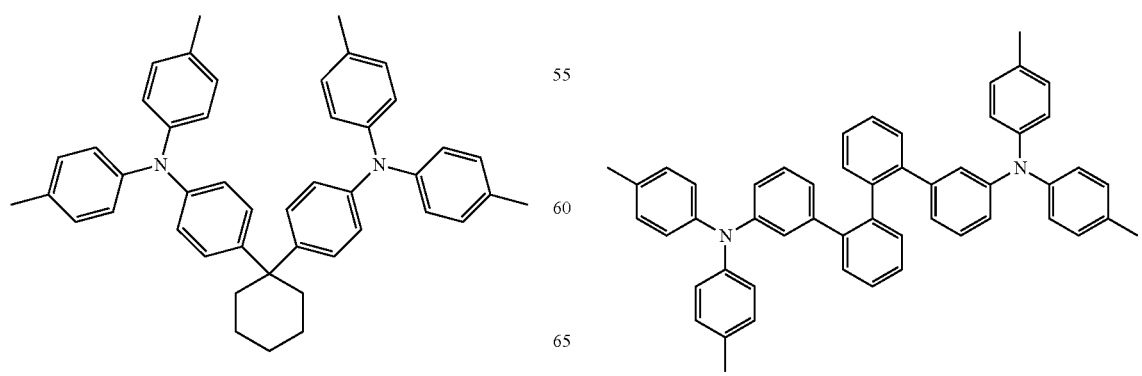

481
-continued
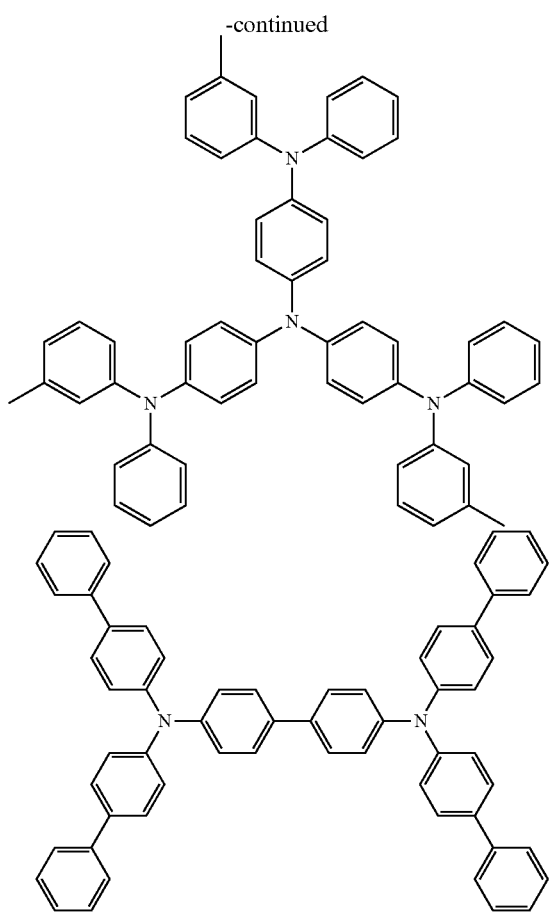
Preferred examples of a compound that may be used as the hole barrier material are shown below.
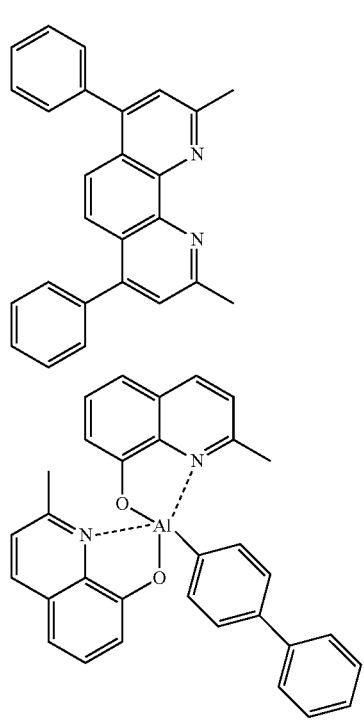
482
-continued
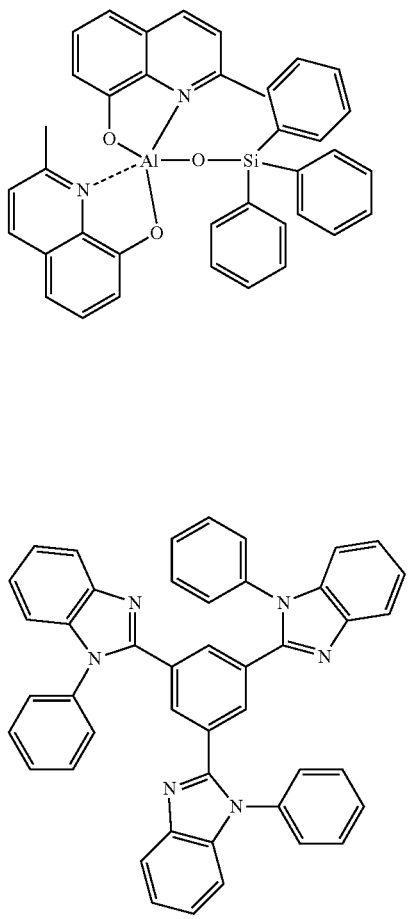
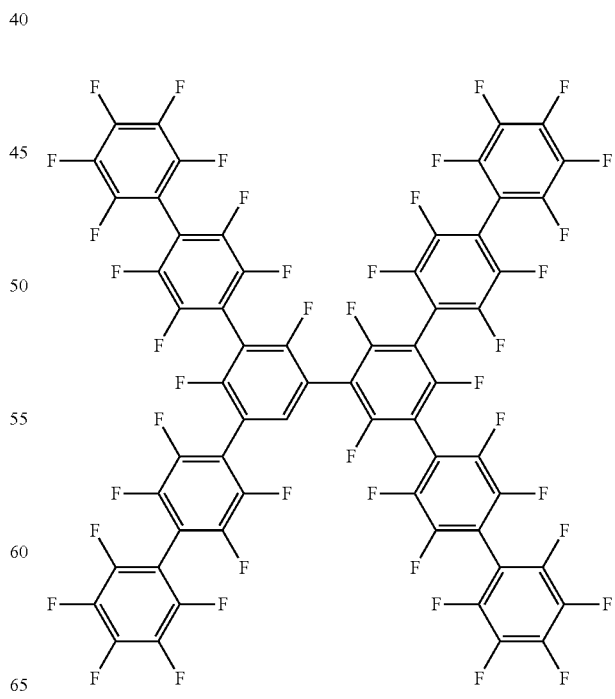

483
-continued
484
-continued
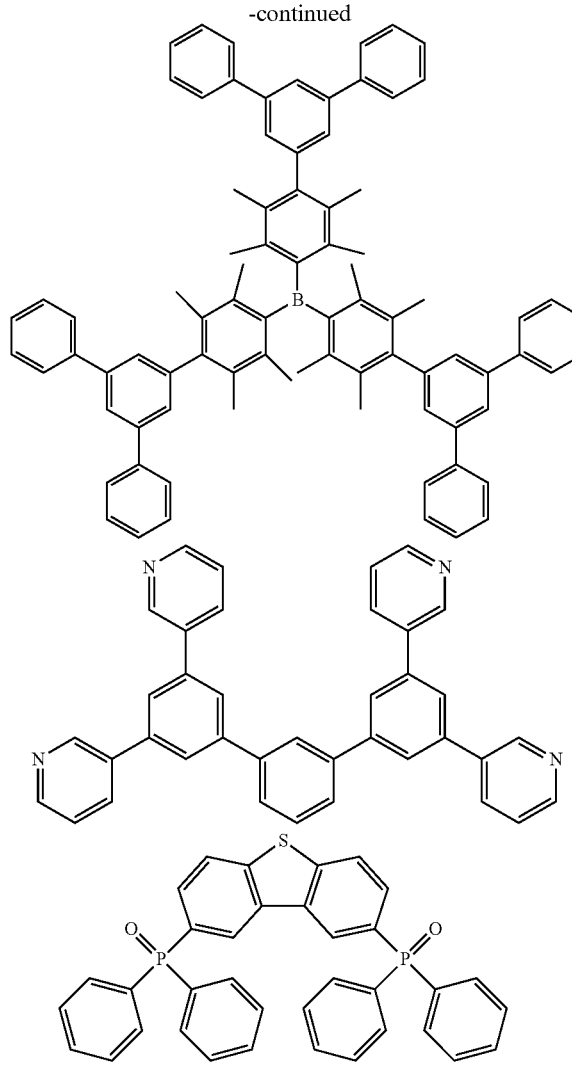
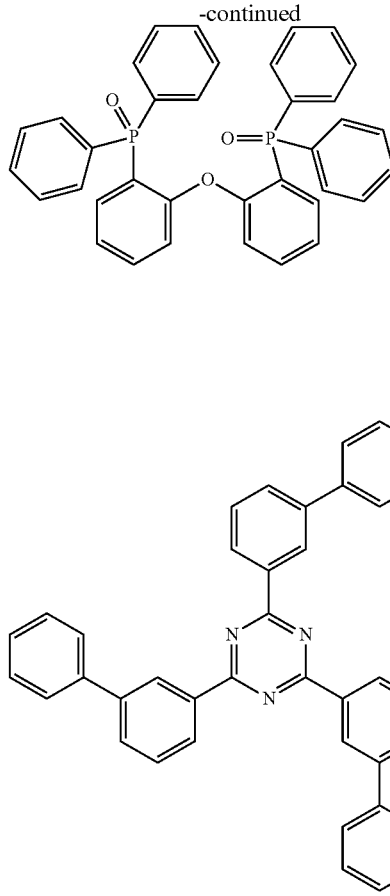
Preferred examples of a compound that may be used as the electron transporting material are shown below.
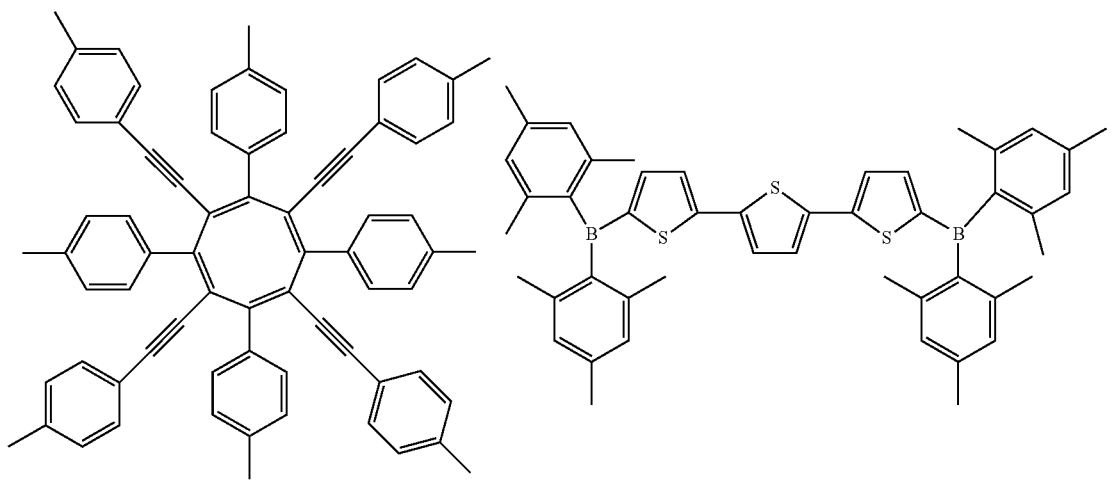

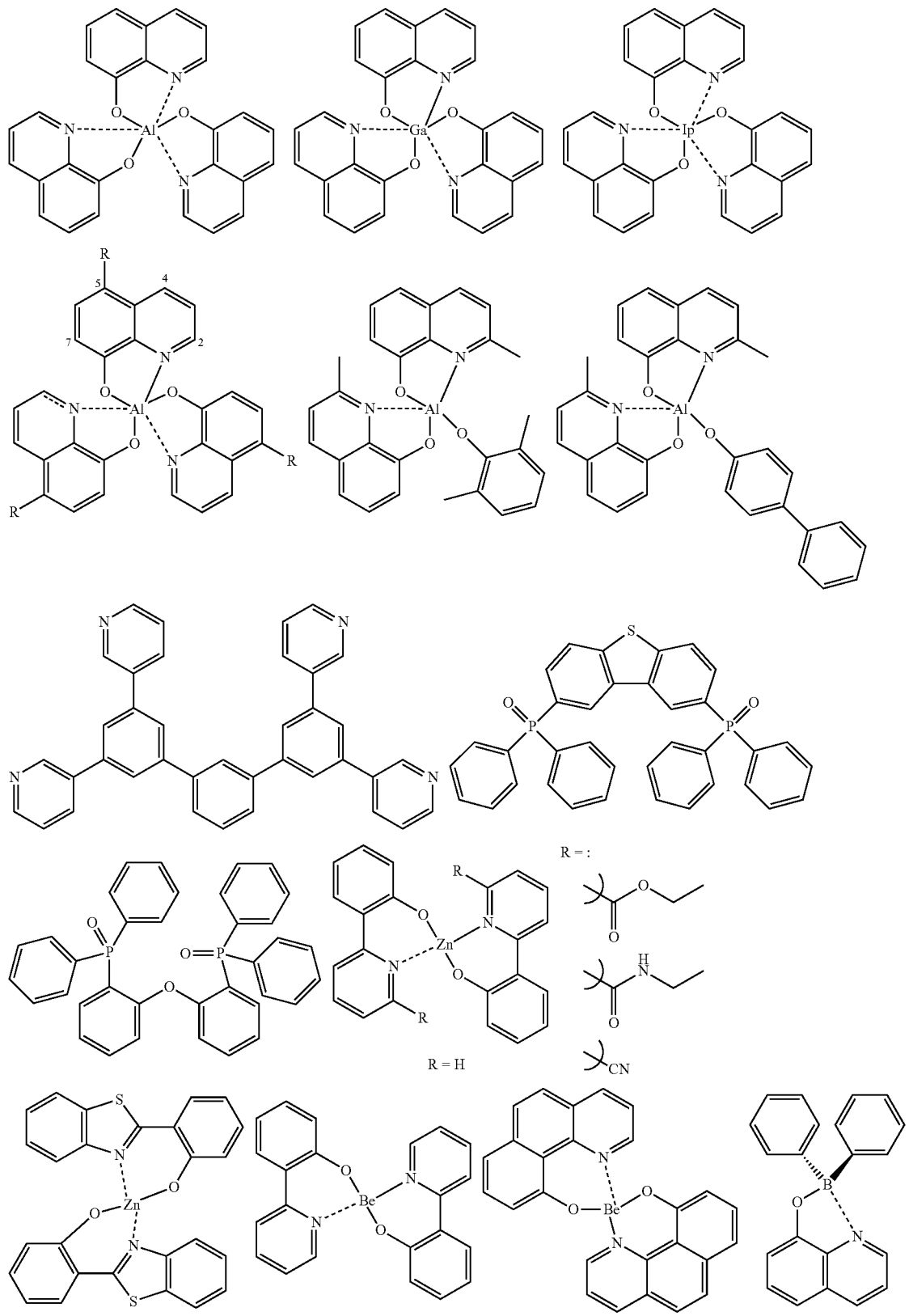

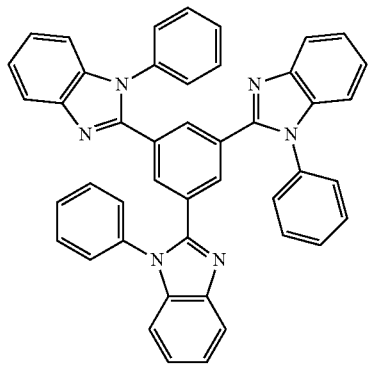
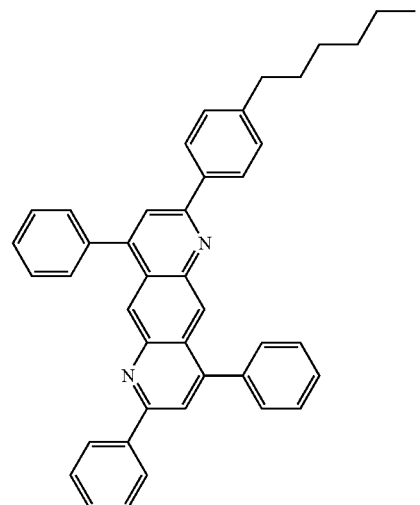
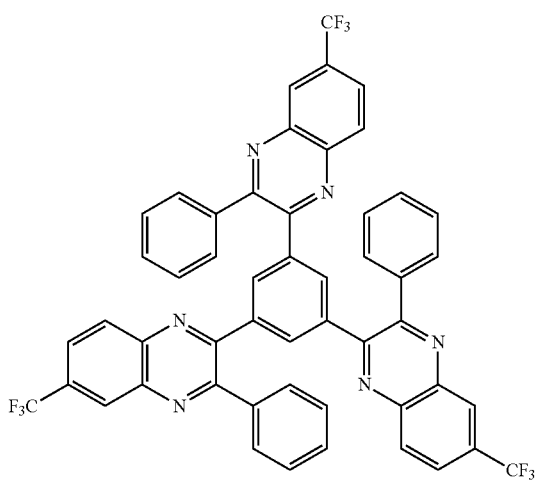
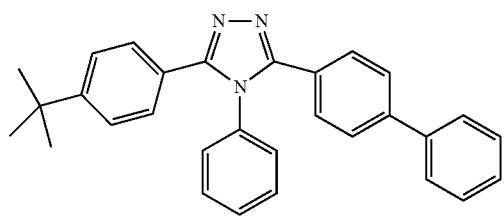
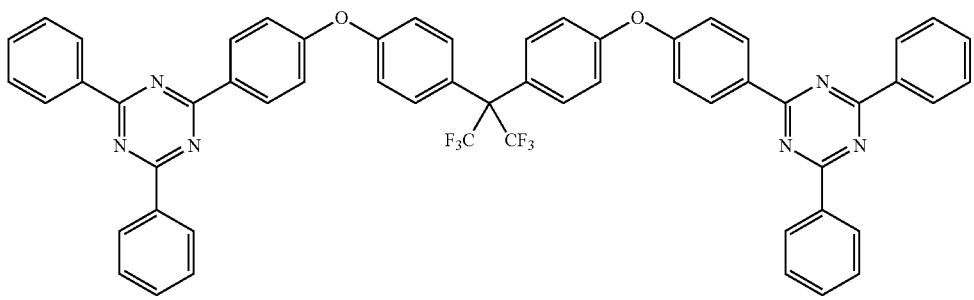

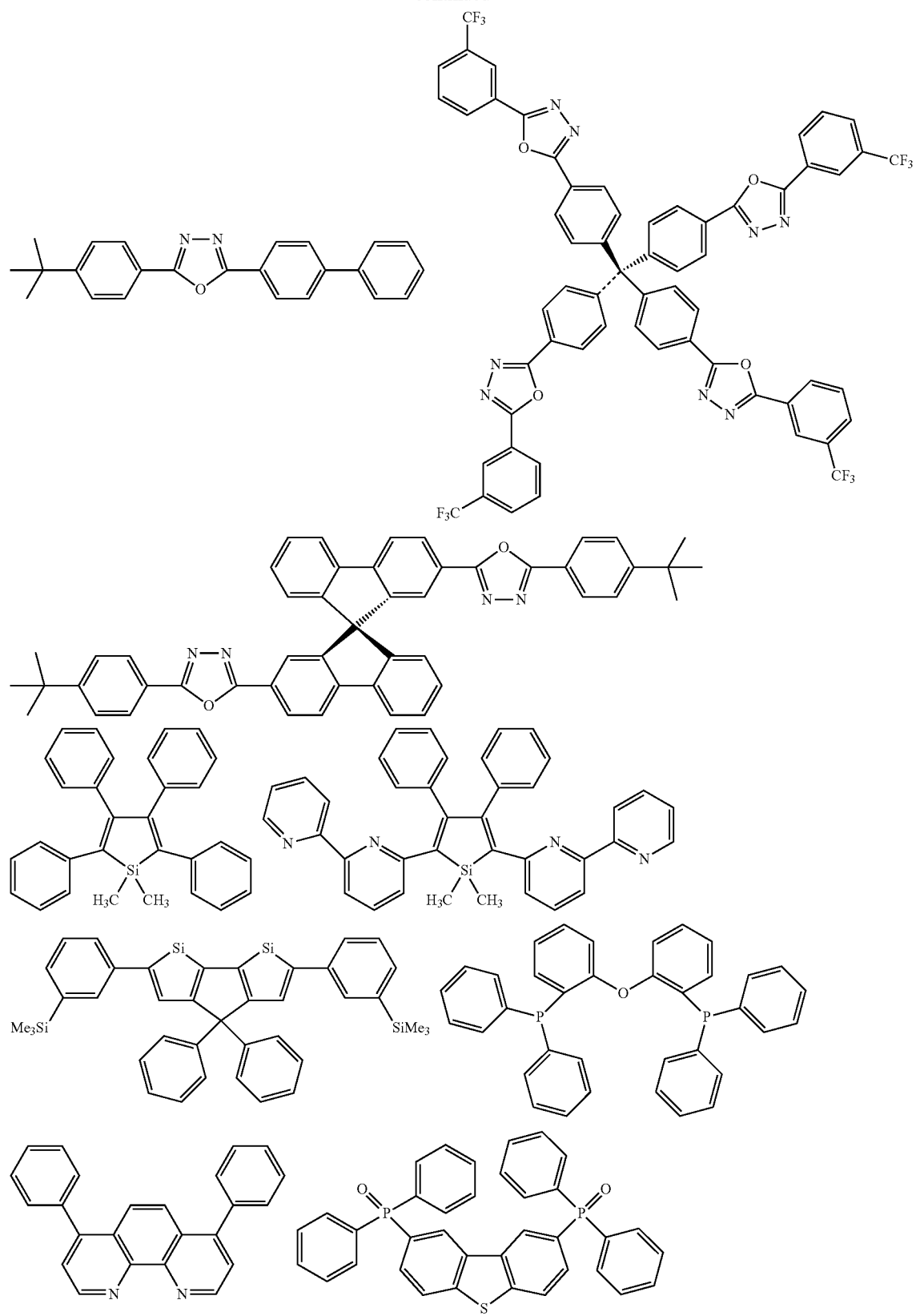

Preferred examples of a compound that may be used as the electron injection material are shown below.

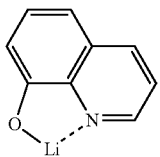

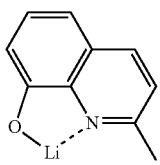

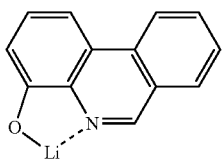

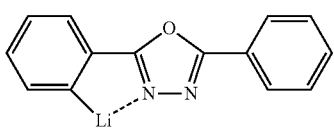

Preferred examples of a compound as a material that may be added are shown below. For example, the compound may be added as a stabilizing material.

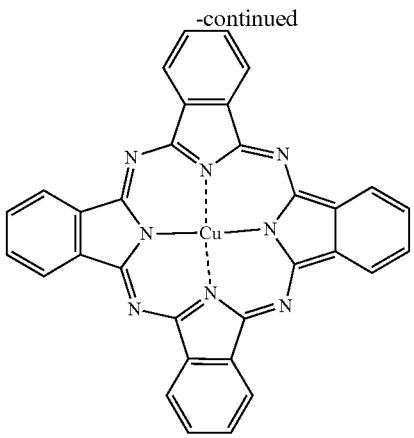

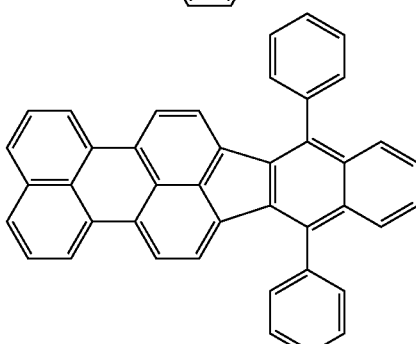

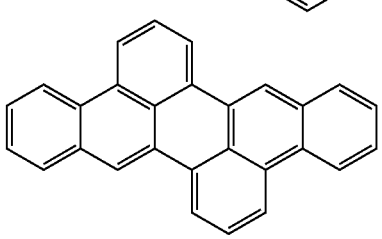

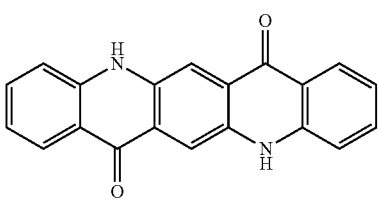

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

Synthesis Example 1

Synthesis of Compound 1

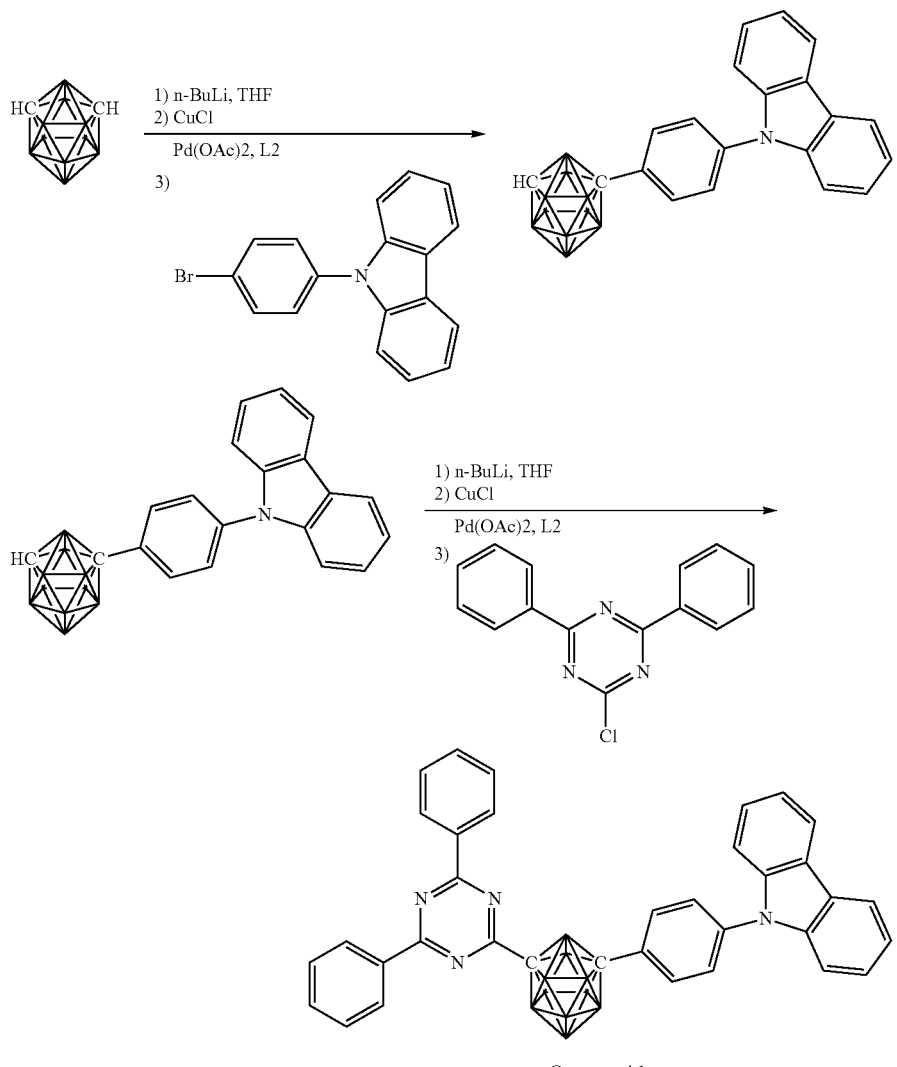

Compound 1 m-Carborane (1.87 g, 13.0 mmol) was placed in a three-neck flask, which was then replaced by nitrogen. Thereafter, 80 mL of tetrahydrofuran was added thereto, the mixture was cooled to −78° C., and a 1.60 M n-butyllithium hexane solution (9.80 mL, 26.0 mmol) was slowly added dropwise thereto, followed by agitating at −78° C. for 15 minutes. Thereafter, the mixture was agitated at 0° C. for 1 hour, and copper (I) chloride (1.39 g, 14.3 mmol) was added thereto, followed by agitating at room temperature for 30 minutes. Thereafter, 100 mL of a tetrahydrofuran solution containing palladium(II) acetate (0.15 g, 0.676 mmol), trismethoxytriphenylphosphine (0.75 g, 2.13 mmol), and 9-(4-bromophenyl)carbazole (5.00 g, 15.6 mmol) was added, followed by agitating at room temperature for 48 hours. Thereafter, water and chloroform were added to the mixture, which was extracted therewith. The organic layer separated was dried over sodium sulfate, and suction-filtered to provide a filtrate. The resulting filtrate was purified by column chromatography and recrystallization, thereby providing 1-(4-carbazol-9-ylphenyl)-m-carborane (yield: 37.1%).

1-(4-Carbazolylphenyl)-m-carborane (1.56 g, 4.0 mmol) was placed in a three-neck flask, which was then replaced by nitrogen. Thereafter, 80 mL of tetrahydrofuran was added thereto, the mixture was cooled to −78° C., and a 1.60 M n-butyllithium hexane solution (5.0 mL, 8.0 mmol) was slowly added dropwise thereto, followed by agitating at −78° C. for 15 minutes. Thereafter, the mixture was agitated at 0° C. for 1 hour, and copper(I) chloride (0.52 g, 5.2 mmol) was added thereto, followed by agitating at room temperature for 30 minutes. Thereafter, 100 mL of a tetrahydrofuran solution containing palladium(II) acetate (0.047 g, 0.208 mmol), trismethoxytriphenylphosphine (0.23 g, 0.656 mmol), and 2-chloro-4,6-diphenyl-1,3,5-triazine (1.3 g, 4.8 mmol) was added, followed by agitating at room temperature for 48 hours. Thereafter, water and chloroform were added to the mixture, which was extracted therewith. The organic layer separated was dried over sodium sulfate, and suction-filtered to provide a filtrate. The resulting filtrate was purified by column chromatography, thereby providing the compound 1 (yield: 44.5%) The compound was identified by $^1$H-NMR and elemental analysis.

$^1$H-NMR (500 MHz, CDCl$_3$, TMS, δ): 8.68 (d, J=7.0 Hz, 4H), 8.14 (d, J=7.5 Hz, 2H), 7.77 (d, J=8.5 Hz, 2H), 7.65-7.62 (m, 2H), 7.58-7.53 (m, 6H), 7.47-7.40 (m, 4H) 7.30 (t, J=9.0 Hz, 2H), 3.89-1.75 (br, 10H, B—H)

Elemental analysis: Anal. Calcd. for $C_{35}H_{32}B_{10}N_4$: C, 68.16%; H, 5.23%; N, 9.08%; found: C, 68.25%; H, 5.21%; N, 9.17%.

Synthesis Example 2

Synthesis of Compound 2

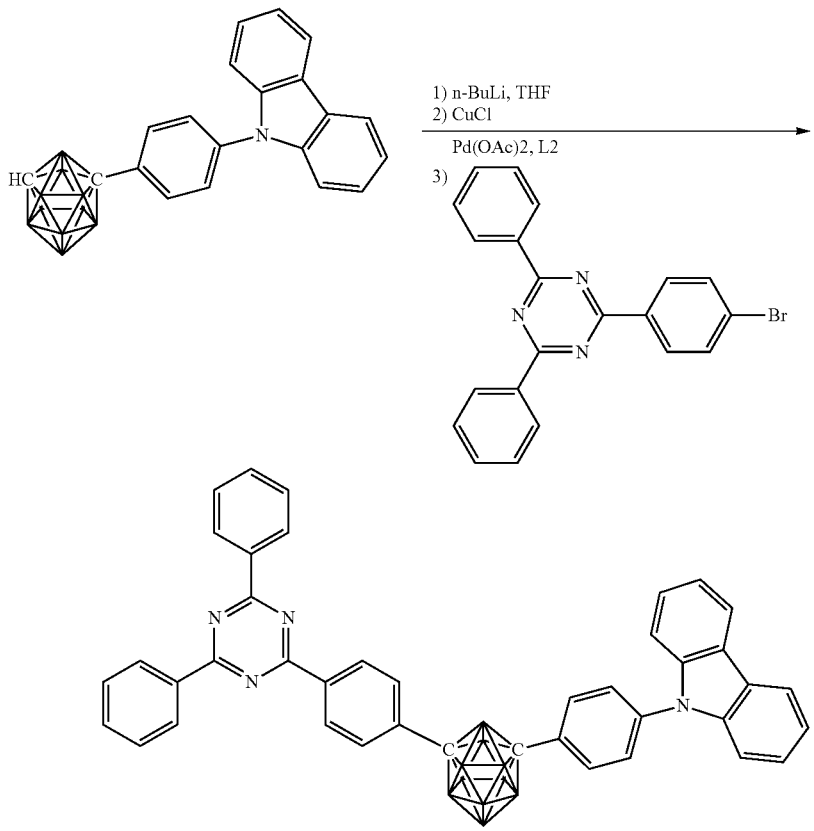

Compound 2

1-(4-Carbazolylphenyl)-m-carborane (1.56 g, 4.0 mmol) was placed in a three-neck flask, which was then replaced by nitrogen. Thereafter, 80 mL of tetrahydrofuran was added thereto, the mixture was cooled to −78° C., and a 1.60 M n-butyllithium hexane solution (5.0 mL, 8.0 mmol) was slowly added dropwise thereto, followed by agitating at −78° C. for 15 minutes. Thereafter, the mixture was agitated at 0° C. for 1 hour, and copper(I) chloride (0.52 g, 5.2 mmol) was added thereto, followed by agitating at room temperature for 30 minutes. Thereafter, 100 mL of a tetrahydrofuran solution containing palladium(II) acetate (0.047 g, 0.208 mmol), trismethoxytriphenylphosphine (0.23 g, 0.656 mmol), and 2-(4-bromophenyl)-4,6-diphenyl-1,3,5-triazine (1.86 g, 4.8 mmol) was added, followed by agitating at room temperature for 48 hours. Thereafter, water and chloroform were added to the mixture, which was extracted therewith. The organic layer separated was dried over sodium sulfate, and suction-filtered to provide a filtrate. The resulting filtrate was purified by column chromatography, thereby providing the compound 2 (yield: 10.8%). The compound was identified by 1H-NMR and elemental analysis.

$^{1}$H-NMR (500 MHz, CDCl$_3$, TMS, δ): 8.77 (d, J=9.7 Hz, 4H), 8.69 (d, J=8.7 Hz, 2H), 8.14 (d, J=7.7 Hz, 2H), 7.75-7.72 (m, 4H), 7.65-7.57 (m, 6H), 7.53 (d, J=8.7 Hz, 2H), 7.47-7.40 (m, 4H), 6.5 (t, J=8.7 Hz, 2H), 3.80-1.76 (br, 11H, B—H)

Synthesis Example 3

Synthesis of Compound 3

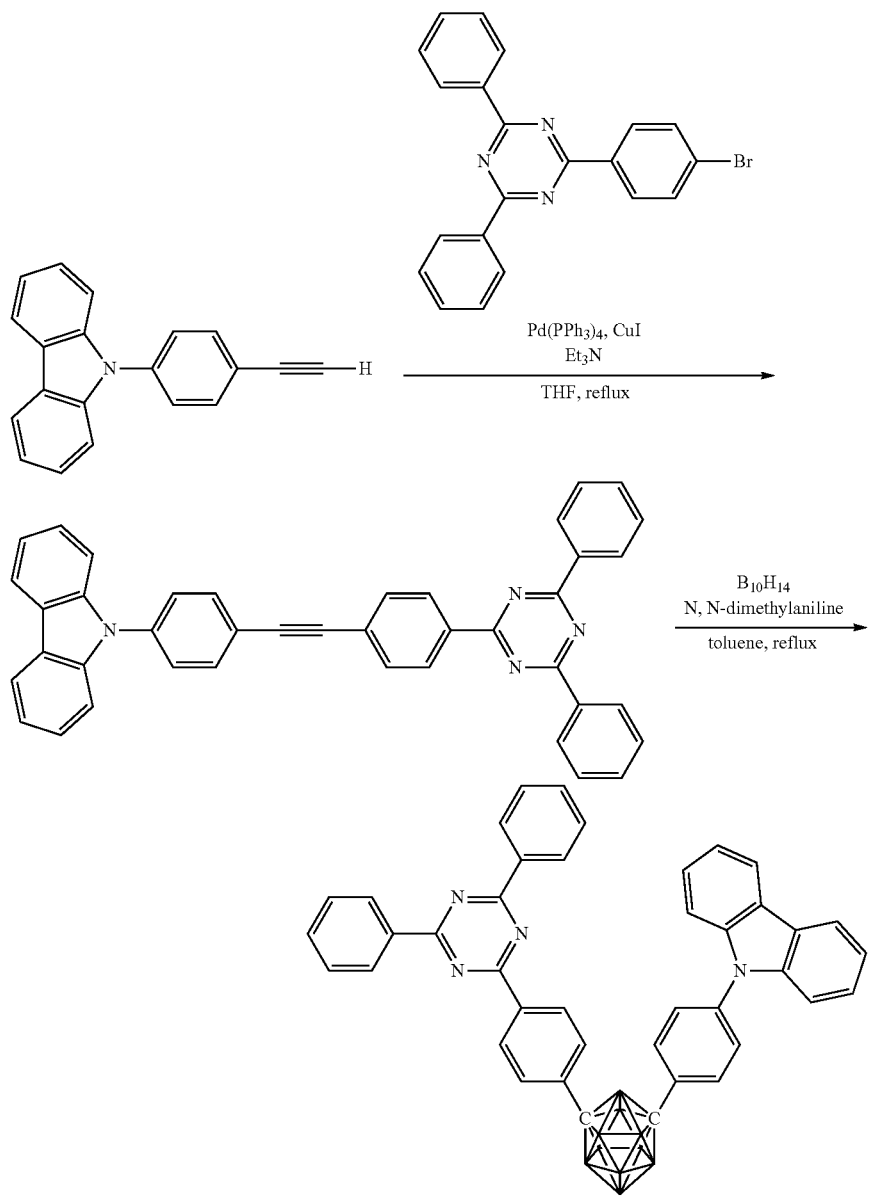

Compound 3

9-(4-Ethynylphenyl)-9H-carbazole (2.13 g, 8.0 mmol) and brominated triphenyltriazine (2.06 g, 5.3 mmol) were placed in a three-neck flask, which was then replaced by nitrogen. Thereafter, 180 mL of triethylamine and 100 mL of tetrahydrofuran were added thereto for dissolution, and then tetrakis(triphenylphosphine) palladium(0) (0.31 g, 0.0266 mmol) and copper(I) iodide (0.05 g, 5.57 mmol) were added, followed by refluxing for 24 hours. Thereafter, water and chloroform were added to the mixture, which was extracted therewith. The organic layer separated was dried over sodium sulfate, and suction-filtered to provide a filtrate. The resulting filtrate was purified by column chromatography, thereby providing 9-(4-((4,6-diphenyl-1,3,5-triazin-2-yl)phenyl)ethynyl)phenyl)-9H-carbazole (yield: 39.3%).

Decaborane (0.234 g, 1.91 mmol) and N,N-dimethylaniline (0.580 g, 4.79 mmol) were placed in a 100 mL three-neck flask having been replaced by nitrogen, and dissolved with 50 mL of toluene. The solution was agitated at room temperature for 30 minutes, and then heated for refluxing under agitating for 2 hours. Thereafter, the temperature thereof was lowered to 40° C., to which 9-(4-((4,6-diphenyl-1,3,5-triazin-2-yl)phenyl)ethynyl)phenyl)-9H-carbazole (1.0 g, 1.74 mmol) was added, followed by refluxing for 24 hours. Thereafter, water and chloroform were added to the mixture, which was extracted therewith. The organic layer separated was dried over sodium sulfate, and suction-filtered to provide a filtrate. A solid was obtained by reprecipitation and purified by sublimation, thereby providing the compound 3 (yield: 21.8%). The compound was identified by $^1$H-NMR and elemental analysis. $^1$H-NMR (500 MHz, CDCl$_3$, TMS, δ): 8.72 (d, J=8.5 Hz, 4H), 8.64 (d, J=8.5 Hz, 2H), 8.02 (d, J=7.5 Hz, 2H), 7.72-7.69 (m, 4H), 7.63-7.54 (m, 6H), 7.39 (d, J=8.5 Hz, 2H), 7.24-7.14 (m, 6H), 3.83-1.78 (br, 10H, B—H)

Example 1

Production and Evaluation of Organic Photoluminescent Device Using Compound 1 as Host Material A light-emitting material containing 4CzIPN, and the compound 1 were vapor-deposited from separate vapor deposition sources on a quartz substrate by a vacuum vapor deposition method under condition of a vacuum degree of from 2 to 7.0×10$^{-4}$ Pa, so as to form a thin film having a concentration of 4CzIPN of 3.0% by weight to a thickness of 100 nm, thereby providing an organic photoluminescent device.

Figure 2:
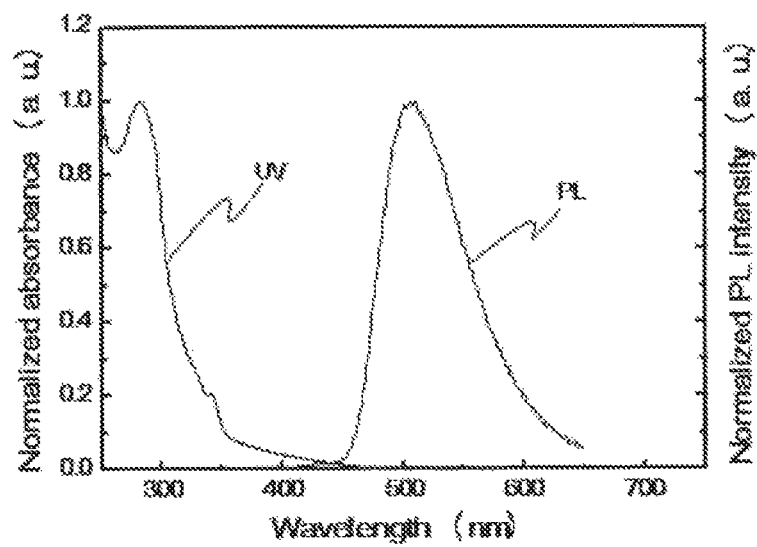
FIG. 2 shows the light emission and absorption spectra of the thin film organic photoluminescent device of 4CzIPN and the compound 1 in Example 1.

FIG. 2 shows the light emission and absorption spectra of the organic photoluminescent device thus produced with excitation light of 280 nm. The photoluminescence quantum efficiency was 84.9%.

Example 2

Production and Evaluation of Organic Electroluminescent Device Using Compound 1 as Host Material Thin films were laminated on a glass substrate having formed thereon an anode formed of indium tin oxide (ITO) having a thickness of 100 nm, by a vacuum vapor deposition method at a vacuum degree of from 2 to 7.0×10$^{-4}$ Pa. Firstly, α-NPD was formed to a thickness of 35 nm on ITO, and then mCP was formed to a thickness of 10 nm thereon. Subsequently, a light-emitting material containing 4CzIPN and the compound 1 were co-deposited thereon from separate vapor deposition sources to form a layer having a thickness of 20 nm, which was designated as a light-emitting layer. At this time, the concentration of 4CzIPN was 3.0% by weight. PPT was then formed to a thickness of 40 nm, further lithium fluoride (LiF) was vacuum vapor-deposited to a thickness of 0.8 nm, and then aluminum (Al) was vapor-deposited to a thickness of 80 nm to form a cathode, thereby completing an organic electroluminescent device.

Figure 3:
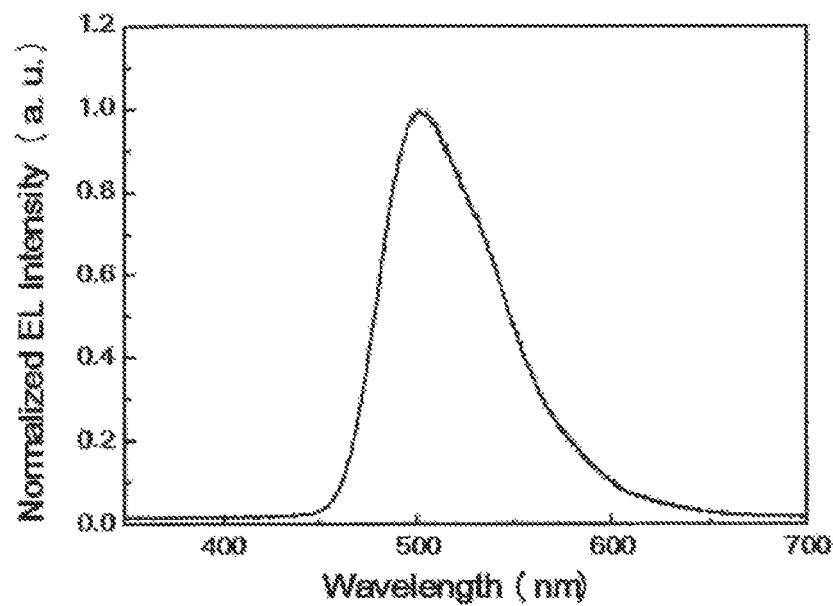
FIG. 3 shows the light emission spectrum of the organic electroluminescent device of 4CzIPN and the compound 1 in Example 2.
Figure 4:
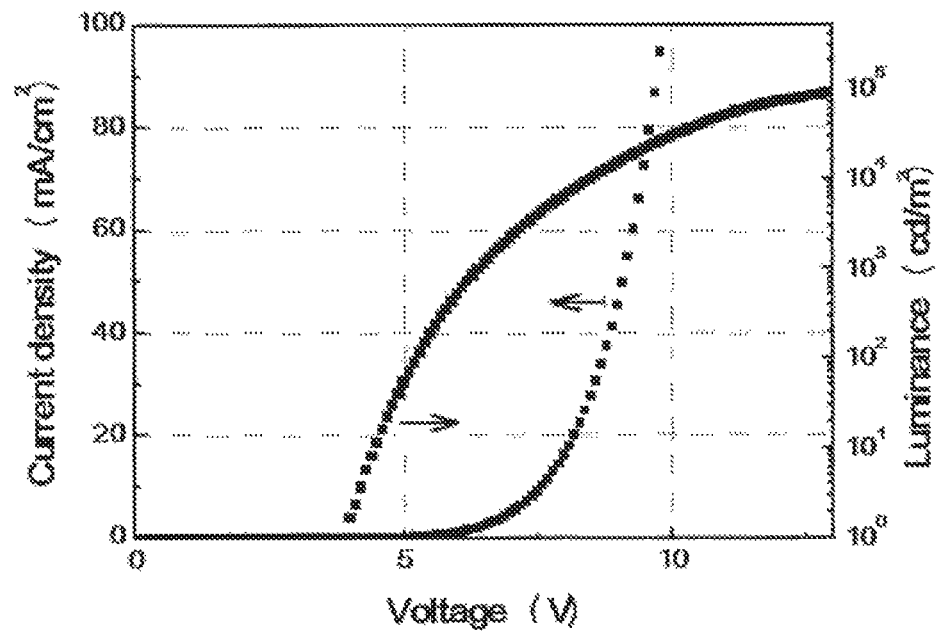
FIG. 4 is a graph showing the voltage-current density-luminance characteristics of the organic electroluminescent device of 4CzIPN and the compound 1 in Example 2.
Figure 5:
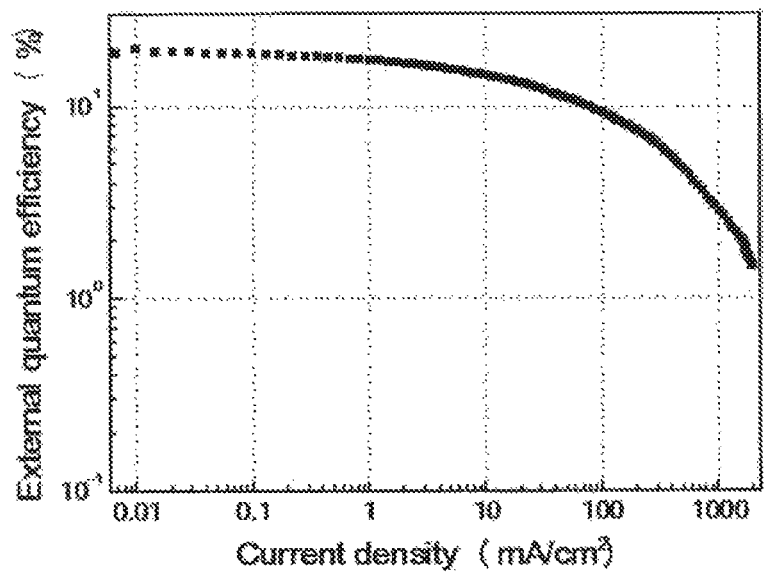
FIG. 5 is a graph showing the current density-external quantum efficiency characteristics of the organic electroluminescent device of 4CzIPN and the compound 1 in Example 2.

FIG. 3 shows the light emission spectrum of the organic electroluminescent device thus produced at 10 mA/cm$^2$, FIG. 4 shows the voltage-current density-luminance characteristics thereof, and FIG. 5 shows current density-external quantum efficiency characteristics thereof. The organic electroluminescent device using the compound 1 as a host material exhibited a voltage of 3.9 V at a light emission wavelength of 501 nm at 1 cd/m$^2$, a voltage of 7.6 V at 10 mA/cm$^2$, a luminance of 28,980 cd/m$^2$ at 10 V, and an external quantum efficiency of 19.4% at 0.01 mA/cm$^2$, which indicated a high external quantum efficiency.

Example 3

Production and Evaluation of Organic Photoluminescent Device Using Compound 1 as Light-Emitting Material Toluene solutions of the compound 1 having a concentrations of 10$^{-3}$ M, 10$^{-4}$ M, and 10$^{-5}$ M were prepared in a glove box under an Ar atmosphere.

The compound 1 was vapor-deposited on a quartz substrate by a vacuum vapor deposition method under condition of a vacuum degree of from 2 to 7.0×10$^{-4}$ Pa to form a thin film of the compound 1 to a thickness of 100 nm, thereby providing an organic photoluminescent device.

Figure 6:
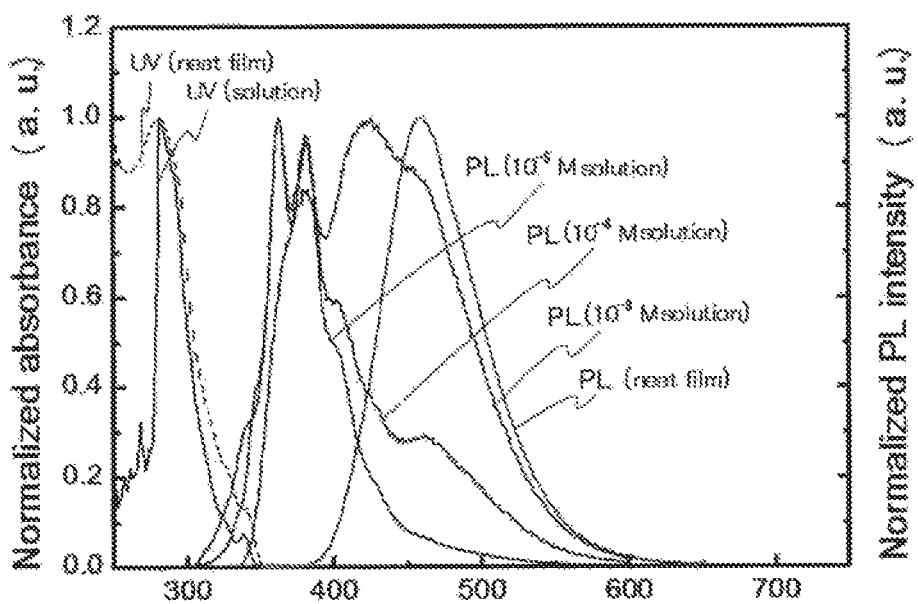
FIG. 6 shows the light emission and absorption spectra of the toluene solutions before bubbling with nitrogen and the thin film organic photoluminescent device of the compound 1 in Example 3.
Figure 7:
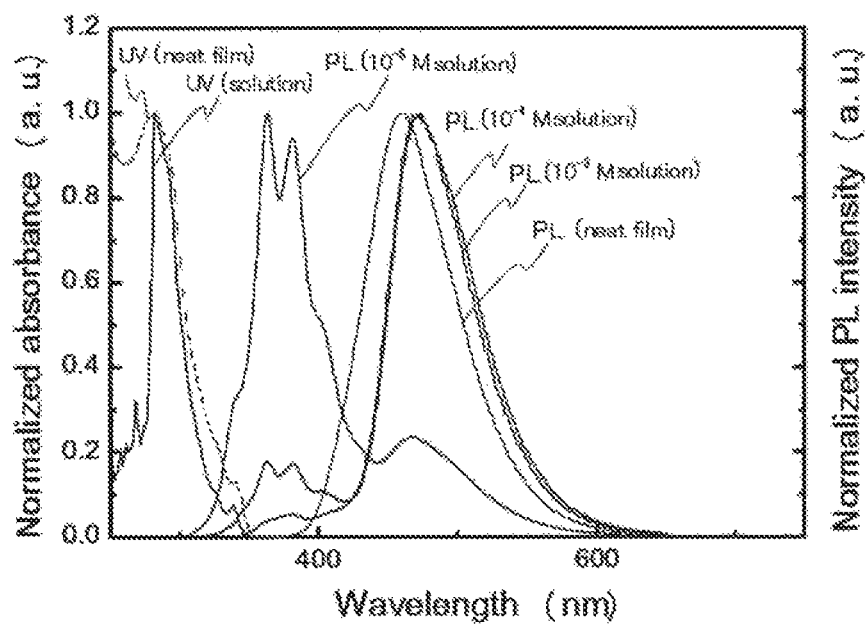
FIG. 7 shows the light emission and absorption spectra of the toluene solutions after bubbling with nitrogen and the thin film organic photoluminescent device of the compound 1 in Example 3.

The specimens using the compound 1 were measured for light emission and absorption spectra with excitation light of 280 nm. FIG. 6 shows the light emission and absorption spectra of the toluene solutions before bubbling with nitrogen and the organic photoluminescent device measured in the air, and FIG. 7 shows the light emission and absorption spectra of the toluene solutions after bubbling with nitrogen and the thin film organic photoluminescent device measured in a nitrogen-containing atmosphere.

The photoluminescence quantum efficiency of the toluene solution of the compound 1 before bubbling with nitrogen was 1.9% for the toluene solution of 10$^{-3}$ M, 2.1% for the toluene solution of 10$^{-4}$ M, and 2.7% for the toluene solution of 10$^{-5}$M, and that after bubbling with nitrogen was 76.3% for the toluene solution of 10$^{-3}$ M, 17.8% for the toluene solution of 10$^{-4}$ M, and 5.3% for the toluene solution of 10$^{-5}$ M. The photoluminescence quantum efficiency of the organic photoluminescent device having the thin film of the compound 1 was 33.9% measured in the air, and 47.0% measured in a nitrogen-containing atmosphere.

Figure 8:
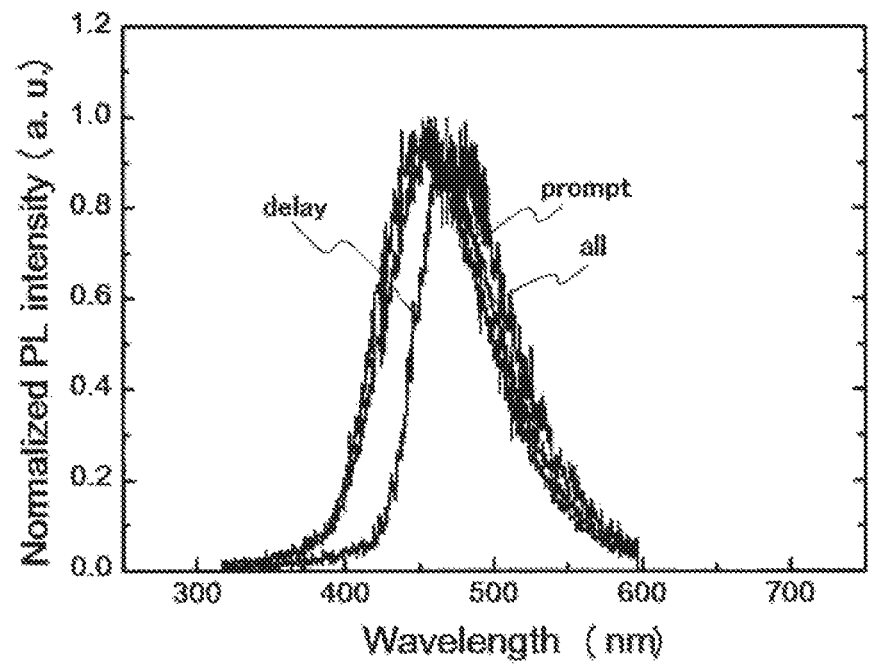
FIG. 8 shows the light emission spectra for fluorescent light, delayed fluorescent light, and total fluorescent light of the organic photoluminescent device of the compound 1 in Example 3.
Figure 9:
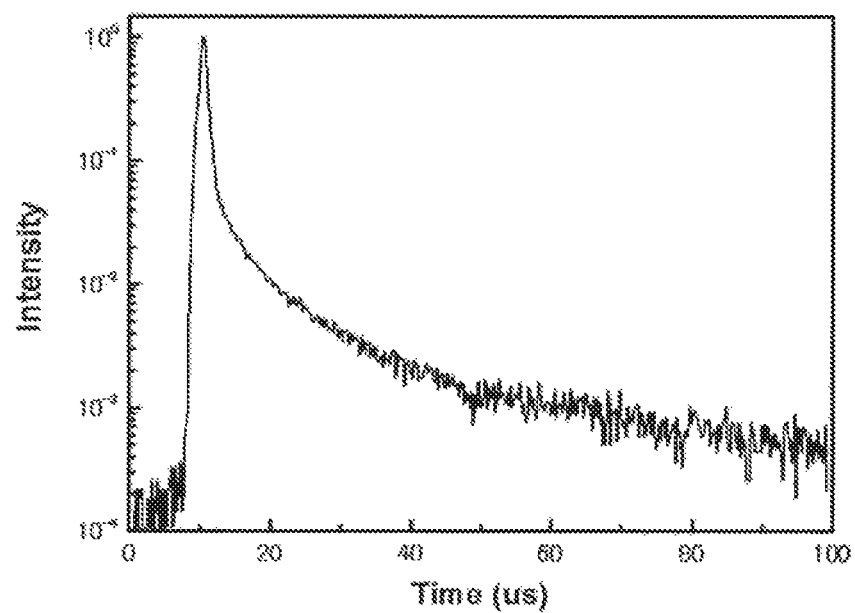
FIG. 9 shows the transient decay curve of the organic photoluminescent device of the compound 1 in Example 3.

FIG. 8 shows the light emission spectra for fluorescent light, delayed fluorescent light, and total fluorescent light of the organic photoluminescent device having the thin film of the compound 1, and FIG. 9 shows the transient decay curve measured at 300 K thereof. The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the compound 1 shown in FIG. 9, while a linear component (fluorescent light) was observed in the initial stage of observation, a component that deviated from the linearity appeared after several microseconds. The later component is light emission of the delayed component, and the signal thereof added to the initial component appears as a long tail curve on the longer time side. Thus, the measurement of the light emission lifetime revealed that the compound 1 was a light-emitting material that contained a delayed component in addition to a fluorescent component.

Example 4

Production and Evaluation of Organic Photoluminescent Device Using Compound 2 as Light-Emitting Material A toluene solution having a concentration of $10^{-3}$ mol/L was prepared in the same manner as in Example 3 except that the compound 2 was used instead of the compound 1.

Figure 10:
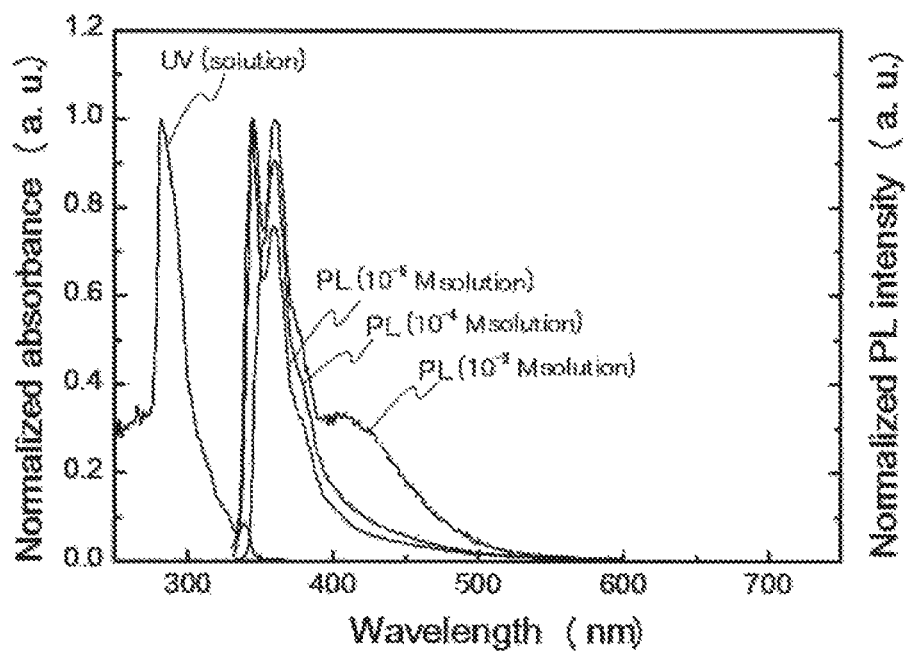
FIG. 10 shows the light emission and absorption spectra of the toluene solution of the compound 2 in Example 4.

FIG. 10 shows the light emission and absorption spectra of the toluene solution of the compound 2 thus prepared, with excitation light of 320 nm after bubbling with nitrogen. The photoluminescence quantum efficiency was 12.8%.

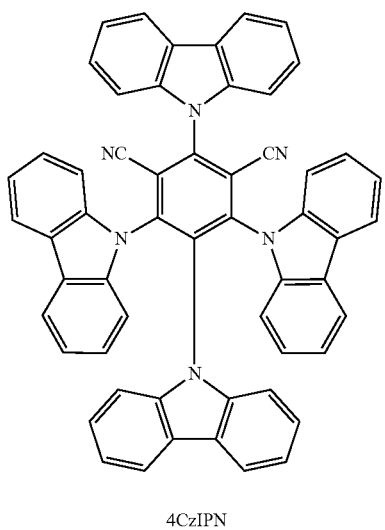

4CzIPN

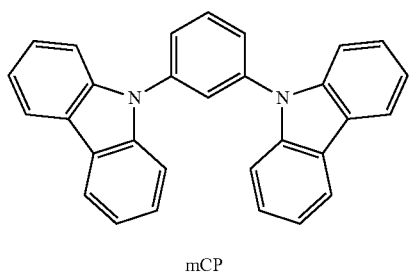

mCP

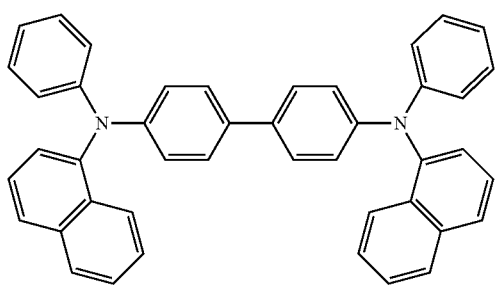

α-NPD

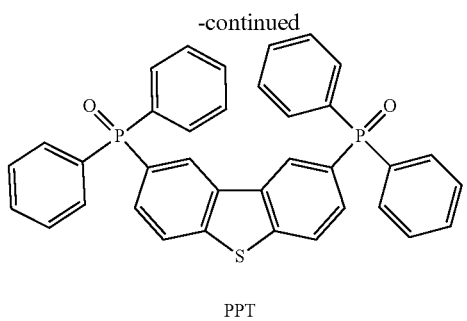

PPT

INDUSTRIAL APPLICABILITY

The compound represented by the general formula (1) is useful as a host material or a light-emitting material. Accordingly, the compound of the invention may be effectively used as a host material or a light-emitting material of an organic light-emitting device, such as an organic electroluminescent device. The compound of the invention includes a compound that emits delayed fluorescent light, and thus may be capable of providing an organic light-emitting device having a high light emission efficiency. Thus, the invention has high industrial applicability.

REFERENCE SIGNS LIST 1 substrate
2 anode
3 hole injection layer
4 hole transporting layer
5 light-emitting layer
6 electron transporting layer
7 cathode

The invention claimed is:
1. An organic light-emitting device comprising a compound represented by the following general formula (1) in a light-emitting layer:

General Formula (1)

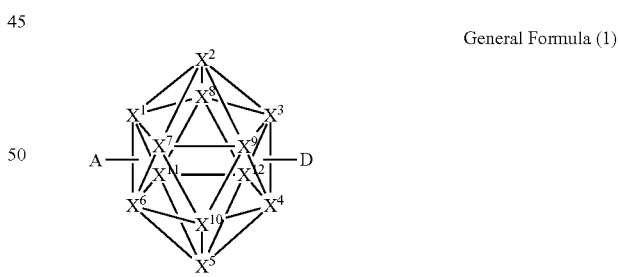

wherein in the general formula (1), $X^1$ to $X^{12}$ each independently represent C or BH constituting carborane, provided that among $X^1$ to $X^{12}$, the bonding positions to A and D each represent C, and the other thereof each represent BH; A represents an acceptor bonded to the carborane through an aromatic ring or a heteroaromatic ring; and D represents a donor bonded to the carborane through an aromatic ring or a heteroaromatic ring, and the compound represented by the general formula (1) emits light.

2. The organic light-emitting device according to claim 1, wherein the organic light-emitting device contains the compound represented by the general formula (1) as a host material.

3. The organic light-emitting device according to claim 2, wherein the light-emitting layer further contains a delayed fluorescent emitter.

4. The organic light-emitting device according to claim 1, wherein the organic light-emitting device contains the compound represented by the general formula (1) as a light-emitting material.

5. The organic light-emitting device according to claim 1, wherein in the general formula (1), D is bonded to the carborane through a benzene ring.

6. The organic light-emitting device according to claim 1, wherein in the general formula (1), D has a diphenylamino group or a carbazolyl group.

7. The organic light-emitting device according to claim 1, wherein in the general formula (1), D represents a group represented by the following general formula (2):

$[(R^1)(R^2)N]_{n1}-Ar^1-$        General Formula (2)

wherein in the general formula (2), $R^1$ and $R^2$ each independently represent a substituent, provided that $R^1$ and $R^2$ may be bonded to each other to form a cyclic structure; n1 represents an integer of from 1 to 4; and $Ar^1$ represents a substituted or unsubstituted aromatic group having a valence of (n1+1).

8. The organic light-emitting device according to claim 7, wherein in the general formula (2), n1 represents 1 or 2.

9. The organic light-emitting device according to claim 1, wherein in the general formula (1), A has a heteroaromatic ring containing a nitrogen atom.

10. The organic light-emitting device according to claim 9, wherein in the general formula (1), A has a triazine ring.

11. The organic light-emitting device according to claim 10, wherein the triazine ring is substituted with a phenyl group.

12. The organic light-emitting device according to claim 9, wherein in the general formula (1), A is bonded to the carborane through the heteroaromatic ring containing a nitrogen atom.

13. The organic light-emitting device according to claim 9, wherein in the general formula (1), A represents a group represented by the following general formula (3):

$(Het)_{n2}-Ar^2-$        General Formula (3)

wherein in the general formula (3), Het represents a substituted or unsubstituted heteroaromatic ring group (provided that the heteroaromatic ring group contains a nitrogen atom as a ring structure constituting atom); n2 represents an integer of from 1 to 4; and $Ar^2$ represents a substituted or unsubstituted aromatic group having a valence of (n2+1).

14. The organic light-emitting device according to claim 13, wherein in the general formula (3), n2 represents 1 or 2.

15. The organic light-emitting device according to claim 1, wherein the compound represented by the general formula (1) is an o-carborane compound or a m-carborane compound.

16. The organic light-emitting device according to claim 1, wherein the organic light-emitting device is an organic electroluminescent device.

17. The organic light-emitting device according to claim 1, wherein the organic light-emitting device emits delayed fluorescent light.

* * * * *